US008486634B2

(12) United States Patent
Lim et al.

(10) Patent No.: US 8,486,634 B2
(45) Date of Patent: *Jul. 16, 2013

(54) AMPLIFYING BISULFITE-TREATED TEMPLATE

(75) Inventors: Mark J. Lim, Reading, MA (US); Kenneth J. Rothschild, Newton, MA (US)

(73) Assignee: Ambergen, Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/291,178

(22) Filed: Nov. 6, 2008

(65) Prior Publication Data

US 2010/0311042 A1   Dec. 9, 2010

Related U.S. Application Data

(60) Provisional application No. 61/002,013, filed on Nov. 6, 2007.

(51) Int. Cl.
*C12Q 1/68* (2006.01)
*C12P 19/34* (2006.01)
*C07H 21/04* (2006.01)

(52) U.S. Cl.
USPC ............ 435/6.12; 435/91.2; 536/24.33

(58) Field of Classification Search
USPC .................. 435/6, 91.2; 536/22.1, 24.33
See application file for complete search history.

(56) References Cited

U.S. PATENT DOCUMENTS

| | | | |
|---|---|---|---|
| 5,641,658 A | 6/1997 | Adams et al. ............. | 435/91.3 |
| 5,643,722 A | 7/1997 | Rothschild et al. ......... | 435/6.13 |
| 5,807,522 A | 9/1998 | Brown et al. ............. | 422/50 |
| 5,922,858 A | 7/1999 | Rothschild et al. ......... | 536/24.1 |
| 5,986,076 A | 11/1999 | Rothschild et al. ......... | 536/22.1 |
| 6,057,096 A | 5/2000 | Rothschild et al. ......... | 435/6.13 |
| 6,210,941 B1 | 4/2001 | Rothschild et al. ......... | 435/183 |
| 6,306,628 B1 | 10/2001 | Rothschild et al. ......... | 435/91.3 |
| 6,589,736 B1 | 7/2003 | Rothschild et al. ......... | 435/6.13 |
| 6,596,481 B1 | 7/2003 | Rothschild et al. ......... | 435/6.13 |
| 7,101,662 B2 | 9/2006 | Rothschild et al. ......... | 435/6.13 |
| 7,285,394 B2 | 10/2007 | Lofton-Day et al. ........ | 435/18 |
| 2006/0148853 A1* | 7/2006 | Liu et al. ................. | 514/336 |

FOREIGN PATENT DOCUMENTS

WO    WO 2005082098 A2 *  9/2005

OTHER PUBLICATIONS

U.S. Appl. No. 60/499,082, filed Aug. 29, 2003, Boyd, et al.
U.S. Appl. No. 60/499,106, filed Aug. 29, 2003, Zon, et al.
U.S. Appl. No. 60/499,113, filed Aug. 29, 2003, Zon, et al.
U.S. Appl. No. 60/520,942, filed Nov. 17, 2003, Zon, et al.
U.S. Appl. No. 60/523,054, filed Nov. 17, 2003, Zon, et al.
U.S. Appl. No. 60/523,056, filed Nov. 17, 2003, Boyd, et al.
Adessi, et al., "Solid phase DNA amplification: characterisation of primer attachment and amplification mechanisms." *Nucleic Acids Res*, 28:E87 (2000).
Ahuja, et al., "Association between CpG Island Methylation and Microsatellite Instability in Colorectal Cancer." *Cancer Res*, 57:3370-3374 (1997).
Alivisatos, "The Use of Nanocrystals in Biological Detection." *Nature Biotech.*, 22:47-52 (2004).
Atherton, et al., "Solid Phase Peptide Synthesis." IRL Press, Oxford (1989).
Badal, et al., "CpG Methylation of Human Papillomavirus Type 16 DNA in Cervical Cancer Cell Lines and in Clinical Specimens: Genomic Hypomethylation Correlates with Carcinogenic Progression." *J Virol*, 77:6227-6234 (2003).
Baldwin, et al., "New photolabile phosphate protecting group." *Tetrahedron* 46:6879 (1990).
Barone, et al., "Photolithographic synthesis of high-density oligonucleotide probe arrays." *Nucleosides Nucleotides Nucleic Acids* 20:525-531 (2001).
Bazan and Rapoport, Methodological considerations for the measurement of protein kinase C translocation in intact smooth muscle. *J Pharm Tox Meth*, 36:87-95 (1996).
Bing, et al., "Bridge amplification: a solid phase PCR system for the amplification and detection of allelic differences in single copy genes." In *Genetic Identity Conference Proceedings, Seventh International Symposium on Human Identification*, Phoenix AZ by Promega Corporation (1996).
Bottger, et al., "Molecular characterization of the hdm2-p53 interaction." *J Mol Biol*, 269:744-756 (1997).
Brenan, et al., "Chemical imaging with a confocal scanning Fourier-transform-Ramam microscope." *Appl. Opt.*, 33:7520 (1994).
Bruchez, et al., "Semiconductor Nanocrystals as Fluorescent Biological Labels." *Science*, 281:2013-2016 (1998).
Chan, et al., "Quantum Dot Bioconjugates for Ultrasensitive Nonisotopic Detection." *Science* 281:2016-2018 (1998).
Chen, et al., "Detection in Fecal DNA of Colon Cancer—Specific Methylation of the Nonexpressed Vimentin Gene." *J Natl Cancer Inst* 97:1124-1132 (2005).
Chiang, et al., "NFkB translocation in human microvessel endothelial cells using a four-compartment subcellular protein redistribution assay." *J Biochem Biophys Methods* 46:53-68 (2000).
Colarusso, et al., "Infrared Spectroscopic Imaging: From Planetary to Cellular Systems." *Appl. Spectrosc.* 52:106A (1998).
Colvin, et al., "Semiconductor Nanocrystals Covalently Bound to Metal Surfaces with Self-Assembled Monolayers." *J. Am. Chem. Soc.* 114:5221-5230 (1992).
Darder, et al., "Dithiobissuccinimidyl propionate as an anchor for assembling peroxidases at electrodes surfaces and its application in a H2O2 biosensor." *Anal Chem* 71:5530-5537 (1999).
Den Dunne, et al., "The protein truncation test: A review." *Hum Mutat* 14:95-102 (1999).
Diehl, et al., "Detection and quantification of mutations in the plasma of patients with colorectal tumors." *Proc Natl Acad Sci USA* 102:16368-16373 (2005).

(Continued)

*Primary Examiner* — Prabha Chunduru
(74) *Attorney, Agent, or Firm* — Medlen & Carroll, LLP

(57) ABSTRACT

Methods of amplifying nucleic acid are described. Primers on solid support, e.g. a population of beads, are employed. A population of nucleic acid template molecules, wherein the nucleic acid template molecules have been treated with bisulfite, is amplified so as to create loaded beads comprising amplified nucleic acid.

39 Claims, 65 Drawing Sheets
(15 of 65 Drawing Sheet(s) Filed in Color)

OTHER PUBLICATIONS

Dressman, et al., "Transforming single DNA molecules into fluorescent magnetic particles for detection and enumeration of genetic variations." *Proc Natl Acad Sci USA* 100:8817-8822 (2003).

Empedocles, et al., "Influence of Spectral Diffusion on the Line Shapes of Single CdSe Nanocrystallite Quantum Dots." *Phys. Rev. Lett.* 77(18):3873 (1996).

Fenniri, et al., "Preparation, Physical Properties, On-Bead Binding Assay and Spectroscopic Reliability of 25 Barcoded Polystyrene—Poly(ethylene glycol) Graft Copolymers." *J Am Chem* Soc 125, 10546-10560 (2003).

Finn, et al., "Isolation and Characterization of Hormone Receptors." *Methods Enzymol.* 184:244 (1990).

Fraga and Esteller, "DNA methylation: a profile of methods and applications." *Biotechniques* 33:632, 634, 636-649 (2002).

Frommer, et al., "A genomic sequencing protocol that yields a positive display of 5-methylcytosine residues in individual DNA strands." *Proc Nall Acad Sci USA* 89:1827-1831 (1992).

Futreal, et al., "BRCA1 mutations in primary breast and ovarian carcinomas." *Science* 266:120-122 (1994).

Garvin, et al., "A complete protein truncation test for BRCA1 and BRCA2." *Eur J Hum Genet.* 6:226-234 (1998).

Gite, et al., "Ultrasensitive fluorescence-based detection of nascent proteins in gels." *Anal Biochem* 279:218-225 (2000).

Gite, et al., "A high-throughput nonisotopic protein truncation test." *Nat Biotechnol* 21:194-197 (2003).

Gonzalez, et al., "Extremely high thermal stability of streptavidin and avidin upon biotin binding." *Biomol Eng* 16, 67-72 (1999).

Gonzalgo and Jones, "Rapid quantitation of methylation differences at specific sites using methylation-sensitive single nucleotide primer extension (Ms-SNuPE)." *Nucleic Acids Res* 25:2529-2531 (1997).

Green, et al., "Microfabricated tip arrays for improving force measurements." Phys. Rev. Letts 74:1489 (1999).

Groden, et al., Identification and characterization of the familial adenomatous polyposis coli gene. *Cell* 66:589-600 (1991).

Gunderson, et al., "Decoding randomly ordered DNA arrays." *Genome Res* 14:870-877 (2004).

Hahner, et al., "Matrix-assisted laser desorption/ionization mass spectrometry of DNA using photocleavable biotin." *Biomol Eng* 16:127-133 (1999).

Han, et al., "Quantum-dot-tagged microbeads for multiplexed optical coding of biomolecules." *Nat Biotechnol* 19:631-635 (2001).

Happ, "Aminoacyl derivatives of nucleosides, nucleotides and polynucleotides. 43. New approach to synthesis of 2'(3')-O-aminoacyl oligoribonucleotides." *J. Org. Chem.* 52:5387 (1987).

Harlow and Lane, "Antibodies: A Laboratory Manual." Cold Spring Harbor Laboratory Press: USA (1988).

Hazum, "Purification of gonadotropin-releasing hormone receptors." *Methods Enzymol.* 184:285, (1990).

Heim, et al., "Distribution of 13 truncating mutations in the neurofibromatosis 1 gene." *Hum Mol Genet.* 4:975-981 (1995).

Hesson, et al., "CpG island promoter hypermethylation of a novel Ras-effector gene RASSF2A is an early event in colon carcinogenesis and correlates inversely with K-ras mutations." *Oncogene* 24:3987-3994 (2005).

Hogervorst, et al., "Rapid detection of BRCA1 mutations by the protein truncation test." *Nat Genet.* 10:208-212 (1995).

Hudson, et al., "Methodological implications of simultaneous solid-phase peptide synthesis. 1. Comparison of different coupling procedures." *J. Org. Chem.* 53:617 (1988).

Hughes, et al., "DNA microarray-based transcriptomic profiling of an isogenic cell culture model of breast tumour cell invasion." *Anticancer Res* 27:1353-1359 (2007).

Isakov, et al., "Purification and Characterization of Human ZAP-70 Protein-tyrosine Kinase from a Baculovirus Expression System." *J Biol Chem* 271:15753-15761 (1996).

Jacobs and Dahlman, "Enhancement of the quality of MALDI mass spectra of highly acidic oligosaccharides by using a nafion-coated probe." *Anal Chem* 73:405-410 (2001).

Johansson, et al., "Time gating improves sensitivity in energy transfer assays with terbium chelate/dark quencher oligonucleotide probes." *J Am Chem Soc* 126:16451-16455 (2004).

Kane, et al., "Methylation of the hMLH1 promoter correlates with lack of expression of hMLH1 in sporadic colon tumors and mismatch repair-defective human tumor cell lines." *Cancer Res* 57:808-811 (1997).

Katari, et al., "X-ray Photoelectron Spectroscopy of CdSe Nanocrystals with Applications to Studies of the Nanocrystal Surface." *J. Phys. Chem.* 98:4109-4117 (1994).

Kiernan, et al., "High-Throughput Analysis of Hemoglobin from Neonates Using Matrix-assisted Laser Desorption/Ionization Time-of-Flight Mass Spectrometry." *Clin Chem* 48:947-949 (2002).

Kinzler, et al., "Identification of a gene located at chromosome 5q21 that is mutated in colorectal cancers." *Science* 251:1366-1370 (1991).

Kojima, et al., "PCR amplification from single DNA molecules on magnetic beads in emulsion: application for high-throughput screening of transcription factor targets." *Nucleic Acids Res* 33:e150 (2005).

Koopmann & Blackburn, "High affinity capture surface for matrix-assisted laser desorption/ionisation compatible protein microarrays." *Rapid Commun Mass Spectrom* 17:455-462 (2003).

Koster, et al., "A strategy for rapid and efficient DNA sequencing by mass spectrometry." *Nat Biotechnol* 14:1123-1128 (1996).

Kurzchalia, et al., "tRNA-mediated labelling of proteins with biotin: A nonradioactive method for the detection of cell-free translation products." *Eur. J. Biochem.* 172:663-68 (1988).

Li, et al., "SLC5A8, a sodium transporter, is a tumor suppressor gene silenced by methylation in human colon aberrant crypt foci and cancers." *Proc Natl Acad Sci USA* 100:8412-8417 (2003).

Lingerfelt, et al., "Preparation of quantum dot-biotin conjugates and their use in immunochromatography assays." *Anal Chem* 75:4043-4049 (2003).

Liu, et al., "Promoter hypermethylation: an important epigenetic mechanism for hMLH1 gene inactivation in head and neck squamous cell carcinoma." *Otolaryngol Head Neck Surg* 126:548-553 (2002).

MacBeath, et al., "Printing proteins as microarrays for high-throughput function determination." *Science* 289:1760-1763 (2000).

Malik, et al., "Fourier transform multipixel spectroscopy for quantitative cytology." *J. Microsc.* 182(2):133-140 (1996).

Mamaev, et al., "Cell-free N-terminal protein labeling using initiator suppressor tRNA." *Anal Biochem* 326:25-32 (2004).

Mayer, et al., "Aptamers: Multifunctional tools for target validation and drug discovery." *DrugPlus International*, Nov./Dec., 2:6-10 (2003).

Mehlmann, et al., "Reflectometric interference spectroscopy combined with MALDI-TOF mass spectrometry to determine quantitative and qualitative binding of mixtures of vancomycin derivatives." *Anal Bioanal Chem* 382:1942-1948 (2005).

Mercier, et al., "Solid Phase DNA Amplification: A Simple Monte Carlo Lattice Model." Biophysical Journal 85:2075-2086 (2003).

Michael, et al., "Randomly ordered addressable high-density optical sensor arrays." *Anal Chem* 70:1242-1248 (1998).

Michaud, et al., "Analyzing antibody specificity with whole proteome microarrays." *Nat Biotechnol* 21:1509-1512 (2003).

Miliotis, et al., "Development of silicon microstructures and thin-film MALDI target plates for automated proteomics sample identifications." *J Neurosci Methods* 109:41-46 (2001).

Miliotis, et al., "Ready-made matrix-assisted laser desorption/ionization target plates coated with thin matrix layer for automated sample deposition in high-density array format." *Rapid Commun Mass Spectrom* 16:117-126(2002).

Mitterer, et al., "Microarray-Based Identification of Bacteria in Clinical Samples by Solid-Phase PCR Amplification of 23S Ribosomal DNA Sequences." *J Clin Microbiol* 42:1048-1057 (2004).

Moinova, et al., "HLTF gene silencing in human colon cancer." *Proc Natl Acad Sci USA* 99:4562-4567 (2002).

Nakamura, et al., "Ca:+/calmodulin activated protein phosphatas (PP2B) of *Saccharomyces cerevisiae* PP2B activity is not essential for growth." *FEBS Lett* 309:103-106 (1992).

Nakano, et al., "Single-molecule PCR using water-in-oil emulsion." *J Biotechnol* 102:117-124 (2003).

Nakano, et al., "Single-molecule reverse transcription polymerase chain reaction using water-in-oil emulsion." *J Biosci Bioeng* 99:293-295 (2005).

Nargeot, et al., "Time course of the increase in the myocardial slow inward current after a photochemically generated concentration jump of intracellular cAMP." *Proc. Natl. Acad. Sci. USA* 80:2395 (1983).

Neu, et al., "Release of Surface Enzymes in *Enterobacteriaceae* by Osmotic Shock." *J. Biol. Chem.* 239:2927-34 (1964).

Neubert, et al., "Enhanced Affinity Capture MALDI-TOF MS:Orientation of an Immunoglobulin G Using Recombinant Protein G." *Anal Chem* 74:3677-3683 (2002).

Newman, et al., "Biotinylated Parathyroid Hormone as a Probe for the Parathyroid Hormone Receptor." *Methods Enzymol.* 184:275 (1990).

Nord, et al., "Microbead display of proteins by cell-free expression of anchored DNA." *J Biotechnol* 106:1-13 (2003).

Olejnik, et al., "Photocleavable Biotin derivatives: A Versatile Approach for the Isolation of Biomolecules." *Proceedings of the National Academy of Science (USA)* 92:7590-7594 (1995).

Olejnik, et al., "Photocleavable biotin phosphoramidite for 5'-end-labeling, affinity purification and phosphorylation of synthetic oligonucleotides." *Nucleic Acids Research* 24:361-366 (1996).

Olejnik, et al., "Photocleavable peptide-DNA conjugates: synthesis and applications to DNA analysis using MALDI-MS." *Nucleic Acids Res* 27:4626-4631 (1999).

Pandori, et al., "Photochemical control of the infectivity of adenoviral vectors using a novel photocleavable biotinylation reagent." *Chem Biol* 9:567-573 (2002).

Park, et al., "Correlation between hypermethylation of the RASSF2A promoter and K-ras/BRAF mutations in microsatellite-stable colorectal cancers." *Int J Cancer* 12:7-12 (2007).

Parry, et al., "Germ-line mutations in the neurofibromatosis 2 gene: correlations with disease severity and retinal abnormalities." *Am J Hum Genet.* 59:529-539 (1996).

Peral, et al., "Identification of mutations in the duplicated region of the polycystic kidney disease 1 gene (PKD1) by a novel approach." *Am J Hum Genet.* 60:1399-1410 (1997).

Pillai, "Photoremovable protecting groups in organic synthesis." *Synthesis* 1:1-26 (1980).

Powell, et al., Molecular diagnosis of familial adenomatous polyposis. N Engl J Med 329:1982-1987 (1993).

Rabani, et al., "Drying-mediated self-assembly of nanoparticles." *Nature* 426:271-274 (2003).

Ramachandran, et al., "Self-Assembling Protein Microarrays." *Science* 305:86-90 (2004).

Ramsby, et al., "Differential detergent fractionation of isolated hepatocytes: biochemical, immunochemical and two-dimensional gel electrophoresis characterization of cytoskeletal and noncytoskeletal compartments." *Electrophoresis* 15:265-277 (1994).

Ramsby and Makowski, "Differential Detergent Fractionation of Eukaryotic Cells." p. 53-66 From: *Methods Mol Biol*, 112:53-6: 2-D Proteome Analysis Protocols Edited by: A. J. Link © Humana Press Inc., Totowa, NJ (1999).

Robertson, "DNA Methylation and Human Disease." *Nat Rev Genet.* 6:597-610 (2005).

Robinson, et al., "Autoantigen microarrays for multiplex characterization of autoantibody responses." *Nat Med* 8:295-301 (2002).

Robinson, et al., "Protein microarrays guide tolerizing DNA vaccine treatment of auto immune encephalomyelitis." *Nat Biotechnol* 21:1033-1039 (2003).

Roest, et al., "Protein truncation test (PTT) to rapidly screen the DMD gene for translation terminating mutations." *Neuromuscul Disord* 3:391-39 (1993).

Ross and Joyner, "Resting distribution and stimulated translocation of protein kinase C isoforms alpha, epsilon and zeta in response to bradykinin and TNF in human endothelial cells." *Endothelium* 5:321-332 (1997).

Ross, et al., "High level multiplex genotyping by MALDI-TOF mass spectrometry." *Nat Biotechnol* 16:1347-1351 (1998).

Rothschild, et al., "tRNA-mediated protein engineering." *Curr Opin Biotechnol* 10:64-70 (1999).

Sampson, et al., "Biochemical and physical characterization of an unmodified yeast phenylalanine transfer RNA transcribed in vitro." *Proc. Natl. Acad. Sci. USA* 85:1033 (1988).

Shapero, et al., "SNP Genotyping by Multiplexed Solid-Phase Amplification and Fluorescent Minisequencing." *Genome Res* 11:1926-1934 (2001).

Shendure, et al., "Accurate multiplex polony sequencing of an evolved bacterial genome." *Science* 309:1728-1732 (2005).

Sheridan, "Protein chip companies turn to biomarkers." *Nat Biotechnol* 23:3-4 (2005).

Singer-Sam, et al., "A quantitative HpaII-PCR assay to measure methylation of DNA from a small number of cells." *Nucleic Acids Res* 18:687 (1990).

Sinha, et al., "A new silver staining apparatus and procedure for matrix-assisted laser desorption/ionization-time of flight analysis of proteins after two-dimensional electrophoresis." *Proteomics* 1:835-840 (2001).

Steigerwald, et al., "Surface derivatization and isolation of semiconductor cluster molecules." J. Am. Chem. Soc. 110:3046 (1988).

Thomas, et al., "Sensitive mutation detection in heterogeneous cancer specimens by massively parallel picoliter reactor sequencing." *Nat Med* 12:852-855 (2006).

Tillib, et al., "Integration of Multiple PCR Amplifications and DNA Mutation Analyses by Using Oligonucleotide Microchip." *Anal Biochem* 292:155-160 (2001).

Traverso, et al., "Detection of APC mutations in fecal DNA from patients with colorectal tumors." *N Engl J Med* 346:311-320 (2002).

van der Luijt, et al., Rapid detection of translation-terminating mutations at the adenomatous polyposis coli (APC) gene by direct protein truncation test. *Genomics* 20:1-4 (1994).

Wilchek, et al., "Direct Incorporation of Biotin into DNA." Methods Enzymol. 184:243 (1990).

Xiao, et al., "A multi-array multi-SNP genotyping algorithm for Affymetrix SNP microarrays." *Bioinformatics* 23:1459-1467 (2007).

Xiong and Laird, "COBRA: A sensitive and quantitative DNA assay." *Nucleic Acids Res.*, 25:2532-2534 (1997).

Xu, et al., "Multiplexed SNP genotyping using the Qbead™ system: a quantum dot-encoded microsphere-based assay." *Nucleic Acids Res.* 31(8):e43 (2003).

Yazlovitskaya & Melnykovych, "Selective farnesol toxicity and translocation of protein kinase C in neoplastic HeLa-S3K and non-neoplastic CF-3 cells." *Cancer Lett* 88:179-183 (1995).

Zhang and Orlando, "Solid-Phase Extraction/MALDI-MS: Extended Ion-Pairing Surfaces for the On-Target Cleanup of Protein Samples." *Anal Chem* 71:4753-4757 (1999).

Zhu, et al., "Analysis of yeast protein kinases using protein chips." *Nat Genet.* 26:283-289 (2000).

Zhu, et al., "Protein arrays and microarrays." *Curr Opin Chem Biol* 5:40-45 (2001); and.

Zhu, et al., "Global analysis of protein activities using proteome chips." *Science* 293:2101-2105 (2001).

\* cited by examiner

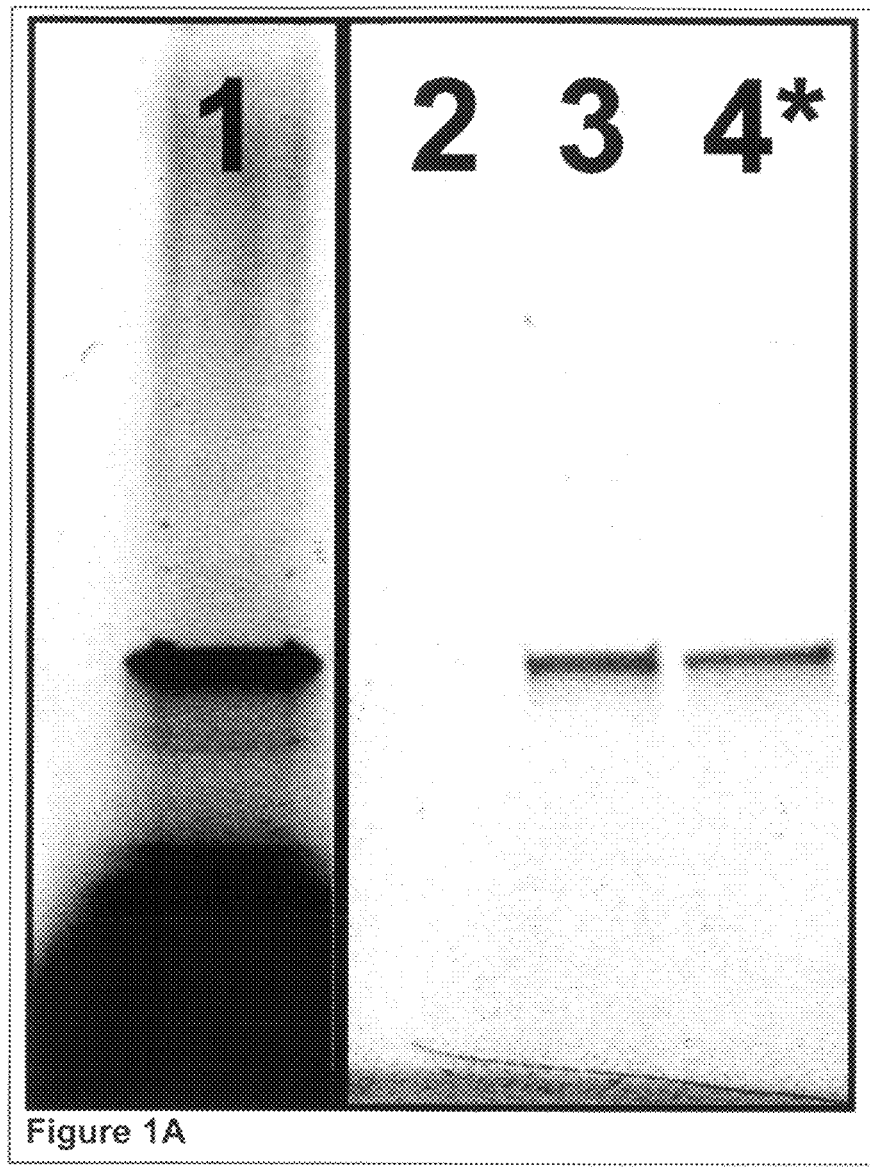

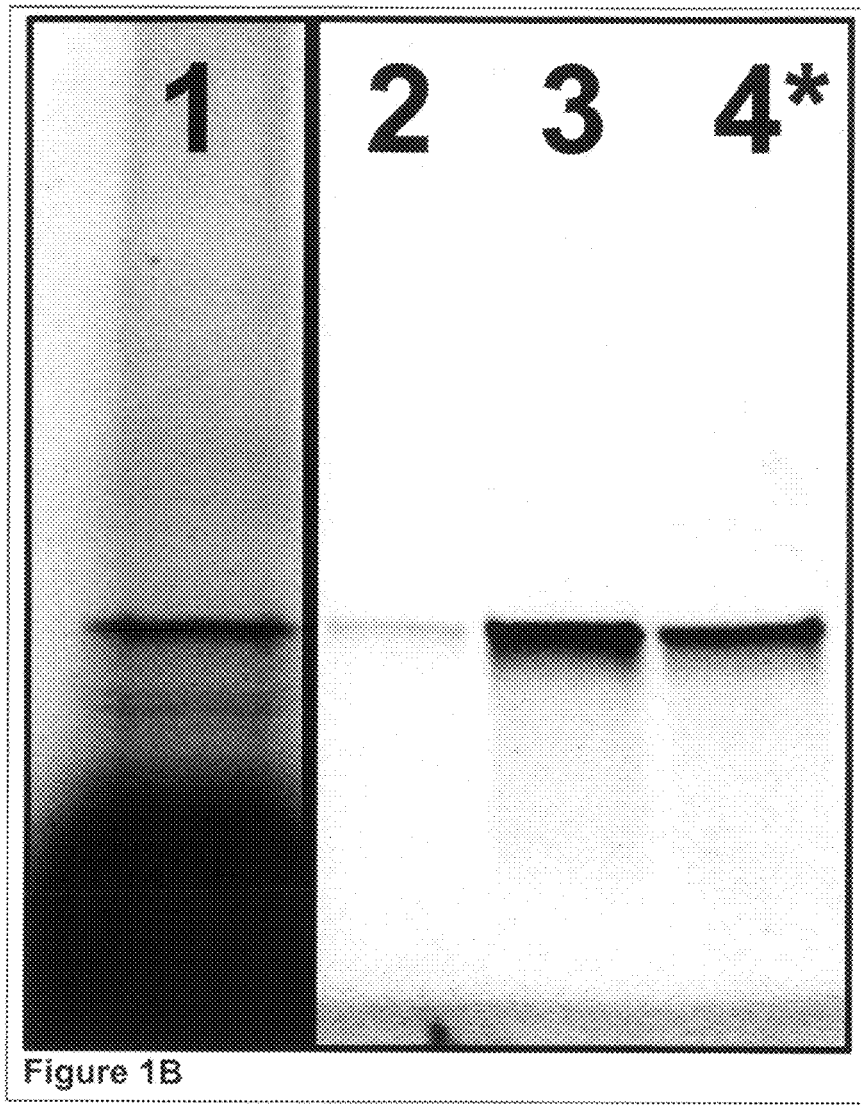

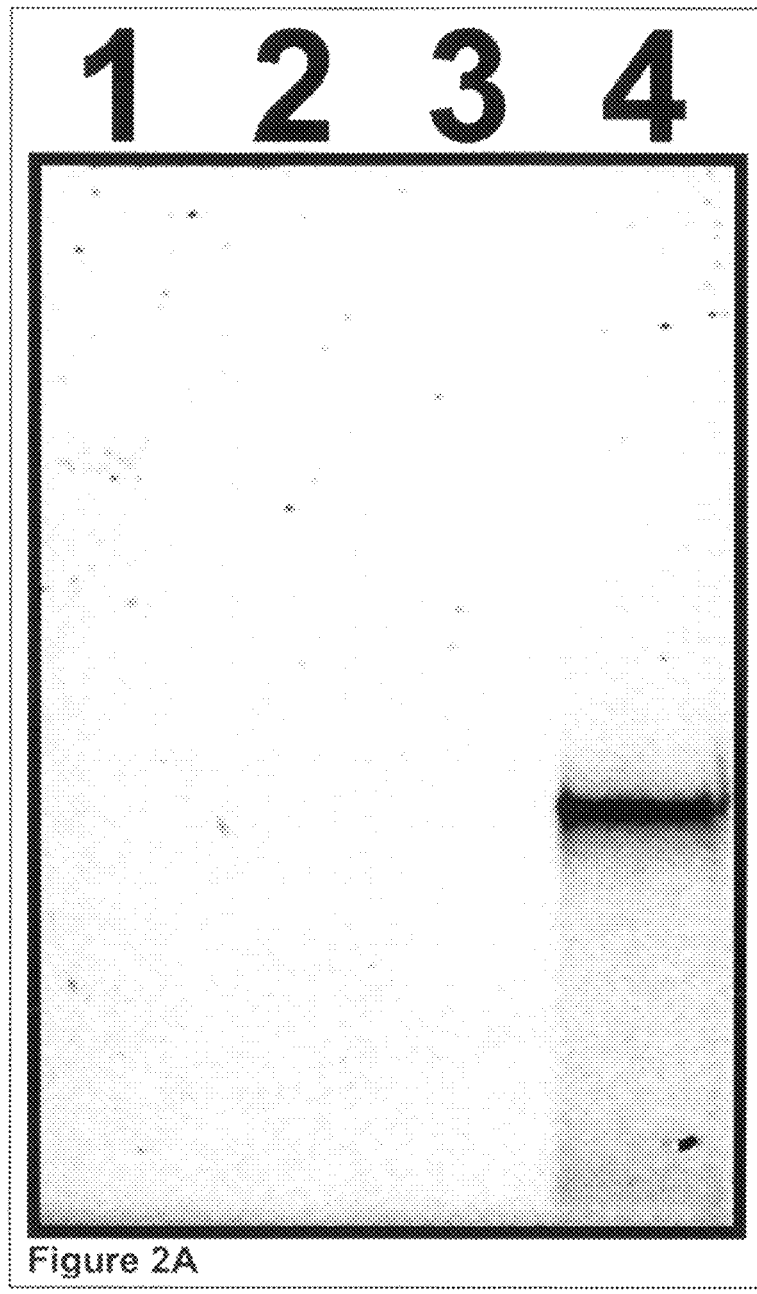

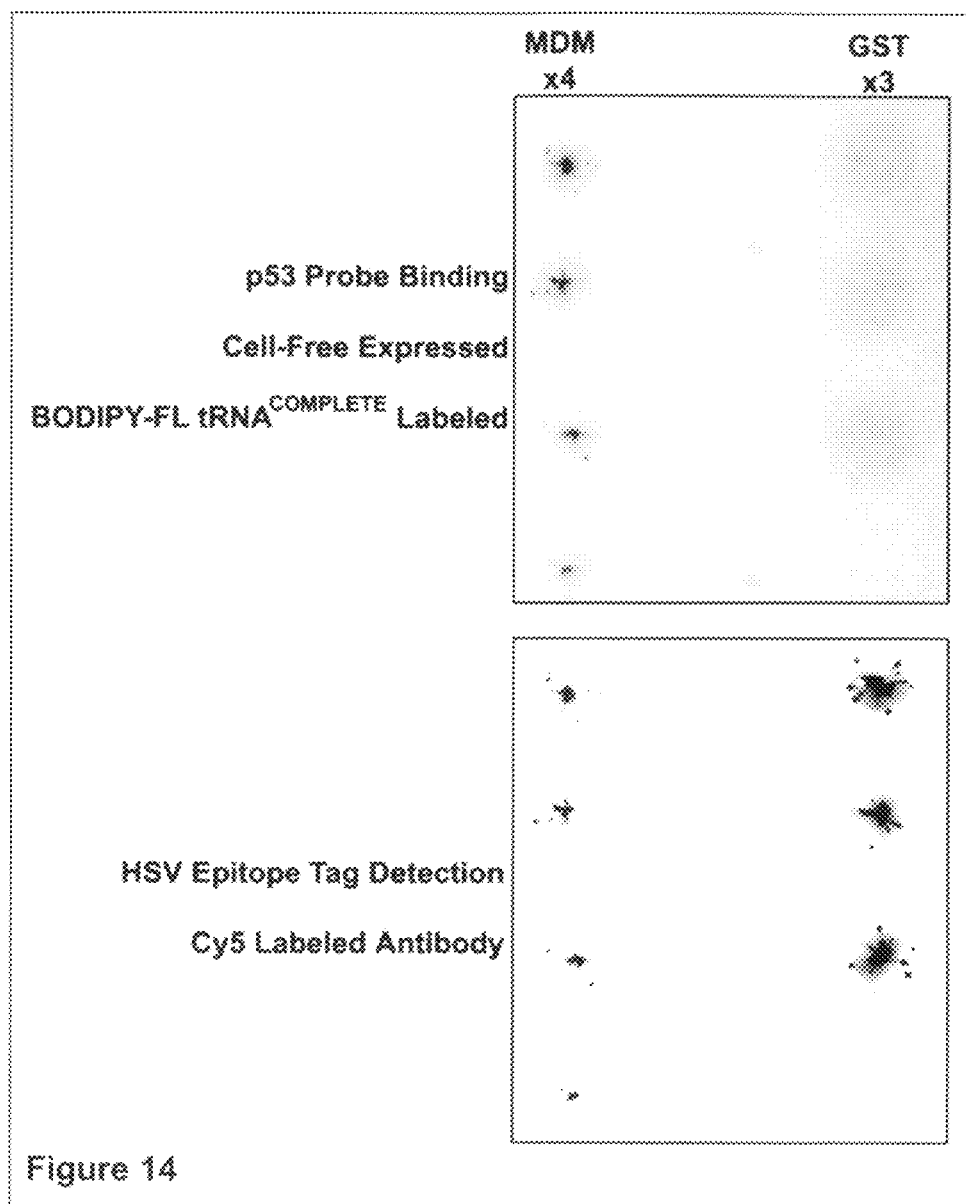

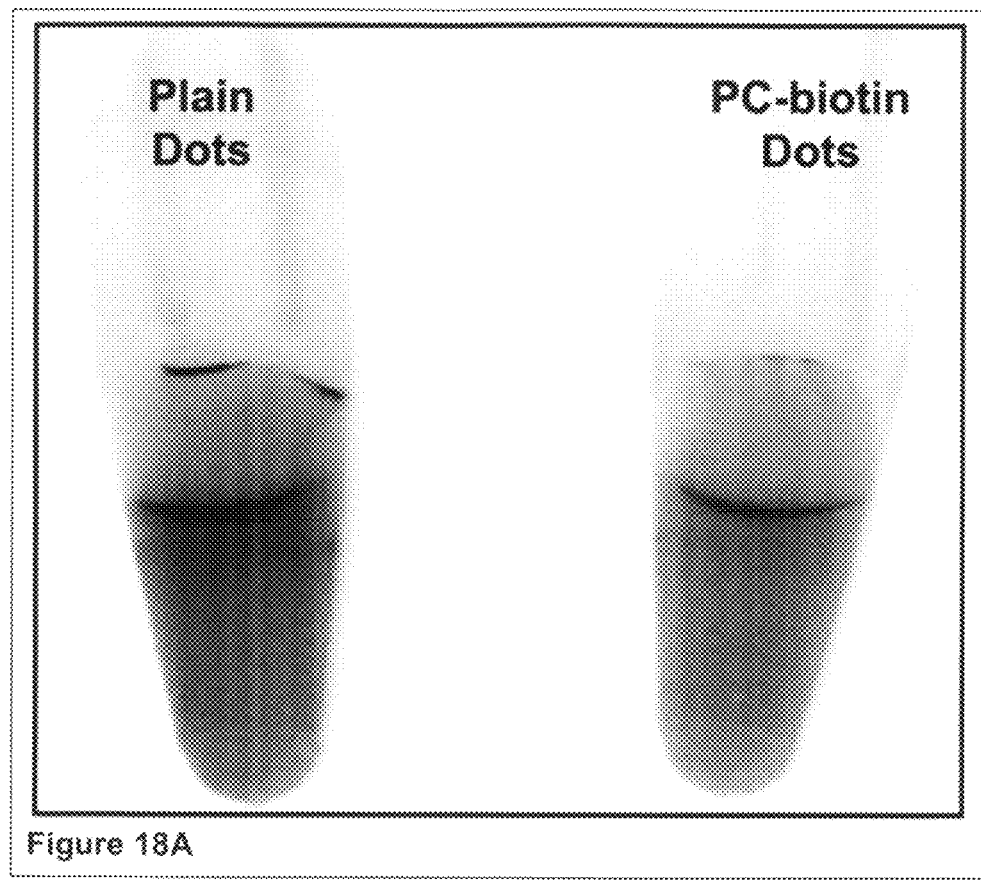

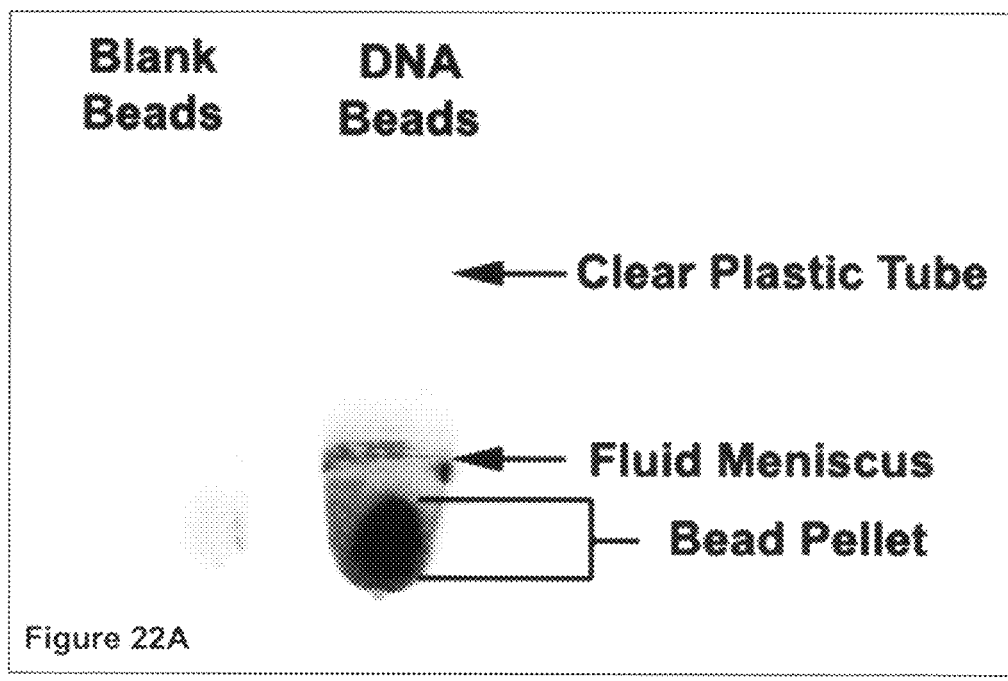

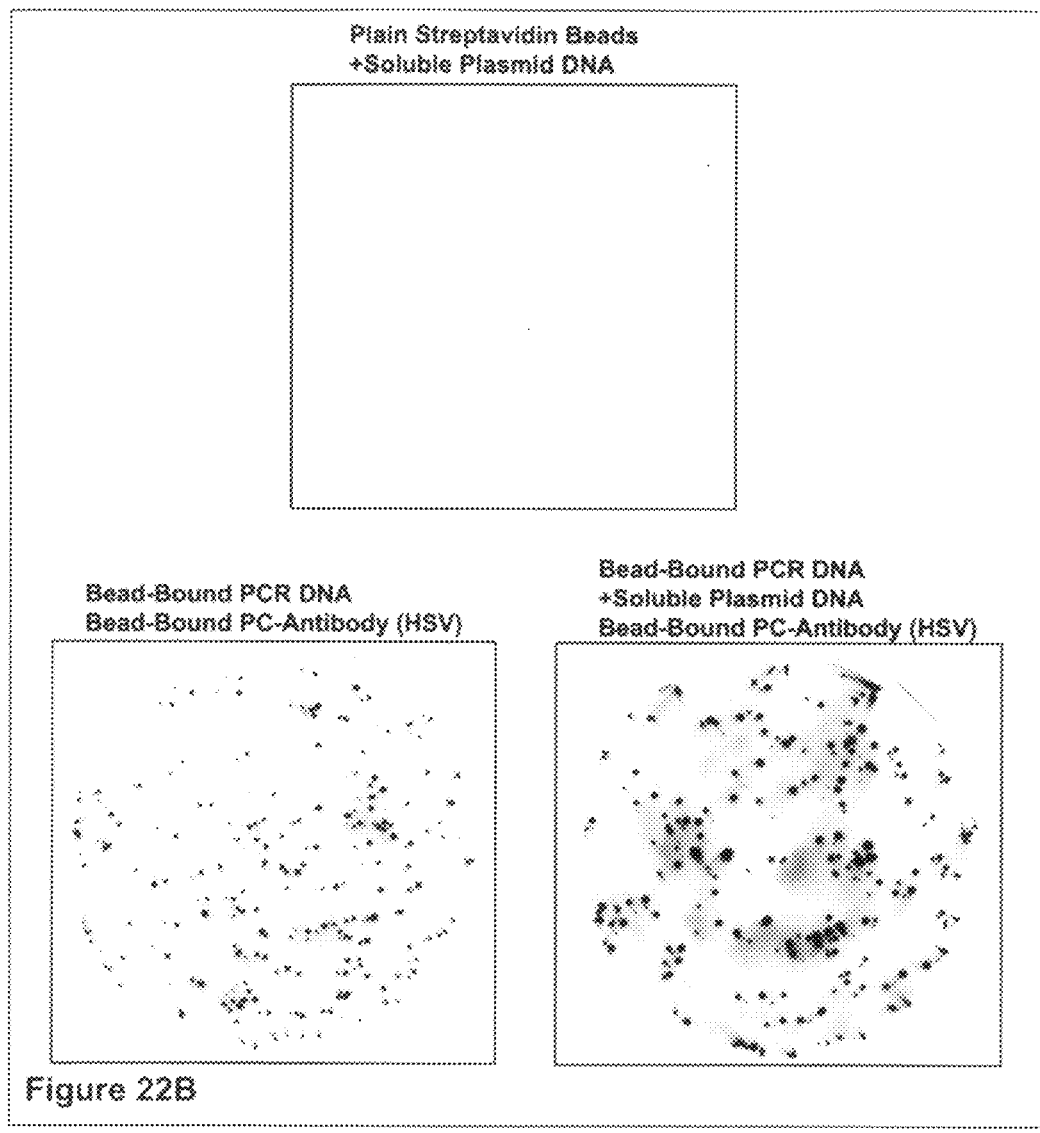

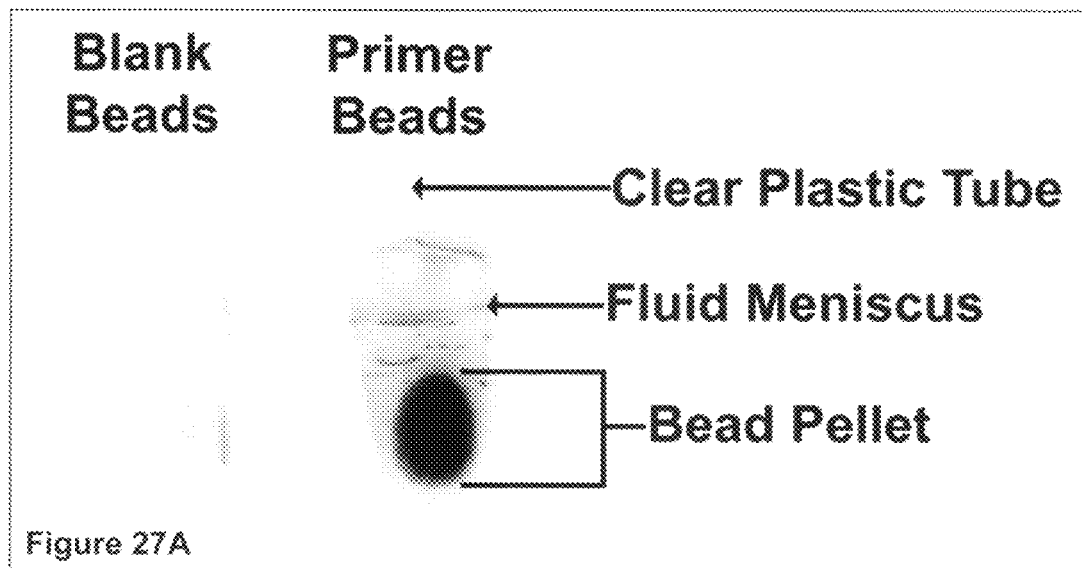

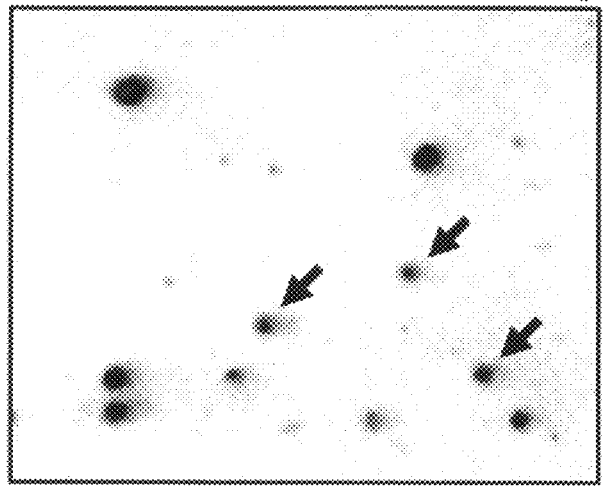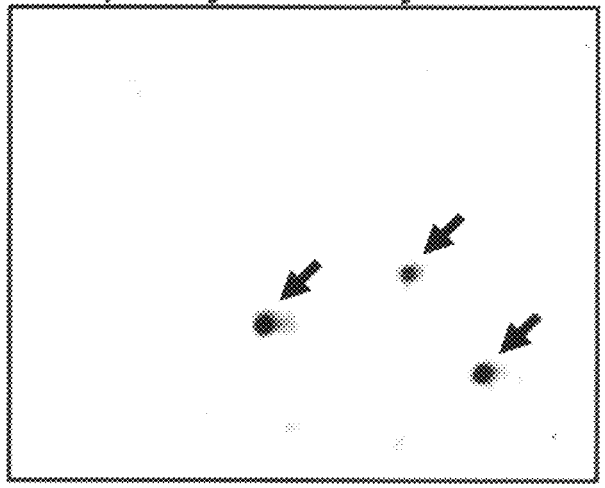
Figure 28

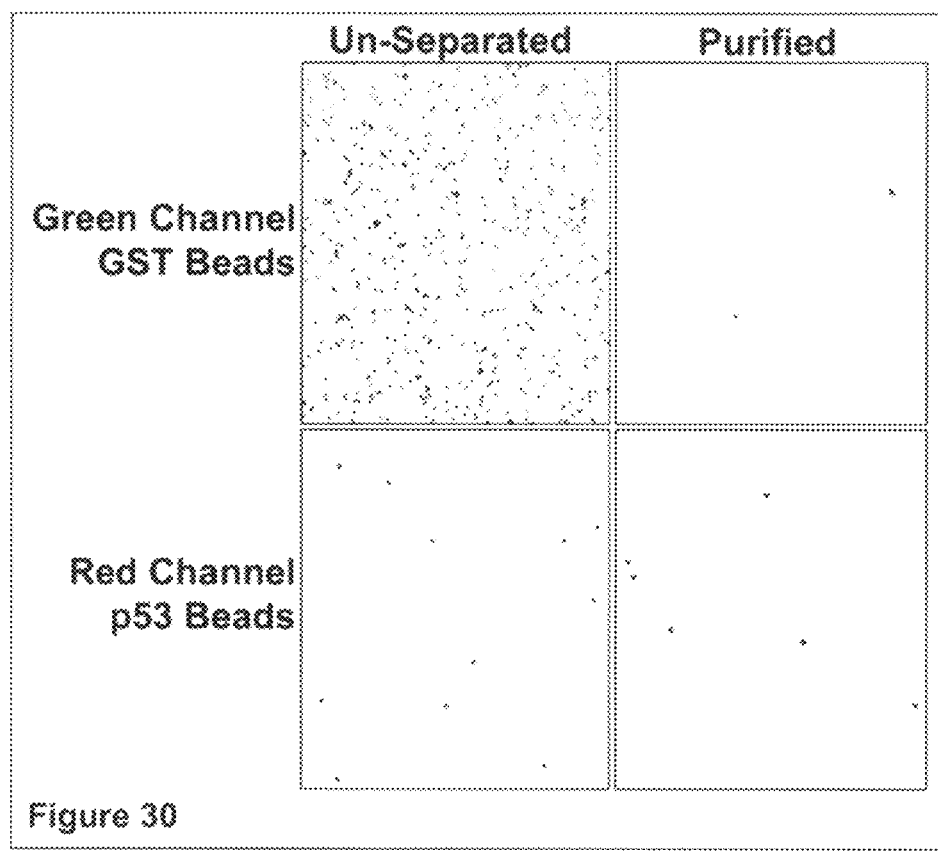

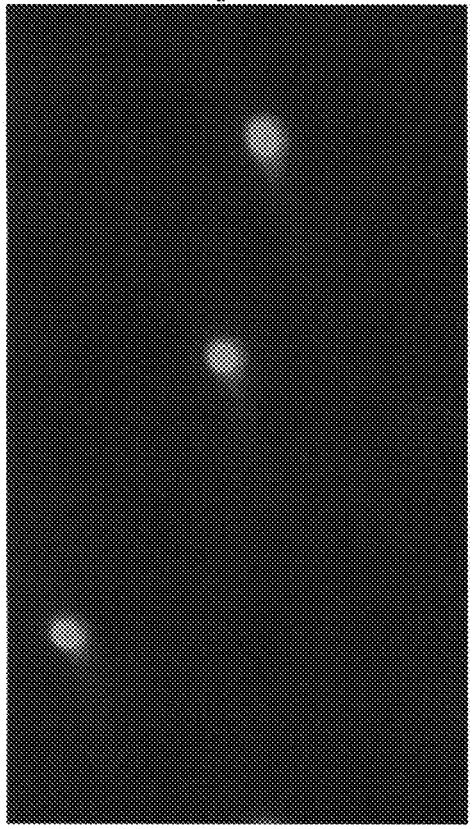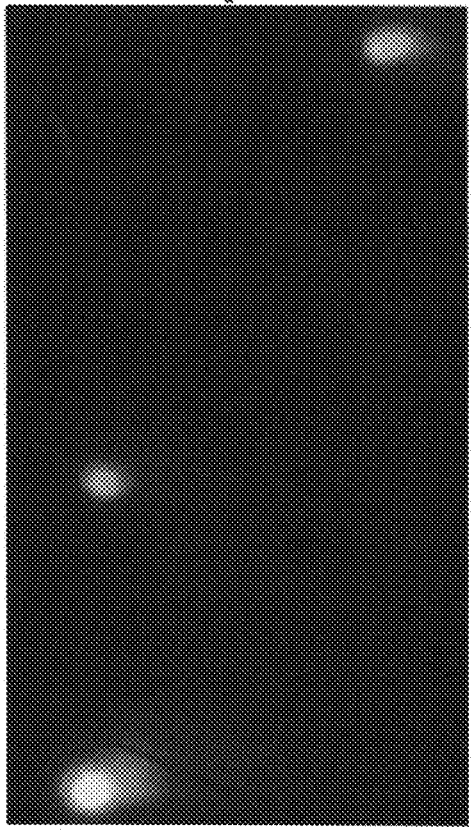
Figure 37

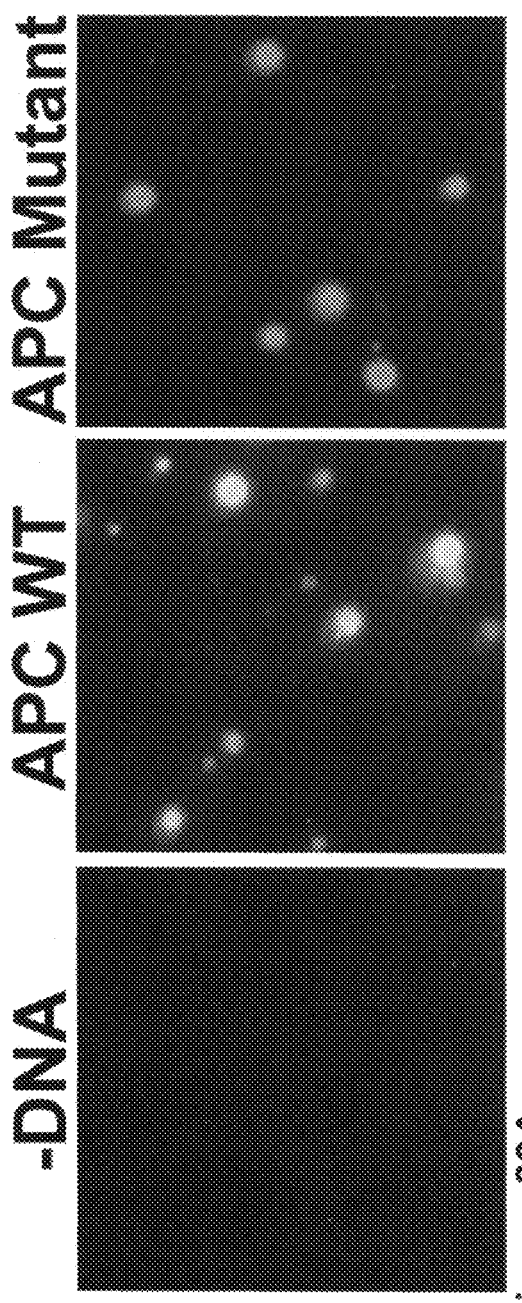

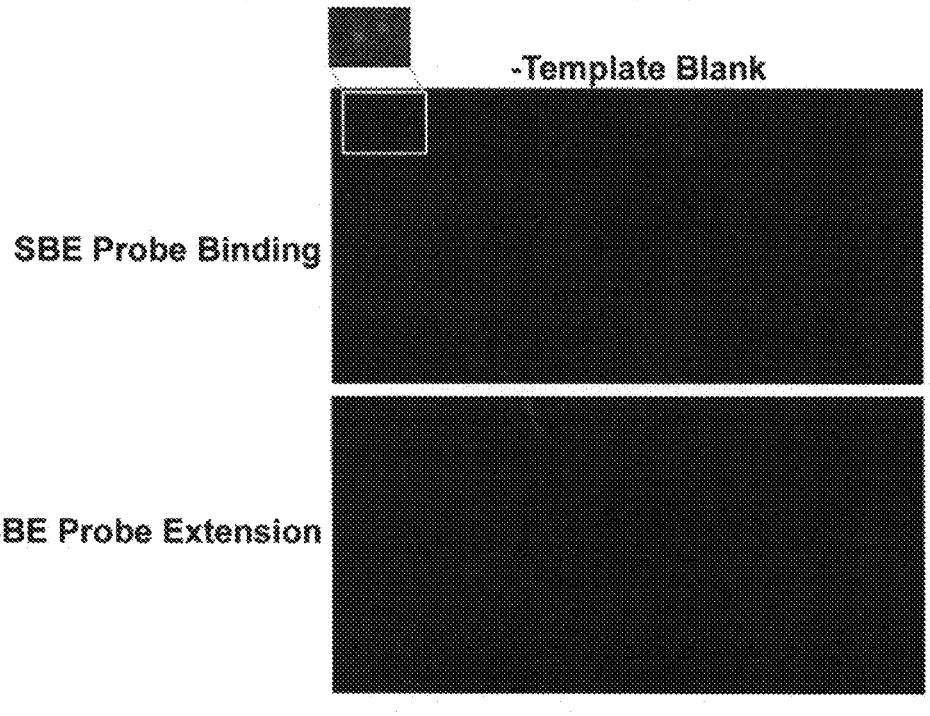
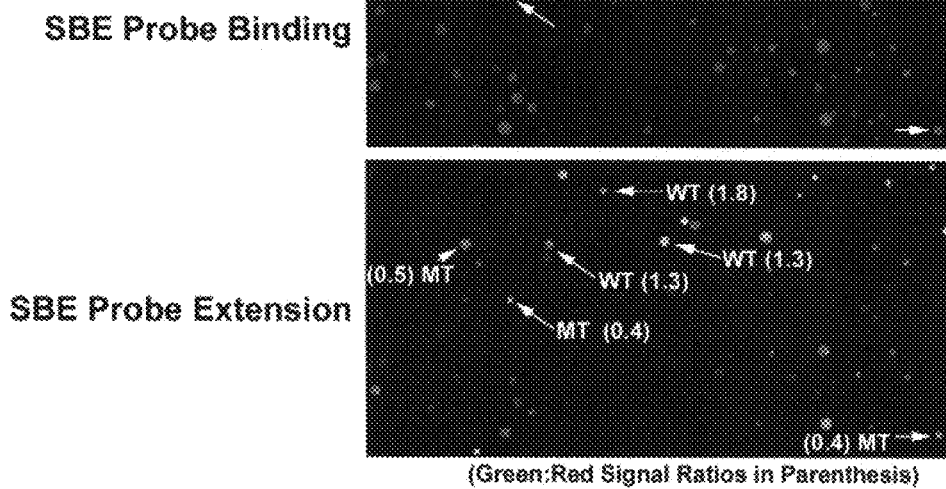
Figure 41

AMPLIFYING BISULFITE-TREATED TEMPLATE

The present application claims priority to U.S. Provisional Application No. 61/002,013, filed Nov. 6, 2007, which is incorporated by reference in its entirety.

FIELD OF THE INVENTION

The present invention relates to methods and compositions for the production of biomolecules on beads or particles, for example by amplification or de novo synthesis (e.g. by enzymatically mediated replication or enzymatically mediated synthesis, respectively). This invention also relates to methods and compositions for the photo-transfer of substances and compounds, such as biomolecules, from one surface to another. This invention has applications in many fields including, but not limited to, the fields of microarrays and micro-bead technologies, for applications such as parallel DNA sequencing, mRNA or protein expression profiling, single nucleotide polymorphism (SNP) and other genetic analyses, biomarker discovery, diagnostics, prognostics, personalized medicine, protein interaction analysis, drug discovery and proteomics.

BACKGROUND OF THE INVENTION

Microarray and micro-bead technologies can be used as tools to conduct biological, chemical or biochemical analyses in a parallel, massively parallel or multiplexed fashion because of the large number of different compounds or substances that can be fabricated or deposited on the microarray substrate or beads. As is also well known in the art, microarrays and micro-bead technologies are applicable to a variety of such analyses including, but not limited to, mRNA or protein expression profiling, parallel DNA sequencing, protein-protein interaction mapping, protein-drug interaction analysis, antibody specificity testing, enzyme substrate profiling and single nucleotide polymorphism (SNP) detection as well as various other applications in the fields of biomarker discovery, diagnostics, prognostics, personalized medicine, protein interaction analysis, drug discovery and proteomics (See for example [Ramachandran et al. (2004) Science 305, 86-90; Zhu et al. (2001) Science 293, 2101-2105; MacBeath & Schreiber. (2000) Science 289, 1760-1763; Zhu et al. (2000) Nat Genet. 26, 283-289; Michaud et al. (2003) Nat Biotechnol 21, 1509-1512; Sheridan. (2005) Nat Biotechnol 23, 3-4; Robinson et al. (2003) Nat Biotechnol 21, 1033-1039; Robinson et al. (2002) Nat Med 8, 295-301; Xiao et al. (2007) Bioimformatics 23, 1459-1467; Hughes et al. (2007) Anticancer Res 27, 1353-1359]).

The plurality of compounds or substances arrayed or displayed on the microarray substrate or micro-beads can be of a variety of types and for a variety of uses. These compounds or substances are not intended to be limited to any one type or for any one use, and henceforth will be referred to "features", as is commonly used in the art of microarrays. Microarray or micro-bead features can include, but are not limited to proteins, peptides, DNA, nucleic acids, nucleosides, nucleotides or polymers thereof, drug or other chemical compounds, polymers, cells, tissues, particles, nanoparticles or nanocrystals. Microarray or micro-bead features may be used as, for example, analytes, probes or targets in various applications, assays or analyses.

Microarrays currently exist as two-dimensional feature arrays fabricated on solid glass (plain or chemically activated/modified) or nylon substrates for instance. A variety of additional substrates such as nitrocellulose, polystyrene, polymeric or metallic materials provided as solid substrates, coatings, films, membranes or matrices are also available. Due to the massively parallel or multiplexed nature of microarrays, far more information is obtained from a single experiment compared to other non-parallel or non-multiplexed methods. Furthermore, because the samples to be analyzed are generally in limited supply, hard to produce and/or expensive, it is highly desirable to perform experiments on as many components in a mixture as possible on as many features as possible, on a single microarray. This calls for a significant increase in feature density and quantity on a single substrate. In general, microarrays with densities larger than 400 features per square centimeter are referred as "high density" microarrays, otherwise, they are "low density" microarrays. Affymetrix Inc. (Santa Clara, Calif.) for example, currently offers several commercial high density oligonucleotide microarrays having as much as 1 million or more ~10 µm features, for feature densities reaching ~1 million/cm$^2$ [Barone et al. (2001) Nucleosides Nucleotides Nucleic Acids 20, 525-531]. Applications of these commercial microarrays include mRNA expression profiling or single nucleotide polymorphism (SNP) detection.

Production of microarray or micro-bead features can be achieved by a variety of methods, either by in situ production, or by deposition/binding of off-line produced feature substances onto microarray substrates, beads or particles. Current methods however, suffer from various deficiencies.

For microarrays, there are two categories of techniques on the market, photolithographic and mechanical printing. Photolithography is an in situ method, while mechanical printing techniques require off-line production of the feature substances followed by deposition of the features onto the microarray substrate. The photolithographic technique adapts the same fabrication process used for electronic integrated circuits, in order to in situ synthesize compounds or substances, monomer-by-monomer for example (e.g. nucleic acid monomers), directly on the microarray substrate. This technique requires a large capital outlay for equipment, running up to hundreds of millions of dollars. The initial setup of new microarray designs is also very expensive due to the high cost of producing photo masks. This technique is therefore only viable in mass production of standard microarrays at a very high volume. Even at high volumes, the complexity in synthesis still limits the production throughput resulting in a high microarray cost. This method has typically been employed for high density DNA microarrays. The complexity of the process however, also limits the length of the synthesized DNA to the level of short oligonucleotide sequences of about 25 bases.

The established mechanical printing technique [U.S. Pat. No. 5,807,522] uses a specially designed mechanical robot, which produces a feature spot on the microarray by dipping a pin head into a fluid, i.e. the bulk stocks of the feature substances, such as DNA or protein solutions, and then printing it onto the substrate at a predetermined position. Washing and drying of the pins are required prior to printing a different feature onto the microarray substrate. In current designs of such robotic systems, the printing pin, and/or the stage carrying the microarray substrates move along the XYZ axes in coordination to deposit samples at controlled positions on the substrates. Other mechanical printing techniques, either contact or non-contact, use quills, pins with built-in sample channels, non-contact ink jet/piezoelectric devices or capillaries as the means of feature deposition. Because a microarray contains a very large number of different features, these techniques, although highly flexible, are inherently very slow.

Even though the speed can be enhanced by employing multiple pin-heads (or printing devices) and printing multiple substrates before washing, production throughput remains very low. Furthermore, the printing instrumentation is susceptible to mechanical failure due to the large number of moving parts. Non-contact methods additionally suffer from difficulties in controlling the microarray quality. Mechanical printing methods are therefore not suitable for high volume mass production of microarrays.

Mechanical printing also requires that the materials comprising the features be produced off-line, prior to printing. Typically, bulk stocks of the feature substances are produced and used to print multiple spots and/or microarrays. However, such production has a variety of limitations. For example, conventional off-line production of DNA (e.g. oligonucleotides) uses chemical synthesis, but is limited to approximately 150 bases in length, and although can be done in parallel, is not truly multiplexed. Conventional methods for DNA production beyond this length (e.g. full-length genes or large portions thereof), involves slow, laborious, and non-multiplexed standard DNA cloning practices. Adams and Kron [U.S. Pat. No. 5,641,658] disclose a general multiplexed method for producing DNA on beads or other surfaces by using solid-phase bridge PCR (i.e. where both PCR primers, forward and reverse, are attached to the surface). However, this approach is rarely used and has not been adapted for cloning (amplification of single template molecules) or downstream production of protein, for example. For recombinant proteins for instance, off-line production typically involves all the aforementioned conventional DNA cloning procedures in addition to labor intensive and non-multiplexed steps such as transfection, cell culture and purification reactions for each protein species. It is particularly important yet challenging to deposit the produced feature substances in pure and active form on the microarray substrate. Prior to deposition, feature substances are usually produced in heterogeneous mixtures and hence require purification. The production, purification and deposition process can readily inactivate delicate feature substances such as proteins. Furthermore, contaminants on the microarray surface can yield false signals in downstream analyses.

Feature size is another limiting factor of high density microarray production. With either microarray fabrication technique, photolithography or mechanical printing, the microarrays cannot easily be extended to spot sizes (i.e. features) at the nanometer level. Such nanoarrays would be highly advantageous, since they could dramatically increase the level of multiplexing for example. Photolithography represents the state-of-the-art in terms of spot size (10 µm) and density, but is limited to short polymers such as oligonucleotides and short peptides, and is essentially only used in practice for DNA microarrays.

Micro-bead technologies are analogous to microarrays except that the features are spatially segregated on different beads or particles. The experiment, analysis and/or readout can be formatted like a microarray, for example, with the beads arrayed or embedded on the surface or in wells of a device such as a microscope slide or plate. The experiment, analysis and/or readout can alternatively be performed with the beads suspended in a solution for example. The working density of features for micro-bead technologies is potentially far greater than for microarrays, depending primarily on the minimum usable bead size and maximum usable bead concentration or density. For example, 0.3 µm beads have been arrayed in etched wells at densities of $4 \times 10^9$ beads/cm$^2$ [Michael et al. (1998) *Anal Chem* 70, 1242-1248], three orders of magnitude better than the current high density DNA microarrays from Affymetrix Inc. (Santa Clara, Calif.). However, because the beads are random, a decoding method is typically required to determine the identity of the feature on each bead in a given experiment or analysis. Several commercial entities utilize micro-bead technologies to achieve parallel or multiplexed assays in a fashion similar to microarrays. For example, Luminex Corporation (Austin, Tex.) markets a flow cytometry based bead platform for multiplexed assays, such as SNP detection and various immunoassays. Beads are fluorescently coded to facilitate the multiplexing and production of the bead "features", e.g. analytes, is up to the end-user. Illumina Incorporated (San Diego, Calif.) has created a bar-coded bead-array platform for genetic analyses, such as multiplexed SNP and DNA methylation detection. 454 Life Sciences™ (Branford, Conn.) offers a bead-based parallel sequencing platform whereby beads carrying the DNA "features", in this case DNA analytes for sequencing, are arrayed in microscopic wells and analyzed by massively parallel DNA pyrosequencing, for applications such as whole genome sequencing and detection of low abundance mutations.

In general, production of a plurality of beads with different features, whether the features are to serve as probes, targets or analytes for example, suffers from analogous problems as described for microarrays. For instance, different feature substances are typically produced off-line and can then be bound to beads in separate reactors, in a mechanical process of mixing solutions containing the feature substances with beads containing some binding capacity. This can be done in separate test tubes, vials or wells of a microtiter plate for example. Liquid handling robotics may be used to perform this process in parallel, however, it is again not truly multiplexed (e.g. does not produce the complete population of beads with different features, using a single reaction or few reactions within a single reactor).

The present invention overcomes the problems and disadvantages associated with current strategies and designs for the fabrication and utilization of microarrays, micro-bead technologies and a variety of other parallel, massively parallel or multiplexed biological sensing methodologies or devices.

SUMMARY OF THE INVENTION

The present invention relates to methods and compositions for the production of biomolecules on beads or particles, for example by amplification or de novo synthesis (e.g. by enzymatically mediated replication or enzymatically mediated synthesis, respectively). This invention also relates to methods and compositions for the transfer (e.g. photo-transfer) of substances and compounds, such as biomolecules, from one surface to another. This invention has applications in many fields including, but not limited to, the fields of microarrays and micro-bead technologies, for applications such as parallel DNA sequencing, mRNA or protein expression profiling, single nucleotide polymorphism (SNP) and other genetic analyses, biomarker discovery, diagnostics, prognostics, personalized medicine, protein interaction analysis, drug discovery and proteomics.

In one embodiment, the present invention contemplates transferring compounds from one surface to another. While it is not intended that the present invention be limited by the nature of the compound (e.g. drug, ligand, etc.), preferred compounds are biomolecules (e.g. proteins, protein fragments, peptides, nucleic acid, oligonucleotides, etc.). In one embodiment, the present invention contemplates a method for transferring a compound from a first surface to a second surface, comprising: a) providing i) a compound attached to a first surface through a photocleavable linker; ii) a source of electromagnetic radiation; and iii) a second surface; b) contacting said second surface with said compound; and c) illuminating said compound with radiation from said radiation source under conditions such that compound is photocleaved from said first surface and transferred to said second surface. Electromagnetic radiation includes x-rays, ultraviolet rays, visible light, infrared rays, microwaves, radio waves, and combinations thereof.

In one embodiment, said first surface is part of a particle. In a preferred embodiment, said particle is a bead and said contacting comprising depositing said bead onto said second surface. In a preferred embodiment, the method further comprises, after step c), the step d) removing said bead(s) from said second surface. Of course, the efficiency of removing the beads need not be 100%; some beads (preferably less than 50%, more preferably less than 20%, and most preferably not more than 1%) may remain after the removing step.

In some embodiments, it is not strictly necessary that said compound be in physical contact with said second surface. Without limiting the present invention to any particular mechanism, it is believed that it is sufficient that the compound be in proximity (e.g. to a distance of less than $10^6$ Angstroms, more preferably between 0.1 and 1000 Angstroms) to said second surface. In one embodiment, the compound is brought into proximity simply by bringing the surfaces into proximity (without actual contact between the surfaces). In one embodiment, the compound is brought into proximity via a carrier, such as a particle or bead. For example, the present invention, in one preferred embodiment, contemplates a method for transferring substances from a bead to a surface, comprising: a) providing i) a compound attached to a bead through a photocleavable linker; ii) a source of electromagnetic radiation; and iii) a surface; b) bringing said bead into contact with (or in proximity to) said surface; and illuminating said bead with radiation from said radiation source under conditions such that compound is photocleaved from said bead and transferred to said surface. In one embodiment, step b) comprises depositing said bead onto said surface (whether by hand or by robotic spotting or by inkjet spraying or by sedimentation or the like).

It is not intended that the present invention be limited to particular surfaces. In one embodiment, the surface is part of a solid support. For example, in one embodiment said first surface is part of a particle or nanoparticle. In one embodiment, the particle is a bead. In one embodiment, said nanoparticle is a nanocrystal. Indeed, surfaces can be beads, glass slides and surfaces used for biomolecular detection (e.g. surfaces used for mass spec). In one embodiment, said second surface is selected from glass surfaces, metal surfaces, surfaces coated with antibodies, surfaces coated with streptavidin, surfaces coated with cells, hydrogel surfaces, nitrocellulose surfaces, polymeric surfaces, gold coated surfaces, surfaces suitable for surface plasmon resonance, surfaces suitable for MALDI, surfaces coated with nucleic acid, and surfaces coated with protein.

It is not intended that the present invention be limited by the nature of the surfaces employed. A variety of surface types (e.g. coated, charged, absorbing, non-absorbing, etc.) and surface configurations (e.g. flat, curved, indented, etc.) are contemplated. Where coated surfaces are used, the surface may be coated with a variety of molecules (whether nucleic acids, proteins, carbohydrates or other types). In a preferred embodiment, the surface is coated with molecules having affinity to another molecule (e.g. binding partner) such as antibodies, lectins, avidin, streptavidin, and the like. In some embodiments, the surface is coated with a metal (such as gold, platinum, copper, etc.) or metal ions. In some embodiments, metal ion-chelate derivatives, nickel nitrilo-triacetic acid (Ni-NTA), or cobalt nitrilo-triacetic acid complexes are employed. In some embodiments, said surfaces are coated with cells. Surface types such as hydrated matrix coated surfaces (e.g. polyacrylamide gels or HydroGel coated microarray substrates; PerkinElmer Life and Analytical Sciences, Inc., Boston, Mass.), nitrocellulose surfaces, polymeric surfaces, surfaces suitable for surface plasmon resonance, and surfaces suitable for mass spectrometry (e.g. MALDI) are specifically contemplated. In some embodiments, polymer surfaces are used (e.g. polyvinylidene fluoride (PVDF) or polystyrene). In other embodiments, plastic or ceramic surfaces are used. In some embodiments, simple surfaces such as glass, crystal, and silicon dioxide surfaces are used (e.g. in one embodiment of the above described method, said second surface may be a glass surface). In some embodiments, the surface is modified with a compound to make the surface more hydrophilic. Rain-X antifog (commercially available) is a surface treatment which makes surfaces hydrophilic. Hydrophobic surfaces (such as Teflon) can also be employed. In some embodiments, the surface is modified with a magnetic or paramagnetic coating. In some embodiments, the surface is modified so as to comprise reactive groups (e.g. amine reactive groups, esters, epoxy groups, etc.).

In one embodiment, said second surface is selected from glass surfaces, metal surfaces, surfaces coated with antibodies, surfaces coated with streptavidin, surfaces coated with cells, hydrogel surfaces, nitrocellulose surfaces, polymeric surfaces, gold coated surfaces, surfaces suitable for surface plasmon resonance, surfaces suitable for MALDI, surfaces coated with nucleic acid, and surfaces coated with protein.

Where beads are used, it is not intended that the present invention be limited to the particular type. A variety of bead types are commercially available, including but not limited to, beads selected from agarose beads, streptavidin-coated beads, NeutrAvidin-coated beads, antibody-coated beads, paramagnetic beads, magnetic beads, electrostatic beads, electrically conducting beads, fluorescently labeled beads, colloidal beads, glass beads, semiconductor beads, and polymeric beads.

Importantly, a variety of compounds can be photo-transferred using the methods of the present invention, including but not limited to compounds selected from the group consisting of proteins, peptides, antibodies, amino acids, amino acid analogs, drug compounds, nucleic acids, nucleosides, nucleotides, lipids, fatty acids, saccharides, polysaccharides, inorganic molecules, and metals. In one embodiment, said compound is selected from the group consisting of proteins, nascent proteins, peptides, antibodies, amino acids, amino acid analogs, drug compounds, nucleic acids, nucleosides, nucleotides, protein-nucleic acid complexes, lipids, fatty acids, saccharides, polysaccharides, inorganic molecules, and metals. In one embodiment, the compound is a conjugate comprising two or more different molecules. For example, in one embodiment, said conjugate comprises an antibody-protein complex, and in particular, and antibody-nascent protein complex.

Photocleavage of the photoconjugate may cause the compound or compounds to be released in a modified or unmodified form. For example, the photocleavage may leave part of the linker attached to the compound.

It is not intended that the present invention be limited to particular photocleavable linkers. There are a variety of known photocleavable linkers. Preferred comprise a 2-nitrobenzyl moiety. U.S. Pat. No. 5,643,722 describes a variety of such linkers and is hereby incorporated by reference.

In one embodiment, the present invention contemplates a method for transferring substances from a bead to a surface, comprising: a) providing i) a compound attached to a bead through a photocleavable linker; ii) a source of electromagnetic radiation; and iii) a surface; b) bringing said bead into contact (or in proximity to) with said surface; and c) illuminating said bead with radiation from said radiation source under conditions such that compound is photocleaved from said bead and transferred to said surface. In one embodiment, step b) comprises depositing said bead onto said surface. In a preferred embodiment, the method further comprises, after step c), the step d) removing said bead from said surface. Again, not all beads need be removed; some (e.g. 1-10%) can remain after washing. Again, the bead can be of any type (see above) and the compound can be of any type, including biomolecules (see above) and conjugates of biomolecules.

In one embodiment, the method also involves the use of a coding agent (discussed in more detail below). For example, in one embodiment, the present invention contemplates a method for transferring substances from a bead to a surface, comprising: a) providing i) a compound attached to a bead through a photocleavable linker, said bead further comprising a coding agent attached to said bead through a photocleavable linker; ii) a source of electromagnetic radiation; and iii) a surface; b) bringing said bead into contact with said surface; and c) illuminating said bead with radiation from said radiation source under conditions such that said compound and said coding agent are photocleaved from said bead and transferred to said surface. In one embodiment, step b) comprises depositing said bead onto said surface. In a preferred embodiment, the method further comprises, after step c), the step d) removing said bead from said surface. Again, not all beads need be removed; some (e.g. 1-10%) can remain after washing. Again, the bead can be of any type (see above) and the compound can be of any type, including biomolecules (see above) and conjugates of biomolecules. In one embodiment, the method further comprises, after step d), the step e) using said coding agent to determine the identity of said compound.

It is not intended that the present invention be limited to the nature of the coding agent. In one embodiment, said coding agent is selected from the group consisting of nucleic acid, protein, nanoparticles, quantum dots, mass coding agents, and fluorescent molecules. In one embodiment, the coding agent has identifiable spectral properties and the identifiable spectral property is detecting using a method selected from fluorescence spectroscopy, absorption spectroscopy, infrared spectroscopy, Raman spectroscopy, nuclear magnetic resonance, mass spectrometry.

As mentioned above, the compound can be a ligand. In one embodiment, the present invention contemplates a method for transferring a compound from a bead to a surface, comprising: a) providing i) a photocleavable biotin-labeled compound attached to an avidin-coated bead; ii) a source of electromagnetic radiation; and iii) a surface; b) bringing said bead into contact with (or in proximity to) said surface; and c) illuminating said bead with radiation from said radiation source under conditions such that compound is photocleaved from said bead and transferred to said surface. In a preferred embodiment, the method further comprises, after step c), the step d) removing said bead from said surface. Again, not all beads need be removed; some (e.g. 1-10%) can remain after washing. Again, the bead can be of any type (see above) and the compound can be of any type, including biomolecules (see above) and conjugates of biomolecules. In one embodiment, said photocleavable biotin comprises a 2-nitrobenzyl moiety. In one embodiment, said compound is a nascent protein labeled with photocleavable biotin during translation.

The transfer (e.g. photo-transfer) of compounds and substances has many uses, including but not limited to, the formation of arrays. For example, in one embodiment, the present invention contemplates a method of making an array, comprising: a) providing i) a plurality of beads (or other particles or nanoparticles), each bead comprising a group of compounds, each compound of said group attached to a bead through a photocleavable linker; ii) a source of electromagnetic radiation; and iii) a surface; b) bringing said plurality of beads into contact with (or in proximity to) said surface; and c) illuminating said beads with radiation from said radiation source under conditions such that at least a portion of said compounds is photocleaved from said beads and transferred to said surface to form a plurality of transferred groups of compounds on said surface, at least a portion of said plurality of transferred groups positioned in different locations on said surface (so as to create an array). In one embodiment, said photocleavable linker comprises a 2-nitrobenzyl moiety.

It is not intended that the present invention be limited to the nature of compounds employed or the makeup of compounds within a group. For example, the present invention contemplates an embodiment wherein each compound in any one group of compounds of step a) is identical. In another embodiment, two or more different compounds are in a group. In another embodiment, each transferred group of step c) has fewer compounds than any one group of compounds of step a). In another embodiment, at least a portion of said plurality of transferred groups are positioned at different predetermined locations on said surface. In another embodiment, step b) comprises depositing single beads at different locations on said surface. In another embodiment, step b) comprises depositing more than one bead at each location on said surface. In a preferred embodiment, the method further comprises, after step c), the step d) removing at least a portion of said beads from said surface (some, e.g. 1-10%, of the beads can remain). All types of compounds are contemplated, including biomolecules. For example, in one embodiment, each compound of every transferred group is a peptide, and in particular, a peptide of between 6 and 50 amino acids in length. In another, embodiment, each compound of every transferred group is an oligonucleotide, and in particular, an oligonucleotide of between 18 and 150 nucleotides in length. In one embodiment, each compound of every transferred group comprises nucleic acid derived from a single nucleic acid template. In one embodiment, each group consists of the amplified product from a single nucleic acid template.

As noted above, coding agents can be employed in the methods of the present invention. Coding agents are particularly useful in the context of arrays, and in particular, random arrays (in a way, ordered arrays are already coded by position, e.g. a compounds x-y location on the surface). In one embodiment, the present invention contemplates a method of making an array, comprising: a) providing i) a plurality of beads (or other particles or nanoparticles), each bead comprising a group of compounds and at least one coding agent, each compound of said group attached to a bead through a photocleavable linker, said coding agent attached to said bead through a photocleavable linker; ii) a source of electromagnetic radiation; and iii) a surface; b) bringing said plurality of beads into contact with said surface; and c) illuminating said beads with radiation from said radiation source under conditions such that at least a portion of said compounds is photocleaved from said beads and transferred to said surface to form a plurality of transferred groups of compounds on said surface (so as to create an array), at least a portion of said plurality of transferred groups positioned in different locations on said surface and associated with a transferred coding agent. In one embodiment, the method further comprises, after step d), the step e) using said coding agent to determine the identity of said compounds in said portion of said transferred groups. In one embodiment, each compound in any one group of compounds of step a) is identical. In another embodiment, two or more different compounds are in a group. In another embodiment, each transferred group of step c) has fewer compounds than any one group of compounds of step a). In another embodiment, at least a portion of said plurality of transferred groups are positioned at different predetermined locations on said surface. In another embodiment, step b) comprises depositing single beads at different locations on said surface. In another embodiment, step b) comprises depositing more than one bead at each location on said surface. In a preferred embodiment, the method further comprises after step c), the step d) removing at least a portion of said beads from said surface (some, e.g. 1-10%, of the beads can remain). All types of compounds are contemplated, including biomolecules. For example, in one embodiment, each compound of every transferred group is a peptide, and in particular, a peptide of between 6 and 50 amino acids in length. In another, embodiment, each compound of every transferred group is an oligonucleotide, and in particular, an oligonucleotide of between 18 and 150 nucleotides in length. In one embodiment, each compound of every transferred group comprises nucleic acid derived from a single nucleic acid template. In one embodiment, each group consists of the amplified product from a single nucleic acid template.

It is not intended that the present invention be limited by the nature of the particle or bead. In one embodiment, the bead is selected from agarose beads, streptavidin-coated beads, NeutrAvidin-coated beads, antibody-coated beads, paramagnetic beads, magnetic beads, electrostatic beads, electrically conducting beads, fluorescently labeled beads, colloidal beads, glass beads, semiconductor beads, nanocrystalline beads and polymeric beads.

It is not intended that the present invention be limited by the nature of the surface. In one embodiment, said surface is selected from charged surfaces, hydrophobic surfaces, and hydrophilic surfaces. In one embodiment, said surface is a chemically treated surface. In one embodiment, said surface is an epoxy-activated surface. In one embodiment, said surface is selected from surfaces coated with antibodies, surfaces coated with streptavidin, surfaces coated with cells, surfaces coated with nucleic acid, and surfaces coated with protein. In one embodiment, said surface is selected from glass surfaces, hydrogel surfaces, nitrocellulose surfaces, polymeric surfaces, gold coated surfaces, surfaces suitable for surface plasmon resonance, and surfaces suitable for MALDI. On the other hand, embodiments are also contemplated wherein said surface is an untreated surface. In one embodiment, said untreated surface is a polymer. In one embodiment, said polymer is selected from the group consisting of polystyrene and polyvinylidene fluoride.

In another embodiment, the present invention contemplates a method of making an array, comprising: providing i) a plurality of avidin-coated beads (or other particles or nanoparticles), each bead comprising a group of photocleavable biotin-labeled compounds attached to said bead through a biotin-avidin attachment; ii) a source of electromagnetic radiation; and iii) a surface; bringing said plurality of beads into contact with said surface; and illuminating said beads with radiation from said radiation source under conditions such that at least a portion of said compounds is photocleaved from said beads and transferred to said surface to form a plurality of transferred groups of compounds on said surface, at least a portion of said plurality of transferred groups positioned in different locations on said surface. In one embodiment, each compound in any one group of compounds of step a) is identical. In another embodiment, two or more different compounds are in a group. In another embodiment, each transferred group of step c) has fewer compounds than any one group of compounds of step a). In another embodiment, at least a portion of said plurality of transferred groups are positioned at different predetermined locations on said surface. In another embodiment, step b) comprises depositing single beads at different locations on said surface. In another embodiment, step b) comprises depositing more than one bead at each location on said surface. In a preferred embodiment, the method further comprises, after step c), the step d) removing at least a portion of said beads from said surface (some, e.g. 1-10%, of the beads can remain). All types of compounds are contemplated, including biomolecules. For example, in one embodiment, each compound of every transferred group is a peptide, and in particular, a peptide of between 6 and 50 amino acids in length. In another, embodiment, each compound of every transferred group is an oligonucleotide, and in particular, an oligonucleotide of between 18 and 150 nucleotides in length. In one embodiment, each compound of every transferred group comprises nucleic acid derived from a single nucleic acid template. In one embodiment, each group consists of the amplified product from a single nucleic acid template.

In some embodiments, amplification on a solid support (such as a bead or other particle) is useful for particular templates, including treated templates (e.g. treated enzymatically, chemically, etc.). In one embodiment, the present invention contemplates a method of amplifying nucleic acid on a solid support, comprising: a) providing a population of beads, each bead comprising one or more amplification primers, a population of nucleic acid template molecules, wherein said nucleic acid template molecules have been treated with bisulfite; and b) contacting said population of beads with said population of nucleic acid template molecules under conditions such that at least a portion of said nucleic acid is amplified to create loaded beads comprising immobilized amplified nucleic acid. In one embodiment, the method further comprises: c) treating said immobilized amplified nucleic acid so as to release at least a portion from said loaded beads so as to create free amplified nucleic acid. In one embodiment, the method further comprises: c) transferring at least a portion of said immobilized amplified nucleic acid to a non-bead solid support. In one embodiment, the method further comprises: c) detecting at least a portion of said immobilized amplified nucleic acid. In one embodiment, the method further comprises: c) determining at least a portion of the sequence of the immobilized amplified nucleic acid on one or more beads. In one embodiment, determining at least a portion of the sequence comprises use of nucleic acid hybridization probes, single base extension, DNA sequencing and mass spectrometry (or other assay). In one embodiment, the method further comprises: c) transcribing and translating the immobilized amplified nucleic acid. In one embodiment, each bead of step (a) comprises a forward and a reverse PCR primer. While it is not intended that the present invention be limited to particular chemistries, in one embodiment, prior to step (a) said forward and reverse PCR primers comprised 5' amine modifications and were attached to agarose beads comprising a plurality of primary amine reactive functional groups. It is not intended that the present invention be limited to the nature of the primers. In one embodiment, the primers have a region of complementarity to a gene associated with methylation and/or methylation differences associated with disease. In one embodiment, said forward and reverse PCR primers have a region that is completely complementary to a portion of the vimentin gene. In another embodiment, said forward and reverse PCR primers have a region that is completely complementary to a portion of the RASF2A gene. In one embodiment, said forward primer comprises a portion encoding an N-terminal epitope tag and said reverse primer comprises a portion encoding a C-terminal epitope tag. In some embodiments, the amount of beads and template is known. For example, in one embodiment, the known number of beads and the known number of nucleic acid template molecules is such that less than five template molecules contact any one bead. In another embodiment, the known number of beads and the known number of nucleic acid template molecules is such that less than two template molecules contact any one bead. In still another embodiment, the known number of beads and the known number of nucleic acid template molecules is such that less than one template molecule contacts any one bead. In one embodiment, the bisulfite for said bisulfite-treated template was an aqueous solution of a bisulfite salt (e.g. sodium bisulfite, magnesium bisulfite, etc.).

The present invention contemplates still other embodiments where treated template is employed in the context of amplifying on a solid support. In one embodiment, the present invention contemplates a method of amplifying nucleic acid on a solid support, comprising: a) providing a population of a known number of beads, and a population of a known number of nucleic acid template molecules treated with bisulfite, wherein said known number of nucleic acid template molecules is less than the known number of beads; b) contacting said population of beads with said population of nucleic acid template molecules under conditions such that at least a portion of said nucleic acid is non-covalently attached so as to create loaded beads comprising immobilized template; and c) amplifying at least a portion of said immobilized template so as to create immobilized amplified nucleic acid. In one embodiment, the method further comprises: d) treating said immobilized amplified nucleic acid so as to release at least a portion from said loaded beads so as to create free amplified nucleic acid. In one embodiment, the method further comprises: d) transferring at least a portion of said immobilized amplified nucleic acid to a non-bead solid support. In one embodiment, the method further comprises: d) detecting at least a portion of said immobilized amplified nucleic acid. In one embodiment, the method further comprises: d) determining at least a portion of the sequence of the immobilized amplified nucleic acid on one or more beads. In one embodiment, determining at least a portion of the sequence comprises use of nucleic acid hybridization probes, single base extension, DNA sequencing and mass spectrometry (or other assay). In one embodiment, the method further comprises: d) transcribing and translating the immobilized amplified nucleic acid. In one embodiment, each bead of step (a) comprises a forward and a reverse PCR primer. While it is not intended that the present invention be limited to particular chemistries, in one embodiment, prior to step (a) said forward and reverse PCR primers comprised 5' amine modifications and were attached to agarose beads comprising a plurality of primary amine reactive functional groups. It is not intended that the present invention be limited to the nature of the primers. In one embodiment, the primers have a region of complementarity to a gene associated with methylation and/or methylation differences associated with disease. In one embodiment, said forward and reverse PCR primers have a region that is completely complementary to a portion of the vimentin gene. In another embodiment, said forward and reverse PCR primers have a region that is completely complementary to a portion of the RASF2A gene. In one embodiment, said forward primer comprises a portion encoding an N-terminal epitope tag and said reverse primer comprises a portion encoding a C-terminal epitope tag. In one embodiment, the bisulfite for said bisulfite-treated template was an aqueous solution of a bisulfite salt (e.g. sodium bisulfite, magnesium bisulfite, etc.).

In yet another embodiment employing treated template, the present invention contemplates a method of amplifying nucleic acid on a solid support, comprising: a) providing a population of a known number of beads, each bead comprising forward and reverse PCR primers linked to the bead through a photocleavable linker, a population of a known number of nucleic acid template molecules treated with bisulfite, wherein said known number of nucleic acid template molecules is less than the known number of beads; and b) contacting said population of beads with said population of nucleic acid template molecules under conditions such that at least a portion of said nucleic acid is amplified to create loaded beads comprising immobilized amplified nucleic acid linked to the beads through a photocleavable linker. In one embodiment, the method further comprises: c) exposing at least a portion of said immobilized amplified nucleic acid to light so as to create free amplified nucleic acid. In one embodiment, the method further comprises: c) exposing at least a portion of said immobilized amplified nucleic acid to light so as to transfer at least a portion of said immobilized amplified nucleic acid to a non-bead solid support. In one embodiment, the method further comprises: c) treating said immobilized amplified nucleic acid so as to release at least a portion from said loaded beads so as to create free amplified nucleic acid. In one embodiment, the method further comprises: c) transferring at least a portion of said immobilized amplified nucleic acid to a non-bead solid support. In one embodiment, the method further comprises: c) detecting at least a portion of said immobilized amplified nucleic acid. In one embodiment, the method further comprises: c) determining at least a portion of the sequence of the immobilized amplified nucleic acid on one or more beads. In one embodiment, determining at least a portion of the sequence comprises use of nucleic acid hybridization probes, single base extension, DNA sequencing and mass spectrometry (or other assay). In one embodiment, the method further comprises: c) transcribing and translating the immobilized amplified nucleic acid. While it is not intended that the present invention be limited to particular chemistries, in one embodiment, prior to step (a) said forward and reverse PCR primers comprised 5' amine modifications and were attached to agarose beads comprising a plurality of primary amine reactive functional groups. It is not intended that the present invention be limited to the nature of the primers. In one embodiment, the primers have a region of complementarity to a gene associated with methylation and/or methylation differences associated with disease. In one embodiment, said forward and reverse PCR primers have a region that is completely complementary to a portion of the vimentin gene. In another embodiment, said forward and reverse PCR primers have a region that is completely complementary to a portion of the RASF2A gene. In one embodiment, said forward primer comprises a portion encoding an N-terminal epitope tag and said reverse primer comprises a portion encoding a C-terminal epitope tag.

In some embodiments, it is desirable to control the amplification of template on a solid support. For example, where it is desired that the amplification product on a bead (or other particle or nanoparticle) be homogeneous (or at least substantially homogeneous), it is useful to limit the concentration of template such that the ratio of beads to template results in between 0 and 10 template molecules, more preferably between 1 and 5 template molecules, hybridizing to the primers. This is particularly useful where multiplexing is desired (i.e. the simultaneous amplification of different templates). For multiplexing, the beads (or other particle or nanoparticle) can initially be treated separately, but thereafter mixed for simultaneous amplification. For example, in one embodiment, first and second beads are mixed (after they were initially treated with first and second templates in the manner described herein) and thereafter amplified under conditions such that the amplified product on said first bead comprises greater than 90% first template, and the amplified product on said second bead comprises greater than 90% second template. Unlike the prior art, such mixing of first and second beads can be done under non-emulsion conditions. In one embodiment, the present invention contemplates a method comprising a) providing template in a primer-free solution and beads, said beads comprising covalently attached forward and reverse PCR primers, b) mixing said beads and template under conditions such that said primers are extended, so as to create covalently attached extended products, c) washing said beads under conditions such that they are substantially free of template, and c) thermally cycling said beads such that said extended products are amplified. In one embodiment, the present invention contemplates a method of amplifying nucleic acid on a solid support, comprising: a) providing i) a population of beads (or other particle or nanoparticle), each bead comprising one or more amplification primers, ii) a solution of amplification reagents comprising a thermostable polymerase (but preferably primer-free), and iii) a population of nucleic acid template molecules (again, preferably primer-free), b) mixing said beads and said template molecules in a first aliquot of said solution of amplification reagents so as to create a mixture; c) treating the mixture under conditions such that at least a portion of said template molecules non-covalently bind to at least a portion of said beads to create bound template, and at least a portion of said primers on at least a portion of said beads are extended by said polymerase, so as to create treated beads; d) manipulating said treated beads so as to remove at least a portion of said bound template so as to create manipulated beads; and e) contacting said manipulated beads with a second aliquot of said solution of amplification reagents under conditions such that at least a portion of said extended primers is amplified to create loaded beads comprising immobilized amplified nucleic acid and unloaded beads lacking amplified nucleic acid. In one embodiment, said manipulating of step d) comprises washing said treated beads with a denaturing solution (e.g. a solution comprising NaOH). In one embodiment, prior to step d) between 1 and 10 primers per bead are extended. In one embodiment, prior to step d) some beads comprise no extended primers. In one embodiment, at step a) a known concentration of beads is provided. In one embodiment, at step a) a known concentration of nucleic acid template molecules is provided. In one embodiment, at step b) the number of template molecules to beads is less than one. In one embodiment, at step c) fewer than 50% of the beads comprise non-covalently bound template. In one embodiment, the amplification primers comprise a sequence which provides a code. In one embodiment, said code identifies the origin of the nucleic acid templates. In one embodiment, the origin of the nucleic acid template is a patient and the code identifies the patient. In one embodiment, said code identifies the bead. In one embodiment, each bead of step (a) comprises a forward and a reverse PCR primer.

In some embodiments, it is useful to have conditions that create loaded beads comprising immobilized amplified nucleic acid and unloaded beads lacking amplified in order to control for homogeneity of the amplified product. In one embodiment, the present invention contemplates a method of amplifying nucleic acid on a solid support, comprising: a) providing i) a population of beads (or other particle or nanoparticle), each bead comprising forward and reverse PCR primers primers, ii) a solution of amplification reagents comprising a thermostable polymerase, and iii) a population of nucleic acid template molecules, b) mixing said beads and said template molecules in a first aliquot of said solution of amplification reagents so as to create a mixture; c) treating the mixture under conditions such that at least a portion of said template molecules non-covalently bind to at least a portion of said beads to create bound template, and at least a portion of said primers on at least a portion of said beads are extended by said polymerase, so as to create treated beads; d) washing said treated beads with a denaturing solution so as to create manipulated beads; and e) contacting said manipulated beads with a second aliquot of said solution of amplification reagents under conditions such that at least a portion of said extended primers is amplified to create loaded beads comprising immobilized amplified nucleic acid and unloaded beads lacking amplified nucleic acid. In one embodiment, the method further comprises: (f) treating said immobilized amplified nucleic acid so as to release at least a portion from said loaded beads so as to create free amplified nucleic acid. In another embodiment, the method further comprises: (f) transferring at least a portion of said immobilized amplified nucleic acid to a non-bead solid support. In one embodiment, prior to step (a) said forward and reverse PCR primers comprised 5' amine modifications and were attached to agarose beads comprising a plurality of primary amine reactive functional groups. In one embodiment, said forward and reverse PCR primers have a region that is completely complementary to a portion of disease-related gene (e.g. the APC gene segment 3). In one embodiment, said forward primer comprises a portion encoding an N-terminal epitope tag and said reverse primer comprises a portion encoding a C-terminal epitope tag. In one embodiment, said mixture is created under the conditions such that the ratio of the number of nucleic acid template molecules to the number of beads is between 0.1:1 and 2:1. In one embodiment, said mixture is created under the conditions such that the ratio of the number of nucleic acid template molecules to the number of beads is between 2:1 and 500,000:1. In one embodiment, the ratio of the number of nucleic acid template molecules to the number of beads is between 1000:1 and 100,000:1. In one embodiment, the ratio of the number of nucleic acid template molecules to the number of beads is between 10,000:1 and 100,000:1. In one embodiment, the ratio of the number of nucleic acid template molecules to the number of beads is between 1000:1 and 10,000:1. In one embodiment, the percentage of unloaded beads is between approximately 50% and 95%, as measured by fluorescence. In one embodiment, the percentage of loaded beads is between approximately 1% and 5%, as measured by fluorescence. In one embodiment, the percentage of loaded beads is between approximately 5% and 50%, as measured by fluorescence (an assay for which is described below).

The present invention contemplates other embodiments of the method for creating loaded and unloaded beads (or particles or nanoparticles). In one embodiment, the present invention contemplates a method amplifying nucleic acid on a solid support, comprising: a) providing i) a population of a known concentration of beads (or particles or nanoparticles), each bead comprising one or more amplification primers, ii) a solution of amplification reagents comprising a thermostable polymerase, and iii) a population of a known concentration of nucleic acid template molecules; b) mixing said beads and said template molecules in a first aliquot of said solution of amplification reagents so as to create a mixture under the conditions such that the ratio of the number of nucleic acid template molecules to the number of beads is between 1:1 and 10,000:1; c) treating the mixture under conditions such that at least a portion of said template molecules non-covalently bind to at least a portion of said beads to create bound template, and at least a portion of said primers on at least a portion of said beads are extended by said polymerase, so as to create treated beads; d) manipulating said treated beads so as to remove at least a portion of said bound template so as to create manipulated beads; and e) contacting said manipulated beads with a second aliquot of said solution of amplification reagents under conditions such that at least a portion of said extended primers is amplified to create loaded beads comprising immobilized amplified nucleic acid and unloaded beads lacking amplified nucleic acid. In one embodiment, the method further comprises: (f) treating said immobilized amplified nucleic acid so as to release at least a portion from said loaded beads so as to create free amplified nucleic acid. In another embodiment, the method further comprises: (f) transferring at least a portion of said immobilized amplified nucleic acid to a non-bead solid support. In one embodiment, each bead of step (a) comprises a forward and a reverse PCR primer. In one embodiment, said manipulating comprises washing said treated beads with a denaturing solution (e.g. a solution comprising NaOH). In one embodiment, said washing removes the majority of said non-covalently bound template. In one embodiment, prior to step (a) said forward and reverse PCR primers comprised 5' amine modifications and were attached to agarose beads comprising a plurality of primary amine reactive functional groups. In one embodiment, said forward and reverse PCR primers have a region that is completely complementary to a portion of disease-related gene (e.g. the APC gene segment 3). In one embodiment, said forward primer comprises a portion encoding an N-terminal epitope tag and said reverse primer comprises a portion encoding a C-terminal epitope tag. In one embodiment, the percentage of unloaded beads is between approximately 50% and 95%, as measured by fluorescence. In one embodiment, the percentage of loaded beads is between approximately 1% and 5%, as measured by fluorescence. In one embodiment, the percentage of loaded beads is between approximately 5% and 50%, as measured by fluorescence (an assay for which is described below). In one embodiment, the ratio of the number of nucleic acid template molecules to the number of beads is between 1:1 and 10:1. In one embodiment, the ratio of the number of nucleic acid template molecules to the number of beads is between 10:1 and 100:1. In one embodiment, the ratio of the number of nucleic acid template molecules to the number of beads is between 100:1 and 1,000:1.

Still other embodiments of methods creating loaded and unloaded beads (or other particle or nanoparticle) employ lower ratios. In one embodiment, the present invention contemplates A method of amplifying nucleic acid on a solid support, comprising: a) providing i) a population of a known concentration of beads, each bead comprising one or more amplification primers, ii) a solution of amplification reagents comprising a thermostable polymerase, and iii) a population of a known concentration of nucleic acid template molecules, b) mixing said beads and said template molecules in a first aliquot of said solution of amplification reagents so as to create a mixture under the conditions such that the ratio of the number of nucleic acid template molecules to the number of beads is between 0.1:1 and 2:1; c) treating the mixture under conditions such that at least a portion of said template molecules non-covalently bind to at least a portion of said beads to create bound template, and at least a portion of said primers on at least a portion of said beads are extended by said polymerase, so as to create treated beads; d) exposing said treated beads to a denaturing solution so as to create manipulated beads; and e) contacting said manipulated beads with a second aliquot of said solution of amplification reagents under conditions such that at least a portion of said extended primers is amplified to create loaded beads comprising immobilized amplified nucleic acid and unloaded beads lacking amplified nucleic acid. In one embodiment, the method further comprises: (f) treating said immobilized amplified nucleic acid so as to release at least a portion from said loaded beads so as to create free amplified nucleic acid. In another embodiment, the method further comprises: (f) transferring at least a portion of said immobilized amplified nucleic acid to a non-bead solid support. In one embodiment, each bead of step (a) comprises a forward and a reverse PCR primer. In one embodiment, said denaturing solution comprises NaOH and said exposing comprises at least two washings of the beads. In one embodiment, said washings remove at least a portion of said non-covalently bound template. In one embodiment, said washings removes the majority of said non-covalently bound template. In one embodiment, the percentage of unloaded beads is between approximately 50% and 99%, as measured by fluorescence. In one embodiment, the percentage of loaded beads is between approximately 0.1% and 2%, as measured by fluorescence (an assay for which is described below).

In one embodiment, the present invention contemplates generating and capturing nascent proteins (or portions thereof) or peptides on the same solid support. In one embodiment, the present invention contemplates a surface comprising captured nascent protein, or fragment thereof, and amplified product encoding said nascent protein or fragment thereof (and methods of making such a surface). In one embodiment, the present invention contemplates a method of generating and capturing nascent proteins (or portions thereof) and peptides, comprising: a) providing nucleic acid encoding a protein (or portions thereof), and a plurality of beads (or other particle or nanoparticle), each bead comprising one or more amplification primers; b) contacting said beads with said nucleic acid under conditions such that at least a portion of said nucleic acid is amplified to create treated beads comprising immobilized amplified nucleic acid; and c) producing nascent protein from at least a portion of said immobilized amplified nucleic acid on said treated beads by (preferably cell free) expression to create expressed beads, wherein at least a portion of said nascent protein (or portion thereof) is captured on said expressed beads. It is not intended that the present invention be limited by the manner in which said protein (or portion thereof) is captured. In one embodiment, each of said beads, prior to step c), comprises a plurality of first binding agents on the bead surface, said first binding agents capable of binding said nascent protein. In one embodiment, said first binding agents comprise chemical moieties.

It is not intended that the present invention be limited to particular chemical moieties; a variety are contemplated. For example, in one embodiment, said chemical moieties are selected from the group consisting of amines, sulfhydryls, carboxyls, epoxy, and aldehyde moieties.

In one embodiment, said binding agents are ligands. For example, in one embodiment, said first binding agents are selected from the group consisting of antibodies, aptamers, streptavidin and avidin. It is not intended that the present invention be limited to only one binding agent. For example, in one embodiment, each of said beads, prior to step c), comprises a plurality of first binding agents on the bead surface, said first binding agents capable of binding a plurality of second binding agents, said second binding agents capable of binding said nascent protein. In yet another embodiment, each of said beads, prior to step c), comprises a plurality of first binding agents on the bead surface, said first binding agents capable of binding a plurality of second binding agents, said second binding agents capable of binding a plurality of third binding agents, said third binding agents capable of binding said nascent protein. In one embodiment, said first binding agent comprises biotin, said second binding agent comprises avidin, and said third binding agent comprises biotinylated antibody. In the latter embodiment, it is preferred that said avidin is a tetramer.

While not intending to limit the invention to any particular mechanism, the present invention contemplates, in one embodiment, that said contacting of step b) results in at least a portion of said nucleic acid annealing to said one or more amplification primers. Moreover, in one embodiment, after said annealing at least a portion of said primers are extended (e.g. wherein said conditions comprise use of a polymerase). It is preferred that after said primers are extended, the beads are treated under denaturing conditions.

Once the protein (or portions thereof) or peptide is captured, the bead can be used in a variety of assays. For example, in one embodiment, the method (above) further comprises, after step c), sequencing at least a portion of said nascent protein. In another embodiment, the method (above) further comprises after step c), determining whether said nascent protein comprises truncated protein (which can be done by ELISA using antibodies, mass spec, etc.).

Once the protein (or portions thereof) or peptide is captured, it can be transferred to another solid support, including but not limited to non-bead solid supports. For example, in one embodiment, the method (above) further comprises, after step c), transferring at least a portion of said nascent protein to a non-bead solid support, so as to create transferred nascent protein. In some embodiments, the assaying of the protein (or portions thereof) is done after such a transfer. For example, in one embodiment, the method (above) further comprises the step of sequencing at least as portion of said transferred nascent protein (or portion thereof) or peptide.

It is not intended that the present invention be limited to only transferring captured protein. In one embodiment, the method further comprises, after step c), transferring at least a portion of said nascent protein and at least a portion of said amplified nucleic acid to a non-bead solid support, so as to create transferred nascent protein and transferred nucleic acid. In some embodiments, the assaying of the nucleic acid (or portions thereof is done after such a transfer. For example, in one embodiment, the method further comprises the step of sequencing at least a portion of said transferred nucleic acid.

In one embodiment, the present invention contemplates, as a composition of matter, "loaded beads," i.e. beads (or other particle or nanoparticle) with captured protein(s) or peptide(s). In one embodiment, the "loaded beads" further comprises nucleic acid encoding said captured protein(s) or peptide(s). It is not intended that the present invention be limited by the methods by which this is achieved. Nonetheless, an illustrative embodiment is a method of generating and capturing nascent proteins, comprising: a) providing i) nucleic acid encoding a protein or fragment thereof, ii) a plurality of beads (or other particle or nanoparticle), each bead comprising one or more amplification primers and one or more first binding molecules, and iii) a population of second binding molecules capable of binding to said protein and said first binding molecules; b) contacting said beads with said nucleic acid under conditions such that at least a portion of said nucleic acid is amplified to create treated beads comprising immobilized amplified nucleic acid; c) contacting said treated beads with said second binding molecules under conditions such that at least a portion of said first binding molecules bind to at least a portion of said second binding molecules so as to create capture beads; and d) producing nascent protein or fragments thereof from at least a portion of said immobilized amplified nucleic acid on said capture beads by cell free expression, at least a portion of said nascent protein or fragments thereof interacting with at least a portion of said second binding molecules so as to generate loaded beads comprising captured nascent protein or captured fragments thereof. In one embodiment, the present invention contemplates the loaded beads generated according to this method as a composition of matter.

As mentioned above, it is not intended that the present invention be limited to particular chemical moieties; a variety are contemplated. For example, in one embodiment, said chemical moieties are selected from the group consisting of amines, sulfhydryls, carboxyls, epoxy, and aldehyde moieties.

In one embodiment, said binding agents are ligands. For example, in one embodiment, the present invention contemplates that said first binding agents comprise biotin. In another embodiment, the present invention contemplates that said second binding agents comprise antibody having affinity for said nascent protein or fragments thereof.

As with other embodiments discussed above, the protein or fragment thereof can be assayed after capture, either before or after transfer (e.g. transfer to another solid support, including non-bead supports). For example, in one embodiment, the method further comprises e) sequencing at least a portion of said nascent protein. In another embodiment, the method further comprises e) transferring at least a portion of said captured nascent protein to a non-bead solid support, so as to create transferred nascent protein, and thereafter f) sequencing at least a portion of said transferred nascent protein (or fragment thereof).

As with other embodiments discussed above, more than just the protein (or fragment) can be transferred. In one embodiment, the method further comprises e) transferring at least a portion of said captured nascent protein and at least a portion of said amplified nucleic acid, so as to create transferred nascent protein and transferred nucleic acid. In one embodiment, the method further comprises f) sequencing at least a portion of said transferred nucleic acid.

As with other embodiments discussed above, it is not intended that the present invention be limited by the nature of the assay. In one embodiment, the method further comprises after step d) determining whether said nascent protein comprises truncated protein. Such determining can be done by a variety of methods, including sequencing, ELISA (with antibodies to the C-terminus), or mass spec (in order to detect a smaller peptide).

In one embodiment, the method further comprises: (e) treating said captured nascent protein so as to release at least a portion from said loaded beads so as to create free nascent protein. It is not intended that the present invention be limited by the configuration which permits transfer. In a preferred embodiment, transfer is photo-transfer. In one embodiment, biotin (or another ligand) is linked to said beads via a photocleavable linker and the treating of step e) comprises exposing said photocleavable linker to light.

In one embodiment, each bead (or other particle or nanoparticle) of step (a) comprises a forward and a reverse PCR primer. It is not intended that the present invention be limited by the chemistry by which the primers are attached. In one embodiment, prior to step (a) said forward and reverse PCR primers comprised 5' amine modifications and were attached to beads (e.g. agarose beads) comprising a plurality of primary amine reactive functional groups.

The present invention contemplates other embodiments for generating "loaded beads." For example, in one embodiment, the present invention contemplates a method of generating and capturing nascent proteins (or fragments thereof), comprising: a) providing nucleic acid encoding a protein or fragment thereof, a plurality of beads (or other particle or nanoparticle), each bead comprising one or more amplification primers and one or more first binding molecules, a population of second binding molecules capable of binding to said first binding molecules, and a population of third binding molecules capable of binding to said second binding molecules and said protein or fragment thereof; b) contacting said beads with said nucleic acid under conditions such that at least a portion of said nucleic acid is amplified to create treated beads comprising immobilized amplified nucleic acid; c) contacting said treated beads with said second binding molecules under conditions such that at least a portion of said first binding molecules bind to at least a portion of said second binding molecules so as to create conjugated beads; d) contacting said conjugated beads with said third binding molecules under conditions such that at least a portion of said second binding molecules bind to at least a portion of said third binding molecules so as to create capture beads; and e) producing nascent protein or fragment thereof from at least a portion of said immobilized amplified nucleic acid on said capture beads by cell free expression, at least a portion of said nascent protein or fragment thereof interacting with at least a portion of said third binding molecules so as to generate loaded beads comprising captured nascent protein or captured fragment thereof.

As with other embodiments discussed above, the protein or fragment thereof can be assayed after capture, either before or after transfer (e.g. transfer to another solid support, including non-bead supports). In one embodiment, the method further comprises f) sequencing at least a portion of said nascent protein. In another embodiment, the method further comprises f) transferring at least a portion of said captured nascent protein to a non-bead solid support, so as to create transferred nascent protein and g) sequencing at least a portion of said transferred nascent protein.

As with other embodiments discussed above, more than just the protein (or fragment) can be transferred. For example, in one embodiment, the method further comprises f) transferring at least a portion of said captured nascent protein and at least a portion of said amplified nucleic acid, so as to create transferred nascent protein and transferred nucleic acid. In one embodiment, after transferring, the method further comprises g) sequencing at least a portion of said transferred nucleic acid.

As with other embodiments discussed above, it is not intended that the present invention be limited by the nature of the assay. In one embodiment, the method further comprises after step e) determining whether said nascent protein comprises truncated protein. Such determining can be done by a variety of methods, including sequencing, ELISA (with antibodies to the C-terminus), or mass spec (in order to detect a smaller peptide).

In one embodiment, the binding molecules are ligands. For example, in one embodiment said first binding molecules comprise biotin, said second binding molecules comprise streptavidin and said third binding molecules comprise biotinylated antibody, said antibody having affinity for said nascent protein or fragment thereof.

In one embodiment, the method further comprises: (f) treating said captured nascent protein or fragment thereof so as to release at least a portion from said loaded beads so as to create free nascent protein or free fragment thereof. It is not intended that the present invention be limited to the method of transfer. In one embodiment of phototransfer, said biotinylated antibody comprises biotin linked via a photocleavable linker to said antibody and said treating of step f) comprises exposing said photocleavable linker to light.

In one embodiment, each bead of step (a) comprises a forward and a reverse PCR primer. The attachment can be done in a variety of ways. In one embodiment, prior to step (a) said forward and reverse PCR primers comprised 5' amine modifications and were attached to agarose beads comprising a plurality of primary amine reactive functional groups.

In yet another embodiment of creating "loaded beads," the present invention contemplates a method of generating and capturing truncated protein, comprising: a) providing nucleic acid encoding a truncated protein, a plurality of beads (or other particle or nanoparticle), each bead comprising one or more amplification primers and one or more first binding molecules, a population of second binding molecules capable of binding to said first binding molecules, and a population of third binding molecules capable of binding to said second binding molecules and capturing said truncated protein; b) contacting said beads with said nucleic acid under conditions such that at least a portion of said nucleic acid is amplified to create treated beads comprising immobilized amplified nucleic acid; c) contacting said treated beads with said second binding molecules under conditions such that at least a portion of said first binding molecules bind to at least a portion of said second binding molecules so as to create conjugated beads; d) contacting said conjugated beads with said third binding molecules under conditions such that at least a portion of said second binding molecules bind to at least a portion of said third binding molecules so as to create capture beads; and e) producing truncated protein from at least a portion of said immobilized amplified nucleic acid on said capture beads by cell free expression, said third binding molecules capturing at least a portion of said truncated protein so as to generate loaded beads comprising captured truncated protein.

As with other embodiments discussed above, the protein or fragment thereof can be assayed after capture, either before or after transfer (e.g. transfer to another solid support, including non-bead supports). In one embodiment, the method further comprises f) sequencing at least a portion of said nascent protein. In another embodiment, the method further comprises f) transferring at least a portion of said captured nascent protein to a non-bead solid support, so as to create transferred nascent protein and g) sequencing at least a portion of said transferred nascent protein.

As with other embodiments discussed above, more than just the protein (or fragment) can be transferred. For example, in one embodiment, the method further comprises f) transferring at least a portion of said captured nascent protein and at least a portion of said amplified nucleic acid, so as to create transferred nascent protein and transferred nucleic acid. When nucleic acid is transferred, it can also be assayed. In one embodiment, the method further comprises g) sequencing at least a portion of said transferred nucleic acid.

In one embodiment, the method further comprises after step e) determining whether said nascent protein comprises truncated protein. As with other embodiments discussed above, it is not intended that the present invention be limited by the nature of the assay (e.g. gel electrophoresis, ELISA with antibodies to the C-terminus, mass spec, etc.).

As with other embodiments, the binding molecules may be ligands. In one embodiment, said first binding molecules comprise biotin, said second binding molecules comprise streptavidin and said third binding molecules comprise biotinylated antibody.

In one embodiment, the method further comprising: (f) treating said captured truncated protein so as to release at least a portion from said loaded beads so as to create free truncated protein. As with other embodiments, it is not intended that the invention be limited to any particular transfer mechanism. Nonetheless, a preferred transfer is phototransfer. In one embodiment, said biotinylated antibody comprises biotin linked via a photocleavable linker to said antibody. Thus, in one embodiment, the method comprises exposing said photocleavable linker to light.

In one embodiment, each bead of step (a) comprises a forward primer encoding a first epitope and a reverse PCR primer encoding a second epitope. Again, it is not intended that the invention be limited by the attachment chemistry. Nonetheless, in one embodiment, prior to step (a) said forward and reverse PCR primers comprised 5' amine modifications and were attached to agarose beads comprising a plurality of primary amine reactive functional groups.

In all of the above-discussed embodiments, the protein, protein portion, protein fragment, truncated protein or peptide can be encoded by a variety of disease related genes or portions of such genes. In one embodiment, at least a portion of said truncated protein is encoded by a portion of the APC gene.

In one embodiment, a plurality of biomolecule species are produced, sorted on beads, in multiplexed fashion, i.e. using one or a few reactions, each within a single reactor. It is not intended that the present invention be limited by the nature of the biomolecules. In one embodiment, the biomolecules are peptides or proteins. In one embodiment, the biomolecules are nucleic acids, nucleosides, nucleotides or polymers thereof which are useful directly or used to subsequently direct de novo protein synthesis, hence producing, in multiplexed fashion, a plurality protein or peptide biomolecules also sorted on the same beads.

The produced biomolecules on beads can be used as probes, targets or analytes, for example, for various parallel, massively parallel or multiplexed analyses such as DNA sequencing and/or mutation detection as well as various genome-wide and proteome-wide analyses.

However, the plurality of produced biomolecules can be for a variety of uses. These biomolecules are not intended to be limited to any one use, and henceforth will be referred to "features", as is commonly used in the art of microarrays. Compared to conventional approaches, it is far more desirable to utilize truly multiplexed methods to produce said features on beads, with one or a few reactions, each within a single reactor for example.

In one preferred embodiment, a method is disclosed for the multiplexed production of a plurality of DNA features, sorted on beads, using solid-phase bridge PCR amplification with a given amplification primer set on each bead species. Each bead can amplify a plurality template DNA molecules or more preferably, each bead can clone (amplify) a single template molecule, all performed with the entire bead population in a single reactor. In either case, the DNA amplicon on the beads can subsequently be used for multiplexed cell-free (in vitro) protein synthesis on the beads, producing a bead-sorted library of in vitro expressed proteins (BS-LIVE-PRO). This is achieved by cell-free (in vitro) transcription and translation of the entire bead population and capturing molecules of each produced protein species on the same DNA-encoded bead from which they were made, all in a single reactor (e.g. in a single tube).

The single-molecule solid-phase bridge PCR amplification approach is particularly useful, since in that embodiment a single primer set (pair) on a population of beads can be used to amplify a plurality of different DNA templates in a single reactor (e.g. amplify different cDNAs from a cDNA library pertaining to different gene coding sequences), yet the different amplicon species, arising from the single template molecules, remain sorted on different beads (for example, all template molecules having some common sequences, e.g. on 5' and 3' ends of the template DNA). This can be useful in the highly multiplexed manufacturing of probe or target type features for beads, e.g. to produce proteome libraries sorted on beads. However, the method is also useful in the production of analyte type "features" for diagnostic applications, for example, where a population of molecules (e.g. population of molecules corresponding to a particular gene or fragment thereof) needs to be queried for sub-populations (e.g. a minor sub-population of those gene molecules containing a disease causing mutation).

Furthermore, in one embodiment, the solid-phase bridge PCR uses amplification primers attached to the beads, with no soluble primers (i.e. it is preferred that free primers are not added), and hence the PCR amplicon is also restricted to the beads. This facilitates full multiplexing, should the need exist to target single molecules of a plurality of different DNA template species, using different specific primer sets. For example, with this approach, it is possible to clone (amplify) single template molecules on beads, whereby the different primer sets on different beads target single template molecules corresponding to different fragments of a gene, all performed with the entire bead and template population within a single reactor (using one or a few reactions).

Methods are also disclosed that pertain to the photo-transfer of features, produced as described above or in any other manner, from beads to planar substrates (or to wells into which the beads fit), such as microarray substrates, in order to create microarray features from said beads.

More broadly however, this invention also relates to methods and compositions for the photo-transfer of substances and compounds from one surface to another, without restrictions on the types or numbers of substances and compounds, and without restrictions on the types surfaces, and is therefore also applicable to a much wider range of fields.

In a preferred embodiment, compounds such as macromolecules or substances such as nanoparticles (particles of between 1 and 100 nm in diameter) or cells, which serve as probes, analytes or targets for example, are attached to a surface through photocleavable linkers, said surface allowed to contact a second surface and then said substances or compounds photo-released under conditions to allow transfer to said second surface. Surfaces can be, but are not limited to, beads, glass slides, metallic surfaces, plastic or polymeric surfaces and other surfaces used for biomolecular detection. In some embodiments, it is not strictly necessary that said photo-transferred compounds or substances be in physical contact with said second surface, but in close proximity instead.

In one embodiment, the method also involves the phototransfer of a coding agent. For example, in one preferred embodiment, the present invention contemplates a method for co-transferring coding agents and compounds or substances from a bead to a surface and using said coding agents to determine the identity of said co-transferred compound or substance or the identity of said bead.

In some instances, it is desired to photo-transfer more than just one compound or substance. For example, in some embodiments, any combination of various substances and/or compounds are photo-transferred.

The present invention also contemplates sorting out and/or enriching subpopulations of biomolecules on solid supports, including enriching subpopulations of beads containing biomolecules. In one embodiment, the present invention contemplates method of enriching a subpopulation of beads in a mixture, comprising: a) providing a mixture comprising i) a plurality of first beads, said first beads comprising immobilized first amplified product, said first amplified product encoding a first nascent protein or fragment thereof, and ii) a plurality of second beads, said second beads comprising immobilized second amplified product, said second amplified product encoding a second nascent protein or fragment thereof, b) exposing said mixture to translation system under conditions such that said first and second nascent proteins or fragments thereof are generated from at least a portion of said first and second immobilized amplified products, c) capturing at least a portion of said first nascent protein or fragment thereof on said first bead and capturing at least a portion of said second nascent protein or fragment thereof on said second bead, so as to create a mixture of beads comprising captured proteins or fragments thereof, and d) contacting said mixture of beads comprising captured proteins or fragments thereof with a ligand with affinity for said first nascent protein or fragment thereof, said contacting performed under conditions such that at least a portion of said first beads are separated from said mixture, thereby enriching a subpopulation of beads. In one embodiment, each of said beads, prior to step c), comprises a plurality of reactive chemical moieties on the bead surface, said moieties capable of reacting with said nascent protein. In one embodiment, said ligand comprises an antibody. In one embodiment, said antibody is attached to magnetic beads. In one embodiment, said conditions of step d) comprise exposure of said mixture to a magnet. In one embodiment, said exposure to a magnet creates precipitated beads and a supernatant. In one embodiment, said conditions of step d) further comprise removing said supernatant or substantially all (e.g. 90% or more) of said supernatant, so as to create an isolated precipitate. In one embodiment, said conditions of step d) further comprise removing said precipitated beads or substantially all (e.g. 90% or more) of said precipitated beads, so as to create a depleted supernatant. In one embodiment, the ratio of first beads to second beads in said mixture of step a) is 50:50. In one embodiment, said isolated precipitate is contaminated with less than 30% of second beads. In one embodiment, said isolated precipitate is contaminated with less than 10% of second beads. In one embodiment, said isolated precipitate is contaminated with less than 1% of second beads. In one embodiment, said mixture of step a) further comprises a plurality of third beads. In one embodiment, said third beads lack immobilized amplified product. In one embodiment, said third beads comprise immobilized third amplified product, said third amplified product encoding a third nascent protein or fragment thereof. In one embodiment, said first immobilized amplified product comprises at least a portion of a disease-related (including but not limited to cancer-related) gene. In one embodiment, said disease-related gene is selected from the group consisting of the APC gene, the NF1 gene, the NF2 gene, the BRCA1 gene, the BRCA2 gene, the Kras gene, and the p53 gene. In one embodiment, the number of second beads in said mixture is less than the number of said first beads.

It is not intended that the present invention be limited to the number or nature of ligands employed to enrich or sort subpopulations. In one embodiment, the present invention contemplates a method of enriching a subpopulation of beads (or other particle or nanoparticle) in a mixture, comprising: a) providing a mixture comprising i) a plurality of first beads, said first beads comprising immobilized first amplified product, said first amplified product encoding a first nascent protein or fragment thereof, and ii) a plurality of second beads, said second beads comprising immobilized second amplified product, said second amplified product encoding a second nascent protein or fragment thereof; b) exposing said mixture to a translation system under conditions such that said first and second nascent proteins or fragments thereof are generated from said first and second immobilized amplified products, c) capturing said first nascent protein or fragment thereof on said first bead and capturing said second nascent protein or fragment thereof on said second bead, so as to create a mixture of beads comprising captured proteins or fragments thereof; d) contacting said mixture of beads comprising captured proteins or fragments thereof with a first ligand with affinity for said first nascent protein or fragment thereof, so as to create a mixture of treated beads; e) contacting said mixture of treated beads with a second ligand, said second ligand having affinity for said first ligand, said contacting performed under conditions such that at least a portion of said first beads are separated from said mixture, thereby enriching a subpopulation of beads. In one embodiment, each of said beads, prior to step c), comprises a plurality of reactive chemical moieties on the bead surface, said moieties capable of reacting with said nascent protein. In one embodiment, said first ligand comprises a first antibody. In one embodiment, said second ligand comprises a second antibody. In one embodiment, said second antibody is attached to magnetic beads. In one embodiment, said conditions of step e) comprise exposure of said mixture to a magnet. In one embodiment, said exposure to a magnet creates precipitated beads and a supernatant. In one embodiment, said conditions of step e) further comprise removing said supernatant or substantially all (90% or more) of said supernatant, so as to create an isolated precipitate. In one embodiment, said conditions of step e) further comprise removing said precipitated beads or substantially all (90% or more) of said precipitated beads, so as to create a depleted supernatant. In one embodiment, the ratio of first beads to second beads in said mixture of step a) is 50:50. In one embodiment, said isolated precipitate is contaminated with less than 30% of second beads. In one embodiment, said isolated precipitate is contaminated with less than 10% of second beads. In one embodiment, said isolated precipitate is contaminated with less than 1% of second beads. In one embodiment, said mixture of step a) further comprises a plurality of third beads. In one embodiment, said third beads lack immobilized amplified product. In one embodiment, said third beads comprise immobilized third amplified product, said third amplified product encoding a third nascent protein or fragment thereof. In one embodiment, said first immobilized amplified product comprises at least a portion of a disease-related (including but not limited to cancer-related) gene. In one embodiment, said disease-related gene is selected from the group consisting of the APC gene, the NF1 gene, the NF2 gene, the BRCA1 gene, the BRCA2 gene, the Kras gene, and the p53 gene. In one embodiment, the number of second beads in said mixture is less than the number of said first beads.

In one embodiment, the present invention contemplates sorting out or enriching populations such that wild-type full-length protein is separated from truncated protein. In one embodiment, the present invention contemplates a method of enriching a subpopulation of beads, comprising: a) providing a mixture comprising i) a plurality of first beads, said first beads comprising immobilized first amplified product, said first amplified product encoding a truncated version of a first protein, and ii) a plurality of second beads, said second beads comprising immobilized second amplified product, said second amplified product encoding an untruncated version of said first protein, wherein the number of first beads in said mixture is less than the number of said second beads; b) exposing said mixture to a translation system under conditions such that said truncated and untruncated versions of said first protein are generated from at least a portion of said first and second immobilized amplified products, c) capturing said truncated version of said first protein on said first bead and capturing said untruncated version of said first protein on said second bead, so as to create a mixture of beads comprising captured proteins or truncated fragments thereof; and d) contacting said mixture of beads comprising captured proteins or truncated fragments thereof with a ligand with affinity for said untruncated version of said first protein, so as to create a mixture of treated beads, said contacting performed under conditions such that at least a portion of said second beads are separated from said mixture, thereby enriching a subpopulation of beads comprising truncated protein. In one embodiment, each of said beads, prior to step c), comprises a plurality of reactive chemical moieties on the bead surface, said moieties capable of reacting with and capturing said nascent protein. In one embodiment, said ligand comprises an antibody. In one embodiment, said antibody has affinity for a region of said untruncated version of said first protein that is lacking in said truncated protein said antibody is attached to magnetic beads. In one embodiment, said conditions of step d) comprise exposure of said mixture to a magnet. In one embodiment, said exposure to a magnet creates precipitated beads and a supernatant. In one embodiment, said conditions of step d) further comprise removing said supernatant or substantially all (905 or more) of said supernatant, so as to create an isolated precipitate. In one embodiment, said conditions of step d) further comprise removing said precipitated beads or substantially all (90% or more), so as to create a depleted supernatant. In one embodiment, the ratio of first beads to second beads in said mixture of step a) is less than 1:10. In one embodiment, said isolated precipitate is contaminated with less than 5% of said first beads. In one embodiment, said isolated precipitate is contaminated with less than 2% of said first beads. In one embodiment, said isolated precipitate is contaminated with less than 1% of said first beads. In one embodiment, said mixture of step a) further comprises a plurality of third beads. In one embodiment, said third beads lack immobilized amplified product. In one embodiment, said third beads comprise immobilized third amplified product, said third amplified product encoding a third nascent protein or fragment thereof. In one embodiment, said first immobilized amplified product comprises at least a portion of a disease-related (including but not limited to cancer-related) gene. In one embodiment, said disease-related gene is selected from the group consisting of the APC gene, the NF1 gene, the NF2 gene, the BRCA1 gene, the BRCA2 gene, the Kras gene, and the p53 gene.

In yet another embodiment of sorting out and/or enriching for truncated protein, the present invention contemplates a method of enriching a subpopulation of beads, comprising: a) providing a mixture comprising i) a plurality of first beads, said first beads comprising immobilized first amplified product, said first amplified product encoding a truncated version of a first protein, and ii) a plurality of second beads, said second beads comprising immobilized second amplified product, said second amplified product encoding an untruncated version of said first protein, wherein the number of first beads in said mixture is less than the number of said second beads; b) exposing said mixture to a translation system under conditions such that said truncated and untruncated versions of said first protein are generated from at least a portion of said first and second immobilized amplified products, c) capturing said truncated version of said first protein on said first bead and capturing said untruncated version of said first protein on said second bead, so as to create a mixture of beads comprising captured proteins or truncated fragments thereof; d) contacting said mixture of beads comprising captured proteins or truncated fragments thereof with a first ligand with affinity for said untruncated version of said first protein, so as to create a mixture of treated beads; and e) contacting said mixture of treated beads with a second ligand, said second ligand having affinity for said first ligand, said contacting performed under conditions such that at least a portion of said first beads are separated from said mixture, thereby enriching a subpopulation of beads comprising truncated protein. In one embodiment, each of said beads, prior to step c), comprises a plurality of reactive chemical moieties on the bead surface, said moieties capable of reacting with said nascent protein. In one embodiment, said first ligand comprises a first antibody. In one embodiment, said antibody has affinity for a region of said untruncated version of said first protein that is lacking in said truncated protein. In one embodiment, said second ligand comprises a second antibody. In one embodiment, said second antibody is attached to magnetic beads. In one embodiment, said conditions of step e) comprise exposure of said mixture to a magnet. In one embodiment, said exposure to a magnet creates precipitated beads and a supernatant. In one embodiment, said conditions of step e) further comprise removing said supernatant or substantially all (90% or more) of said supernatant, so as to create an isolated precipitate. In one embodiment, said conditions of step e) further comprise removing said precipitated beads or substantially all (90% or more), so as to create a depleted supernatant. In one embodiment, the ratio of first beads to second beads in said mixture of step a) is less than 1:10. In one embodiment, said isolated precipitate is contaminated with less than 5% of said first beads. In one embodiment, said isolated precipitate is contaminated with less than 2% of said first beads. In one embodiment, said isolated precipitate is contaminated with less than 1% of said first beads. In one embodiment, said mixture of step a) further comprises a plurality of third beads. In one embodiment, said third beads lack immobilized amplified product. In one embodiment, said third beads comprise immobilized third amplified product, said third amplified product encoding a third nascent protein or fragment thereof. In one embodiment, said first immobilized amplified product comprises at least a portion of a disease-related (including but not limited to cancer-related) gene. In one embodiment, said disease-related gene is selected from the group consisting of the APC gene, the NF1 gene, the NF2 gene, the BRCA1 gene, the BRCA2 gene, the Kras gene, and the p53 gene.

In yet another embodiment, the present invention contemplates bead-ligand-nascent protein complexes (including but not limited to bead-ligand-nascent protein fluorescent complexes) as well as methods of creating and detecting a bead-ligand-nascent protein complex (including but not limited to a bead-ligand-nascent protein fluorescent complex). In one embodiment, the present invention contemplates a method, comprising: a) providing i) a population of template molecules, each template molecule encoding a nascent protein or protein fragment, and ii) at least one surface comprising forward and reverse PCR primers attached to said surface; b) amplifying at least a portion of said population of template molecules so as to create amplified product attached to said surface; c) generating nascent protein or protein fragment from said amplified product, said nascent protein or protein fragment comprising an affinity tag or first epitope, and d) capturing said nascent protein or protein fragment on said surface via a first ligand, said first ligand attached to said bead and reactive with said affinity tag or first epitope. In one embodiment, said at least one surface is on a bead. In one embodiment, the present invention contemplates the bead-ligand-nascent protein complex created by the method (as a composition of matter). In one embodiment, said first ligand is attached to said bead after step b) and prior to step c). In one embodiment, said first ligand comprises an antibody. In one embodiment, said first ligand comprises a metal chelator. In one embodiment, said affinity tag comprises biotin and said first ligand is selected from the group consisting of avidin and streptavidin. In one embodiment, said antibody is attached to said bead through a biotin-streptavidin linkage. In one embodiment, said amplifying of step b) comprises i) mixing a plurality of beads in solution with said template under conditions such that at least a portion of said template hybridizes to at least a portion of said PCR primers on at least a portion of said beads to create hybridized primers, ii) extending at least a portion of said hybridized primers to created treated beads, iii) washing said treated beads so as to create washed beads, said washed beads being substantially free (e.g. 90% or more removed) of template, and iv) thermally cycling said washed beads in the presence of amplification reagents. In one embodiment, said amplification reagents comprise a thermostable polymerase. In one embodiment, the nascent protein or fragment thereof generated in step c) is generated in a cell-free translation reaction. In one embodiment, said affinity tag is introduced into said nascent protein during said translation reaction. In one embodiment, said antibody reacts with said first epitope on said nascent protein. In one embodiment, the nucleic acid encoding said first epitope is introduced during amplification in step b). In one embodiment, said first epitope is encoded by a nucleic acid sequence of one of said PCR primers. In one embodiment, said forward PCR primer comprises i) a sequence corresponding to a promoter, ii) a sequence corresponding to a ribosome binding site, iii) a start codon, and iv) said sequence coding for said first epitope. In one embodiment, said forward PCR primer further comprises v) a sequence complementary to at least a portion of said template molecules. In one embodiment, said template sequence comprises at least a region of a gene, said gene selected from the group consisting of the APC gene, the NF1 gene, the NF2 gene, the BRCA1 gene, the BRCA2 gene, the Kras gene, the p53 gene, and the BCR-able gene. In one embodiment, said reverse PCR primer comprises i) at least one stop codon, and ii) a sequence coding for a second epitope. In one embodiment, said first ligand is attached via a photocleavable linker. In one embodiment, said captured nascent protein or protein fragment of step d) is photoreleased. In one embodiment, said captured nascent protein of step d) comprises a second epitope. In one embodiment, said first epitope is an N-terminal epitope and said second epitope is a C-terminal epitope. In one embodiment, the method further comprises e) reacting said captured nascent protein with a second ligand, said second ligand having affinity for said second epitope. In one embodiment, said nascent protein or protein fragment is photoreleased onto a non-bead surface. In one embodiment, said non-bead surface is compatible with mass spectrometry. In one embodiment, the mass of said nascent protein or protein fragment is measured by mass spectrometry. In one embodiment, said bead-ligand-nascent protein complex is detected by flow cytometry. In one embodiment, said bead-ligand-nascent protein complex is fluorescent. In one embodiment, said fluorescent bead-ligand-nascent protein complex is analyzed under a microscope capable of detecting fluorescence. In one embodiment, said fluorescent bead-ligand-nascent protein complex is analyzed by a fluorescent activated cell sorter. In one embodiment, said fluorescent bead-ligand-nascent protein complex is analyzed under a microarray reader capable of detecting fluorescence. In one embodiment, said fluorescent bead-ligand-nascent protein complex is detected by microfluidics.

The present invention contemplates still other embodiments of bead-ligand-nascent protein complexes (including but not limited to bead-ligand-nascent protein fluorescent complexes) as well as other embodiments of methods for creating and detecting a bead-ligand-nascent protein complex (including but not limited to a bead-ligand-nascent protein fluorescent complex). In one embodiment, the present invention contemplates a method, comprising: a) providing 1) a template sequence encoding a nascent protein or fragment thereof and 2) a surface comprising a PCR primer, said PCR primer comprises i) a promoter sequence, ii) a ribosome binding site sequence, iii) a start codon sequence, iv) a sequence coding for a first epitope, and v) a sequence complementary to at least a portion of said a template sequence; b) amplifying said template so as to create amplified product immobilized on said surface, said amplified product encoding a nascent protein or fragment thereof, and encoding said first epitope; c) attaching a first ligand capable of capturing said nascent protein or fragment thereof by reacting with said first epitope; d) generating said nascent protein or fragment thereof comprising said first epitope from said amplified product, and e) capturing said nascent protein or fragment thereof on said surface via said first ligand, thereby generating a surface comprising captured nascent protein, or fragment thereof, and amplified product coding said nascent protein or fragment thereof. In one embodiment, said surface is a bead surface. In one embodiment, the present invention contemplates the bead-ligand-nascent protein complex created by the method (as a composition of matter). In one embodiment, said first ligand comprises an antibody. In one embodiment, said first ligand comprises a metal chelator. In one embodiment, said template sequence comprises at least a region of a gene, said gene selected from the group consisting of the APC gene, the NF1 gene, the NF2 gene, the BRCA1 gene, the BRCA2 gene, the Kras gene, the p53 gene, and the BCR-able gene. In one embodiment, said first ligand is attached via a photocleavable linker. In one embodiment, said captured nascent protein or fragment thereof of step e) is photoreleased. In one embodiment, said captured nascent protein of step e) further comprises a second epitope. In one embodiment, said first epitope is an N-terminal epitope and said second epitope is a C-terminal epitope. In one embodiment, the method further comprises f) reacting said captured nascent protein with a second ligand, said second ligand having affinity for said second epitope.

The present invention contemplates still other embodiments of bead-ligand-nascent protein complexes (and in particular, bead-ligand-nascent protein fluorescent complexes) as well as other embodiments of methods for creating and detecting bead-ligand-nascent protein fluorescent complexes. In one embodiment, the present invention contemplates a method of creating and detecting a bead-ligand-nascent protein fluorescent complex, comprising: a) providing 1) a template sequence encoding a nascent protein or fragment thereof and 2) a bead comprising first and second PCR primers, said first PCR primer comprising i) a promoter sequence, ii) a ribosome binding site sequence, iii) a start codon sequence, iv) a sequence coding for a first epitope, and v) a sequence complementary to at least a portion of said a template sequence, and said second PCR primer comprising i) at least one stop codon, and ii) a sequence coding for a second epitope; b) amplifying said template so as to create amplified product immobilized on said bead, said amplified product encoding a nascent protein or fragment thereof, and encoding said first and second epitopes; c) attaching to said bead a first ligand capable of capturing said nascent protein or fragment thereof by reacting with said first epitope; d) generating said nascent protein or fragment thereof comprising said first epitope from said immobilized amplified product, e) capturing said nascent protein or fragment thereof on said bead via said first ligand, thereby generating a bead-ligand-nascent protein complex; f) contacting said bead-ligand-nascent protein complex with a second ligand capable of binding to said second epitope, said second ligand comprising a fluorescent moiety, thereby creating a bead-ligand-nascent protein fluorescent complex; and g) detecting said fluorescent moiety of said bead-ligand-nascent protein fluorescent complex. The present invention contemplates, as a composition of matter, the bead-ligand-nascent protein fluorescent complex made according to the above method. In one embodiment, said first ligand comprises an antibody. In one embodiment, said bead-ligand-nascent protein complex is detected by flow cytometry. In one embodiment, said fluorescent moiety of said bead-ligand-nascent protein fluorescent complex comprises Cy3. In one embodiment, said fluorescent bead-ligand-nascent protein complex is detected under a microscope capable of detecting fluorescence. In one embodiment, said fluorescent bead-ligand-nascent protein complex is detected by a fluorescent activated cell sorter. In one embodiment, said fluorescent bead-ligand-nascent protein complex is detected under a microarray reader capable of detecting fluorescence. In one embodiment, said fluorescent bead-ligand-nascent protein complex is detected by microfluidics.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A. tRNA mediated labeling, isolation by incorporated PC-biotin and photo-release into solution of cell-free expressed proteins. Lane 1 is the initial unbound fraction corresponding to nascent GST not binding the NeutrAvidin beads (wash factions were also collected and analyzed but contained negligible quantities). Lane 2 is the negative control elution in the absence of the proper light. Lane 3 is the photo-released fraction following illumination with the proper light. Lane 4 is the fraction remaining bound to the beads that was subsequently released by denaturation of the NeutrAvidin (asterisk indicates 2× more loading to gel relative to other lanes).

FIG. 1B. tRNA mediated labeling, isolation by photocleavable antibodies and photo-release into solution of cell-free expressed proteins. Lane 1 is the initial unbound fraction corresponding to nascent GST not binding the photocleavable antibody beads (wash factions were also collected and analyzed but contained negligible quantities). Lane 2 is the negative control elution in the absence of the proper light. Lane 3 is the photo-released fraction following illumination with the proper light. Lane 4 is the fraction remaining bound to the beads that was subsequently released by denaturation of the antibody (asterisk indicates 2× more loading to gel relative to other lanes).

FIG. 2A. Purity of cell-free proteins following photo-isolation by incorporated PC-biotin. Fluorescence image of electrophoretic gel (pre-staining). Lane 1 is plain SDS-PAGE gel loading buffer as a negative control. Lane 2 is the plain buffer used in the isolation as a negative control. Lane 3 is a negative control corresponding to the photo-released fraction derived from a cell-free expression reaction where only the added DNA (GST gene in plasmid) was omitted. Lane 4 is the photo-released fraction derived from a cell-free expression reaction where the GST DNA was included.

FIG. 14. Contact photo-transfer of pre-formed protein-protein complexes from single 100 micron agarose beads by incorporated PC-biotin. Advanced 2 color fluorescence p53-MDM protein-protein interaction assay. Importantly, protein-protein complexes between MDM and p53 are formed prior to contact photo-transfer to activated microarray substrates. Both the "bait" proteins (MDM and GST) and the p53 probe were expressed in a cell-free reaction, each with appropriate tRNA mediated labels needed for the assay.

FIG. 18A. Preparation of photocleavable fluorescent Quantum Dot nanocrystals by conjugation to PC-biotin. Selective capture on 100 micron NeutrAvidin agarose beads. Shown here is the total Quantum Dot fluorescence of the NeutrAvidin agarose bead suspension prior to washing away any unbound Quantum Dots.

FIG. 22A. Verification of binding of biotin labeled PCR amplified DNA to streptavidin agarose beads as detected using the PicoGreen fluorescence staining reagent selective for double stranded DNA.

FIG. 22B. Cell-free protein synthesis from expression DNA bound to agarose beads and in situ capture of the nascent proteins by PC-antibody also immobilized on the same agarose beads. After expression, in situ protein capture and isolation, proteins were applied to a microarray substrate by contact photo-transfer and the internal tRNA mediated BODIPY-FL fluorescence labels were imaged.

Figure 25:
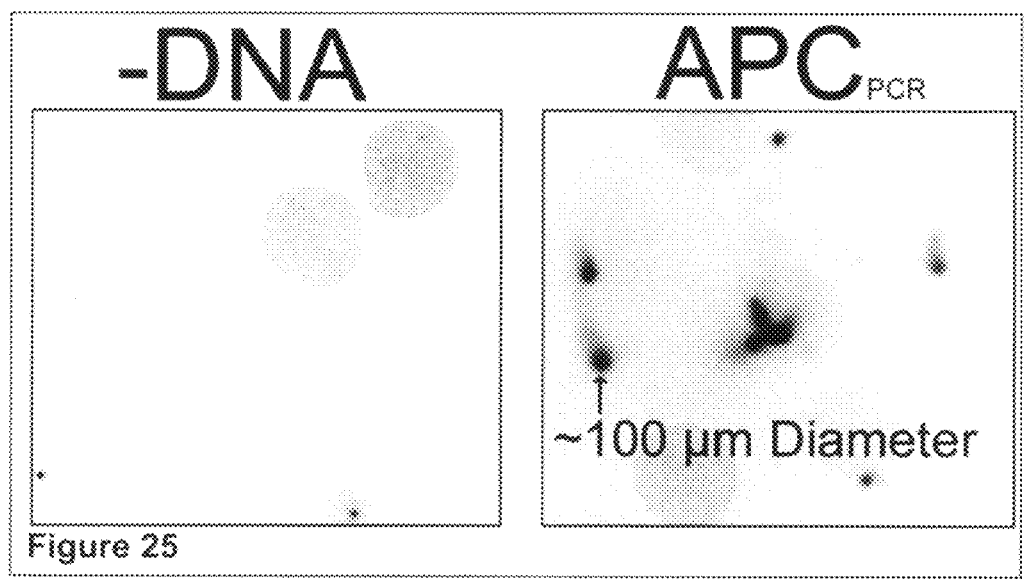

FIG. 25. Contact photo-transfer for molecular diagnostic assays. Cell-free expression from a PCR template of segment 3 of the APC gene amplified from human genomic DNA. Truncating mutations in APC are linked to the pathogenesis of colorectal cancer. Protein based cell-free expression assays can be performed with N- and C-terminal tags to detect the relative amount of truncated gene product for diagnostic purposes. Here, the tRNA mediated, BODIPY-FL internal labeling of cell-free expressed APC segment 3 protein is shown following contact photo-transfer from individually resolved beads. Bead-derived microarray features of about 100 microns in diameter are created. −DNA=the procedure performed where only the PCR derived expression DNA is omitted from the cell-free translation step. $APC_{PCR}$=the procedure performed where the PCR derived expression DNA for segment 3 of the human APC gene is included in the cell-free translation step.

Figure 26A:
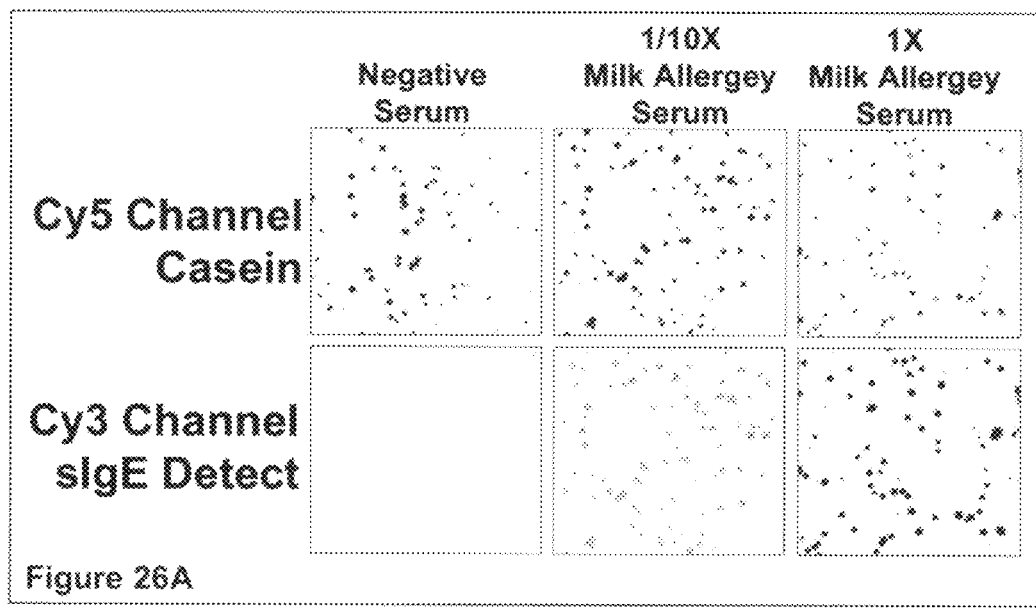

FIG. 26A. Contact photo-transfer based microarray assays for detection of allergen-specific IgE in human sera from allergy patients. The milk allergen casein was contact photo-transferred from beads to a microarray substrate and the allergen-specific IgE assay performed on the microarray substrate. "Negative Serum" corresponds to an assay of serum from a non-allergic patient while "Milk Allergy Serum" corresponds to an assay of serum from a patient with a verified casein-dependant milk allergy. Both undiluted ("1×") and 10-fold diluted ("1/10×") serum was tested. The "Negative Serum" was undiluted. The "Cy5 Channel" shows the fluorescence signal from the transferred casein itself, which contained a direct Cy5 label. The "Cy3 Channel" shows detection of allergen-specific IgE (sIgE) bound to the transferred casein from patient sera.

Figure 26B:
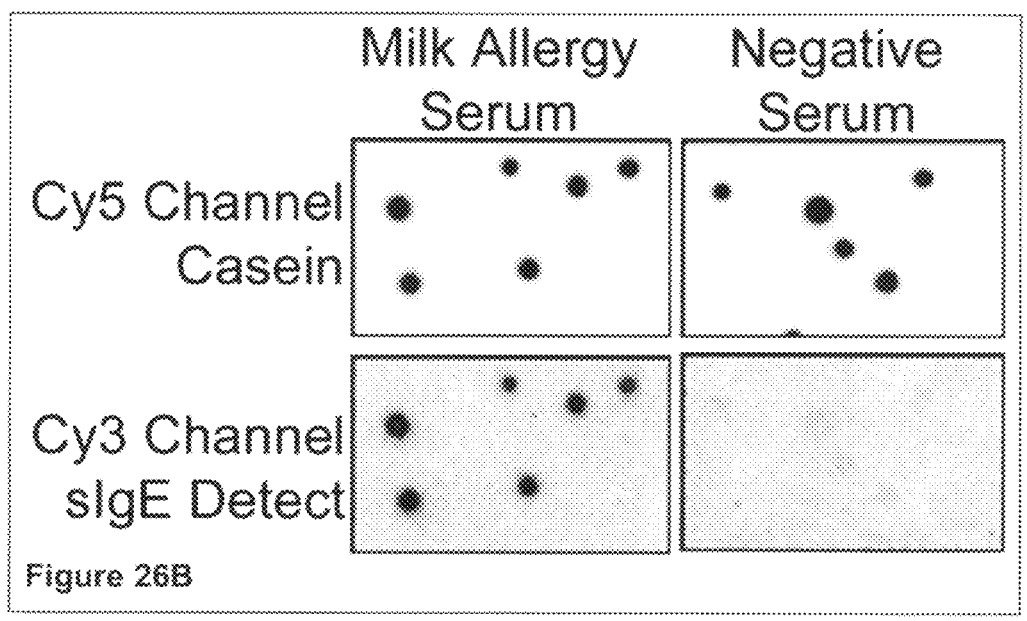

FIG. 26B. Contact photo-transfer based microarray assays for detection of allergen-specific IgE in human sera from allergy patients. The milk allergen casein was tethered to beads with a photocleavable linker and the allergen-specific IgE assay performed directly on the beads. The bound material on the beads was then contact photo-transferred to a microarray substrate for signal readout. "Negative Serum" corresponds to an assay of serum from a non-allergic patient while "Milk Allergy Serum" corresponds to an assay of serum from a patient with a verified casein-dependant milk allergy. The "Cy5 Channel" shows the fluorescence signal from the transferred casein itself, which contained a direct Cy5 label. The "Cy3 Channel" shows detection of allergen-specific IgE (sIgE) bound to the casein from patient sera.

FIG. 27A. Verification of binding of amine functionalized PCR primers to amine-reactive NHS ester activated agarose beads as detected using the OliGreen fluorescence staining reagent selective for single stranded DNA. The beads were prepared for the downstream purposes of solid-phase bridge PCR.

Figure 27B:
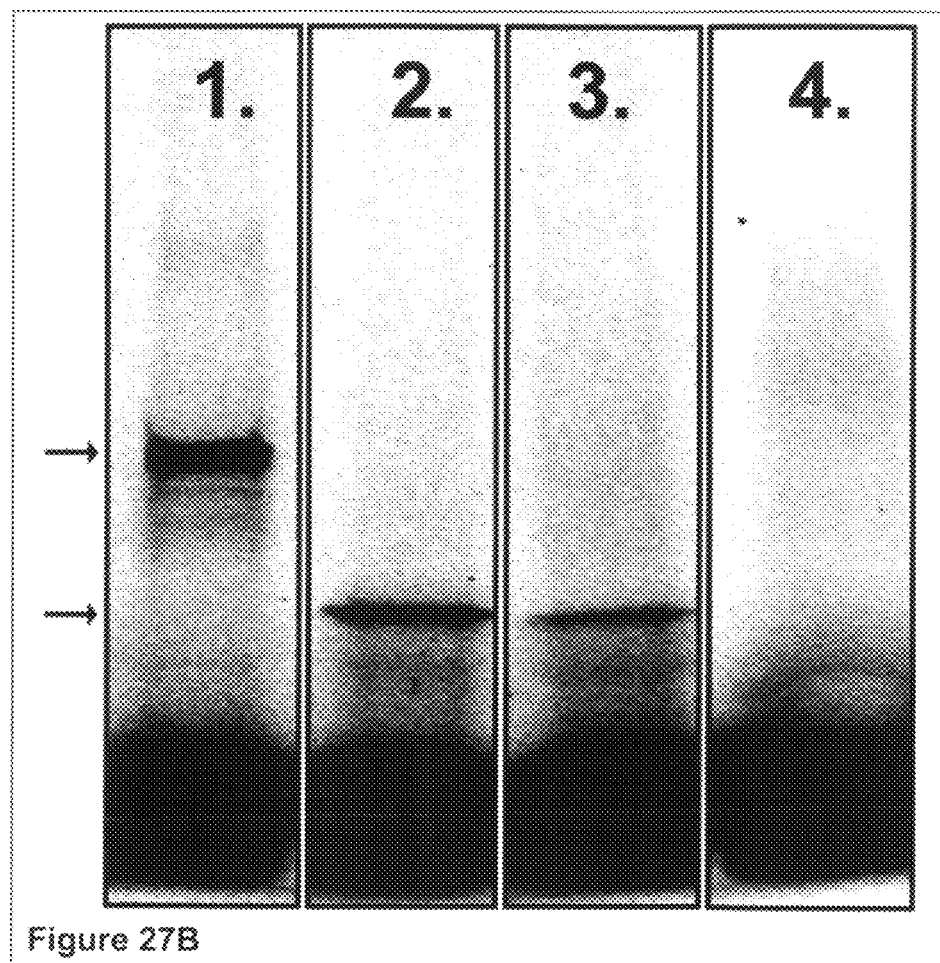

FIG. 27B. Cell-free expression of human glutathione-s-transferase A2 from bead-bound DNA which was created by primer-conjugated agarose beads used in a solid-phase bridge PCR reaction (Lane 3). Comparisons were made to beads lacking the bound solid-phase bridge PCR primers (Lane 4) and expression reactions of human p53 and human glutathione-s-transferase A2 using soluble plasmid DNA instead of bead-bound DNA (Lanes 1 and 2 respectively). Arrows indicate the positions of the fluorescently labeled expressed target protein bands on the SDS-PAGE gel.

FIG. 28. Cell-free protein synthesis from immobilized DNA created by solid-phase bridge PCR on agarose beads and in situ capture of the nascent proteins by PC-antibody also immobilized on the same agarose beads. A mixed population of beads coated with primer sets to either γ-actin or p53 were used in a single-tube, multiplex, solid-phase bridge PCR reaction with a HeLa cell cDNA library as template. The resultant beads, now encoded with either γ-actin DNA or p53 DNA were loaded with PC-antibody and co-expressed in a single multiplex cell-free reaction. After expression, in situ protein capture and isolation, proteins were then applied to a microarray substrate by contact photo-transfer. The microarray substrate was further probed with a Cy5 labeled anti-p53 specific antibody. The internal tRNA mediated BODIPY-FL fluorescence labels (Green Fluorescence Channel) as well as binding of the Cy5 labeled p53 antibody (Red Fluorescence Channel) were imaged. The figure shows the identical region of the microarray substrate in the 2 different fluorescence channels. Arrows denote the p53 spots.

Figure 29:
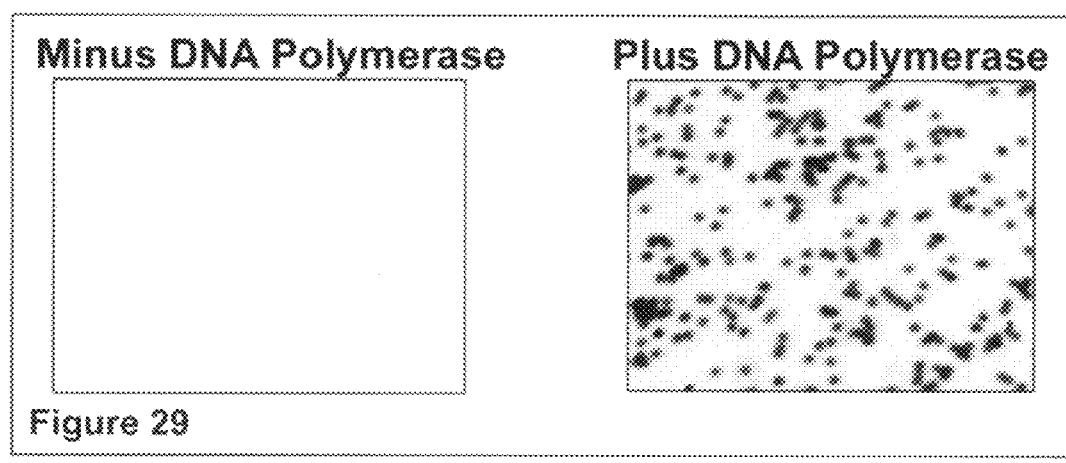

FIG. 29. Solid-phase bridge PCR on 7 micron diameter biotin-BSA and primer coated beads with on-bead detection of the solid-phase bridge PCR amplicon using BODIPY-FL-dUTP labeling. Solid-phase bridge PCR reactions were performed either minus or plus the needed DNA polymerase. The minus DNA polymerase solid-phase bridge PCR reaction provides the background levels related to bead autofluorescence and the BODIPY-FL-dUTP labeling reagent.

FIG. 30. 7 micron diameter plastic beads: solid-phase bridge PCR, cell-free protein expression, in situ protein capture, antibody probing and isolation of the antibody targeted bead sub-population. Solid-phase bridge PCR beads carrying amplified and expressible DNA for the p53 and GST genes were separately cell-free expressed, with in situ protein capture onto the same beads, using a bead-bound rabbit anti-HSV antibody against a common epitope tag in both proteins. Beads were then mixed at 1% p53 beads and 99% GST beads followed by probing the mixed beads with a mouse monoclonal anti-p53 antibody. The p53 bead sub-population, targeted by the anti-p53 antibody, was then purified using 1 micron magnetic particles which were coated with an anti-[mouse IgG] species-specific secondary antibody (magnetic particles not visible in figure). The un-separated and purified beads were embedded in a polyacrylamide film on a microscope slide and the fluorescence bead labels then imaged. The same regions of the microscope slide were imaged in both the green fluorescence channel (GST beads) and red fluorescence channel (p53 beads).

Figure 31A:
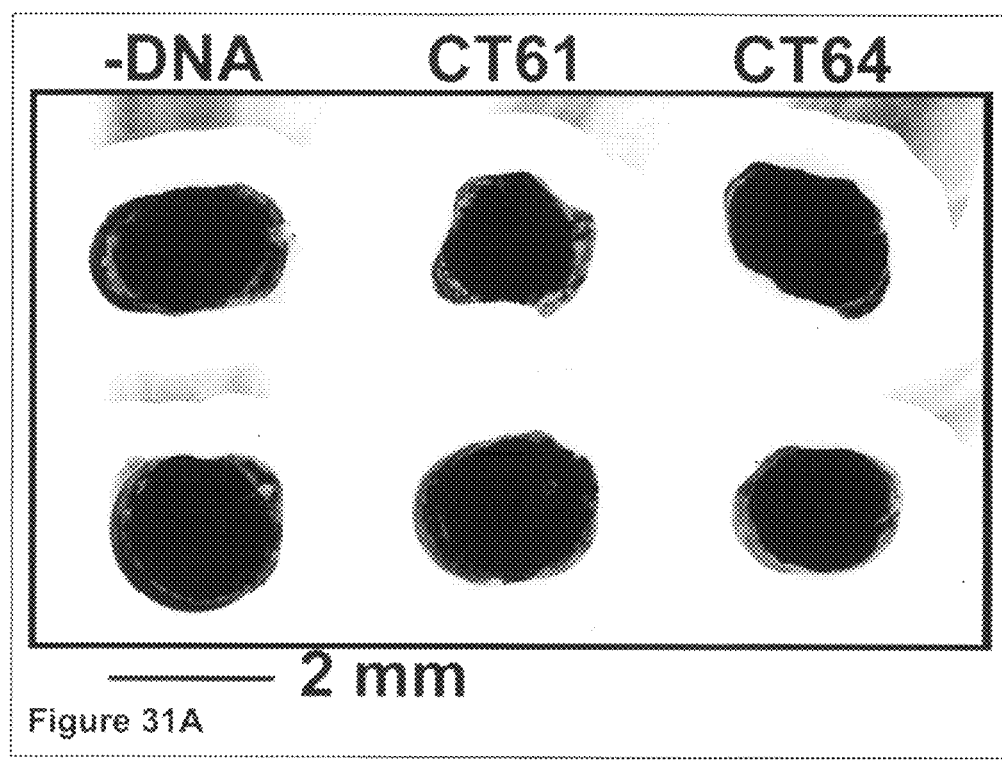

FIG. 31A. Contact photo-transfer of cell-free expressed peptides onto glass microarray slides followed by mass spectrometry analysis (MALDI-TOF). FLAG epitope tagged CT61 and CT64 test peptides were cell-free expressed and isolated on beads that carry a photocleavably linked and fluorescently labeled anti-FLAG antibody. The beads were then used to contact photo-transfer the peptide-antibody complexes to an epoxy activated-microarray slide. The microarray slide was first imaged fluorescently. The minus DNA (−DNA) negative control corresponds to a parallel sample differing only by omission of the expression DNA from the cell-free reaction.

Figure 31B:
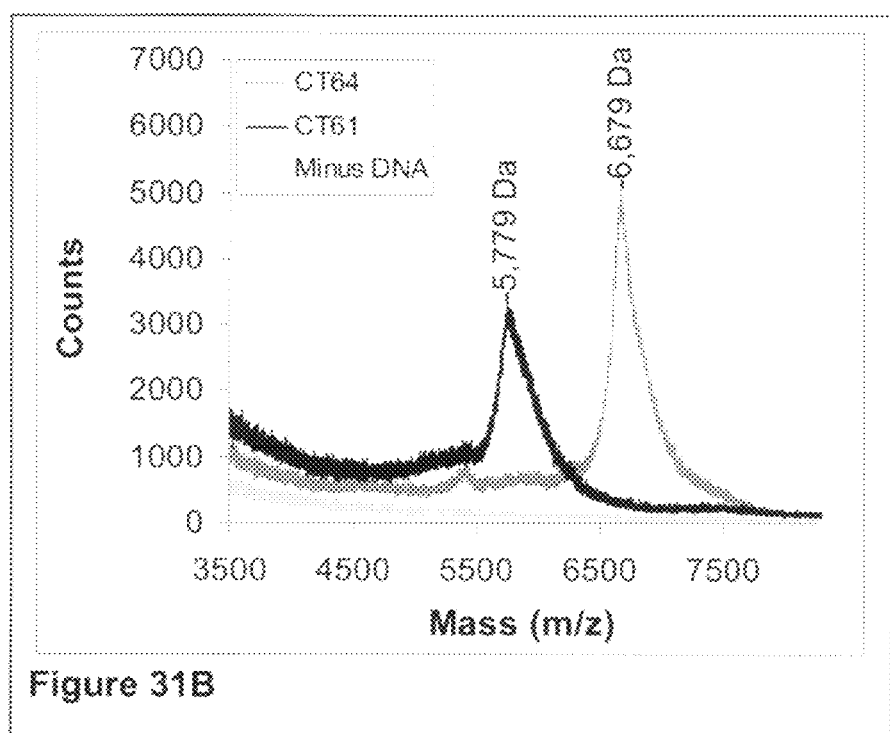

FIG. 31B. Contact photo-transfer of cell-free expressed peptides onto glass microarray slides followed by mass spectrometry analysis (MALDI-TOF). FLAG epitope tagged CT61 and CT64 test peptides were cell-free expressed and isolated on beads that carry a photocleavably linked and fluorescently labeled anti-FLAG antibody. The beads were then used to contact photo-transfer the peptide-antibody complexes to an epoxy activated microarray slide. After fluorescence imaging (see FIG. 31A), the microarray slide was then subjected to MALDI-TOF mass spectrometric analyses. The minus DNA (−DNA) negative control corresponds to a parallel sample differing only by omission of the expression DNA from the cell-free reaction. The black spectrum is CT61, the dark gray spectrum CT64 and the light gray is the minus DNA (−DNA).

Figure 32A:
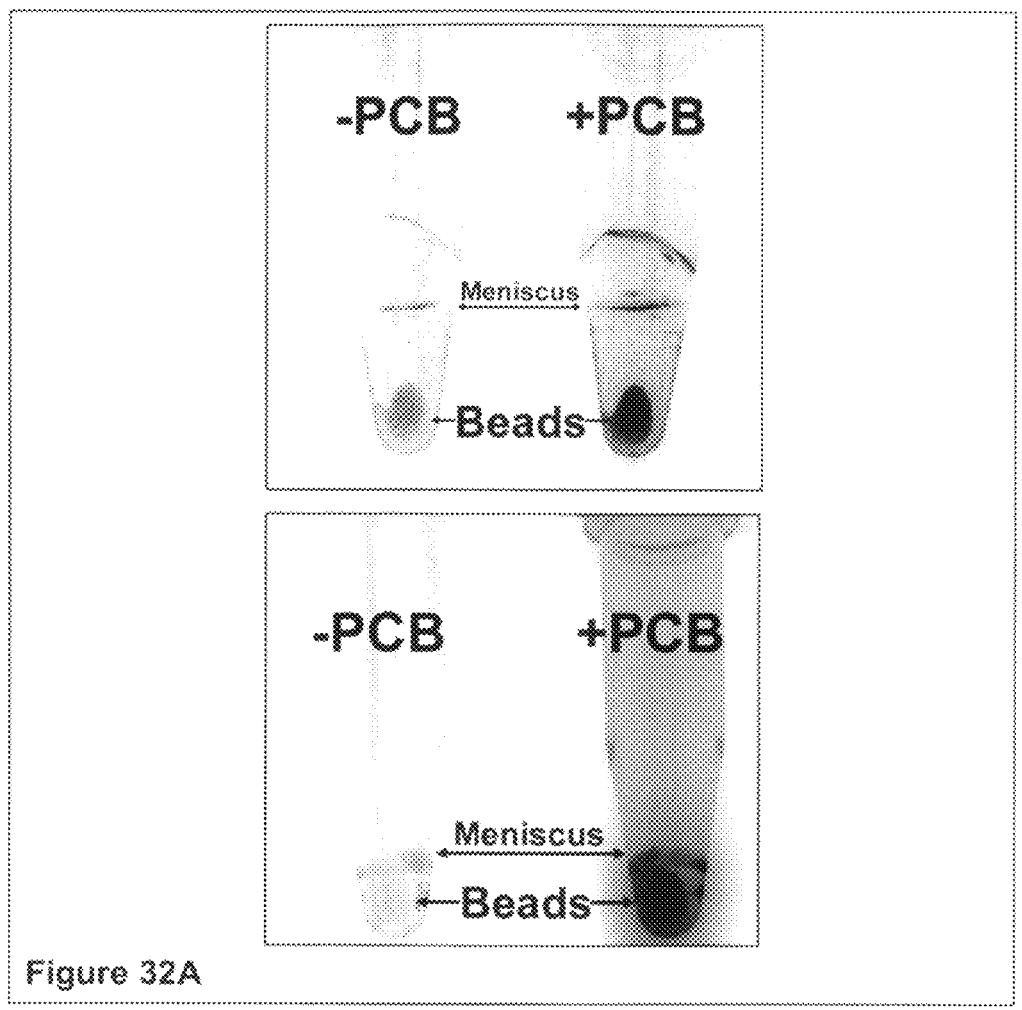

FIG. 32A. Contact photo-transfer of DNA from beads to an activated microarray slide. DNA was either labeled with PC-biotin (+PCB) or left unlabeled (—PCB). NeutrAvidin agarose beads were then used to capture the DNA. The beads were subsequently used for contact photo-transfer (see FIG. 32B). Prior to contact photo-transfer, DNA binding to the beads was first verified using either the ssDNA fluorescence stain Oli-Green (upper panels) or a Cy5 fluorescence labeled complementary oligonucleotide probe (lower panels). The bead pellets (Beads) were imaged directly in 0.5 mL micro-centrifuge tubes.

Figure 32B:
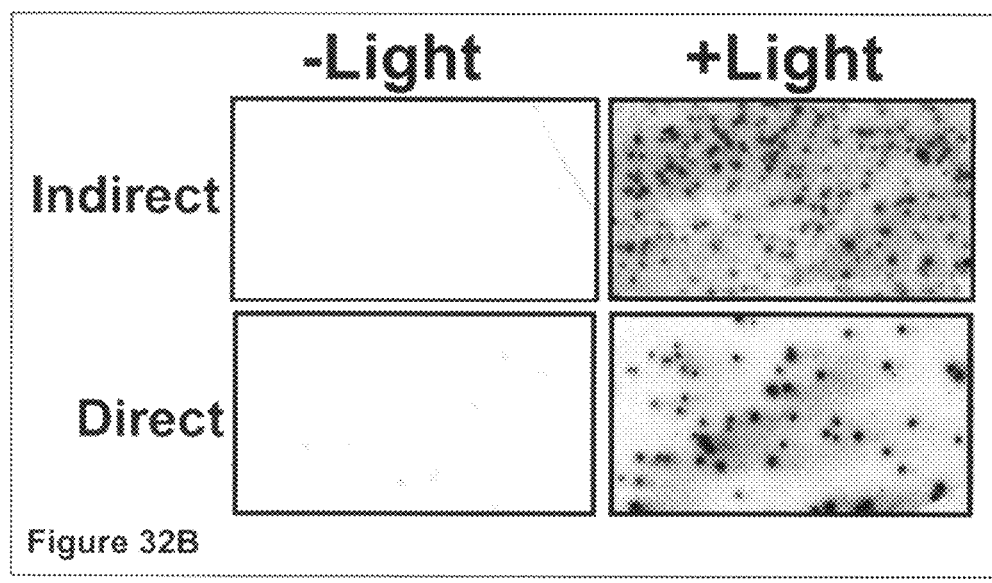

FIG. 32B. Contact photo-transfer of DNA from beads to an activated microarray slide. DNA was labeled with PC-biotin and NeutrAvidin agarose beads were then used to capture the DNA. The beads were subsequently used for contact photo-transfer. Beads loaded with the PC-biotin labeled DNA, but not previously stained with OliGreen or a complementary oligonucleotide probe (as done in FIG. 32A), were used for contact photo-transfer. Contact photo-transfer was performed with (+Light) or without (−Light) the proper light illumination. After contact photo-transfer onto epoxy activated microarray slides, the slides were probed with either a biotin labeled complementary oligonucleotide followed by a NeutrAvidin-Cy5 conjugate (upper panels) or a directly Cy5 labeled complementary oligonucleotide (lower panels).

Figure 33A:
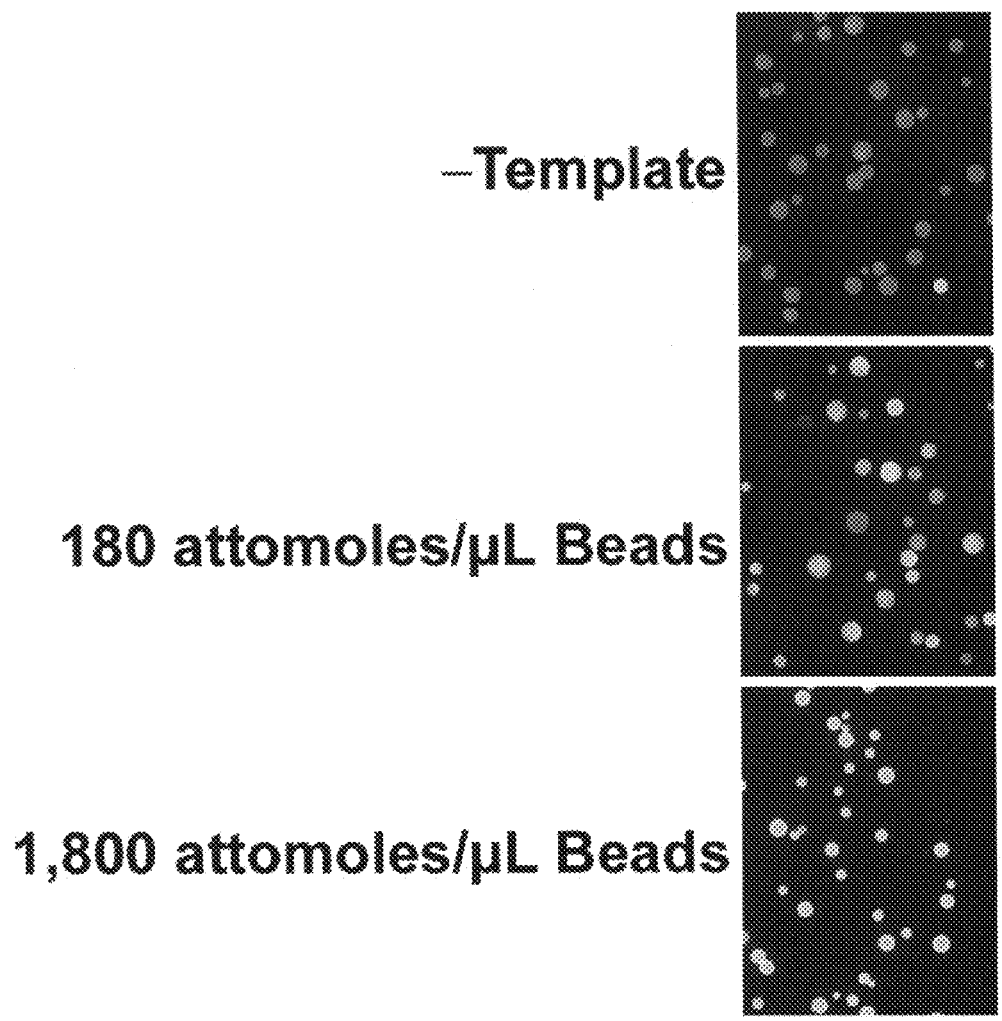

FIG. 33A. Effective single template molecule solid-phase bridge PCR: Amplicon detection through fluorescence dUTP labeling during the PCR reaction. Conditions were targeted to achieve solid-phase bridge PCR amplification of one or a few template DNA molecules per bead, on agarose beads that were covalently conjugated to both the forward and reverse PCR primers. The added template solution was a mixture of 50% human GST A2 (gene fragment) and 50% human p53 (gene fragment), with both gene fragments flanked by universal sequences to which the solid-phase primers were directed. Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Labeling of the PCR amplicon (product) on the beads was achieved by using BODIPY-FL conjugated fluorescent dUTP (green) in the PCR reaction mix. Following solid-phase bridge PCR, the beads were washed and then probed with a NeutrAvidin-Cy5 fluorescent conjugate (red), which binds to biotin labels which were uniformly covalently attached directly to the agarose bead surface during the earlier primer attachment procedure; thus detecting all beads regardless of the presence of PCR amplicon (red). The beads were washed again then embedded in a polyacrylamide film on a standard microscope slide for imaging in a fluorescence microarray reader. The images correspond to 2-color fluorescence image overlays (same image contrast settings) of the minus template (−Template) and plus template (180 and 1,800 attomoles of template per μL of agarose bead volume) solid-phase bridge PCR reaction samples. In the 2-color fluorescence image overlay, a yellow-orange color indicates the presence of both the green and red signals, however, at higher amplicon levels, the green signal masks the red in the overlaid images.

Figure 33B:
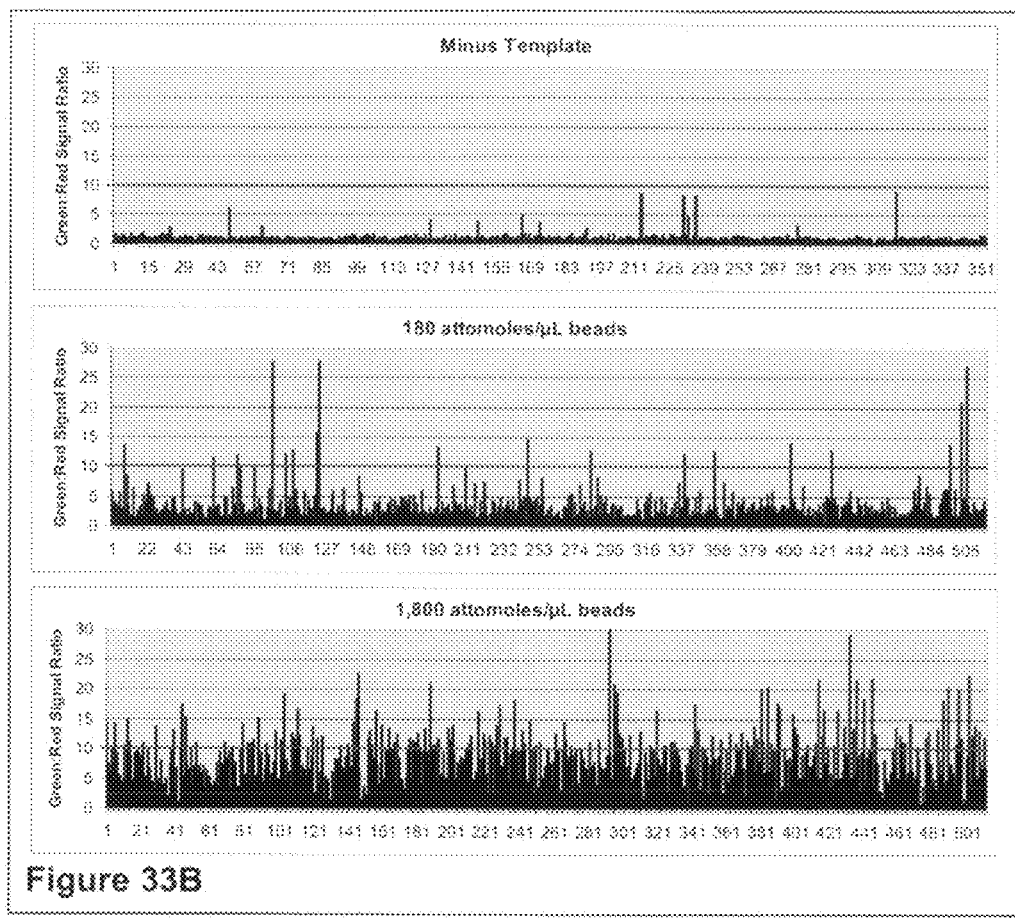

FIG. 33B. Effective single template molecule solid-phase bridge PCR: Amplicon detection through fluorescence dUTP labeling during the PCR reaction. Conditions were targeted to achieve solid-phase bridge PCR amplification of one or a few template DNA molecules per bead, on agarose beads that were covalently conjugated to both the forward and reverse PCR primers. The added template solution was a mixture of 50% human GST A2 (gene fragment) and 50% human p53 (gene fragment), with both gene fragments flanked by universal sequences to which the solid-phase primers were directed. Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Labeling of the PCR amplicon (product) on the beads was achieved by using BODIPY-FL conjugated fluorescent dUTP (green) in the PCR reaction mix. Following solid-phase bridge PCR, the beads were washed and then probed with a NeutrAvidin-Cy5 fluorescent conjugate (red), which binds to biotin labels which were uniformly covalently attached directly to the agarose bead surface during the earlier primer attachment procedure; thus detecting all beads regardless of the presence of PCR amplicon (red). The beads were washed again then embedded in a polyacrylamide film on a standard microscope slide for imaging in a fluorescence microarray reader. More than 350 beads per each sample permutation were quantified by computer-assisted image analysis and the green:red signal ratios were calculated and plotted. Permutations were the minus template (−Template) and plus template (180 and 1,800 attomoles of template per μL of agarose bead volume) solid-phase bridge PCR reaction samples. The Y-axis is the green:red signal ratio and the X-axis is the bead number. The red line indicates the cut-off, at or above which the beads are scored as "strong positives".

Figure 34A:
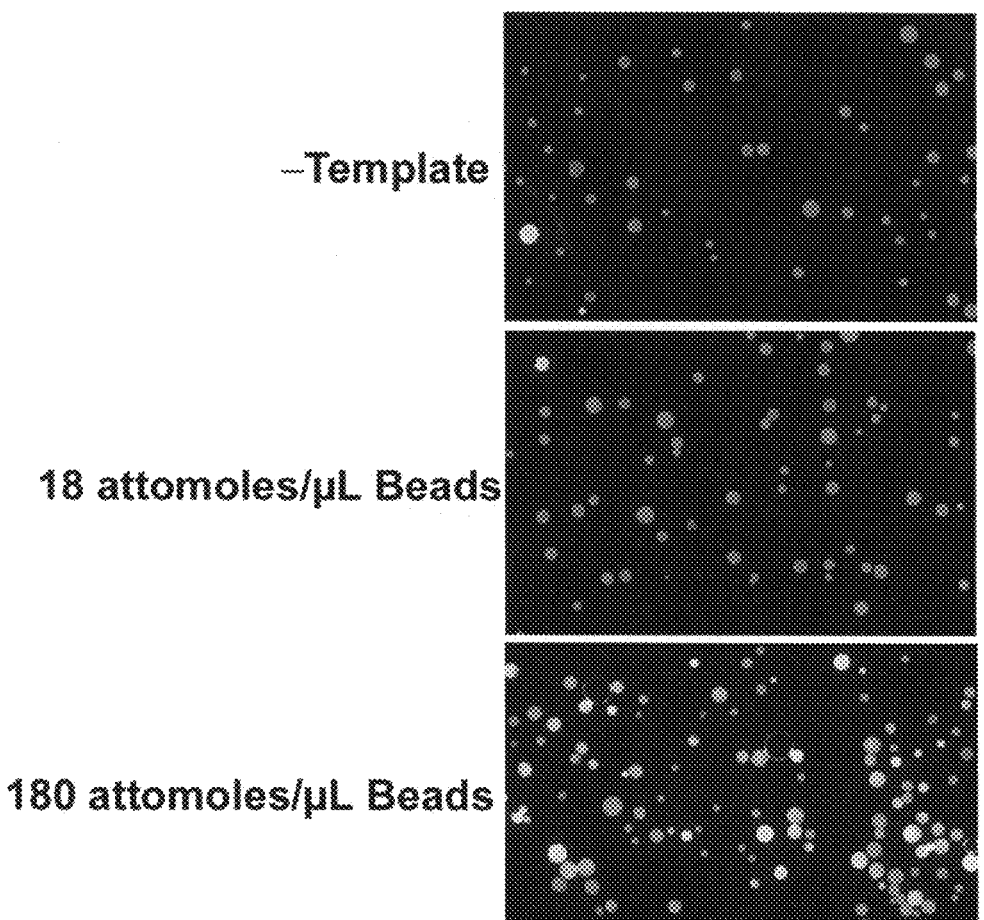

FIG. 34A. Effective single template molecule solid-phase bridge PCR: Amplicon detection through fluorescence dUTP labeling during the PCR reaction. Conditions were targeted to achieve solid-phase bridge PCR amplification of one or a few template DNA molecules per bead, on agarose beads that were covalently conjugated to both the forward and reverse PCR primers. The added template solution was a mixture of 75% human GST A2 (gene fragment) and 25% human p53 (gene fragment), with both gene fragments flanked by universal sequences to which the solid-phase primers were directed. Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Labeling of the PCR amplicon (product) on the beads was achieved by using BODIPY-FL conjugated fluorescent dUTP (green) in the PCR reaction mix. Following solid-phase bridge PCR, the beads were washed and then probed with a NeutrAvidin-Cy5 fluorescent conjugate (red), which binds to biotin labels which were uniformly covalently attached directly to the agarose bead surface during the earlier primer attachment procedure; thus detecting all beads regardless of the presence of PCR amplicon (red). The beads were washed again and embedded in a polyacrylamide film on a standard microscope slide for imaging in a fluorescence microarray reader. The images correspond to 2-color fluorescence image overlays (same image contrast settings) of the minus template (−Template) and plus template (18 and 180 attomoles of template per μL of agarose bead volume) solid-phase bridge PCR reaction samples. In the 2-color fluorescence image overlay, a yellow-orange color indicates the presence of both the green and red signals, however, at higher amplicon levels, the green signal masks the red in the overlaid images.

Figure 34B:
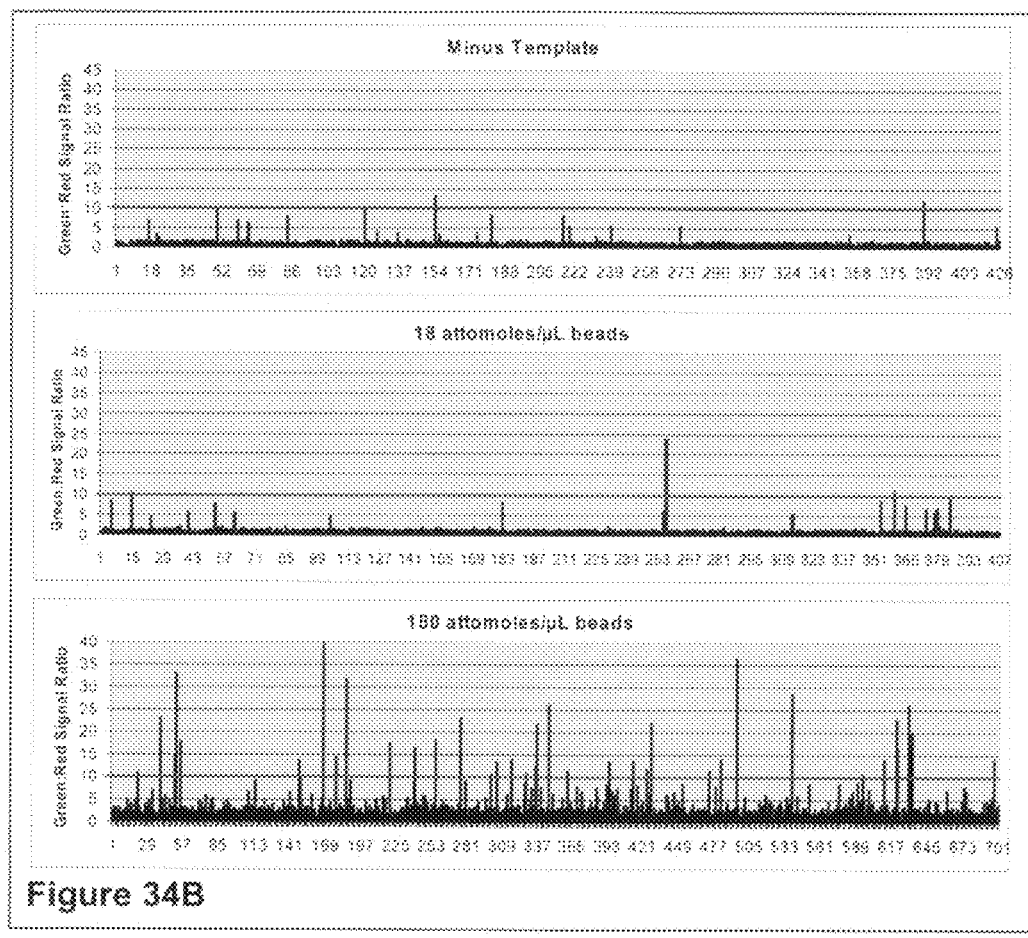

FIG. 34B. Effective single template molecule solid-phase bridge PCR: Amplicon detection through fluorescence dUTP labeling during the PCR reaction. Conditions were targeted to achieve solid-phase bridge PCR amplification of one or a few template DNA molecules per bead, on agarose beads that were covalently conjugated to both the forward and reverse PCR primers. The added template solution was a mixture of 75% human GST A2 (gene fragment) and 25% human p53 (gene fragment), with both gene fragments flanked by universal sequences to which the solid-phase primers were directed. Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Labeling of the PCR amplicon (product) on the beads was achieved by using BODIPY-FL conjugated fluorescent dUTP (green) in the PCR reaction mix. Following solid-phase bridge PCR, the beads were washed and then probed with a NeutrAvidin-Cy5 fluorescent conjugate (red), which binds to biotin labels which were uniformly covalently attached directly to the agarose bead surface during the earlier primer attachment procedure; thus detecting all beads regardless of the presence of PCR amplicon (red). The beads were washed again and embedded in a polyacrylamide film on a standard microscope slide for imaging in a fluorescence microarray reader. More than 350 beads per each sample permutation were quantified by computer-assisted image analysis and the green:red signal ratios were calculated and plotted. Permutations were the minus template (−Template) and plus template (18 and 180 attomoles of template per μL of agarose bead volume) samples. The Y-axis is the green:red signal ratio and the X-axis is the bead number. The red line indicates the cut-off, at or above which the beads are scored as "strong positives".

Figure 35:
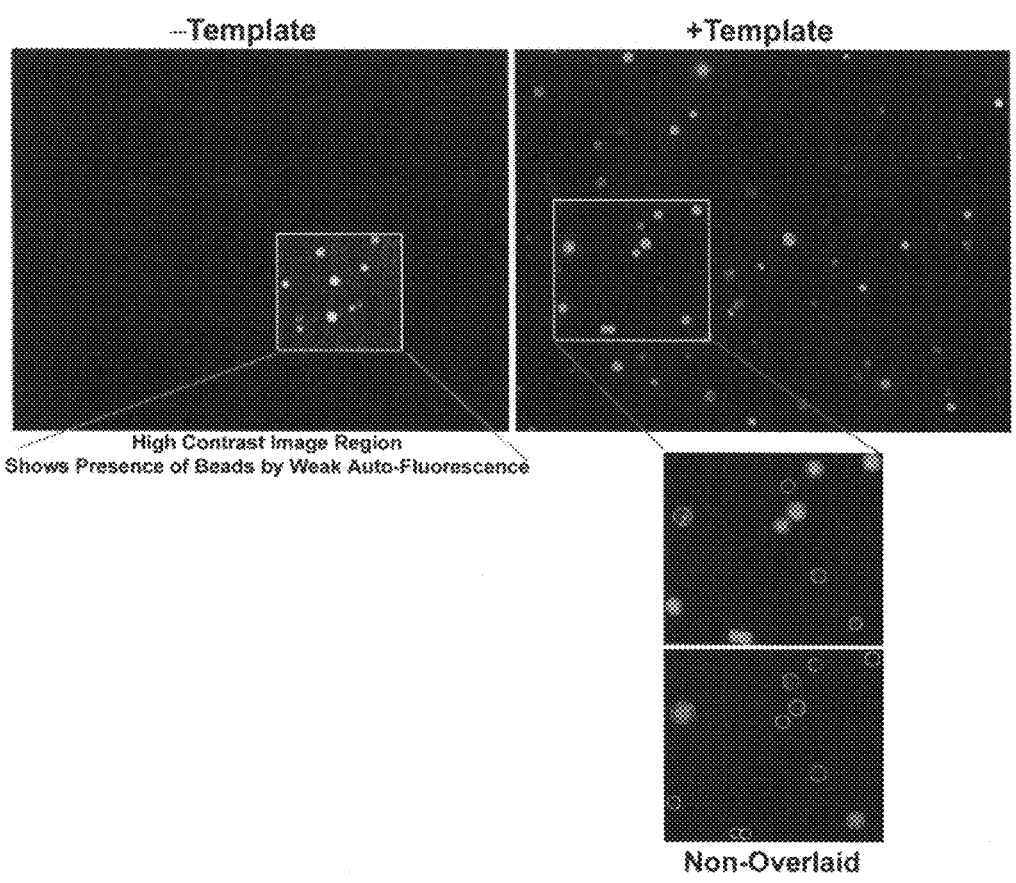

FIG. 35. Effective single template molecule solid-phase bridge PCR: Amplicon detection by dual oligonucleotide hybridization probing. Conditions were targeted to achieve solid-phase bridge PCR amplification of one or a few template DNA molecules per bead, on agarose beads that were covalently conjugated to both the forward and reverse PCR primers. The added template solution was a mixture of 75% human GST A2 (gene fragment) and 25% human p53 (gene fragment), with both gene fragments flanked by universal sequences to which the solid-phase primers were directed. Template was added at 180 attomoles per μL of agarose bead volume. Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Following solid-phase bridge PCR, the beads were simultaneously hybridization-probed with gene-specific complementary oligonucleotides that were fluorescently labeled. The beads were embedded in a polyacrylamide film on a standard microscope slide for imaging in a fluorescence microarray reader. The main left and right image panels correspond to 2-color fluorescence image overlays (same image contrast settings) of the minus template (−Template) and plus template (+Template) solid-phase bridge PCR reaction samples respectively, following hybridization-probing of the beads. Human GST A2 PCR product was detected on the beads via the Cy3 fluorophore (green) attached to the gene-specific hybridization probe and the human p53 PCR product via the Cy5 fluorophore (red) attached to the gene-specific hybridization probe. In the 2-color fluorescence image overlay, a yellow-orange color indicates the presence of both the green and red signals. The inset box in the main left panel (−Template) shows the presence of beads (present throughout entire main left panel), visible in this selected region only by their weak auto-fluorescence at extremely high image contrast settings. The inset box in the main right panel (+Template) shows the non-overlaid green and red fluorescence images of the selected boxed region (circular outlines denote the position of beads both visible and not visible in that particular fluorescence channel).

Figure 36A:
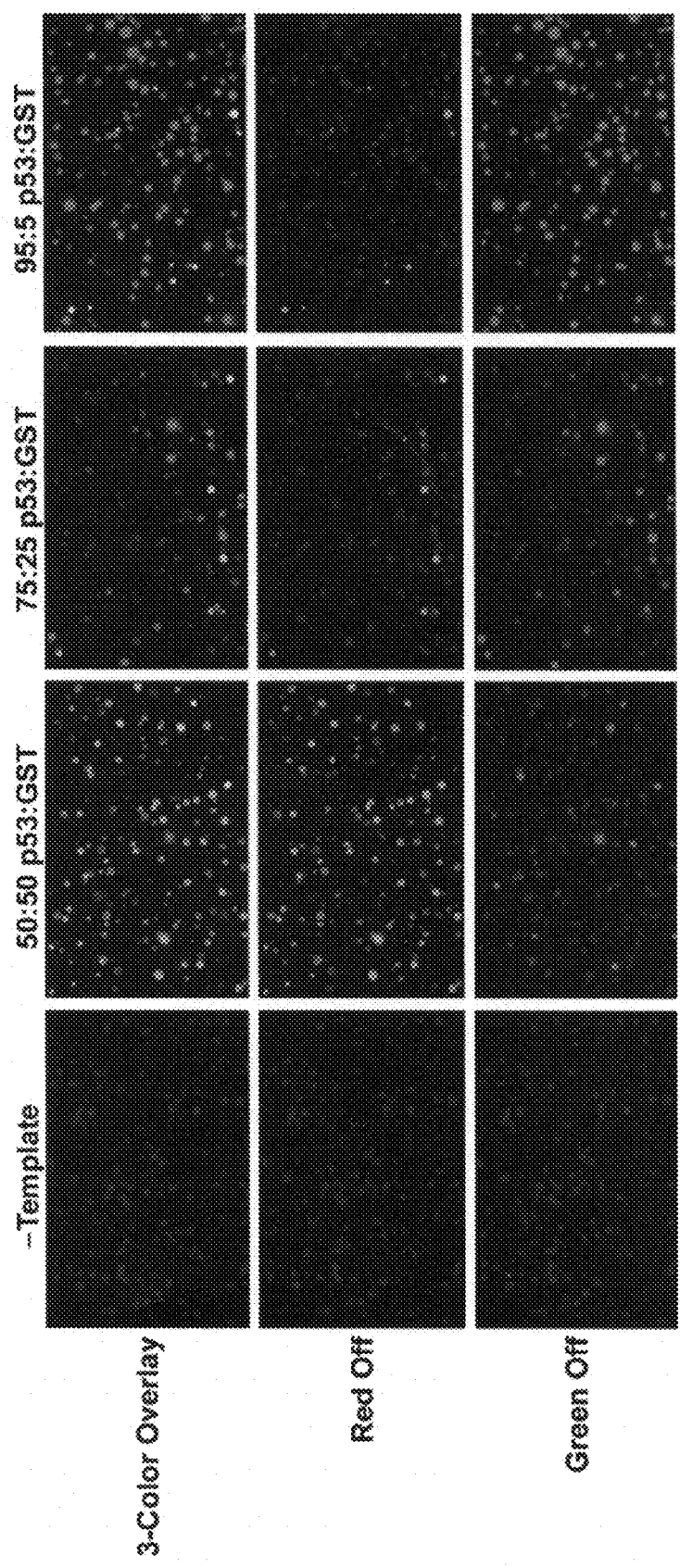

FIG. 36A. Effective single template molecule solid-phase bridge PCR: Titration of template ratios and amplicon detection by dual oligonucleotide hybridization probing. Conditions were targeted to achieve solid-phase bridge PCR amplification of only one or a few template DNA molecules per bead, on agarose beads that were covalently conjugated to both the forward and reverse PCR primers. The added template solution was a mixture of human p53 (gene fragment) and human GST A2 (gene fragment), with both gene fragments flanked by universal sequences to which the solid-phase primers were directed. Ratios of human p53 to human GST A2 within the added template solution were 50:50, 75:25 and 95:5. Template was added at 180 attomoles per μL of agarose bead volume or template DNA was omitted from the solid-phase bridge PCR reaction as a negative control (−Template). Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Following solid-phase bridge PCR, the beads were simultaneously hybridization-probed with gene-specific complementary oligonucleotides that were fluorescently labeled. The beads were embedded in a polyacrylamide film on a standard microscope slide for imaging in a fluorescence microarray reader. The upper row of image panels correspond to 3-color fluorescence image overlays. Human p53 PCR product was detected on the beads via the Cy5 fluorophore (red) attached to the gene-specific hybridization probe and the human GST A2 PCR product via the Cy3 fluorophore (green) attached to the gene-specific hybridization probe. The blue signal is a total bead fluorescence stain that is independent of the presence or absence of PCR product, thereby allowing detection of all beads. In the 3-color fluorescence image overlay, a yellow-orange color indicates the presence of both the green and red signals. The lower 2 rows of image panels are 2-color fluorescence image overlays, with either the red (human p53) or green (human GST A2) fluorescence images turned off (i.e. omitted from image overlay).

Figure 36B:
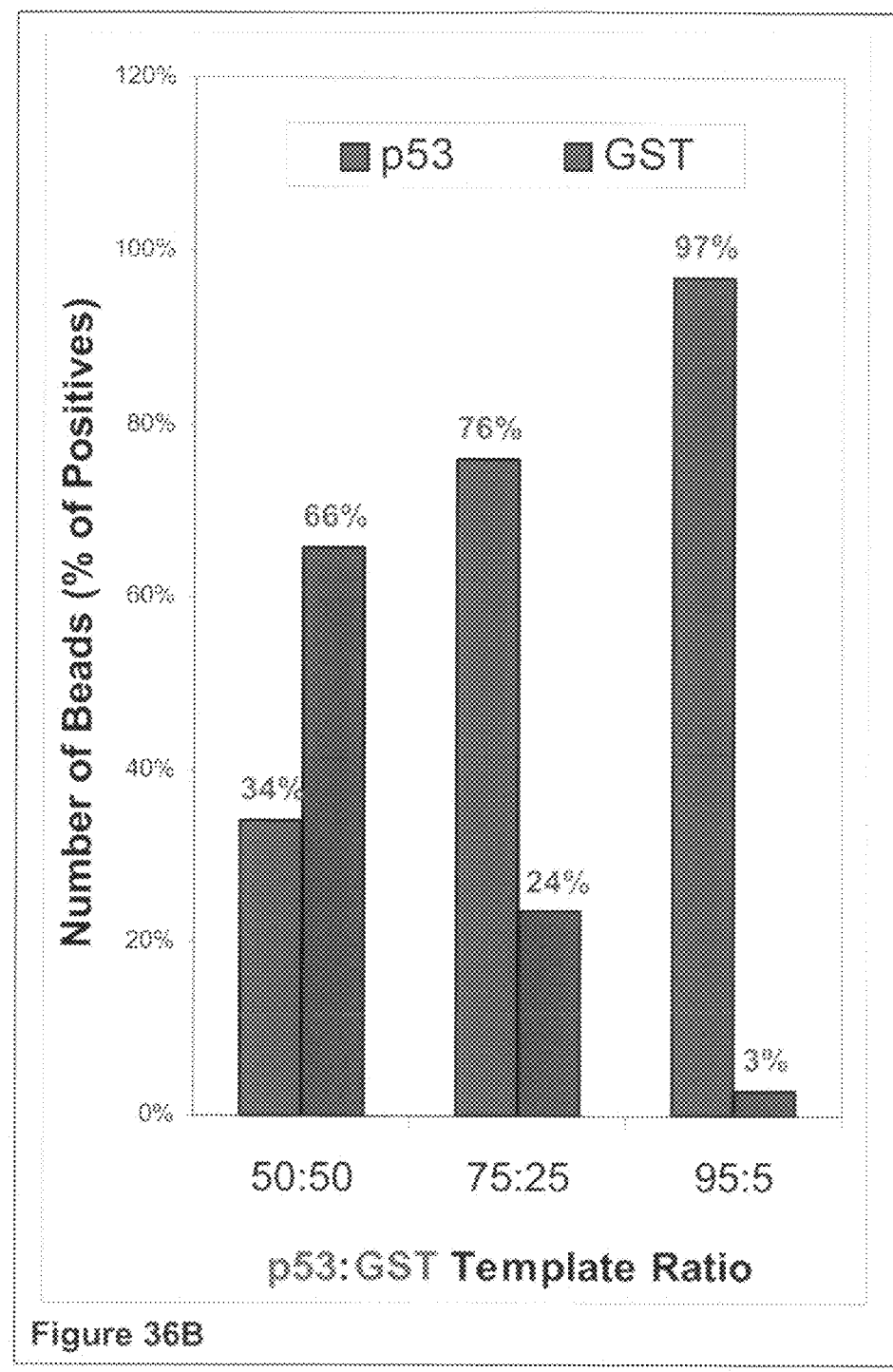

FIG. 36B. Effective single template molecule solid-phase bridge PCR: Titration of template ratios and amplicon detection by dual oligonucleotide hybridization probing. Conditions were targeted to achieve solid-phase bridge PCR amplification of only one or a few template DNA molecules per bead, on agarose beads that were covalently conjugated to both the forward and reverse PCR primers. The added template solution was a mixture of human p53 (gene fragment) and human GST A2 (gene fragment), with both gene fragments flanked by universal sequences to which the solid-phase primers were directed. Ratios of human p53 to human GST A2 within the added template solution were 50:50, 75:25 and 95:5. Template was added at 180 attomoles per μL of agarose bead volume or template DNA was omitted from the solid-phase bridge PCR reaction as a negative control (−Template). Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Following solid-phase bridge PCR, the beads were simultaneously hybridization-probed with gene-specific complementary oligonucleotides that were fluorescently labeled. The beads were embedded in a polyacrylamide film on a standard microscope slide for imaging in a fluorescence microarray reader. Beads were quantified and scored. Beads were scored positive if the signal to noise ratio was 0:1. For each sample permutation, the p53 and GST A2 positive scores are plotted as a percentage of the total positive scores.

FIG. 37. Effective single template molecule solid-phase bridge PCR: Multiplexed cell-free expression with in situ protein capture, contact photo-transfer of the expressed protein and antibody detection. Conditions were targeted to achieve solid-phase bridge PCR amplification of one or a few template DNA molecules per bead, on agarose beads that were covalently conjugated to both the forward and reverse PCR primers. The added template solution was a mixture of 75% human GST A2 (gene fragment) and 25% human p53 (gene fragment), with both gene fragments flanked by universal sequences to which the solid-phase primers were directed. Template was added at 180 attomoles per μL of agarose bead volume. Template DNAs also contained sequences necessary to support cell-free protein expression of the gene fragments in addition to common N- and C-terminal antibody epitope tags. Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Following solid-phase bridge PCR, the beads were uniformly coated with a photocleavable antibody against the common N-terminal FLAG epitope tag. The beads were then used in a multiplexed cell-free expression reaction with in situ protein capture, whereby expressed proteins are captured simultaneously onto their parent beads, as they are produced from the bead-bound solid-phase bridge PCR product. Contact photo-transfer was then performed from the beads and the resultant random microarray probed with fluorescent antibodies. The left and right image panels correspond to 2-color fluorescence image overlays (same image contrast settings) of the minus template (−Template) and plus template (+Template) solid-phase bridge PCR reaction samples respectively, following expression, contact phototransfer and fluorescence antibody probing. Although a representative region is shown, approximately 60-100 spots were analyzed in each of the 2 samples. The green signal is the detection of the photo-transferred FLAG antibody, and shows all spots, regardless of the presence of detectible expressed protein. The red signal shows detection of the common VSV epitope tag present at the C-terminal of both the human GST A2 and human p53 gene fragments. In the 2-color fluorescence image overlay, a yellow-orange color indicates the presence of both the green and red signals.

Figure 38:
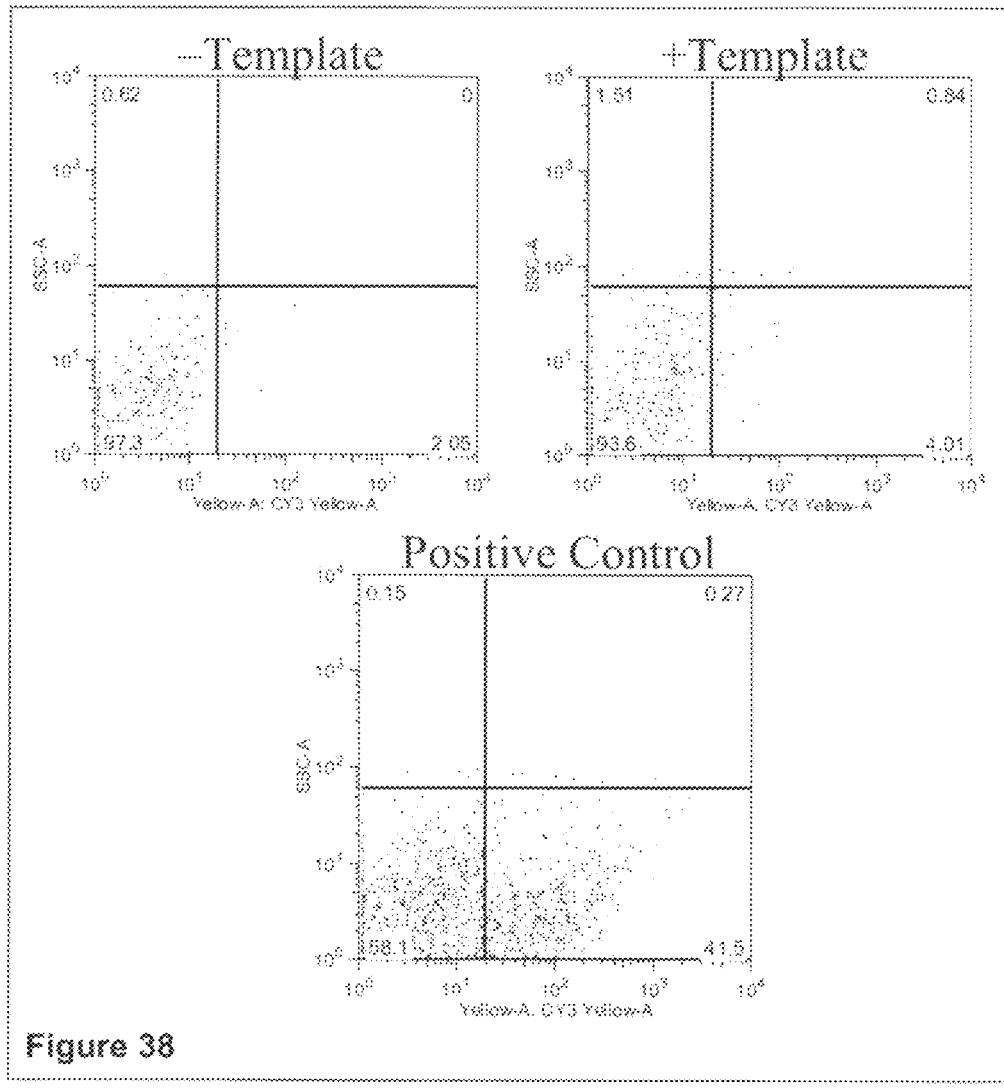

FIG. 38. Effective single template molecule solid-phase bridge PCR: Multiplexed cell-free expression with in situ protein capture, on-bead antibody detection and flow cytometry. Conditions were targeted to achieve solid-phase bridge PCR amplification of one or a few template DNA molecules per bead, on agarose beads that were covalently conjugated to both the forward and reverse PCR primers. The added template solution was a mixture of 75% human GST A2 (gene fragment) and 25% human p53 (gene fragment), with both gene fragments flanked by universal sequences to which the solid-phase primers were directed. Template was added at 180 attomoles per μL of agarose bead volume. Template DNAs also contained sequences necessary to support cell-free protein expression of the gene fragments in addition to common N- and C-terminal antibody epitope tags. Following template capture (annealing) and extending the primers only once in the presence of DNA polymerase, any free or hybridized template DNA was washed from the beads in 0.1 N NaOH, leaving only covalently attached unused and extended primers. The beads were then subjected to full PCR thermocycling in a high-fidelity PCR reaction mixture, to facilitate solid-phase bridge PCR amplification. Following solid-phase bridge PCR, the beads were uniformly coated with a photocleavable antibody against the common N-terminal FLAG epitope tag. The beads were then used in a multiplexed cell-free expression reaction with in situ protein capture, whereby expressed proteins are captured simultaneously onto their parent beads, as they are produced from the bead-bound solid-phase bridge PCR product. The beads were then probed with a Cy3 labeled antibody against the common VSV epitope tag present at the C-terminal of both the human GST A2 and human p53 gene fragments. The beads were then analyzed by flow cytometry. The upper left and upper right image panels correspond to the minus template (−Template) and plus template (+Template) solid-phase bridge PCR reaction samples respectively, following expression, fluorescence antibody probing and flow cytometry analysis. "Positive Control" refers to a sample which did not involve solid-phase bridge PCR, but instead expression was from soluble PCR derived DNA with protein capture onto FLAG antibody coated agarose beads as with the other samples. The Y-axis corresponds to the side-scatter (bead detection regardless of fluorescence signal) and the X-axis the fluorescence signal intensity from the Cy3 labeled VSV antibody probe. The values denoted in the lower corners of each quadrant indicate the percent of beads falling within that quadrant.

FIG. 39A. Microarray protein truncation test on the APC gene associated with colorectal cancer: Contact photo-transfer and fluorescence antibody detection. A segment of the human APC gene was amplified by standard solution-phase PCR on cell-line genomic DNA, using gene-specific PCR primers. Non-native DNA sequences necessary for cell-free protein expression and epitope tag detection were also incorporated (added) via the PCR primers, by way of the non-hybridizing portions of the primers. The DNA was then cell-free expressed in a coupled transcription/translation rabbit reticulocyte system. Following expression, proteins were captured on agarose beads coated with a photocleavable antibody against the common N-terminal HSV binding epitope tag. Beads were then used for contact photo-transfer and the resultant random microarray probed simultaneously with fluorescently labeled antibodies against the N- and C-terminal detection epitope tags. The images above are 2-color fluorescence overlays, whereby the green corresponds to the N-terminal detection epitope tag probed with an anti-VSV antibody labeled with the Cy3 fluorophore and the red corresponds to the C-terminal detection epitope tag probed with an anti-p53 antibody labeled with the Cy5 fluorophore. In the 2-color fluorescence image overlay, a yellow-orange color indicates the presence of both the green and red signals. "APC WT" refers to a 100% wild-type sample derived from cell-line DNA lacking any mutations in the APC gene segment. "APC Mutant" refers to a 100% mutant sample derived from cell-line DNA containing a truncation mutation within the APC gene segment tested (i.e. nonsense mutation to stop codon). "−DNA" refers to a negative control, identical to the other samples except that only the DNA was omitted from the cell-free expression reaction.

Figure 39B:
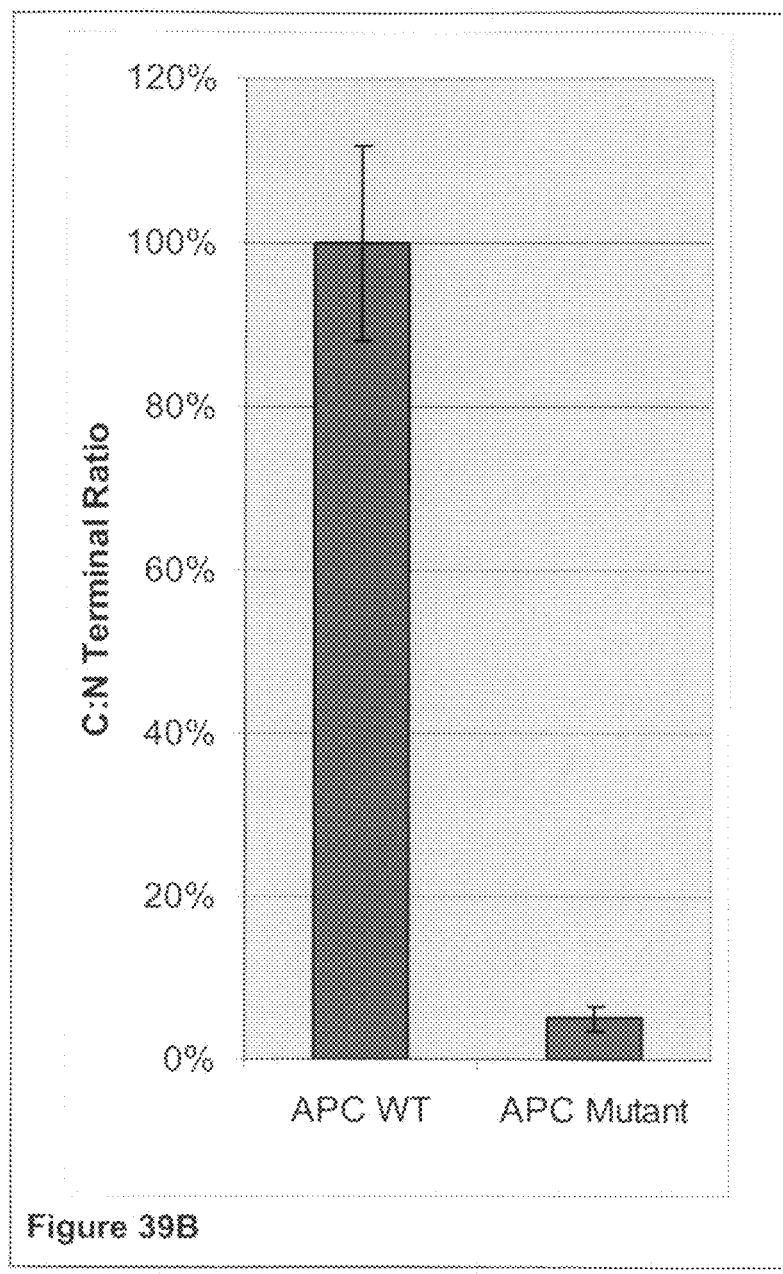

FIG. 39B. Microarray protein truncation test on the APC gene associated with colorectal cancer: Contact photo-transfer and fluorescence antibody detection. A segment of the human APC gene was amplified by standard solution-phase PCR on cell-line genomic DNA, using gene-specific PCR primers. Non-native DNA sequences necessary for cell-free protein expression and epitope tag detection were also incorporated (added) via the PCR primers, by way of the non-hybridizing portions of the primers. The DNA was then cell-free expressed in a coupled transcription/translation rabbit reticulocyte system. Following expression, proteins were captured on agarose beads coated with a photocleavable antibody against the common N-terminal HSV binding epitope tag. Beads were then used for contact photo-transfer and the resultant random microarray probed simultaneously with fluorescently labeled antibodies against the N- and C-terminal detection epitope tags. Each spot was quantified and the C-terminal to N-terminal ratio (C:N Ratio) calculated. "APC WT" refers to a 100% wild-type sample derived from cell-line DNA lacking any mutations in the APC gene segment. "APC Mutant" refers to a 100% mutant sample derived from cell-line DNA containing a truncation mutation within the APC gene segment tested (i.e. nonsense mutation to stop codon). "−DNA" refers to a negative control, identical to the other samples except that only the DNA was omitted from the cell-free expression reaction. All spots were averaged for each sample permutation (n>300), the data were normalized to set the C:N ratio of the APC WT to 100% and the data then plotted. In the bar graph, the error bars represent the standard deviation.

Figure 40:
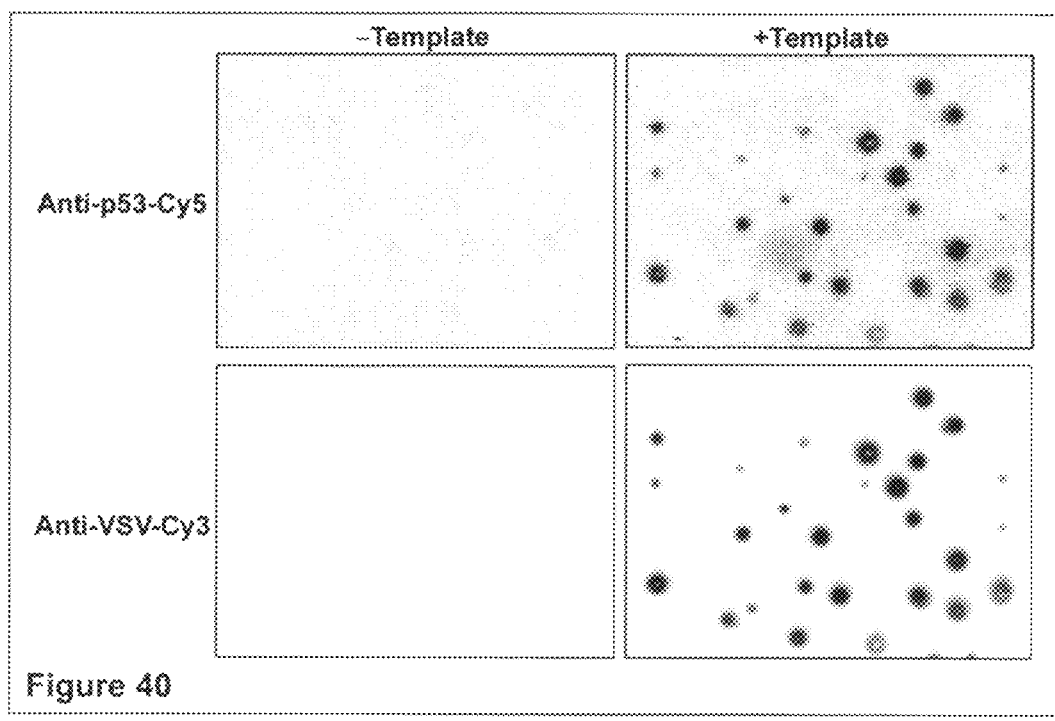

FIG. 40. Solid-phase bridge PCR on the APC gene associated with colorectal cancer: Cell-free protein expression, contact photo-transfer and fluorescence antibody detection. The solid-phase bridge PCR template DNA was first prepared by amplifying a segment of the human APC gene using standard solution-phase PCR on cell-line genomic DNA, with gene-specific PCR primers. These PCR primers also serve to introduce (add) a portion of the non-native DNA sequences needed for cell-free protein expression and epitope tag detection, via the non-hybridizing portion of the primers. Next, a universal forward and reverse PCR primer set, directed against these added non-native sequences, was covalently conjugated to agarose beads and used for solid-phase bridge PCR amplification of the aforementioned template DNA. The solid-phase universal primers also serve to introduce (add) the remaining portion of non-native DNA sequences necessary for cell-free expression and epitope tag detection. For the solid-phase bridge PCR, the template DNA was captured (annealed) onto the beads in non-limiting amounts, and was a mixture of 75% wild-type APC and 25% mutant APC, containing a truncation mutation within the APC gene segment tested (i.e. nonsense mutation to stop codon). Following solid-phase bridge PCR, the beads were uniformly coated with a photocleavable antibody against the common N-terminal HSV binding epitope tag. The beads were then used in a cell-free protein expression reaction, whereby proteins expressed from the bead-bound solid-phase bridge PCR product are then captured onto the beads via the photocleavable HSV antibody. Beads were then used for contact photo-transfer and the resultant random microarray probed simultaneously with fluorescently labeled antibodies against the N- and C-terminal detection epitope tags. "Anti-p53-Cy5" denotes results from the C-terminal detection epitope tag (p53) probed using a p53 antibody labeled with the Cy5 fluorophore. "Anti-VSV-Cy3" denotes results from the N-terminal detection epitope tag (VSV) probed using a VSV antibody labeled with the Cy3 fluorophore (same region of microarray). "+Template" refers to the test sample, where the appropriate template DNA was indeed added to the solid-phase bridge PCR reaction. "−Template" refers to a negative control, identical to the test sample except that only the template DNA was omitted from the solid-phase bridge PCR reaction.

FIG. 41. Effective single template molecule solid-phase bridge PCR on the APC gene associated with colorectal cancer: Validation of effective amplification of single template molecules per bead using 2 template species and a single-base extension reaction as the ultimate assay. The solid-phase bridge PCR template DNA was first prepared by amplifying a segment of the human APC gene using standard solution-phase PCR on cell-line genomic DNA, with gene-specific PCR primers. These PCR primers also serve to introduce (add) a portion of the non-native DNA sequences needed for cell-free protein expression and epitope tag detection, via the non-hybridizing portion of the primers. Next, a universal forward and reverse PCR primer set, directed against these added non-native sequences, was covalently conjugated to agarose beads and used for solid-phase bridge PCR amplification of the aforementioned template DNA. The solid-phase universal primers also serve to introduce (add) the remaining portion of non-native DNA sequences necessary for cell-free expression and epitope tag detection. For the solid-phase bridge PCR, the template DNA was initially added at a ratio of roughly 1 molecule per bead. The initially added template was a mixture of 50% wild-type APC and 50% mutant APC, containing a truncation mutation within the APC gene segment tested (i.e. nonsense mutation to stop codon). Following solid-phase bridge PCR, the beads were subjected to a fluorescence based single-base extension (SBE) reaction to distinguish the single-base change between wild-type and mutant APC amplicons on the beads. The top pair of image panels indicates the minus template sample permutation while the bottom pair of image panels the plus template sample. The top image in each pair corresponds to the fluorescein fluorescence channel and hence the binding of the fluorescein labeled SBE probe. The inset box shows the presence of beads in the minus template sample, visible only at extremely high image intensity settings via their extremely weak auto-fluorescence. The bottom image in each pair corresponds to a 2-color fluorescence image overlay of the Cy3 (wild-type extension product; green) and the Cy5 (mutant extension product; red) fluorescence channels. Arrows indicate selected beads for which the green:red signal ratios are shown.

Figure 42:
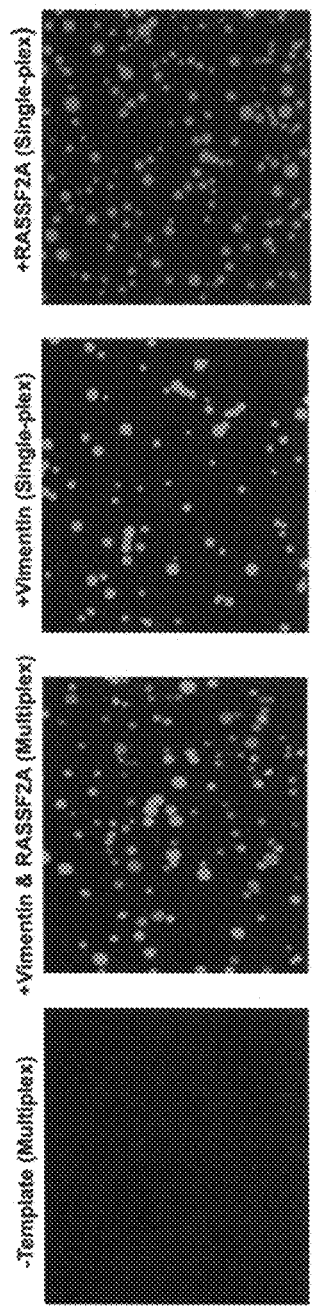

FIG. 42. Multiplexing methylation specific PCR (MSP) using solid-phase bridge PCR on beads: Application to the colorectal cancer associated markers vimentin and RASSF2A. As a model system, the solid-phase bridge PCR template DNA was first prepared by solution-phase MSP amplification of regions of bisulfite treated wild-type human genomic DNA corresponding to the vimentin and RASSF2A markers associated with colorectal cancer. Next, primers directed at the key bisulfite converted sequences (regions that are unmethylated at CpG islands in the wild-type and methylated in the disease state) were covalently conjugated to agarose beads and used for solid-phase bridge PCR amplification of the aforementioned template DNA. Two primer bead species, for vimentin and RASSF2A, were prepared separately. Following solid-phase bridge PCR amplification on the beads, the amplicon was detected on the beads by dual probing with fluorescently labeled complementary oligonucleotides. The vimentin probe was labeled with Cy3 (green) and the RASSF2A with Cy5 (red). Image panels marked "Multiplex" correspond to samples where both primer bead species were used in the solid-phase bridge PCR reaction at a 50:50 ratio. Image panels marked "Single-Plex" correspond to samples were only one bead species was used. "−Template" indicates that only the template DNA was omitted from the solid-phase bridge PCR reaction (negative control). When template was included, "Multiplex" samples received both templates while "Single-Plex" samples received only the corresponding template.

Figure 43:
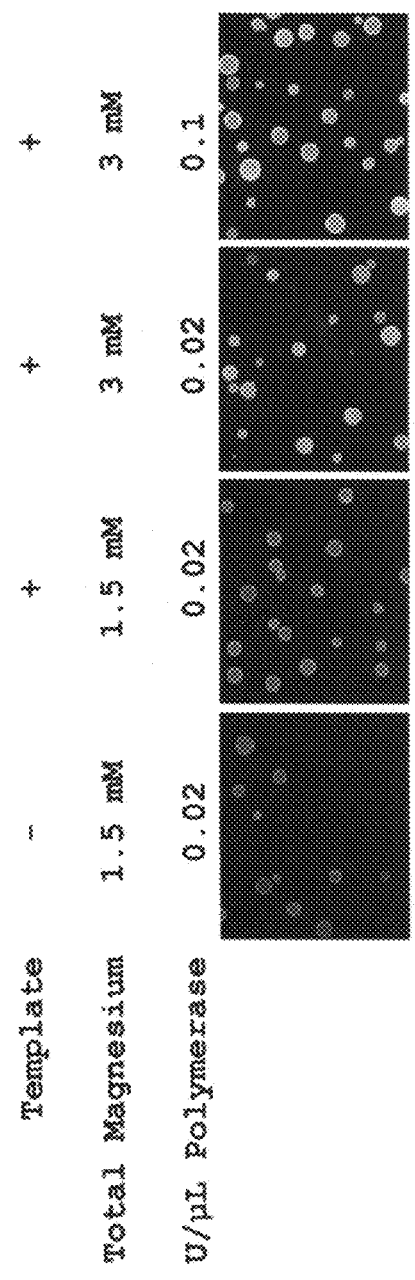

FIG. 43. Solid-Phase bridge PCR on the APC gene associated with colorectal cancer: Direct use of genomic DNA templates in the solid-phase bridge PCR reaction. Solid-Phase bridge PCR was performed on agarose beads using fragmented genomic DNA as a template. To do so, agarose beads covalently conjugated to an APC gene-specific primer set were prepared. Non-hybridizing regions of the primers also incorporate all necessary untranslated regions for downstream cell-free protein expression and epitope tag detection of the N- and C-terminals of the expressed protein. Supplementation with magnesium and DNA polymerase in the solid-phase bridge PCR reaction was tested. Following completion of the solid-phase bridge PCR reaction, all beads, which also contain conjugated biotin moieties, were stained with streptavidin Alexa Fluor 488 (green). Beads were then probed (hybridized) with a complementary Cy5 labeled oligonucleotide direct against internal sequences of the APC solid-phase bridge PCR amplicon (red). 2-color overlays of the green and red fluorescence images are presented.

Figure 44A:
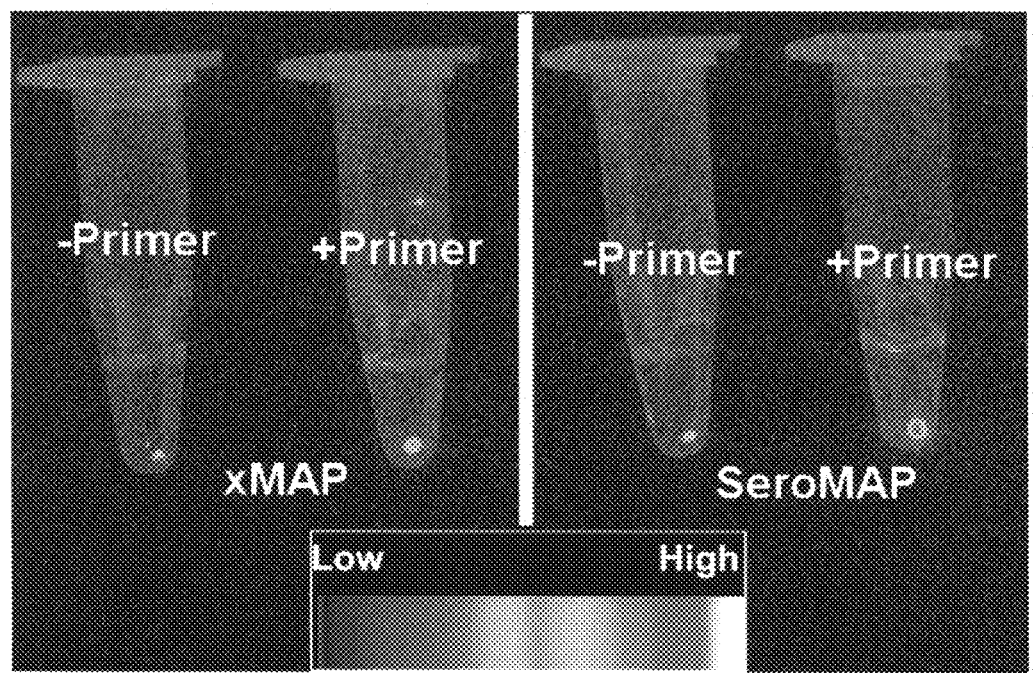

FIG. 44A. Solid-Phase bridge PCR on 6 micron diameter, non-porous, fluorescently bar-coded plastic beads from Luminex Corporation: Verification of primer attachment to the beads prior to solid-phase bridge PCR. Both forward and reverse primers directed against a template derived from the human APC gene were covalently attached to the beads by their 5' ends for later use of the beads in solid-phase bridge PCR reactions. Two types of fluorescently bar-coded beads from Luminex Corporation (Austin, Tex.) were tested, xMAP and SeroMAP, which were designed for multiplexed assays (e.g. multiplexed SNP or immunoassays). To verify successful primer attachment to the beads, the beads were stained with the fluorescent single-stranded DNA detection agent OliGreen (Invitrogen Corporation, Carlsbad, Calif.). Stained bead pellets (~0.125 µL actual bead pellet volume) were fluorescently imaged directly in 0.5 mL thin-wall polypropylene PCR tubes. "+Primer" indicates beads that were chemically conjugated to the primers, while "−Primer" indicates beads that were subjected to the chemical conjugation procedure, but omitting only the primers from the reaction. The image was artificially colorized in Pseudocolor using ImageQuant quantitative image analysis software (Molecular Dynamics; Amersham Biosciences Corp., Piscataway, N.J.) to better show differences in fluorescence intensity and the corresponding scale is shown.

Figure 44B:
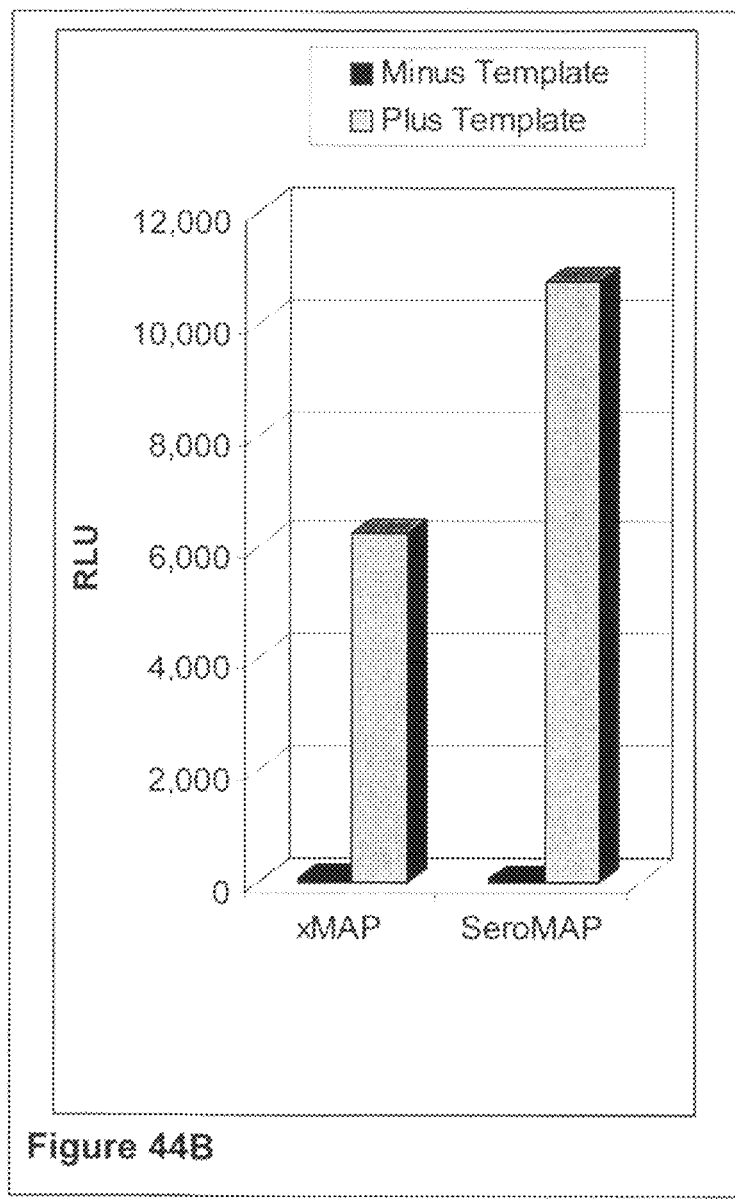

FIG. 44B. Solid-Phase bridge PCR on 6 micron diameter, non-porous, fluorescently bar-coded plastic beads from Luminex Corporation: Detection of the solid-phase bridge PCR amplicon on the beads by biotin-dUTP labeling. Both forward and reverse primers directed against a template derived from the human APC gene were covalently attached to the beads by their 5' ends. Solid-phase bridge PCR was performed in the presence of biotin-16-dUTP for labeling of the amplicon. Following solid-phase bridge PCR, amplicon was detected on the beads via chemiluminescence using a NeutrAvidin-HRP conjugate. The data was plotted in bar chart form and RLU represents the Relative Luminescence Units (arbitrary units). "Plus Template" refers to samples where template DNA was included in the solid-phase bridge PCR reaction. "Minus Template" refers to parallel samples whereby only the template DNA was omitted from the solid-phase bridge PCR reaction, but were otherwise identical to the "Plus Template" samples. Two types of fluorescently bar-coded beads from Luminex Corporation (Austin, Tex.) were tested, xMAP and SeroMAP, which were designed for multiplexed assays (e.g. multiplexed SNP or immunoassays).

Figure 45:
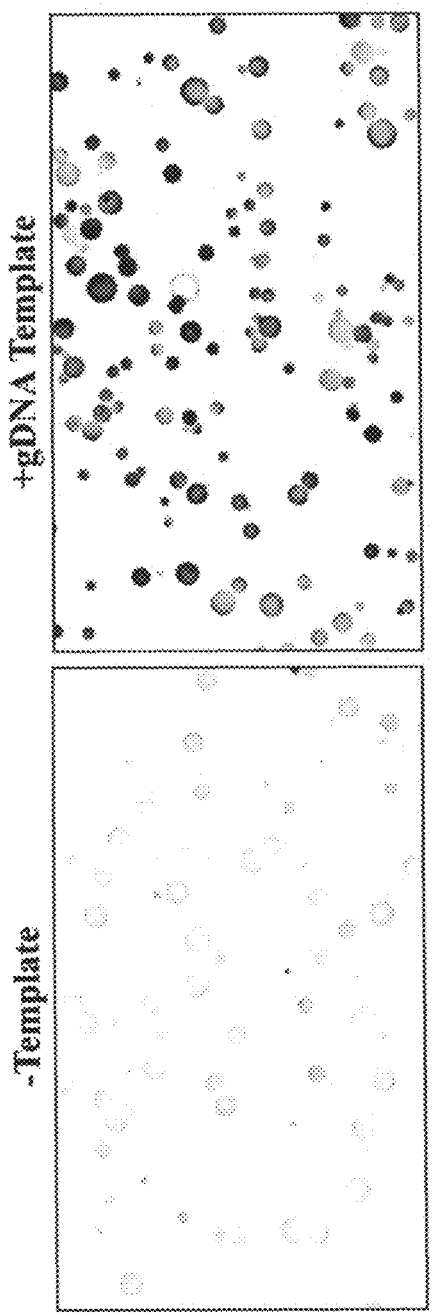

FIG. 45. Solid-Phase bridge PCR for detection of the bisulfite converted wild-type vimentin DNA marker directly from genomic DNA: Applications in colorectal cancer diagnosis. Template for the solid-phase bridge PCR reaction was wild-type human genomic DNA that was fragmented and bisulfite converted to distinguish between methylated and unmethylated sequences. Next, primers directed at the key bisulfite converted sequences in the vimentin marker (regions that are unmethylated at CpG islands in the wild-type and methylated in the disease state) were covalently conjugated to agarose beads and used for solid-phase bridge PCR amplification of the aforementioned template DNA. Following solid-phase bridge PCR amplification on the beads, the amplicon was detected on the beads by probing with a fluorescently labeled complementary oligonucleotide. This vimentin probe was labeled with Cy3 fluorescence. "+gDNA Template" indicates when the fragmented and bisulfite converted genomic DNA template was added to the solid-phase bridge PCR reaction. "−Template" indicates that only the template DNA was omitted from the solid-phase bridge PCR reaction (negative control).

Figure 46A:
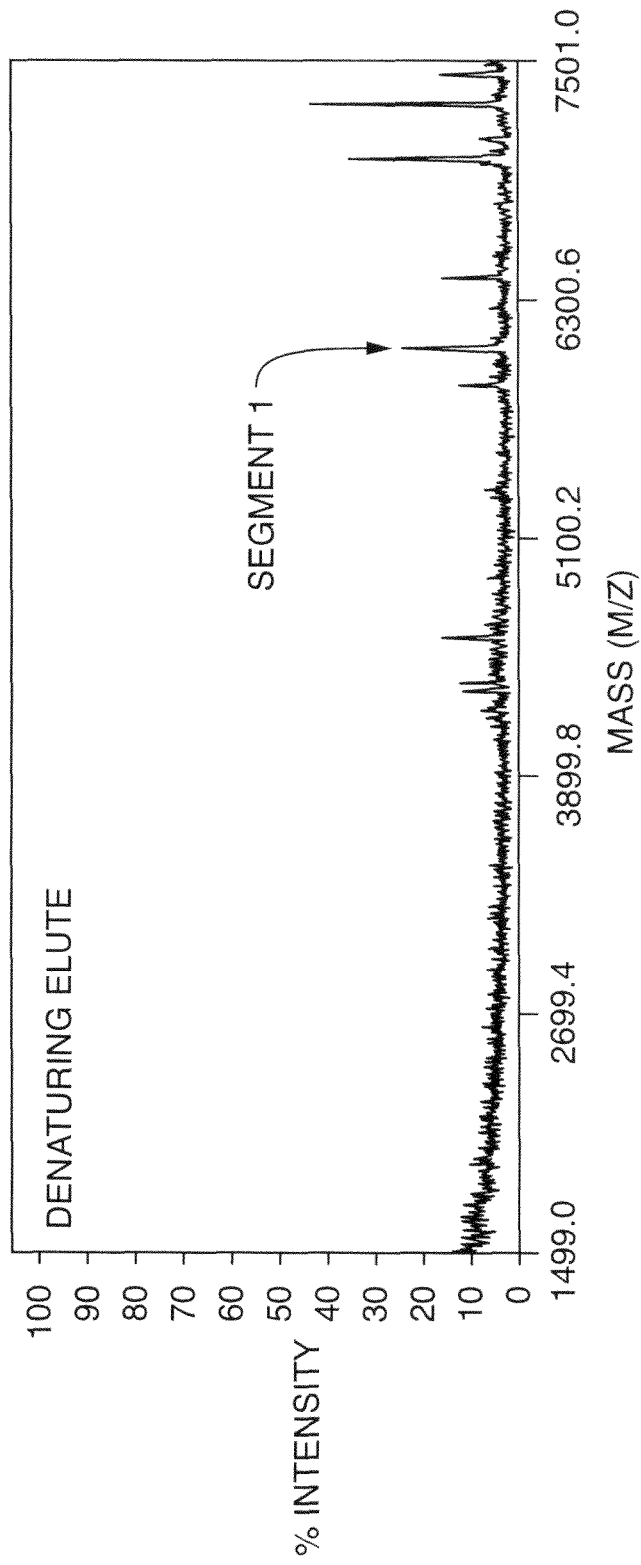
Figure 46B:
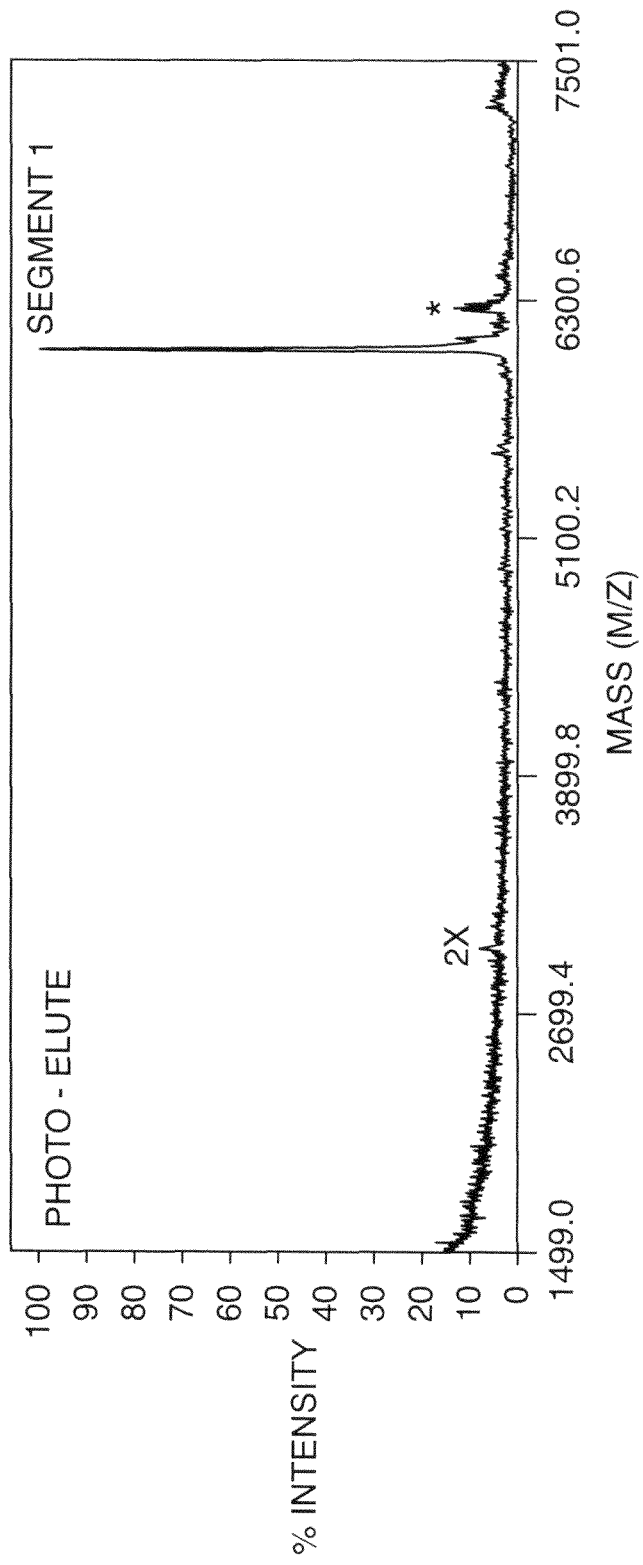

FIG. 46. Solid-Phase bridge PCR followed by cell-free expression with in situ protein capture on PC-antibodies: Background reduction in mass spectrometry analysis by subsequent photo-release. Solid-phase bridge PCR was performed on beads to amplify a segment of the BCR-ABL tyrosine kinase domain (designated Segment 1 in this Example). The solid-phase bridge PCR primers additionally incorporated sequences for cell-free protein expression as well as an N-terminal FLAG epitope tag. Following solid-phase bridge PCR, a photocleavable antibody (PC-antibody), directed against the FLAG epitope tag, was bound to the beads and the beads used to mediate cell-free protein expression. The expressed peptide was in situ captured onto the same beads, during the expression reaction. Following extensive washing, the captured peptide was eluted from the beads either by denaturation of the PC-antibody (46A) or by photo-release (46B) of the PC-antibody. The eluted peptide was then analyzed by MALDI-TOF mass spectrometry. The asterisk and "2×" in the figure denote the plus matrix adduct and doubly charged versions of the Segment 1 peptide, respectively, and hence are not contaminants.

Figure 47:
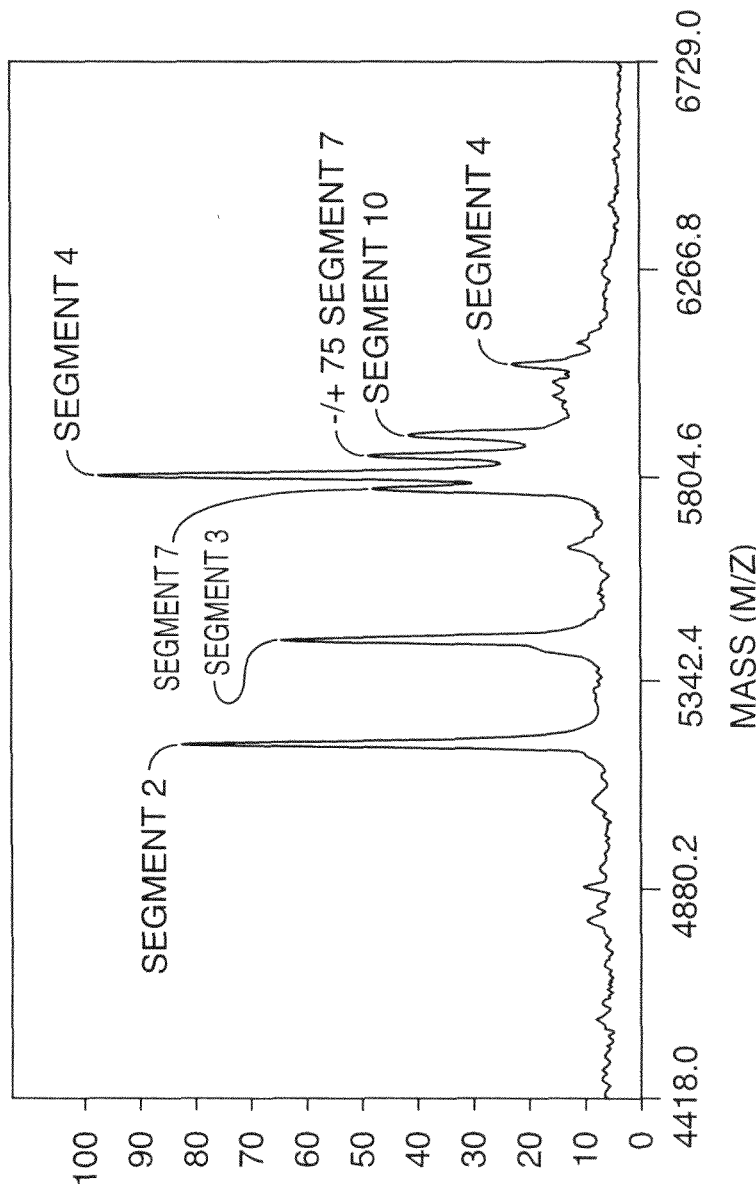

FIG. 47. Solid-phase bridge PCR followed by cell-free expression and mass spectrometry analysis: Multiplex cell-free expression. A single multiplexed solid-phase bridge PCR reaction was performed on 6 different segments of the BCR-ABL transcript involved in Chronic Myeloid Leukemia (CML). The solid-phase bridge PCR primers additionally incorporated sequences needed for efficient cell-free protein expression and epitope tagging. A single multiplexed cell-free protein expression reaction was then performed using the post solid-phase bridge PCR beads as the template DNA source (bead mixture of all 6 segments). Following expression, the crude peptides were affinity co-purified via their common N-terminal FLAG epitope tag and analyzed by MALDI-TOF mass spectrometry. Peptide peaks in the mass spectrum are labeled with their corresponding segment number. All segments were clearly identified with a 1 Dalton mass accuracy. The +75 peak was putatively identified as a SNP of Segment 7.

Figure 48:
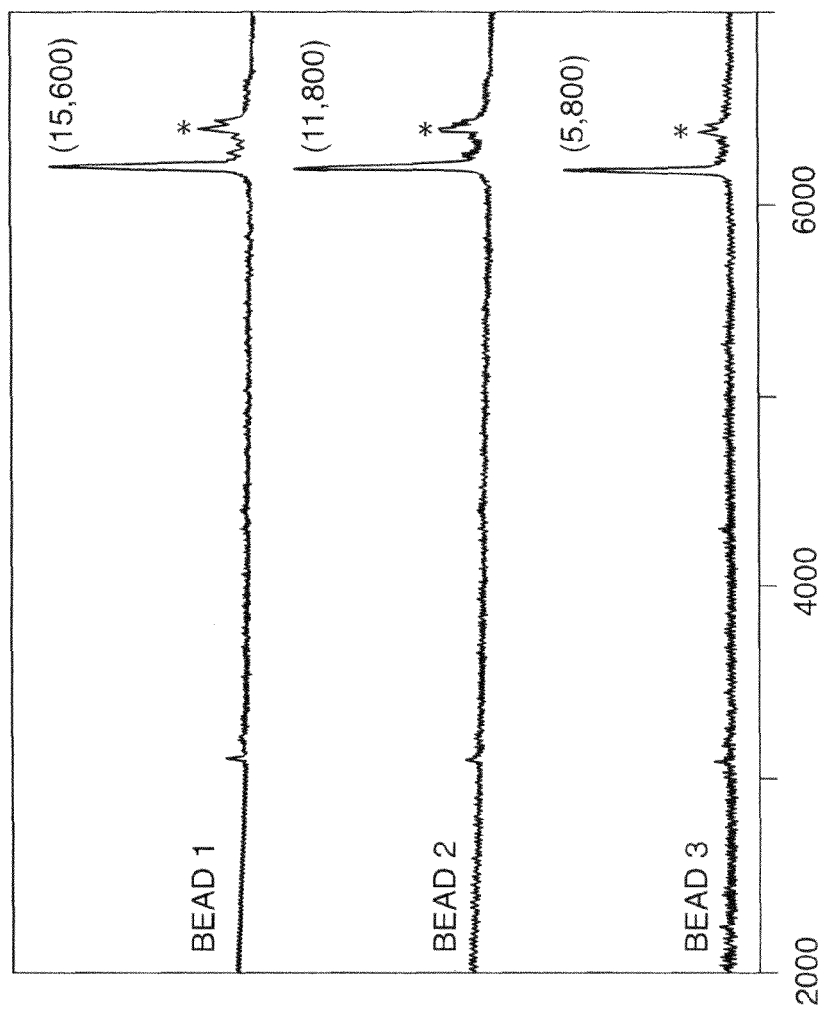

FIG. 48. Affinity purification of cell-free expressed peptides onto an agarose bead affinity resin followed by mass spectrometry detection from single beads. A conventional solution-phase PCR reaction was performed on a segment of the APC gene involved in colorectal cancer. The PCR primers additionally incorporated sequences needed for efficient cell-free protein expression and epitope tagging. The PCR product DNA was then used to mediate cell-free protein expression. Following expression, the crude peptide was affinity purified via its N-terminal FLAG epitope tag and analyzed by MALDI-TOF mass spectrometry. The labels in parenthesis correspond to the signal intensity of the expected target peak (arbitrary units). The asterisks indicate the minor plus matrix adduct of the target peak. Spectra from 3 different individual 100 micron diameter agarose beads are shown.

DETAILED DESCRIPTION OF THE INVENTION

The present invention features methods and compositions for the production of biomolecules on beads or particles. In one embodiment, the biomolecules are peptides and proteins. In some embodiments, biomolecules are produced on beads and include, but are not limited to, nucleic acids, nucleosides, nucleotides or polymers thereof (e.g. DNA or RNA). The nucleic acids, nucleosides, nucleotides or polymers thereof (e.g. DNA or RNA) can optionally be used to direct subsequent protein synthesis on the beads. The beads can optionally be selected, enriched or separated based on characteristics of the biomolecules present on the beads. In some embodiments, the biomolecules are utilized directly on the beads for downstream assays, analyses or experiments. In other embodiments, biomolecules are subsequently photo-transferred from the beads to a surface, as described below.

The present invention also features methods and compositions for the photo-transfer of compounds and/or substances from a first surface to a second surface. In some embodiments, the photo-transferred compounds and/or substances are deposited in highly purified and active forms. Often, the compounds and/or substances can serve as probes, targets or analytes for bio-detection devices such as microarrays. The invention is also directed to compositions and methods for facilitating the interaction of compounds and/or substances. The compounds and/or substances can be present in a heterogeneous mixture such as blood, plasma or sera and constitute probes, targets or analytes for a bio-detection device such as a microarray. Surfaces include but are not limited to surfaces of a microarray, diagnostic devices, biochip or bio-detector. Probes, targets or analytes (so-called "features") can comprise compounds, substances, molecules, macromolecules and cells. Molecules and macromolecules comprise but are not limited to proteins, peptides, amino acids, amino acid analogs, nucleic acids, nucleosides, nucleotides, lipids, vesicles, detergent micelles, cells, virus particles, fatty acids, saccharides, polysaccharides, inorganic molecules and metals.

Direct Contact Photo-Transfer of Molecules to Surfaces

One embodiment of the invention is directed to methods for depositing compounds and/or substances such as molecules, biomolecules, macromolecules, nanoparticles and cells from a first surface onto a second surface. The compounds and/or substances are initially attached to the first surface, such as present on a bead, using a photocleavable linker or photocleavable conjugate. The first surface is then allowed to directly contact the second surface (as distinct from another embodiment wherein the first surface is merely brought into proximity to second surface). The compounds and/or substances are then photo-released from the first surface facilitating transfer of the compounds and/or substances to the second surface. The first surface is then removed from direct contact with the second surface. This method is referred to as direct contact photo-transfer.

In some embodiments, it is not strictly necessary that said photo-transferred compounds and/or substances be in physical contact with said second surface, but in close proximity instead. Without limiting the present invention to any particular mechanism, it is believed that it is sufficient that the compounds and/or substances be in proximity (e.g. to a distance of less than $10^6$ Angstroms, more preferably between 0.1 and 1000 Angstroms) to said second surface. In one embodiment, the compounds and or substances are brought into proximity simply by bringing the surfaces into proximity (without actual contact between the surfaces). In one embodiment, the compound is brought into proximity via a carrier, such as a particle or bead.

In one preferred embodiment, the first surface is the surface of a bead and the second surface is chosen from substrates such as glass or plastic slides coated with nitrocellulose, PVDF or polystyrene or derivatized with aldehyde, epoxy, carboxyl, sulfhydryl or amine moieties. In one embodiment, beads are in a solution (i.e. in suspension) before contacting the second surface and are diluted sufficiently so that a majority of the beads deposited on the second surface can be individually identified. Photo-transfer of the compounds and/or substances from the beads to the second surface, i.e. to the substrate, results in individually identifiable (resolved) spots on the surface of the substrate (i.e. second surface).

In another preferred embodiment the bead is formed from agarose and is coated with (strept)avidin or derivatives thereof. The compound transferred is a protein to which is attached covalently a photocleavable biotin which binds to the (strept)avidin residing on the bead surface. The beads are deposited on epoxy coated glass slides in a solution and allowed to settle on said slides. The slide is then illuminated with light with wavelengths longer than 300 nm (e.g. between 300 nm and 400 nm, more preferably between 300 nm and 360 nm) for a period of time (less than one hour, more preferably less than 30 minutes, still more preferably between 1 and 10 minutes, or even 1 second to 1 minute). The beads are then washed from the slide with a stream of water, solution or buffer.

It is to be understood that this invention is not limited by the type of surface that the compounds are transferred to (second surface). Such a surface may comprise glass, plastic/polymer, ceramic, or metallic materials either plain or additionally coated or chemically derivatized/conjugated with the following: antibodies; (strept)avidin/avidin or derivatives thereof such as NeutrAvidin; proteins or peptides; nucleic acids; cells; 3-dimensional matrices such as polyacrylamide (e.g. HydroGel coated microarray substrates from PerkinElmer Life and Analytical Sciences, Inc., Boston, Mass.) or agarose (cross-linked and non-cross-linked); membrane or film coatings such as nitrocellulose, polyvinylidene fluoride (PVDF) or polystyrene; polymers; chemically reactive derivitization such as activation with aldehyde, epoxy, N-hydroxy-succinimide (NHS) esters or other amine-reactive esters such as other succinimidyl esters, tetrafluorophenyl (TFP) esters or carbonyl azides, isothiocyanate, sulfonyl chloride, cyanogen bromide, iodoacetamide or maleimide chemistries; activated surfaces such as those derivatized with amines (e.g. GAPS microarray substrates from Corning Lifesciences, Acton, Mass.) or carboxyl groups; metal ion or metal ion-chelate derivitization such as nickel nitrilo-triacetic acid (Ni-NTA) or cobalt nitrilo-triacetic acid complexes/chelates; hydrophilic or hydrophobic coatings for non-specific biomolecule absorption; gold or metal coatings such as those suitable for MALDI-TOF or Surface Plasmon Resonance.

Where beads or particles are used (e.g. first surface), the invention is also not limited by the types of bead or particle used. Beads and particles can be composed of a variety of materials including but not limited to organic or inorganic molecules, polymer, solid-state materials such as metals or semiconductors, biological materials, sol gels, colloids, glass, magnetic materials, paramagnetic materials, electrostatic materials, electrically conducting materials, insulators, fluorescent materials, absorbing material and combinations thereof. The beads or particles may also vary in size, shape and density. For example beads may range in size from 20 nanometers to hundreds of microns depending on the application and spot size desired for different applications. The beads may also be polydisperse in regards to size, shape, material composition, optical, magnetic, electrical properties. Beads may also comprise of aggregates of smaller beads. A variety of bead types are commercially available, including but not limited to, beads selected from agarose beads, (strept) avidin-coated beads, NeutrAvidin-coated beads, antibody-coated beads, paramagnetic beads, magnetic beads, electrostatic beads, electrically conducting beads, fluorescently labeled beads, colloidal beads, glass beads, semiconductor beads and polymeric beads.

In addition to beads, first surface could be provided by nanoparticles having dimensions of 1-100 nm and more preferably 10-40 nm. Nanoparticles are a collection of atoms or molecules which are normally in the size range of 1-100 nm and more preferable 10-50 nm. An example of a nanometer particle is an aggregate of several proteins or a semiconductor particle both in the size range of 1-100 nm. Compounds are bound to the surface of nanoparticles through a photocleavable linker. For example, proteins such as streptavidin can be linked through photocleavable linkers to the surface of nanoparticles by using photocleavable biotin which can be attached to the surface through covalent interaction and to streptavidin through non-covalent interaction. This provides a means to release small numbers of streptavidin molecules in spots with a dimension approximately equal to the projected surface areas of the nanoparticles.

Patterns of molecules can be photo-transferred onto the second surface based on the methods of this invention and self-assembly of the nanoparticles. The process of self-assembly of nanoparticles on a surface is well known to those working in the field of nanoparticles and for example allows various complex patterns to be formed on a surface [Rabani, E., Reichman, D. R., Geissler, P. L., and Brus, L. E. (2003) *Nature* 426, 271-274]. This phenomenon thus provides a means to pattern the molecules which are photo-released from the surface of self-assembled nanoparticles (first surface) in contact with the second surface.

The first surface can also comprise a flat surface such as found on a slide or surfaces with a high radius of curvature such as found on a tip. Specific tips compatible with this invention include tips from atomic force microscopes or scanning tunneling microscopes.

Regardless of what types of surfaces are employed, importantly, a variety of compounds and/or substances can be photo-transferred using the methods of the present invention, including but not limited to compounds selected from the group consisting of proteins, peptides, antibodies, amino acids, amino acid analogs, drug compounds, nucleic acids, nucleosides, nucleotides, lipids, fatty acids, saccharides, polysaccharides, inorganic molecules, and metals. Photocleavage of the photoconjugate may cause the compound or compounds to be released in a modified or unmodified form. For example, the photocleavage may leave part of the linker attached to the compound.

Furthermore, regardless of what types of surfaces are employed, the present invention contemplates embodiments wherein more than one type of affinity reagent is used. For example, in one embodiment an antibody (a first affinity reagent) is covalently conjugated to a photocleavable biotin (a second affinity reagent). The antibody is directed against one or more epitopes which are part of a protein. The protein then becomes bound to (strept)avidin coated agarose beads (a third affinity reagent) through the interaction of biotin on the antibody with (strept)avidin on the beads and interaction of the antibody with the protein.

It is to be understood that either a single homogeneous compound or substance, or a mixture of different compounds and/or substances can be bound to the first surface through photocleavable linkers. In the case where first surface comprises beads or nanoparticles, a mixture of beads or nanoparticles, each containing different compounds and/or substances, can be used to photo-transfer the compound(s) and/or substance(s) onto the second surface. For example, in the case of beads, each spot resulting from photo-transfer may thus contain a mixture of compounds and/or substances or each spot may contain one compound and/or substance which is different from another spot.

In one preferred embodiment, the compound to be deposited on the second surface is a target molecule present in a biological fluid such as whole blood or sera. An antibody directed against the target molecule is bound through a photocleavable conjugate to a bead (first surface). After contacting the biological fluid, the beads are separated from the biological fluid and allowed to directly contact the second surface. The beads are then illuminated at preferred wavelengths of light which causes photo-transfer of the antibody-target molecule complex to the second surface.

Other useful biological fluids include but are not limited to saliva, cerebrospinal fluid, synovial fluid, urine and sweat. Additional biological samples include but are not limited to stool samples and tumors (e.g. biopsies, tumor cell lines, primary cultures, lysates, etc.). The photo-conjugate can comprise of a photocleavable biotin covalently bound to an antibody which is directed against an antigen. The bead (first surface) comprises a (strept)avidin or avidin or derivatives thereof such as NeutrAvidin, coated onto a porous polymer matrix such as agarose, Sepharose or polyacrylamide. The photo-conjugate is linked to the bead through a biotin-(strept) avidin interaction. After the beads are washed away from the second surface, a labeled antibody which selectively interacts with the antigen is added for detection purposes.

In comparison to a conventional sandwich immunoassay, well known in the field for detection of analytes, the present invention avoids the potential transfer of non-specifically bound materials present in the blood, plasma, sera or biological fluid for example, from the first surface to the second surface, due to selective and gentle release of the target analyte from the first surface using photocleavage.

In another preferred embodiment, the compound to be deposited on the second surface is a target antibody present in a biological fluid such as whole blood or sera. An antigen for the target antibody (e.g. a specific allergen which interacts with a target specific IgE) is bound through a photocleavable linker to a bead (first surface). After contacting the biological fluid to allow the antibody-antigen interaction, the beads are separated from the biological fluid and allowed to directly contact the second surface. The beads are then illuminated at preferred wavelengths of light under conditions such that said antigen-antibody complexes are photocleaved from said beads and transferred to said second surface.

In an additional preferred embodiment, a nascent protein is synthesized in a cellular or cell-free transcription/translation system, whereby the nascent protein contains one or more affinity markers. Beads coated with an affinity agent which selectively binds to the affinity marker are allowed to contact the cellular or cell-free transcription/translation system. The beads are then separated from the transcription/translation system and allowed to directly contact the second surface. The beads are then illuminated under conditions such that said nascent proteins are photocleaved from said beads and transferred to said second surface.

In one preferred embodiment, compounds and/or substances (e.g. the proteins) are transferred from a multiarray probe device such as present on an AFM tip array described previously (Green, J-B D., Novoradovsky, A et al., *Phys. Rev. Letts* 74, 1999, 1489) to a second surface. Compounds and/or substances are bound to the tips through a photocleavable linker. The tips are allowed to contact a second surface and then illuminated with light to facilitate the transfer of said compounds and/or substances to the second surface. Since the tips are nanometer scale or less, only small nanometer scale spots comprising the compounds and/or substances (e.g. protein) will be transferred to the second surface.

In another preferred embodiment, a suspension of nanoparticles is spotted onto the second surface using a conventional robotic spotter (microarray printing device), or randomly dispersed on a second surface. Different compounds and/or substances are linked to different nanoparticles through photocleavable linkers. The nanoparticles are illuminated with radiation under conditions such that the compounds and/or substances are photocleaved from said nanometer particles and transferred to said second surface.

As described in U.S. Pat. No. 5,643,722, which is specifically incorporated by reference, and variations thereof described in U.S. Pat. No. 6,306,628, which is also specifically incorporated by reference, affinity markers containing photocleavable bonds can be incorporated into nascent proteins during their cell-free synthesis. In one example, specially prepared tRNAs are used to incorporate a photocleavable biotin in place of one or more normal residues in the proteins amino acid sequence. Such photocleavable linkers can also be incorporated specifically at the N-terminal end of the protein by using initiator suppressor tRNA. This provides a means to capture these nascent proteins selectively from the rest of the protein synthesis system, onto the first surface, followed by protein transfer to the second surface using the methods described in this invention.

Affinity markers in the form of epitopes can also be incorporated into a nascent proteins by designing the message or DNA coding for the nascent protein to have a nucleic acid sequence corresponding to the particular epitope. This can be accomplished by using primers that incorporate the desired nucleic acid sequence into the DNA coding for the nascent protein using the polymerase chain reaction (PCR). A variety of epitope tag sequences can be utilized in the methods of the present invention, including $His_6$ (or other polyhistidine tags), c-myc, a p53-tag (derived from the P53 sequence), HSV, HA, FLAG, VSV-G, Fil-16 (filamin derived) and StrepTag.

In addition to proteins, methods and compositions of this invention are directed to depositing nucleic acid molecules or macromolecules containing nucleic acids (heretofore "nucleic acid" is meant to include all complexes containing nucleic acids) onto a second surface. The nucleic acid molecules are initially attached to a different surface (first surface), such as present on a bead, with the attachment being by a photocleavable linker or conjugate. The first surface is then allowed to directly contact the second surface. The nucleic acid molecules are then photo-released from the first surface facilitating transfer of the nucleic acid to the second surface. The first surface is then removed from direct contact with the second surface.

In one preferred embodiment, a nucleic acid molecule is synthesized with a photocleavable affinity tag. Beads coated with an affinity agent which binds to the affinity marker are allowed to contact a solution containing the nucleic acid molecules or nucleic acid complexes. Beads are then separated from the solution and allowed to directly contact the second surface. The beads are then illuminated at preferred wavelength which causes photo-transfer of the nucleic acids molecules to the second surface. It will be understood by those skilled in the art of nucleic acid chemistry there exists a number of methods to incorporate photocleavable tags into nucleic acid molecules during or after their synthesis, including methods based on enzymatic incorporation or chemical synthesis.

In one example, photocleavable biotins are incorporated into nucleic acids or nucleic acid complexes. The incorporation of photocleavable biotin and other photocleavable affinity markers are described in U.S. Pat. No. 5,643,722 which is specifically incorporated by reference, and variations thereof described in U.S. Pat. Nos. 5,986,076 and 6,057,096, which are also specifically incorporated by reference.

As described in U.S. Pat. No. 6,057,096, the isolation of nucleic acids is based on three basic steps. First, a photocleavable biotin derivative is attached to a nucleic acid molecule by enzymatic or chemical means or, alternatively, by incorporation of a photocleavable biotin nucleotide into a nucleic acid by enzymatic or chemical means. The choice of a particular photocleavable biotin depends on which molecular groups are to be derivatized on the nucleic acid. For example, attachment of photocleavable biotin to a nucleic acid can be accomplished by forming a covalent bond with the aromatic amine, sugar hydroxyls or phosphate groups. Photocleavable biotin can also be incorporated into oligonucleotides through chemical or enzymatic means.

In some embodiments, there is no need for external printing methods such as performed by conventional robotic printing. Instead, a spot is formed on the second surface in the immediate vicinity of where the beads or nanoparticles (first surface) contact the second surface. Furthermore, the shape (i.e. morphology) of the spot is directly related to the size and shape of the contacting surface (first surface) such as from a bead or nanoparticles.

As in the case of conventional printing, the interaction between the photo-released molecule and the second surface determines in part how well the molecule will adhere to the second. For example, proteins will form covalent linkage with some specific surfaces which have present at their surface specifically activated (i.e. reactive) molecules. For example, commercially available glass slides, such as those derivatized with epoxy or aldehyde moieties, have particular chemical groups allowing particular interactions. A second example involves proteins which interact strongly with nitrocellulose, PVDF or polystyrene surfaces, mainly through hydrophobic interactions. A third example is the use of a secondary antibody bound to a surface, which is chosen to interact selectively with the primary antibody involved in the photocleavable conjugate. An fourth example involves hydrated matrix coated slides which bind proteins (e.g. polyacrylamide gels or HydroGel coated microarray substrates; PerkinElmer Life and Analytical Sciences, Inc., Boston, Mass.). A fifth example involves surfaces (e.g. slides, chips, etc.) with charged chemical groups such as amines or carboxyls, which can non-covalently bind proteins through ionic interactions, or can be covalently linked to proteins with the aid of chemically reactive cross-linkers.

In one preferred embodiment, the second surface comprises a MALDI substrate which is normally coated with gold. The gold surface is activated by chemically incorporating reactive groups which interact with different types of molecules including hydrophobic, hydrophilic and molecules containing specific chemical groups [Koopmann & Blackburn. (2003) Rapid Commun Mass Spectrom 17, 455-462; Zhang & Orlando. (1999) Anal Chem 71, 4753-4757; Neubert et al. (2002) Anal Chem 74, 3677-3683; Kiernan et al. (2002) Clin Chem 48, 947-949; Darder et al. (1999) Anal Chem 71, 5530-5537].

Conventional microarray printers (e.g. spotters) can be used to deposit one or more beads (first surface) at specific positions on a second surface. In some cases it is desirable to deposit a single bead per spot. This can be achieved, in one embodiment, by diluting the beads solution so that each liquid spot deposited (e.g. by the robot) has at most one bead. The density of beads deposited per spot can be controlled by a number of factors well known in the field. For example, the diameter of capillary fibers used in the printing process can be controlled so that the inner diameter of the fiber is restricted to a single file of beads. Alternatively, the drop size in the case of ink jet printing technology can be used to control the number of beads deposited per spot. Alternatively, beads can be deposited on a surface comprising wells, wherein said wells are dimensioned to permit one bead or particle, and not more than one bead or particle, to fit or at least partially fit or settle.

The present invention also contemplates methods which do not require mechanical microarray printers. For example, beads (first surface) which contain photocleavable conjugates that link various molecules can be allowed to contact the second surface by introducing all of the beads together in solution form, i.e. in suspension, which contacts the second surface. The bead deposition in this case will cause a random or semi-random pattern. In order to control the average 2-dimensional density of beads on the second surface, the solution of beads which contacts the surface can be diluted to a desired concentration. Other methods of introducing the beads without the use of a mechanical microarray printer include spraying the beads onto the surface.

Alternatively, beads or nanoparticles (first surface) can be guided to specific positions on the second surface without the use of conventional mechanical microarray printers, using preexisting features on the second surface. For example, interaction of beads or nanoparticles with preformed elements on the second surface include but are not limited to mechanical (e.g. etched wells, dimples or holes), electrostatic, magnetic, surface tension, capillarity, molecular interactions, covalent interacts, DNA hybridization and protein-protein interactions.

A variety of approaches can be used to modify a second surface to guide beads (first surface) to specific positions. One example of preformed features on a second surface which can be used to guide beads to specific positions is based on utilization of small etched pits which hold the beads. Such a mechanism is used for example in the case of Illumina's (Illumina Incorporated; San Diego, Calif.) coded bead array technology [Gunderson, K. L. et al., (2004) Genome Res 14, 870-877].

Regardless of the methods, compounds, substances and/or surfaces used in this invention, it is not intended that the present invention be limited to particular photocleavable linkers used in the photo-transfer process. There are a variety of known photocleavable linkers. Preferred comprise a 2-nitrobenzyl moiety. U.S. Pat. No. 5,643,722 describes a variety of such linkers and is hereby incorporated by reference.

Identifying Molecules Deposited by Direct Contact Photo-Transfer of Coding Agents Another embodiment of the invention is directed to methods for determining the identity of compounds deposited in a plurality of spots on a second surface using the methods of direct contact photo-transfer. A plurality of beads or nanoparticles are prepared with coding agents such that different compounds or mixture of compounds are linked using photocleavable conjugates to different beads containing different coding agents. The coding agents allow beads (and the photo-transferred compound(s)) to be uniquely identified on the basis of unique spectral, mechanical, magnetic or electrical properties which identifies on coding agent from another. Following methods of this invention for preparing these beads, the beads are allowed to directly contact the second surface. In one embodiment, the coding properties of each bead are then recorded as a function of position on the bead on the second surface. The beads are then illuminated causing photo-transfer of the compounds from each bead to the second surface. The beads are then removed from the surface. Later the information recorded about bead coding as a function of position is used to identify the compound or compounds deposited in each spot.

It is not intended that the present invention be limited to the nature of the particular coding method. A variety of methods are known for coding beads some of which are commercially available. In general, several categories of coding options can be used in the context of direct contact photo-transfer, including but not limited to:

Spectral Coding:

Agents having unique and distinguishable spectral properties can be used for decoding following contact photo-transfer. One embodiment for spectral coding utilizes fluorescent quantum dot nanocrystals. Based on published reports, such as by Han et al. [Han et al. (2001) Nat Biotechnol 19, 631-635], highly fluorescent quantum dot nanocrystals can be used for spectral bar coding on beads. As many as 40,000 distinct codes can be created by adjusting the ratio of the intensities of different quantum dot species having different fluorescence emissions ("colors"). For example, nearly 1,000 distinct codes can be achieved using 3 colors of quantum dot nanocrystals at 10 different intensity levels ($10^3-1=999$ codes). Quantum dot nanocrystal codes can be photocleavably attached to a first surface (e.g. bead) to facilitate contact photo-transfer to a receiving surface (second surface). In one embodiment, to facilitate photocleavable attachment to the first surface (e.g. bead), protein or amine functionalized quantum dot nanocrystals (e.g. from Quantum Dot Corporation, Hayward, Calif.) can be labeled with AmberGen's amine reactive photocleavable biotin (PC-biotin) reagent (AmberGen Incorporated, Waltham, Mass.) [Olejnik et al. (1995) *Proceedings of the National Academy of Science* (*USA*) 92, 7590-7594; Pandori et al. (2002) *Chem Biol* 9, 567-573].

DNA Coding:

DNA decoding schemes have been previously reported for bead-based fiber-optic microarray devices used in detection of single-nucleotide polymorphisms (SNPs) (Illumina Inc., San Diego, Calif.) [Gunderson et al. (2004) *Genome Res* 14, 870-877]. In this approach, each bead is encoded with a unique DNA sequence (code) which can be read by hybridization probes consisting of fluorescently labeled complementary oligonucleotides (decoders). A highly efficient algorithm has been developed which allows thousands of different sequences to be identified with just a few color probes and several cycles of hybridization. For example, 1,520 unique DNA sequences have been decoded using 3 colors (blank, red and green) and 7 sequential hybridization steps (with each hybridization step containing 1,520 decoder probes, each carrying one of the 3 possible colors; color on decoder probes is modulated for each sequential hybridization step to achieve all 1,520 codes).

DNA codes can be photocleavably attached to a first surface (e.g. bead) to facilitate contact photo-transfer to a receiving surface (second surface). DNA coding elements can be manually attached to the first surface or generated via solid-phase bridge PCR for example. In one embodiment, a photocleavable amine phosphoramidite reagent, sold commercially by Glen Research (Sterling, Va.; world wide web.glenres.com), can be used to photocleavably attach DNA codes. This phosphoramidite will generate a photocleavable 5' amine modified oligonucleotide, which can then be attached to amine-reactive beads or attached to beads via amine-based cross-linking chemistries (e.g. carbodiimide based coupling to carboxyl functionalized beads).

Protein/Peptide Coding:

Proteins, polypeptides or peptides which can be distinguished based on certain characteristics can also serve as coding agents following contact photo-transfer. In one embodiment, peptide/protein codes of unique and distinguishable masses are contact photo-transferred to a receiving surface (second surface) and subsequently detected using matrix-assisted laser desorption/ionization mass spectrometry (MALDI-MS). A similar application of photocleavable mass tags for multiplexed assays has been previously reported by AmberGen [Olejnik et al. (1999) *Nucleic Acids Res* 27, 4626-4631; Hahner et al. (1999) *Biomol Eng* 16, 127-133]. Only relatively small peptides (e.g. 10 amino acids) are required to create tens of thousands of mass tags with unique masses that can be easily distinguished with a high resolution mass spectrometer.

Protein/Peptide codes can be photocleavably attached to a first surface (e.g. bead) to facilitate contact photo-transfer to a receiving surface (second surface). Protein/Peptide coding elements can be manually attached to the first surface or generated, for example, via cell-free protein synthesis from DNA on the first surface, whereby in situ protein/peptide capture [Ramachandran et al. (2004) *Science* 305, 86-90; Nord et al. (2003) *J Biotechnol* 106, 1-13] is used to isolate the protein/peptide code onto the same bead from which it was produced; using for example, a photocleavably linked antibody for capture of the protein/peptide codes (proteins/peptides can be comprised of a common epitope tag for antibody capture and a variable region for coding).

One specific example of spectral coding involves the use of Qbeads offered by Quantum Dot Corporation (Hayward, Calif.). Qbeads coding is based on spectral bar-coding. In the case of Qbeads, microspheres are dyed with Qdot® nanocrystals (referred to a as quantum dots) which are small crystals ranging in size from 10-30 nm. Different nanocrystals have different distinct fluorescent excitation spectra, thus allowing codes to be created on the basis of the different types of nanocrystals and their relative ratio attached to a particular Qbead. When illuminated with UV or visible light, these encoded spheres emit with the characteristics of the underlying quantum dots. Different populations of beads can be encoded with different ratios and different combinations of quantum dots colors. Beads can then be mixed but their individual identity can be determined by measuring the fluorescent properties of the beads. This can be performed for example using a fluorescence microscope or microarray scanner with multicolor capability such as the ArrayWoRx scanner manufactured by Applied Precision Inc. In principle, the number of quantum dots available with different spectral properties can allow as many as a million different unique spectral codes to be created enabling multiplexed read-out of large numbers of beads.

Previously, Qbeads have been used for a number of biotechnological applications including SNP genotyping (Xu et al. (2003) "Multiplexed SNP genotyping using the Qbead™ system: a quantum dot-encoded microsphere-based assay," *Nucleic Acids Res.* 31 (8):e43). A variety of methods of probing quantum dots can be used for the decoding process and have been described in the literature (Alivisatos, A. P. (2004) "The Use of Nanocrystals in Biological Detection," *Nature Biotech.* 22:47-52).

It is to be understood that it is not intended that the present invention be limited to coding agents that are quantum dots and the use of fluorescent spectral properties. For example, beads can be coded based on their infrared, Raman or resonance Raman spectrum by adding a variety of compounds with easily identifiable vibrational spectral features (Fenniri, H., Chun, S., Ding, L., Zyrianov, Y., and Hallenga, K. (2003) *J Am Chem Soc* 125, 10546-10560). Beads can also be coded using a combination of molecules with unique absorption spectra in the visible or UV spectral range. An additional spectral property useful for coding beads is the nuclear magnetic resonance spectrum of one or more compounds. Beads can also be coded by attaching a unique polymer which can be sequenced. In one embodiment, unique sequences of nucleic acids are attached to beads, removed and sequenced or alternatively removed, amplified using polymerase chain reaction and sequenced. In yet another approach, beads can be coded by attaching molecules with unique molecular masses and detected using mass spectrometry.

Coding may also be provided by the intrinsic properties of the compound to be photo-transferred to second surface. For example, the compound can be identified on the basis of a unique molecular mass by using mass spectrometry. Compounds to be photo-transferred may also have unique spectral characteristics including V, visible, infrared absorption or fluorescent emission spectra and NMR spectrum. In one embodiment, unique combinations of different species of green fluorescent protein which have different emission and excitation spectra are used for coding.

Another preferred embodiment of the invention is directed to methods for determining the identity of compounds deposited in a plurality of spots on a surface by incorporating on the bead coding agents which are photo-transferred along with the compounds to the second surface. A plurality of coded beads are prepared such that different compounds or mixture of compounds are linked using photocleavable conjugates to different beads with unique coding. In addition, the coding agents are attached to the beads using photocleavable conjugates. The beads are then isolated and allowed to directly contact second surface. The beads are then illuminating with preferred wavelengths causing photo-release and deposition of the compounds and the coding agents. The beads are then removed from the second surface. The identity of the compounds deposited in each spot is then determined by measuring some property of the photo-transferred coding agents.

A variety of methods and compositions are contemplated in this invention for producing photo-transferable coding agents which are used to determine the identity of compounds photo-transferred from beads onto second surface. In one example, these coding agents comprise nanocrystals with distinct spectral properties such as Qdot®. Different nanocrystals have different distinct fluorescent excitation spectra, thus allowing codes to be created on the basis of the different types of nanocrystals and their relative ratio.

In one preferred embodiment, both the compounds to be photo-transferred along quantum dots are linked through photocleavable conjugates to beads. The beads are then allowed to contact second surface. The beads are then illuminated with preferred wavelengths to photo-release both the compounds and the quantum dots. The beads are then removed by washing leaving behind spots containing both the photodeposited compounds and quantum dots which serve as coding agents allowing identification of the compounds.

For example, Quantum Dot Corporation offers a Qdot® antibody conjugation kits for 565, 605, 655 and 705 nm fluorescent emitting nanoocrystals. Quantum Dot Corporation introduced this kit to allow researchers to conjugate their antibody of choice to nanocrystals. However, a similar procedure can be used to create nanocrystals which contain photocleavable linkers to beads. In particular Qdots nanocrystals contain a number of amine groups on their surfaces. In the prescribed procedures included in the kit, the amine groups are converted to thiol-reactive maleimide groups for the purpose of linking antibodies. However, these amine groups are also reactive against specific PC-linker reagents such as NHS-PC-biotin and other photocleavable affinity markers which are described in U.S. Pat. No. 5,986,076 which is specifically incorporated by reference, and variations thereof described in U.S. Pat. No. 6,057,096, which is also specifically incorporated by reference.

In a typical procedure designed to create photocleavable nanocrystals which can be linked to a variety of beads and surfaces, the Qdots described above are treated with NHS-PC-biotin. After conjugation, unreacted NHS-PC-biotin is removed. The purified nanocrystal-PC-biotin conjugate is then contacted with beads or a surface to which streptavidin or derivatives are bound in order to link the nanocrystals to the beads. The present invention specifically contemplates, as compositions of matter, nanocrystal photocleavable biotin conjugates as well as beads comprising nanocrystal-photocleavable-biotin conjugates.

It is understood that this invention is not limited to the nature of the nanocrystals, photolinker or bead. For example, a variety of methods have been reported for coating nanocrystals with surfaces which can be made specifically reactive thereby allowing photocleavable linkers to be conjugated (Lingerfelt, B. M., Mattoussi, H., Goldman, E. R., Mauro, J. M., and Anderson, G. P. (2003) *Anal Chem* 75, 4043-4049).

Polymeric microspheres or beads can be prepared from a variety of different polymers, including but not limited to polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers and epoxies. The materials have a variety of different properties with regard to swelling and porosity, which are well understood in the art. Preferably, the beads are in the size range of approximately 10 nm to 1 mm (and more preferably in the size range between approximately 50 nm and 500 nm), and can be manipulated using normal solution techniques when suspended in a solution.

A plurality of such beads or mixtures of different bead populations can be immobilized on a planar surface such that they are regularly spaced in a chosen geometry using any suitable method. For example, beads can be immobilized by micromachining wells in which beads can be entrapped into the surface, or by patterned activation of polymers on the surface using light activation to cross-link single beads at particular locations. Suitable wells can be created by ablating circles in a layer of parylene deposited on a glass surface using a focused laser. In one embodiment, the well dimensions are chosen such that a single bead can be captured per well. For example, 7 micron wells can be readily used for analysis of beads about 4 microns to about 6 microns in diameter. This can be performed (if desired) on the end of an optical fiber. On the other hand, the well dimensions in other embodiments may be chosen such that two or more beads can be captured per well. Whether the well dimensions accommodate one bead or a plurality of beads, it is preferred that the wells not be so deep that the beads remain trapped when a lateral flow of fluid passes across the surface. On the other hand, in some embodiments, it may be desirable to dimension the wells so as to cause the beads to remain trapped when a lateral flow of fluid passes across the surface.

The present invention contemplates beads comprising coding agents to as to create spectrally encoded microspheres. Microspheres can be spectrally encoded through incorporation of semiconductor nanocrystals (or SCNCs). The desired fluorescence characteristics of the microspheres may be obtained by mixing SCNCs of different sizes and/or compositions in a fixed amount and ratio to obtain the desired spectrum, which can be determined prior to association with the microspheres. Subsequent treatment of the microspheres (through for example covalent attachment, co-polymerization, or passive absorption or adsorption) with the staining solution results in a material having the designed fluorescence characteristics.

A number of SCNC solutions can be prepared, each having a distinct distribution of sizes and compositions, to achieve the desired fluorescence characteristics. These solutions may be mixed in fixed proportions to arrive at a spectrum having the predetermined ratios and intensities of emission from the distinct SCNCs suspended in that solution. Upon exposure of this solution to a light source, the emission spectrum can be measured by techniques that are well established in the art. If the spectrum is not the desired spectrum, then more of the SCNC solution needed to achieve the desired spectrum can be added and the solution "titrated" to have the correct emission spectrum. These solutions may be colloidal solutions of SCNCs dispersed in a solvent, or they may be pre-polymeric colloidal solutions, which can be polymerized to form a matrix with SCNCs contained within.

The SCNCs can be attached to the beads by covalent attachment as well as by entrapment in swelled beads, or can be coupled to one member of a binding pair the other member of which is attached to the beads. For instance, SCNCs are prepared by a number of techniques that result in reactive groups on the surface of the SCNC. See, e.g., Bruchez et al. (1998) *Science* 281:2013-2016, Chan et al. (1998) *Science* 281:2016-2018, Colvin et al. (1992) *J. Am. Chem. Soc.* 114: 5221-5230, Katari et al. (1994) *J. Phys. Chem.* 98:4109-4117, Steigerwald et al. (1987) *J. Am. Chem. Soc.* 110:3046.

The reactive groups present on the surface of the SCNCs can be coupled to reactive groups present on a surface of the material. For example, SCNCs which have carboxylate groups present on their surface can be coupled to beads with amine groups using a carbodiimide activation step. Any cross-linking method that links a SCNC to a bead and does not adversely affect the properties of the SCNC or the bead can be used. In a cross-linking approach, the relative amounts of the different SCNCs can be used to control the relative intensities, while the absolute intensities can be controlled by adjusting the reaction time to control the number of reacted sites in total. After the beads are crosslinked to the SCNCs, the beads are optionally rinsed to wash away unreacted SCNCs.

In some embodiments, a sufficient amount of fluorophore must be used to encode the beads so that the intensity of the emission from the fluorophores can be detected by the detection system used and the different intensity levels must be distinguishable, where intensity is used in the coding scheme but the fluorescence emission from the SCNCs or other fluorophores used to encode the beads must not be so intense to as to saturate the detector used in the decoding scheme.

The beads or other substrate to which one or more different known capture probes are conjugated can be encoded to allow rapid analysis of bead, and thus capture probe, identity, as well as allowing multiplexing. The coding scheme preferably employs one or more different SCNCs, although a variety of additional agents, including chromophores, fluorophores and dyes, and combinations thereof can be used alternatively or in combination with SCNCs. For organic dyes, different dyes that have distinguishable fluorescence characteristics can be used. Different SCNC populations having the same peak emission wavelength but different peak widths can be used to create different codes if sufficient spectral data can be gathered to allow the populations to be distinguished. Such different populations can also be mixed to create intermediate linewidths and hence more unique codes.

The number of SCNCs used to encode a single bead or substrate locale can be selected based on the particular application. Single SCNCs can be detected; however, a plurality of SCNCs from a given population is preferably incorporated in a single bead to provide a stronger, more continuous emission signal from each bead and thus allow shorter analysis time.

Different SCNC populations can be prepared with peak wavelengths separated by approximately 1 nm, and the peak wavelength of an individual SCNC can be readily determined with 1 nm accuracy. In the case of a single-peak spectral code, each wavelength is a different code. For example, CdSe SCNCs have a range of emission wavelengths of approximately 490-640 nm and thus can be used to generate about 150 single-peak codes at 1 nm resolution.

A spectral coding system that uses only highly separated spectral peaks having minimal spectral overlap and does not require stringent intensity regulation within the peaks allows for approximately 100,000 to 10,000,000 or more unique codes in different schemes.

A binary coding scheme combining a first SCNC population having an emission wavelength within a 490-565 nm channel and a second SCNC population within a 575-650 nm channel produces 3000 valid codes using 1-nm resolved SCNC populations if a minimum peak separation of 75 nm is used. The system can be expanded to include many peaks, the only requirement being that the minimum separation between peak wavelengths in valid codes is sufficient to allow their resolution by the detection methods used in that application.

A binary code using a spectral bandwidth of 300 nm, a coding-peak resolution, i.e., the minimum step size for a peak within a single channel, of 4 nm, a minimum interpeak spacing of 50 nm, and a maximum of 6 peaks in each code results in approximately 200,000 different codes. This assumes a purely binary code, in which the peak within each channel is either "on" or "off." By adding a second "on" intensity, i.e., wherein intensity is 0, 1 or 2, the number of potential codes increases to approximately 5 million. If the coding-peak resolution is reduced to 1 nm, the number of codes increases to approximately $1 \times 10^{10}$.

Valid codes within a given coding scheme can be identified using an algorithm. Potential codes are represented as a binary code, with the number of digits in the code corresponding to the total number of different SCNC populations having different peak wavelengths used for the coding scheme. For example, a 16-bit code could represent 16 different SCNC populations having peak emission wavelengths from 500 nm through 575 nm, at 5 nm spacing. A binary code 1000 0000 0000 0001 in this scheme represents the presence of the 500 nm and 575 nm peaks. Each of these 16-bit numbers can be evaluated for validity, depending on the spacing that is required between adjacent peaks; for example, 0010 0100 0000 0000 is a valid code if peaks spaced by 15 nm or greater can be resolved, but is not valid if the minimum spacing between adjacent peaks must be 20 nm. Using a 16-bit code with 500 to 575 nm range and 5 nm spacing between peaks, the different number of possible valid codes for different minimum spectral spacings between adjacent peaks is shown in Table 1.

TABLE 1

The number of unique codes with a binary 16-bit system.

| | Spectral Separation | | | | | |
|---|---|---|---|---|---|---|
| | 5 nm | 10 nm | 15 nm | 20 nm | 25 nm | 30 nm |
| Number of unique codes | 65535 | 2583 | 594 | 249 | 139 | 91 |

If different distinguishable intensities are used, then the number of valid codes dramatically increases. For example, using the 16-bit code above, with 15 nm minimum spacing between adjacent peaks in a code, 7,372 different valid codes are possible if two intensities, i.e., a ternary system, are used for each peak, and 38,154 different valid codes are possible for a quaternary system, i.e., wherein three "on" intensities can be distinguished.

Codes utilizing intensities require either precise matching of excitation sources or incorporation of an internal intensity standard into the beads due to the variation in extinction coefficient exhibited by individual SCNCs when excited by different wavelengths.

In some embodiments, it is preferred that the light source used for the encoding procedure be as similar as possible (preferably of the same wavelength and intensity) to the light source that will be used for decoding. The light source may be related in a quantitative manner, so that the emission spectrum of the final material may be deduced from the spectrum of the staining solution.

An example of an imaging system for automated detection of nanocrystals for use with the present methods comprises an excitation source, a monochromator (or any device capable of spectrally resolving the image, or a set of narrow band filters) and a detector array. The excitation source can comprise blue or UV wavelengths shorter than the emission wavelength(s) to be detected. This may be: a broadband UV light source, such as a deuterium lamp with a filter in front; the output of a white light source such as a xenon lamp or a deuterium lamp after passing through a monochromator to extract out the desired wavelengths; or any of a number of continuous wave (cw) gas lasers, including but not limited to any of the Argon Ion laser lines (457, 488, 514, etc. nm) or a HeCd laser; solid state diode lasers in the blue such as GaN and GaAs (doubled) based lasers or the doubled or tripled output of YAG or YLF based lasers; or any of the pulsed lasers with output in the blue.

The emitted light can be detected with a device that provides spectral information for the substrate, e.g., grating spectrometer, prism spectrometer, imaging spectrometer, or the like, or use of interference (bandpass) filters. Using a two-dimensional area imager such as a CCD camera, many objects may be imaged simultaneously. Spectral information can be generated by collecting more than one image via different bandpass, longpass, or shortpass filters (interference filters, or electronically tunable filters are appropriate). More than one imager may be used to gather data simultaneously through dedicated filters, or the filter may be changed in front of a single imager. Imaging based systems, like the Biometric Imaging system, scan a surface to find fluorescent signals.

A scanning system can be used in which the sample to be analyzed is scanned with respect to a microscope objective. The luminescence is put through a single monochromator or a grating or prism to spectrally resolve the colors. The detector is a diode array that then records the colors that are emitted at a particular spatial position. The software then recreates the scanned image.

When imaging samples labeled with multiple fluorophores, it is desirable to resolve spectrally the fluorescence from each discrete region within the sample. Such samples can arise, for example, from multiple types of SCNCs (and/or other fluorophores) being used to encode beads, from a single type of SCNC being used to encode beads but bound to a molecule labeled with a different fluorophore, or from multiple molecules labeled with different types of fluorophores bound at a single location. Many techniques have been developed to solve this problem, including Fourier transform spectral imaging (Malik et al. (1996) J. Microsc. 182:133; Brenan et al. (1994) Appl. Opt. 33:7520) and Hadamard transform spectral imaging, or simply scanning a slit or point across the sample surface (Colarusso et al. (1998) Appl. Spectrosc. 52: 106A), all of which are capable of generating spectral and spatial information across a two-dimensional region of a sample.

One-dimensional spectral imaging can easily be achieved by projecting a fluorescent image onto the entrance slit of a linear spectrometer. In this configuration, spatial information is retained along the y-axis, while spectral information is dispersed along the x-axis (Empedocles et al. (1996) Phys. Rev. Lett. 77(18):3873). The entrance slit restricts the spatial position of the light entering the spectrometer, defining the calibration for each spectrum. The width of the entrance slit, in part, defines the spectral resolution of the system.

Two-dimensional images can be obtained by eliminating the entrance slit and allowing the discrete images from individual points to define the spatial position of the light entering the spectrometer. In this case, the spectral resolution of the system is defined, in part, by the size of the discrete images. Since the spatial position of the light from each point varies across the x-axis, however, the calibration for each spectrum will be different, resulting in an error in the absolute energy values. Splitting the original image and passing one half through a dispersive grating to create a separate image and spectra can eliminate this calibration error. With appropriate alignment, a correlation can be made between the spatial position and the absolute spectral energy.

To avoid ambiguity between images that fall along the same horizontal line, a second beam-splitter can be added, with a second dispersive element oriented at 90 degrees to the original. By dispersing the image along two orthogonal directions, it is possible to unambiguously distinguish the spectra from each discrete point within the image. The spectral dispersion can be performed using gratings, for example holographic transmission gratings or standard reflection gratings. For example, using holographic transmission gratings, the original image is split into 2 (or 3) images at ratios that provide more light to the spectrally dispersed images, which have several sources of light loss, than the direct image. This method can be used to spectrally image a sample containing discrete point signals, for example in high throughput screening of discrete spectral images such as single molecules or ensembles of molecules immobilized on a substrate, and for highly parallel reading of spectrally encoded beads. The images are then projected onto a detector and the signals are recombined to produce an image that contains information about the amount of light within each band-pass.

Alternatively, techniques for calibrating point spectra within a two-dimensional image are unnecessary if an internal wavelength reference (the "reference channel") is included within the spectrally encoded material. The reference channel is preferably either the longest or shortest wavelength emitting fluorophore in the code. The known emission wavelength of the reference channel allows determination of the emission wavelengths of the fluorophores in the dispersed spectral code image. In addition to wavelength calibration, the reference channel can serve as an intensity calibration where coding schemes with multiple intensities at single emission wavelengths are used. Additionally, a fixed intensity of the reference channel can also be used as an internal calibration standard for the quantity of label bound to the surface of each bead.

In one system for reading spectrally encoded beads or materials, a confocal excitation source is scanned across the surface of a sample. When the source passes over an encoded bead, the fluorescence spectrum is acquired. By raster-scanning the point-excitation source over the sample, all of the beads within a sample can be read sequentially.

Optical tweezers can optionally be used to "sweep" spectrally encoded beads or any other type of bead into an ordered array as the beads are read. The "tweezers" can either be an infrared laser that does not excite any fluorophores within the beads, or a red laser that simultaneously traps the beads and also excites the fluorophores. Optical tweezers can be focused to a tight spot in order to hold a micron-size bead at the center of this spot by "light pressure."

Optical tweezers can be used to hold spectrally encoded beads and to order them for reading. The tweezers can be focused near the bottom of a well located at the center of the detection region of a point-scanning reader, which can use the same optical path. The reader and tweezers can be scanned together so that they are always in the same position relative to each other. For example, if the tweezers are turned on at spot-1, any bead contacted by the tweezers will be pulled into the center of the trap, ensuring an accurate quantitative measure of the assay label intensity. After reading the first bead, the tweezers are turned off to release it, and the scanner advances to the right just far enough to prevent the first bead from being retrapped before the tweezers are turned on again and then moved immediately to spot-2. In the process, any bead contacted by the tweezers would be trapped and brought to spot-2, where it is read. Choosing a scan distance that corresponds to the average interbead spacing can minimize bead loss from multiple beads occurring between sampling points.

Alternatively, the optical tweezers can be focused within the solution away from the surface of the well. As the tweezers are turned on and off, the solution is mixed, so that different beads are brought into the detection region and held while they are scanned. In another alternative, the optical tweezers can be focused in only one dimension, i.e., to a line rather than a spot, thus creating a linear trap region. This type of system can be used to sweep beads into distinct lines that can be scanned by a "line scanning" bead reader.

In another preferred embodiment, the photo-transferable coding agents comprise a mixture of different photocleavable nanocrystals conjugates, each with distinct spectral properties. The nanocrystals are coated with a surface such as an amine reactive polymer which allows covalent bonding of NHS-PC-biotin. The PC-biotin is used to link the nanocrystals to streptavidin-coated beads. Different compounds are attached to different coded beads using photocleavable conjugates described in this invention. The beads are allowed to directly contact the second surface. The beads are then illuminating causing photo-release and deposition of the compound and coding agents in the immediate vicinity of the bead. The beads are then removed from the surface leaving spots on second surface containing both the transferred compound and coding agents. Since the nanocrystals used in this embodiment contain amine reactive groups they will react with a variety of surfaces. The identity of the compound or compound mixture deposited in each spot is then determined by the spectral properties of the photo-transferred quantum dots.

Detection of Biomarkers

An additional embodiment of the invention is directed to the detection of biomarkers in a heterogeneous biological mixture including but not limited to blood, serum, stool, tissue, prenatal samples, fetal cells, nasal cells, urine, saliva and cerebrospinal fluid. Biomarkers can comprise of a variety of biomolecules or biomolecular complexes including proteins, nucleic acids, carbohydrates, steroids and combinations thereof. Biomarkers can also comprise of specific types of cells including but not limited to pathogens, bacteria, viruses, tissue cells, blood cells, colonocytes, fetal cells and tumor cells.

In one preferred embodiment, beads contain a coupling agent which selectively binds to the biomarker. The coupling agent is linked to the bead through a photocleavable conjugate. The beads are allowed to contact the heterogeneous sample which can contain the biomarker, separated from the heterogeneous sample and allowed to directly contact the second surface. The beads are then illuminated at preferred wavelengths which causes photo-transfer of the biomarker in a modified or unmodified form to the second surface. Conventional methods are then used to detect the presence of the biomarkers deposited on the second surface. Detection methods can include but are not limited to absorption spectroscopy, fluorescence spectroscopy, fluorescent resonance energy transfer, Raman spectroscopy, mass spectrometry, addition of a labeled antibody directed against the biomarker or addition to a fluorescent label which selectively interacts with the biomarker and not the affinity agent.

In another preferred embodiment, a plurality of beads comprising separately different coupling agents, each of which selectively binds to different biomarkers. The coupling agents are linked to the bead through one or more types of photocleavable conjugates. The beads are allowed to contact the heterogeneous sample which can contain one or more of the biomarkers, separated from the heterogeneous sample and allowed to directly contact the second surface. The beads are then illuminated at preferred wavelengths which causes photo-transfer of the biomarkers in a modified or unmodified form to the second surface. Conventional methods are then used to detect the presence of the different biomarkers deposited on the second surface. Detection methods can include but are not limited to absorption spectroscopy, fluorescence spectroscopy, fluorescent resonance energy transfer, Raman spectroscopy, mass spectrometry, addition of a labeled antibody directed against the biomarker or addition to a fluorescent label which selectively interacts with the biomarker and not the affinity agent.

In another preferred embodiment, a plurality of beads comprise different coupling agents which selectively bind to different biomarkers. The coupling agents are linked to the bead through one or more types of photocleavable conjugates. The beads are allowed to contact the heterogeneous sample which can contain one or more of the biomarkers, separated from the heterogeneous sample and allowed to directly contact the second surface. The beads are then illuminated at preferred wavelengths which causes photo-transfer of the biomarkers in a modified or unmodified form to the second surface. Conventional methods are then used to detect the presence of the different biomarkers deposited on the second surface. Detection methods can include but are not limited to absorption spectroscopy, fluorescence spectroscopy, fluorescent resonance energy transfer, Raman spectroscopy, mass spectrometry, addition of a labeled antibody directed against the biomarker or addition to a fluorescent label which selectively interacts with the biomarker and not the affinity agent.

In another preferred embodiment, a plurality of beads comprise different coupling agents which selectively bind to different biomarkers. In addition, the beads comprise coding agents which allow the identification of the beads and said coupling agents. The coupling agents are linked to the bead through one or more types of photocleavable conjugates. The beads are allowed to contact the heterogeneous sample which can contain one or more of the biomarkers, separated from the heterogeneous sample and allowed to directly contact the second surface. The beads are then illuminated at preferred wavelengths which causes photo-transfer of the biomarkers in a modified or unmodified form to the second surface. The coding agents are then used to determine the identity of the photo-transferred biomarker.

It is not intended that the present invention be limited to any particular type of coupling agent or biomarkers. Examples of useful coupling agents include molecules such as haptens, immunogenic molecules, biotin and biotin derivatives, and fragments and combinations of these molecules. For example, coupling agents can enable the selective binding or attachment of newly formed nascent proteins to facilitate their detection or isolation. Coupling agents may contain antigenic sites for a specific antibody, or comprise molecules such as biotin which is known to have strong binding to acceptor molecules such as streptavidin.

In addition, biomarkers may be (but are not limited to) small organic molecules, proteins, nucleic acids, carbohydrates and combinations thereof which are distinctive or change their concentrations in response to a disease, therapeutic or other stimulus. Examples include compounds sometimes found in an increased amount in the blood, other body fluids, or tissues and that may suggest the presence of some types of cancer. Biomarkers include CA 125 (ovarian cancer), CA 15-3 (breast cancer), CEA (ovarian, lung, breast, pancreas, and GI tract cancers), and PSA (prostate cancer) also called tumor markers.

A variety of coupling agents are available that can be used to selectively bind biomarkers. In many case, the biomarker will have antigenic properties reflecting one or more antigenic sites which will interact with antibodies, both polyclonal and monoclonal, directed at the particular antigenic site or sites on the biomarker.

In one embodiment, the attachment of the coupling agent to the bead occurs through a photocleavable conjugate. There are a variety of compositions which can be used to achieve such attachments. For example, photocleavable biotin may be covalently linked to a component of the coupling agent. Photocleavable biotin contains a photoreactive moiety which comprises a phenyl ring derivatized with functionalities represented in FIG. 12 in U.S. Pat. No. 5,922,858 specifically incorporated here by reference by X, Y and Z where X allows linkage of PCB to the bimolecular substrate through the reactive group X'. Examples of X' include Cl, O—N-hydroxysuccinimidyl, $OCH_2$ CN, $OPhF_5$, $OPhCl_5$, $N_3$. Y represents a substitution pattern of a phenyl ring containing one or more substitutions such as nitro or alkoxyl. The functionality Z represents a group that allows linkage of the cross-linker moiety to the photoreactive moiety.

The photoreactive moiety has the property that upon illumination, it undergoes a photoreaction that results in cleavage of the PCB molecule from the substrate. If the coupling agent is an antibody this can occur through a covalent bond to one or more amino acids present in the antibody. The presence of the photocleavable biotin will allow high affinity binding of the antibody coupling agent to avidin molecules coated onto a bead. In addition to beads, such suitable surfaces include resins for chromatographic separation, plastics such as tissue culture surfaces for binding plates, microtiter dishes, ceramics and glasses, particles including magnetic particles, polymers, quantum dots, nanocrystals and other matrices.

Figure 5:
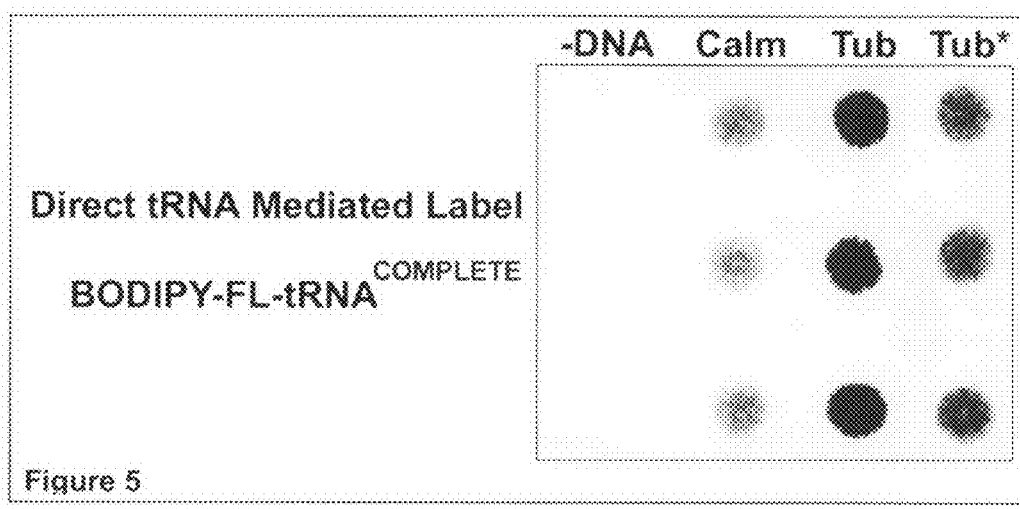
FIG. 5. Contact photo-transfer by incorporated PC-biotin of cell-free expressed, tRNA labeled and isolated proteins. Detection via the directly incorporated tRNA mediated fluorescence label.

One example of an antigenic site which illustrates the methods of this invention and can be present on a specially prepared biomarker is dansyllysine (FIG. 5 of U.S. Pat. No. 6,596,481 specifically incorporated here by reference). Antibodies which interact with the dansyl ring are commercially available (Sigma Chemical; St. Louis, Mo.) or can be prepared using known protocols such as described in Antibodies: A Laboratory Manual (E. Harlow and D. Lane, editors, Cold Spring Harbor Laboratory Press, 1988) which is hereby specifically incorporated by reference. Many conventional techniques exist which would enable proteins containing the dansyl moiety to be separated from other proteins on the basis of a specific antibody-dansyl interaction. For example, the antibody could be immobilized onto the packing material of a chromatographic column. This method, known as affinity column chromatography, accomplishes protein separation by causing the target protein to be retained on the column due to its interaction with the immobilized antibody, while other proteins pass through the column. The target protein is then released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.).

Separation can also be performed through an antibody-dansyl interaction using other biochemical separation methods such as immunoprecipitation and immobilization of the antibodies on filters or other surfaces such as beads, plates or resins. For example, protein could be isolated by coating magnetic beads with a protein-specific antibody. Beads are separated from the extract using magnetic fields. A specific advantage of using dansyllysine as an affinity marker is that once a protein is separated it can also be conveniently detected because of its fluorescent properties.

In addition to antibodies, a variety of other coupling agents are envisioned which can be coupled to beads through a photocleavable conjugate. One example are aptamers, which comprise single-stranded nucleic acids that form three-dimensional structures which specially bind to target molecules with high affinity and specificity (Mayer G, Grättinger M, and Blind M. Aptamers: Multifunctional tools for target validation and drug discovery. *DrugPlus international,* 2003, November-December, 6-10). A wide range of applications which normally use monoclonal antibodies can be substituted with aptamers. However, unlike antibodies which are proteins and will interact and stain with similar properties to biomarkers comprising (completely or in part) polypeptides, aptamers will not, thereby allowing detection of the bound biomarker. In contrast, detection of a biomarker using antibodies normally requires a second antibody. While this sandwich approach to detection of antigens is widely used in a variety of applications, the requirement of two antibodies which interact with the antigen is often difficult to achieve while maintaining strong binding and selectivity.

In one preferred embodiment, an aptamer which is selective for a specific biomarker is linker using a photocleavable conjugate to a bead. The bead is then allowed to contact a heterogeneous sample which could potentially contain the biomarker. The bead is then isolated and allowed to directly contact the surface. The beads are then illuminated causing photo-transfer of the biomarker-aptamer complex from each bead to the surface. The beads are then removed from the surface. The presence or absence of a biomarker is then determined using a dye which labels the biomarker selectively.

Mass Spectrometry

Another preferred embodiment of this invention is directed at analysis of target molecules by mass spectrometry. Mass spectrometry (MS) has become increasingly attractive as an analytical technique in biomedical research. Matrix assisted laser desorption time of flight mass spectrometry (MALDI-TOF MS) is now the core technology underlying the proteomics field because this method can quickly and accurately measure the masses of peptides in a mixture. Mass spectrometry also holds substantial potential for the rapid screening of disease causing genetic defects and the discovery of biomarkers (Koster, H., Tang, K., Fu, D. J., Braun, A., van den Boom, D., Smith, C. L., Cotter, R. J., and Cantor, C. R. (1996) *Nat Biotechnol* 14, 1123-1128). Importantly, very high throughputs are obtained because separation times are measured in microseconds rather than minutes or hours for conventional methods such as gel electrophoresis (Ross, P., Hall, L., Smirnov, I., and Haff, L. (1998) *Nat Biotechnol* 16, 1347-1351).

Mass spectrometry can be of great value in the detection and discovery of biomarkers, provided methods can be developed that can be used to rapidly isolate biomarkers from heterogeneous mixtures in a form suitable for mass spectrometric analysis. Methods which can isolate multiple biomarkers from a biological sample in a form suitable for mass spectrometric analysis are particularly advantageous due to the rapid ability of mass spectrometry to analyze each sample.

A variety of methods exist for selective absorption of biomolecules on a MALDI substrate from a heterogeneous mixture. Many of these methods depend on selective binding of molecules with particular physical properties such as hydrophobicity or hydrophilic to the surface. Other methods involve selective binding through coupling agents present on the surface of the MALDI substrate or on beads. Additional methods utilize affinity chromatography to select particular molecules from a heterogeneous mixture. However, these methods all suffer from various degrees of non-specific binding of non-target biomolecules to the affinity medium and ultimately deposition on the MALDI substrate. This problem can be particularly complicated when fingerprint analysis of the biomarker is performed via proteolysis such as tryptic digestion well known in the field of mass spectrometry. In this case, a protein is proteolyzed into smaller fragments and the molecular mass of the proteolytic fragments used to identify the target protein or target complex.

These problems are significantly reduced through the use of the methods and compositions of the present invention. Because only molecules that are linked to a surface (B) through a photocleavable conjugate are released to bind to a second MALDI surface (A), non-specific absorption is greatly reduced. Furthermore the use of a plurality of beads containing different coupling agents (e.g. antibodies) provides a means to perform multiplex biomarker detection. Alternatively, beads with common coupling agents can also be advantageously utilized in many applications as described later.

In one preferred embodiment, beads contain a coupling agent which selectively binds to a biomarker which may be present in a heterogeneous mixture. The said coupling agent is linked to the bead through a photocleavable conjugate. The beads are allowed to contact the heterogeneous sample which can contain the biomarker, separated from the heterogeneous sample and allowed to directly contact the MALDI second surface. The beads are then illuminated at preferred wavelengths which cause photo-transfer of the biomarker in a modified or unmodified form to the MALDI substrate. Mass spectrometry is then used to detect the presence of the biomarkers deposited on the second surface.

In another preferred embodiment, a plurality of beads contain different coupling agents which selectively bind to different biomarkers. In addition, the beads contain coding agents which allow the identification of the beads and said coupling agents. The said coupling agents are linked to the bead through one or more types of photocleavable conjugates. The beads are allowed to contact the heterogeneous sample which can contain one or more of the biomarkers, separated from the heterogeneous sample and allowed to directly contact the second surface. The beads are then illuminated at preferred wavelengths which causes photo-transfer of the biomarkers in a modified or unmodified form to the second surface. The coding agents are then used to determine the identity of the photo-transferred biomarker.

In one embodiment the method used to identify the photo-transferred coding agents, biomarker or biomarker complex is based on the use of mass spectrometry. For example, small polypeptides can serve as coding agents if they have unique masses compared to other coding agents. The mass of the proteolytic fragments from a transferred substance such as a biomarker or biomarker complex can also be used in order to uniquely identify it.

It is to be understood that the present invention is not limited to a particular MALDI substrate. However, some MALDI substrates are preferred because of the ability to adhere to a variety of biomarkers. In one preferred embodiment, a MALDI substrate is utilized which contains chemically reactive groups which form covalent bonds with a variety of biomolecules. One method which could be used to activate MALDI plates coated with gold, consists of soaking the surface with 4 mM solution of (Dithiobis-succinimidyl-proprionate (DTSP) in DMSO which results in the absorption of the N-succinimidyl-3-thiopropionate Darder, M., Takada, K., Pariente, F., Lorenzo, E., and Abruna, H. D. (1999) *Anal Chem* 71, 5530-5537. These groups will result in a MALDI plate surface which is expected to be highly reactive with amide groups in proteins. Another approach is to coat the MALDI plate with a nitrocellose surface. Such a surface is well known as advantageous for protein absorption. In one report (Miliotis, T., Marko-Varga, G., Nilsson, J., and Laurell, T. (2001) *J Neurosci Methods* 109, 41-46), nitrocellulose was coated on a MALDI target plate. An acetone solution consisting of matrix (10 mg/ml) and nitrocellose membrane (0.5 mg/ml) was precoated as thin film on the targets using an air-brush device. (Miliotis, T., Kjellstrom, S., Nilsson, J., Laurell, T., Edholm, L. E., and Marko-Varga, G. (2002) *Rapid Commun Mass Spectrom* 16, 117-126.).

Photo-Release of Targets from Beads for Improved Detection

An additional embodiment of the invention is directed to the detection of target molecules by a biomolecular detection device such as a microarray-based device. Target molecules are normally present in heterogeneous biological mixture including but not limited to blood, serum, stool, tissue, prenatal samples, fetal cells, nasal cells, urine, saliva and cerebrospinal fluid. Targets can also comprise agents in the environment including but not limited to allergens, toxins, pathogens, biowarfare agents. Environmental targets can be present in air, liquid, soil, surfaces, solids that are part of environment. Targets can comprise a variety of biomolecules or biomolecular complexes including biomarkers, proteins, nucleic acids, carbohydrates, steroids and combinations thereof. Targets can also consist of specific types of cells including but not limited to pathogens, bacteria, viruses, tissue cells, blood cells, colonocytes, fetal cells and tumor cells. Typically, targets are detected by their interaction with probes which are used as part of the target detection process. For example, probes are deposited on microarray substrates for subsequent possible interaction with targets in the sample comprising a heterogeneous mixture.

A major limitation of current microarray technology and more generally biomolecular detection is the difficulty of detecting with sufficient sensitivity and accuracy low levels of target molecules, especially when present in heterogeneous mixtures. For example, in the field of medical diagnostics the target biomolecule, which often serves as a biomarker include but are not limited to proteins, antigens, antibodies, cells and nucleic acid. These molecules are often present at very low concentrations in the presence of a complex mixture of other biomolecules.

In the case of basic research, a similar need exists for increased sensitivity to detect target biomolecules that are present in a heterogeneous mixture. For example, it is often essential to monitor the change in the level of biological molecules in specific cells, cell cultures or tissues in response to various stimuli. Furthermore, the volume of the fluid analyzed by the biomolecular detection device such as a microarray is often small, in the range of 10-100 microliters, thus limiting the number of target molecules available for binding to the probes. In the case of portable diagnostic devices such as glucose meters even smaller volumes, e.g. 1 microliters of blood are analyzed. The low volume and low concentration of target molecules can necessitate the use of time consuming, expensive techniques in order to concentrate the target molecules without destroying their activity. These methods are normally not compatible with the need for rapid measurements of targets.

In one preferred embodiment of this invention, the targets present in a heterogeneous mixture are bound to the bead using a photocleavable conjugate. The beads are then isolated and concentrated in a preferred solution. The target is then photo-released from the bead in a modified or unmodified form and the beads removed. The photo-released target molecules are then allowed to interact with the probes.

In another preferred embodiment of the invention, the targets present in a heterogeneous mixture are bound to the bead using a photocleavable conjugate. The beads are then isolated and concentrated in a preferred solution. The target is then allowed to interact with the probes and subsequently photo-released from the bead in a modified or unmodified form.

In another preferred embodiment of the invention, the targets present in a heterogeneous mixture are bound to the bead using a photocleavable conjugate. The beads are then isolated and concentrated in a preferred solution which is introduced to the biomolecular detection device.

It is to be understood that in these embodiments, the method is not limited by the nature of the target. Targets can consist but not limited to compounds, molecules, biomolecules, macromolecules and cells which are ordinarily present in a heterogeneous mixture such as blood sera and. Molecules and macromolecules comprise but are not limited to proteins, peptides, amino acids, amino acid analogs, nucleic acids, nucleosides, nucleotides, lipids, vesicles, detergent micelles, cells, virus particles, fatty acids, saccharides, polysaccharides, inorganic molecules and metals.

The invention is also not limited by the nature of the beads, which could be composed of a variety of materials including but not limited to organic or inorganic molecules, polymer, solid-state materials such as metals or semiconductors, biological materials, sol gels, colloids, glass, paramagnetic and magnetic materials, electrostatic materials, electrically conducting materials, insulators, fluorescent materials, absorbing material and combinations thereof. The beads may also vary in size, shape and density. For example beads may range in size from 20 nanometers to hundreds of microns depending on the application and spot size desired for different applications. The beads may also be polydisperse in regards to size, shape, material composition, optical, magnetic, electrical properties. Beads may also consist of aggregates of smaller beads.

In one preferred embodiment the target is a specific IgE antibody which is present in blood. The beads contain an anti-IgE antibody attached to the bead through a photocleavable conjugate. The beads are allowed to contact the blood sample and then are isolated and concentrated in a buffer solution. The IgE-anti IgE complex is then photo-released from the beads into the buffer solution. The solution is then introduced into the microarray chamber for subsequent detection of IgE molecules which have a specificity to interact with specific probe allergens on the array surface.

In another preferred embodiment the target is a specific IgE antibody which is present in blood. The beads contain a specific allergen which serves as an antigen for the specific IgE target molecules. The allergen is attached to the bead through a photocleavable conjugate. The beads are allowed to contact the blood sample and then are isolated and concentrated in a buffer solution. The IgE-allergen complex is then photo-released from the beads into the buffer solution. The solution is then introduced into the microarray device for subsequent detection of the IgE allergen complex by a probe molecule. Probe molecules can consist of an antibody directed against the allergen.

In another preferred embodiment the target is a protein biomarker present in blood. The beads contain an antibody directed against the biomarker which is attached to the bead through a photocleavable conjugate. The beads are allowed to contact the blood sample and then are isolated and concentrated in a buffer. The biomarker-antibody complex is then photo-released from the bead into the buffer solution and the beads removed. The solution is then introduced into the microarray device for subsequent detection of biomarker-antibodies complex by specific probe antibodies present on the microarray surface.

It is to be understood that the invention is not limited by the number targets detected. For example, a plurality of beads can be prepared such that some beads are coated with antibodies directed towards target X, while other beads contain antibodies directed towards target Y. In the general case where the microarray is designed to detect N different targets, N different types of beads, each bead type with a corresponding antibody, are prepared. Each of the antibodies are attached to the beads through a photocleavable conjugate using for example photocleavable biotin. In addition to antibodies, aptamers can be utilized for capture of the target molecule.

Photocleavable Conjugates

Probes as referred to herein, as those compounds being deposited on a surface using the agents, conjugates and methods of the invention. Targets are referred to herein as those compounds detected using the agents, conjugates and methods of the invention. Substrates, as referred to herein, are those compounds which are covalently attached to the bioreactive agent. Substrates may also be referred to as targets when the target being identified specifically binds to the bioreactive agent.

Photocleavable conjugates are described in U.S. Pat. No. 5,986,076, which is specifically incorporated by reference, and variations thereof described in U.S. Pat. Nos. 6,057,096 and 6,589,736 which are also specifically incorporated by reference. Photocleavable conjugates comprise bioreactive agents photocleavable coupled to substrates. Conjugates have the property that they can be selectively cleaved with electromagnetic radiation to release the substrate. Substrates are those chemicals, compounds, macromolecules, cells and other compounds which are or can be used to couple probes or targets. Substrates that are selectively cleaved from conjugates may be modified by photocleavage or may be released from the conjugate completely unmodified by photocleavage. Substrates may be coupled with agents, uncoupled and recoupled to new agents at will.

Agents of the invention comprise a detectable moiety and a photoreactive moiety, and can be covalently coupled to a variety of substrates to form a photocleavable conjugate. A covalent bond between agent and substrate can be created from a wide variety of chemical moieties including amines, hydroxyls, imidazoles, aldehydes, carboxylic acids, esters and thiols. Agent-substrate combinations are referred to herein as conjugates. Through the presence of the detectable moiety, conjugates can be quickly and accurately bound to a bead or used to isolate a probe or target. Further, these conjugates are selectively cleavable which provides unique advantages in isolation procedures and release of the probe or target for subsequent deposition on the array surface or detection. Substrate can be separated from agent quickly and efficiently. Complex technical procedures and highly trained experts are not required. New attachment and separation procedures do not need to be developed for every new probe or target to be used with a microarray. Following isolation of probe or target, it is a relatively simple matter to treat the conjugate with electromagnetic radiation and release the substrate. Released substrate is preferably functionally active and structurally unaltered. Nevertheless, minor chemical alterations in the structure may occur depending on the point of attachment. It is generally preferred that such alterations not affect functional activity. However, when functional activity does not need to be preserved, such changes are of no considerations and may even be useful to for delivering probe or target to microarray by methods of the invention.

It is not intended that the present invention be limited to the nature of the particular photocleavable conjugates. A variety of photocleavable conjugates are contemplated, including conjugates that photocleave over a variety of infrared, visible and UV wavelengths. Nonetheless, compared to many other photocleavable conjugates, several have been empirically found to have very efficient quantum yields for photocleavage and are not sensitive under normal laboratory conditions to photocleavage. They include reagents and compounds described in U.S. Pat. No. 5,986,076 "Photocleavable agents and conjugates for the detection and isolation of biomolecules" and U.S. Pat. Nos. 6,057,096 and 6,589,736, hereby incorporated by reference.

Useful substrates are any chemical, macromolecule or cell that can be attached to a bioreactive agent. Examples of useful substrates include proteins, peptides, amino acids, amino acid analogs, nucleic acids, nucleosides, nucleotides, lipids, vesicles, detergent micells, cells, virus particles, fatty acids, saccharides, polysaccharides, inorganic molecules and metals. Substrates may also comprise derivatives and combinations of these compounds such as fusion proteins, protein-carbohydrate complexes and organo-metallic compounds. Substrates may also be pharmaceutical agents such as cytokines, immune system modulators, agents of the hematopoietic system, recombinant proteins, chemotherapeutic agents, radio-isotopes, antigens, anti-neoplastic agents, enzymes, PCR products, receptors, hormones, vaccines, haptens, toxins, antibiotics, nascent proteins, synthetic pharmaceuticals and derivatives and combinations thereof. Substrates may also be aptamers comprised of nucleic acid.

Substrates may be probes or targets or part of the probes or targets such as an amino acid in the synthesis of nascent polypeptide chains wherein substrates may be amino acid or amino acid derivative which becomes incorporated into the growing peptide chain. Substrates may also be nucleotides or nucleotide derivatives as precursors in the synthesis of a nucleic acid. Constructs useful in creating synthetic oligonucleotide conjugates may contain phosphoramidites or derivatives of DATP, dCTP, dTTP and dGTP, and also ATP, CTP, UTP and GTP. Resulting nucleic acid-conjugates can be used in hybridization technology as both targets and probes.

Photocleavage of conjugates of the invention should preferably not damage released substrate or impair substrate activity. Proteins, nucleic acids and other protective groups used in peptide and nucleic acid chemistry are known to be stable to most wavelengths of radiation above 300 nm. PCB carbamates, for example, undergo photolysis upon illumination with long-wave UV light (320-400 nm), resulting in release of the unaltered substrate and carbon dioxide. The yield and exposure time necessary for release of substrate photo-release are strongly dependent on the structure of photoreactive moiety. In the case of un-substituted 2-nitrobenzyl PCB derivatives the yield of photolysis and recovery of the substrate are significantly decreased by the formation of side products which act as internal light filters and are capable of reacting with amino groups of the substrate. In this case, illumination times vary from about 1 minute to about 24 hours, preferably less than 4 hours, more preferably less than two hours, and even more preferably less than one hour, and yields are between about 1% to about 95% (V. N. R. Pillai, Synthesis 1, 1980). In the case of alpha-substituted 2-nitrobenzyl derivatives (methyl, phenyl), there is a considerable increase in rate of photo-removal as well as yield of the released substrate (J. E. Baldwin et al., Tetrahedron 46:6879, 1990; J. Nargeot et al., Proc. Natl. Acad. Sci. USA 80:2395, 1983).

It is not intended that the present invention be limited to the nature of the attachment of the photocleavable conjugate to a bead surface. Examples of the chemical structure of conjugates of the invention include: a structure described in U.S. Pat. No. 5,986,076 (Structure 5) specifically incorporated here by reference wherein SUB comprises a substrate; $R_1$ and $R_2$ are selected from the group consisting of hydrogen, alkyls, substituted alkyls, aryls, substituted aryls, —$CF_3$, —$NO_2$, —COOH and —COOR, and may be the same or different; A is a divalent functional group selected from the group consisting of —O—, —S— and —$NR_1$; Y comprises one or more polyatomic groups which may be the same or different; V comprises one or more optional monoatomic groups which may be the same or different; Q comprises an optional spacer moiety; m1 and m2 are integers between 1-5 which can be the same or different; and D comprises a selectively detectable moiety which is distinct from $R_1$ and $R_2$.

Figure 8:
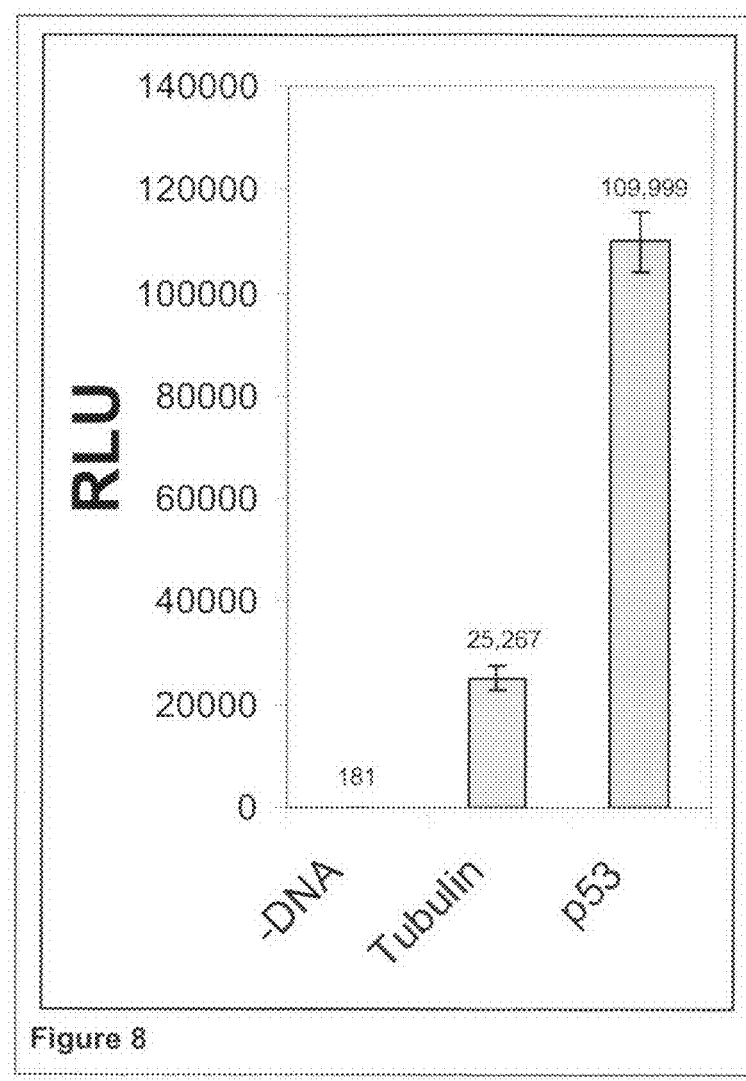
FIG. 8. Photo-transfer by incorporated PC-biotin of cell-free expressed, tRNA labeled and isolated proteins. Transfer to the uncoated surface of 96-well polystyrene microtiter plates. Detection by antibody.

As discussed above, the polyatomic group may be one or more nitro groups, alkyl groups, alkoxyl groups, or derivatives or combinations thereof. The optional monoatomic group may be one or more fluoro, chloro, bromo or iodo groups, or hydrogen. The polyatomic and monoatomic groups and the chemical moieties at $R_1$ and $R_2$ may effect the photocleavage reaction such as the frequency of radiation that will initiate photocleavage or the exposure time needed to execute a cleavage event. The spacer moiety (Q) may be a branched or unbranched hydrocarbon or a polymeric carbohydrate and is preferably represented by the formula described in U.S. Pat. No. 5,986,076 (Structure 6 specifically incorporated here by reference) wherein W and W' are each selected from the group consisting of —CO—, —CO—NH—, —HN—CO—, —NH—, —O—, —S— and —$CH_2$-, and may be the same or different; and n1 and n2 are integers from 0-10 which can be the same or different and if either n1 or n2 is zero, then W and W' are optional. Specific examples of conjugates of the invention are depicted in FIG. 8 of U.S. Pat. No. 5,986,076 specifically incorporated here by reference.

In addition, it is not intended that the invention be limited to only bead surfaces. Conjugates of the invention may be attached to a solid support via the detectable moiety, the substrate or any other chemical group of the structure. The solid support may comprise constructs of glass, ceramic, plastic, metal or a combination of these compounds. In addition to beads and microbeads, useful structures and constructs include plastic structures such as microtiter plate wells or the surface of sticks, paddles, alloy and inorganic surfaces such as semiconductors, two and three dimensional hybridization and binding chips, and magnetic beads, chromatography matrix materials and combinations of these materials.

Nascent Proteins

One of the preferred embodiments of the invention relates to the deposition of protein on a surface. In one application of this embodiment, photocleavable biotin (PCB) is reacted with a protein through the formation of covalent bonds with specific chemicals groups of the protein thereby forming a conjugate. The protein may be either the target to be isolated or detected or a probe for the target protein such as an antibody. The target protein can then be isolated using streptavidin affinity methodology. For example beads that are coated with streptavidin are used to capture the target or probe protein. This protein is then photo-released for subsequent transfer to a surface such as part of a microarray device.

Another application of this embodiment is directed to the use of photocleavable biotin to deposit nascent proteins that can be created from in vitro or in vivo protein synthesis on a surface. Basically, in this embodiment, photocleavable biotins are synthesized and linked to amino acids (PCB-amino acids) containing special blocking groups. These conjugates are charged to tRNA molecules and incorporated into peptides and proteins using a translation or coupled transcription/translation system. PCB-amino acids of the invention have the property that once illuminated with light, a photocleavage occurs that produces a native amino acid plus the free biotin derivative. Such proteins can be photo-released in a structurally and/or functionally unaltered form for contact photo-transfer to a surface or for detection by a biomolecular device.

The detailed procedure for the production of photocleavable biotin amino acids and their incorporation into the nascent proteins involves a few basic steps. First, photocleavable biotin is synthesized and linked to an amino acid with an appropriate blocking group. These PCB-amino acid conjugates are charged to tRNA molecules and subsequently incorporated into nascent proteins in an in vivo or in vitro translation system. Alternatively, a tRNA molecule is first charged enzymatically with an amino acid such as lysine which is then coupled to a reactive PCB. Nascent proteins are separated and isolated from the other components of synthesis using immobilized streptavidin. Photocleavage of PCB-streptavidin complex from the nascent protein generates a pure and native, nascent protein.

Figure 9:
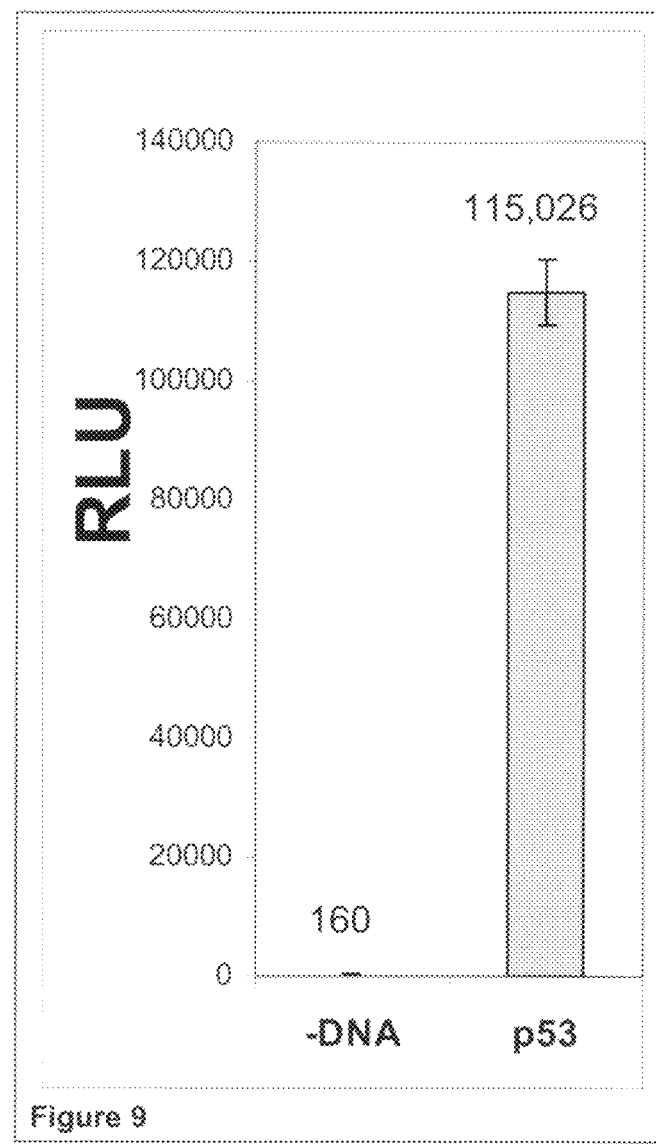
FIG. 9. Photo-transfer by incorporated PC-biotin of cell-free expressed, tRNA labeled and isolated proteins. Transfer to the antibody coated surface of 96-well polystyrene microtiter plates. Both capture on plate and detection achieved with antibodies in a standard sandwich ELISA format.

PCB is attached to an amino acid using, for example, the side-chain groups such as an amino group (lysine), aliphatic and phenolic hydroxyl groups (serine, threonine and tyrosine), sulfydryl group (cysteines) and carboxylate group (aspartic and glutamic acids) (FIG. 9 of U.S. Pat. No. 5,986,076 specifically incorporated here by reference). Synthesis can be achieved by direct condensations with appropriately protected parent amino acids. For example, lysine side chain amino group can be modified with PCB by modification of the epsilon amino group. The synthesis of, for example, PCB-methionine involves primarily alpha amino group modification. PCB-methionine can be charged to an initiator tRNA which can participate in protein synthesis only at initiation sites which results in single PCB incorporation per copy of the nascent protein.

Figure 10:
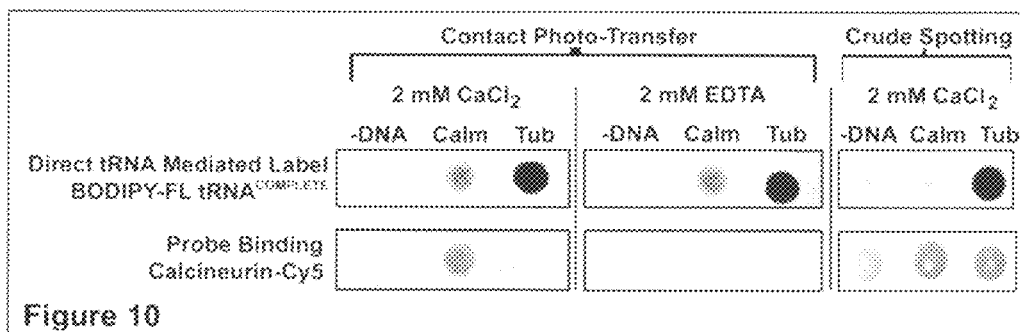
FIG. 10. Advanced 2 color fluorescence calcineurin-calmodulin protein-protein interaction assays on microarrays prepared with and without the contact photo-transfer method.

One method for incorporation of a photocleavable biotin amino acid into a nascent protein involves misaminoacylation of tRNA. Normally, a species of tRNA is charged by a single, cognate native amino acid. This selective charging, termed here enzymatic aminoacylation, is accomplished by enzymes called aminoacyl-tRNA synthetases and requires that the amino acid to be charged to a tRNA molecule be structurally similar to a native amino acid. Chemical misaminoacylation can be used to charge a tRNA with a non-native amino acids such as photocleavable amino acids. The specific steps in chemical misaminoacylation of tRNAs are depicted in FIG. 10 of U.S. Pat. No. 5,986,076 specifically incorporated here by reference.

As shown, tRNA molecules are first truncated to remove the 3'-terminal residues by successive treatments with periodate, lysine (pH 8.0) and alkaline phosphate (Neu et al., J. Biol. Chem. 239:2927-34, 1964). Alternatively, truncation can be performed by genetic manipulation, whereby a truncated gene coding for the tRNA molecule is constructed and transcribed to produce truncated tRNA molecules (Sampson et al., Proc. Natl. Acad. Sci. USA 85:1033, 1988). Second, protected acylated dinucleotides, pdCpA, are synthesized (Hudson, J. Org. Chem. 53:617, 1988; E. Happ, J. Org. Chem. 52:5387, 1987). PCB-amino acids blocked appropriately at their side chains and/or at a-amino groups, using standard protecting groups like Fmoc, are prepared and coupled with the synthetic dinucleotide in the presence of carboxy group activating reagents. Subsequent deprotection of Fmoc groups yields aminoacylated dinucleotide.

Third, the photocleavable biotin amino acid is ligated to the truncated tRNA through the deprotected dinucleotide. The bond formed by this process is different from that resulting from tRNA activation by an aminoacyl-tRNA synthetase, however, the ultimate product is the same. T4 RNA ligase does not recognize the O-acyl substituent, and is thus insensitive to the nature of the attached amino acid (FIG. 10 of U.S. Pat. No. 5,986,076 specifically incorporated here by reference). Misaminoacylation of a variety of non-native amino acids can be easily performed. The process is highly sensitive and specific for the structures of the tRNA and the amino acid.

Aminoacylated tRNA linked to a photocleavable biotin amino acid can also be created by employing a conventional aminoacyl synthetase to aminoacylate a tRNA with a native amino acid or by employing specialized chemical reactions which specifically modify the native amino acid linked to the tRNA to produce a photocleavable biotin aminoacyl-tRNA derivative. These reactions are referred to as post-aminoacylation modifications. Such post-aminoacylation modifications do not fall under the method of misaminoacylation, since the tRNA is first aminoacylated with its cognate described amino acid.

In contrast to chemical aminoacylation, the use of post-aminoacylation modifications to incorporate photocleavable biotin non-native amino acids into nascent proteins is very useful since it avoids many of the steps including in misaminoacylation. Furthermore, many of the photocleavable biotin derivatives can be prepared which have reactive groups reacting specifically with desired side chain of amino acids. For example, postaminoacylation modification of lysine-tRNA.sup.Lys, an N-hydroxysuccinimide derivative of PCB can prepared that would react with easily accessible primary epsilon amino and minimize reactions occurring with other nucleophilic groups on the tRNA or alpha-amino groups of the amino acylated native amino acid. These other non-specific modifications can alter the structure of the tRNA structure and severely compromise its participation in protein synthesis. Incomplete chain formation could also occur when the alpha-amino group of the amino acid is modified. Post-aminoacylation modifications to incorporate lysine-biotin non-native amino acids into nascent proteins has been demonstrated (Promega's Transcend tRNA; Promega; Madison, Wis.) used for the detection of nascent protein containing biotin using Western Blots followed by enzymatic assays for biotin (T. V. Kurzchalia et al., Eur. J. Biochem. 172:663-68, 1988). However, these biotin derivatives are not photocleavable which, in the case of NHS-derivatives of PCB, allows the biotin linkage to the lysine to be photochemically cleaved.

PCB-amino acids can also be incorporated into polypeptide by means of solid-support peptide synthesis. First, PCB-amino acids are derivatized using base labile fluorenylmethyloxy carbonyl (Fmoc) group for the protection of alpha-amino function and acid labile t-butyl derivatives for protection of reactive side chains. Synthesis is carried out on a polyamide-type resin. Amino acids are activated for coupling as symmetrical anhydrides or pentafluorophenyl esters (E. Atherton et al., Solid Phase Peptide Synthesis, IRL Press, Oxford, 1989). Second, amino acids and PCB are coupled and the PCB-amino acid integrated into the polypeptide chain. Side chain PCB-derivatives, like epsilon-amino-Lys, side chain PCB-amino acid esters of Glu and Asp, esters of Ser, Thr and Tyr, are used for incorporation at any site of the polypeptide. PCB-amino acids may also be incorporated in a site-specific manner into the chain at either predetermined positions or at the N-terminus of the chain using, for example, PCB-derivatized methionine attached to the initiator tRNA.

A wide range of polypeptides can be formed from PCB-amino acids cytokines and recombinant proteins both eukaryotic and prokaryotic (e.g. alpha-, beta- or gamma-interferons; interleukin-1, -2, -3, etc.; epidermal, fibroblastic, stem cell and other types of growth factors), and hormones such as the adrenocorticotropic hormones (ACTHs), insulin, the parathyroid hormone (bPTH), the transforming growth factor .beta. (TGF-.beta.) and the gonadotropin releasing hormone (GnRH) (M. Wilchek et al., Methods Enzymol. 184: 243, 1990; F. M. Finn et al., Methods Enzymol. 184:244, 1990; W. Newman et al., Methods Enzymol. 184:275, 1990; E. Hazum, Methods Enzymol. 184:285, 1990). These hormones retain their binding specificity for the hormone receptor. One example is the GnRH hormone where a biotin was attached to the epsilon amino group Lys-6 through reaction of a d-biotin p-nitophenyl ester. This biotinylated hormone can be used for isolation of the GnRH receptor using avidin coated columns.

After incorporation or attachment of PCB into a protein, protein-complex or other amino acid-containing target, the target is isolated using a simple four step procedure (FIG. 11 of U.S. Pat. No. 5,986,076 specifically incorporated here by reference). First, a bioreactive agent (PCB) is synthesized. Second, a substrate is coupled to the bioreactive agent forming a conjugate. Third, target is separated from other materials in the mixture through the selective interaction of the photocleavable biotin with avidin, streptavidin or their derivatives. Captured targets may be immobilized on a solid support such as magnetic beads, affinity column packing materials or filters which facilitates removal of contaminants. Finally, the photocleavable biotin is detached from the target by illumination of a wavelength which causes the photocleavable biotin covalent linkage to be broken. Targets are dissolved or suspended in solution at a desired concentration. In those situations wherein conjugate coupled targets are not attached to solid supports, release of targets can be followed by another magnetic capture to remove magnetic particles now containing avidin/streptavidin bound biotin moiety released form the photocleavage of PCB. Thus, a completely unaltered protein is released in any solution chosen, in a purified form and at nearly any concentration desired.

In one embodiment of this invention, nascent proteins are produced in an in vitro or in vivo translation system using misaminoacylated tRNAs to incorporate photocleavable biotin. The nascent protein is captured using beads coated with streptavidin. The beads are used to contact a surface and illuminated with light to transfer said nascent proteins to surface.

Another embodiment of this invention is directed at constructing a proteomic microarray which is used to probe protein-protein interactions. The conventional method of protein expression profiling/identification in normal and diseased states relies on the use of 2D gel electrophoresis and mass spectrometry. While this approach has been invaluable in proteomics, recent studies show that approximately 40% of cellular proteins, many involved in key process such as transcription control, are missed because of their low concentrations (e.g. low copy number) in the cell. In addition, 2D gel electrophoresis is a relatively slow process and not compatible with the high throughput needed to map the vast number of protein-protein interactions that occur in the cell. It is also not suitable for use in clinical studies where large numbers of patients are involved. Finally, 2D gel technology is unable to probe the function of each of the proteins comprising the proteome, a critical requirement for future progress.

As an alternative to gel electrophoresis, many researchers and commercial companies have begun exploring the use of protein microarrays (Zhu, H., Bilgin, M., Bangham, R., Hall, D., Casamayor, A., Bertone, P., Lan, N., Jansen, R., Bidlingmaier, S., Houfek, T., Mitchell, T., Miller, P., Dean, R. A., Gerstein, M., and Snyder, M. (2001) Science 293, 2101-2105; Zhu, H., and Snyder, M. (2001) Curr Opin Chem Biol 5, 40-45). Such arrays have the advantage that they in principle can provide the high sensitivity and speed not available using gel electrophoresis. In addition, protein arrays can be used to study protein function. However, unlike DNA arrays, where oligonucleotide probes for each gene can be readily synthesized, creating a set of capture elements for most proteins in the proteome is significantly more difficult.

An attractive alternative is to array the proteome of a specific organism on a chip. Such a proteome array would be highly suitable for mapping protein-protein interactions, probing the function of specific proteins in the array, and discovering biomarkers of specific diseases. For example, many protein components of a particular cell are likely to interact and in some cases enzymatically modify proteins from the array. Such interactions/modifications provide a specific profile which is likely to change between normal and diseased state. Clinical samples such as blood and urine are also likely to contain protein biomarkers, especially in the case of infectious disease where components of the pathogen or antibodies which are developed against it are present.

In one embodiment aimed a fabricating a proteomic array, a plurality of nascent proteins are expressed by in vitro or in vivo protein synthesis systems and attached to beads through photocleavable conjugates. Beads may contain a single species of protein or a mixture of different species. Beads are deposited on a surfaces using the direct contact photo-transfer method described in this invention. The deposited nascent proteins are then used as probes for a microarray that can detect possible interaction of specific biomolecules with the nascent protein array.

A major advantage of this approach is that custom made microarrays can be rapidly produced by selecting only those beads which carry the probes which are desired to be used for the microarray experiment. Until this decision is made, proteins are stored on beads and then deposited on a microarray substrate by direct contact photo-transfer.

In one example, an assortment of beads carrying different nascent proteins are mixed together in a small volume of buffer and allowed to contact the microarray surface. The beads are then irradiated and removed. This results in a set of spots on the microarray surface, each containing a different protein.

Cell-Free Synthesis of Nascent Proteins on Beads for Probes, Targets and Coding Agents One preferred embodiment of this invention is directed at the synthesis of nascent proteins on the surface of a bead, the attachment of said protein to said bead through a photocleavable linker and the subsequent photo-release of said nascent protein. In this embodiment, the coding DNA or RNA (nucleic acid template) for the nascent protein is attached directly to the bead along with a coupling agent for said nascent protein. A photocleavable linker is incorporated directly into the nascent protein during its synthesis using tRNA based methods described in this invention. Alternatively, the said coupling agent is attached to bead through a photocleavable linker. A preferred embodiment is the incorporation of the photocleavable linkers NHS-PC-biotin into said nascent protein, whereas the coupling agent on the bead is streptavidin. A second preferred embodiment is the use of an antibody which is directed at an epitope incorporated into said nascent proteins and encoded by the attached nucleic acid template through a photocleavable linker such as NHS-PC-biotin which binds to streptavidin on the bead surface. The synthesis of nascent proteins using nucleic acid template attached to a planar surface and its subsequent capture by tethered non-photocleavable antibodies has already been described (Ramachandran, N., Hainsworth, E., Bhullar, B., Eisenstein, S., Rosen, B., Lau, A. Y., Walter, J. C., and LaBaer, J. (2004) *Science* 305, 86-90).

It is to be understood that this invention allows for a plurality of nascent proteins to be synthesized and attached to a plurality of beads. For example, different nucleic acid templates can be attached to different beads thereby allowing the nascent proteins which each template codes for to become photocleavable attached to the corresponding bead. Thus bead type A which attaches nucleic acid template A and codes for nascent protein A, will capture primarily nascent protein A. Whereas, bead type B which attaches nucleic acid template B and codes for nascent protein B, will capture primarily nascent protein B. Using this method, a large number of different nascent proteins can be synthesized in a cell free mixture and become attached to a large number of specific beads containing the corresponding nucleic acid template coding for said nascent protein.

In one preferred embodiment, each bead has a DNA template and streptavidin or NeutrAvidin attached to the surface. The beads are placed in a coupled rabbit reticulocyte transcription/translation system such as sold by Promega Corp. along with tRNA which incorporates PC-biotin into various amino acid positions in the protein as described in U.S. Pat. No. 6,210,941 and is hereby incorporated by reference. After incubation of the beads for less than 1 hour (e.g. between 15 and 45 minutes, more preferably for 30 minutes), the beads are removed from the rabbit reticulocyte system and washed. The beads are then deposited on Epoxy coated glass in a solution and allowed to settle on said slide. The slide is then illuminated with light with wavelengths longer than 300 nm (e.g. between 300 nm and 400 nm, more preferably between 300 nm and 360 mm) for a period of time (less than one hour, more preferably less than 30 minutes, still more preferably between 1 and 10 minutes). The beads are then washed from the slide with a stream of water.

In one preferred embodiment, the DNA template is attached to the streptavidin through a photocleavable biotin. There are a variety of methods which will be known to those skilled in the area of nucleic acid chemistry to attach photocleavable biotin to DNA. One such method involves incorporating photocleavable biotin at the 5' end of the DNA which is chemically synthesized using a PC-biotin phosphoramidite as described previously [Olejnik, J., Krzymanska-Olejnik, E., and Rothschild, K. J. (1996) *Nucleic Acids Research* 24, 361-366] and sold commercially by Glen Research Corporation and also described in U.S. Pat. No. 5,986,076 and hereby incorporated by reference. An alternative method is to utilize primers containing the 5' PC-biotin in order to amplify a DNA sequence of interest. In both cases, after incubation of the beads for less than 1 hour (e.g. between 15 and 45 minutes, more preferably for 30 minutes), the beads are removed from the rabbit reticulocyte system and washed. The beads are then deposited on a slide in a solution and allowed to settle on said slide. The slide is then illuminated with light with wavelengths longer than 300 nm (e.g. between 300 nm and 400 nm, more preferably between 300 nm and 360 nm) for a period of time (less than one hour, more preferably less than 30 minutes, still more preferably between 1 and 10 minutes) thereby allowing both the said nascent protein and DNA template to be transferred to said slide. The beads are then removed from the slide.

The transfer of the template DNA and the nascent protein for which it codes to the same spot on a slide provides an effective coding agent for the nascent protein. For example, the identity of the template DNA can be subsequently determined using a number of methods well known in the field including the use of polymerase chain reaction, hybridization probes or a combination of both. One such method is part of the Illumina's SNP decoding technology and recently described [Gunderson, K. L., Kruglyak, S., Graige, M. S., Garcia, F., Kermani, B. G., Zhao, C., Che, D., Dickinson, T., Wickham, E., Bierle, J., Doucet, D., Milewski, M., Yang, R., Siegmund, C., Haas, J., Zhou, L., Oliphant, A., Fan, J. B., Barnard, S., and Chee, M. S. (2004) *Genome Res* 14, 870-877].

In another preferred embodiment the nascent proteins synthesized on a bead using the attached template nucleic acid are coded for using a variety of other coding agents which are attached to the bead and described previously in this invention. In one embodiment, the coding agents consist of quantum dots which are specifically attached to the bead through a photocleavable linker, thereby allowing direct contact photo-transfer of the quantum dots to a surface along with the said nascent proteins. It is to be understood that all of the methods and compositions described under section II can be applied equally as well to coding for nascent proteins synthesized on a bead using an attached nucleic acid template.

In one especially preferred embodiment, the coding agent is a nascent protein that is synthesized on the bead surface. For example, a nucleic acid which codes for one of a variety of different green fluorescent protein can be used to produce the green fluorescent protein that serves as a coding agent.

The concept of cell-free synthesis of a protein on the surface of a bead which can be photo transferred to a surface is useful in a variety of applications including molecular diagnostics and proteomics. One preferred embodiment is related to the creation of a customized protein arrays. The creation of such protein arrays are especially attractive when a differential gene expression analysis reveals that particular disease related cell types exhibit abnormal gene expression. In such cases it is highly desirable to move beyond transcriptional activity in order to understand the basis of the disease state. In this case, the state of individual proteins and their interactions in a diseased cell which correspond to those proteins coded by abnormally expressed genes can be explored.

Libraries of In Vitro Expressed Proteins

In one preferred embodiment, primer pairs are attached to individual beads. Said primer pairs are designed to amplify specific nucleic acid sequences in a sample such as genomic DNA or mRNA using BRIDGE amplification, a solid phase PCR amplification technology also referred to as solid phase amplification (SPA). (see Promega Catolog; Adessi, C., G. Matton, G. Ayala, G. Turcatti, J.-J. Mermod, P. Mayer, and E. Kawashima. 2000. Solid phase amplification: characterisation of primer attachment and amplification mechanisms. Nucleic Acids Res. 28:e87 and Bing, D. H., C. Boles, F. N. Rehman, M. Audeh, M. Belmarsh, B. Kelley, and C. P. Adams; 1996. Bridge amplification: a solid phase PCR system for the amplification and detection of allelic differences in single copy genes In Genetic Identity Conference Proceedings, Seventh International Symposium on Human Identification; Jean-Francois Mercier, Gary W. Slater, and Pascal Mayer, Biophysical Journal Volume 85 October 2003 2075-2086). In this embodiment, the beads are then exposed to genomic DNA or mRNA and BRIDGE PCR(SAP) performed under conditions that are designed to amplify specific nucleic acid sequences in the sample including but not limited to entire genes or regions of genes. The beads which will have after the previous step amplified DNA attached to them are then placed in a cell-free protein synthesis system and the attached DNA sequences used as templates for protein transcription and translation as described previously. One example of such a cell-free protein system is rabbit reticulocyte which is capable of supporting both transcription and translation. A second system is a reconstituted *E. coli* an example of which is the reconstituted system available from Post Genome Institute Co., Ltd. (Japan) called PURESYSTEM. The systems was originally developed at the University of Tokyo and comprises approximately 30 purified enzymes (enzymes made recombinantly) necessary for transcription and translation. Because all the components are tagged with a hexahistidine, the preferred N-terminal and C-terminal epitopes for the wild-type and truncated polypeptides (discussed in various embodiments of the method below) are preferably not Histags. The system is advertised as "essentially free of protease," however, there is significant protease activity that interferes with detection of small polypeptides by mass spectrometry. In one embodiment, the present invention contemplates supplementing a reconstituted system with a protease inhibitor.

In order to capture the translated protein on the same bead as the template nucleic acid produced using BRIDGE amplification, an affinity coupling agents is utilized which can be attached to the bead surface and in addition may include the bead interior. Since some coupling agents such as ordinary proteins will denature under high temperature conditions which might be encountered during the BRIDGE amplification step, a variety of coupling agent which are not damaged by the high temperature conditions can be utilized. One example of a coupling agent which will not lose its native affinity after being heated to high temperature even above 100 C are nucleic acid aptamers described previously. Such aptamers will unfold at high temperature but refold when the temperature is lowered, thereby preserving the native affinity and high selectivity of the aptamer for specific target biomolecules. In the case of translated proteins, a common epitope tag can be added by modification of the primers which is recognized by the aptamer with high affinity. Additional example of coupling agents which are compatible with BRIDGE amplification are single domain antibodies sometimes referred to as nanobodies. Such single domain antibodies display stability at much higher temperatures than ordinary antibodies. An additional example is of a affinity agents possessing stability to temperature are certain chelating agents such as $Ni^{2+}$ which are attached to the bead surface and display an affinity to so-called histidine tags consisting of several histidine residues positioned at either the N or C-terminal end of a protein. In all of these examples, coupling agents can be directed to a specific epitope which is produced during translation of the protein, thereby providing a means for binding of the translated protein to the same beads which have attached the nucleic acid sequences coding for said translated protein.

Coupling agents can also be attached to beads after BRIDGE amplification is performed in order to avoid damage to the coupling agent that might occur due to high temperatures. For example, a variety of methods well-known in the literature exist for attaching coupling agents to beads. Since, in most applications the same coupling agent is used for all beads, the coupling agent can be attached in one step to the beads subsequent to BRIDGE amplification. In one preferred embodiment, biotin is used with a chemically active moieties forms covalent bonds with amino group on a bead surface. After BRIDGE, a streptavidin conjugated through photocleavable biotin to an antibody directed at a specific epitope is added to the bead population under conditions such that the streptavidin interacts with the biotin preattached to the bead surface. This method provides a convenient method to create a photocleavable linker between the antibody and the bead surface after BRIDGE amplification.

One preferred embodiment of this invention is directed to a method for conversion of a cDNA library to a complete or partial protein bead library such that different proteins or polypeptides which are coded by elements of the cDNA library are attached to individual beads. This so-called bead sorted library of in vitro expressed proteins (BS-LIVE-PRO) is produced by providing a cDNA library and a set of beads, said beads each containing a set of forward and reverse primers designed to amplify using BRIDGE specific elements of the cDNA library. Each beads also has attached an affinity coupling element which exhibits stability to high temperature up to 100 C and is directed against a common epitope which is coded for by at least one element each primer pair attached to beads. The cDNA and beads are then introduced to the beads and solid phase polymerase amplification (SPA) performed. The beads are subsequently introduced into a cell-free protein synthesis system and coupled transcription and translation performed under conditions suitable to produce proteins which become attached through the said primer coded epitope to the said affinity coupling agent attached to the bead.

In one preferred embodiment, the proteins that are captured onto the bead surface using the methods described herein can be photo-released. This can be accomplished by using a coupling agent such as a single domain antibody which is attached to the bead through a photocleavable linker. It is important for the creation of a bead sorted protein library that this photocleavable linker does not lose its properties during SPA. One example is the utilization of beads coated with streptavidin which bind a photocleavable biotin attached photoreversibly to a high temperature stable coupling agent such as described previously in this invention. One example is the utilization of streptavidin-photocleavable biotin linkage. It has been shown that streptavidin-biotin complexes exhibit unusual thermal stability up to 117° C. (Gonzalez, M., Argarana, C. E., and Fidelio, G. D. (1999) *Biomol Eng* 16, 67-72). The ability to photocleavable release of the translated proteins captured on a bead surface is especially useful for direct contact photo-transfer of said proteins to a surface for subsequent analysis and utilization in biomolecular detection applications.

Application to the Multiplex Detection of Mutations in Genes

One preferred embodiment of this invention is directed to the multiplex detection of mutations in one or more genes such as part of a clinical diagnostic assay. A library of beads each containing specific proteins or fragments of proteins is prepared from a sample of genomic DNA using the methods described in this invention including BRIDGE amplification of specific genes or regions of genes on individual beads, cell-free translation of proteins or polypeptides coded for by the BRIDGE amplified DNA on separate beads and capture of proteins on beads which attach the coding DNA through a photocleavable coupling agent. The proteins or polypeptides on the bead are then transferred to a surface through the method of direct photocleavage contact printing described previously in this invention.

In one embodiment, the proteins are transferred to a surface suitable to perform MALDI analysis as previously described. It is to be understood that since each bead contains a homogeneous population of protein or polypeptide which was coded for by the BRIDGE amplified nucleic acid also attached to the bead, direct photocleavage contact printing as described previously will produce a plurality of spots on the surface, each spot containing a distinct species of protein or polypeptide. The identity of the protein or polypeptide as well as the presence of mutations can then be determined by measuring the molecular weight of the proteins/polypeptides as well as any possible shift in molecular weight caused by a mutation. The presence of a peak in the mass spectrum due to the unaltered wild-type species not containing the mutation is assured as long as the mutation appears in only one of two chromosomes present in all cases of heterozygous mutations.

In one preferred embodiment directed at the detection of APC mutations which are associated with both inherited and sporadic forms of colorectal cancer, a sample of genomic DNA derived from either blood or stool is provided. Specific regions of the APC gene are amplified using BRIDGE amplification methods whereby primer pairs are provided on beads which are designed to amplify specific regions of the APC gene to be scanned for mutations. Primer pairs also incorporate sequences for promoters for efficient transcription of the coded proteins as well as a variety of sequences encoding one or more epitopes for capture and analysis of the protein. After BRIDGE amplification, the beads are incorporated in a cell-free protein synthesis system suitable for translation of the encoded proteins/polypeptides. Due to the selective capture of proteins on beads containing the coding DNA, each bead will contain a homogeneous population (or nearly homogeneous, i.e. at least 90% identical with 10% or less: contaminating, more preferably at least 95% identical with 5% or less contaminating, still more preferably at least 99% identical with 1% or less contaminating) of proteins/polypeptides which can then be transferred by photo-release of the proteins to a MALDI surface using the methods described in this invention. By analyzing each transferred spot separately by MALDI, mutations in specific regions of the APC gene can be detected.

Application to the High Sensitivity Detection of Mutations

One further embodiment of the present invention applies to the detection of chain truncation mutations which are known to be associated with a variety of genetically related diseases including but not limited to cancers such as colorectal, lung and breast cancer. Very often mutated genes that are either inherited or produced somatically in individual cells can trigger cancer either alone or in conjunction with other causes such as additional mutations. The detection of such mutations, especially when they are present at very low concentration in a biological sample, relative to the wild-type gene sequence (unmutated gene) is an important challenge and goal in biotechnology. This is especially true in the case of colorectal cancer, where the detection of chain truncating mutations in the APC gene is correlated with the presence of polyps, precancerous adenomas or cancerous tumors in the colon.

One embodiment of the present invention facilitates the detection of cancer by creating a bead sorted library of in vitro expressed proteins or polypeptides (BS-LIVE-PRO) from a patient sample containing DNA. Patient samples can include but are not limited to urine, stool, tumor tissue, saliva, buccal scrapes or washes, cerebrospinal fluid or synovial fluid. The said BS-LIVE-PRO are created from the patient sample DNA using methods described in this invention such that each bead contains either predominantly full-length (untruncated peptides) reflecting the presence of a wild-type sequence of a target gene or predominantly truncated peptides reflecting the presence of a mutant sequence causing a chain-truncation. The beads are then probed for the presence of the full-length or truncated protein using a variety of assays.

One such assay which is highly advantageous for this application is similar to the ELISA protein truncation test (ELISA-PTT) reported by Gite et al. in 2003 [Gite et al. (2003) Nat Biotechnol 21, 194-197]. This test can be configured to utilize fluorescently labeled antibodies to probe the C- and N-terminal portions of the peptides bound to individual beads.

In one preferred embodiment of this invention directed at detecting with high sensitivity chain truncating mutations occurring anywhere in a gene or portion of a gene the following is provided: i) a patient sample containing DNA and ii) beads which contain at least one of a set of forward and reverse primers designed to amplify a specific genetic sequence contained in said patient DNA and an affinity coupling element which is directed against a nascent protein expressed from the sequence which is amplified by said primers. Alternatively, specific chemical moieties are present on the beads before amplification or created on the beads during amplification and used to attach the affinity coupling element after amplification, whereby the affinity coupling agent is directed against a nascent protein expressed from the sequence which is amplified by said primers. The DNA from the patient sample (patient DNA) is added to the said beads and polymerase amplification is performed under conditions such that the surface attached amplicon on said bead is derived from a few copies of patient DNA (preferably 10 but more optimal 3, and even more optimal 1). The beads are subsequently introduced into a cell-free protein synthesis system and coupled transcription and translation performed under conditions suitable to produce nascent proteins which become attached through the affinity coupling agent to the bead. The nascent proteins on individual beads are then probed to determine the presence or absence of truncated polypeptides. The ratio of beads with detected chain truncated polypeptide to those where such chain truncated polypeptide is not detected is used to determine the fraction of patient DNA containing chain truncating mutations in the targeted genetic sequence.

A variety of methods can be utilized to capture DNA on individual beads which are derived from a single copy chain reactions. One such method utilizes solid phase polymerase amplification (SPA) and BRIDGE as described previously. In this case, the concentration of DNA from the patient sample is diluted sufficiently so that the solid phase polymerase amplification on each bead is initiated by a single template using primer pairs that are immobilized on the bead surface. A second approach (e.g [Dressman et al. (2003) Proc Natl Acad Sci USA 100, 8817-8822]), utilizes emulsions which trap single copies of the sample DNA for subsequent amplification and immobilization of the product on the bead surface. In either case, the amplified DNA can then be utilized in a coupled cell-free transcription/translation reaction to express nascent proteins ultimately derived from the product of the single copy PCR reaction.

Once a BS-LIVE-PRO is produced using the methods described above, the detection of beads containing predominantly chain-truncated polypeptides can be detected using a variety of methods. In one embodiment [Gite et al. (2003) Nat

*Biotechnol* 21, 194-197] described in U.S. Pat. No. 7,101,662 which is specifically incorporated by reference, two different antibodies are used which are directed towards the N- and C-terminal portions of the expressed nascent protein. The binding of both antibodies indicates a full-length peptide whereas binding of only the N-terminal directed antibody indicates a truncated peptide. Binding of the antibodies can be detected using a variety of different methods including a fluorescent or chemiluminescent read-out. For example, duel or single labeled nascent proteins bound to individual beads can be detected using a sensitive microarray scanner or with flow cytometry.

Even if only a small proportion of the DNA in the patient sample encodes for a chain truncated polypeptide, these should be detectable by probing the individual beads. For example, if 1 out of 100 copies of DNA encoded for a gene contain a chain truncating mutations, approximately 1 out of 100 beads should contain predominantly polypeptides which were altered due to the chain truncating mutation. Importantly, this approach allows rapid scanning for chain truncating mutations in an entire sequence of a gene without pre-knowledge of the mutation in contrast with reported methods which are designed to detect specific mutations or single nucleotide polymorphisms (SNPs) at the DNA level [Dressman et al. (2003) *Proc Natl Acad Sci USA* 100, 8817-8822; Diehl et al. (2005) Proc Natl Acad Sci USA 102, 16368-16373].

The methods described in this invention can also be utilized to transfer the nascent proteins from individual beads onto discrete spots on the surface by means of phototransfer. In this case, each individual spot can be probed to determine if it contains predominantly truncated or full-length peptide or protein.

One preferred method of determining if a photo-transferred spot on a surface contains a predominantly truncated or full-length peptide is the use of mass-spectrometry and more preferably MALDI mass spectrometry as described previously in this invention. In this case, a shift in mass of the polypeptide from that predicted for the WT sequence would indicate the presence of a mutation.

It will be understood by those skilled in the use of mass spectrometry to probe proteins and polypeptides that many mass spectrometer which have high sensitivity and high mass resolution would allow not only chain truncation mutations to be detected but any mutation which resulted in a shift in the mass of the expressed peptide. For example, many commercially available MALDI mass spectrometers such as the ABI 4800 have sensitivity sufficient to detect mass shifts of much less than 1 dalton. Thus, beads which have bound predominantly nascent protein expressed from the normal wild-type sequence of a gene will produce easily distinguished signal from those beads which have bound predominantly mutant protein expressed from a mutant sequence provided that the mutation produced a peptide with a mass shift of at least 1 dalton. It will be also recognized by those skilled in the art of mass spectrometry of proteins and polypeptides that in many cases the actual change in the amino acid sequence of the polypeptide can be determined by utilizing peptide sequencing capabilities of many commercially available mass spectrometers such as the ABI 4800.

In one preferred embodiment of this invention directed at detecting at scanning with high sensitivity mutations occurring anywhere in a gene or portion of a gene the following is provided: i) a patient sample containing DNA and ii) beads which contain at least one of a set of forward and reverse primers designed to amplify a specific genetic sequence contained in said patient DNA and an affinity coupling element which is directed against the nascent protein expressed from the sequence which is amplified by said primers. The DNA from the patient sample (patient DNA) is added to the said beads and polymerase amplification is performed under conditions such that the surface attached amplicon on said bead is derived from a few copies of patient DNA (preferably 10 but more optimally, 3 and even more optimally 1). The beads are subsequently introduced into a cell-free protein synthesis system and coupled transcription and translation performed under conditions suitable to produce nascent proteins which become attached through the affinity coupling agent to the bead. The nascent proteins on individual beads are then probed to determine the presence or absence of mutant polypeptides. The ratio of beads with detected mutant polypeptide to those where such mutant polypeptide is not detected is used to determine the fraction of patient DNA containing mutations in the targeted genetic sequence.

In addition to mass spectrometry a variety of methods exist to assay the nascent protein derived from each bead. This includes assaying nascent protein bound directly to a bead or photo-transferred to a surface. Useful methods well know to those skilled in the area of protein analysis, biotechnology and biophysics include but are not limited to using fluorescence, chemiluminescence, absorption, Raman spectroscopy, infrared spectroscopy, mass spectrometry, flow cytometry, multiphoton spectroscopy, multiphoton microscopy, single molecule detection, functional analysis and microarray analysis. For example, as described previously proteins nascent proteins which have altered sequences can often be detected by mass spectrometry provided the mass of the altered sequence is not degenerate with the wild-type sequence. In the case of chain truncated polypeptides fluorescent labeled antibodies or antibodies which have a chemiluminescent readout can be utilized to probe the relative proportion of the N-terminal and C-terminal ends of the nascent protein. In some cases, the nascent protein can be probed for functional activity which is disrupted by changes in the wild type sequence. For example, it is well known that many mutations will alter the binding property of p53 for specific sequences of DNA. Raman and infrared spectroscopy can be used to detect changes in the overall structure and amino composition of proteins and polypeptides. Multiphoton spectroscopy and multiphoton microscopy can provide a means to probe with high spatial resolution the presence of specific chromophores which might be present or interacted with a nascent protein and with long wavelength non-damaging light.

Application to a Protein Truncation Test

One preferred embodiment of this invention is directed to the detection of chain truncating mutations in genes using methods described in this invention. Chain truncating mutations which result in truncated gene product, are prevalent in a variety of disease-related genes [Den Dunnen & Van Ommen. (1999) *Hum Mutat* 14, 95-102], including APC (colorectal cancer) [Powell et al. (1993) *N Engl J Med* 329, 1982-1987; van der Luijt et al. (1994) *Genomics* 20, 1-4; Traverso et al. (2002) *N Engl J Med* 346, 311-320; Kinzler et al. (1991) *Science* 251, 1366-1370; Groden et al. (1991) *Cell* 66, 589-600.], BRCA1 and BRCA2 (breast and ovarian cancer) [Hogervorst et al. (1995) *Nat Genet*. 10, 208-212; Garvin. (1998) *Eur J Hum Genet*. 6, 226-234; Futreal et al. (1994) *Science* 266, 120-122.], PKD1 (polycystic kidney disease) [Peral et al. (1997) *Am J Hum Genet*. 60, 1399-1410.], NF1 and NF2 (neurofibromatosis) [Heim et al. (1995) *Hum Mol Genet*. 4, 975-981; Parry et al. (1996) *Am J Hum Genet*. 59, 529-539.] and DMD (Duchenne muscular dystrophy) [Roest et al. (1993) *Neuromuscul Disord* 3, 391-394.]. Such chain truncating mutations can be detected using the protein truncation test (PTT), well known in the diagnostic filed. However, this test is based on cell-free transcription/translation of PCR(RT-PCR) amplified portions of the target gene (or target mRNA) followed by analysis of the translated product(s) for shortened polypeptide fragments. However, conventional PTT is not easily adaptable to high-throughput applications since it involves SDS-PAGE followed by autoradiography or Western blot. It is also subject to human error since it relies on visual inspection to detect mobility-shifted bands.

To overcome these limitations, a solid-phase PTT (so-called ELISA-PTT) was developed [Gite et al. (2003) Nat Biotechnol 21, 194-197]. One embodiment of ELISA-PTT uses a combination of misaminoacylated tRNAs [Rothschild & Gite. (1999) Curr Opin Biotechnol 10, 64-70; Gite et al. (2000) Anal Biochem 279, 218-225.], which incorporate affinity tags for surface capture of the cell-free expressed protein fragments, and specially designed PCR primers, which introduce N- and C-terminal markers for measuring the relative level of shortened polypeptide produced by the chain truncation mutation. After cell-free translation of the protein fragments, capture and detection is accomplished in a single-well using a standard 96-well microtiter plate ELISA format and chemiluminescence readout. The technique was demonstrated for the detection of chain truncation mutations in the APC gene using DNA or RNA from cancer cell lines as well as DNA of individuals pre-diagnosed with familial adenomatous polyposis (FAP) [Gite et al. (2003) Nat Biotechnol 21, 194-197].

A second version of this approach uses three epitopes described in U.S. Pat. No. 7,101,662 which is specifically incorporated by reference. In this approach, two epitopes located near the N-terminal end of the cell-free expressed protein or protein fragment are incorporated using a specially designed forward primer during PCR. These epitopes serve the purpose of binding the expressed protein or protein fragment to a surface and detection of the N-terminus. A third epitope tag, incorporated at the C-terminal end of the protein or protein fragment, by the reverse primer during PCR, is used for detection of the C-terminal end which is absent in the case of chain truncation mutations.

In the case of the present embodiment regarding a bead-based PTT, a method is used comprising: a) providing i) a population of template molecules, each template molecule encoding a nascent protein or protein fragment, and ii) at least one surface comprising forward and reverse PCR primers attached to said surface; b) amplifying at least a portion of said population of template molecules so as to create amplified product attached to said surface; c) generating nascent protein or protein fragment from said amplified product, said nascent protein or protein fragment comprising an affinity tag or first epitope, an N-terminal detection tag or second epitope and a C-terminal detection tag or third epitope; d) capturing said nascent protein or protein fragment on said surface via a first ligand, said first ligand attached to said bead and reactive with said affinity tag or first epitope; e) detecting N-terminal end of said nascent protein or protein fragments via a second ligand, said second ligand attached to a detection moiety; and f) detecting C-terminal end of said nascent protein or protein fragment via a third ligand, said third ligand attached to a detection moiety.

In one embodiment, the template molecules are derived from genomic DNA or fragmented genomic DNA that are present in common patient samples including but not limited to blood, plasma, serum, urine, sputum, saliva, stool, mouth lavage and buccal scrape/swab. The affinity binding tag consists of an HSV epitope sequence, the N-terminal detection tag a VSV epitope sequence and the C-terminal detection tag a p53 epitope sequence. The cell-free expressed protein or protein fragment is captured on a bead surface using an antibody directed against the HSV epitope. In order to distinguish between full-length and truncated polypeptides on a bead, two fluorescently labeled antibody ligands directed against the VSV and p53 epitopes are employed, each with a different wavelength of fluorescence emission which can be detected separately without significant wavelength overlap. For example, the combination of red and green fluorescence from the N-terminal and C-terminal antibodies indicates a full-length peptide whereas only green fluorescence indicates a truncated polypeptide. As described in this invention, individual beads can be read using a microarray scanner, fluorescence microscope or flow cytometer.

In one embodiment, the second ligand directed against the N-terminal epitope (second epitope) and third ligand directed against the C-terminal epitope (third epitope) are labeled with detection moieties which are chosen to act as donor and acceptor pairs, for fluorescence resonance energy transfer (FRET). For example, if the detection moiety on the second ligand is a donor and the detection moiety on the third ligand an acceptor, then the fluorescence from the donor will be quenched when excited at the wavelength of maximum excitation as long as the donor/acceptor pair are close to each other (e.g. within 100 Angstroms and more preferably within 50 Angstroms). In this case, only the acceptor will fluoresce at its characteristic wavelength normally red-shifted from the donor fluorescence or if it is a "dark" quencher [Johansson et al. (2004) J Am Chem Soc 126, 16451-16455], it will quench the donor but not itself fluoresce. It will be readily understood by those skilled in the art that the use of FRET detection pairs as described above enables preferential detection of chain truncated peptides from full-length peptides since the N-terminal ligand labeled with a donor will only fluoresce when the C-terminal ligand with the acceptor moiety is not present.

In order to demonstrate the process of bead-based fluorescence PTT, a test assay was designed using PCR amplification of segments of the APC gene from cell-line genomic DNA. The corresponding polypeptide was expressed in a rabbit reticulocyte cell-free transcription/translation system (RRL) and captured on 100 micron diameter NeutrAvidin coated agarose beads, which were loaded with a capture antibody. Note that the capture antibody was bound to the NeutrAvidin coated agarose beads through AmberGen's proprietary photocleavable biotin, to facilitate photo-release or contact photo-transfer in cases where desired. The PCR primers were designed to amplify APC segment 3 of Exon 15, which corresponds to codons 1,099 to 1,696. In addition to the wild-type (WT) sequence (HeLa cell line), cell-line genomic DNA containing a chain truncation mutation at codon 1,338 of APC(CAg→TAg) was used as the template for PCR(SW480 cell line). Similar to the ELISA-PTT assay, three epitope tags were incorporated into the PCR amplified DNA via the specially designed primers. These included an HSV epitope tag for binding to the corresponding antibody on the beads, a VSV epitope tag for N-terminal readout and AmberGen's proprietary p53 epitope tag for C-terminal readout. Exploiting the photocleavable biotin linkage of the binding (capture) antibody, APC polypeptides were contact photo-transferred from the beads to a microarray substrate prior to detection with the fluorescence antibodies.

In one embodiment, the present invention contemplates 2-color fluorescence overlays which show N-terminal and C-terminal detection (for example, in one embodiment, green is the anti-VSV-Cy3 N-terminal detection and red is the anti-p53-Cy5 C-terminal detection, with yellow being the combination of both colors). The minus DNA negative control sample (no DNA during cell-free protein expression) shows zero signal due to the use of contact photo-transfer, which eliminates auto-fluorescence arising from the beads themselves as well as fluorescence on the beads due to non-specific binding (e.g. of the detection antibodies). Importantly, the chain-truncating mutant displays only the VSV signal (green) while the WT has both VSV and p53 (red and green which appears yellow in the overlay). Intrinsic fluorescent labeling of the APC polypeptide (both full-length and truncated) using FluoroTect tRNA labeling was also detected confirming that polypeptide was bound to bead independent of N-terminal measurement. Details of this experiment are described in Example 42 of the Experimental section.

Bead-Based PCR Amplification of DNA Combined with Polypeptide Cell-free Expression An additional embodiment of this invention is the production of beads coated with polypeptide from beads coated with specific primers plus templates coding for a specific gene or gene fragment. In one example, customized primers attached to beads (both forward and reverse) are used to capture target DNA through hybridization (step 1). These primers are designed to amplify specific regions of a particular gene, for example, a portion of the DNA coding for the APC gene, as well as incorporate the 3 epitope tags and comprise additional sequences which promote cell-free translation (optimized for specific cell-free reaction systems such as E. coli or rabbit reticulocyte). Beads are also coated with an affinity agent, such as biotin, which is used for attachment of the capture antibody later in the process. After hybridization-capture of the target DNA directly on the bead (e.g. fecal DNA isolated from stool samples or alternatively freely circulating DNA present in other assay samples such blood or urine) the DNA may be separated from non-hybridizing DNA by removing the beads from the assay solution followed by a washing step. The target DNA captured on each bead is then selectively amplified using the BRIDGE PCR process (step 2), thereby yielding beads coated with template DNA coding for the desired polypeptide sequence to be probed. A capture antibody is then attached to the beads (step 3) through a (strept) avidin-biotin interaction (using the tetrameric (strept)avidin as a bridge between biotin on the beads and biotin on the capture antibody). Note that the antibody may optionally be connected through photocleavable biotin described in this invention for the purpose of contact photo-transfer. This DNA is then transcribed/translated, for example in some cases in an ultra-low protease protein expression system, and the polypeptide subsequently captured on the same bead from which it was made. Capture is achieved via the capture antibody on the beads and the incorporated N-terminal epitope in the expressed proteins.

An important feature of the method of this embodiment is the ability to perform multiplexed solid-phase PCR (SP-PCR) (e.g. BRIDGE) reactions followed by multiplex cell-free protein expression reactions. Since mixing of the resulting proteins from a particular bead (parent bead) to another bead (non-parent bead) during this process is minimized, the expressed proteins are essentially sorted on individual beads (on their parent DNA coated beads). This is especially valuable for multiplexing of different segments of a gene (e.g. specific exons or other fragments), for example in a bead-based PTT assay.

As an example of this process including a simple 2-fold multiplexing, an experiment was performed which was designed to express two different model proteins, p53 and γ-actin, separately on individual beads. Details of each step used including primer design, primer binding to beads, solid-phase PCR and the cell-free expression reaction are described in Example 31 of the Experimental section.

1) Primers: First, gene-specific primers were designed similar to that used in a recent AmberGen publication [Gite et al. (2003) Nat Biotechnol 21, 194-197] which included regulatory sequences necessary to convert the DNA template to a form which can be expressed in a rabbit reticulocyte cell-free system. The overall sequences included a T7 promoter, a Kozak ribosome binding sequence (forward primer) and an HSV epitope tag (reverse primer).

2) Primer Attachment to Beads: Primers were purchased commercially (Sigma-Genosys), each with 5' amine modifications for bead attachment. Both primers, along with a biotin-amine linker (Biotin-PEO-Amine; Pierce Biotechnology), were then covalently attached to ~100 μm amine-reactive NHS ester activated 4% agarose beads (Amersham Biosciences). The co-attachment of biotin provides a heat stable molecular "handle" for later attachment of (strept)avidin and photocleavable biotin (PC-biotin) conjugated PC-antibodies.

3) BRIDGE PCR: After completing all covalent bead modifications and extensive washing, successful primer and biotin attachment was separately confirmed. Beads with different gene-specific primer sets were then pooled and a single-tube SP-PCR reaction was performed under standard PCR conditions (no soluble primers). An in-house prepared cDNA library was used as the PCR template.

4) Adding the Capture Antibody: A PC-biotin conjugated PC-antibody against the common HSV epitope tag was bulk loaded onto the beads using a NeutrAvidin bridge. Successful loading was confirmed using a secondary detection antibody.

5) Protein Expression and Microarray Printing: Fully prepared DNA-beads were then cell-free expressed using BODIPY-FL-tRNA$^{COMPLETE}$ (TRAMPE) to label all nascent protein (green). Following contact photo-transfer of the beads to an epoxy activated microarray slide, the microarray was then probed with the p53 antibody clone Bp53-12 (B-P3) (BioSource International) which was in-house labeled with Cy5 fluorescence (red) (Amersham Biosciences).

Bead-Based Digital PCR without Limiting Dilution or Encapsulation

Digital PCR, especially when applied to a bead format, is an important advance in biotechnology. It facilitates a variety of applications including massively parallel DNA sequencing, for example of genomes [Dressman et al. (2003) Proc Natl Acad Sci USA 100, 8817-8822; Kojima et al. (2005) Nucleic Acids Res 33, e150; Nakano et al. (2003) J Biotechnol 102, 117-124; Nakano et al. (2005) J Biosci Bioeng 99, 293-295; Shendure et al. (2005) Science 309, 1728-1732; Thomas et al. (2006) Nat Med 12, 852-855]. This relies on the ability to amplify single copies or a most a few copies of template DNA on a single bead. However, single copy PCR has only been demonstrated up to now using an emulsion method whereby beads are trapped in an emulsion with approximately one molecule of DNA by using limiting dilution; e.g. diluting the concentration of the solution so that the average number of molecules encapsulated along with a single bead is one [Dressman et al. (2003) Proc Natl Acad Sci USA 100, 8817-8822].

One embodiment of this invention is directed at the performance of bead-based digital PCR without the need for limiting dilution or encapsulation of the bead. Such an approach avoids many of the limitations of conventional bead-based digital PCR, for example:
1. Limiting dilution requires careful adjustment of the DNA at very low concentration, a process difficult and expensive to automate.
2. The bead encapsulation introduces extra steps in any assay resulting in higher cost.
3. The small 1 micron beads used in conjunction with bead encapsulation are difficult to read with a standard microarray scanners with a resolution greater than 3 microns.
4. With regards to digital PTT, in order to perform cell-free transcription/translation, the bead encapsulation needs to be removed in order to allow large macromolecules such as polymerases and ribosomes to have access to the bound template.

Although embodiments of this invention are directed at molecular assays performed at the protein level, such as bead-based digital PTT, it will be realized by those skilled in the field that this embodiment facilitates a variety of other useful applications at the DNA level including bead-based massively parallel DNA sequencing or SNP/mutation analysis, for example by single-base extension.

One very desirable feature of this embodiment is the ability to perform amplification of DNA and subsequent production of proteins (e.g. polypeptides) without encapsulation methods. This is possible because: i) the PCR amplification is confined to the solid-phase on individual beads due to the intrinsic nature of the BRIDGE process. This limits the possibility that amplicon escapes from the bead and binds to other beads in the vicinity of the local reaction. ii) The transcription/translation reaction occurs at or near the surface of the bead since the template DNA is covalently attached to the bead surface. iii) Capture antibodies directed at an affinity tag on the translated polypeptide act to capture the said polypeptide before it escapes from the bead thereby minimizing mixing with other beads. Together these factors ensure that even without encapsulation, the overall PCR amplification and subsequent polypeptide translation is confined to the bead.

Another advantageous feature of this embodiment is the ability to perform amplification on a few copies or ideally a single copy of a template DNA on a single bead despite the fact that the template to bead ratio in solution is initially much higher than a 1:1 ratio.

The ability to obtain a higher ratio relates to the ability of the template DNA to hybridize to the covalently bound primer on the bead surface. Under certain well defined conditions, this requires a much higher ratio of template to bead than the normal 1:1 conditions used for bead encapsulation (e.g. 5:1 or preferably higher than 10:1). For example, the binding of single copies of target DNA to the bead depends on a number of factors including melting temperature of the primer molecules and target DNA template, the relative net charge and hydrophobicity of the bead, as well as in the case of agarose beads the properties of the intrinsic polymer matrix which both limit the ability of the target DNA to penetrate into the bead and hybridize with the primers. These factors can be controlled for example by adjusting the agarose density, hybridization temperature and melting temperature of the template DNA-primer.

An additional useful step in this embodiment is the removal of excess template copies in the solution bathing the beads, prior to performing additional PCR amplification cycles. For this purpose, after initial hybridization-based capture of a few copies of the template on the bead surface and a subsequent first cycle of BRIDGE PCR amplification (i.e. extend the primers only once), the initial non-covalently attached template is then removed from the bead (leaving only the covalently attached primer extension products, i.e. PCR products); assuring that the subsequent solid-phase BRIDGE PCR reaction (additional cycles) is confined to the bead surface and does not involve additional templates, as in the case of the conventional bead-based PCR reaction which occurs partially in the solution phase.

The overall method comprises of several steps:
1) A few (preferably one) target DNA molecules are captured on a single bead through hybridization with specially designed primers which hybridize with regions of the DNA which is to be analyzed (e.g. for chain truncation mutations).
2) A single cycle of PCR is performed so that each captured copy of target DNA serves as a template to extend the primer which is covalently linked to the bead surface.
3) All non-covalently bound copies of the target DNA are de-hybridized for example by denaturation in NaOH and removed by washing to prevent further "seeding" of the bead ($2^{nd}$ panel).
4) Additional cycles of the BRIDGE PCR amplification reaction are then performed in a PCR solution devoid of additional template (bottom two panels show only two cycles).

Application to Massively Parallel Sequencing Systems

BS-LIVE-PRO as produced using the methods described above can be used and analyzed in conjunction with a new generation of bead based massively parallel DNA sequencing systems to provide many important advantages in the fields of proteomics and molecular diagnostics. For example, several instruments which are commercially available can be used in their existing form or with some modification for proteomic and diagnostic applications due to the unique features of BS-LIVE-PRO and the methods engendered by this invention.

For example, the Genome Sequencer 20™ System, developed by 454 Life Sciences can be used in conjunction with BS-LIVE-PRO for both proteomic and molecular diagnostic applications. This system is an ultra-high-throughput automated DNA sequencing system capable of resolving hundreds of thousands of DNA sequences in one run. The basic chemistry utilizes the release of pyrophosphate (PPi) that occurs with each nucleotide addition during DNA-directed DNA synthesis to generate an amount of light commensurate with the amount of PPi released; this light is captured by a CCD camera and converted into a digital signal. The combination of signal intensity and positional information over the PicoTiterPlate™ device (see below) allows the Sequencer's Linux-based computer, equipped with an onboard Field Programmable Gate Array processor, to determine the sequence of hundreds of thousands of individual reactions simultaneously, producing millions of nucleotides of sequence per hour.

In one preferred embodiment of this invention which utilizes a bead based massively parallel sequencing system such as the Genome Sequencer 20™ System, a cDNA library is converted using the methods described in this invention into a complete or partial protein bead library such that different proteins or polypeptides which are coded by elements of the cDNA library are both attached to individual beads. In other words each bead contains the coding DNA and protein or polypeptide from which it is derived. This so-called bead sorted in vitro expressed protein library (BS-LIVE-PRO) is then analyzed using the capabilities of a bead based massively parallel sequencing system.

In one preferred embodiment of this invention which utilizes a bead based massively parallel sequencing system, before the DNA residing on each bead is sequenced, the protein which is coded for by the DNA is analyzed for example to determine if a particular target protein or molecule interact with any particular protein on specific beads comprising the BS-LIVE-PRO. Once the proteins on the beads have been analyzed, the identity of the protein residing on the bead is then determined by sequencing the DNA residing on the bead. This normally requires sequencing of only a small portion of the actual DNA sequence residing on each bead in order to determine the identity of the protein. For example, for a 454 system only 100 base pairs and even more preferentially 25 base pairs are only needed to establish the unique identity of each protein residing on the bead.

There are a variety of means for which the beads can be analyzed and subsequently sequenced which is compatible with the bead based approach for massively parallel sequencers and with specific components typically incorporated in such systems. For example, many sequencers utilize beads deposited onto a surface or into preformed pits. Because the sequencers are designed to detect light originating from individual beads, this capability can be used to measure the interaction of the proteins on the bead with molecules which are directly or indirectly labeled with light emitting substances such as fluorophores or chemiluminescent markers. Those skilled in this field will recognize that this capability derives from the use of fiber optics where individual fibers collect light from individual beads or through the use of high resolution scanners which are able to resolve the light being emitted from individual beads.

In one application, the beads comprising the BS-LIVE-PRO are exposed to a fluid sample containing a putative interactor such as a single protein which may interact with one or more of the proteins residing on specific beads or a more complex mixture such as serum from the blood of a patient which may contain antibodies which may interact with one or more of the proteins residing on specific beads. Other examples include candidate drug compounds which may interact with one or more of the proteins residing on specific beads. In each case, the beads which the putative interactors may interact with can easily be measured using the ability of the sequencer instrument to measure light emitted from individual beads by attaching directly or indirectly a marker such as a fluorophore or chemilumiscent molecule to the putative interactor In particular, once an interactor has bound to a particular bead, the light emitted from the interactor is detected. This information plus the positional information and sequence information from the individual bead uniquely identified the protein on the bead.

It will be understood by those familiar with DNA sequencers that it is possible to perform many cycles of bead analysis using the process described above. For example, a potential interactor which is fluorescently labeled can introduced into a chamber which encloses the DNA sequencer substrate where the beads will reside (e.g. PicoTiterPlate™ device in case of the Genome Sequencer 20™ System), washed out without displacing individual beads and then a second fluorescently labeled interactor introduced in the chamber. This cycle can be repeated multiple times and information determined about the position of which beads interact with the fluorescently labeled interactor followed by sequencing of the individual beads. In this way, the profile of how each protein residing on the beads interacts with multiple interactors can be determined. It is also possible to use multiple fluorophores which emit at different wavelengths to introduce more then a single interactor during each cycle.

In addition to bead based massively parallel DNA sequencing systems, a number of parallel sequencing systems utilize non-bead technology based on binding of single DNA molecules or islands of DNA derived from single DNA molecules to substrates. Examples include the Solexa technology (Illumina Genome Analyzer) and the Helicos Biosystems, Inc. technology. The methods and compositions of this invention can be used advantageously with these non-bead based sequencing systems. For example, in one preferred embodiment, a BS-LIVE-PRO is created and DNA and proteins are PC-printed onto a substrate which is subsequently analyzed using the non-bead based sequencing methods.

In a second example, proteins are generated using methods described in this invention directly from DNA randomly deposited onto the surface of the sequencing substrate as employed by both Helicos and Solexa and the proteins analyzed prior to performing DNA sequencing. In this case, the combination of analysis of the proteins derived from the sequenced DNA provides a unique advantages in terms of performing efficiently diagnostic applications discussed above in conjunction with beads.

This contrasts for example, with methods reported previously of printing known sequences of DNA on a surface followed by protein translation. In this case, DNA amplification must be performed for each species of DNA in separate PCR reactions prior to deposition on a surface. For an entire genome this might require as many as 20,000 separate PCR reactions. The methods presented in this invention avoid the need for such large number of reactions by using random deposition of single molecules of DNA on beads or surfaces followed by amplification and then translation to protein. Decoding is then performed using a massively parallel sequencing system.

DNA is immobilized on a proprietary flow cell surface designed to present the DNA in a manner that facilitates access to enzymes while ensuring high stability of surface-bound template and low non-specific binding of fluorescently labeled nucleotides. Solid phase amplification is employed to create up to 1,000 identical copies of each single molecule in close proximity (diameter of one micron or less). Because this process does not involve photolithography, mechanical spotting or positioning of beads into wells, Solexa sequencing technology can achieve densities of up to millions of single molecule clusters per square centimeter.

Identification Tags in Primer Sequences for Simultaneous Analysis of Multiple Patient DNA The methods and compositions described in this invention can also be advantageously applied to analyze mutations present in multiple patients by introducing identification tags into primer(s) which are bound to beads. Such identification tags comprise of a unique sequence of bases that serve to code the origin of the template DNA from individual patients which is amplified on the bead. By incorporating the unique identifier sequence into primers, the amplified DNA which is covalently bound to the surface of the bead as well as the expressed protein from that DNA can be uniquely identified with an individual patient even though beads carrying amplified DNA from multiple patients are pooled (e.g. mixed) together.

The number of bases used for the identifier sequence is determined by the number of patients which will be simultaneously be analyzed. For example, 1000 patients can be uniquely identified by using only a sequence of only 5 bases which yields 1064 unique sequence combinations. Additional bases might also be added in order to code additional information such as the sample number from a particular patient where more then one sample has been collected, date, time and status of patient. Additional bases might also be added to the sequence in order to provide a "check sum" which is determined using an algorithm based on the prior sequence in order to test its validity.

One example would be the case of 1000 different patients where the primer contains a sequence of 6 bases. The first 5 bases can uniquely determine which patients DNA has been amplified since there are 1064 possible sequences using 4 different bases A=adenine, T=thymine, C=cytosine and G=guanine. The sixth base might be based on a simple algorithm whereby each base is assigned a number A=1, T=2, C=3 and G=4. The numbers are summed and divided by 5 and rounded off to the nearest none zero integer which determines the sixth base. Hence ATGGC=14 and when divided by 5 and rounded of to the nearest none zero integer is 3, thus the sixth base would also be a C. Thus skilled in the area of computer science will recognize there are many possible algorithms possible to develop check sums to increase the read reliability of the patient tag identifiers.

Each patient sample containing DNA is amplified separately on beads using the methods described in this invention and then the resulting beads containing the immobilized amplified DNA pooled together for simultaneous analysis. Thus for example, in the case where beads are analyzed for the presence of DNA coding for chain truncated peptides, subsequent sequencing of all beads using a preferred method such as a massively parallel DNA sequencer will reveal not only the segment of DNA where the mutation resides in the gene but also the identity of the patient where the DNA template used for amplification of the DNA on the bead originated.

The use of identifier tags in primers immobilized on beads is particularly advantageous in cases where massively parallel DNA sequencers are used to sequence the DNA on multiple beads simultaneously. For example, many of the new generation of DNA sequencers can sequence simultaneously over 1 million beads however the number of beads necessary to analyze the DNA from an individual patient may be far less (e.g. 1000 beads). The use of identification tags in primer sequences provides a means whereby many patients (e.g. 1000) can be simultaneously analyzed without the need to segregate the beads from individual into different sequencing compartments on the sequencer. Such compartmentalization requires segregation of beads at each step in the sequencing process including introduction of the beads associated with each patient on the sequencing substrate (e.g. slide).

The use of identification tags in primers to code for individual patients also does not require that the amplified DNA remain bound to the individual bead. As described in this invention, DNA can be transferred directly to spots on a substrate from the beads using PC-print methods described in this invention. For example, the DNA may be amplified on the surface of a bead but analyzed on a surface other than the bead provided that the DNA from each individual bead remains in separate deposited spots.

Identification tags in primers can also be used advantageously in conjunction with DNA sequencing methods that do not employ beads, yet still capable of analyzing in parallel millions of individual DNA templates as for example employed by Solexa or Helicos Bioscience, Inc. In the case of Solexa, individual DNA templates are amplified by surface PCR directly on a substrate to produce a series of individual islands of DNA which are derived from a single template. These islands are then sequenced in parallel. For the purpose of analyzing specific regions of multiple patients DNA for particular mutations sequence identification tags incorporated into primers can again be used to amplify the specific region of a patients DNA which one wishes to sequence. In this case, solution PCR is performed in separate reactions for each patient DNA and then the resulting amplified DNA can be pooled and applied to the sequencing system. In the case of Helicos Bioscience, Inc. single strands of DNA are sequenced, however, identification tags can still be employed at the stage where specific regions of a patients DNA is amplified.

DEFINITIONS

The terms "bead", "sphere", "microbead" and "microsphere" are used interchangeably herein. Polymeric microspheres or beads can be prepared from a variety of different polymers, including but not limited to polystyrene, crosslinked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers and epoxies. The materials have a variety of different properties with regard to swelling and porosity, which are well understood in the art. Preferably, the beads are in the size range of approximately 10 nm to 1 mm, and can be manipulated using normal solution techniques when suspended in a solution. Beads may be porous or non-porous. In some embodiments where porous beads are employed, ligands may be attached within the bead as well as on the bead.

Terms such as "connected," "attached," "linked," and "conjugated" are used interchangeably herein and encompass direct as well as indirect connection, attachment, linkage or conjugation unless the context clearly dictates otherwise. In one embodiment, the present invention contemplates bead-ligand-nascent protein conjugates or complexes. The attachment of the ligand to the bead may be covalent, while the attachment of the ligand to the nascent protein may be non-covalent. In a preferred embodiment, compounds, ligands, etc. are covalently attached to beads through a photocleavable linker. However, in some embodiments, there may be additional functional groups at one or more sites along the linker.

As used herein, "binding agents" can be of any type. In one embodiment, the can be comprise chemical moieties. In a preferred embodiment, binding agents are ligands, such as antibodies, lectins, aptamers, streptavidin and avidin (and the like).

A "portion" can be with reference to a population or a molecule (e.g. a gene), depending on the context. For example, where contacting results in at least a "portion" of said nucleic acid annealing to said one or more amplification primers, it should be clear that portion is with reference to a population. Similarly, where at least a "portion" of said primers is extended, the term is with reference to a population. Similarly, when transferring at least a portion of said nascent protein to a non-bead solid support, the term is with reference to a population. By contrast, a portion of a disease-related gene ("encoded by a portion of the APC gene") is a region (e.g. larger than 4 bases, typically 8-15 bases or more, preferably 20 bases or more).

As used herein, "bisulfite-treated" means exposure to a bisulfite containing reagent. Typically, bisulfite is used as an aqueous solution of a bisulfite salt (e.g. sodium bisulfite, sodium metabisulphite). It has been discovered that bisulfite methods that employ magnesium bisulfite, polyamine compounds, and/or quaternary amine compounds provide useful alternatives to sodium bisulfite conversion reactions. See "Method And Materials For Polyamine Catalyzed Bisulfite Conversion Of Cytosine To Uracil" (U.S. application Ser. No. 60/499,113 filed Aug. 29, 2003, and also application Ser. No.

60/520,942 having the same title and filed Nov. 17, 2003), "Method And Materials For Quaternary Amine Catalyzed Bisulfite Conversion Of Cytosine To Uracil" (U.S. application Ser. No. 60/499,106 filed Aug. 29, 2003, and also application application Ser. No. 60/520,942 having the same title and filed Nov. 17, 2003), "Method And Materials For Quaternary Amine Catalyzed Bisulfite Conversion Of Cytosine To Uracil" (U.S. application Ser. No. 60/499,106 filed Aug. 29, 2003, and also application Ser. No. 60/523,054 having the same title and filed Nov. 17, 2003), and "Method and Materials for Bisulfite Conversion of Cytosine to Uracil (U.S. application Ser. No. 60/499,082 filed Aug. 29, 2003, and also application Ser. No. 60/523,056 (5180P2) having the same title and filed Nov. 17, 2003), all of which are hereby incorporated by reference in their entirety.

In one embodiment, the present invention contemplates labeling cytosine bases in methylated CpG dinucleotides. U.S. Pat. No. 7,285,394, hereby incorporated by reference, describes that 5-methylcytosine DNA glycosylase, in combination with art-recognized DNA repair enzymes, and in particular embodiments with DNA methyltransferase, to specifically label cytosine bases in methylated CpG dinucleotides in genomic DNA sequences. Such labeling occurs through enzymatic substitution of 5-methylcytosine with labeled cytosine, and allows, inter alia, for selection and cloning of sequences originally containing methylated CpG dinucleotides

EXPERIMENTAL

The following examples illustrate embodiments of the invention, but should not be viewed as limiting the scope of the invention.

Example 1

Isolation and Photo-Release of Protein Produced in a Cell-Free Expression System Using Incorporated PC-biotin Cell-Free Expression and tRNA Mediated Labeling:

Glutathione-s-transferase (GST) was expressed in a cell-free reaction and co-translationally labeled using AmberGen's PC-biotin-tRNA$^{COMPLETE}$ (PC-biotin=photocleavable biotin) and BODIPY-FL-tRNA$^{Lys}$ misaminoacylated tRNA reagents. AmberGen's BODIPY-FL-tRNA$^{Lys}$ misaminoacylated tRNA and PC-biotin reagents are described in the scientific literature [Gite et al. (2003) Nat Biotechnol 21, 194-197; Olejnik et al. (1995) Proceedings of the National Academy of Science (USA) 92, 7590-7594]. Although not used in this Example, BODIPY-FL-tRNA$^{COMPLETE}$ is also used in later Examples instead of BODIPY-FL-tRNA$^{Lys}$. "tRNA$^{Lys}$" refers to a pure preparation of E. coli lysine specific aminoacyl tRNA that is conjugated to the BODIPY-FL or PC-biotin label at the ε-amine group of the amino acid side chain. "tRNA$^{COMPLETE}$" refers to a complete mixture of yeast tRNAs (i.e. tRNAs for all 20 amino acids) that is chemically misaminoacylated uniformly with a lysine conjugated to the BODIPY-FL or PC-biotin label at the ε-amino group of the amino acid side chain. The basic chemical aminoacylation methodology used to prepare the misaminoacylated "tRNA$^{COMPLETE}$" reagents is described by AmberGen in the scientific literature [Mamaev et al. (2004) Anal Biochem 326, 25-32]. In brief, these specialized misaminoacylated tRNA reagents have the ability to co-translationally incorporate the non-native labeled amino acids that they carry into cell-free expressed proteins at various positions and frequencies. Expression reactions were performed using a transcription/translation coupled rabbit reticulocyte lysate system (TNT® T7 Quick for PCR DNA; Promega, Madison, Wis.) with the following modifications to the manufacturer's instructions: Plasmid DNA was used at a final concentration of approximately 25 ng/μL. Expression plasmids used were either the pETBlue-2 (EMD Biosciences, Inc., San Diego, Calif.) containing a C-terminal polyhistidine and HSV epitope tag or the pIVEX-WG (Roche Applied Science, Indianapolis, Ind.) containing only a C-terminal polyhistidine tag. Gene cloning (open reading frames) into the expression plasmids was performed according to the manufacturer's instructions and plasmid amplification/isolation achieved using standard molecular biology practices. For plasmid expression in the cell-free reaction, a complete amino acid mixture was added to a final concentration of 50 μM each. The final concentration PC-biotin-tRNA$^{COMPLETE}$ and BODIPY-FL-tRNA$^{Lys}$ was 1 μM and 0.6 μM respectively. Total expression reaction volume was 200 μL per sample. The reaction was carried out for 30 min at 30° C. and stopped by chilling on an ice bath and the addition of equal volume of Translation Dilution Buffer (TDB) [2×PBS pH 7.5, 2 mM DTT, 0.2% (w/v) BSA and 0.4% (v/v) of a mammalian protease inhibitor cocktail (cocktail in DMSO, Sigma-Aldrich, St. Louis, Mo.)] for a final 400 μL volume per sample (PBS=50 mM sodium phosphate pH 7.5 and 100 mM NaCl). The stopped translations were equilibrated at +4° C. for 15 min and clarified by spinning 1 min 13,000 rpm in a microcentrifuge prior to further processing. The fluid supernatant containing the soluble material was kept and used in the subsequent steps and the insoluble pellet was discarded.

Isolation of Labeled Nascent Proteins:

PC-biotin labeled nascent GST was captured and isolated on 10 μL packed bead volume of NeutrAvidin agarose beads having an approximate biotin binding capacity of 800 pmoles (Pierce Biotechnology, Inc., Rockford, Ill.). The isolation procedure was performed in batch mode using a micro-centrifuge and polypropylene tubes to manipulate the affinity matrix and exchange the buffers. All steps were performed at +4° C. or on an ice water bath and all reagents and samples were also kept under these conditions during the procedure. After capture on the NeutrAvidin beads for 1 hr, beads were washed by mixing 2× briefly (briefly=5 sec vortex mix) and 2× for 5 min in 45 bead volumes per wash. The buffer used for washing the beads was PBS pH 7.5, 1 mM DTT and 0.1% (w/v) BSA. Prior to photo-release of the captured and isolated GST, the washed pellet of 10 μL of NeutrAvidin agarose beads was suspended in a final volume of 400 μL thereby keeping the volume equal to the volume of starting material (i.e. volume just prior to addition of sample to NeutrAvidin agarose beads).

Photo-Release:

Photo-release of the captured GST was achieved via illumination of the NeutrAvidin bead suspension, with mixing, for 5 min with near-UV light (365 nm peak UV lamp, Blak-Ray Lamp, Model XX-15, UVP, Upland, Calif.) at a 5 cm distance. Importantly, light illumination was performed directly in uncovered/uncapped polypropylene micro-centrifuge tubes, such that there was no solid barrier between the bead suspension and the light source. The power output under these conditions was 2.6 mW/cm$^2$ at 360 nm, 1.0 mW/cm$^2$ at 310 nm and 0.16 mW/cm$^2$ at 250 nm. Fractions (i.e. fluid supernatant with no beads) were collected at each step of the isolation and photo-release procedures and GST content was analyzed by standard SDS-PAGE and imaging of the fluorescent BODIPY labels using a FluorImager SI laser-based gel scanner (Molecular Dynamics/Amersham Biosciences Corp., Piscataway, N.J.).
Results:
Results are shown in FIG. 1A. Lane 1 is the initial unbound fraction corresponding to nascent GST not binding the NeutrAvidin beads (wash factions were also collected and analyzed but contained negligible quantities). Lane 2 is the negative control elution in the absence of the proper light. Lane 3 is the photo-released fraction following illumination with the proper light. Lane 4 is the fraction remaining bound to the beads that was subsequently released by denaturation of the NeutrAvidin (asterisk indicates 2× more loading to gel relative to other lanes). Quantification of the gel shows 81% of the total GST does not bind the NeutrAvidin beads for a calculated binding of 19%. 68% of the bound GST is photo-released with light for a 13% overall recovery. For the negative control, in the absence of the proper light, 3% of the bead-bound GST "leaks" from the affinity matrix.

Example 2

Isolation and Photo-Release of Protein Produced in a Cell-Free Expression System Using Photocleavable Antibodies Preparation of a Photocleavable Antibody Affinity Matrix:
A "photocleavable" antibody (PC-antibody) is defined, in all Examples provided, as an antibody conjugated to a photocleavable chemical linker, in this case photocleavable biotin (PC-biotin), that mediates attachment of the antibody to a solid affinity matrix [in this case (strept)avidin coated beads] in a photo-reversible fashion. With proper light treatment, the antibody is photo-released from the solid affinity matrix, with the antibody intact and still bound to any antigen that was bound prior to photo-release.

400 μg of mouse monoclonal anti-HSV tag antibody (EMD Biosciences, Inc., San Diego, Calif.) at 1 μg/μL was dialyzed extensively against 200 mM sodium bicarbonate (no pH adjustment) and 200 mM NaCl. The resultant recovered antibody (~200 μg at 0.3-0.4 μg/μL) was labeled using 20 molar equivalents of AmberGen's PC-biotin-NHS reagent (added from 5 mM stock in DMF) for 1 hr with mixing. The reaction was quenched for 15 min by adding one-fifth volume of a 1M glycine stock. Without additional purification, the resultant antibody conjugate solution is mixed 1:1 with 0.1% BSA (w/v) in TBS [TBS=50 mM Tris (2-amino-2-(hydroxymethyl)-1,3-propanediol) pH 7.5 and 200 mM NaCl] and captured on NeutrAvidin agarose beads (Pierce Biotechnology, Inc., Rockford, Ill.) at a ratio of 0.25 μg of antibody conjugate per μL of packed beads. Capture is allowed to proceed for 30 min with mixing. Beads are washed 4×5 min with 10 bead volumes each wash using 0.1% BSA (w/v) in TBS and resuspended to a 50% slurry (v/v) in the same buffer. Sodium azide is added as a preservative to 1.5 mM and the beads stored protected from light at +4° C.
Cell-Free Expression and tRNA Mediated Labeling:
Glutathione-s-transferase (GST) containing an HSV epitope tag on the C-terminus was expressed in a cell-free reaction as described earlier in Example 1 except that only AmberGen's BODIPY-FL-tRNA$^{COMPLETE}$ was used at 1 μM for labeling.
Isolation of Labeled Nascent Proteins and Photo-Release:
Isolation and photo-release of GST was performed as described earlier in Example 1 except that the anti-HSV photocleavable antibody affinity matrix was substituted for the NeutrAvidin beads in Example 1.

Results:
Results are shown in FIG. 1B. Lane 1 is the initial unbound fraction corresponding to nascent GST not binding the photocleavable antibody beads (wash factions were also collected and analyzed but contained negligible quantities). Lane 2 is the negative control elution in the absence of the proper light. Lane 3 is the photo-released fraction following illumination with the proper light. Lane 4 is the fraction remaining bound to the beads that was subsequently released by denaturation of the antibody (asterisk indicates 2× more loading to gel relative to other lanes). Quantification of the gel shows 25% of the total GST does not bind the photocleavable antibody beads for a calculated binding of 75%. 78% of the bound GST is photo-released with light for a 58% overall recovery. For the negative control, in the absence of the proper light, 3% of the bead-bound GST "leaks" from the affinity matrix.

Example 3

Purity of Proteins Isolated by Incorporated PC-Biotin and Photo-Released

Figure 2B:
FIG. 2B. Purity of cell-free proteins following photo-isolation by incorporated PC-biotin. Silver stain total protein image of same electrophoretic gel (post-staining). Lane 1 is plain SDS-PAGE gel loading buffer as a negative control. Lane 2 is the plain buffer used in the isolation as a negative control. Lane 3 is a negative control corresponding to the photo-released fraction derived from a cell-free expression reaction where only the added DNA (GST gene in plasmid) was omitted. Lane 4 is the photo-released fraction derived from a cell-free expression reaction where the GST DNA was included. The asterisk denotes an unknown global contamination originating either in the electrophoretic gel itself or the SDS-PAGE loading buffer but not attributable to the cell-free expressed samples or isolation process.

Cell-Free Expression and tRNA Mediated Labeling:
Glutathione-s-transferase (GST) was expressed in a cell-free reaction as described earlier in Example 1 except that the Translation Dilution Buffer (TDB) was modified as follows: i) DTT was not used, ii) 4 mM cycloheximide was included to ensure the expression reaction is completely stopped and iii) 0.02% (w/v) Triton X-100 detergent was used as a carrier instead of BSA to avoid interference with purity analysis.
Isolation of Labeled Nascent Proteins and Photo-Release.
Isolation and photo-release of GST was performed as described earlier in Example 1 except that 0.01% (w/v) Triton X-100 detergent was used as a carrier in all buffers instead of BSA to avoid interference with purity analysis. Additionally, to ensure detection of all possible contaminants, the volume of buffer used during photo-release was reduced such that the isolated GST was concentrated by a factor of approximately 5.
Electrophoresis Based Analysis of Purity:
20 μL of purified and concentrated photo-released GST was separated using standard SDS-PAGE (8-16% gradient gel for comprehensive coverage) (FIG. 2). The electrophoretic gel was scanned for the selective fluorescent labeling of nascent GST (FIG. 2A) as described in Example 1. The gel was subsequently stained for total protein using a high sensitivity silver stain method according to published reports [Sinha et al. (2001) *Proteomics* 1, 835-840] as shown in FIG. 2B.
Results:
Results are shown in FIG. 2. Lane 1 is plain SDS-PAGE gel loading buffer as a negative control. Lane 2 is the plain buffer used in the isolation as a negative control. Lane 3 is a negative control corresponding to the photo-released fraction derived from a cell-free expression reaction where only the added DNA (GST gene in plasmid) was omitted. Lane 4 is the photo-released fraction derived from a cell-free expression reaction where the GST DNA was included. The data show a GST band present only in Lane 4 as expected. The asterisk denotes an unknown global contamination originating either in the electrophoretic gel itself or the SDS-PAGE loading buffer but not attributable to the cell-free expressed samples or isolation process. Disregarding the global contaminant, the GST band is shown to be highly pure with only a few contaminating bands of negligible relative intensities (all contaminant bands >10-fold weaker than GST band).

Example 4

Yield of Proteins Isolated by Incorporated PC-Biotin and Photo-Released

Western Blot Analysis of Absolute Yield:

Various human proteins were expressed and labeled in a rabbit reticulocyte cell-free reaction system, captured and photo-released in pure form as described in Example 1. In cases where co-migration during SDS-PAGE of the BSA carrier used in the isolation procedure (66 kDa) with the expressed test protein was of concern, the BSA carrier was replaced with a β-casein carrier (~24 kDa) to avoid this. After isolation and photo-release, test proteins were separated by standard SDS-PAGE and analyzed using standard Western blotting practices. Western blotting was achieved with antibodies either to endogenous epitopes or to the HSV epitope tag present at the C-terminus of most expressed proteins. Linearity of the Western blot signals and quantification of the isolated test proteins was achieved by generating standard curves from known quantities of purified commercial recombinant proteins (e.g. recombinant human PKA from Invitrogen Corporation, Carlsbad, Calif. and recombinant Firefly luciferase from Promega, Madison, Wis.) or known quantities of a recombinant protein bearing the HSV epitope tag (EMD Biosciences, Inc., San Diego, Calif.).

Results:

Results indicate yields of 522 pg (luciferase), 399 pg (human c-jun), 267 pg (human p53), 132 pg (human MDM2), 383 pg (human $PKA_{c\alpha}$) and 247 pg (human GST A2) per every μL of cell-free expression reaction for an overall average yield of 325±137 pg/μL across all tested proteins.

Example 5

Contact Photo-Transfer of Cell-Free Expressed Proteins from Beads to Solid Surfaces Using Incorporated PC-Biotin: UV Light Dependence Cell-Free Expression and tRNA Mediated Labeling:

The human p53 oncoprotein (tumor antigen) was expressed and labeled in a rabbit reticulocyte cell-free reaction system as described in Example 1 with the following exceptions: PC-biotin-tRNA$^{COMPLETE}$ was used at 2 μM instead of 1 μM. The BODIPY-FL-tRNA$^{Lys}$ was not used. The expression reaction carried out for 1 hr instead of 30 min. The composition of the Translation Dilution Buffer (TDB) was 2×TBS, pH 7.5, 0.2% (w/v) Triton X-100 and 20 mM EDTA.

Isolation of Labeled Nascent Proteins by Incorporated PC-Biotin and Contact Photo-Transfer:

PC-biotin labeled nascent p53 was captured and isolated on 50 μL packed bead volume of NeutrAvidin agarose beads (Pierce Biotechnology, Inc., Rockford, Ill.). All steps were performed at +4° C. The isolation procedure was performed in batch mode using a micro-centrifuge and polypropylene tubes to manipulate the affinity matrix and exchange the buffers. After capture on the NeutrAvidin beads for 30 min, beads were washed by mixing 3× for 5 min each in TBS pH 7.5, 0.1% (w/v) Triton X-100, 10 mM EDTA and then washed 3× briefly (briefly=5 sec vortex mix) in PBS all at 20 bead volumes per wash. Lastly, the beads were washed 2× briefly (briefly=5 sec vortex mix) with 100 bead volumes each of 40% glycerol in PBS and resuspended to a 10% bead suspension (v/v) in the same glycerol/PBS buffer.

For contact photo-transfer, the beads were resuspended by mixing and 1 μL of the bead suspension was manually pipetted onto the surface of an amine-reactive aldehyde activated glass microarray substrate (i.e. activated glass slide) (Super-Aldehyde substrates, TeleChem International, Inc. ArrayIt™ Division, Sunnyvale, Calif.). The substrates were then illuminated, without agitation, for 5 min with near-UV light (365 nm peak UV lamp, Blak-Ray Lamp, Model XX-15, UVP, Upland, Calif.) at a 5 cm distance to photo-release and transfer the p53 protein. The power output of the lamp under these conditions was 2.6 mW/cm$^2$ at 360 nm, 1.0 mW/cm$^2$ at 310 nm and 0.16 mW/cm$^2$ at 250 nm. As a negative control, replicate samples on the same substrate were protected from the incident UV light. After light treatment, the glass substrates were incubated for 30 min at 37° C. in a sealed and humidified chamber to fully ensure photo-released proteins react with the activated solid surface. The beads and any unbound protein were then washed away and the substrates simultaneously blocked in TBS, pH 7.5, 0.05% (w/v) Tween-20 (TBS-T) plus 5% BSA (w/v) for 15 min at 37° C. Importantly, phase-contrast light microscopy reveals that the easily visible ~100 μm agarose beads do not remain bound to any of the solid surfaces tested (see later examples for different surfaces).

Detection of Photo-Transferred Protein:

Contact photo-transferred p53 was detected on the glass substrate by probing with a mouse monoclonal antibody against the HSV epitope tag (EMD Biosciences, Inc., San Diego, Calif.) present at the C-terminal of the protein. This was followed by probing with a fluorescent Alexa Fluor® 488 conjugated secondary antibody (Invitrogen Corporation, Carlsbad, Calif.). Unbound antibody was washed away and the substrates were imaged using a FluorImager SI laser-based scanner (Molecular Dynamics/Amersham Biosciences Corp., Piscataway, N.J.).

Figure 3:
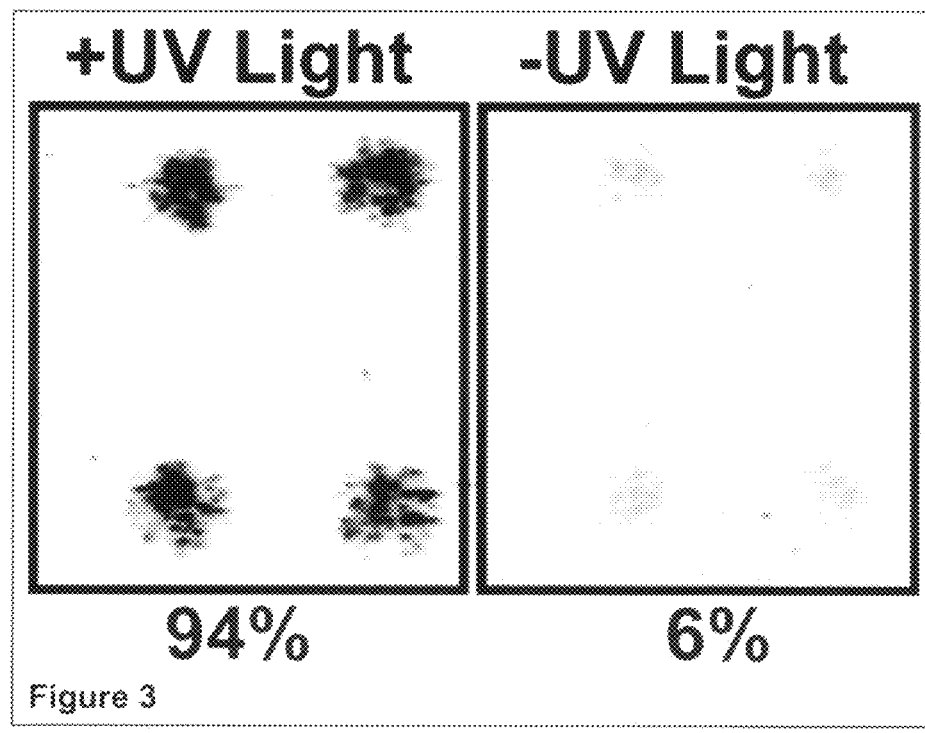
FIG. 3. Contact photo-transfer by incorporated PC-biotin of cell-free expressed, tRNA labeled and isolated proteins (antibody detection). UV light dependence of the transfer is shown.

Results:

Results are shown in FIG. 3 and quantification of the image shows that 94% of the total signal is dependent on illumination with the proper light while only 6% of the p53 protein is transferred without light.

Example 6

Incorporated PC-Biotin: Contact Photo-Transfer Versus Release from Beads into Solution Followed by Mechanical Protein Array Printing Cell-Free Expression and tRNA Mediated Labeling:

Various human proteins were expressed and labeled in a rabbit reticulocyte cell-free reaction system as described in Example 1 with the following exceptions: PC-biotin-tRNA$^{COMPLETE}$ was used at 2 μM instead of 1 μM. The BODIPY-FL-tRNA$^{Lys}$ was not used. The expression reaction carried out for 1 hr instead of 30 min. The composition of the Translation Dilution Buffer (TDB) was 2×TBS, pH 7.5, 0.2% (w/v) Triton X-100 and 20 mM EDTA. Furthermore, the cell-free expression reaction size for each protein was varied to normalize for the differences in expression yield.

Isolation of Labeled Nascent Proteins by) Incorporated PC-Biotin and Contact Photo-Transfer:

Performed as described in Example 5. Additionally, as a comparison to contact photo-transfer, an aliquot of the bead suspension (at the same bead to fluid ratio) containing the captured proteins was illuminated off-line (i.e. separately prior to application to surface) in low protein binding 1.5 mL polypropylene micro-centrifuge tubes (Maxymum Recovery Tubes; Axygen Scientific, Inc., Union City, Calif.) with mixing. Light illumination was otherwise performed under the same conditions described in Example 5. Importantly, light illumination was performed in uncovered/uncapped tubes, such that there was no solid barrier between the bead suspension and the light source. Note that no protein carriers were used during photo-release (e.g. BSA) in order to facilitate direct covalent immobilization of the isolated protein on the amine-reactive activated microarray substrate. After photo-release, the beads were spun down in a micro-centrifuge and only the fluid supernatant was pipetted ("printed") onto the microarray substrate. All subsequent procedures were the same as for the contact photo-transfer described in Example 5.

Detection of Photo-Transferred Protein:
Detection of the common C-terminal HSV epitope tag was performed as described in Example 5.

Figure 4:
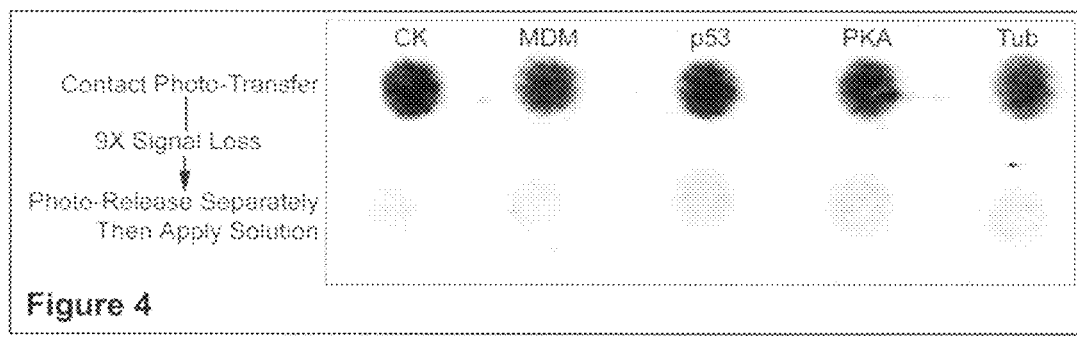
FIG. 4. Contact photo-transfer by incorporated PC-biotin of cell-free expressed, tRNA labeled and isolated proteins (antibody detection). Comparison to separate photo-release into solution followed by application of the fluid elution to the activated solid microarray surface.

Results:
Results are shown in FIG. 4. The 5 contact photo-transferred proteins were CK=casein kinase II; MDM=ubiquitin-protein ligase E3 MDM2; p53=cellular tumor antigen p53; PKA=protein kinase A catalytic subunit alpha; Tub=alpha-tubulin. Averaged over all 5 proteins, the contact photo-transfer method achieves 9±3 fold more protein transferred to and immobilized on the microarray substrate as compared to the method of photo-release into solution then immobilization. Contact photo-transfer also avoids the need for proteinaceous carriers (additives), normally used in solution to prevent losses of the target protein via non-specific adsorption (e.g. to the walls of the storage vial/tube). The lack of a need for proteinaceous carriers facilitates efficient immobilization on protein binding surfaces, such the aldehyde activated glass slides in this Example (or other surfaces such as epoxy activated or PVDF, polystyrene or nitrocellulose surfaces or membranes/films), without competition for binding from the carrier. It also eliminates the need for chemical carriers like detergents which my harm protein folding and function. Improved protein transfer/immobilization can be attributed to i) since the protein is directly transferred from the beads to the surface, no non-specific loss (adsorption) of the protein occurs on the walls of a storage vial/tube, in the absence of a carrier; ii) the target protein is maintained in high concentration on the bead which rests on the microarray surface, upon photo-release the protein is at a high local concentration near the binding surface and thus more efficiently captured/immobilized. Experiments involving contact photo-transfer from individually resolved beads shown later in FIGS. 12, 13 and 14 (Examples 14, 15 and 16) further support that the protein is largely captured on the surface prior to diffusion into the fluid medium. In contrast, pre-photo-release into solution pre-dilutes the protein prior to application to the microarray surface; iii) better light delivery as the beads form a monolayer on the microarray substrate.

Example 7

Contact Photo-Transfer to Activated Microarray Surfaces Using Incorporated PC-Biotin: Detection of a tRNA Mediated Direct Fluorescence Label Cell-Free Expression and tRNA Mediated Labeling:
Human calmodulin and alpha-tubulin were expressed in a rabbit reticulocyte cell-free reaction and co-translationally labeled with both BODIPY-FL and PC-biotin as in Example 1 with the following exceptions: BODIPY-FL-tRNA$^{COMPLETE}$ was used for fluorescence labeling instead of BODIPY-FL-tRNA$^{Lys}$. As a negative control, an expression reaction was performed lacking only the added DNA for the gene of interest (Minus DNA blank). The Translation Dilution Buffer (TDB) used to stop the reaction and prepare the sample contained no BSA or any other protein carriers.

Isolation of Labeled Nascent Proteins:
The isolation procedure only (see later for contact photo-transfer) was performed as in Example 1 with the following exceptions: The buffers used in the procedure contained no BSA or other protein carriers at any step. Capture on the NeutrAvidin beads was for 30 min. After washing the unbound material from the NeutrAvidin beads as described in Example 1 the beads were further washed 3× briefly (briefly=5 sec vortex mix) with 45 bead volumes each of plain PBS and 1×5 min with 45 bead volumes of 40% glycerol in PBS. The washed bead pellet was then suspended with equal volume of 40% glycerol in PBS to yield a 50% bead slurry (v/v).

Contact Photo-Transfer:
For contact photo-transfer, the beads were resuspended by mixing and 1 μL of the bead suspension was manually pipetted onto the surface of a reactive epoxy activated glass microarray substrate (i.e. activated glass slide) (SuperEpoxy substrates, TeleChem International, Inc. ArrayIt™ Division, Sunnyvale, Calif.). Note that 1 μL of bead suspension deposited on the substrate (corresponding to one spot in FIG. 5) contained roughly 400 agarose beads prior to removal/washing. The substrates were then illuminated, without agitation, for 5 min with near-UV light (365 nm peak UV lamp, Blak-Ray Lamp, Model XX-15, UVP, Upland, Calif.) at a 5 cm distance to photo-release and transfer the target proteins. The power output of the lamp under these conditions was 2.6 mW/cm$^2$ at 360 nm, 1.0 mW/cm$^2$ at 310 nm and 0.16 mW/cm$^2$ at 250 nm. After light treatment, the glass substrates were incubated for 30 min at 37° C. in a sealed and humidified chamber to fully ensure photo-released proteins react with the activated solid surface. The beads and any unbound protein are then washed away from the microarray substrate surface, in a tray, with several rounds of excess buffer (e.g. 20 mL per substrate of TBS or PBS with or without 0.05% w/v Tween-20 detergent). Phase contrast light microscopy reveals that the easily visible 100 micron NeutrAvidin agarose beads were completely washed/removed from the glass substrates. In fact, when 1 μL of a 50% (v/v) bead suspension is applied per spot to the glass substrates, the bead monolayer is even plainly visible by eye prior to washing/removal without the need for a microscope; and the monolayer is clearly observed to be gone immediately after submersion even in the first wash. The glass substrates were further rinsed in excess purified water to remove salts prior to drying and imaging.

Detection of Photo-Transferred Protein:
Detection of the directly incorporated tRNA mediated BODIPY-FL fluorescence labeling was achieved by imaging the dry microarray substrates on an ArrayWoRx$^e$ BioChip fluorescence reader (Applied Precision, LLC, Issaquah, Wash.).

Results:
Results are shown in FIG. 5. –DNA=minus DNA blank derived from expression reaction lacking only the added DNA for gene of interest (all other processing steps otherwise performed same as with DNA containing expressed protein samples); Calm=calmodulin; Tub=alpha-tubulin; *=decreased sample loading to roughly normalize signal to calmodulin. The results show that the directly incorporated BODIPY-FL fluorescence label is easily detectable following contact photo-transfer compared to the minus DNA blank. Signal to noise ratios exceed 6:1 in all cases and reach 29:1 in the case of tubulin (full loading). Note that calmodulin binds relatively poorly to the glass substrate due to it's highly acidic nature (pI=3; low lysine content; epoxy activated surfaces primarily react with primary amines).

Example 8

Figure 6:
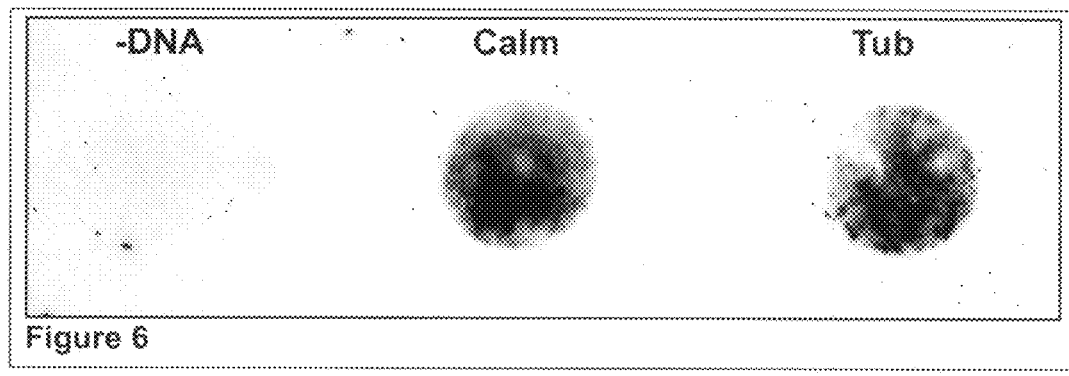
FIG. 6. Contact photo-transfer by incorporated PC-biotin of cell-free expressed, tRNA labeled and isolated proteins. Transfer to 3-dimensional HydroGel matrix coated microarray substrates and detection via the directly incorporated tRNA mediated fluorescence label.

Contact Photo-Transfer to 3-Dimensional Matrix Coated Microarray Surfaces Using Incorporated PC-Biotin: Detection of a tRNA Mediated Direct Fluorescence Label Cell-Free Expression and tRNA Mediated Labeling:
Human calmodulin and alpha-tubulin were expressed in a rabbit reticulocyte cell-free reaction and co-translationally labeled with both BODIPY-FL and PC-biotin as in Example 1 with the following exceptions: BODIPY-FL-tRNA$^{COMPLETE}$ was used for fluorescence labeling instead of BODIPY-FL-tRNA$^{Lys}$. As a negative control, an expression reaction was performed lacking only the added DNA for the gene of interest (Minus DNA blank). The Translation Dilution Buffer (TDB) used to stop the reaction and prepare the sample contained no BSA or any other protein carriers.
Isolation of Labeled Nascent Proteins:
The isolation procedure only (see later for contact photo-transfer) was performed as in Example 1 with the following exceptions: The buffers used in the procedure contained no BSA or other protein carriers at any step. Capture on the NeutrAvidin beads was for 30 min. After washing the unbound material from the NeutrAvidin beads as described in Example 1 the beads were further washed 3× briefly (briefly=5 sec vortex mix) with 45 bead volumes each of plain PBS and 1×5 min with 45 bead volumes of 40% glycerol in PBS. The washed bead pellet was then suspended with equal volume of 40% glycerol in PBS to yield a 50% bead slurry (v/v).
Contact Photo-Transfer:
Performed as in Example 7 with the following exceptions: Proteins were contact-photo transferred onto 3-dimensional polyacrylamide based HydroGel coated microarray substrates (PerkinElmer Life and Analytical Sciences, Inc., Boston, Mass.). Prior to contact photo-transfer, the HydroGel slides were re-hydrated according to the manufacturers instructions. Following contact photo-transfer, the proteins were allowed to bind to the HydroGel matrix for overnight at +4° C. prior to washing away the beads and unbound material.
Detection of Photo-Transferred Protein:
Detection of the directly incorporated tRNA mediated BODIPY-FL fluorescence labeling was achieved as described in Example 7.
Results:
Results are shown in FIG. 6. −DNA=minus DNA blank derived from expression reaction lacking only the added DNA for gene of interest (all other processing steps otherwise performed same as with DNA containing expressed protein samples); Calm=calmodulin; Tub=alpha-tubulin. The results show that the directly incorporated BODIPY-FL fluorescence label is easily detectable following contact photo-transfer compared to the minus DNA blank. Signal to noise ratios are 4:1 in both cases. Compatibility with matrix coated surfaces such as the HydroGel substrates is important as they may more effectively maintain function of the immobilized proteins versus the essentially flat solid glass substrates for example. Better maintenance of protein function is expected, for example, with surfaces that are hydrophilic, do not chemically react with the protein, and/or maintain the protein in a hydrated state.

Example 9

Contact Photo-Transfer From Magnetic Beads to Antibody Coated Microarray Surfaces Using Incorporated PC-Biotin: Detection of a tRNA Mediated Direct Fluorescence Label Cell-Free Expression and tRNA Mediated Labeling:
Human GST was expressed in a rabbit reticulocyte cell-free reaction and co-translationally labeled with both BODIPY-FL and PC-biotin as in Example 1 with the following exceptions: BODIPY-FL-tRNA$^{COMPLETE}$ was used for fluorescence labeling instead of BODIPY-FL-tRNA$^{Lys}$. As a negative control, an expression reaction was performed lacking only the added DNA for the gene of interest (Minus DNA blank). The Translation Dilution Buffer (TDB) used to stop the reaction and prepare the sample also contained 0.02% Triton X-100 detergent (w/v) in addition to the 0.2% BSA (w/v) as carriers to prevent non-specific adhesion or aggregation of the 1 micron magnetic beads. TDB was also supplemented with 4 mM cycloheximide.
Isolation of Labeled Nascent Proteins:
The isolation procedure only (see later for contact photo-transfer) was performed as in Example 1 with the following exceptions: The buffers used in the procedure contained no BSA or other protein carriers at any step. Capture on the NeutrAvidin beads was for 30 min. After washing the unbound material from the NeutrAvidin beads as described in Example 1 the beads were further washed 3× briefly (briefly=5 sec vortex mix) with 45 bead volumes each of plain PBS and 1×5 min with 45 bead volumes of 40% glycerol in PBS. The washed bead pellet was then suspended with equal volume of 40% glycerol in PBS to yield a 50% bead slurry (v/v).
Furthermore, all Examples prior to this used NeutrAvidin conjugated cross-linked agarose beads (~100 micron) as the affinity matrix for capture of the PC-biotin labeled expressed proteins. However, magnetic beads are desirable due to their ease of manipulation with magnetic devices and are readily available in various relatively small and uniform sizes. In this example, proteins were captured/isolated on streptavidin conjugated 1 micron diameter magnetic beads (Dynabeads® MyOne™ Streptavidin; Dynal Biotech LLC, Brown Deer, Wis.). 114 µg of beads was used for each sample which corresponds to roughly 1×10$^8$ beads with a biotin binding capacity of approximately 400 pmoles. For all processing steps, beads were separated from the fluid in the polypropylene micro-centrifuge tubes using the appropriate manufacturer supplied magnetic device. In contrast to Examples 1 and 7 involving agarose beads, the buffer used during capture on the streptavidin magnetic beads contained both 0.1% BSA (w/v) and 0.01% Triton X-100 detergent (w/v) as carriers to prevent non-specific adhesion or aggregation of the beads. Also in contrast to Examples 1 and 7, following capture of the target protein on the beads, the full washing regimen was as follows: 2× briefly (briefly 5 sec vortex mix) and 2×5 min in 0.5 mL per sample of 1 mM DTT, 0.1% w/v BSA and 0.01% w/v Triton X-100 in PBS then 1× briefly (briefly=5 sec vortex mix) in 0.5 mL per sample of 0.1% BSA w/v in PBS and 1× briefly (briefly=5 sec vortex mix) in 1 mL per sample of plain PBS. Lastly, each washed bead pellet was suspended in 45 µL (~2.5 µg/µL bead concentration) of 50% glycerol and 1% BSA w/v in PBS.
Preparation of Anti-HSV Monoclonal Antibody Coated Microarray Substrates:
The commercially available mouse monoclonal anti-HSV tag antibody (EMD Biosciences, Inc., San Diego, Calif.) at 1

μg/μL was diluted ⅛ in PBS and 64 μL was applied to reactive epoxy activated glass microarray substrates (i.e. activated glass slide) (SuperEpoxy substrates, TeleChem International, Inc. ArrayIt™ Division, Sunnyvale, Calif.). The solution was spread evenly over the substrate surface by overlaying a 22×60 mm cover glass. Binding to the surface was allowed to occur for 30 min at 37° C. in a humidified chamber without agitation. Slides were then washed 4×2 min with excess (>20 mL) TBS-T and blocked in TBS-T supplemented freshly with 0.1M glycine. Slides were rinsed 4× briefly (5 sec) in purified water and dried.

Contact Photo-Transfer:

Performed as in Example 7 except that the 1 micron streptavidin magnetic beads were used here and transfer and immobilization was onto the anti-HSV monoclonal antibody coated microarray substrates. Note that 1 μL of bead suspension deposited onto the substrate (corresponding to one spot in FIG. 7) contained roughly 2×10$^6$ beads prior to removal/washing. Phase contrast light microscopy reveals that the 1 micron magnetic beads, also visible under the microscope, were completely washed/removed from the glass substrates. However, omission of the BSA carrier from the contact photo-transfer buffer results in non-specific adhesion of the 1 micron streptavidin magnetic beads to the substrate surface, unlike with the 100 micron NeutrAvidin agarose beads.

Detection of Photo-Transferred Protein:

Performed as in Example 7.

Figure 7:
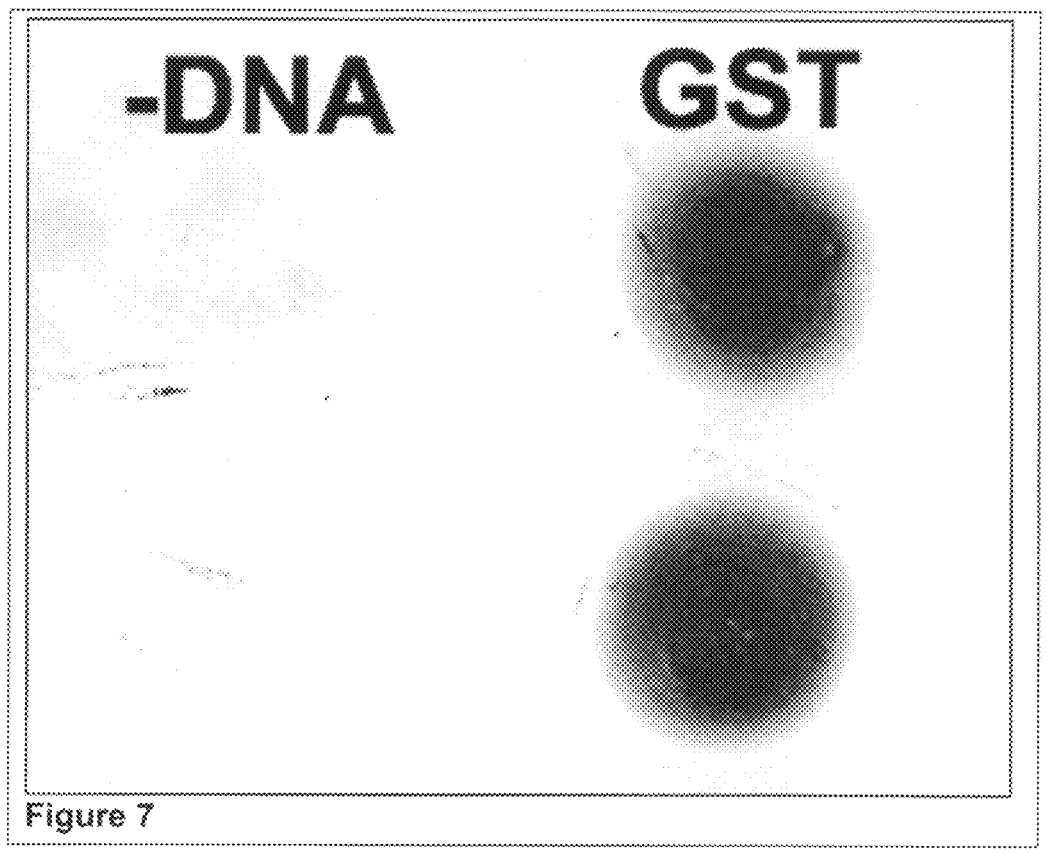
FIG. 7. Contact photo-transfer by incorporated PC-biotin of cell-free expressed, tRNA labeled and isolated proteins. Transfer from 1 micron magnetic beads to an antibody coated surface and detection via the directly incorporated tRNA mediated fluorescence label.

Results:

Results are shown in FIG. 7. −DNA=minus DNA blank derived from expression reaction lacking only the added DNA for gene of interest (all other processing steps otherwise performed same as with DNA containing expressed protein samples); GST=glutathione-s-transferase. The results show that the directly incorporated BODIPY-FL fluorescence label is easily detectable following contact photo-transfer compared to the minus DNA blank with a signal to noise ratio of 9:1. This example importantly demonstrates 2 achievements, i) contact photo-transfer from magnetic beads which are desirable due to their readily available small and uniform sizes and their ease of manipulation for automated assays for example; ii) contact photo-transfer onto antibody coated microarray substrates rather than chemically reactive substrates (e.g. epoxy).

Example 10

Photo-Transfer to Polystyrene 96-Well Microtiter Plates Using Incorporated PC-Biotin: Detection by Antibody Cell-Free Expression and tRNA Mediated Labeling Human p53 oncoprotein (tumor antigen) and alpha-tubulin proteins were expressed and labeled in a rabbit reticulocyte cell-free reaction system as described in Example 1 with the following exceptions: PC-biotin-tRNA$^{COMPLETE}$ was used at 3 μM instead of 1 μM. The BODIPY-FL-tRNA$^{Lys}$ was not used. 100 μL of total expression reaction was used instead of 200 μL. The expression reaction carried out for 1 hr instead of 30 min. The composition of the Translation Dilution Buffer (TDB) was 2×TBS, pH 7.5, 0.2% (w/v) Triton X-100 and 20 mM EDTA.

Isolation of Labeled Nascent Proteins:

PC-biotin labeled nascent proteins were captured and isolated on 50 μL packed bead volume of NeutrAvidin agarose beads (Pierce Biotechnology, Inc., Rockford, Ill.). The isolation procedure was performed in batch mode using a microcentrifuge and polypropylene tubes to manipulate the affinity matrix and exchange the buffers. After capture on the NeutrAvidin beads for 1 hr, beads were washed by mixing 3× briefly (briefly=5 sec vortex mix) in TBS pH 7.5, 0.1% (w/v) Triton X-100 and 10 mM EDTA at 20 bead volumes per wash. Beads were then washed 3× briefly (briefly=5 sec vortex mix) in 50 mM sodium carbonate, pH 9.5 and 50 mM NaCl at 40 bead volumes per wash and lastly prepared to a 5% bead suspension (v/v) in the same buffer.

Photo-Transfer to Wells of a Microtiter Plate:

100 μL/well of the 5% bead suspension, corresponding to each captured target protein, was loaded into opaque white polystyrene 96-well microtiter plates (Microlite 2+; Thermo Labsystems, Franklin, Mass.) for photo-release and subsequent protein adsorption (transfer) to the polystyrene well surface. For photo-release, the plate was illuminated from the top for 5 min with near-UV light (365 nm peak UV lamp, Blak-Ray Lamp, Model XX-15, UVP, Upland, Calif.) at a 5 cm distance while mixing on an orbital plate shaker. The power output of the lamp under these conditions was 2.6 mW/cm$^2$ at 360 nm, 1.0 mW/cm$^2$ at 310 nm and 0.16 mW/cm$^2$ at 250 nm. After light treatment, mixing was continued for 1 hr to allow the photo-released proteins to bind the well surface.

Detection of Photo-Transferred Protein:

For detection purposes, the commercially available mouse monoclonal anti-HSV tag antibody (EMD Biosciences, Inc., San Diego, Calif.) was conjugated to an alkaline phosphatase enzyme reporter using a commercially available maleimide activated alkaline phosphatase reagent (Pierce Biotechnology, Inc., Rockford, Ill.) essentially according to the manufacturer's instructions.

Following photo-transfer of the target proteins to the microtiter plate wells, the bead suspension was removed and the wells washed 4× briefly (5 sec) in 300 μL/well of TBS-T. Wells were then blocked for 30 min in 5% BSA (w/v) in TBS-T. Detection was achieved by adding the anti-HSV alkaline phosphatase conjugate at 0.1 ng/μL in 5% BSA (w/v) in TBS-T for 30 min. Plates were washed again and signal was generated using a commercially available chemiluminescence alkaline phosphatase substrate (Roche Applied Science, Indianapolis, Ind.) according to the manufacturer's instructions. Signal was read in a LumiCount luminescence plate reader (Packard/PerkinElmer Life and Analytical Sciences, Inc., Boston, Mass.).

Results:

Results are shown in FIG. 8. −DNA=minus DNA blank derived from expression reaction lacking only the added DNA for gene of interest (all other processing steps otherwise performed same as with DNA containing expressed protein samples); Tubulin=alpha-tubulin; p53=cellular tumor antigen p53; RLU=raw relative luminescence units. The results show clear detection of the photo-transferred proteins by way of the common C-terminal HSV epitope tag with signal to noise ratios of 140:1 and 609:1 for alpha-tubulin and p53 respectively compared to the minus DNA negative control sample.

Example 11

Photo-Transfer to Antibody Coated 96-Well Microtiter Plates Using Incorporated PC-Biotin: Detection by Antibody in Sandwich ELSIA Format Cell-Free Expression and tRNA Mediated Labeling:

Human p53 oncoprotein (tumor antigen) was expressed and labeled in a rabbit reticulocyte cell-free reaction system as described in Example 1 with the following exceptions:

PC-biotin-tRNA$^{COMPLETE}$ was used at 1.5 μM instead of 1 μM. The BODIPY-FL-tRNA$^{Lys}$ was used, for quality control purposes only, at 1.5 μM instead of 0.6 μM. 100 μL of total expression reaction was used instead of 200 μL. The expression reaction carried out for 1 hr instead of 30 min. The composition of the Translation Dilution Buffer (TDB) was 2×TBS, pH 7.5, 0.2% (w/v) Triton X-100 and 20 mM EDTA.

Isolation of Labeled Nascent Proteins:

PC-biotin labeled nascent p53 was captured and isolated on 10 μL packed bead volume of NeutrAvidin agarose beads (Pierce Biotechnology, Inc., Rockford, Ill.). The isolation procedure was performed in batch mode using a micro-centrifuge and polypropylene tubes to manipulate the affinity matrix and exchange the buffers. After capture on the NeutrAvidin beads for 30 min, beads were washed by mixing 3×5 min each in TBS pH 7.5, 0.1% (w/v) Triton X-100 and 10 mM EDTA at 45 bead volumes per wash. Beads were then washed 3× briefly (briefly=5 sec vortex mix) with 40% glycerol in PBS with 45 bead volumes per wash. For quality control purposes at this point, the washed bead pellets were imaged in the tube using the FluorImager SI laser-based fluorescence scanner (Molecular Dynamics/Amersham Biosciences Corp., Piscataway, N.J.) and the signal from the p53 sample compared to the minus DNA negative control to confirm the expression and isolation was successful. The bead pellet was then further washed 3× briefly (briefly=5 sec vortex mix) in TBS-T at 45 bead volumes each and the beads ultimately prepared to an approximate 5% suspension (v/v) in the same buffer.

Photo-Transfer to Wells of an Antibody Coated Microtiter Plate:

The commercially available mouse monoclonal anti-HSV tag antibody (EMD Biosciences, Inc., San Diego, Calif.) was adsorbed/coated onto the wells of opaque white polystyrene 96-well microtiter plates (Microlite 2+; Thermo Labsystems, Franklin, Mass.) and the plates washed then blocked [5% BSA (w/v) in TBS-T] using standard ELISA procedures. 100 μL/well of the 5% bead suspension corresponding to the captured p53 protein was loaded into the anti-HSV coated microtiter plate for photo-release and subsequent protein capture via the C-terminal HSV epitope tag. For photo-release, the plate was illuminated from the top for 5 min with near-UV light (365 nm peak UV lamp, Blak-Ray Lamp, Model XX-15, UVP, Upland, Calif.) at a 5 cm distance while mixing on an orbital plate shaker. The power output of the lamp under these conditions was 2.6 mW/cm$^2$ at 360 nm, 1.0 mW/cm$^2$ at 310 nm and 0.16 mW/cm$^2$ at 250 nm. After light treatment, mixing was continued for 30 min to allow the photo-released protein to bind the antibody coated well surface.

Detection of Photo-Transferred Protein:

Following photo-transfer of the target protein to the antibody coated microtiter plate wells, the bead suspension was removed and the wells washed 4× briefly (5 sec) in 300 μL/well of TBS-T. Wells were then blocked for 30 min in 5% BSA (w/v) in TBS-T. Detection was achieved in a sandwich ELISA format with a well characterized monoclonal anti-p53 horseradish peroxidase (HRP) conjugate (antibody clone BP53-12 custom ordered from Santa Cruz Biotechnology, Inc., Santa Cruz, Calif.). The antibody was added at 50 pg/μL in 5% BSA (w/v) in TBS-T for 30 min. Plates were washed again and signal was generated using a commercially available chemiluminescence HRP substrate (SuperSignal Femto ELISA Substrate; Pierce Biotechnology, Inc., Rockford, Ill.) according to the manufacturer's instructions. Signal was read in a LumiCount luminescence plate reader (Packard/PerkinElmer Life and Analytical Sciences, Inc., Boston, Mass.).

Results:

Results are shown in FIG. 9. −DNA=minus DNA blank derived from expression reaction lacking only the added DNA for gene of interest (all other processing steps otherwise performed same as with DNA containing expressed protein samples); p53=cellular tumor antigen p53; RLU=raw relative luminescence units. The results show clear detection of the photo-transferred p53 with a signal to noise ratio of 719:1 compared to the minus DNA negative control sample.

Example 12

Contact Photo-Transfer to Activated Microarray Surfaces Using Incorporated PC-Biotin: Application to Advanced 2 Color Protein-Protein Interaction Assays Cell-Free Expression and tRNA Mediated Labeling:

Human calmodulin and alpha-tubulin were expressed in a rabbit reticulocyte cell-free reaction and co-translationally labeled with both BODIPY-FL and PC-biotin as in Example 1 with the following exceptions: BODIPY-FL-tRNA$^{COMPLETE}$ was used for fluorescence labeling instead of BODIPY-FL-tRNA$^{Lys}$. As a negative control, an expression reaction was performed lacking only the added DNA for the gene of interest (Minus DNA blank). The Translation Dilution Buffer (TDB) used to stop the reaction and prepare the sample contained no BSA or any other protein carriers.

Isolation of Labeled Nascent Proteins:

The isolation procedure only (see later for contact photo-transfer) was performed as in Example 1 with the following exceptions: The buffers used in the procedure contained no BSA or other protein carriers at any step. Capture on the NeutrAvidin beads was for 30 min. After washing the unbound material from the NeutrAvidin beads as described in Example 1 the beads were further washed 3× briefly (briefly=5 sec vortex mix) with 45 bead volumes each of plain PBS and 1×5 min with 45 bead volumes of 40% glycerol in PBS. The washed bead pellet was then suspended with equal volume of 40% glycerol in PBS to yield a 50% bead slurry (v/v).

Contact Photo-Transfer:

Performed as in Example 7.

Spotting of Crude Expression Reaction to Microarray Surface for Comparison:

To demonstrate one advantage of the contact photo-transfer method, a comparison was made to microarray immobilized proteins that were not pre-purified by the incorporated PC-biotin and not applied to the microarray surface via contact photo-transfer. Instead, proteins were applied to the microarray surface directly in the crude expression reaction. Because the samples were applied in crude format, the immobilization method could not be via a non-specific protein-reactive chemically activated substrate (e.g. epoxy activated glass substrates). Instead, the immobilization needed to be via a selective affinity interaction. For this, microarray substrates coated with the anti-HSV epitope tag antibody were used to capture via the common C-terminal epitope tag present in the expressed proteins. This antibody was chosen due to its proven effectiveness in protein capture as demonstrated in several former and later Examples.

Microarray substrates were coated with the anti-HSV antibody as described earlier in Example 9. Proteins were expressed as described earlier in this Example except that only BODIPY-FL-tRNA$^{COMPLETE}$ was used for labeling at 4 μM and not the PC-biotin-tRNA$^{COMPLETE}$. After cell-free protein expression, the reactions were diluted with equal volume of 80% glycerol, 2 mM DTT, 20 mM EDTA and 2% (v/v)

of a mammalian protease inhibitor cocktail (Sigma-Aldrich, St. Louis, Mo.) in 2×PBS. 1 μL of the prepared crude expression reactions was applied to the anti-HSV antibody coated microarray substrates and allowed to bind for 1 hr at 37° C. in a humidified chamber.

Preparation of a Cy5 Conjugated Calcineurin Probe for Fluorescence Detection of Protein-Protein Interaction:

In order to measure the known biological binding interaction between the microarray deposited calmodulin "bait" and calcineurin, a fluorescently labeled calcineurin-Cy5 conjugate/probe was prepared as follows: A commercially available 100 Unit vial of calcineurin purified from bovine brain (Sigma-Aldrich, St. Louis, Mo.; Catalog# C1907) corresponding to approximately 20 μg was used for fluorescence labeling. Calcineurin was dissolved in 50 μL of 200 mM sodium bicarbonate and 200 mM NaCl. A 2.7 mM stock of Cy5-NHS monoreactive ester (Amersham Biosciences Corp., Piscataway, N.J.) was prepared in DMSO fresh before use and enough added to the calcineurin solution to achieve a 10-fold molar excess of the Cy5-NHS ester. The labeling reaction was allowed to proceed by gentle mixing for 30 min protected from light with aluminum foil. $\frac{1}{9}^{th}$ volume freshly prepared 100 mM L-lysine monohydrochloride in 200 mM sodium bicarbonate and 200 mM NaCl was added to quench the reaction and mixed for 15 min protected from light with aluminum foil. BSA was then added from a 10% stock as a carrier to a final 0.05% (w/v) concentration. Unreacted/hydrolyzed labeling reagent, quenched labeling reagent, and L-lysine contaminants were removed from the labeled calcineurin protein using a MicroSpin G-25 desalting column (Amersham Biosciences Corp., Piscataway, N.J.) according to the manufacturers instructions. (except that the column was additionally pre-washed 1×350 μL with TBS). Protein recovery was estimated at 0.16 μg/L and the probe stock stored frozen long term at −70° C. Note that initially, a similar calcineurin labeling procedure was done except using a BODIPY-FL-SSE labeling reagent (Invitrogen Corporation, Carlsbad, Calif.) instead of the Cy5-NHS monoreactive ester. This allowed analysis of the conjugate via SDS-PAGE and fluorescence imaging of the gel using a FluorImager SI argon laser-based scanner (Molecular Dynamics/Amersham Biosciences Corp., Piscataway, N.J.) in order to verify successful conjugation and estimate protein concentration using known standards.

Probing the Proteins on the Microarray with the Calcineurin-Cy5 Conjugate:

The calmodulin and tubulin proteins immobilized on the microarray substrates as described earlier in this Example were subsequently probed with the calcineurin-Cy5 conjugate to test for its expected biological interaction with calmodulin. To do so, microarray substrates were rinsed 3× briefly (5 sec) with excess TBS directly following transfer and binding to the substrate surface. The microarray substrates were then blocked 10 min with an excess of 1% BSA (w/v) in TBS. The calcineurin-Cy5 probe stock prepared as described earlier in this Example was diluted 1/30 in 1% BSA (w/v) and 2 mM CaCl₂ in TBS. Each microarray substrate was probed with 75 μL of the diluted calcineurin-Cy5 solution by overlaying with a 22×60 mm glass coverslip and incubating for 45 min in a humidified chamber. Unbound probe was then removed by washing 3×1 min each with excess 2 mM CaCl₂ in TBS and then 1× briefly (5 sec) with 2 mM CaCl₂ in purified water. The microarray substrates were then dried. Since the binding interaction is calcium dependant, as a negative control, a separate permutation was performed whereby the CaCl₂ was omitted from all buffers where present and replaced with the same concentration of EDTA (minus calcium permutation).

Detection of Photo-Transferred Protein:

Detection of the directly incorporated tRNA mediated BODIPY-FL fluorescence labeling as well as binding of the fluorescent calcineurin-Cy5 probe was achieved by imaging the dry microarray substrates on an ArrayWoRx$^e$ BioChip fluorescence reader (Applied Precision, LLC, Issaquah, Wash.) using the appropriate standard built-in filter sets to discriminate between the 2 color fluorophores.

Results:

Results are shown in FIG. 10. −DNA=minus DNA blank derived from expression reaction lacking only the added DNA for gene of interest (all other processing steps otherwise performed same as with DNA containing expressed protein samples); Calm=calmodulin; Tub=alpha-tubulin; Contact Photo-Transfer=microarrays prepared by contact photo-transfer then probed; Crude Spotting=microarrays prepared by applying the crude cell-free expression reaction to anti-HSV antibody coated substrates and then probed; 2 mM CaCl₂=the plus calcium calcineurin probing permutation; 2 mM EDTA=the minus calcium calcineurin probing permutation. In the case of the contact photo-transfer permutation, the results clearly show the expected binding of the calcineurin probe only to calmodulin, in correlation with the known biological interaction as reported in the literature [Nakamura et al. (1992) *FEBS Lett* 309, 103-106], and not tubulin. The direct tRNA mediated BODIPY-FL labeling confirms that both calmodulin and tubulin are present on the array surface compared to the minus DNA control (in fact tubulin is more abundant although it does not bind the probe as expected). Furthermore, as expected, the calcium dependant calcineurin interaction is abolished in the absence of calcium and presence of the metal chelator EDTA. However, in the so-called "Crude Spotting" permutation, while the direct tRNA mediated BODIPY-FL labeling confirms the presence of tubulin, the calmodulin is essentially equal to background. This is likely explained by the lack of a concentrating pre-purification step as with the contact photo-transfer or inaccessibility of the HSV epitope due to protein folding. More importantly, both the BODIPY-FL and Cy5 fluorescence images show measurable signal in the minus DNA negative control, indicating non-specific binding of components from the crude expression reaction to the microarray substrate that are not washed away. Importantly, these non-specifically bound contaminants, likely present in excessive quantities, mediate non-specific binding of the calcineurin probe to the spot areas in all applied samples, effectively masking any potential specific signal from the calcineurin-calmodulin interaction.

Example 13

Contact Photo-Transfer to Microarray Surfaces Using Incorporated PC-Biotin: Advanced Kinase Substrate Profiling Assays Cell-Free Expression and tRNA Mediated Labeling:

Various human proteins were expressed and labeled in a rabbit reticulocyte cell-free reaction system as described in Example 1 with the following exceptions: PC-biotin-tRNA$^{COMPLETE}$ was used at 2 μM instead of 1 μM. The BODIPY-FL-tRNA$^{Lys}$ was not used (nor any other tRNA mediated fluorescence labeling). The volume of expression reaction for each protein species was varied to approximately normalize for differences in expression efficiencies. The expression reaction carried out for 1 hr instead of 30 min. The composition of the Translation Dilution Buffer (TDB) was 2×TBS, pH 7.5, 0.2% (w/v) Triton X-100 and 20 mM EDTA.

Isolation of Labeled Nascent Proteins by Incorporated PC-Biotin and Contact Photo-Transfer:

PC-biotin labeled nascent p53 was captured and isolated on 50 µL packed bead volume of NeutrAvidin agarose beads (Pierce Biotechnology, Inc., Rockford, Ill.). All steps were performed at +4° C. The isolation procedure was performed in batch mode using a micro-centrifuge and polypropylene tubes to manipulate the affinity matrix and exchange the buffers. After capture on the NeutrAvidin beads for 30 min, beads were washed by mixing 3× for 5 min each in TBS pH 7.5, 0.1% (w/v) Triton X-100, 10 mM EDTA and then washed 2× briefly (briefly=5 sec vortex mix) in PBS all at 20 bead volumes per wash. Lastly, the beads were washed 1× briefly (briefly=5 sec vortex mix) with 20 bead volumes of 40% glycerol in PBS and resuspended to a 50% bead slurry (v/v) in the same glycerol/PBS buffer.

For contact photo-transfer, the beads were resuspended by mixing and 1 µL of the bead suspension was manually pipetted onto the surface of an amine-reactive aldehyde activated glass microarray substrate (i.e. activated glass slide) (Super-Aldehyde substrates, TeleChem International, Inc. ArrayIt™ Division, Sunnyvale, Calif.). The slides were then illuminated, without agitation, for 5 min with near-UV light (365 nm peak UV lamp, Blak-Ray Lamp, Model XX-15, UVP, Upland, Calif.) at a 5 cm distance to photo-release and transfer the p53 protein. The power output of the lamp under these conditions was 2.6 mW/cm$^2$ at 360 nm, 1.0 mW/cm$^2$ at 310 nm and 0.16 mW/cm$^2$ at 250 nm. After light treatment, the glass slides were incubated for 30 min at 37° C. in a sealed and humidified chamber to fully ensure photo-released proteins react with the activated solid surface. The beads and any unbound protein were then washed away and the unreacted aldehyde groups on the slides simultaneously blocked for 15 min in 0.25% sodium borohydride (w/v) prepared immediately before use in PBS. Importantly, phase-contrast light microscopy reveals that the easily visible ~100 µm agarose beads do not remain bound to any of the solid surfaces tested (see later examples for different surfaces). The slides were further washed 4× briefly (5 sec) in excess PBS and again blocked for 15 min at 37° C. with 0.1M glycine in TBS-T. Slides were rinsed 4× briefly (5 sec) in excess purified water and dried prior to further processing.

Kinase Treatment of Photo-Transferred Proteins on Microarray Slide:

Kinase solutions were prepared fresh immediately prior to use as follows: ZAP-70 Tyrosine Kinase—979.5 µL of ZAP-70 Base Buffer [50 mM Tris (2-amino-2-(hydroxymethyl)-1,3-propanediol), pH 7.0, 150 mM NaCl and 10 mM MnCl$_2$] was further supplemented with 5 µL of a 1M MnCl$_2$ stock (Sigma-Aldrich, St. Louis, Mo.), 1 µL of a 1M DTT stock (stock stored in aliquots at −70° C.), 10 µL of a 10% Triton X-100 detergent stock and 4.5 µL of a commercially available 230 ng/µL human recombinant ZAP-70 tyrosine kinase stock (Invitrogen Corporation, Carlsbad, Calif.). Just prior to application to the microarray slide, 1 mL of this kinase mixture was supplemented with 53 µL of a 20 mM ATP stock (stock stored in aliquots at −70° C.).

Src pp$^{60}$ Tyrosine Kinase—972.2 µL of ZAP-70 Base Buffer [50 mM Tris (2-amino-2-(hydroxymethyl)-1,3-propanediol), pH 7.0, 150 mM NaCl and 10 mM MnCl$_2$] was further supplemented with 5 µL of a 1M MnCl$_2$ stock (Sigma-Aldrich, St. Louis, Mo.), 1 µL of a 1M DTT stock (stock stored in aliquots at −70° C.), 10 µL of a 10% Triton X-100 detergent stock, 10 µL of a 1M MgCl$_2$ stock (Sigma-Aldrich, St. Louis, Mo.) and 1.8 µL of a commercially available 580 ng/µL human recombinant Src pp$^{60}$ tyrosine kinase stock (Invitrogen Corporation, Carlsbad, Calif.). Just prior to application to the microarray slide, 1 mL of this kinase mixture was supplemented with 53 µL of a 20 mM ATP stock for a 1 mM final (stock stored in aliquots at −70° C.).

Dried microarray slides containing the photo-transferred proteins as described earlier in this Example were overlaid with 1 mL of the aforementioned kinase mixtures and incubated for 30 min at 37° C. in a humidified chamber. This was to allow the kinase to phosphorylate any potential enzyme substrates (photo-transferred proteins) on the microarray slide surface. The kinase reaction was stopped and any kinase solution removed by washing the slides 4×2 min each with excess 10 mM EDTA in TBS-T. Any potentially bound kinase was stripped from the slides by treating the slides for 30 min at 65° C. in a denaturing buffer [2% SDS (w/v) and 5 mM DTT in 50 mM Tris, pH 6.8]. The denaturing buffer was removed by washing the slides 4× briefly (5 sec) in excess TBS-T.

Detection of Phosphorylation:

To detect phosphorylation of any potential kinase substrates (i.e. phosphorylation of photo-transferred proteins) on the microarray slide, the slides were probed with a universal anti-phosphotyrosine antibody. The antibody used was a recombinant derivative of the well known and established PY20 monoclonal anti-phosphotyrosine antibody, the commercially available so-called RC20 antibody clone which was supplied labeled with biotin to allow secondary detection (BD Biosciences, San Jose, Calif.). The microarray slides were first pre-blocked for 15 min at 37° C. with 5% BSA (w/v) in TBS-T. The RC20 anti-phosphotyrosine biotin conjugated antibody was used at 0.5 ng/µL diluted with 5% BSA (w/v) in TBS-T and the slides treated for overnight at +4° C. with gentle mixing. After antibody binding, the slides are washed 4×2 min each with excess TBS-T and secondary fluorescence detection is performed using a streptavidin-Alexa Fluor® 488 dye conjugate (Invitrogen Corporation, Carlsbad, Calif.) at a concentration of 0.2 ng/µL diluted in 5% BSA (w/v) in TBS-T. Secondary detection was performed for 1 hr with gentle mixing. Slides were then washed 4×2 min each with excess TBS-T, rinsed 4× briefly (5 sec) in purified water and dried.

Phosphorylation Controls:

As a negative control, the aforementioned kinase reactions on the microarray slides were performed except only the necessary ATP was omitted from the kinase reaction mixture. Additionally, as a positive control, commercially available phosphotyrosine conjugated to BSA (Sigma-Aldrich, St. Louis, Mo.) was also pre-spotted onto the microarray slide prior to the kinase reaction. Detection of phosphorylation was performed as described earlier in this Example except that instead of a biotin conjugated RC20 anti-phosphotyrosine antibody, a horse radish peroxidase (HRP) conjugated antibody was used (BD Biosciences, San Jose, Calif.) and thus secondary detection was not needed. In this case, fluorescence signal was generated using an Alexa Fluor® 488 Tyramide/TSA HRP substrate mediated fluorescence amplification kit for better sensitivity (Invitrogen Corporation, Carlsbad, Calif.). After imaging the fluorescence signals corresponding to detection of phosphotyrosine (see imaging details later in this example), the slides were further probed with an anti-HSV antibody and fluorescent secondary antibody as described in Example 5 to determine the amount of total photo-transferred protein based on their common C-terminal HSV epitope tags.

Detection of Fluorescence Signals:

All fluorescence signals were imaged on a FluorImager SI argon laser-based scanner (Molecular Dynamics/Amersham Biosciences Corp., Piscataway, N.J.).

Figure 11A:
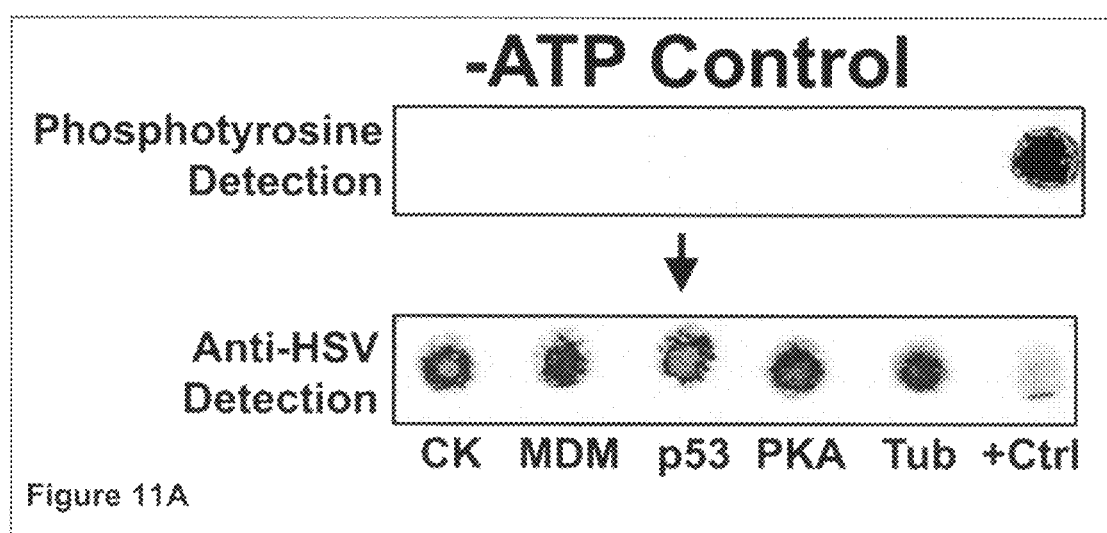
FIG. 11A. Advanced kinase substrate profiling assays using proteins as substrates printed to microarray surfaces by contact photo-transfer. Minus ATP negative control kinase reaction and phosphotyrosine detection followed by anti-HSV total photo-transferred protein detection.
Figure 11B:
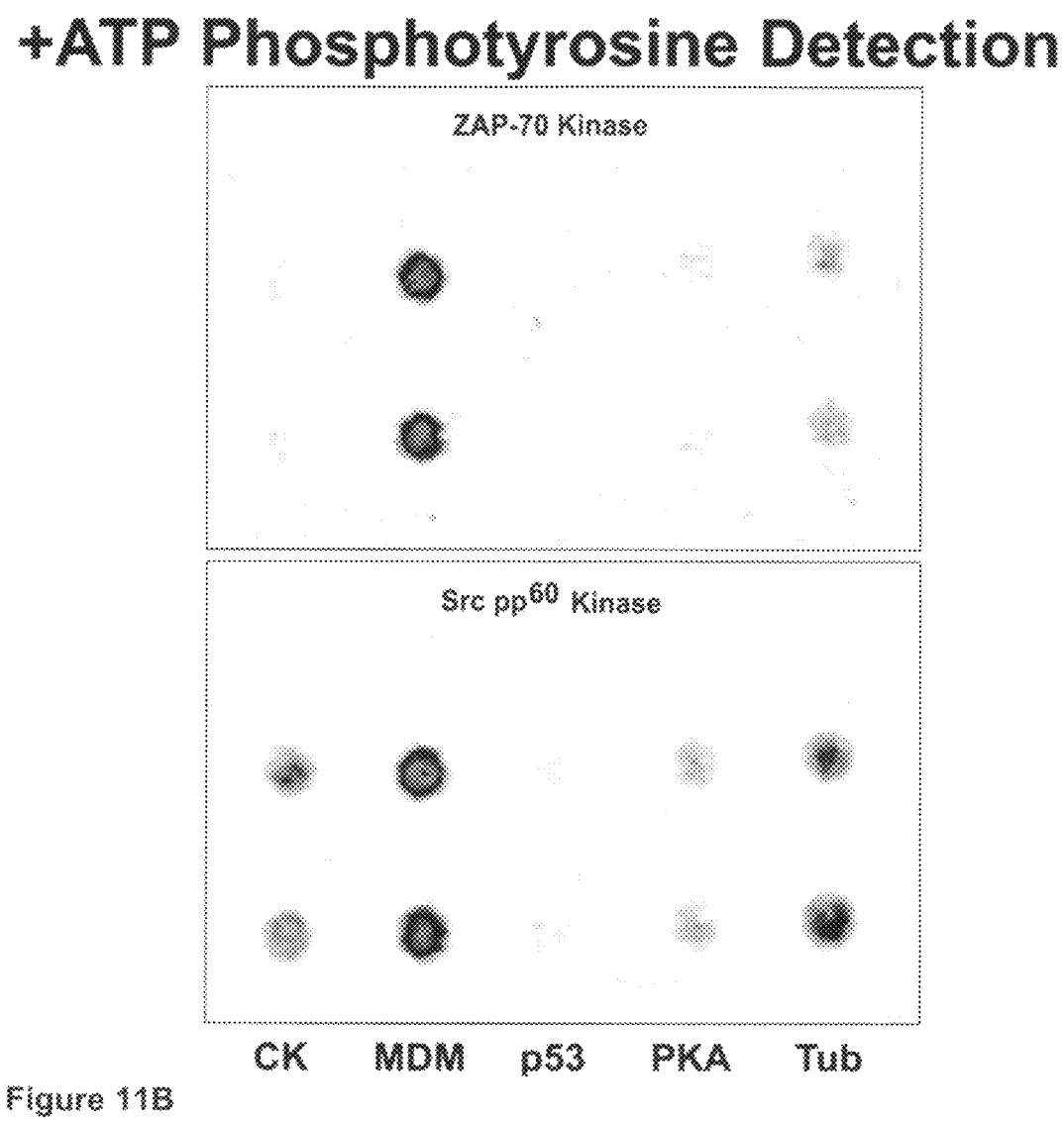
FIG. 11B. Advanced kinase substrate profiling assays using proteins as substrates printed to microarray surfaces by contact photo-transfer. Plus ATP kinase reaction for 2 kinases followed by phosphotyrosine detection.

Results:

Results are shown in FIG. 11. CK casein kinase II; MDM=ubiquitin-protein ligase E3 MDM2; p53=cellular tumor antigen p53; PKA=protein kinase A catalytic subunit alpha; Tub=alpha-tubulin. FIG. 11A shows the minus ATP kinase reaction negative control, the phosphotyrosine positive control and the confirmation of successful contact photo-transfer. As expected, when only the needed ATP is omitted from the kinase reaction, no phosphorylation of the photo-transferred proteins is detected. However, the artificial pre-made and spotted phosphotyrosine-BSA conjugate positive control clearly shows the antibody based phosphotyrosine detection method works. Subsequent probing of the microarray slide with an anti-HSV antibody against the common HSV epitope tag present in all expressed proteins confirms successful photo-transfer of all proteins, which are shown to be present in similar quantities on the array surface. FIG. 11B shows the results of the plus ATP kinase reaction for 2 different human recombinant tyrosine kinases, ZAP-70 and Src $pp^{60}$. The results show differential phosphorylation of the various photo-transferred proteins (substrates) by the 2 kinases. Both kinases heavily phosphorylate the MDM protein and to a lesser degree alpha-tubulin. However, Src $pp^{60}$ shows a broader substrate preference, with significant phosphorylation of CK and PKA. In contrast, ZAP-70 does not phosphorylate CK and phosphorylates PKA to a very slight, nearly undetectable degree. For partial verification of the assay, alpha-tubulin was included as a substrate since it is known in the literature to be phosphorylated by the ZAP-70 tyrosine kinase [Isakov et al. (1996) *J Biol Chem* 271, 15753-15761], and as expected, is indeed targeted by the ZAP-70 kinase. Furthermore, as a negative control, p53 is not phosphorylated by either kinase in correlation with the fact that p53 is a major serine/threonine kinase substrate but not tyrosine kinase substrate.

Example 14

Contact Photo-Transfer from Individually Resolved Beads to Microarray Surfaces Using Incorporated PC-Biotin: Detection of Internal tRNA Mediated Label and by Antibody Cell-Free Expression and tRNA Mediated Labeling:

Human MDM2 and alpha-tubulin were expressed in a rabbit reticulocyte cell-free reaction and co-translationally labeled with both BODIPY-FL and PC-biotin as in Example 1 with the following exceptions: BODIPY-FL-tRNA$^{COMPLETE}$ was used for fluorescence labeling instead of BODIPY-FL-tRNA$^{Lys}$. As a negative control, an expression reaction was performed lacking only the added DNA for the gene of interest (Minus DNA blank). The Translation Dilution Buffer (TDB) used to stop the reaction and prepare the sample contained 0.2% (w/v) beta-casein (pure from bovine milk; Sigma-Aldrich, St. Louis, Mo.) instead of BSA as a carrier, 10 mM DTT instead of 2 mM and additionally contained 20 mM EDTA added from a 500 mM pH 8.0 stock and 4 mM cycloheximide (Sigma-Aldrich, St. Louis, Mo.) added from a 355 mM stock in DMSO.

Isolation of Labeled Nascent Proteins:

The isolation procedure only (see later for contact photo-transfer) was performed as in Example 1 with the following exceptions: Capture on the NeutrAvidin beads was for 30 min. After capture, beads were washed 2× briefly (briefly=5 sec vortex mix) with 45 bead volumes each of PBS pH 7.5, 5 mM DTT and 0.1% (w/v) beta-casein and 2×5 min with 45 bead volumes of 40% glycerol and 5 mM DTT in PBS (room temperature). The washed bead pellet was then prepared with 40% glycerol and 5 mM DTT in PBS to yield a 1% bead suspension (v/v).

Contact Photo-Transfer from Individually Resolved Beads:

For contact photo-transfer from individually resolved beads, the beads were resuspended by mixing and 1 µL of the bead suspension was manually pipetted onto the surface of a reactive epoxy activated glass microarray substrate (i.e. activated glass slide) (SuperEpoxy substrates, TeleChem International, Inc. ArrayIt™ Division, Sunnyvale, Calif.). Note that 1 µL of the 1% bead suspension deposited on the substrate (so-called "parent spots"; ~2 mm diameter) contained roughly 5 to 8 individual agarose beads (~100 micron diameter) prior to removal/washing. The individual beads (prior to washing) within the parent spots were easily visible using a phase contrast light microscope and were typically not clustered/aggregated at this density (i.e. did not contact each other). Prior to photo-release, the beads were allowed to settle onto (contact) the microarray substrate surface by leaving the substrates for 5 min without disturbance/agitation. Note that in this buffer system, the more dense beads do visibly settle at unit gravity in this time frame. The substrates were then illuminated, without agitation, for 5 min with near-UV light (365 nm peak UV lamp, Blak-Ray Lamp, Model XX-15, UVP, Upland, Calif.) at a 5 cm distance to photo-release and transfer the target proteins. The power output of the lamp under these conditions was 2.6 mW/cm$^2$ at 360 nm, 1.0 mW/cm$^2$ at 310 nm and 0.16 mW/cm$^2$ at 250 nm. After light treatment, the glass substrates were incubated without disturbance for 30 min at 37° C. in a sealed and humidified chamber to fully ensure photo-released proteins react with the activated solid surface. The beads and any unbound protein was then removed with 3× brief (5 sec) washes in TBS-T followed by 4× brief (5 sec) washes in purified water. Phase contrast light microscopy reveals that the easily visible 100 micron NeutrAvidin agarose beads were completely washed/removed from the glass substrates. The slides were dried prior to fluorescence imaging.

Detection of Photo-Transferred Protein:

Detection of the directly incorporated tRNA mediated BODIPY-FL fluorescence labeling was achieved by imaging the dry microarray substrates on an ArrayWoRx$^e$ BioChip fluorescence reader (Applied Precision, LLC, Issaquah, Wash.) using the appropriate manufacturer supplied standard filter set and the resolution set to 9.7 microns.

Preparation of a Cy5 Conjugated Anti-HSV Antibody for Fluorescence Detection:

After imaging the signal from the directly incorporated tRNA mediated BODIPY-FL fluorophores, the photo-transferred proteins on the microarray substrate were then probed with an antibody to the common C-terminal HSV epitope tag. For this, a fluorescently labeled Cy5 antibody conjugate was prepared. 120 µg of mouse monoclonal anti-HSV tag antibody (EMD Biosciences, Inc., San Diego, Calif.) at 1 µg/µL was kept in it's manufacturer supplied buffer (PBS/glycerol) and supplemented with ⅑$^{th}$ volume of 1M sodium bicarbonate stock for a final 100 mM. The Cy5-NHS monoreactive ester (Amersham Biosciences Corp., Piscataway, N.J.) labeling reagent was added to a 20-fold molar excess relative to the antibody from a 27 mM stock prepared in DMSO. The reaction was allowed to occur for 30 min with gentle mixing protected from light. Unreacted or hydrolyzed labeling reagent was removed using a NAP-10 Sepharose G-25 desalting column (Amersham Biosciences Corp., Piscataway, N.J.) against a PBS buffer according to the manufacturer's instructions except that only the visibly blue colored (Cy5) protein elution fraction was collected. The antibody conjugate was analyzed in a standard spectrophotometer and found to be 0.07 mg/mL antibody concentration at 1 mL total with an average of 3.5 Cy5 dyes per antibody molecule. The antibody conjugate was then supplemented with a BSA carrier to a final 0.1% (w/v) from a 10% stock and stored protected from light at +4° C.

Probing the Photo-Transferred Proteins with the Cy5 Fluorescently Labeled Anti-HSV Antibody:

Microarray substrates were blocked for 15 min at 37° C. using 5% BSA (w/v) in TBS-T and then probed for 30 min at 37° C. with the anti-HSV-Cy5 probe at 0.7 ng/μL in the same buffer. Substrates were then washed 4×2 min with excess TBS-T, 4× briefly (5 sec) with purified water and then dried. Detection of the anti-HSV-Cy5 signal was achieved by imaging the dry microarray substrates on an ArrayWoRx$^e$ BioChip fluorescence reader using the appropriate manufacturer supplied standard filter set (Applied Precision, LLC, Issaquah, Wash.) and the resolution set to 9.7 microns.

Figure 12:
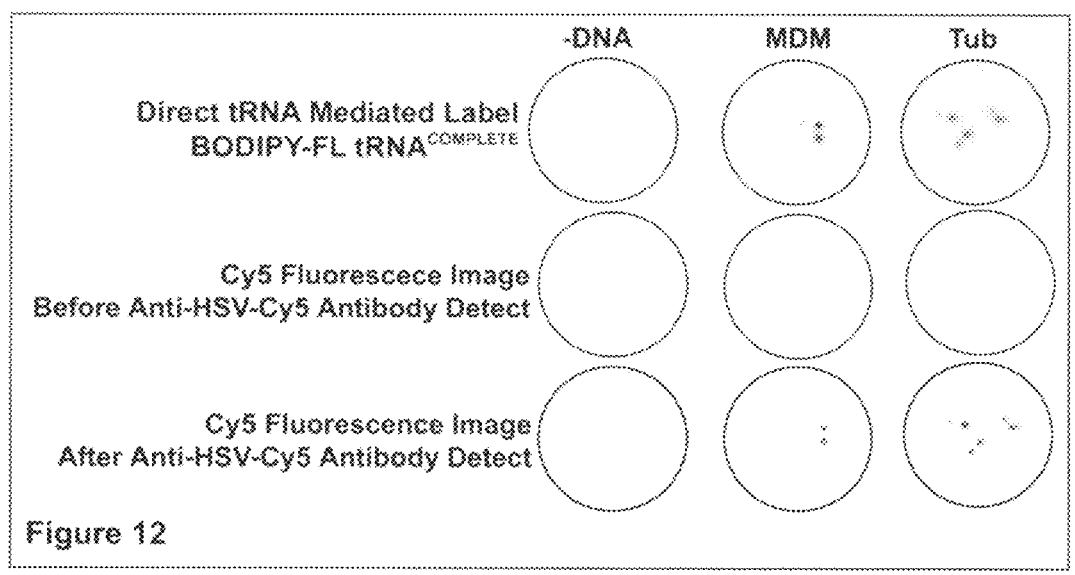
FIG. 12. Contact photo-transfer from single 100 micron agarose beads by incorporated PC-biotin of cell-free expressed, tRNA labeled and isolated proteins. Transfer to activated microarray substrates. Detection via the directly incorporated tRNA mediated fluorescence label and by antibody.

Results:

Results are shown in FIG. 12. −DNA=minus DNA blank derived from expression reaction lacking only the added DNA for gene of interest (all other processing steps otherwise performed same as with DNA containing expressed protein samples); MDM=ubiquitin-protein ligase E3 MDM2; Tub=alpha-tubulin. The results show that the directly incorporated BODIPY-FL fluorescence label is easily detectible following contact photo-transfer of expressed proteins from individual ~100 micron agarose beads compared to the minus DNA blank. Individual spot diameters were measured using the manufacturer supplied software for the ArrayWoRx$^e$ BioChip fluorescence reader (Applied Precision, LLC, Issaquah, Wash.) and were approximately 100 microns (note that agarose beads are supplied mesh filtered and somewhat heterogeneous in size). Approximately 3-8 individual spots originating from individual beads were observed within each 1 μL (2 mm) parent spot in correlation with the number and pattern of beads observed by phase contrast light microscopy prior to washing the beads away. Prior to probing the microarrays with the anti-HSV Cy5 antibody, the arrays were imaged using the Cy5 filter set (channel) in the reader as a negative control. No cross-talk of the BODIPY-FL fluorescence from the tRNA mediated labels was observed in the Cy5 filter set (channel) of the reader. Following probing the microarrays with the anti-HSV Cy5 antibody, the arrays were again imaged with the Cy5 filter set (channel) in the reader. Specific signal from the photo-transferred HSV tagged proteins is clearly observed again with spotting patterns that precisely match that observed from the tRNA mediated fluorescence labeling. Clearly/sharply resolved and robust 100 micron fluorescent spots suggests that the photo-released proteins are largely captured/transferred directly onto the microarray surface without significant diffusion into the fluid medium of the 1 μL parent spots.

Example 15

Contact Photo-Transfer from Individually Resolved Beads to Microarray Surfaces Using Incorporated PC-Biotin: Advanced 2 Color p53-MDM Protein-Protein Interaction Assays Cell-Free Expression and tRNA Mediated Labeling:

The lower sample volume requirements per microarray-feature of the method comprising contact photo-transfer from individually resolved beads facilitates significant scaling down of the expression reaction. Therefore the expression reaction was scaled down 10× compared to Example 1, from 200 μL to 20 μL. Note that with the isolation procedures used (see later in this example) 20 μL of expression reaction yields ~750 agarose beads and therefore a theoretical maximum of 750 microarray features. Human MDM2 and GST were expressed in a rabbit reticulocyte cell-free reaction and co-translationally labeled with both BODIPY-FL and PC-biotin as in Example 1 (scaled down proportionally to 20 μL reaction) with the following additional exceptions:

BODIPY-FL-tRNA$^{COMPLETE}$ was used for fluorescence labeling instead of BODIPY-FL-tRNA$^{Lys}$. As a negative control, an expression reaction was performed lacking only the added DNA for the gene of interest (Minus DNA blank). The Translation Dilution Buffer (TDB) used to stop the reaction and prepare the sample contained 0.2% (w/v) beta-casein (pure from bovine milk; Sigma-Aldrich, St. Louis, Mo.) instead of BSA as a carrier, 10 mM DTT instead of 2 mM and additionally contained 20 mM EDTA added from a 500 mM pH 8.0 stock and 4 mM cycloheximide (Sigma-Aldrich, St. Louis, Mo.) added from a 355 mM stock in DMSO. Note that due to the scaled down reaction size, after TDB addition the total sample volume was 40 μL prior subsequent steps.

Isolation of Labeled Nascent Proteins:

PC-biotin labeled nascent proteins were captured and isolated on 1 μL packed bead volume of NeutrAvidin agarose beads having an approximate biotin binding capacity of 80 pmoles (Pierce Biotechnology, Inc., Rockford, Ill.). To facilitate addition of small bead volumes to the samples, the beads were initially prepared to a 5% (v/v) bead suspension in 0.1% (w/v) beta-casein, 1% (w/v) BSA and 5 mM DTT in PBS. The prepared 40 μL of samples (see earlier in this Example) were then mixed with 20 μL of the 5% (v/v) bead suspension corresponding to addition of 1 μL packed bead volume. The isolation procedure was performed in batch mode using 0.45 micron pore size, PVDF membrane, micro-centrifuge Filtration Devices to facilitate manipulation of the small volumes of affinity matrix (~100 micron beads) and exchange the buffers (Ultrafree-MC Durapore Micro-centrifuge Filtration Devices, 400 μL capacity; Millipore, Billerica, Mass.). All steps were performed at +4° C. or on an ice water bath and all reagents and samples were also kept under these conditions during the procedure. After capture on the NeutrAvidin beads for 30 min, beads were washed by mixing 2× briefly (briefly=5 sec vortex mix) and 2× for 5 min in 400 bead volumes per wash. The buffer used for washing the beads was PBS pH 7.5 and 5 mM DTT. The beads were then additionally washed 1× briefly (briefly=5 sec vortex mix) in 400 bead volumes of 40% glycerol and 5 mM DTT in PBS. Prior to contact photo-transfer of the captured and isolated proteins, the washed pellet of 1 μL of NeutrAvidin agarose beads was suspended in a final volume of 100 μL of 40% glycerol and 5 mM DTT in PBS thereby resulting in a 1% (v/v) bead suspension that can be stored long-term at −20° C. without freezing of the sample and thus without damage to the NeutrAvidin agarose beads.

Contact Photo-Transfer from Individually Resolved Beads:

Performed as in Example 14 with the following exceptions: 0.5 μL instead of 1 μL of the 1% (v/v) bead suspension was applied to the microarray substrates to create the parent spots and application was to aldehyde activated glass microarray substrates instead of epoxy (i.e. activated glass slide) (Super-Aldehyde substrates, TeleChem International, Inc. ArrayIt™ Division, Sunnyvale, Calif.). Note that 0.5 μL of the 1% bead suspension deposited on the substrate (so-called "parent spots"; ~1-2 mm diameter) contained roughly 3 to 5 individual agarose beads (~100 micron diameter) prior to removal/washing. After contact photo-transfer from individually resolved beads, the beads and any unbound protein were then removed and the substrates simultaneously blocked with a 15 min wash, with mixing, using 5 mM DTT, 100 mM glycine and 6% (w/v) BSA in PBS. Phase contrast light microscopy reveals that the easily visible 100 micron NeutrAvidin agarose beads were completely washed/removed from the glass substrates.

Preparation of a Cy5 Conjugated p53 Probe for Fluorescence Detection of Protein-Protein Interaction:

In order to measure the known biological binding interaction between the microarray deposited MDM "bait" and p53, a fluorescently labeled p53-Cy5 conjugate/probe was prepared as follows: 100 µL of a commercially available recombinant human p53-GST fusion protein (Santa Cruz Biotechnology, Inc., Santa Cruz, Calif.) at 1 µg/µL (100 µg) was used for fluorescence labeling. The manufacturer supplied p53 solution was clarified in a micro-centrifuge at 13,000 rpm for 5 min. The p53 was then dialyzed against 200 mM sodium bicarbonate, 200 mM NaCl, 5 mM DTT and 10 mM EDTA (added from a 500 mM pH 8.0 stock). Dialysis was performed at +4° C. in 400 µL capacity 10 kDa molecular weight cut-off (MWCO) Slide-A-Lyzer MINI Dialysis Units (Pierce Biotechnology, Inc., Rockford, Ill.). Reservoir buffer was 250-500 mL for each round of dialysis and dialysis was for 1× overnight and 1×1 hr with mixing of the reservoir buffer using a standard magnetic stir bar device. The resultant dialyzed p53 sample is collected and mixed with 0.5 µL of a 27 mM stock of Cy5-NHS monoreactive ester (Amersham Biosciences Corp., Piscataway, N.J.) which was prepared in DMSO. With an estimated 50% protein recovery after dialysis, this constitutes an approximate 20-fold molar excess of labeling reagent. The labeling reaction was allowed to proceed by gentle mixing for 30 min protected from light with aluminum foil. $\frac{1}{9}^{th}$ volume freshly prepared 100 mM L-lysine monohydrochloride in PBS was added to quench the reaction and mixed for 1 hr protected from light with aluminum foil. After quenching, the sample is mixed with equal volume of 10 mM DTT and 0.2% (w/v) beta-casein in 2×PBS prior to processing on a desalting column. Unreacted or hydrolyzed labeling reagent was removed using a NAP-10 Sepharose G-25 desalting column (Amersham Biosciences Corp., Piscataway, N.J.) against 5 mM DTT and 0.1% (w/v) beta-casein in PBS according to the manufacturer's instructions except that only the visibly blue colored (Cy5) protein elution fraction was collected. Estimated p53-Cy5 conjugate concentration is 25-50 ng/µL (protein concentration). Note that initially, a similar p53 labeling procedure was done except using a BODIPY-FL-SSE labeling reagent (Invitrogen Corporation, Carlsbad, Calif.) instead of the Cy5-NHS monoreactive ester. This allowed analysis of the conjugate via SDS-PAGE and fluorescence imaging of the gel using a FluorImager SI argon laser-based scanner (Molecular Dynamics/Amersham Biosciences Corp., Piscataway, N.J.) in order to verify successful conjugation and estimate protein concentration using known standards. This p53-Cy5 probe stock was stored in single to double use aliquots at −70° C.

Probing the Photo-Transferred Proteins with the Cy5 Fluorescently Labeled p53 Probe:

The MDM and GST proteins were immobilized/transferred onto the microarray substrates which were then washed and blocked as described earlier in this Example. The microarray substrates were subsequently probed with the p53-Cy5 conjugate to test for its expected biological interaction with MDM. To do so, microarray substrates were first further washed 3× briefly (5 sec) with excess TBS. The p53-Cy5 probe stock prepared as described earlier in this Example was thawed and diluted 1:1 with 10% BSA (w/v) and 5 mM DTT and further supplemented with $\frac{1}{49}^{th}$ volume of a 5M NaCl stock. The final buffer composition of the diluted p53-Cy5 probe was 5% BSA (w/v), 150 mM NaCl, 0.05% beta-casein (w/v) and 5 mM DTT in 25 mM sodium phosphate pH 7.5. Insoluble, aggregated or particulate material/contamination was removed from the probe solution by running it through a 0.45 micron pore size, PVDF membrane, micro-centrifuge Filtration Device (Ultrafree-MC Durapore Microcentrifuge Filtration Devices, 400 µL capacity; Millipore, Billerica, Mass.) in addition to further spinning the filtrate in a micro-centrifuge at 13,000 rpm and collecting the fluid supernatant. Each microarray substrate was probed with ~75 µL of the diluted p53-Cy5 probe solution by overlaying with a 22×60 mm glass coverslip and incubating for 30 min in a humidified chamber. Unbound probe was then removed by washing 3×1 min each with excess PBS and then 1× briefly (5 sec) purified water. The microarray substrates were then dried.

Detection of Photo-Transferred Protein:

Detection of the directly incorporated tRNA mediated BODIPY-FL fluorescence labeling as well as binding of the fluorescent p53-Cy5 probe was achieved by imaging the dry microarray substrates on an ArrayWoRx$^e$ BioChip fluorescence reader (Applied Precision, LLC, Issaquah, Wash.) using the appropriate standard built-in filter sets to discriminate between the 2 color fluorophores and the resolution set to 9.7 microns.

Figure 13:
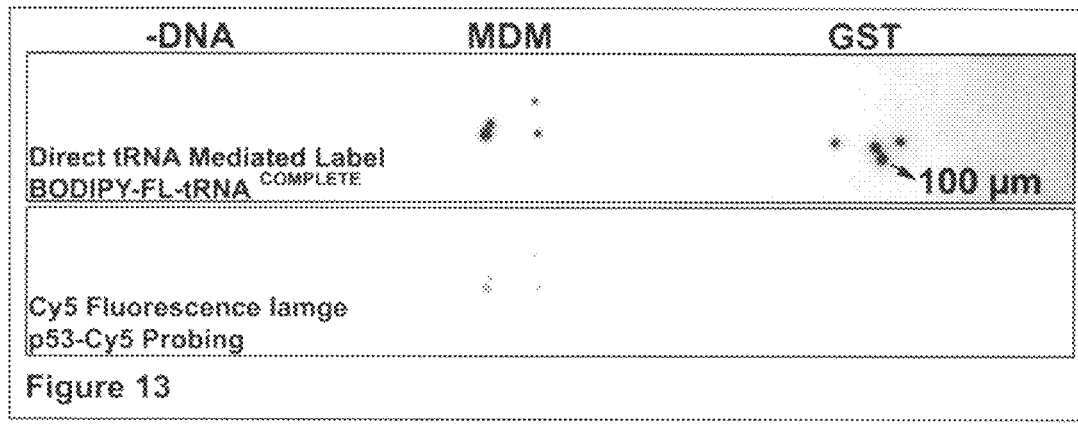
FIG. 13. Contact photo-transfer from single 100 micron agarose beads by incorporated PC-biotin of cell-free expressed, tRNA labeled and isolated proteins. Transfer to activated microarray substrates. Advanced 2 color fluorescence p53-MDM protein-protein interaction assay.

Results:

Results are shown in FIG. 13. −DNA=minus DNA blank derived from expression reaction lacking only the added DNA for gene of interest (all other processing steps otherwise performed same as with DNA containing expressed protein samples); MDM=ubiquitin-protein ligase E3 MDM2; GST=glutathione-s-transferase. The results show that the directly incorporated BODIPY-FL fluorescence label is easily detectable following contact photo-transfer of expressed proteins from individual ~100 micron agarose beads compared to the minus DNA blank. Individual spot diameters were measured using the manufacturer supplied software for the ArrayWoRx$^e$ BioChip fluorescence reader (Applied Precision, LLC, Issaquah, Wash.) and were approximately 100 microns. The arrow in FIG. 13 denotes a single spot derived from the contact photo-transfer from individually resolved beads that was specifically measured at 100 microns in diameter. Four individual spots originating from individual beads were observed within each 0.5 µL (1-2 mm) parent spot in correlation with the number and pattern of beads observed by phase contrast light microscopy prior to washing the beads away. Query of the microarray substrate with the p53-Cy5 probe clearly shows the probe only interacts with MDM as expected, in correlation with the literature [Bottger et al. (1997) *J Mol Biol* 269, 744-756], and not the GST negative control protein present in equal amounts based on the BODIPY-FL signals. Clearly/sharply resolved and robust 100 micron fluorescent spots suggests that the photo-released proteins are largely captured/transferred directly onto the microarray surface without significant diffusion into the fluid medium of the 0.5 µL parent spots.

Example 16

Contact Photo-Transfer from Individually Resolved Beads of Pre-Formed Protein-Protein Complexes to Microarray Surfaces Using Incorporated PC-Biotin: Protein-Protein Interaction Assays Using Only Cell-Free Expressed and tRNA Labeled Proteins Throughout Cell-Free Expression and tRNA Mediated Labeling:

The lower sample volume requirements per microarray-feature of the method comprising contact photo-transfer from individually resolved beads facilitates significant scaling down of the expression reaction. Therefore the expression reaction was scaled down 10× compared to Example 1, from 200 μL to 20 μL. Note that with the isolation procedures used (see later in this example) 20 μL of expression reaction yields ~750 agarose beads and therefore a theoretical maximum of 750 microarray features. Human MDM2, GST and p53 were expressed in a rabbit reticulocyte cell-free reaction and co-translationally labeled with BODIPY-FL or PC-biotin as in Example 1 (scaled down proportionally to 20 μL reaction) with the following additional exceptions:

BODIPY-FL-tRNA$^{COMPLETE}$ was used for fluorescence labeling (at 2 μM) instead of BODIPY-FL-tRNA$^{Lys}$. The cell-free expressed p53 "probe" was labeled only with BODIPY-FL using the BODIPY-FL-tRNA$^{COMPLETE}$ and was not labeled with PC-biotin in any way. Note that 40 μL of p53 was expressed and processed such that 20 μL could be used to probe each of the 2 "bait" proteins (MDM2 and GST). The "bait" proteins were labeled only with PC-Biotin-tRNA$^{COMPLETE}$ (at 1 μM) and not with BODIPY-FL in any way. The Translation Dilution Buffer (TDB) used to stop the reaction and prepare the sample contained no BSA or other protein carrier, 10 mM DTT instead of 2 mM and additionally contained 20 mM EDTA added from a 500 mM pH 8.0 stock and 4 mM cycloheximide (Sigma-Aldrich, St. Louis, Mo.) added from a 355 mM stock in DMSO. Note that due to the scaled down reaction size, after TDB addition the total sample volume was 40 μL (for "bait" proteins) prior subsequent steps (80 μL for p53 "probe").

Protein-Protein Interaction Assay:

All steps were performed at +4° C. or on an ice water bath and all reagents and samples were also kept under these conditions during the procedure. 40 μL of the processed/diluted p53 "probe" solution was mixed with each of the 40 μL of the processed/diluted "bait" proteins (MDM2 and GST) and incubated for 15 min at +4° C. with gentle mixing to allow any binding to occur. PC-biotin labeled "bait" proteins (MDM2 and GST), along with any bound BODIPY-FL labeled p53 "probe", were then captured and isolated on 1 μL packed bead volume of NeutrAvidin agarose beads having an approximate biotin binding capacity of 80 pmoles (Pierce Biotechnology, Inc., Rockford, Ill.). To facilitate addition of small bead volumes to the samples, the beads were initially prepared to a 10% (v/v) bead suspension with 5 mM DTT in PBS. The samples, now 80 μL each, were then mixed with 10 μL of the 10% (v/v) bead suspension corresponding to addition of 1 μL packed bead volume. After capture on the NeutrAvidin beads for 1 hr, beads were washed by mixing 3× briefly (briefly=5 sec vortex mix) in 400 bead volumes per wash of PBS pH 7.5 and 5 mM DTT. The washing procedure was performed in batch mode using 0.45 micron pore size, PVDF membrane, micro-centrifuge Filtration Devices to facilitate manipulation of the small volumes of affinity matrix (~100 micron beads) and exchange the buffers (Ultrafree-MC Durapore Micro-centrifuge Filtration Devices, 400 μL capacity; Millipore, Billerica, Mass.). Prior to contact photo-transfer of the captured and isolated proteins, the washed pellet of 1 μL of NeutrAvidin agarose beads was suspended in a final volume of 50 μL of 50% glycerol and 5 mM DTT in PBS thereby resulting in a 2% (v/v) bead suspension.

Contact Photo-Transfer from Individually Resolved Beads:

Performed as in Example 14 except that after contact photo-transfer from individually resolved beads to epoxy activated microarray substrates, the beads and any unbound protein were then removed by washing only 1× briefly (5 sec) in purified water. Phase contrast light microscopy reveals that the easily visible 100 micron NeutrAvidin agarose beads were completely washed/removed from the glass substrates. Substrates were dried prior to fluorescence imaging.

Detection of Protein-Protein Interaction After Contact Photo-Transfer:

Detection of the directly incorporated tRNA mediated BODIPY-FL fluorescence signal arising from selective binding of the cell-free expressed p53 "probe" to the MDM "bait" was achieved by imaging the dry microarray substrates on an ArrayWoRx$^e$ BioChip fluorescence reader (Applied Precision, LLC, Issaquah, Wash.) using the appropriate standard built-in filter set.

Detection of Total Photo-Transferred Protein Using an Anti-HSV-Cy5 Antibody:

After determining binding of the p53 "probe" by fluorescence imaging, the successful photo-transfer of all proteins was verified using an anti-HSV-Cy5 fluorescently labeled antibody against the common C-terminal HSV epitope tag present in all expressed proteins as described in Example 14.

Results:

Results are shown in FIG. 14. MDM=ubiquitin-protein ligase E3 MDM2 ("×4" refers to application of 4 parent spots at 1 μL each); GST=glutathione-s-transferase ("×3" refers to application of 3 parent spots at 1 μL each). The results show that the directly incorporated BODIPY-FL fluorescence label corresponding to selective binding of the p53 "probe" to the MDM "bait", in correlation with the literature [Bottger et al. (1997) *J Mol Biol* 269, 744-756], is easily detectible following contact photo-transfer of the expressed/isolated proteins and complexes from individual ~100 micron agarose beads. In contrast, the GST negative control "bait" shows no signal indicating no binding of the added p53 "probe" as expected. Note that in comparison to Examples 14 and 15, the beads were 2× more concentrated and thus somewhat clustered within the parent spots and therefore not all beads are fully resolved with this lower magnification image (although many are). Further query of the microarray substrate with the anti-HSV-Cy5 antibody against the common C-terminal epitope tag present in all expressed proteins clearly shows that both the MDM and GST "baits" were successfully photo-transferred although only the MDM binds the p53 "probe". Note that GST expresses more efficiently than p53 or MDM and therefore provides a stronger anti-HSV-Cy5 signal than even the p53-MDM complexes.

Example 17

Contact Photo-Transfer to Activated Microarray Surfaces Using Photocleavable Antibodies:
Detection of a tRNA Mediated Direct Fluorescence Label Preparation of a Photocleavable Antibody Affinity Matrix:

For photo-isolation of expressed proteins, an antibody against the common C-terminal HSV epitope tag was conjugated to PC-biotin and loaded to a NeutrAvidin agarose bead affinity matrix as done in Example 2.

Cell-Free Expression and tRNA Mediated Labeling:

Human p53 oncoprotein (tumor antigen) and glutathione-s-transferase (GST) proteins containing a common HSV epitope tag at the C-terminus were expressed and labeled in a rabbit reticulocyte cell-free reaction system as described in Example 1 except that only BODIPY-FL-tRNA$^{COMPLETE}$ was used for labeling at 1 μM and the BSA protein carrier was omitted from the TDB buffer used to stop the reaction and prepare the sample.

Isolation of Labeled Nascent Proteins:

The isolation procedure only (see later for contact photo-transfer and solution photo-release) was performed as in Example 1 with the following exceptions: 20 μL of the anti-HSV photocleavable antibody affinity matrix was substituted for the NeutrAvidin beads in Example 1. The buffers used in the procedure contained no BSA or other protein carriers at any step. 50 bead volumes per wash was used to remove the unbound material. The washed bead pellet was then suspended to a 50% bead slurry (v/v) in 40% glycerol and 1 mM DTT in PBS.

Contact Photo-Transfer:

Performed as in Example 7 except that amine-reactive aldehyde activated glass microarray substrates (i.e. activated glass slide) (SuperAldehyde substrates, TeleChem International, Inc. ArrayIt™ Division, Sunnyvale, Calif.) were used instead of the epoxy activated substrates.

Solution Photo-Release for SDS-PAGE Analysis:

For quality control confirmation, the remaining sample/beads (50% suspension) not used for contact photo-transfer were diluted to an approximate 10% bead suspension (v/v) in 0.1% BSA (w/v) and 1 mM DTT in PBS. Photo-release of this bead suspension and SDS-PAGE analysis was performed as described in Example 1. An aliquot of the crude non-isolated cell-free expression reaction was also analyzed in parallel via standard SDS-PAGE.

Detection of Proteins:

Detection of the directly incorporated tRNA mediated BODIPY-FL fluorescence labeling was achieved by imaging either the dry microarray substrates or the electrophoretic gel on a FluorImager SI laser-based scanner (Molecular Dynamics/Amersham Biosciences Corp., Piscataway, N.J.).

Figure 15A:
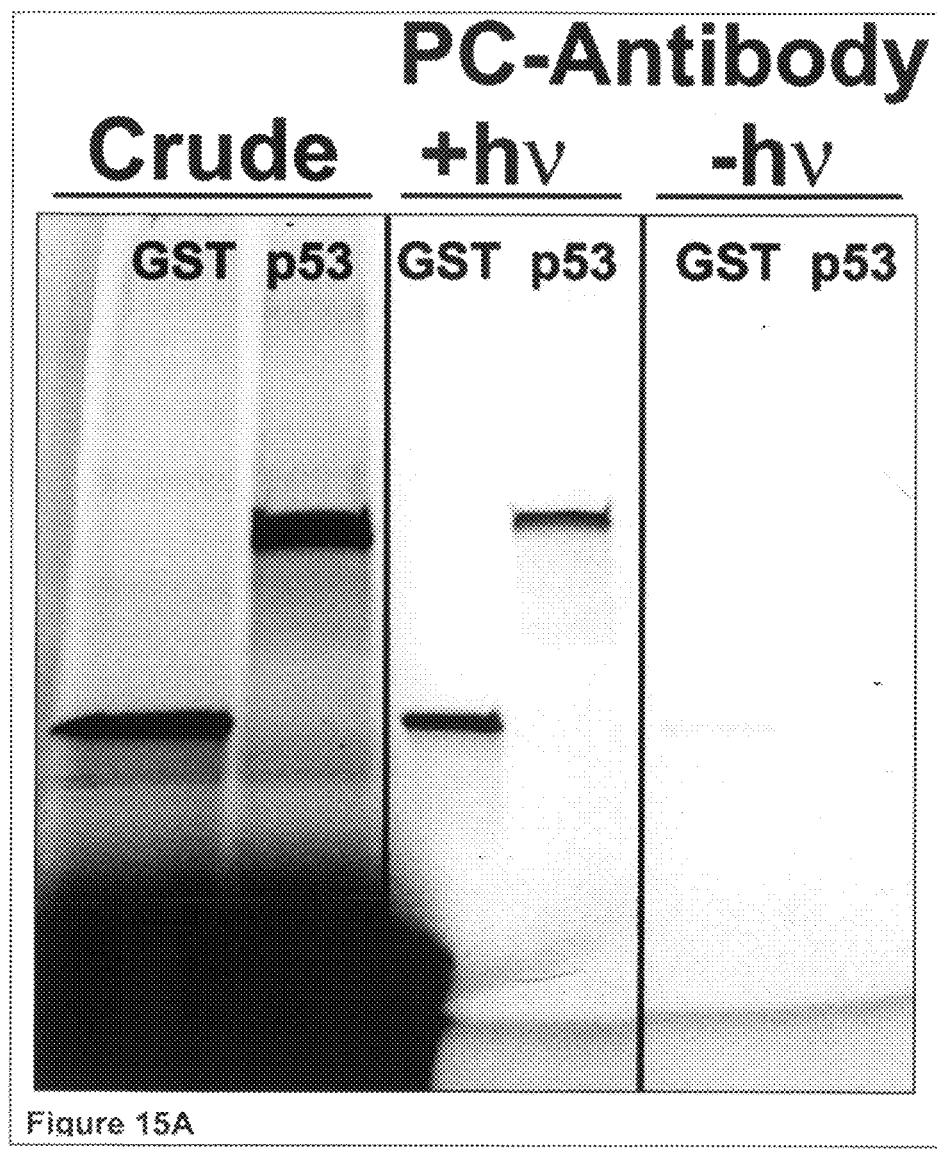
FIG. 15A. Photo-release and contact photo-transfer of cell-free expressed, tRNA labeled and photocleavable antibody isolated proteins. Confirmation of successful photocleavable antibody mediated isolation and subsequent photo-release into solution.
Figure 15B:
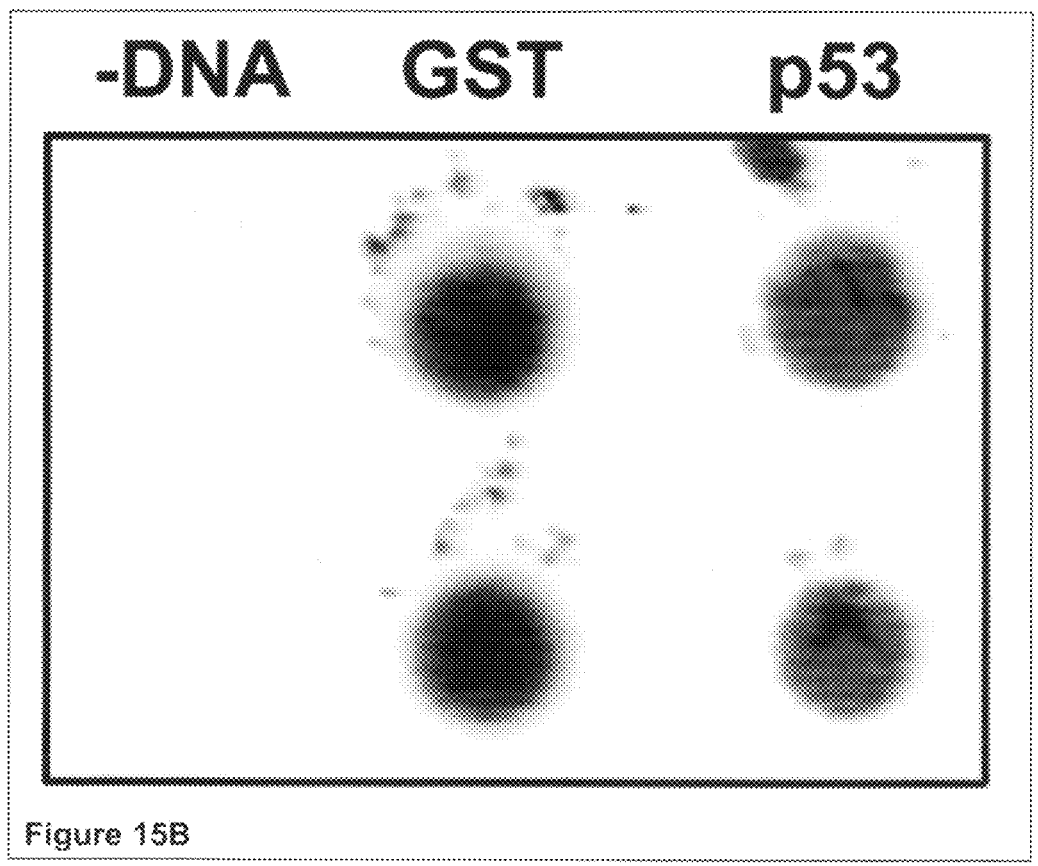
FIG. 15B. Photo-release and contact photo-transfer of cell-free expressed, tRNA labeled and photocleavable antibody isolated proteins. After validation of successful photocleavable antibody mediated isolation and the ability to photo-release into solution (see FIG. 15A), compatibility with contact photo-transfer from beads to an aldehyde activated glass microarray substrate was also demonstrated. Detection on the microarray substrate was via the directly incorporated tRNA mediated fluorescence label.

Results:

Results are shown in FIG. 15. PC-Antibody=photocleavable HSV antibody isolated fractions; Crude=crude non-isolated cell-free expression reaction (equivalent loading to PC-Antibody fractions); +hv=elution (photo-release) with proper light illumination; -hv=elution procedure without light illumination; -DNA=minus DNA blank derived from expression reaction lacking only the added DNA for gene of interest (all other processing steps otherwise performed same as with DNA containing expressed protein samples); GST=glutathione-s-transferase; p53=cellular tumor antigen p53. FIG. 15A shows the fluorescence SDS-PAGE bands corresponding to the GST and p53 proteins at the correct approximate molecular weight positions. The highly fluorescent unresolved zone at the bottom of the gel in the crude samples corresponds to unused fluorescence tRNA and byproducts as well as auto-fluorescence from large quantities of hemoglobin in the rabbit reticulocyte cell-free expression lysate. The photo-release lanes show recovery of the purified proteins only when the appropriate light illumination is used, with only negligible trace quantities "leached" from the affinity matrix in the absence of light illumination. FIG. 15B shows the contact photo-transfer to an aldehyde activated microarray substrate. The internal tRNA mediated fluorescence label is clearly detectible in the transferred proteins with signal to noise ratios of 10:1 and 8:1 for GST and p53 respectively.

Example 18

Photo-Transfer to Nickel Metal Chelate Coated Microtiter Plates Using Photocleavable Antibodies: Detection of the Already-Bound Photocleaved Antibody Preparation of a Photocleavable Antibody Affinity Matrix:

For photo-isolation of expressed proteins, an antibody against the common C-terminal HSV epitope tag was conjugated to PC-biotin and loaded to a NeutrAvidin agarose bead affinity matrix as done in Example 2.

Cell-Free Expression and tRNA Mediated Labeling:

Human casein kinase II (CK) and human dihydrofolate reductase (DHFR) proteins containing a common HSV and polyhistidine epitope tag at the C-terminus were expressed in a rabbit reticulocyte cell-free reaction system as described in Example 1 except that no misaminoacylated tRNAs were used (no labeling), the expression was carried out for 1 hr and the BSA protein carrier was omitted from the TDB buffer used to stop the reaction and prepare the sample.

Isolation of Labeled Nascent Proteins:

The isolation procedure only (see later for photo-transfer) was performed as in Example 1 with the following exceptions: 20 μL of the anti-HSV photocleavable antibody affinity matrix was substituted for the NeutrAvidin beads in Example 1. The buffers used in the procedure contained no BSA or other protein carriers at any step. 50 bead volumes per wash was used to remove the unbound material. The washed bead pellet was then suspended to a 50% bead slurry (v/v) in 40% glycerol and 1 mM DTT in PBS.

Photo-Transfer to Wells of a Nickel Metal Chelate Coated Microtiter Plate:

The 50% bead slurry corresponding to the captured protein samples was further diluted to a 2.5% bead suspension in TBS-T and loaded at 100 μL/well to commercially available nickel metal chelate coated/derivatized opaque white 96-well microtiter plates (Pierce Biotechnology, Inc., Rockford, Ill.). Photo-transfer from the affinity beads to the wells of the microtiter plate was achieved as in Example 10 except that the capture mechanism onto the plate was via the C-terminal polyhistidine tag present in the photo-released protein and the capture step was allowed to occur for 30 min.

Detection of Photo-Transferred Protein:

Following photo-transfer of the target proteins to the metal chelate coated microtiter plate wells, the bead suspension was removed and the wells washed 4× briefly (5 sec) in 300 μL/well of TBS-T. Detection of the already-bound HSV mouse monoclonal antibody (from the photocleavable antibody isolation step) was achieved using a secondary rabbit anti-[mouse IgG] horseradish peroxidase (HRP) conjugate (Pierce Biotechnology, Inc., Rockford, Ill.). The detection antibody was added at a 1/50,000 dilution of the manufacturer's stock in 1% BSA (w/v) in TBS-T for 30 min. Plates were washed again and signal was generated using a commercially available chemiluminescence HRP substrate (SuperSignal Femto ELISA Substrate; Pierce Biotechnology, Inc., Rockford, Ill.) according to the manufacturer's instructions. Signal was read in a LumiCount luminescence plate reader (Packard/PerkinElmer Life and Analytical Sciences, Inc., Boston, Mass.).

Figure 16:
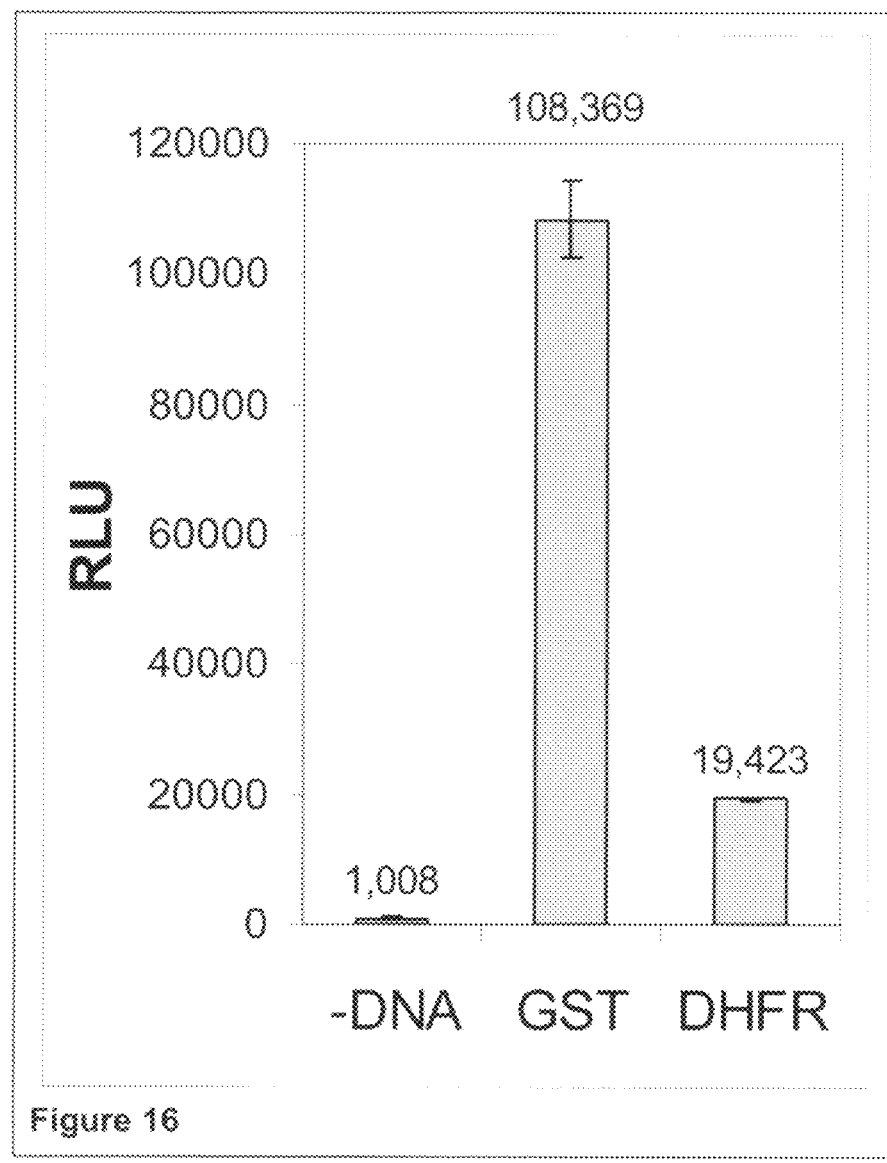
FIG. 16. Photo-transfer of cell-free expressed and photocleavable antibody isolated proteins. Transfer to the nickel metal chelate coated surface of 96-well microtiter plates using a polyhistidine tag binding mechanism (tag in expressed proteins). Detection of the already-bound photocleavable antibody via a secondary antibody reporter conjugate.

Results:

Results are shown in FIG. 16. -DNA=minus DNA blank derived from expression reaction lacking only the added DNA for gene of interest (all other processing steps otherwise performed same as with DNA containing expressed protein samples); GST=glutathione-s-transferase; DHFR=dihydrofolate reductase; RLU=raw relative luminescence units. The results show clear detection of the photo-transferred GST and DHFR with signal to noise ratios of 108:1 and 19:1 respectively compared to the minus DNA negative control sample. It is important to note that like the expressed protein samples, the minus DNA control would also contain photo-released anti-HSV antibody that is not bound to any expressed protein. Therefore, the results demonstrate that the specific signal achieved for the GST and DHFR proteins is indeed a result of detection of only photoreleased anti-HSV antibody that is bound to the expressed proteins which are in turn themselves bound to the nickel metal chelate coated plate via their polyhistidine tag proteins have HSV and polyhistidine tags); and any photo-released anti-HSV antibody not bound to it's target protein is effectively washed out of the wells of the plate since it lacks any metal chelate binding tag.

Example 19

Figure 17:
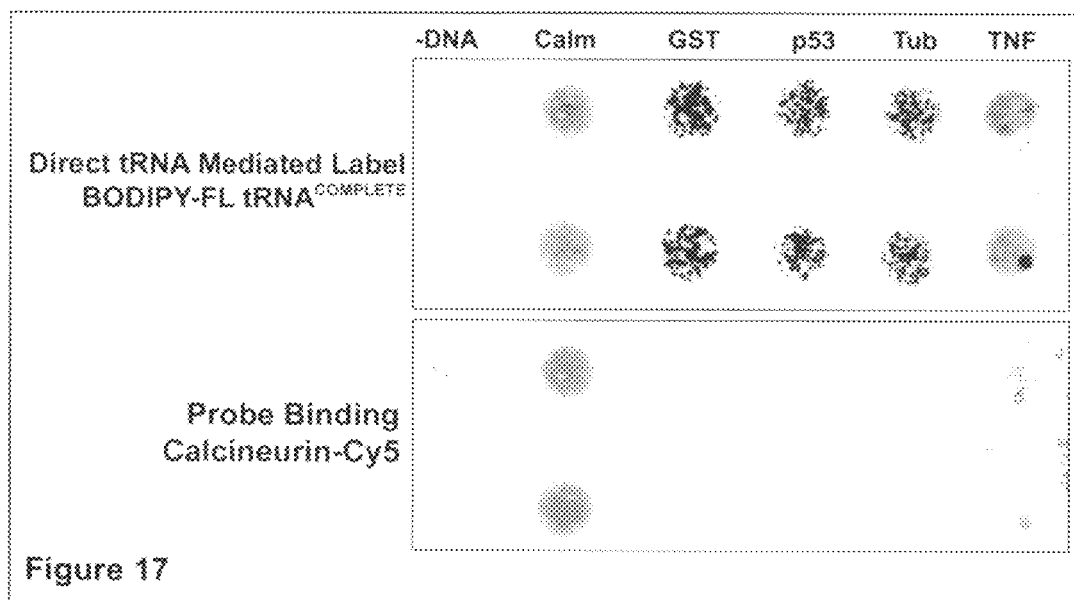
FIG. 17. Contact photo-transfer of cell-free expressed, tRNA labeled and photocleavable antibody isolated proteins. Transfer to activated microarray substrates. Advanced 2 color fluorescence calmodulin-calcineurin protein-protein interaction assay.

Contact Photo-Transfer to Activated Microarray Surfaces Using Photocleavable Antibodies: Application to Advanced 2 Color Protein-Protein Interaction Assays Cell-Free Expression and tRNA Mediated Labeling
Various human proteins containing a common HSV epitope tag at the C-terminus were expressed in a rabbit reticulocyte cell-free reaction and co-translationally labeled with BODIPY-FL as in Example 1 with the following exceptions: BODIPY-FL-tRNA$^{COMPLETE}$ was used for fluorescence labeling instead of BODIPY-FL-tRNA$^{Lys}$. PC-Biotin-tRNA$^{COMPLETE}$ was not used for direct labeling since isolation was via a photocleavable antibody instead (see later in this Example). As a negative control, an expression reaction was performed lacking only the added DNA for the gene of interest (Minus DNA blank). The Translation Dilution Buffer (TDB) used to stop the reaction and prepare the sample contained no BSA or any other protein carriers.
Preparation of a Photocleavable Antibody Affinity Matrix:
An anti-HSV tag photocleavable antibody conjugated agarose bead affinity matrix was prepared as in Example 2.
Isolation of Labeled Nascent Proteins:
The isolation procedure only (see later for contact photo-transfer) was performed as in Example 1 with the following exceptions: The buffers used in the procedure contained no BSA or other protein carriers at any step. Capture was on 10 µL of the anti-HSV photocleavable antibody beads. After washing the unbound material from the NeutrAvidin beads as described in Example 1 the beads were further washed 3× briefly (briefly=5 sec vortex mix) with 45 bead volumes each of plain PBS and 1×5 min with 45 bead volumes of 40% glycerol in PBS. The washed bead pellet was then suspended with equal volume of 40% glycerol in PBS to yield a 50% bead slurry (v/v).
Contact Photo-Transfer:
Performed as in Example 7 except that some protein samples (GST, p53 and Tub) were further diluted with unused/plain anti-HSV photocleavable antibody beads (beads still in 40% glycerol and PBS) to decrease the total integrated amount of transferred protein in the applied 1 µL (~2 mm) parent spot to a level roughly similar (although not exact) to the lower expressing and poorer substrate binding Calm and TNF proteins.
Preparation of a Calcineurin-Cy5 Directly Labeled Fluorescence Probe:
In order to measure the known biological binding interaction between the microarray deposited calmodulin "bait" and calcineurin, a fluorescently labeled calcineurin-Cy5 conjugate/probe was prepared as described in Example 12.
Probing the Proteins on the Microarray with the Calcineurin-Cy5 Conjugate:
The cell-free expressed proteins subsequently photo-transferred onto the microarray substrates as described earlier in this Example were then probed with the calcineurin-Cy5 conjugate to test for its expected biological interaction with calmodulin. This was done as described in Example 12 except that no minus calcium permutation was performed.
Detection of Photo-Transferred Protein:
Detection of the directly incorporated tRNA mediated BODIPY-FL fluorescence labeling as well as binding of the fluorescent calcineurin-Cy5 probe was achieved by imaging the dry microarray substrates on an ArrayWoRx$^e$ BioChip fluorescence reader (Applied Precision, LLC, Issaquah, Wash.) using the appropriate standard built-in filter sets to discriminate between the 2 color fluorophores.
Results:
Results are shown in FIG. 17. –DNA=minus DNA blank derived from expression reaction lacking only the added DNA for gene of interest (all other processing steps otherwise performed same as with DNA containing expressed protein samples); Calm=calmodulin; GST=glutathione-s-transferase; p53=cellular tumor antigen p53; Tub=alpha-tubulin; TNF=tumor necrosis factor alpha. The direct tRNA mediated BODIPY-FL labeling confirms that all proteins are present on the array surface in amounts equal to or greater than the amount of the calmodulin "bait". It is important to note that the GST, p53 and Tub protein samples were further diluted with unused agarose beads prior to photo-transfer to roughly normalize the total integrated amount of transferred proteins in the 1 µL (~2 mm) parent spot. Importantly, in those pre-diluted samples, the beads are dispersed sufficiently that transfer from individual ~100 micron agarose beads can be resolved (speckled appearance of parent spot), again supporting that after photo-release, the proteins are directly transferred due to the close bead-surface contact and that diffusion of the proteins away from the bead area is minimal. Furthermore, as expected, the calcineurin-Cy5 probe interacts only with the calmodulin spots on the microarray surface, in correlation with the known biological interaction as reported in the literature [Nakamura et al. (1992) *FEBS Lett* 309, 103-106], and not with the other non-calmodulin binding proteins.

Example 20

Preparation of PC-Biotin Conjugated Quantum Dot Nanocrystals and Binding to NeutrAvidin Agarose Beads Preparation of PC-Biotin Conjugated Quantum Dot 605 Nanocrystals:
Antibody (IgG) conjugated Quantum Dot nanocrystals were obtained commercially (QDot® 605 Sheep anti-Digoxigenin Conjugate [Fab Fragment] catalog number 1600-1; Quantum Dot Corp., Hayward, Calif.) and were provided from the manufacturer at 1 µM concentration in borate buffer pH 8.3. The binding specificity of the Quantum Dot conjugated antibody (IgG), against digoxigenin, was irrelevant in this case since the small molecule antigen digoxigenin occurs naturally only in plants. The antibody (IgG) coating in this case served only as an irrelevant protein medium in order to mediate conjugation of PC-biotin using AmberGen's proprietary protein/amine reactive PC-biotin NHS ester labeling reagent. Quantum Dots conjugated to other irrelevant proteins such as BSA or simply amine derivatized (also available from Quantum Dot Corp., Hayward, Calif.) would also be suitable. A 2 mM stock of the PC-biotin NHS ester labeling reagent was prepared in anhydrous dimethyl formamide (DMF) and 1 µL added to 100 µL of the manufacturer supplied Quantum Dots for an approximate 20-fold molar excess labeling reagent relative to the Quantum Dots. The reaction was allowed to proceed for 30 min with gentle mixing. Unreacted or hydrolyzed labeling reagent was removed using a NAP-10 Sepharose G-25 desalting column (Amersham Biosciences Corp., Piscataway, N.J.) against a TBS buffer according to the manufacturer's instructions except that only the visibly orange colored (Quantum Dot) size-excluded elution fraction was collected. The resultant PC-biotin Quantum Dot conjugate was analyzed on a standard spectrophotometer and the yielded Quantum Dot concentration calculated to be 0.17 µM at ~500 µL total (85% recovery) using the appropriate extinction coefficient.

Selective Binding of PC-Biotin Conjugated Quantum Dot 605 Nanocrystals to NeutrAvidin Beads:

PC-biotin conjugated Quantum Dots were selectively captured and isolated on 10 µL packed bead volume of NeutrAvidin agarose beads (~100 micron diameter) having an approximate total biotin binding capacity of 800 pmoles (Pierce Biotechnology, Inc., Rockford, Ill.). The isolation procedure was performed in batch mode using a micro-centrifuge and polypropylene tubes to manipulate the affinity matrix (beads) and exchange the buffers (note that under the micro-centrifuge conditions used, ~10 sec at 13,000 rpm, the Quantum Dots do not precipitate but remain in solution). Beads were first pre-washed 2× briefly (briefly=5 sec vortex mix) with 45 bead volumes per wash using 5 mM DTT and 0.01% (w/v) Triton X-100 detergent in PBS. The beads were suspended with 100 µL of the same buffer and 24 µL of the prepared 0.17 µM PC-biotin conjugated Quantum Dots was added, therefore constituting an approximate theoretical maximum 1 to 2% level of the total available binding capacity of the 10 µL of NeutrAvidin beads (assuming that for steric reasons, a roughly 1:1 binding ratio of NeutrAvidin tetramer to Quantum Dots, which are the size of large proteins, will occur). 1-2% of saturation was used since the Quantum Dots are anticipated to be ultimately employed for photo-transferable spectral bar-coding of the NeutrAvidin beads, and the remaining binding capacity of the NeutrAvidin beads will be needed for capture of other PC-biotin conjugated biomolecules (e.g. cell-free expressed proteins described in previous Examples). Additionally, as a negative control (blank), a parallel sample was performed but by adding the same amount of plain Quantum Dots, i.e. not conjugated to PC-biotin but otherwise identical. Binding was allowed to occur for 30 min at +4° C. with gentle shaking.

Prior to washing away the unbound Quantum Dots from the NeutrAvidin agarose beads, the bead suspension was imaged directly in the clear polypropylene micro-centrifuge tubes using a FluorImager SI argon laser-based fluorescence scanner (Molecular Dynamics/Amersham Biosciences Corp., Piscataway, N.J.) and the standard manufacturer supplied 610 nm emissions filter. Unbound Quantum Dots where then removed from the NeutrAvidin agarose beads by washing the beads 3× briefly (briefly=5 sec vortex mix) and 1×1 hr (+4° C.) at 45 bead volumes per wash using 5 mM DTT and 0.01% (w/v) Triton X-100 detergent in PBS. The washed bead pellet was imaged using a FluorImager SI argon laser-based fluorescence scanner (Molecular Dynamics/Amersham Biosciences Corp., Piscataway, N.J.) and the standard manufacturer supplied 610 nm emissions filter.

Figure 18B:
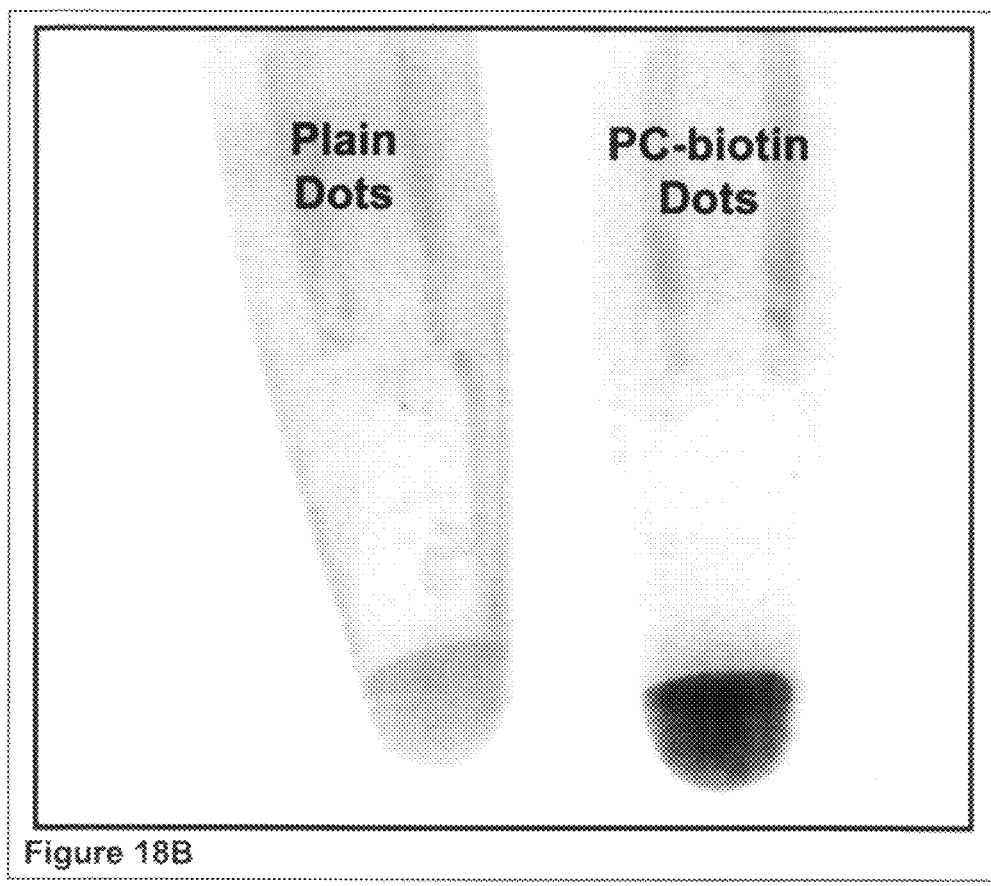
FIG. 18B. Preparation of photocleavable fluorescent Quantum Dot nanocrystals by conjugation to PC-biotin. Selective capture on 100 micron NeutrAvidin agarose beads. Shown here is the Quantum Dot fluorescence bound to the NeutrAvidin agarose bead pellet after extensive washing away of any unbound Quantum Dots and removing the fluid supernatant.

Results:

Results are shown in FIG. 18. FIG. 18A shows the NeutrAvidin bead suspension prior to washing away the unbound Quantum Dots. The fluorescence signal arising from the total amount of added Quantum Dots is the same for both the plain non-PC-biotin and the PC-biotin conjugated Quantum Dots as expected. FIG. 18B shows the NeutrAvidin bead pellets only, after washing away the unbound Quantum Dots. Significant binding of the Quantum Dots only occurs in the case where they are conjugated to PC-biotin, with a 6-fold greater signal intensity than for the plain non-PC-biotin Quantum Dots. The background signal in the plain non-PC-biotin scenario does not arise from non-specifically bound Quantum Dots (as confirmed later in Example 21), but is the typical background fluorescence from plain untreated NeutrAvidin agarose beads (not shown in FIG. 18) likely due to autofluorescence and light scattering effects.

Example 21

Contact Photo-Transfer of Photocleavable Quantum Dot Nanocrystals to Activated Microarray Substrates: UV Dependence of Transfer and Fluorescence Specificity Contact Photo-Transfer of PC-Biotin Conjugated Quantum Dot Nanocrystals:

The same 10 µL NeutrAvidin agarose beads loaded with PC-biotin conjugated Quantum Dots prepared as described in Example 20 were further washed 1× briefly (briefly=5 sec vortex mix) at 45 bead volumes with 5 mM DTT and 40% glycerol in PBS and resuspended to a 50% (v/v) slurry with the same buffer. Negative control beads treated with the same amount of plain Quantum Dots, i.e. not conjugated to PC-biotin as described in Example 20, were also processed in this way. Using these bead slurrys, contact photo-transfer was performed as described in Example 7 with the following exceptions: As a negative control, additional spots of bead slurry that were applied to the same microarray substrate were not illuminated with the appropriate near-UV light by employing shielding with an opaque aluminum foil covered barrier. After binding of the transferred material to the microarray substrate, the substrates were washed 4×1 min with excess TBS-T and 4× briefly (5 sec) with purified water prior to drying and imaging.

Detection of Photo-Transferred Quantum Dots:

Detection of the Quantum Dot 605 nm fluorescence emissions was achieved by imaging the dry microarray substrates on an ArrayWoRx$^e$ BioChip fluorescence reader (Applied Precision, LLC, Issaquah, Wash.) using the standard built-in (manufacturer supplied) filter sets. The Cy3 filter set was used here to selectively image the Quantum Dot fluorescence. Although not optimal, these particular Quantum Dots (~400 nm optimal but broad excitation and 605 nm emissions peak) can be imaged using a standard Cy3 excitation-emissions filter set, albeit with 5× less signal intensity than Quantum Dot optimized fluorescence filters.

Figure 19:
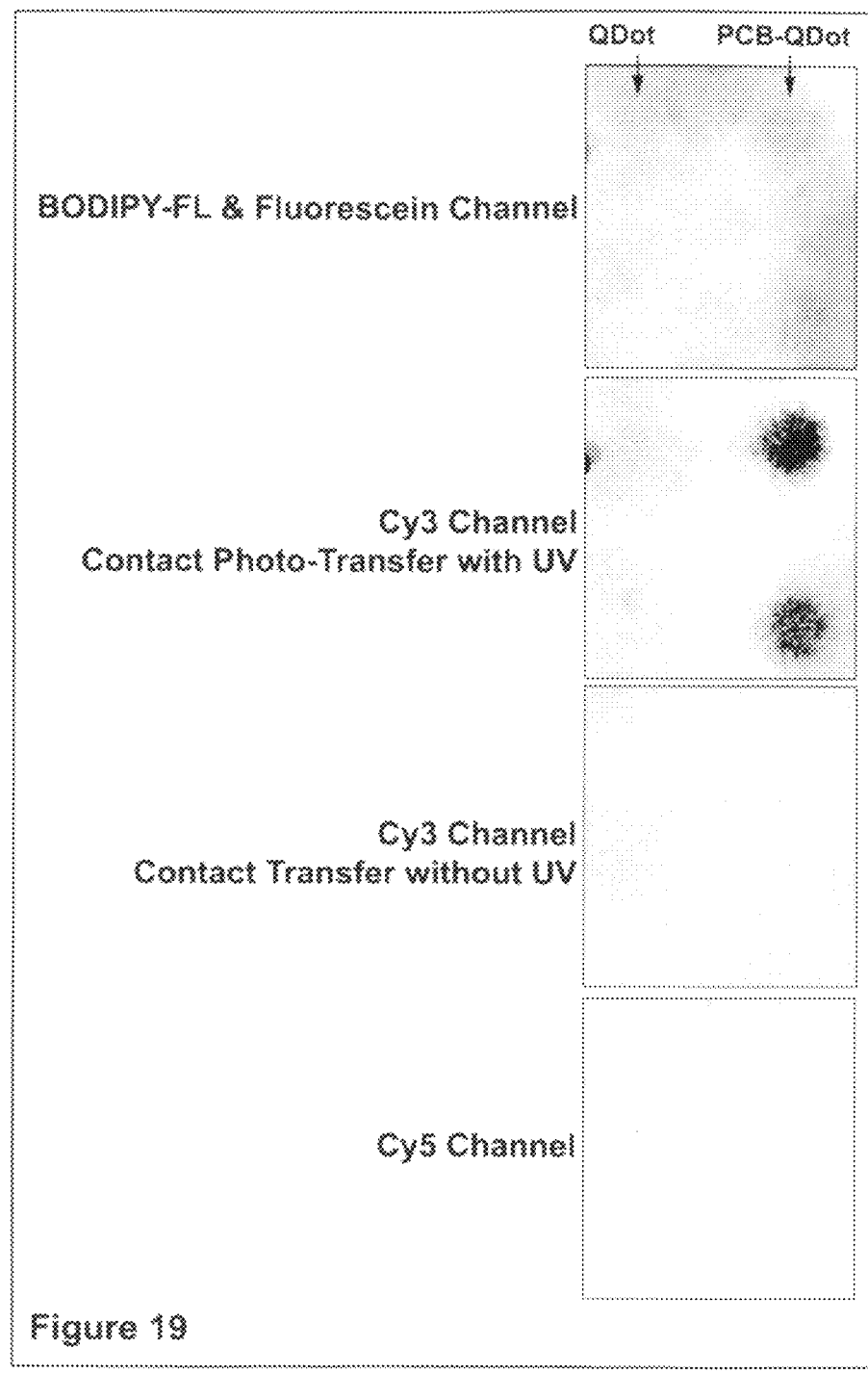
FIG. 19. Contact photo-transfer of photocleavable fluorescent Quantum Dot nanocrystals from 100 micron NeutrAvidin agarose beads. Light dependence of transfer and fluorescence emissions specificity (605 nm peak emissions Quantum Dots).

Results:

Results are shown in FIG. 19. "QDot"=refers to the procedure performed on plain Quantum Dots, i.e. not conjugated to PC-biotin; "PCB-QDot" refers to the procedure performed on PC-biotin (PCB) conjugated Quantum Dots; "Channel"=refers to the various fluorescence filter sets used to obtain images; "UV"=the near-UV light illumination required for photocleavage of the PC-biotin. FIG. 19 shows fluorescence images obtained by scanning the microarray substrates in the ArrayWoRx$^e$ BioChip fluorescence reader (Applied Precision, LLC, Issaquah, Wash.), whereby signal from the photo-transferred Quantum Dot 605 nm emissions is only expected with the Cy3 filter set (channel). As anticipated, when attempts are made to load plain non-PC-biotin Quantum Dots to NeutrAvidin agarose beads, no binding occurs (Quantum Dots washed away from beads in isolation step) and thus no measurable photo-transfer occurs from the beads to the microarray substrate. However, when PC-biotin conjugated Quantum Dots are loaded to the NeutrAvidin agarose beads, binding does occur as demonstrated previously in Example 20, and thus photo-transfer does occur as shown in FIG. 19. Fluorescence signal is only observed in the Cy3 channel as expected and no fluorescence cross-talk occurs in the "BODIPY-FL & Fluorescein" channel or the "Cy5" channel. As an additional negative control, when illumination with the proper near-UV light is not done, transfer of the PC-biotin conjugated Quantum Dots from the NeutrAvidin agarose beads to the microarray substrate does not occur and signal is not observed in any fluorescence channels (Cy3 channel is shown in FIG. 19). Note that the high density of beads per 1 µL parent spot on the substrates does not afford good resolution of photo-transfer from individual beads at this magnification (although speckled appearance indicates individual beads). Nonetheless, an example involving contact photo-transfer of Quantum Dots from individual beads is possible as shown in Examples 14-16 and 19 for other PC-biotin conjugates.

Example 22

Isolation of Analytes Using Photocleavable Affinity Capture Agents: Analyte Pre-Purification and Pre-Enrichment for Improved Signal to Noise Ratios in Downstream Assays The goal will be to improve signal to noise ratios and eliminate interference in downstream assays, such as traditional "sandwich" immunoassays, by pre-purifying and pre-enriching an analyte (e.g. antigen) using photocleavable antibodies. For example, as compared to traditional sandwich immunoassays (e.g. ELISA or microarray) where analyte pre-purification and pre-enrichment is not performed.
Preparation of a Photocleavable Antibody Affinity Matrix:

400 µg of Alexa Fluor® 488 conjugated rat anti-mouse IL-2 antibody purchased from BD Biosciences (San Jose, Calif.; clone JES6-5H4 supplied in 10 mM phosphate buffer 150 mM NaCl and 0.09% azide without protein carrier; catalog number 557725) will be dialyzed, conjugated to PC-biotin, and pre-loaded to NeutrAvidin agarose beads in the same manner as described in Example 2 for the anti-HSV antibody. The antibody will be pre-loaded at saturating levels (5× molar excess) to ensure maximum antibody density per unit volume of NeutrAvidin agarose beads. Note that according to the manufacturer's specifications, this antibody is immunoprecipitation compatible as well as tested for detection in sandwich ELISA assays. Additionally, the Alexa Fluor® 488 fluorescent label will be chosen due to its resistance to photo-bleaching. The manufacturer supplied antibody solution is free of unlabeled antibody and uncoupled fluorophore.
Antibody Microarray Printing:

A different and unlabeled rat anti-mouse IL-2 monoclonal antibody, clone JES6-1A12, recognizing an epitope different from that of the photocleavable IL-2 antibody prepared as described in the previous paragraph, will also be purchased from BD Biosciences (San Jose, Calif.; catalog 554424) and left untreated. The antibody will be left undiluted in its supplied phosphate buffer and printed to various microarray surfaces using a GMS 417 robotic pin-and-ring microarraying instrument (Genetic Microsystems/AffyMetrix; Santa Clara, Calif.). As a negative control, pre-immune non-specific rat IgG will be printed in equal amounts. Spots will be approximately 200 microns in diameter and approximately 50 pL of applied volume each. Coated or activated glass microarray surfaces for printing will be amine-reactive aldehyde or epoxy activated substrates (SuperAldehyde or SuperEpoxy substrates, TeleChem International, Inc. ArrayIt™ Division, Sunnyvale, Calif.), amine derivatized substrates (GAPS II substrates, Corning Incorporated Life Sciences, Acton, Mass.) and nitrocellulose coated substrates (SuperNitro Substrates, TeleChem International, Inc. ArrayIt™ Division, Sunnyvale, Calif.). Following printing, substrates will be washed 4×2 min each with excess TBS-T and subsequently blocked for 30 min in 5% BSA (w/v) in TBS-T. Slides will then be rinsed 4× briefly (5 sec) in purified water and dried.
Microarray Sandwich Immunoassay on Photocleavable Antibody Enriched and Concentrated Antigen:

As the test analyte (antigen), recombinant mouse IL-2 will be purchased from R&D Systems (Minneapolis, Minn.; catalog number 402-ML-020/CF). The IL-2 will then be exogenously added into normal mouse serum that is devoid of detectable endogenous mouse IL-2 (i.e. validated sera from non-infected or compromised animals). The recombinant mouse IL-2 will be supplemented (diluted) into the serum from the high concentration stock (i.e. minimum 100× stock) to various final concentrations over the normal range of sandwich immunoassay detection sensitivity (i.e. low ng/mL to pg/mL range) to determine the limits of sensitivity of the microarray sandwich assay. The IL-2 will then be purified from the various supplemented sera using the photocleavable antibody affinity matrix prepared as described earlier in this example (i.e. beaded affinity matrix that is pre-loaded with a fluorescently labeled anti-mouse IL-2 photocleavable antibody). For purification, just enough affinity matrix will be added to the various supplemented sera to provide a 2-fold molar excess binding capacity relative to the amount of IL-2 present. At each IL-2 dilution tested, the total volume of IL-2 supplemented serum added to the affinity matrix will be 100 µL, 1 mL or 10 mL to ultimately yield concentrating factors of 1×, 10× and 100× respectively following photo-release (see later) of the isolated IL-2 into 100 µL volume. Binding (capture) will be allowed to occur for 1 hr with gentle mixing and the beaded affinity matrix will be washed 2×5 min each then 2× briefly (briefly=5 sec vortex mix) with 50 bead volumes of 0.1% BSA (w/v) in PBS. The fluorescently labeled antibody-antigen complexes will then be photo-released from the beaded affinity matrix via illumination of the bead suspension, with mixing, for 5 min with near-UV light (365 nm peak UV lamp, Blak-Ray Lamp, Model XX-15, UVP, Upland, Calif.) at a 5 cm distance. Importantly, light illumination will be performed directly in uncovered/uncapped polypropylene micro-centrifuge tubes, such that there will be no solid barrier between the bead suspension and the light source. The power output under these conditions is 2.6 mW/cm at 360 nm, 1.0 mW/cm$^2$ at 310 nm and 0.16 mW/cm$^2$ at 250 nm. Photo-release will be performed into 100 µL of solution, just enough to overlay a standard sized microarray substrate (slide), and will be performed with 0.1% BSA (w/v) in TBS as the buffer. The photo-released antibody-antigen complexes, now in solution (and separated from beads), will then be applied to the antibody printed microarray substrate for recapture (thus forming the antibody-antigen-antibody "sandwich" on the array surface). Alternatively, the 100 µL suspension of beaded affinity matrix will be spread over the surface of the microarray substrate prior to photo-release (e.g. using an overlaid glass coverslip that is transparent to near-UV) and photo-release will be performed by directly exposing the overlaid microarray substrate to the light source. Recapture of the photo-released (fluorescent) antibody-antigen complexes onto the microarray-printed antibody will be allowed to occur for 1 hr. Unbound materials (and beads where applicable) will then be removed from the microarray substrate by 4× washes for 2 min each in TBS-T followed by 4× brief (5 sec) rinses in purified water. The microarray will be dried and the fluorescence signal read using an ArrayWoRx$^e$ BioChip fluorescence reader (Applied Precision, LLC, Issaquah, Wash.) with the appropriate standard manufacturer supplied filter sets.

The anticipated results will be improvements in the signal to noise ratios and elimination of assay interference by pre-purifying and pre-enriching the analyte (the IL-2 antigen in this case) using a photocleavable antibody prior to application to the microarray surface (note: photocleavable antibody serves dual purpose as detection antibody). Comparisons will be made to the traditional sandwich immunoassay format where analyte pre-purification and pre-enrichment is not performed (e.g. crude analyte will be directly applied onto the antibody-printed microarray substrate, capture will be allowed to occur, the microarray will be washed and then treated with the fluorescently labeled detection antibody).

Example 23

Isolation of Protein Kinase C from Crude Cell Lysates Using Secondary Photocleavable Antibodies Followed by Downstream Kinase Activity Assay Cell Activation:

Cultured HeLa cells (ATCC; Manassas, Va.) were stimulated for 5 min with 200 nM Phorbol-12-Myristate-13-Acetate (PMA; EMD Biosciences, Inc., San Diego, Calif.) and subsequently detergent fractionated into sub-cellular compartments according to reported procedures [Ramsby et al. (1994) *Electrophoresis* 15, 265-277; Ramsby & Makowski. (1999) *Methods Mol Biol* 112, 53-66; Chiang et al. (2000) *J Biochem Biophys Methods* 46, 53-68]. PMA is a potent activator of PKCα and is well known to cause translocation of the kinase from the cytosolic to the membrane sub-cellular compartments [Ross & Joyner. (1997) *Endothelium* 5, 321-332; Bazan & Rapoport. (1996) *J Pharmacol Toxicol Methods* 36, 87-95; Yazlovitskaya & Melnykovych. (1995) *Cancer Lett* 88, 179-183].

Kinase Isolation and Functional Assay:

A photocleavable antibody conjugated solid affinity matrix was prepared and used to isolate and photo-release the antigen into solution essentially as described in Example 2 except that in this case, a photocleavable anti-IgG secondary antibody was used to immobilize the unlabeled primary antibody onto the solid affinity matrix. This antibody affinity matrix was used to isolate and photo-release endogenous PKCα from the undiluted detergent fractionated HeLa cell extracts. PKCα activity, following photocleavable antibody mediated purification, was assayed using a non-isotopic heterogeneous ELISA-type kit available from EMD Biosciences, Inc. (San Diego, Calif.) consisting of an immobilized peptide substrate and an anti-phospho-peptide antibody mediated detection system (calorimetric signal generation).

Figure 20:
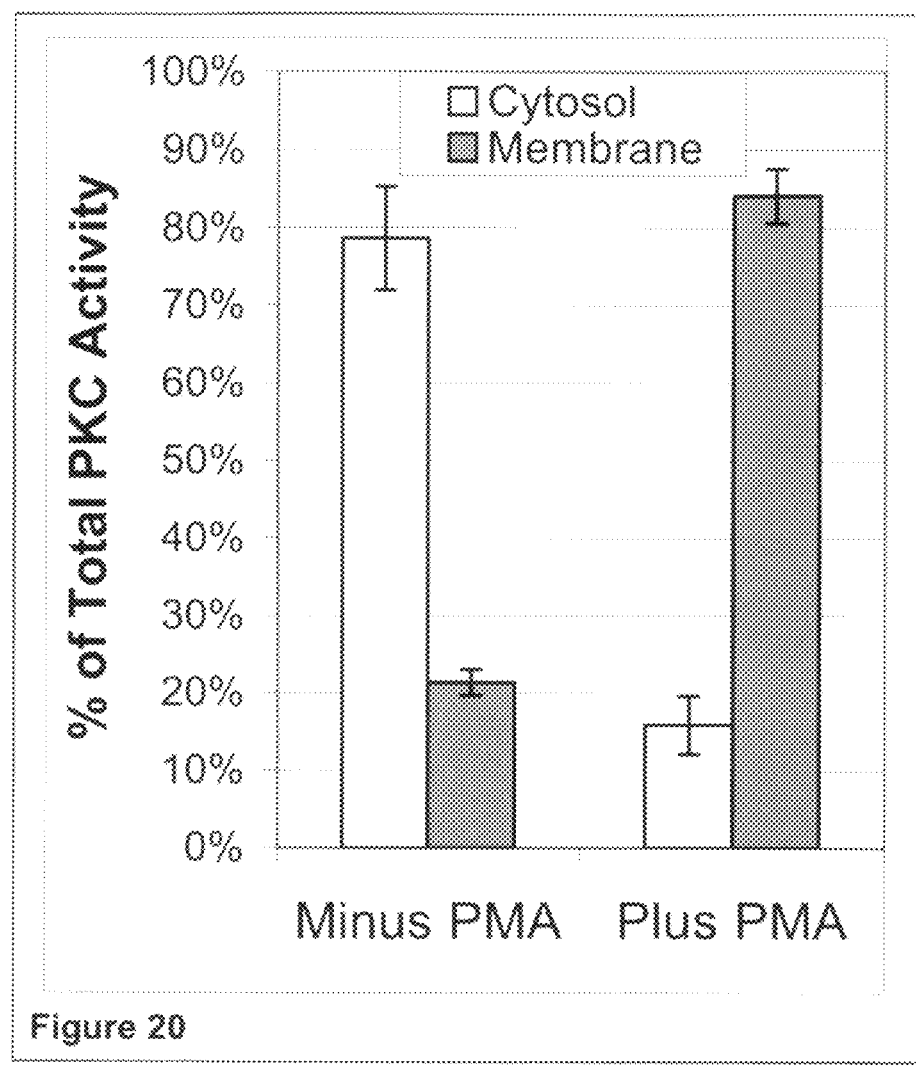
FIG. 20. Phorbol ester (PMA) mediated protein kinase Cα (PKCα) sub-cellular translocation as measured by functional activity following isolation with photocleavable antibodies. Cultured HeLa cells were stimulated with 200 nM PMA for 5 min and detergent fractionated into the cytosol and membrane compartments prior to isolation and purification with the photocleavable antibodies. The graph shows relative sub-cellular distribution of PKCα based on kinase activity of the photocleavable antibody isolated protein.

Results:

The goal is to improve signal to noise ratios and eliminate potential interference from contaminants or similar kinases (e.g. other PKC isoforms specific for the same substrates, such as PKCβ) by employing a pre-purification step based on photocleavable antibodies. The results in FIG. 20 demonstrate that, based on functional activity measurements of photocleavable antibody isolated HeLa cell PKCα, translocation of the kinase from the cytosol to the membrane compartments was clearly observed in correlation with the scientific literature [Ross & Joyner. (1997) *Endothelium* 5, 321-332; Bazan & Rapoport. (1996) *J Pharmacol Toxicol Methods* 36, 87-95; Yazlovitskaya & Melnykovych. (1995) *Cancer Lett* 88, 179-183]. FIG. 20 shows a baseline PKCα distribution of 79±7% cytosol and 21±2% membrane which shifts to 16±4% cytosol and 84±3% membrane following PMA stimulation of the cultured HeLa cells (t-test p value of 0.000003; n=4) (distribution confirmed by Western blot).

Example 24

Contact Photo-Transfer from Individually Resolved Beads in a Thin Liquid Film Under a Cover Glass Using a PC-Antibody Preparation of a Photocleavable Antibody Affinity Matrix:

The photocleavable antibody beaded affinity matrix was prepared using the monoclonal anti-HSV tag antibody (EMD Biosciences, Inc., San Diego, Calif.) as described in Example 2.

Cell-Free Expression and tRNA Mediated Labeling:

Human glutathione-s-transferase (GST) and the p53 oncoprotein, both containing an HSV epitope tag on the C-terminus, were expressed in a cell-free reaction as described earlier in Example 1 with the following exceptions: Only AmberGen's BODIPY-FL-tRNA$^{COMPLETE}$ was used at 2 μM for labeling and not the PC-biotin-tRNA$^{COMPLETE}$ or any other misaminoacylated tRNA labeling reagents. The 2 different DNA species, for GST and p53, were mixed at a 1:1 ratio and co-expressed in the same reaction. The expression reaction size was only 50 μL instead of 200 μL. Importantly, the aforementioned anti-HSV tag photocleavable antibody affinity beads were added directly into the expression reaction, at the start of the expression reaction, as the last component. To do this, 5 μL of the beads was washed 3×400 μL briefly (briefly 5 sec vortex mix) in TBS using 0.45 micron pore size, PVDF membrane, micro-centrifuge Filtration Devices to facilitate manipulation of the small volume of affinity matrix (~100 micron beads) and exchange the buffer (Ultrafree-MC Durapore Micro-centrifuge Filtration Devices, 400 μL capacity; Millipore, Billerica, Mass.). The expression reaction mixture was used to resuspend the washed bead pellet and the bead suspension transferred to a fresh 0.5 mL polypropylene tube. The expression reaction was carried out in the presence of the beads for 45 min at 30° C. The TDB buffer used to stop the expression reaction and prepare the sample contained no BSA or any other protein carrier and additionally contained 4 mM cycloheximide. After addition of the TDB buffer, the samples were immediately processed for washing and isolation.

Isolation of Labeled Nascent Proteins:

The washing and isolation procedure was performed in batch mode using 0.45 micron pore size, PVDF membrane, micro-centrifuge Filtration Devices to facilitate manipulation of the small volumes of affinity matrix (~100 micron beads) and exchange the buffers (Ultrafree-MC Durapore Microcentrifuge Filtration Devices, 400 μL capacity; Millipore, Billerica, Mass.). All steps were performed at +4° C. or on an ice water bath and all reagents and samples were also kept under these conditions during the procedure. After cell-free expression in the presence of the anti-HSV tag photocleavable antibody affinity beads, beads were washed by mixing 2× briefly (briefly=5 sec vortex mix) and 1× for 5 min in 400 bead volumes per wash. The buffer used for washing the beads was PBS pH 7.5 and 5 mM DTT. The beads were then additionally washed 1× briefly (briefly=5 sec vortex mix) in 400 bead volumes of 50% glycerol and 5 mM DTT in PBS. Prior to contact photo-transfer of the captured and isolated proteins, the washed pellet of 1 μL of beads was suspended in a final volume of 200 μL with 50% glycerol and 5 mM DTT in PBS thereby resulting in a 0.5% (v/v) bead suspension that can be stored long-term at −20° C. without freezing of the sample and thus without damage to the agarose beads.

Contact Photo-Transfer from Individually Resolved Beads:

The 0.5% bead suspension containing the captured proteins was resuspended by vortex mixing and 10 µL of suspension was manually pipetted to the surface of epoxy activated glass microarray substrates (slides) (SuperEpoxy substrates, TeleChem International, Inc. ArrayIt™ Division, Sunnyvale, Calif.). The 10 µL pool containing the beads was then overlaid with a standard circular 12 mm microscope cover glass, creating a thin film of fluid between the cover glass and the microarray substrate. The microarray substrate overlaid with the cover glass was allowed to stand for 5 min without disturbance. The substrates were then illuminated, through the cover glass, without agitation or disturbance, for 5 min with near-UV light (365 nm peak UV lamp, Blak-Ray Lamp, Model XX-15, UVP, Upland, Calif.) at a 5 cm distance to photo-release and transfer the target proteins. The power output of the lamp under these conditions was 2.6 mW/cm$^2$ at 360 nm, 1.0 mW/cm$^2$ at 310 nm and 0.16 mW/cm$^2$ at 250 nm. After light treatment, the microarray substrate overlaid with the cover glass was incubated without disturbance for 30 min at 37° C. in a sealed and humidified chamber to fully ensure photo-released proteins react with the activated solid surface. The beads and any unbound protein as well as the overlaid cover glass was then removed with 3× brief (5 sec) washes in TBS-T followed by 4× brief (5 sec) washes in purified water. Phase contrast light microscopy reveals that the easily visible 100 micron agarose beads were completely washed/removed from the glass substrates. The slides were dried prior to fluorescence imaging.

Detection of Photo-Transferred Protein:

Detection of the directly incorporated tRNA mediated BODIPY-FL fluorescence labeling was achieved by imaging the dry microarray substrates on an ArrayWoRx$^e$ BioChip fluorescence reader (Applied Precision, LLC, Issaquah, Wash.) using the appropriate manufacturer supplied standard filter set and the resolution set to 9.7 microns.

Figure 21:
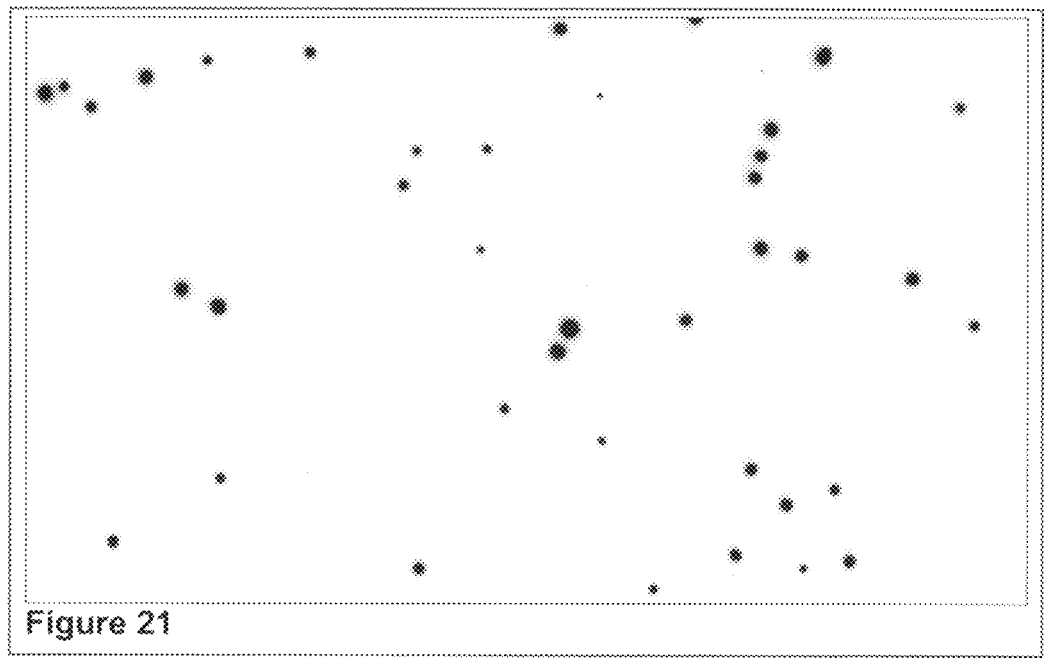
FIG. 21. Contact photo-transfer from individually resolved beads in a thin liquid film under a cover glass. A liquid suspension of 100 micron agarose beads bearing the photocleavably linked and fluorescently labeled protein is applied to an activated microarray substrate. The droplet of bead suspension is then overlaid with a circular microscope cover glass forming a thin liquid film between the cover glass and the microarray substrate. The fluorescent protein is then contact photo-transferred from the beads to the microarray substrate by light treatment through the overlaid cover glass.

Results:

Results are shown in FIG. 21. The BODIPY-FL fluorescence image shows multiple sharply resolved and non-clustered spots corresponding to the labeled protein material that was contact photo-transferred from the affinity beads. The spots average roughly 100 µm in diameter, correlating with the approximate diameter of the beads.

Example 25

Cell-Free Protein Synthesis and In Situ Protein Immobilization on Beads Followed by Contact Photo-Transfer Using Photocleavable Antibodies Immobilization of Expression DNA on Beads:

Genes encoding human glutathione-s-transferase (GST) and the p53 oncoprotein were used in this example. Cloned and purified expression plasmids described in Example 1 and containing the aforementioned gene inserts were used as the template for PCR amplification with universal primers. Forward and reverse primers were directed against common sequences in the expression plasmid such that the PCR amplicons contained the elements needed for efficient cell-free expression (T7 RNA polymerase promoter and ribosome binding site), the gene insert, as well as the common C-terminal polyhistidine tag and HSV epitope tag. The PCR primers were custom purchased commercially from Sigma-Genosys (The Woodlands, Tex.) and importantly, the reverse primer contained a 5' biotin modification for immobilization of the PCR amplicons. PCR primer sequences were as follows:

```
                                              [SEQ NO. 1]
Forward: 5'CgTCCCgCgAAATTAATACgACTCAC3'

[SEQ NO. 2]
Reverse: 5'[Biotin]gTTAAATTgCTAACgCAgTCAggAg3'
```

PCR was performed using standard practices and a commercially available kit according to the manufacturer's instructions (SuperTae™ DNA Polymerase Kit; Ambion, Austin, Tex.). The following thermocycling steps were used for the PCR reaction: Initially 94° C. 2 min (once) and then 25 cycles of 94° C. 30 s, 55° C. 30 s and 72° C. 30 s to 2 min (depending on DNA length), followed by a final 72° C. 10 mM (once). Purification and concentration of the PCR amplicons was achieved using a commercially available kit according to the manufacturer's instructions (QIAquick PCR Purification Kit; Qiagen, Valencia, Calif.). Resultant purified DNA concentrations ranged from 0.15 to 0.2 µg/µL. The correct size and integrity of the PCR amplified DNA was verified by standard agarose gel electrophoresis and ethidium bromide staining with comparison to a known molecular weight ladder (molecular weight standards). Single sharply resolved bands were observed for each PCR amplicon at the correct molecular weight positions without any detectable contaminants or degradation products. Expression of the soluble PCR amplicons was validated using the rabbit reticulocyte cell-free expression system described in Example 1 coupled with selective labeling with AmberGen's BODIPY-FL-tRNA$^{COMPLETE}$ and followed by SDS-PAGE and fluorescence imaging as described in earlier Examples. Expression efficiency of the PCR amplicons was found to be comparable to the starting plasmid DNA template.

Next, to immobilize the biotin-DNA on beads, 10 µL of streptavidin conjugated 4% cross-linked agarose beads (~100 microns diameter; Sigma-Aldrich; St. Louis, Mo.) were first washed 3×400 µL in TE-NaCl buffer (10 mM Tris-HCl, pH 8.0, 1 mM EDTA, 2M NaCl) using micro-centrifuge Filtration Devices according to the manufacturer's instructions (0.45 micron pore size, PVDF membrane, Ultrafree-MC Durapore Micro-centrifuge Filtration Devices, 400 µL capacity; Millipore, Billerica, Mass.). The washed bead pellets were resuspended with 150 µL of the purified PCR amplified biotin-DNA diluted to 10 ng/µL in TE-NaCl buffer (1.5 µg total DNA). The DNA was allowed to bind for 30 min with gentle mixing. Again using the micro-centrifuge Filtration Devices, the beads were washed 3×400 µL with TE-NaCl buffer followed by 1×400 µL in 50% glycerol/50% TE-NaCl buffer. The beads were then diluted to a 10% suspension (v/v) with the 50% glycerol/50% TE-NaCl buffer and stored at −20° C. The amount of DNA captured was calculated to be 27% (0.04 µg per µL beads) by comparing the absorbance at 260 nm of the starting DNA solution to the DNA solution after incubation with the beads. It is important to note that this level of DNA capture on the streptavidin beads was well below the saturation limit of the streptavidin beads according to the manufacturer's specifications (~30 ng free d-biotin or roughly 2 µg of biotinylated macro-molecule, such as an antibody, per µL of bead volume). Thus, sufficient biotin binding capacity was expected to remain for capture of photocleavable biotin (PC-biotin) labeled antibodies as described later in this Example.

For qualitative verification of DNA binding to the streptavidin agarose beads, the beads were stained with PicoGreen (Invitrogen Corporation, Carlsbad, Calif.). The PicoGreen reagent binds selectively to double-stranded DNA and upon binding undergoes a roughly 1,000 fold fluorescence enhancement. 5 µL bead volume of the prepared beads was washed 3×400 µL with TE (10 mM Tris-HCl, pH 8.0, 1 mM EDTA) using the micro-centrifuge Filtration Devices. The beads were resuspended in 50 µL of PicoGreen reagent diluted 1/200 in TE buffer and the suspension transferred to 0.5 mL clear, thin-walled, polypropylene PCR tubes. The beads were briefly centrifuged to form a pellet and without removing the fluid, the bead pellets were scanned for fluorescence directly in the tubes using a FluorImager SI laser-based scanner (Molecular Dynamics/Amersham Biosciences Corp., Piscataway, N.J.). As a negative control, plain streptavidin beads without bound DNA were also stained with PicoGreen as a blank. Results shown in FIG. 22A. The fluorescence signal coming from the bead-bound DNA is clearly visible from the bead pellet with an integrated signal intensity of 40:1 relative to the plain streptavidin beads (blank beads) without any bound DNA.

Immobilization of PC-Antibody on DNA Encoded Beads:

To generate the photocleavable antibody (PC-antibody), the mouse monoclonal anti-HSV tag antibody (EMD Biosciences, Inc., San Diego, Calif.) directed against the common HSV epitope tag present in all expressed proteins was labeled with photocleavable biotin (PC-biotin). To perform labeling, the antibody was left in the manufacturer supplied buffer (1 µg/µL antibody, 50% glycerol, PBS, 0.02% sodium azide) and supplemented with 1/9 volume of 1M sodium bicarbonate to yield a final sodium bicarbonate concentration of 100 mM. 330 µg of the antibody (now in 367 µL) was then labeled using 20 molar equivalents of AmberGen's PC-biotin-NHS reagent (added from 50 mM stock in DMF) for 30 min with gentle mixing and protected from light. Un-reacted and hydrolyzed PC-biotin-NHS reagent was removed by running the antibody through a NAP-10 Sepharose G-25 desalting column (Amersham Biosciences Corp., Piscataway, N.J.) according to the manufacturer's instructions except that only the first 1 mL of elution was collected and used. For the column, TBS was used as the equilibration and elution buffer. The concentration of the resultant antibody was measured by absorbance at 280 nm to be 0.21 µg/µL. The antibody was separated into aliquots and stored frozen at −70° C.

Next, the prepared PC-antibody was co-immobilized onto the prepared DNA encoded streptavidin beads described earlier in this Example. To do so, 5 µL bead volume of the DNA encoded beads was washed 3×400 µL with TE-Saline (10 mM Tris-HCl, pH 8.0, 1 mM EDTA, 200 mM NaCl) using the micro-centrifuge Filtration Devices. The beads were then transferred to low protein binding 0.5 mL polypropylene PCR tubes (Eppendorf North America, Westbury, N.Y.) and all fluid supernatant was removed leaving only the hydrated bead pellet. The stored PC-antibody preparation at 0.21 µg/mL in TBS, described earlier in this example, was diluted to 0.14 µg/µL with TE buffer (10 mM Tris-HCl, pH 8.0, 1 mM EDTA) and supplemented to 1 mM EDTA final concentration from a 500 mM, pH 8.0 EDTA stock solution. 150 µL of the diluted PC-antibody solution was used to resuspend the washed DNA encoded bead pellet and the suspension was subsequently mixed gently for 15 min protected from light. Using the micro-centrifuge Filtration Devices, the beads were then washed 3×400 µL with TE-Saline buffer followed by 1×400 µL with 50% glycerol/50% TE buffer/200 mM NaCl. Beads were then resuspended to a 10% (v/v) suspension in 50% glycerol/50% TE buffer/200 mM NaCl and stored at −20° C. The binding of the PC-antibody to the beads was monitored by absorbance at 280 nm of the starting diluted antibody solution versus the antibody solution after incubation with the beads. A calculated 26% of the added antibody was captured for a loading of approximately 1 µg of PC-antibody per µL of bead volume.

Expression and In Situ Immobilization of Proteins with DNA Encoded Photocleavable Antibody Beads:

Briefly, the mechanism for multiplexed cell-free protein expression with in situ protein capture involves affinity capture of proteins on a surface, simultaneously as they are cell-free produced using the surface-immobilized DNA as a template (DNA co-immobilized with affinity capture agent), with capture occurring locally at the position of the parent immobilized DNA.

For cell-free protein expression and in situ immobilization, the beads prepared with co-immobilized expression DNA and photocleavable (PC) anti-HSV antibody were used. Preparation of such beads was described earlier in this Example. Beads encoded with GST DNA were used for this particular demonstration. Just prior to the cell-free expression reaction, 1 µL of beads (i.e. 1 µL bead volume; roughly 750 beads) was additionally washed (in addition to washes done in their preparation) 1×400 µL with nuclease free water using the micro-centrifuge Filtration Devices. The rabbit reticulocyte cell-free expression reaction mixture was prepared as described in Example 1 except that only 1 µBODIPY-FL-tRNA$^{COMPLETE}$ was used for labeling the nascent proteins and in one case, soluble expression DNA was not added, but instead was replaced with the 1 µL of GST DNA encoded PC-antibody beads. To add the beads into the cell-free reaction mixture, the reaction mixture was used to resuspend the washed 1 µL bead pellet. 50 µL of expression reaction mixture was used for each 1 µL bead pellet. As a negative control, a second expression reaction received plain streptavidin beads which lacked both the bound GST DNA and bound PC-antibody, but the reaction sample was supplemented with validated soluble plasmid DNA (for expressing GST) as described in Example 1. A third expression reaction received the 1 µL of GST DNA encoded PC-antibody beads but was also additionally supplemented with validated soluble plasmid DNA (for expressing GST).

The expression reaction was carried out for 1 hr at 30° C. with gentle mixing. The reaction was then mixed with equal volume of Translation Dilution Buffer (TDB) as described in Example 1 except that the buffer contained 10 mM DTT instead of 2 mM and additionally contained 20 mM EDTA added from a 500 mM pH 8.0 stock and 4 mM cycloheximide (Sigma-Aldrich, St. Louis, Mo.) added from a 355 mM stock in DMSO. The TDB contained no BSA or other protein carriers. The samples were equilibrated in the buffer for 15 min at +4° C. with gentle mixing. Using the micro-centrifuge Filtration Devices, the beads were washed 3×400 µL with PBS containing 5 mM DTT. The beads were then washed 1×400 µL with 50% glycerol, PBS and 5 mM DTT and diluted with the same buffer to a 0.5% (v/v) bead suspension.

Contact Photo-Transfer from Individually Resolved Beads:

Contact photo-transfer from individually resolved beads onto epoxy activated glass microarray substrates (slides) (SuperEpoxy substrates, TeleChem International, Inc. ArrayIt™ Division, Sunnyvale, Calif.) overlaid with a cover glass was performed as described in Example 24.

Detection of Photo-Transferred Protein.

Detection of the directly incorporated tRNA mediated BODIPY-FL fluorescence labeling was achieved by imaging the dry microarray substrates on an ArrayWoRx$^e$ BioChip fluorescence reader (Applied Precision, LLC, Issaquah, Wash.).

Results:

Results are shown in FIG. 22B. The top center panel shows the fluorescence image following contact photo-transfer from beads that lacked both immobilized GST DNA and PC-antibody, but where validated soluble plasmid DNA was included in the expression reaction to facilitate GST protein production. Note that the expressed GST does not bind the beads and is therefore not transferred to the microarray substrate. The lower left panel shows contact photo-transfer from beads that contained both immobilized DNA and immobilized PC-antibody against the C-terminal HSV epitope tag present in expressed GST. GST is expressed from the immobilized DNA and labeled with the BODIPY-FL-tRNA$^{COMPLETE}$. The nascent GST is bound by the bead-immobilized PC-antibody and is subsequently contact photo-transferred from individual beads to the microarray substrate, leaving ~100 micron diameter fluorescent microarray features. Other Examples and experiments verify that the fluorescence in fact comes from the labeled nascent protein and not the BODIPY-FL-tRNA$^{COMPLETE}$. The lower right panel shows contact photo-transfer from beads that contained both immobilized DNA and immobilized PC-antibody against the C-terminal HSV epitope tag present in expressed GST and where the expression reaction was additionally supplemented with soluble validated plasmid DNA. This permutation shows significantly increased signal due to the added soluble expression DNA and shows that the immobilized DNA alone (lower left panel) does not produce enough protein to saturate the bead-bound PC-antibody.

Example 26

Cell-Free Protein Synthesis and In Situ Protein Immobilization on Beads Followed by Contact Photo-Transfer Using Photocleavable Antibodies or tRNA Mediated Labels: Co-Expression of Mixed DNA Encoded Bead Species in a Single Reaction Immobilization of Expression DNA on Beads:

This Example is similar to Example 25 except that different bead species bearing DNA for expression of different proteins were translated in the same cell-free reaction for multiplexed protein production and in situ protein capture on the parent DNA encoded beads. Additionally, examples are described using either PC-antibodies or tRNA mediated photocleavable labels for in situ protein capture on the parent DNA encoded beads.

Genes encoding human glutathione-s-transferase (GST) and the p53 oncoprotein were amplified by PCR with a biotin modified primer and the amplicons attached to streptavidin agarose beads as described in Example 25.

Immobilization of PC-Antibody on DNA Encoded Beads:

To generate the photocleavable antibody (PC-antibody), the mouse monoclonal anti-HSV tag antibody (EMD Biosciences, Inc., San Diego, Calif.) directed against the common HSV epitope tag present in all expressed proteins was labeled with photocleavable biotin (PC-biotin) and co-immobilized on the aforementioned DNA encoded streptavidin beads as described in Example 25.

Expression and In Situ Immobilization of Proteins with DNA Encoded Photocleavable Antibody Beads:

For cell-free protein expression and in situ immobilization, the beads prepared with co-immobilized expression DNA and photocleavable (PC) anti-HSV antibody were used. Preparation of such beads was described earlier in this Example. Beads encoded with GST DNA or p53 DNA were used for this particular demonstration. Cell-free expression in the presence of the beads was performed essentially as described in Example 25 with the following exceptions: Only the bead-immobilized DNA was used for expression as no soluble DNA was added in any case. To ensure the DNA was tightly bound to the beads, the GST and p53 DNA encoded beads were additionally washed separately (in addition to washes performed in their preparation). Approximately 1 μL bead volume was washed 1×400 μL in TE-Saline (see Example 25) at 30° C. for 30 min with gentle mixing. Beads were then separated from the fluid wash using the micro-centrifuge Filtration Devices (see Example 25; all subsequent bead washings use the Filtration Devices) and washed 1× briefly (briefly=5 sec vortex mix) with 400 μL of TE-Saline. Beads were then resuspended to 300 μL with TE-Saline and the appropriate amount of bead suspension was combined to yield a 1:1 bead mixture containing 0.5 μL bead volume of GST DNA encoded beads and 0.5 μL bead volume of p53 DNA encoded beads. The fluid was removed from the bead mixture using the Filtration Device and the beads washed 1×400 μL with nuclease-free water just prior to combining with the cell-free expression reaction mixture as described in Example 25.

The cell-free expression reaction in the presence of the beads was performed as described in Example 25 except that the reaction was performed for 15 min at 30° C. without mixing or shaking and after the reaction, the samples were not mixed with TDB buffer but were immediately washed. For washing, the expression reaction was immediately transferred to new Filtration Devices and the fluid removed from the beads by filtration (all subsequent bead washes performed in Filtration Devices). Beads were then washed 1×350 μL briefly (briefly=5 sec vortex mix) with ice cold PBS containing 5 mM DTT. The beads were then washed 4×400 μL briefly (briefly=5 sec vortex mix) with the same ice cold buffer. Lastly, beads were washed 1×400 μL briefly (briefly=5 sec vortex mix) with ice cold 50% glycerol, PBS and 5 mM DTT and diluted with the same buffer to a 0.5% (v/v) bead suspension.

Contact Photo-Transfer from Individually Resolved Beads:

Performed as described in Example 25 except that after contact photo-transfer, washing and drying of the microarray slides, the slides were further processed for antibody probing as described in the following paragraphs.

Preparation of an Anti-p53-Cy5 Fluorescent Antibody:

While the BODIPY-FL-tRNA$^{COMPLETE}$ provides green fluorescence labeling of all nascent cell-free expressed proteins, a protein specific antibody was needed to distinguish between the different proteins (GST and p53) that were contact photo-transferred from the different DNA encoded PC-antibody beads. For this, an anti-p53 monoclonal antibody was conjugated to the Cy5 fluorescent dye to be used in probing the microarray substrate containing the contact photo-transferred protein spots. For this mouse monoclonal anti-p53 clone BP53-12 was purchased from Biosource International (Camarillo, Calif.). The antibody is supplied purified at 1 μg/μL (100 μL for 100 μg) in PBS buffer only. The antibody is then supplemented with ⅑ volume of 1M sodium bicarbonate to give a 100 mM final concentration of sodium bicarbonate. The antibody was then labeled by adding the Cy5-NHS monoreactive ester (Amersham Biosciences Corp., Piscataway, N.J.) from a 27 mM stock (stock in DMSO). The Cy5-NHS ester was added to a 12-fold molar excess relative to the antibody. The labeling reaction was allowed to proceed by gentle mixing for 30 min protected from light with aluminum foil. Unreacted/hydrolyzed labeling reagent was removed from the labeled p53 antibody using a MicroSpin G-25 desalting column (Amersham Biosciences Corp., Piscataway, N.J.) according to the manufacturers instructions (except that the column was additionally pre-washed 1×350 µL with TBS). 2 columns were used with a loading of approximately 55 µL per column and the eluted antibody pooled afterwards. The Cy5 labeled and purified p53 antibody was measured in a spectrophotometer for absorbance at 280 nm (protein concentration) and 649 mm (Cy5 concentration). Using the appropriate extinction coefficients, the result was 0.56 µg/µL antibody concentration and a calculated average of 2.8 Cy5 molecules per molecule of antibody.

Probing the Microarray with Anti-p53-Cy5 Antibody:

The aforementioned anti-p53-Cy5 antibody was used to probe the microarray slide. To do so, the slides were first blocked for 30 min at 37° C. with 5% BSA (w/v) in TBS-T. Next, the slide was probed with ~15 mL of the anti-p53-Cy5 antibody diluted ⅟₁,000 (0.56 µg/mL) with 5% BSA (w/v) in TBS-T. Probing was performed with mixing in a tray for 30 min at 37° C. The microarray slides were then washed for 4×2 min each with excess TBS-T (cover glass removed on first wash), followed by 4× briefly (5 sec) with purified water and dried prior to imaging as described later. Separately, using this same procedure, the anti-p53-Cy5 antibody conjugate was validated to selectively stain the cell-free expressed p53 protein and without any detectable cross-reactivity with cell-free expressed GST.

Detection of Photo-Transferred Protein:

Detection of the directly incorporated tRNA mediated BODIPY-FL fluorescence labeling as well as signal from the Cy5 labeled anti-p53 antibody was achieved by imaging the dry microarray substrates on an ArrayWoRx$^e$ BioChip fluorescence reader (Applied Precision, LLC, Issaquah, Wash.) using the appropriate standard manufacturer supplied filter sets.

Figure 23A:
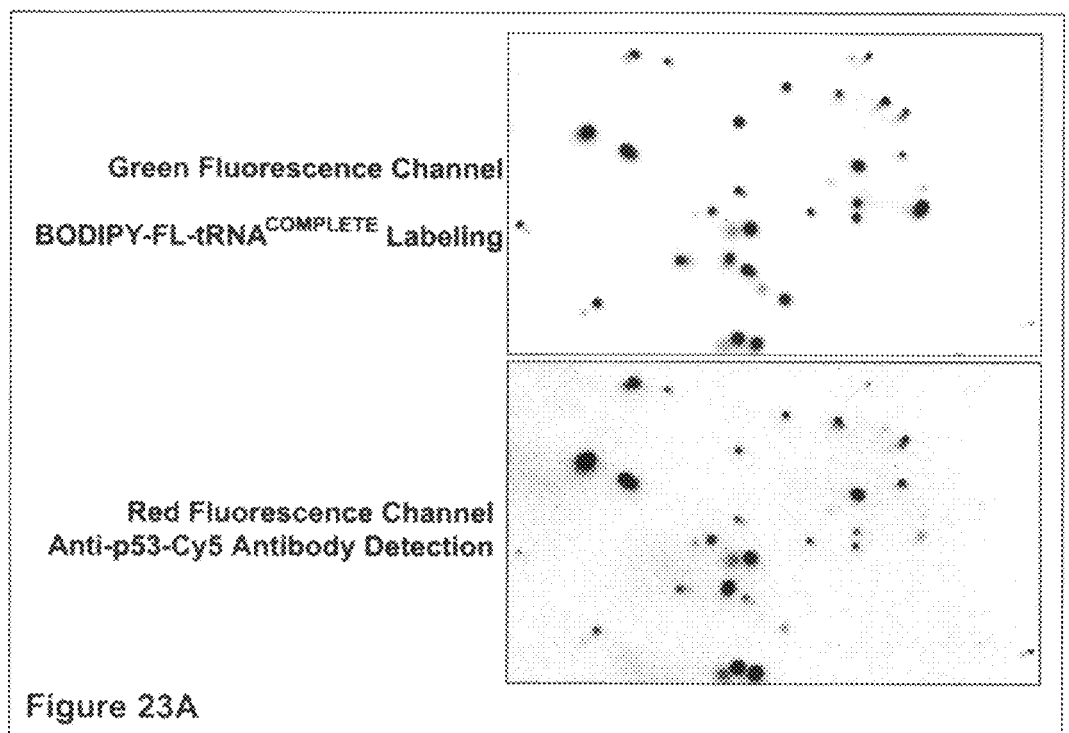
FIG. 23A. Cell-free protein synthesis from expression DNA bound to agarose beads and in situ capture of the nascent proteins by PC-antibody also immobilized on the same agarose beads. A mixed population of beads encoded with either GST DNA or p53 DNA were co-expressed in a single cell-free reaction. After expression, in situ protein capture and isolation, proteins were applied to a microarray substrate by contact photo-transfer. The microarray substrate was further probed with a Cy5 labeled anti-p53 specific antibody. The internal tRNA mediated BODIPY-FL fluorescence labels as well as binding of the Cy5 labeled p53 antibody were imaged.
Figure 23B:
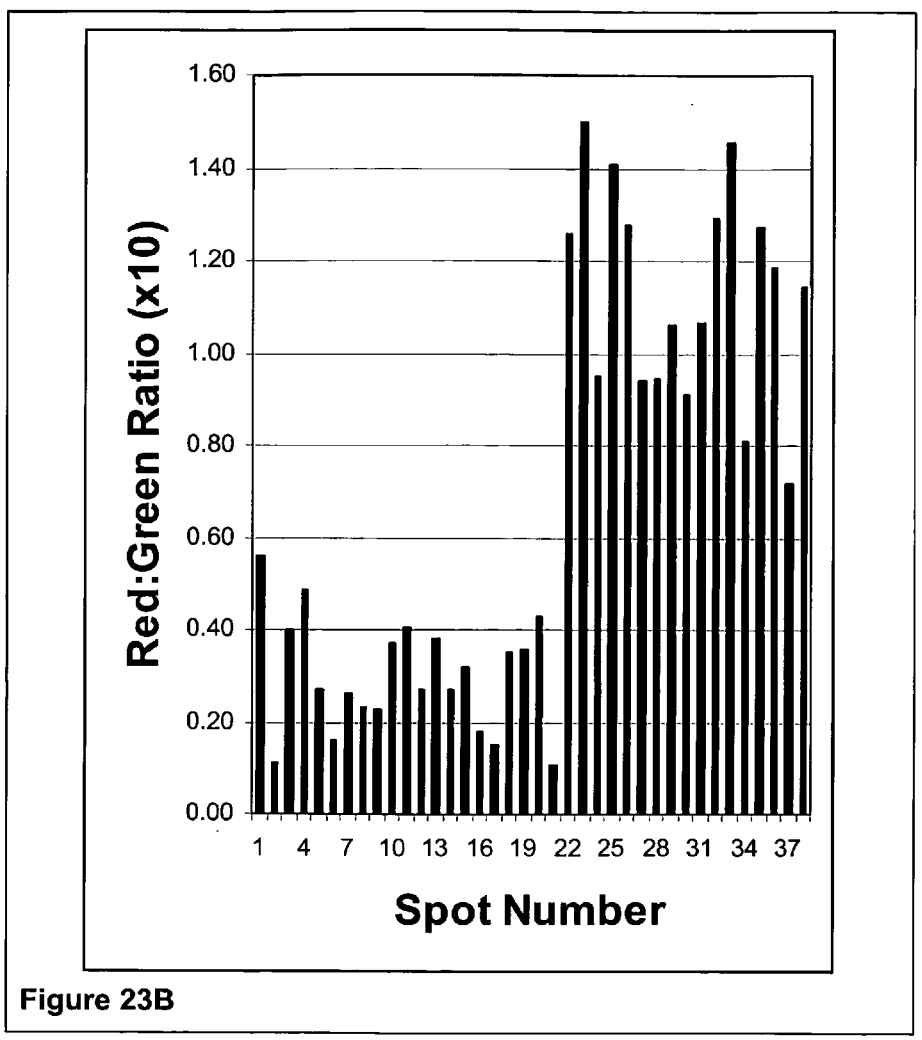
FIG. 23B. Cell-free protein synthesis from expression DNA bound to agarose beads and in situ capture of the nascent proteins by PC-antibody also immobilized on the same agarose beads. A mixed population of beads encoded with either GST DNA or p53 DNA were co-expressed in a single cell-free reaction. After expression, in situ protein capture and isolation, proteins were applied to a microarray substrate by contact photo-transfer. The microarray substrate was further probed with a Cy5 labeled anti-p53 specific antibody. The internal tRNA mediated BODIPY-FL fluorescence labels as well as binding of the Cy5 labeled p53 antibody were imaged. The images were quantified to determine the integrated fluorescence intensities for each spot for both the red (Cy5) and green (BODIPY-FL) fluorescence signals and the ratios calculated.

Results:

Fluorescence microarray images are shown in FIG. 23A. The top panel is a gray-scale image from the green fluorescence channel corresponding to the internal BODIPY-FL tRNA mediated protein labeling. The bottom panel is a gray-scale image of the same slide and same area from the red fluorescence channel corresponding to the binding of the anti-p53-Cy5 antibody to the protein spots on the microarray. Quantification of the integrated intensities for each spot in both the red and green fluorescence images was performed and the ratio of red to green fluorescence is shown for each spot in FIG. 23B. In this Example, partial protein cross-over is observed, i.e. escape of nascent p53 from the parent p53 DNA encoded bead and cross-contamination (capture by PC-antibody) onto the GST DNA encoded beads, and presumably the converse as well. Nonetheless, 2 distinct species of spots originating from the beads (38 beads total analyzed) are observed. The 2 species of spots are identified by differing red fluorescence (p53 content) to green fluorescence (total nascent protein content) ratios as shown in FIG. 23B. The spots arising from p53 DNA encoded beads have a red:green ratio of 1.13±0.23 (visible as yellow spots in the color image overlay FIG. 23A bottom panel) while the spots arising from GST DNA encoded beads have a ratio of 0.30±0.12 (visible as green spots in the color image overlay FIG. 23A bottom panel). The 2 populations of beads were statistically analyzed using an unpaired 2-tailed t-test and determined to be very significantly different with a p value of 0.000000000002 (p value<0.05 considered significant with 95% confidence). Furthermore, the number of each species of spots is at an approximate a 1:1 ratio (17 spots p53 to 21 spots GST) as expected from the 1:1 mixing of the 2 bead species.

As shown earlier, there is some occurrence of nascent proteins escaping from their parent DNA encoded bead resulting in partial cross-contamination of other non-parent beads. This problem arises from mixing and diffusion rates that occur in the 3-dimensional bulk fluid expression reaction as well as from settling of the beads, by gravity, to the bottom of the reaction tube and into very close proximity to each other. This problem can be solved by modulating parameters including the DNA to PC-antibody ratio on the beads as well as the expression reaction times and temperature and the ratio of beads to expression mixture. Additionally, specialized techniques can be used to solve this problem, such as the inclusion of soluble (i.e. not tethered to beads) epitope tag antibody (i.e. anti-HSV antibody in this case) into the expression reaction to bind-up any nascent proteins that escape their micro-porous parent bead matrix (i.e. not captured by the tethered PC-antibody). A more advanced method uses the soluble epitope tag antibody conjugated/attached to a large soluble polar macromolecule (e.g. large dextrans or large irrelevant non-expression DNA plasmids) such that the antibody fails to enter the micro-pores of the cross-linked agarose beads (by size/charge exclusion). With this approach, the soluble free antibody conjugate binds-up only proteins that escape the micro-porous beads but does not interfere with PC-antibody mediated in situ protein capture occurring within the micro-environment (porous matrix) of the beads. This unique design is only effective with micro-porous beads such as cross-linked agarose, and not with non-porous beads such as the streptavidin conjugated 1 micron diameter magnetic beads from Dynal Biotech (Dynabeads® MyOne™ Streptavidin; Dynal Biotech LLC, Brown Deer, Wis.) containing only an external monolayer of streptavidin. Therefore, if these non-porous 1 micron beads are loaded with DNA and PC-antibody for multiplexed expression and in situ protein capture, the cell-free expression reaction can be supplemented with an excess of larger (~100 micron diameter), porous, cross-linked agarose beads (e.g. 4% agarose beads with 30 nm average pore size from Sigma-Aldrich, St. Louis, Mo.) bearing only tethered and non-cleavable epitope tag antibody (i.e. anti-HSV antibody in this case). These larger cross-linked agarose beads bind-up only proteins that are not in situ captured onto the parent DNA encoded 1 micron magnetic beads, thus preventing bead cross-contamination. Since virtually all of the binding capacity of the larger agarose beads is internal to the cross-linked beaded matrix, the tethered antibody will not interact with proteins that do not escape the surface of the parent DNA encoded 1 micron magnetic beads. After the expression reaction, the larger agarose beads can be separated from the smaller magnetic beads by applying a magnet or by simple mesh filtering. An alternative strategy for preventing bead cross-contamination involves expression from the DNA encoded PC-antibody beads in a thin film of fluid (the liquid cell-free expression reaction) containing the beads, such as is created by trapping ("sandwiching") the fluid-bead suspension between a standard glass microscope slide which is overlaid with a standard microscope cover glass. This design disperses the beads as demonstrated in Example 24, which minimizes the possibility of cross-contamination. This design also restricts protein diffusion and hence restricts nascent protein escape from the parent DNA encoded bead and subsequent cross-contamination of non-parent beads.

A variant of the overall bead-based multiplexed protein expression and contact photo-transfer method presented in this Example involves in situ nascent protein capture onto the parent DNA encoded bead [bead also containing bound (strept)avidin with available biotin binding sites] via a directly incorporated PC-biotin label by using AmberGen's PC-biotin-tRNA$^{COMPLETE}$. This variant does not use PC-antibodies (e.g. no PC-antibody to the HSV epitope tag is used) and therefore does not require genetically engineered epitope tags in the expressed proteins. The PC-biotin-tRNA$^{COMPLETE}$ is not pre-bound to the bead surface but instead is included in the solution-phase of the bead containing cell-free expression reaction. Once the expression reaction is initiated, it sets off 2 competing processes, whereby a fraction of the PC-biotin-tRNA$^{COMPLETE}$ is captured on the beads prior to participating in the translation reaction while another fraction of the tRNA is first utilized in the translation reaction to label the nascent protein followed by in situ capture of the labeled nascent protein onto the DNA encoded parent bead. As before, this relies on the ability of the immobilized expression DNA to localize the translation reaction to the parent bead. When this process is performed as otherwise described earlier in this Example (mixed beads in a single expression reaction), in conjunction with the contact photo-transfer method, similar protein segregation onto the parent DNA encoded beads and hence in the photo-transferred spots is observed.

Example 27

Contact Photo-Transfer from 10 Micron Diameter Polymer Beads for High Density Arrays Preparing NeutrAvidin Coated Beads:

The beads used are 10.2±0.09 microns in diameter and composed of a hydrophobic styrene-divinylbenzene co-polymer and are commercially available from Bangs Laboratories, Inc. (Fishers, Ind.). The beads are coated with the biotin binding protein NeutrAvidin (Pierce Biotechnology, Inc., Rockford, Ill.) by passive adsorption. A second set of beads is coated with BSA as a negative control. To do so, 57 mg of beads was washed 3×400 μL each with 20 mM sodium phosphate, pH 6.3 and 150 mM NaCl. Washes were performed by ~5 sec vortex mixing. To wash the beads or exchange the buffers, 0.45 micron pore size, PVDF membrane, micro-centrifuge Filtration Devices were used unless otherwise noted (Ultrafree-MC Durapore Micro-centrifuge Filtration Devices, 400 μL capacity; Millipore, Billerica, Mass.). After washing, the beads were resuspended in 400 μL of NeutrAvidin or BSA at a 2.5 mg/mL concentration in 20 mM sodium phosphate, pH 6.3 and 150 mM NaCl. Binding was allowed to occur for 2 hr at 37° C. with gentle mixing. Beads were then washed for 4×400 μL with 5% BSA (w/v) in TBS. Washes were performed by ~5 sec vortex mixing. Beads were then blocked for 15 min at 37° C. in the same buffer. The beads were then washed for 3×400 μL with 0.1% sodium azide as a preservative in TBS. Washes were performed by ~5 sec vortex mixing. Beads were resuspended to a 10% (v/v) suspension in the same buffer and stored at +4° C.

Conjugating Photocleavable Biotin & Cy5 to the Casein Test Protein:

Bovine casein (sodium salt; Sigma-Aldrich, St. Louis, Mo.) is labeled with both photocleavable biotin (PC-biotin) and the fluorophore Cy5. To do so, the casein was prepared to 2 mg/mL in 200 mM sodium bicarbonate and 200 mM NaCl. Any un-dissolved particulate was removed by passing the solution through 0.45 micron pore size, PVDF membrane, micro-centrifuge Filtration Devices (Ultrafree-MC Durapore Micro-centrifuge Filtration Devices, 400 μL capacity; Millipore, Billerica, Mass.). The filtrate was then collected and desalted on a NAP-10 Sepharose G-25 column (Amersham Biosciences Corp., Piscataway, N.J.) against the same 200 mM sodium bicarbonate and 200 mM NaCl buffer according to the manufacturer's instructions. The protein concentration was then determined by measuring the absorbance at 280 nm on a spectrophotometer (0.84 absorbance units in 1 cm path cuvette=1 mg/mL). The resultant recovered casein (1.2 mg/mL at 1 mL) was labeled using 10 molar equivalents of AmberGen's PC-biotin-NHS reagent (added from 50 mM stock in DMF) for 20 min with mixing. Next, the casein was additionally labeled with the Cy5 fluorophore using a Cy5-NHS monoreactive ester (Amersham Biosciences Corp., Piscataway, N.J.) labeling reagent; The Cy5 labeling reagent was added to a 2.7-fold molar excess relative to the PC-biotin labeled casein from a 27 mM stock prepared in DMSO. The reaction was allowed to proceed for 30 min with gentle mixing and protected from light. The labeled casein was then purified to remove any un-reacted or hydrolyzed labeling reagent by using a NAP-10 Sepharose G-25 column (Amersham Biosciences Corp., Piscataway, N.J.) against a TBS buffer according to the manufacturer's instructions. The labeled casein was stored at +4° C. protected from light.

Loading the PC-Biotin-Casein-Cy5 Conjugate to the NeutrAvidin Coated 10 Micron Beads:

Both the NeutrAvidin coated and negative control BSA coated 10 micron diameter beads are treated with the PC-biotin-casein-Cy5 conjugate to allow binding to occur, which is expected only in the case of the NeutrAvidin beads. To do so, 100 mL of the 10% (v/v) coated bead stocks was mixed with 100 mL of 0.1 μg/μL of the PC-biotin-casein-Cy5 conjugate diluted in 5% BSA (w/v) in TBS. Binding was allowed to occur for 30 min with gentle mixing. Using the aforementioned Filtration Devices, beads were then washed 1×400 mL with 5% BSA (w/v) in TBS, 4×400 μL with PBS and 1×400 μL with 50% glycerol (v/v) and 5 mM DTT in PBS. All washes were for 5 see vortex mixing followed by filtration. The beads were resuspended to a 2% (v/v) suspension with 50% glycerol (v/v) and 5 mM DTT in PBS.

Contact Photo-Transfer from the PC-Biotin-Casein-Cy5 loaded 10 Micron Beads:

For contact photo-transfer, 0.5 mL of the prepared 2% (v/v) bead suspensions were deposited onto the surface of epoxy activated 25×75 mm rectangular microarray substrates (SuperEpoxy substrates, TeleChem International, Inc. ArrayIt™ Division, Sunnyvale, Calif.). The 0.5 μL droplets on the microarray substrates were then each overlaid with 12 mm diameter round microscope cover glasses, which were then pressed gently. This limiting fluid amount per 12 mm cover glass created 7 mm diameter, circle shaped, thin liquid films containing the beads sandwiched between the cover glass and the microarray substrate. The microarray substrates were then placed on a UV transilluminator light box (TMW-20 Transilluminator; Model White/UV; UVP, Upland, Calif.) and the substrates raised, by their edges, off the glass surface of the light box using ~1 mm thick wetted filter papers (wetted to reduce evaporation of bead solutions). The light box was then covered. Prior to powering on the light source, the substrates were allowed to stand, undisturbed, for 5 min to allow equilibration. The substrates were then UV illuminated, from the bottom up, through the glass microarray substrate material for 5 min without disturbance. After UV illumination, the substrates were then left to stand for an additional 10 min without disturbance to allow binding of the photo-released material to the epoxy activated substrate surface. To remove the cover glasses and wash away the beads, the substrates were dropped, face up, into an already-mixing tray of 5% BSA (w/v) in TBS-T and mixed for 1 min on an orbital platform shaker. The microarray substrates were additionally washed 4×30 sec with TBS-T and 4×30 sec with purified water. To confirm that the beads were indeed washed away, the microarray substrates were viewed under a standard phase contrast microscope (note: when present, the 10 micron diameter beads are easily and clearly visible under the microscope). The substrates were dried prior to imaging.

Detection of Photo-Transferred Protein:

Detection of the Cy5 fluorescence labeling in the photo-transferred casein spots was achieved by imaging the dry microarray substrates on an ArrayWoRx$^e$ BioChip fluorescence reader (Applied Precision, LLC, Issaquah, Wash.) with the appropriate standard manufacturer supplied filter set. The optical scanning resolution was set to 3 microns.

Results:

One major advantage of the contact photo-transfer method is the ability to print very high density microarrays, dictated by the bead size, to densities beyond what is possible with conventional mechanical printing instruments. Additionally, unlike conventional mechanical printing, contact photo-transfer is not serial but fully parallel and thus printing time and effort is independent of the number of array features, requiring only 5 min of illumination with the proper light. Mechanical wear-and-tear of conventional robotic printing devices is also eliminated.

Figure 24:
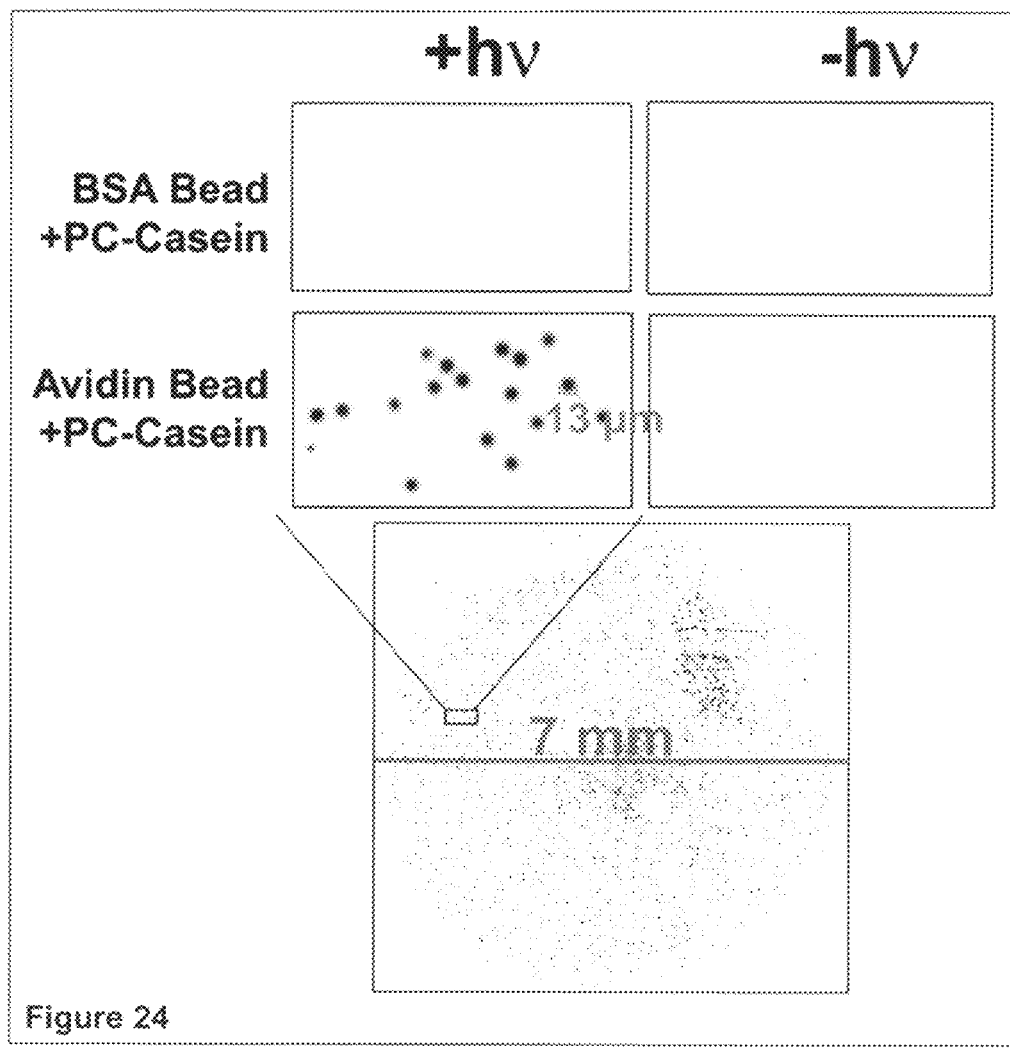
FIG. 24. High density arrays by contact photo-transfer from 10 micron beads. Avidin or negative control BSA coated beads were treated with casein that was dual labeled with PC-biotin and Cy5 ("PC-Casein"). Beads were contact photo-transferred in a 7 mm diameter circular region. At this density, 4,896 spots were counted in the 7 mm circular area which would correspond to 242,004 spots on an entire 25×75 mm microarray substrate. Bead derived spots measure 13 microns diameter. +hv=Contact photo-transfer with proper light. −hv=Negative control contact transfer in the absence of proper light.

Photo-transferred spot diameters were measured using the software supplied by Applied Precision, LLC (Issaquah, Wash.) with their ArrayWoRx$^e$ BioChip reader. Spots in the entire 7 mm diameter printed area were enumerated using simple 2-D electrophoresis spot detection software (ImageQuant; Molecular Dynamics; Amersham Biosciences Corp., Piscataway, N.J.). As shown in FIG. 24, sharp, easily resolved, 13 micron, circular microarray features were generated with this contract photo-transfer method. "+PC-Casein" in FIG. 24 refers to the addition of the PC-biotin-casein-Cy5 conjugate to either the BSA coated negative control beads ("BSA Bead" in FIG. 24) or the NeutrAvidin coated beads ("Avidin Beads" in FIG. 24) prior to the contact photo-transfer process. Spot signal is only observed when NeutrAvidin coated beads were used to capture the PC-biotin-casein-Cy5 conjugate and only when UV light irradiation was used to photo-release and transfer the conjugate to the microarray substrate surface ("+hv" in FIG. 24). When negative control BSA coated beads were used for capture of the PC-biotin-casein-Cy5 conjugate, no signal was observed on the microarray since no conjugate was specifically captured by its PC-biotin label. Observation under a microscope confirmed that the beads were indeed washed away from the microarray substrate prior to imaging. An additional negative control, performed from the NeutrAvidin beads loaded with the PC-biotin-casein-Cy5 conjugate, but without the UV light treatment during the contact photo-transfer process ("−hv" in FIG. 24), also shows no measurable signal. This negative control further confirms that the beads are not bound to the array surface, but are indeed washed away since no signal from the bead-bound fluorescent casein conjugate was observed. At the spot density used, 4,896 spots were counted in the 7 mm circular area which would correspond to 242,004 spots on an entire 25×75 mm microarray substrate (129 spots/mm$^2$).

Example 28

Contact Photo-Transfer for Molecular Diagnostic Assays: Cell-Free Expression from a PCR Template of the APC Gene Amplified from Genomic DNA Preparation of a Photocleavable Antibody Affinity Matrix:

The photocleavable antibody beaded affinity matrix was prepared using the monoclonal anti-HSV tag antibody (EMD Biosciences, Inc., San Diego, Calif.) as described in Example 2.

PCR Amplification of an APC Segment from Genomic DNA.

Isolation of genomic DNA from cultured cells and PCR amplification of segment 3 of the human APC gene was performed as reported by AmberGen in the scientific literature [Gite et al. (2003) Nat Biotechnol 21, 194-197], except that an N-terminal HSV epitope tag (amino acid sequence QPELAPEDPED [SEQ NO. 3]) and an N-terminal VSV-G epitope tag was incorporated into the expressed protein, instead of the N-terminal VSV-G tag alone. The C-terminal p53 derived epitope tag was as previously reported [Gite et al. (2003) Nat Biotechnol 21, 194-197]. Epitope tags and elements necessary for efficient cell-free expression are introduced into the PCR amplicon by way of specialized primers [Gite et al. (2003) Nat Biotechnol 21, 194-197]. APC segment 3 of Exon 15 corresponds to codons 1,099 to 1,696. Wild-type (WT) APC was derived from the HeLa cell line and the mutant, containing a chain truncation mutation at codon 1,338 of APC(CAg→TAg), was derived from the SW480 cell line. The exact primers used are listed below:

```
APC Segment 3 Forward Primer:
                                             [SEQ NO. 4]
5'ggATCCTAATACgACTCACTATAgggAgACCACCATgTACACCgACAT
CgAgATgAACCgCCTgggCAAgggAggACAgCCTgAACTCgCTCCAgAgg
ATCCggAAgATgTTTCTCCATACAggTCACggggA3'

APC Segment 3 Reverse Primer:
                                             [SEQ NO. 5]
5'TTATTACAgCAgCTTgTgCAggTCgCTgAAggTACTTCTgCCTTCTgT
AggAATggTATC3'
```

Cell-Free Expression and tRNA Mediated Labeling:

The APC segment 3 was expressed in a cell-free reaction as described earlier in Example 1 with the following exceptions: Only AmberGen's BODIPY-FL-tRNA$^{COMPLETE}$ was used at 4 μM for labeling and not the PC-biotin-tRNA$^{COMPLETE}$ or any other misaminoacylated tRNA labeling reagents. The expression reaction size was only 20 μL for each sample. Instead of adding expressible purified plasmid DNA for translation, 1 μL of crude PCR amplified APC segment 3 DNA was added. Importantly, the aforementioned anti-HSV tag photo-cleavable antibody affinity beads were added directly into the expression reaction, at the start of the expression reaction, as the last component. To do this, 10 μL of bead volume was washed 2×400 μL briefly (briefly=5 sec vortex mix) with 0.1% BSA (w/v) in PBS. Washes were performed in a polypropylene 0.5 mL micro-centrifuge tube and the beads pelleted in a micro-centrifuge. The washed bead pellet was then diluted to a 50% bead suspension (v/v) with the same buffer. 2 μL of this 50% bead suspension was added to the cell-free expression reaction mixture as the last component. Translation Dilution Buffer (TDB) used to stop the reaction and prepare the sample contained no protein carriers, BSA or otherwise, contained 10 mM DTT instead of 2 mM and additionally contained 20 mM EDTA added from a 500 mM pH 8.0 stock and 4 mM cycloheximide (Sigma-Aldrich, St. Louis, Mo.) added from a 355 mM stock in DMSO. The stopped translations already containing the beads were not equilibrated nor clarified as done in Example 1, but were instead processed for protein isolation as described below.

Isolation of Labeled Nascent Proteins:

All steps were performed at +4° C. or on an ice water bath and all reagents and samples were also kept under these conditions during the procedure. The bead suspension was gently mixed for 30 min to further allow capture of the nascent protein on the anti-HSV tag photocleavable antibody affinity beads. The bead suspensions were then diluted to 400 μL final volume using 5 mM DTT in PBS. The beads were then washed 4× in 400 μL of 5 mM DTT in PBS per wash. The first 2 washes were by 5 sec vortex mixing and the last 2 washes for 5 min with gently mixing. The beads were then additionally washed 1× briefly (briefly=5 sec vortex mix) in 400 µL of 50% glycerol and 5 mM DTT in PBS. All washing procedures were performed in batch mode using 0.45 micron pore size, PVDF membrane, micro-centrifuge Filtration Devices to facilitate manipulation of the small volumes of affinity matrix (~100 micron beads) and exchange the buffers (Utrafree-MC Durapore Micro-centrifuge Filtration Devices, 400 µL capacity; Millipore, Billerica, Mass.). Prior to contact photo-transfer of the captured and isolated proteins, the washed pellet of 1 µL of beads was suspended in a final volume of 100 µL with 50% glycerol and 5 mM DTT in PBS thereby resulting in a 1% (v/v) bead suspension that can be stored long-term at −20° C. without freezing of the sample and thus without damage to the agarose beads.

Contact Photo-Transfer from Individually Resolved Beads:

Contact photo-transfer from individually resolved beads onto epoxy activated microarray substrates using 1 µL droplets of the 1% bead suspension was performed as described in Example 14.

Detection of Photo-Transferred Protein:

Detection of the directly incorporated tRNA mediated BODIPY-FL fluorescence labeling in the photo-transferred APC segment 3 proteins was achieved by imaging the dry microarray substrates on an ArrayWoRx$^e$ BioChip fluorescence reader (Applied Precision, LLC, Issaquah, Wash.) using the appropriate manufacturer supplied standard filter set and the resolution set to 9.7 microns.

Results:

The results in FIG. 25 show that bead-derived 100 micron diameter protein spots are clearly visible for the contact-photo transferred segment 3 of the expressed human APC gene. Phase contrast microscopy confirmed that the easily visible 100 micron beads are indeed washed away from the microarray substrate following contact photo-transfer. The signal from the contact photo-transferred APC protein arises from the internal tRNA mediated BODIPY-FL labels. A negative control, whereby only the needed PCR derived expression DNA was omitted from the cell-free translation step, shows no detectible signal on the microarray substrate. Fluorescently labeled antibodies directed against the genetically engineered N- and C-terminal tags (introduced by PCR primers) can also be used to detect the relative amount of truncated APC protein for diagnostic purposes, analogous to detection with enzyme-labeled antibodies in an ELISA based colorectal cancer diagnostic assay [Gite et al. (2003) Nat Biotechnol 21, 194-197]. In an alternative method, the bead isolated APC protein can be contact photo-transferred to plain, activated (e.g. epoxy or aldehyde) or coated (e.g. hydrophobic coatings or highly charged primary amine coatings) MALDI-TOF mass spectrometry targets. In this case, the mutational or truncation status of the protein is based on molecular weight as determined by mass spectrometry analysis.

Example 29

Contact Photo-Transfer of Allergens to Microarrays for In Vitro Diagnostics

Conjugating Photocleavable Biotin & Cy5 to the Casein Test Allergen:

Performed as described in Example 27.

Loading the PC-Biotin-Casein-Cy5 Conjugate to NeutrAvidin Coated Agarose Beads:

The PC-biotin-casein-Cy5 conjugate is loaded onto 6% cross-linked NeutrAvidin agarose beads (Pierce Biotechnology, Inc., Rockford, Ill.). This was done using 0.45 micron pore size, PVDF membrane, micro-centrifuge Filtration Devices to facilitate manipulation of the small volumes of affinity matrix (~100 micron beads) and exchange the buffers (Ultrafree-MC Durapore Micro-centrifuge Filtration Devices, 400 µL capacity; Millipore, Billerica, Mass.). 50 µL of bead volume was washed 4×400 µL with 1% BSA (w/v) in PBS. The PC-biotin-casein-Cy5 conjugate was then diluted to 12.5 µg/mL with 1% BSA (w/v) in PBS. The diluted conjugate solution was then added to the washed bead pellet and the resultant suspension was gently mixed for 30 min to allow binding. Based on measuring the visible absorbance spectrum of the Cy5 component of the conjugate ($\lambda_{max}$=649 nm; molar extinction coefficient=250,000) in a spectrophotometer, 94% of the added conjugate was captured on the beads. The beads were then washed 2×400 µL with 1% BSA (w/v) in PBS followed by 2×400 µL for 1 min each with 10 mM d-biotin dissolved in a 200 mM sodium bicarbonate and 200 nM NaCl buffer, in order to quench the remaining biotin binding sites on the beads. Lastly the beads were washed 1×400 µL with 50% glycerol (v/v) and 5 mM DTT in PBS. All washes were for 5 sec vortex mixing followed by filtration. The beads were resuspended to a 10% (v/v) suspension with 50% glycerol (v/v) and 5 mM DTT in PBS.

Contact Photo-Transfer Based Microarray Assays for Detection of Allergen-Specific IgE in Human Sera from Allergy Patients:

2 distinct assay formats are demonstrated in this Example: For format #1, the aforementioned prepared bead-bound PC-biotin-casein-Cy5 allergen conjugate is first contact photo-transferred to the microarray substrate and the entire allergen-specific IgE assay performed on the microarray itself. For format #2, the allergen-specific IgE assay is performed on the beads prior to contact photo-transferring the bound material to a microarray substrate for readout.

As mentioned above, for format #1, the bead-bound PC-biotin-casein-Cy5 allergen conjugate must first be contact photo-transferred to the microarray substrate. The contact photo-transfer process was performed as described in Example 24, except that beads were contact photo-transferred over nearly an entire 25×75 mm microarray substrate, instead of a 12 mm diameter circular region. For this, 2 µL bead volume of the aforementioned prepared PC-biotin-casein-Cy5 beads was washed 1×400 µL with 50% glycerol (v/v) and 5 mM DTT in PBS and resuspended to a 1% (v/v) suspension with the same buffer. 100 µL of the bead suspension was applied to the microarray substrate and overlaid with a 22×60 mm rectangular microscope cover glass for the contact photo-transfer process. Following contact photo-transfer, the microarray substrate was washed 4×30 sec with excess TBS-T (cover glass removed) followed by 4×30 sec with purified water. Phase contrast microscopy verifies that the easily visible ~100 micron diameter beads were indeed washed away from the microarray surface. The microarray substrate was dried prior to usage in the allergen assay.

For performing the allergen assay on the microarray (format #1), the aforementioned spotted microarray substrate was subdivided into 16 wells using a commercially available gasket overlay system (ProPlate™ Multiarray Slide System; Grace Bio-Labs, Inc., Bend, Oreg.). The wells were pre-blocked for 1 hr with excess 5% BSA (w/v) in PBS-T [PBS with 0.05% Tween-20 (v/v)]. The wells were then treated with 50 µL of a commercially available verified human serum from a patient with a casein dependant milk allergy (PlasmaLab, Everett, Wash.). 1× concentrated serum or ¹⁄₁₀ diluted serum was used. As a negative control, a separate well was treated with serum from a non-allergic patient. The treatment was performed for 2 hr with gentle mixing to allow binding of the allergen-specific IgE. The wells were then washed 3× with excess PBS-T. The microarray-bound IgE was then detected with 50 µL/well of anti-[human IgE] polyclonal antibody (Bethyl Laboratories, Montgomery, Tex.) conjugated to the Cy3 fluorophore (Amersham Biosciences Corp., Piscataway, N.J.) and diluted to 0.5 µg/mL with 5% BSA (w/v) in PBS-T. Detection was performed for 1 hr with gentle mixing. The wells were then washed 3× with excess PBS-T and then 3× with excess purified water. The microarray substrates were dried prior to imaging.

For performing the allergen assay on the beads (format #2), the beads were first pre-blocked by washing 3× with excess 5% BSA (w/v) in PBS-T using the aforementioned micro-centrifuge Filtration Devices. The beads were then treated with 100 µL of a commercially available verified human serum from a patient with a casein dependant milk allergy (PlasmaLab, Everett, Wash.). As a negative control, a second set of beads was treated with serum from a non-allergic patient. The treatment was performed for 2 hr with gentle mixing to allow binding of the allergen-specific IgE. The beads were then washed 3× with excess PBS-T using the aforementioned micro-centrifuge Filtration Devices. The bead-bound IgE was then detected with an anti-[human IgE] polyclonal antibody (Bethyl Laboratories, Montgomery, Tex.) conjugated to the Cy3 fluorophore (Amersham Biosciences Corp., Piscataway, N.J.) and diluted to 0.5 µg/mL with 5% BSA (w/v) in PBS-T. Detection was performed for 1 hr with gentle mixing. The beads were then washed 3× with excess PBS using the aforementioned micro-centrifuge Filtration Devices and then diluted with 50% glycerol (v/v) and 5 mM DTT in PBS to a 1% (v/v) bead suspension. Contact photo-transfer was then performed as described in Example 24. Following contact photo-transfer, the microarray substrate was washed 4×30 sec with excess PBS-T (cover glasses removed) followed by 4×30 sec with purified water. Phase contrast microscopy verifies that the easily visible ~100 micron diameter beads were indeed washed away from the microarray surface. The microarray substrates were dried prior to imaging.

Detection of Photo-Transferred Protein:

Detection of the Cy5 fluorescence labeling in the photo-transferred casein spots as well as the Cy3 fluorescence for measuring the bound allergen-specific IgE was achieved by imaging the dry microarray substrates on an ArrayWoRx$^e$ BioChip fluorescence reader (Applied Precision, LLC, Issaquah, Wash.) with the appropriate standard manufacturer supplied filter sets.

Results:

Results are shown in FIGS. 26A and B. FIG. 26A (format #1), where the allergen-specific IgE assay was performed on casein that was first photo-transferred to the microarray, shows specific detection of the casein-directed IgE in the 1× and 1/10× diluted test serum ("Milk Allergy Serum") as compared to the blank corresponding to 1× serum from a non-allergic patient ("Negative Serum"). FIG. 26B (format #2), where the allergen-specific IgE assay was performed on the casein-containing beads followed by contact photo-transfer, also shows specific detection of the casein-directed IgE in the 1× test serum as compared to the blank. The slight background signal in the blank samples was determined to arise from fluorescence cross-talk of the intense Cy5 signal in the directly labeled casein conjugate into the Cy3 fluorescence channel of the microarray reader, and not non-specific detection of IgE. This problem can be solved by better fluorescence filtering or lowering the Cy5 labeling ratio of the casein conjugate.

Example 30

Solid-Phase Bridge PCR and Cell-Free Expression of the Solid-Phase Bridge PCR Amplicon Preparation of Beads Covalently Conjugated to PCR Primers:

The following forward and reverse PCR primers were purchased from Sigma-Genosys (The Woodlands, Tex.), both with a 5' primary amine modification following a 6 carbon spacer (see later in this Example for corresponding template):

```
                                            [SEQ NO. 6]
Forward: 5'[Amine]CgTCCCgCgAAATTAATACgACTCAC3'

[SEQ NO. 7]
Reverse: 5'[Amine]gTTAAATTgCTAACgCAgTCAggAg3'
```

Primary amine reactive, NHS ester activated (N-hydroxysuccinimide), 4% cross-linked agarose beads (~100 micron diameter) were purchased from Amersham Biosciences (Amersham Biosciences Corp., Piscataway, N.J.). 100 µL it bead volume was spun down in a micro-centrifuge and the isopropanol storage buffer removed. The remaining procedures, unless otherwise noted, were performed in batch mode using 0.45 micron pore size, PVDF membrane, micro-centrifuge Filtration Devices to facilitate manipulation of the beaded matrix (~100 micron beads) and exchange the buffers (Ultrafree-MC Durapore Micro-centrifuge Filtration Devices, 400 µL capacity; Millipore, Billerica, Mass.). The 100 µL of beads were washed 3× briefly (briefly=5 sec vortex mix) with 400 µL each of ice cold 1 mM HCl prepared in nuclease-free water. The washed bead pellet was then resuspend in 200 µL containing 100 µg of each primer (forward and reverse) prepared in 200 mM sodium bicarbonate and 2M NaCl (all nuclease-free). As a negative control, a second set of beads received plain buffer only (without primers). The binding reaction was allowed to proceed for 1 hour at room temperature with gentle mixing. The beads were then washed 1× briefly (briefly=5 sec vortex mix) with 400 µL of 200 mM sodium bicarbonate, 200 mM glycine, 1 mM EDTA and 2M NaCl (all nuclease-free) and then the remaining reactive sites were quenched by adding 2×400 µL of the same buffer for 30 min each with gentle mixing. The beads were then washed 2× briefly (briefly=5 sec vortex mix) with 200 mM sodium bicarbonate and 2M NaCl (all nuclease-free) followed by 2×5 min each with 10 mM Tris, pH 8.0, 2M NaCl and 1 mM EDTA (all nuclease-free). Beads were lastly washed 1× briefly (briefly=5 sec vortex mix) with 50% glycerol, 5 mM Tris, pH 8.0, 2M NaCl and 0.5 mM EDTA (all nuclease-free) and then diluted to a 20% (v/v) bead suspension in the same buffer. This bead stock was stored in a 0.5 mL PCR tube at −20° C.

Qualitative Analysis of Primer Attachment:

To verify successful primer attachment to the beads, an aliquot of the beads was stained with the single-stranded DNA fluorescence-based detection reagent OliGreen (Invitrogen Corporation, Carlsbad, Calif.). This reagent is essentially non-fluorescent until bound to single-stranded DNA at which point it can be imaged using any standard fluorescein-type fluorescence detection system. The manufacturer supplied reagent was diluted 1/200 in 10 mM Tris, pH 8.0, 1 mM EDTA and 0.01% (v/v) Tween-20 (all nuclease-free). 20 µL of the prepared primer-conjugated bead stock (20% beads for 4 µL actual bead volume) was mixed with 100 µL of the diluted OliGreen reagent in a thin-walled 0.5 mL polypropylene clear PCR tube. As a negative control, beads that were prepared the same except lacked any attached primer were also tested. After approximately 1 min, the beads were spun down in a micro-centrifuge and imaged directly in the tubes using a FluorImager SI laser-based fluorescence scanner (488 nm argon laser excitation and 530 nm emissions filter) (Molecular Dynamics/Amersham Biosciences Corp., Piscataway, N.J.).

Preparation of the Template for Solid-Phase Bridge PCR:

The template DNA for the solid-phase bridge PCR reaction was a linear DNA construct corresponding to the human glutathione-s-transferase A2 gene (GST A2; open reading frame additionally containing epitope tag sequences and untranslated sequences needed for efficient cell-free expression). Using an initial solution-phase PCR reaction (same primers as above in this Example, listed again below), this linear DNA construct itself was created from GST A2 that was cloned into the cell-free expressible pETBlue-2 plasmid (EMD Biosciences, Inc., San Diego, Calif.) (see Example 1 for cloning). The solution-phase PCR was performed according to standard practices and using a commercially available kit according to the manufacturer's instructions (SuperTaq™ DNA Polymerase Kit; Ambion, Austin, Tex.). Prior to serving as the template for subsequent solid-phase bridge PCR, the solution-phase PCR amplicon (product) (i.e. the linear DNA construct) was first purified and concentrated on silica-based columns using a commercially available kit according to the manufacturer's instructions (QIAquick PCR Purification Kit; Qiagen, Valencia, Calif.).

```
Solution-Phase Primers:
                                              [SEQ NO. 8]
Forward: 5'CgTCCCgCgAAATTAATACgACTCAC3'

[SEQ NO. 9]
Reverse: 5'gTTAAATTgCTAACgCAgTCAggAg3'
```

Solid-Phase Bridge PCR with Primer-Conjugated Beads:

Solid-phase "Bridge" PCR was originally developed and patented by Adams and Kron [U.S. Pat. No. 5,641,658] and is used for multiplexed genetic analyses on various solid-surfaces including beads. The mechanism of solid-phase bridge PCR is reported by Adams and Kron [U.S. Pat. No. 5,641,658] as well as in the scientific literature [Tillib et al. (2001) *Anal Biochem* 292, 155-160; Shapero et al. (2001) *Genome Res* 11, 1926-1934; Mitterer et al. (2004) *J Clin Microbiol* 42, 1048-1057; Adessi et al. (2000) *Nucleic Acids Res* 28, E87]. In this Example, immobilized DNA produced by solid-phase bridge PCR is ultimately used as a template for cell-free protein expression.

In this Example, for solid-phase bridge PCR, 5 μL bead volume of the primer-conjugated agarose beads was washed 4×400 μL with nuclease-free water using the 0.45 micron pore size, PVDF membrane, micro-centrifuge Filtration Devices (Ultrafree-MC Durapore Micro-centrifuge Filtration Devices, 400 μL capacity; Millipore, Billerica, Mass.). As a negative control, 5 μL of beads which lack any bound primer (see earlier in this Example for beads) was washed in the same manner. 50 μL of prepared PCR reaction mixture was used to resuspend the washed bead pellets which were then transferred to PCR tubes for thermocycling. Solid-Phase bridge PCR was performed essentially using standard solution-phase PCR practices and a commercially available kit according to the manufacturer's instructions (SuperTaq™ DNA Polymerase Kit; Ambion, Austin, Tex.). However, no soluble primers were added at any step. The human GST A2 template DNA (see earlier in this Example) was used at 10 ng per 50 μL of PCR reaction. The following thermocycling steps were used for the solid-phase bridge PCR reaction: Initially 94° C. 2 min (once) and then 60 cycles of 94° C. 30 s, 60° C. 30 s and 72° C. 2 min, followed by a final 72° C. 10 min (once).

Expression from the Solid-Phase Bridge PCR Beads:

Following the solid-phase bridge PCR reactions, the 5 μL of beads from each PCR reaction sample was then washed 3× with 400 μL each of nuclease free water using the 0.45 micron pore size, PVDF membrane, micro-centrifuge Filtration Devices (Ultrafree-MC Durapore Micro-centrifuge Filtration Devices, 400 μL capacity; Millipore, Billerica, Mass.). Each washed bead pellet was resuspended in 40 μL of complete rabbit reticulocyte cell-free expression mixture and expressed as described in Example 1 with the following exceptions: For expression of solid-phase bridge PCR beads, no soluble DNA was included in the reaction. The reaction mixture containing the beads was gently shaken throughout the expression procedure. Control samples were also performed by expressing soluble plasmid DNA, without any solid-phase bridge PCR beads, as described in Example 1. In all cases, for fluorescent labeling of the nascent protein, only BODIPY-FL-tRNA$^{COMPLETE}$ was included in the reaction at 2 μM final and no other added misaminoacylated tRNAs were used. The crude expression reactions, with and without beads, were processed for and analyzed using standard denaturing SDS-PAGE followed by imaging of the fluorescent BODIPY labels using a FluorImager SI laser-based gel scanner (Molecular Dynamics/Amersham Biosciences Corp., Piscataway, N.J.).

Results:

The results are shown in FIGS. 27A and 27B. FIG. 27A shows the results of qualitative verification of PCR primer attachment to the activated agarose beads. The fluorescent OliGreen DNA detection reagent shows significant positive signal on the beads ("Bead Pellet") in the case where the beads were loaded with amine functionalized PCR primers ("Primer Beads") and negligible background signal from the beads where the PCR primers were omitted in the conjugation reaction ("Blank Beads"). Quantification of the signal shows a 100:1 signal to background (blank) ratio.

FIG. 27B shows fluorescence SDS-PAGE analysis of the cell-free expression of human glutathione-s-transferase A2 from the bead-bound full length DNA which was created by the solid-phase bridge PCR reaction (Lane 3 in the Figure; arrows indicate expressed and labeled nascent protein). As a negative control, beads lacking any bound primers for solid-phase bridge PCR produced no glutathione-s-transferase A2 in the cell-free expression reaction (Lane 4 in Figure). For comparison, positive controls corresponding to human p53 protein (Lane 1 in Figure) and human glutathione-s-transferase A2 (Lane 2 in Figure) that were cell-free expressed from soluble plasmid DNA, without any beads, using standard procedures as described in Example 1. Quantification of the fluorescent protein bands on the SDS-PAGE gel show that the bead-bound glutathione-s-transferase A2 DNA created by solid-phase bridge PCR expresses 2-fold less than the standard soluble plasmid glutathione-s-transferase A2 DNA.

Example 31

Multiplex Solid-Phase Bridge PCR Followed by Multiplex Cell-Free Expression with In Situ Protein Capture and Contact Photo-Transfer to Microarray Surfaces Preparation of Beads Covalently Conjugated to PCR Primers:

Conjugation of 5' amine modified PCR primers to agarose beads was performed as described in Example 30 with the following exceptions: 2 batches of beads were prepared containing 2 different sets of gene-specific PCR primers. The PCR primers also contained elements necessary for efficient cell-free expression (T7 promoter and Kozak sequence) as well as a C-terminal HSV epitope tag. Primers sets for human p53 and γ-actin genes were used and were as follows:

γ-Actin Forward:
[SEQ NO. 10]
5'[Amine]ggATCCTAATACgACTCACTATAgggAgCCACCATggAAgA
AgAgATCgCCgCgCTggTCATTgAC3'

γ-Actin Reverse:
[SEQ NO. 11]
5'[Amine]TTAATCCTCTgggTCTTCAggAgCgAgTTCTggCTggCTgA
AgCATTTgCggTggACgATggAggggCC3' p53 Forward:
[SEQ NO. 12]
5'[Amine]ggATCCTAATACgACTCACTATAgggAgACCACCATggAgg
AgCCgCAgTCAgATCCT3' p53 Reverse:
[SEQ NO. 13]
5'[Amine]TTTTAATCCTCTgggTCTTCAggAgCgAgTTCTggCTggCT
gTCTgAgTCAggCCCTTCTgTC3'

Additionally, during the conjugation of primers to the agarose beads, a biotin-amine linker (EZ-Link Amine-PEO3-Biotin; Pierce Biotechnology, Inc., Rockford, Ill.) was incorporated into the reaction mixture along with the primers. This was achieved by diluting a 20 mg/mL biotin-amine linker stock (prepared in nuclease-free water) 1/100 in nuclease-free water and adding 5 μL to the primer reaction mixture described in Example 30 (biotin-amine linker added prior to adding primer reaction mixture to beads). This level of biotin-amine linker constituted 10-fold less moles relative to the total primer amount. 100-fold less moles of biotin-amine linker can also be used with success.

Qualitative Analysis of Primer Attachment:
Performed as in Example 30.

Solid-Phase Bridge PCR with Primer-Conjugated Beads:
Performed essentially as in Example 30 with the following exceptions: For solid-phase bridge PCR, 2.5 μL bead volume of each bead-bound primer set (p53 and γ-actin; 5 μL bead volume total) was washed 3×400 μL with nuclease-free water, the two different bead species (p53 and γ-actin) were combined and the pellet resuspended in 50 μL of prepared PCR reaction mixture. A single multiplexed solid-phase bridge PCR reaction was performed on the pooled bead species using standard PCR reagents (SuperTaq™ DNA Polymerase Kit; Ambion, Austin, Tex.) and a HeLa cell cDNA library as template. The cDNA template was prepared by extracting total RNA from cultured HeLa cells using a commercially available kit according to the manufacturer's instructions (RNeasy Maxi; Qiagen, Valencia, Calif.). mRNA was then isolated from the total RNA using a commercial kit according to the manufacturer's instructions (Oligotex; Qiagen, Valencia, Calif.). mRNA was then converted to cDNA using standard RT-PCR practices (e.g. using Omniscript RT-PCR kit; Qiagen, Valencia, Calif.). Alternatively, the total RNA can be converted directly to cDNA via RT-PCR instead of using purified mRNA. For solid-phase bridge PCR with the HeLa cell cDNA template, thermocycling was as follows: Initially 94° C. 2 min and then 60 cycles of 94° C. 30 s, 60° C. 30 s and 72° C. 2 min, followed by a final 72° C. 10 min.

Attaching the PC-Antibody to Beads Following Solid-Phase Bridge PCR:
Following the solid-phase bridge PCR reaction, beads were washed briefly 3× with nuclease-free water and 1× with TE-Saline (10 mM Tris-HCl, pH 8.0, 1 mM EDTA, 200 mM NaCl), all at 400 μL (all nuclease-free reagents). Unless otherwise noted, all washes and bead manipulations were performed in batch mode using 0.45 micron pore size, PVDF membrane, micro-centrifuge Filtration Devices to facilitate manipulation of the beaded matrix (~100 micron beads) and exchange the buffers (Ultrafree-MC Durapore Micro-centrifuge Filtration Devices, 400 μL capacity; Millipore, Billerica, Mass.). NeutrAvidin (tetrameric) was then attached to the bead bound biotin-amine linker (see earlier in this Example), in excess, by treatment with 200 μL of a 0.5 μg/μL solution in TE-Saline for 30 min. Beads were washed briefly 4×400 μL with TE-Saline.

The beads were next coated with a polyclonal rabbit anti-HSV tag capture antibody (Bethyl Laboratories, Montgomery, Tex.) which was converted to photocleavable form by conjugation to PC-biotin. Creation of the photocleavable antibody (PC-antibody) was performed similar to as described in Example 2. To first create the PC-antibody (prepared in advance), 400 μg of antibody as supplied by the manufacturer at 1 μg/μL was purified on a NAP-5 desalting column according to the manufacturer's instructions (Amersham Biosciences Corp., Piscataway, N.J.) against a 200 mM sodium bicarbonate and 200 mM NaCl buffer (nuclease-free reagents). The resultant antibody was then reacted with 20 molar equivalents of AmberGen's PC-biotin-NHS labeling reagent (added from a 50 mM stock in anhydrous DMF) (15 to 25 molar equivalents can also be used) for 30-60 min with gentle mixing. The labeled antibody was then purified on a NAP-10 desalting column according to the manufacturer's instructions (Amersham Biosciences Corp., Piscataway, N.J.) against TE-Saline buffer. This prepared polyclonal anti-HSV PC-biotin conjugate was then loaded onto the beads by treatment of the beads with 150 μL of 0.15 μg/μL in TE-Saline for 30 min. Beads were washed briefly 4× and 1×30 min (30° C.) in 400 μL TE-Saline followed by 2× brief washes in nuclease-free water.

Multiplexed Cell-Free Expression of the Beads and In Situ Protein Capture:
The 5 μL bead pellet was then resuspended in 50-100 μL of complete rabbit reticulocyte cell-free expression mixture and expressed essentially as described in Example 1 with the following exceptions: No soluble DNA was included in the reaction and tRNA mediated labeling was with 2 μM BODIPY-FL-tRNA$^{COMPLETE}$ only (i.e. no tRNA mediated PC-biotin labeling). To disperse the beads and limit diffusion during in situ capture, the expression mixture was spread over the surface of a plain glass microscope slide and overlaid with a cover glass (see Examples 25 and 26 for mechanism and details of in situ capture). As detailed earlier, in situ capture was mediated by a common C-terminal HSV epitope tag in all expressed proteins and the anti-HSV PC-antibody on the beads. Expression was carried out in a humidified chamber. After expression, the microscope slide (and cover glass) "sandwich" was placed in a 50 mL polypropylene centrifuge tube and sprayed at the seam with 300 μL of TDB supplemented with 1% BSA (w/v) as the protein carrier and 10 μg of the soluble unlabeled monoclonal anti-HSV antibody. The beads and fluid were then recovered by brief spinning in a clinical centrifuge. Beads were then immediately washed 2× briefly and 2×5 min each with 400 μL of ice cold 5 mM DTT in PBS per wash. The beads were then washed 1× briefly in 400 μL of 40% glycerol, 5 mM DTT in PBS. All washes were performed using the aforementioned micro-centrifuge Filtration Devices. The washed bead pellets were then resuspended to 1% beads (v/v) in 40% glycerol, 5 mM DTT in PBS.

Contact Photo-Transfer from Individually Resolved Beads:

Contact photo-transfer from individually resolved beads onto epoxy activated glass microarray substrates (slides) (SuperEpoxy substrates, TeleChem International, Inc. ArrayIt™ Division, Sunnyvale, Calif.) overlaid with a cover glass was performed as described in Example 24; except that after contact photo-transfer, washing and drying of the microarray slides, the slides were further processed for antibody probing as described in the following paragraphs.

Preparation of an Anti-p53 Cy5 Fluorescent Antibody:

Performed as described in Example 26.

Probing the Microarray with Anti-p53-Cy5 Antibody:

Performed as described in Example 26. Alternatively, a modification to the procedure can be used where the antibody probe is used at a 1/100 dilution. In this case, probing is achieved by applying 100 μL of diluted antibody probe to the microarray slide and overlaying with a 22×60 mm microscope cover glass (binding is then performed in a humidified chamber).

Detection of Photo-Transferred Protein:

Performed as described in Example 26.

Results:

Fluorescence images of the same region of the same microarray slide are shown in FIG. 28. The green fluorescence channel shows the direct tRNA mediated BODIPY-FL labeling, allowing detection of the roughly 100 micron diameter protein spots formed by contact photo-transfer, regardless of whether they are p53 or γ-actin. The red fluorescence channel shows selective detection of the protein spots with the anti-p53-Cy5 antibody, in order to distinguish the p53 spots (red and green fluorescence signal) from the γ-actin spots (only green fluorescence signal). Spots identified as p53 are marked by arrows in FIG. 28 in both the green and red fluorescence channels. Spots identified as γ-actin (unmarked; green signal only) show virtually no detectible red fluorescence signal (p53 antibody), thus demonstrating no cross-contamination. These data clearly demonstrate that the p53 and γ-actin solid-phase bridge PCR amplicons (DNA) are indeed sorted (pure) on their respective (parent) primer-coated beads and hence, by way of in situ protein capture, the expressed proteins are also sorted on their parent beads. The entire process is shown to be compatible with contact photo-transfer fabrication of protein microarrays.

Example 32

Solid-Phase Bridge PCR on 7 Micron Diameter Non-Porous Plastic Beads: On-Bead DNA Detection Primer Attachment to 7 Micron Diameter Non-Porous Plastic Beads 0.5 mL of nuclease-free BSA (100 mg/mL; Invitrogen Corporation, Carlsbad, Calif.) was desalted on a NAP-5 column according to the manufacturer's instructions (Amersham Biosciences Corp., Piscataway, N.J.) versus Conjugation Buffer (200 mM sodium bicarbonate and 200 mM NaCl). The recovered BSA solution was 1 mL at 50 mg/mL. 8 mg of EZ-Link Sulfo-NHS-LC-LC-Biotin powder (Pierce Biotechnology, Inc., Rockford, Ill.) was then dissolved in 239 μL of nuclease-free water and immediately after dissolving, 73 μL was added to the 1 mL of 50 mg/mL BSA. The reaction was carried out for 30 min at room temperature with gentle mixing. The biotinylated BSA was then desalted on NAP-5 columns according to the manufacturer's instructions (Amersham Biosciences Corp., Piscataway, N.J.) versus MES Buffer (0.1 M MES, pH 4.7, 0.9% NaCl; Pierce Biotechnology, Inc., Rockford, Ill.). The biotinylated BSA was then diluted to 3.5 mg/mL in MES Buffer.

The biotinylated BSA solution was then used to coat commercially available 7.16 micron diameter non-porous amine-derivatized polymer (plastic) beads [catalog number PA06N; polymer=poly(MMA\GlycidylMethAcrylate\EDMA)+ EDA; Bangs Laboratories, Inc. Fishers, Ind.]. To wash and manipulate the beads or exchange the buffers, 0.45 micron pore size, PVDF membrane, micro-centrifuge Filtration Devices were used unless otherwise noted (Ultrafree-MC Durapore Micro-centrifuge Filtration Devices, 400 μL capacity; Millipore, Billerica, Mass.). A total 228 mg of beads (divided into 4 equal aliquots) was washed 4×400 μL (each aliquot) with MES Buffer (unless otherwise noted, all washes are brief, 1-3 sec, by vortex mixing). The washed beads were then pooled in a single 1.5 mL micro-centrifuge tube (all supernatant then removed) and the bead pellet (228 mg beads and about 200 μL bead volume) was then pre-chilled on an ice water bath. 10 mg of EDC (1-Ethyl-3-[3-dimethylaminopropyl]carbodiimide hydrochloride powder; Pierce Biotechnology, Inc., Rockford, Ill.) was then dissolved in 0.5 mL of ice-cold nuclease-free water. Immediately after dissolving, 100 μL of the EDC solution was added to the chilled bead pellet. 1 mL of room temperature biotinylated BSA solution (3.5 mg/mL in MES Buffer) was then immediately added to the bead-EDC mixture. The reaction was carried out for 1 hr at room temperature with gentle mixing. Note that subsequent washing of the beads in the 1.5 mL tube involved 1-3 sec vortex mixing, followed by pelleting the beads by micro-centrifugation at maximum speed (13,000 rpm) and discarding the supernatant. All buffers were nuclease-free. After the reaction, the beads were washed in the same 1.5 mL tube at 2×1 mL using Quenching Buffer (200 mM glycine, 1 mM EDTA, 200 mM sodium bicarbonate and 2M NaCl). The beads were then treated for 30 min at room temperature with a fresh 1 mL of Quenching Buffer. Again in the same tube, the beads were washed 2×1 mL with TE-NaCl-Glycine Buffer (10 mM Tris-HCl, pH 8.0, 1 mM EDTA, 2M NaCl, 0.1M glycine). After re-suspension in the second wash, the beads were then pooled in one of the aforementioned Filtration Devices (using filtration to concentrate and pool beads). In the Filtration Device, beads were further washed 4×400 μL with TE-Saline-Tween Buffer (10 mM Tris-HCl, pH 8.0, 1 mM EDTA, 200 mM NaCl, 0.1% Tween-20) and then 2×400 μL with TE-Glycerol-Tween Buffer (50% glycerol, 5 mM Tris-HCl, pH 8.0, 0.5 mM EDTA, 0.1% Tween-20). These biotin-BSA coated beads were then resuspend to 20% (v/v) beads (roughly 200 mg/mL beads) with TE-Glycerol-Tween Buffer and could be stored at −20° C.

These biotin-BSA coated plastic beads were then conjugated to the 5' amine modified solid-phase bridge PCR primers. The primers were the same as described in Example 30. The Working Primer Mix was prepared as follows: A mixture of 100 μg of each amine modified primer (forward and reverse; 200 μg total primer) was freshly prepared in MES Buffer. To do so, 10 μL each of 10 μg/μL primer stocks (forward and reverse primer stocks; stocks prepared in nuclease-free water and stored at −20° C.) was mixed with 180 μL of MES Buffer, thus yielding 1 μg/μL total primer concentration with 200 μg total primer in 90% MES Buffer (200 μL final volume).

Again using the aforementioned Filtration Devices, 25 μL of biotin-BSA coated plastic bead volume was washed 4×400 μL with MES Buffer (unless otherwise noted, all washes are brief, 1-3 sec, by vortex mixing). Directly in the Filtration Devices, to each bead pellet, 200 μL of the previously prepared Working Primer Mix was added. 10 mg of EDC was then immediately dissolved in 200 µL of ice cold nuclease-free water (50 mg/mL EDC stock). Immediately after dissolving the EDC, 86 µL of EDC solution was added to the primer-bead mix in the Filtration Device. The reaction was carried out for 1 hr at room temperature in the upper chamber of the Filtration Device (without yet performing filtration) with mixing. In the Filtration Device, the beads were washed 1×400 µL with TE-NaCl-Glycine Buffer and quenched by treatment for 30 min with mixing in a fresh 400 µL of the same buffer. Beads were then washed 2×400 µL with TE-NaCl (10 mM Tris-HCl, pH 8.0, 1 mM EDTA, 2M NaCl), then 2×400 µL TE-Saline-Tween and lastly 1×400 µL with TE-Glycerol-Tween Buffer. Beads were then resuspended to 20% (v/v) beads in TE-Glycerol-Tween Buffer and could be stored at −20° C.

Solid-Phase Bridge PCR on 7 Micron Diameter Non-Porous Plastic Beads

The prepared 7 micron diameter, biotin-BSA-primer coated beads were then used for solid-phase bridge PCR as described in Example 30 with the following exceptions: 2.5 µL bead volume was used in a 50 µL PCR reaction. Fluorescence BODIPY-FL-dUTP labeling of the solid-phase bridge PCR amplicon was performed by including the reagent (ChromaTide® BODIPY® FL-14-dUTP; Invitrogen Corporation, Carlsbad, Calif.) in the solid-phase bridge PCR reaction (20 µM final concentration added from the manufacturer's stock of 1 mM).

Fluorescence Imaging of Individual 7 Micron Diameter Non-Porous Plastic Beads:

The BODIPY-FL-dUTP labeling of the solid-phase bridge PCR amplicon on the beads was imaged, at the individual bead level, by embedding the beads in a thin polyacrylamide film on top of a microscope slide. Prior to embedding the beads, they were washed following the solid-phase bridge PCR reaction 3×400 µL with TE-Saline-Tween (10 mM Tris-HCl, pH 8.0, 1 mM EDTA, 0.1% v/v Tween-20 and 200 mM NaCl; nuclease-free). The acrylamide mix was prepared by mixing 487 µL TE (10 mM Tris-HCl, pH 8.0, 1 mM EDTA; nuclease-free), 113 µL of a 40% acrylamide and bis-acrylamide mixture (19:1 ratio; Bio-Rad Laboratories, Hercules, Calif.), 1 µL of 100% TEMED (Bio-Rad Laboratories, Hercules, Calif.) and 6 µL of a 10% (w/v) ammonium persulfate solution (prepared in water). This acrylamide mix was used to resuspend the washed bead pellet to form 1% (v/v) beads. Approximately 10-20 µL of the bead suspension was placed on a standard glass microscope slide, overlaid with an 18 mm round microscope cover glass and allowed to polymerize for approximately 10 min. The microscope slides were fluorescently imaged as for other microarrays, such as described in Example 26.

Results:

Results shown in FIG. 29 clearly show detection of the BODIPY-FL-dUTP labeled solid-phase bridge PCR amplicon only when the necessary DNA polymerase was included in the solid-phase bridge PCR reaction (Plus DNA Polymerase). A separate solid-phase bridge PCR reaction, lacking only the necessary DNA polymerase (Minus DNA Polymerase), was performed to provide the background levels related to bead auto-fluorescence and the BODIPY-FL-dUTP labeling reagent. A minus template negative control solid-phase bridge PCR reaction could also be used to assess background levels, with similar results. Upon quantification of the fluorescence signal from several beads, the signal-to-noise ratio was determined to be approximately 10:1.

Example 33

Solid-Phase Bridge PCR on 7 Micron Diameter Non-Porous Plastic Beads: Cell-Free Protein Expression, In Situ Protein Capture and Bead Selection with Magnetic Particles Preparing Anti-[Mouse IgG] Species Specific Secondary Antibody Coated 1 Micron Diameter Magnetic Particles Secondary antibody coated 1 micron diameter magnetic particles were first prepared, in order to be used for isolation of 7 micron diameter plastic beads carrying primary antibody targeted cell-free expressed proteins. For this, amine-reactive p-toluensulphonyl chloride activated, 1 micron diameter, magnetic particles (beads) were purchased commercially and coated with secondary antibody essentially according to the magnetic particle manufacturer's instructions (Dynabeads® MyOne™ Tosylactivated; Dynal Biotech LLC, Brown Deer, Wis.). The antibody was a commercially available donkey anti-[mouse IgG] species-specific secondary antibody (Chemicon International, Inc., Temecula, Calif.; catalog number AP192). First, the antibody, as supplied by the manufacturer (0.5 mL at 2 mg/mL), was desalted on a NAP-5 column versus borate buffer (0.1M sodium tetraborate decahydrate, pH 9.5) according to the column manufacturer's instructions (Amersham Biosciences Corp., Piscataway, N.J.). The resultant antibody solution (0.54 µg/µL) was used for coating the magnetic particles. 12 mg of magnetic particles was pre-washed 2×1 mL with borate buffer. All washes were performed in either 1.5 mL or 0.5 mL polypropylene micro-centrifuge tubes using a commercially available magnet (MPC-S magnet system; Dynal Biotech LLC, Brown Deer, Wis.) to draw the particles to the side-wall of the tube followed by removal of the fluid supernatant. The magnetic particles were then resuspended to 100 µL total volume with borate buffer and mixed with 850 µL of the aforementioned prepared antibody solution (~460 µg antibody). 475 µL of a 3M ammonium sulfate stock solution was then added. Coating of the magnetic particles was carried out for 24 hours at 37° C. with gentle mixing on a tilt rocker/shaker. After coating, the magnet was applied and the unbound antibody solution removed. Magnetic particles were then washed 2×1 mL for 10 min each at 37° C. with gentle mixing using TE-NaCl buffer (10 mM Tris-HCl, pH 8.0, 1 mM EDTA, 2M NaCl) supplemented with 0.1M glycine. Magnetic particles were then rinsed 2× briefly with 1 mL using TE-Saline buffer (10 mM Tris-HCl, pH 8.0, 1 mM EDTA, 200 nM NaCl) supplemented with 0.5% (w/v) BSA and 0.05% (v/v) Tween-20. Magnetic particles were then blocked overnight in 1 mL of the same buffer at 37° C. with gentle mixing on a tilt rocker/shaker. After blocking, magnetic particles were then rinsed 3× briefly in 1 mL using TE-Saline buffer supplemented with 0.01% Tween-20. Lastly, after removing all of the final wash buffer, magnetic particles were resuspended to 120 µL final volume (100 µg/µL; ~20% v/v bead suspension) in 5 mM Tris-HCl, pH 8.0, 0.5 mM EDTA, 200 mM NaCl, 0.01% (v/v) Tween-20 in 50% glycerol for storage at −20° C.

Primer Coating of Beads and Solid-Phase Bridge PCR

Primer attachment to 7 micron diameter non-porous plastic beads was performed as described in Example 32 (see Example 30 for actual primer sequences). Solid-phase bridge PCR with these beads was also performed as described in Example 32 except that BODIPY-FL-dUTP labeling was not performed and 2 separate solid-phase bridge PCR reactions were performed using the plasmid derived template described, containing either human p53 or GST gene inserts.

Attaching the Capture Antibody and Labeling of the Beads

Following the solid-phase bridge PCR reaction, NeutrAvidin was attached to the biotin on the beads followed by attachment of the anti-HSV tag PC-antibody as described in Example 31, except that 2.5 µL bead volume was used per sample and 0.01% Tween-20 (nuclease-free) was included in all buffers (including the NeutrAvidin and PC-antibody solutions) to avoid bead aggregation. Note that the 2 bead species (p53 and GST DNA) were kept separate during these procedures. After loading the anti-HSV tag PC-antibody, the 2 beads species (p53 and GST DNA) were labeled with different fluorophores to enable down stream identification. To wash and manipulate the beads or exchange the buffers, 0.45 micron pore size, PVDF membrane, micro-centrifuge Filtration Devices were used unless otherwise noted (Ultrafree-MC Durapore Micro-centrifuge Filtration Devices, 400 µL capacity; Millipore, Billerica, Mass.). 1 µL packed bead volume of each bead species was washed 3×400 µL briefly with 200 mM sodium bicarbonate, 200 mM NaCl and 0.001% (v/v) Tween-20. Beads were recovered from the aforementioned Filtration Devices in 100 µL of the same buffer, transferred to 0.5 mL micro-centrifuge tubes, spun down briefly in a micro-centrifuge at 13,000 rpm and the fluid supernatant removed. Beads were then resuspended in 10 µL of the same buffer. Fluorescence labeling reagents, either a 25 mM Cy5-NHS monoreactive ester (Amersham Biosciences Corp., Piscataway, N.J.) stock in DMSO or a 12.5 mM Alexa Fluor® 488 5-TFP (Invitrogen Corporation, Carlsbad, Calif.) stock in DMF, were freshly diluted to 250 µM in purified water and 1.6 µL of that was immediately added to the bead suspension. p53 DNA beads were labeled with Cy5 and GST beads with Alexa Fluor® 488. Reactions were carried out for 15 min with mixing and protected from light. After the labeling reaction, each bead suspension was mixed with 400 µL of 200 mM sodium bicarbonate, 2 M NaCl, 0.2M glycine, 1 mM EDTA and 0.001% (v/v) Tween-20 to quench the reaction. The beads were then washed 1×400 µL briefly with the same buffer followed by 2×400 µL briefly with TE-Saline buffer (10 mM Tris-HCl, pH 8.0, 1 mM EDTA, 200 mM NaCl) supplemented with 0.001% Tween-20.

Cell-Free Protein Expression of the Beads

Cell-free protein expression of the beads was then performed as described in Example 30 with the following exceptions: Beads were only pre-washed 1× briefly with 400 µL nuclease-free water prior to expression. 1 µL bead volume was used in a 50 µL cell-free expression reaction. No tRNA mediated labeling was performed, neither with BODIPY-FL nor PC-biotin or otherwise. The reaction was performed for 1 hour with shaking. Since the capture PC-antibody directed against the common HSV epitope tag in all expressed proteins is attached to the beads (see earlier in this Example), in situ protein capture does occur in this case (however, p53 and GST protein expression was performed in separate tubes).

Probing Expressed Beads with an Anti-p53-Cy5 Antibody and Isolation with Magnetic Particles Following expression of the solid-phase bridge PCR beads and in situ protein capture, GST and p53 beads (1 µL bead volume each) were separately washed 1×400 µL with TBS-T follow by 2×400 µL with 5% BSA (w/v) in TBS-T. To wash and manipulate the beads or exchange the buffers, 0.45 micron pore size, PVDF membrane, micro-centrifuge Filtration Devices were used unless otherwise noted (Ultrafree-MC Durapore Micro-centrifuge Filtration Devices, 400 µL capacity; Millipore, Billerica, Mass.). Unless otherwise noted, all washes are brief, 1-3 sec, by vortex mixing. The p53 and GST beads were then suspended to 500 µL total volume with 5% BSA (w/v) in TBS-T. 250 µL of the GST bead suspension was mixed with 2.5 µL of the p53 bead suspension to form a mixture of approximately 1% p53 beads and 99% GST beads.

The fluid was removed from the p53-GST bead mixture using the aforementioned Filtration Devices and the beads probed with a mouse monoclonal anti-p53-Cy5 fluorescence labeled antibody. The antibody was that previously described in Examples 26 and 31 except that the antibody stock was additionally clarified for 1 min in a micro-centrifuge at 13,000 rpm to remove particulate prior to use. The clarified antibody stock was then diluted ½₀ with 5% BSA (w/v) in TBS-T and the diluted antibody again clarified for 1 min in a micro-centrifuge followed by passing the supernatant through the aforementioned Filtration Devices. The filtrate, corresponding to the diluted and clarified antibody, was then used to probe the bead mixture. 100 µL was used to probe the bead mixture for 30 min at room temperature with gentle mixing. The bead mixture was washed 3×400 µL briefly with TBS-T, then resuspended with 100 µL of 5% BSA (w/v) in TBS-T and transferred out of the Filtration Device into a 0.5 mL micro-centrifuge tube.

50 µL of the resultant bead suspension was used for imaging of the un-separated beads and the remaining 50 µL was set aside for magnetic particle isolation (see later in this Example). For imaging the un-separated beads, the beads were spun down briefly in a micro-centrifuge at 13,000 rpm and the supernatant completely removed. The bead pellet was resuspended in 5 µL of acrylamide mix and the entire population was embedded in a thin polyacrylamide film on top of a glass microscope slide under an 18 mm round cover glass, as described in Examples 32 and 34. The embedded beads were fluorescently imaged (see later in this Example).

The remaining 50 µL of un-separated bead mixture (i.e. that which was not embedded) was then used to test selective purification of the bead population bearing the p53 protein and hence the bound mouse anti-p53-Cy5 antibody. This was achieved using 1 micron magnetic particles that were coated with an anti-[mouse IgG] species specific secondary antibody; which selectively bind the mouse anti-p53-Cy5 antibody but not the rabbit anti-HSV PC-antibody also on the beads. First, 1 µL (100 µg) of the secondary antibody coated magnetic particles (prepared as described earlier in this Example) was pre-washed 1×400 µL briefly with 5% BSA (w/v) in TBS-T. All washes involving the magnetic particles were performed in 0.5 mL polypropylene micro-centrifuge tubes and using the magnet system described earlier in this Example, unless otherwise noted. After removing the wash solution, the pellet corresponding to the magnetic particles was gently resuspended with the 50 µL of un-separated p53-GST plastic bead mixture. To allow the magnetic particles to bind the targeted p53 beads, the mixture was allowed to stand for 30 min with gentle intermittent mixing (~every 5 min). Mixing was performed by manually pipetting the suspension up-and-down. The magnetic particles and any beads bound to them were washed 3×400 µL briefly with TBS-T. Washes were performed by gently resuspending the bead and magnetic particle mixture by manually pipetting up-and-down, applying the aforementioned magnet for ~15 sec to draw the magnetic particles and any bound beads to the side-wall of the tube, and then gently removing the fluid containing the suspended 7 micron diameter plastic beads that were not bound to magnetic particles (while magnetic particles remain adherent to the side-walls of the tube). After washing, the magnetic particles and bound beads were spun down briefly in a micro-centrifuge and the supernatant completely removed. The bead pellet was resuspended in 5 µL of acrylamide mix and the entire population was embedded in a thin polyacrylamide film for imaging as described earlier in this Example for the un-separated beads.

Un-separated and purified beads, embedded in a polyacrylamide film, were imaged for fluorescence using the Array-WoRx$^e$ BioChip fluorescence reader (Applied Precision, LLC, Issaquah, Wash.).

Results:

Representative regions of the fluorescence bead images (embedded beads) are shown in FIG. 30. The un-separated 1% p53 and 99% GST bead mix (left panels FIG. 30) and the purified p53 beads (right panels FIG. 30) were imaged in both the green and red fluorescence channels, corresponding to GST beads (labeled with Alexa Fluor® 488) and p53 beads (labeled with Cy5), respectively (upper and lower panels of FIG. 30 respectively). The green fluorescence channel for the un-separated beads is shown in the upper left panel of FIG. 30, corresponding to GST beads. The same region was also imaged in the red fluorescence channel (lower left panel FIG. 30), corresponding to the p53 beads. Although representative regions are shown in FIG. 30, the entire bead populations were enumerated (142,127 total un-separated beads and 1,193 total beads following purification), and the actual measured percentage of p53 beads in the un-separated mixture was indeed 1%. The contaminating green beads (GST) following purification with the magnetic particles are shown in the upper right panel of FIG. 30, while imaging of the same region in the red fluorescence channel (lower right panel FIG. 30) shows the purified red beads (p53). Enumeration of the entire bead population in the purified sample shows that the targeted red beads (p53) are 52.7% pure, thus corresponding to a more than 50-fold enrichment factor and removal of 99.6% of the contaminating green beads (GST) using the magnetic particle purification technique. The yield of targeted red (p53) beads was 42.4% of the starting number of un-separated red (p53) beads.

Example 34

Contact Photo-Transfer of Peptides onto Solid Surfaces used for Downstream MALDI-TOF Mass Spectrometry Analysis Preparation of the Anti-Flag PC-Antibody Affinity Resin A mouse monoclonal anti-FLAG tag antibody clone M2 was purchased commercially (Sigma-Aldrich, St. Louis, Mo.). 242 µL of the antibody solution as provided by the manufacturer (4.9 µg/µL) was desalted on a NAP-10 column according to the manufacturer's instructions (Amersham Biosciences Corp., Piscataway, N.J.) against a 200 mM sodium bicarbonate and 200 mM NaCl buffer. The antibody was then labeled by adding an Alexa Fluor® 488 5-TFP labeling reagent (Invitrogen Corporation, Carlsbad, Calif.) at a 2-fold molar excess from a 12.5 mM stock in DMF. The reaction was carried out for 30 min with gentle mixing. Next, a 20-fold molar excess (relative to antibody) of AmberGen's PC-biotin-NHS labeling reagent was added to the reaction from a 50 mM stock in DMF. The reaction was carried out for an additional 30 min with gentle mixing. 1 mL of the Alexa Fluor® 488 and PC-biotin dual labeled PC-antibody was then separated from the un-reacted labeling reagent using a NAP-10 column according to the manufacturer's instructions (Amersham Biosciences Corp., Piscataway, N.J.) against TBS. The resultant PC-antibody solution (0.42 µg/µL) was supplemented to 0.1% (w/v) with BSA from a 10% stock in water. 750 µL (~300 µg) of this solution was then added to 300 µL packed bead volume of NeutrAvidin agarose beads (Pierce Biotechnology, Inc., Rockford, Ill.) which were pre-washed 4× 1 mL briefly with 0.1% (w/v) BSA in TBS. PC-antibody capture was carried out for 30 min with gentle mixing. The beads were then washed 4× 5 mM each with 1 mL of 0.1% (w/v) BSA in TBS. Beads were then washed 3× 1 mL briefly with TBS followed by 2× 1 mL briefly with 50% TBS, 50% glycerol and 1.5 mM sodium azide and the beads resuspended to a 30% (v/v) suspension in the same buffer for storage at −20° C. Based on measurements of the fluorescence Alexa Fluor® 488 label on the PC-antibody, 82% of the PC-antibody was captured on the beads for 0.8 µg of PC-antibody per 1 µL of packed beads.

Cell-Free Expression of BR CA Peptides and Affinity Capture

Isolation of genomic DNA from cultured cells (HeLa cells; ATCC; Manassas, Va.) and PCR amplification of fragments of the human BRCA2 gene was performed essentially as reported by AmberGen in the scientific literature for the human APC gene [Gite et al. (2003) Nat Biotechnol 21, 194-197], except that an N-terminal FLAG epitope tag (amino acid sequence DYKDDDDK [SEQ NO. 14]) was the only epitope tag incorporated into the expressed sequences. Epitope tags and elements necessary for efficient cell-free expression were introduced into the PCR amplicon by way of specialized primers [Gite et al. (2003) Nat Biotechnol 21, 194-197]. PCR primers for 2 gene fragments, designated CT64 and CT61, of the BRCA2 gene, were as follows:

```
Forward CT64:
                                              [SEQ NO. 15]
5'TAATACgACTCACTATAgggAgAggAggTATATCAATggATTATAAAg
ACgATgATgATAAAAgTACAgCAAgTggAAAgCAA3'

Reverse CT64:
                                              [SEQ NO. 16]
5'TTATTTATTTATTTTTgATACATTTTgTCTAgA3'

Forward CT61:
                                              [SEQ NO. 17]
5'TAATACgACTCACTATAgggAgAggAggTATATCAATggATTATAAAg
ACgATgATgATAAACTTCATAAgTCAgTCTCATCT3'

Reverse CT61:
                                              [SEQ NO. 18]
5'TTATTTATTTATTTCTATTTCAgAAAACACTTg3'
```

Cell-Free protein expression of the crude PCR amplicon was performed in the *E. coli* based PureSystem (Post Genome Institute Co., LTD., Japan) according to the manufacturer's instructions (40 µL expression per sample reacted for 1 hour at 42° C.). A negative control expression reaction (-DNA), lacking only the necessary expressible PCR DNA was also performed. Following cell-free expression, reactions were mixed with equal volume of 2× concentrated PBS with 0.2% (v/v) Triton X-100. Samples were mixed gently for 5 min at +4° C. Samples were clarified at 13,000 rpm in a microcentrifuge for 1 min and the supernatant collected.

To capture the cell-free expressed FLAG epitope tagged peptides from the crude reaction, 5 µL packed bead volume of the aforementioned prepared anti-FLAG PC-antibody beads was pre-washed 2×400 µL briefly with 0.1% (v/v) Triton X-100 in PBS. The aforementioned processed expression samples were then added to the washed bead pellets and mixed for 30 min at +4° C. to allow peptide capture on the beads. Beads were then washed 2×400 µL briefly with PBS then 1×400 µL briefly with 50% glycerol in PBS. For subsequent use in contact photo-transfer, beads were then adjusted to a 50% (v/v) suspension (slurry) in the 50% glycerol and PBS buffer.

Contact Photo-Transfer of Captured BRCA Peptides and Mass Spectrometry

To demonstrate the compatibility of contact photo-transfer with matrix-assisted laser desorption/ionization time of flight (MALDI-TOF) mass spectrometry, a 0.5 µL droplet (~2 mm diameter) of the aforementioned 50% (v/v) bead slurry was applied to the surface of an epoxy activated glass microarray slide (SuperEpoxy substrates, TeleChem International, Inc. ArrayIt™ Division, Sunnyvale, Calif.). Droplets were applied in defined areas outlined with black magic marker to allow later identification. To photo-transfer the antibody and any bound peptide from the beads to the microarray slide (contact photo-transfer), the slide was illuminated from above with near-UV light for 5 min (365 nm peak lamp; Blak-Ray Lamp XX-15, UVP, Upland, Calif.; used at 1 to 3 mW/cm$^2$). After allowing binding of the photo-released material to the epoxy activated slide by incubating for 30 min at 37° C. in a humidified chamber, beads were gently washed away by rinsing 2× briefly in excess 0.1M glycine in TBS followed by 2× briefly in purified water, in a tray with shaking. Bead removal was verified by visible microscopy. Microarray slides were dried by centrifugation in a padded tube and, prior to MALDI-TOF, the slide was imaged for fluorescence in the ArrayWoRx$^e$ BioChip reader (Applied Precision, LLC, Issaquah, Wash.). For MALDI-TOF, a saturated matrix solution was prepared by dissolving 25 mg of α-cyano-4-hydroxycinnamic acid in 1250 µL of 50% (v/v) acetonitrile and 0.3% (v/v) trifluoroacetic acid. The solution was mixed vigorously for 10 min and clarified at 13,000 rpm in a micro-centrifuge. The supernatant was collected and used as the matrix solution. The spots were then overlaid with 0.2 µL of matrix solution which was then allowed to crystallize. Next, the microarray slide was cut and mounted onto a custom designed frame for insertion into the MALDI-TOF instrument (Voyager-DE; Applied Biosystems; Foster City, Calif.). Importantly, MALDI-TOF from glass slides, without the use of contact photo-transfer, has been previously published [Mehlmann et al. (2005) *Anal Bioanal Chem* 382, 1942-1948]. In this Example, MALDI-TOF was performed with the following instrument parameters: Instrument mode linear; positive ion mode; delayed extraction mode at 180 nsec; accelerating voltage 25,000; grid voltage 90.000; guide wire voltage 0.100; and a laser intensity setting of 2,800.

Results:

As shown in FIG. 31A, fluorescence imaging of the microarray slide prior to MALDI-TOF verified successful photo-transfer of the Alexa Fluor® 488 labeled anti-FLAG PC-antibody in all cases. FIG. 31B shows the results of MALDI-TOF on the contact photo-transfer fabricated microarray slides. The minus DNA negative control sample (−DNA) shows no measurable peaks, while the CT61 and CT64 peptides are observed at essentially the correct mass positions (±1%). Other embodiments of this Example are possible where contact photo-transfer is performed onto activated or coated metal MALDI plates or targets, instead of onto activated or coated glass microarray slides. For example, contact photo-transfer will be performed onto activated (chemically reactive), secondary antibody coated (to capture photo-released PC-antibody) or polymer coated metal MALDI plates, which is expected to improve signal-to-noise ratios, peak resolution and mass accuracy. Gold and other metal plates compatible with MALDI-TOF have been reported with various coatings or activations including amine-reactive moieties to attach proteins [Neubert et al. (2002) *Anal Chem* 74, 3677-3683], charged or hydrophobic protein binding polymers such as poly-lysine or nitrocellulose [Jacobs & Dahlman. (2001) *Anal Chem* 73, 405-410; Zhang & Orlando. (1999) *Anal Chem* 71, 4753-4757] and even biotin coatings which have been used for creating protein microarrays for MALDI-TOF readout [Koopmann & Blackburn. (2003) *Rapid Commun Mass Spectrom* 17, 455-462].

Example 35

Contact Photo-Transfer of DNA: Hybridization Probing

Preparing PC-Biotin Labeled DNA and Loading to Beads

A 5' C6 (6-carbon spacer) amine modified oligonucleotide was purchased from Sigma-Genosys (The Woodlands, Tex.) having the following sequence:

[SEQ NO. 19]
5'[Amine]gTTAAATTgCTAACgCAgTCAggAg3'

The oligonucleotide was prepared to a 10 µg/µL stock in nuclease-free water and clarified in a micro-centrifuge for 1 min at 13,000 rpm. 100 µL of the supernatant was then passed through a NAP-5 desalting column according to the manufacturer's instructions (Amersham Biosciences Corp., Piscataway, N.J.) against a 200 mM sodium bicarbonate and 200 mM NaCl buffer (nuclease-free reagents). 400 µL of the resultant 1 µg/µL oligonucleotide was then labeled with a 20-fold molar excess of AmberGen's PC-biotin-NHS labeling reagent (added from a 50 mM stock in anhydrous DMF). The reaction was carried out for 30 min with gentle mixing. As a negative control, an equal amount of oligonucleotide was not labeled, but was otherwise processed in parallel in the same manner. Each sample was then passed through a NAP-5 desalting column according to the manufacturer's instructions (Amersham Biosciences Corp., Piscataway, N.J.) against TE-NaCl buffer (10 mM Tris-HCl, pH 8.0, 1 mM EDTA, 2M NaCl). The resultant oligonucleotides were 0.4-0.5 µL.

To load the oligonucleotides onto beads, 25 µL packed bead volume of NeutrAvidin agarose beads (Pierce Biotechnology, Inc., Rockford, Ill.) was washed 3× 400 µL with TE-NaCl buffer. To wash the beads or exchange the buffers, 0.45 micron pore size, PVDF membrane, micro-centrifuge Filtration Devices were used unless otherwise noted (Ultrafree-MC Durapore Micro-centrifuge Filtration Devices, 400 µL capacity; Millipore, Billerica, Mass.). 400-500 µL of the aforementioned prepared oligonucleotide solutions (PC-biotin labeled or unlabeled DNA) was then used to resuspend the washed bead pellets and bead capture of the oligonucleotides was allowed to occur for 30 min with gentle mixing. Beads were then washed 2×400 W., briefly with TE-NaCl and then 2× 400 µL briefly with 1 mM EDTA in PBS. For final washing and bead storage, either PBS, 1 mM EDTA and 50% glycerol or 50 mM sodium phosphate, pH 7.5, 2M NaCl and 50% glycerol was used with similar results. Final washing was 2×400 µL briefly and beads were stored at −20° C. as 10-20% (v/v) suspensions.

For quality control purposes, 1 µL packed bead volume of the beads loaded with the PC-biotin labeled oligonucleotide or the unlabeled oligonucleotide were stained with the OliGreen ssDNA detection reagent as described in Example 30. To additionally verify the bound oligonucleotide, 5 µL packed bead volume was washed 3×400 µL briefly with 6×SSPE buffer (50 mM sodium phosphate, pH 7.5, 900 mM NaCl and 6 mM EDTA). The beads were then resuspended in 50 µL of a complementary oligonucleotide probe (10 µM in 6×SSPE) labeled on its 5' end with the Cy5 fluorophore (Sigma-Genosys; The Woodlands, Tex.) and having the following sequence:

[SEQ NO. 20]
5'[Cy5]CTCCTgACTgCgTTAgCAATTTAAC3'

The probe was allowed to hybridize with the beads for 30 min at 42° C. with gentle mixing. Beads were then washed 2×400 µL briefly with 6×SSPE, 2×400 µL, briefly with 3×SSPE, 1×400 µL briefly with 50 mM sodium phosphate, pH 7.5, 2M NaCl and 50% glycerol and lastly resuspended in 500 µL of the same buffer. 250 µL of bead suspension (2.5 µL packed beads) was placed in a thin-walled polypropylene 0.5 mL PCR tube and the beads were spun down briefly in a micro-centrifuge at 13,000 rpm. Most of the supernatant was removed (except ~10 µL) and the bead pellet was imaged with a FUJIFILM FLA-2000 fluorescence scanner (Fuji Photo Film Co., LTD., Equipment Product Division, Science Group, Japan) directly in the tubes, using the 633 nm He—Ne laser and a 675 nm emissions filter.

Preparation of a NeutrAvidin-Cy5 Labeled Conjugate

For indirect fluorescence detection of contact photo-transfer fabricated DNA microarrays that are hybridized with biotinylated complementary oligonucleotide probes, as described later in this Example, a NeutrAvidin-Cy5 labeled fluorescent conjugate was first prepared as described in this paragraph. NeutrAvidin powder (Pierce Biotechnology, Inc., Rockford, Ill.) was dissolved to 5 mg/mL in purified water and then 350 µL was passed through a NAP-5 desalting column according to the manufacturer's instructions (Amersham Biosciences Corp., Piscataway, N.J.) against a 200 mM sodium bicarbonate and 200 mM NaCl buffer. The resultant 1 mg/mL NeutrAvidin solution was labeled using 10 molar equivalents of a Cy5-NHS monoreactive ester (Amersham Biosciences Corp., Piscataway, N.J.) that was added from a 27 mM stock in DMSO. The reaction was carried out for 30 min with gentle mixing. The conjugate was then passed through a NAP-10 desalting column according to the manufacturer's instructions (Amersham Biosciences Corp., Piscataway, N.J.) against TBS to remove un-reacted labeling reagent. Measurement of absorbance at 280 nm and 649 nm determined that there was approximately 1 Cy5 molecule per protein molecule on average. The NeutrAvidin-Cy5 conjugate solution was then diluted 1:1 with 100% glycerol for storage at −20° C. (0.38 µg/µL after dilution).

Contact Photo-Transfer of DNA and Detection by Hybridization Probing and Indirect Fluorescence For contact photo-transfer, only the aforementioned beads that were loaded with the PC-biotin labeled DNA were used (i.e. not beads that were treated with the unlabeled DNA). Furthermore, the beads used were those remaining beads that were not stained with OliGreen and not previously probed with the Cy5 labeled complementary oligonucleotide, as described earlier in this Example for quality control purposes. To wash the beads or exchange the buffers, 0.45 micron pore size, PVDF membrane, micro-centrifuge Filtration Devices were used unless otherwise noted (Ultrafree-MC Durapore Micro-centrifuge Filtration Devices, 400 µL capacity; Millipore, Billerica, Mass.). 5 µL packed bead volume was taken and washed 1×400 µL briefly with 6×SSPE then 1×400 µL for 15-45 min at 42° C. with gentle mixing. Next, beads were washed 3×400 µL briefly with nuclease-free water. Beads were then washed 1×400 µL for 15 min at 42° C. using 50 mM sodium phosphate, pH 7.5, 2M NaCl and 50% glycerol with gentle mixing and then rinsed 1×400 µL briefly in the same buffer. Beads were then resuspended to 1-2% beads (v/v) in 50 mM sodium phosphate, pH 7.5, 2M NaCl and 50% glycerol for use in contact photo-transfer.

For contact photo-transfer, 45-50 µL of the aforementioned bead suspension was applied to an epoxy activated microarray slide (SuperEpoxy substrates, TeleChem International, Inc. ArrayIt™ Division, Sunnyvale, Calif.) and overlaid with a standard 18 mm round microscope cover glass. The slide was allowed to stand 5 min undisturbed to allow the beads to settle to the slide surface. Without further disturbance, the slide was then illuminated from above with near-UV light for 5 min (365 nm peak lamp; Blak-Ray Lamp XX-15, UVP, Upland, Calif.; used at 1 to 3 mW/cm$^2$). A minus light negative control was performed on the same slide, by masking a region of the slide with a black plastic opaque lid that was lined with aluminum foil. After light treatment, binding of the photo-released material to the epoxy activated slide was allowed to occur by incubating for 20 min at room temperature in a humidified chamber without disturbance. Beads and cover glasses were then removed and the slides simultaneously washed/blocked by treating 2×15 min with excess 10 mM Tris-HCl, pH 8.0, 1 mM EDTA and 900 mM NaCl at 42° C. in a tray with shaking. Slides were further blocked for 5 min at 42° C. with excess 0.1% (w/v) nuclease-free BSA in 10 mM Tris-HCl, pH 8.0, 1 mM EDTA and 900 mM NaCl. Slides were then rinsed 3× briefly with excess nuclease-free water and dried by centrifugation in a padded tube.

Dried slides were then probed with a complementary oligonucleotide followed by detection by indirect fluorescence. For indirect fluorescence, slides were probed with a complementary oligonucleotide that was 5' labeled with biotin (Sigma-Genosys; The Woodlands, Tex.) and having the following sequence:

[SEQ NO. 21]
5'[Biotin]CTCCTgACTgCgTTAgCAATTTAAC3'

The probing solution was comprised of 10 µM of the biotin labeled complementary oligonucleotide and 10 mM d-biotin in 6×SSPE buffer. Free d-biotin was included as a precautionary measure to prevent binding of the probe to any NeutrAvidin that may have leached from the beads and bound to the microarray slide. Probing the microarray slide was achieved using 120 µL of the solution under a standard 22×60 mm microscope cover glass overlay, for overnight at 42° C. in a humidified chamber. Slides were then allowed to cool to room temperature for 30 min followed by washing with excess 6×SSPE in a tray with mixing for 3× 1 min each. Slides were then treated with 100 µL of the aforementioned prepared NeutrAvidin-Cy5 conjugate diluted to 3.8 µg/mL in 6×SSPE supplemented with 1% (w/v) nuclease-free BSA. Treatment was performed under a standard 22×60 mm microscope cover glass overlay, for 30 min at 37° C. in a humidified chamber. Sides were then washed (cover glass removed) with excess 6×SSPE in a tray with mixing for 3×1 min each. Slides were then dried by centrifugation in a padded tube and imaged for fluorescence (see later in this Example).

Contact Photo-Transfer of DNA and Detection by Hybridization Probing and Direct Fluorescence Direct fluorescence probing of the microarray slides containing the DNA spots was performed essentially the same as with the indirect fluorescence method described above in this Example. After performing contact photo-transfer as described above in this Example, binding of the photo-released material to the epoxy activated slide was allowed to occur by incubating for 20 min at room temperature in a humidified chamber without disturbance. Beads and cover glasses were then removed and the slides simultaneously washed/blocked by treating 2×15 min with excess 10 mM Tris-HCl, pH 8.0, 1 mM EDTA and 900 mM NaCl at 42° C. in a tray with shaking. Slides were further blocked for 10 min at 42° C. with excess 0.1% (w/v) nuclease-free BSA in 10 mM Tris-HCl, pH 8.0, 1 mM EDTA and 900 mM NaCl. Slides were then rinsed 3× briefly with excess nuclease-free water and dried by centrifugation in a padded tube.

Dried slides were then probed with a complementary oligonucleotide which was directly labeled with fluorescence. The oligonucleotide probe was 5' labeled with Cy5 (Sigma-Genosys; The Woodlands, Tex.) and having the following sequence:

[SEQ NO. 22]
5'[Cy5]CTCCTgACTgCgTTAgCAATTTAAC3'

The probing solution was comprised of 10 µM of the Cy5 labeled complementary oligonucleotide in 6×SSPE buffer. Probing the microarray slide was achieved using 100 µL of the solution under a standard 22×60 mm microscope cover glass overlay, for 15 min at 42° C. in a humidified chamber. Slides were then allowed to cool to room temperature for 15 min followed by washing with excess 6×SSPE in a tray with mixing for 4×1 min each. Slides were then dried by centrifugation in a padded tube and imaged for fluorescence (see later in this Example).

Imaging of Contact Photo-Transfer Fabricated DNA Microarrays

Imaging of fluorescent signals from the Cy5 probes was achieved using an ArrayWoRx$^e$ BioChip fluorescence reader (Applied Precision, LLC, Issaquah, Wash.) with the appropriate standard built-in filter set.

Results:

Results in FIG. 32A show verification of DNA attachment to the agarose beads prior to use in contact photo-transfer. Beads that were verified were those that were loaded with either the PC-biotin labeled DNA (+PCB) or beads that were treated with an equivalent amount of unlabeled DNA (−PCB), as a negative control for non-specific binding. The upper panels show detection with the ssDNA fluorescent stain Oli-Green and the lower panels show detection with a directly Cy5 labeled complementary oligonucleotide probe. After detection, the bead pellets were imaged directly in thin-walled 0.5 mL polypropylene micro-centrifuge tubes. In both cases, bound DNA is specifically detected only on beads loaded with the PC-biotin labeled DNA (+PCB).

FIG. 32B shows the DNA spots applied to the microarray slide via contact photo-transfer and detected with either a biotin labeled complementary oligonucleotide probe followed by NeutrAvidin-Cy5 detection upper left and right panels) or DNA spots that were detected with a directly labeled Cy5 fluorescent complementary oligonucleotide probe (lower left and right panels). In either case, a light-dependent transfer of the DNA from the beads to the microarray slide is shown, forming discrete microarray spots (upper and lower right panels). In the case of indirect fluorescence, no detectible spots are visible when contact photo-transfer was performed in the absence of proper light illumination (upper left panel). In the case of direct fluorescence detection, trace signal is observed when contact photo-transfer was performed in the absence of light illumination (lower left panel), likely due to the higher sensitivity of this method. This signal presumably pertains to DNA leaching off the beads during the contact photo-transfer process and quantification shows the signal to be only 18% (~5-fold less) of the total signal achieved when proper light illumination is used for contact photo-transfer (lower right panel).

Example 36

Effective Single Template Molecule Solid-Phase Bridge PCR: Amplicon Detection Through Fluorescence dUTP Labeling During the PCR Reaction Examples 36-39 demonstrate a step-wise process by which to verify, using DNA level assays, that only one or a few of the original template molecules are amplified per bead during solid-phase bridge PCR. One key parameter is the proper concentration of template initially added to the primer coated beads to achieve this result, and this, referred to as the "target template concentration", will vary depending on the characteristics of a given solid-phase bridge PCR system. These characteristics effect the efficiency of initially capturing the template onto the beads and/or the efficiency of template amplification. For example, characteristics of the template and primer pair combination such as template length, sequence-dependent secondary structure of the template and/or primer and primer melting temperature ($T_m$). Characteristics of the beads such as bead composition (e.g. polar, charged or hydrophobic material) and porosity (e.g. whether pores are present and pore size) as well as primer density, will also effect the target template concentration. Lastly, characteristics of the solid-phase bridge PCR reaction itself impact the target template concentration, such as annealing temperatures used and additives such as salt or dimethyl sulfoxide, which effect the primer and template melting temperatures ($T_m$). Therefore, this target template concentration will vary and needs to be systemically determined for any given solid-phase bridge PCR system using the generalized approach detailed in Examples 36-39.

The generalized approach uses a binary system, whereby 2 distinct template DNA species, flanked by common sequences at the 5' and 3' ends to which the primers are directed, are initially added to the primer coated beads for solid-phase bridge PCR amplification. The first stage involves narrowing down the target template concentration using detection of the DNA amplicon (solid-phase bridge PCR amplification product) on individual beads, generically, using incorporation of a fluorescently labeled deoxynucleotide triphosphate during the solid-phase bridge PCR reaction itself (this Example 36 and the subsequent Example 37). The target template concentration is then confirmed by detecting and distinguishing both amplicon species on individual beads using dual fluorescence hybridization probing. The expected result is that individual beads should contain amplicon corresponding to primarily one (e.g. >70%, still more preferably greater than 80%, and preferably 90% or more), but not both of the template DNA species (Example 38). Lastly, the target template concentration is validated by titrating the ratio of the 2 template species initially added to the beads. The expected result after solid-phase bridge PCR amplification is that the ratio of individual beads containing each amplicon should approximately (plus or minus 20%, more preferably, plus or minus 10% or less) reflect the ratio of template species initially added to the beads (Example 39).

Preparing the Solid-Phase Bridge PCR Template DNA:

Note: All buffers and reagents used throughout this entire Example, unless otherwise noted, were minimally DNAse, RNAse and protease free, referred to as Molecular Biology Grade (MBG), including the water, referred to as MBG-Water.

Full length human p53 (GeneBank NM_000546) and GST A2 (GeneBank NM_000846) genes (open reading frame) were cloned into the pETBlue-2 plasmid (EMD Biosciences, Inc., San Diego, Calif.) according to standard practices and the manufacturer's instructions. Plasmids were then used as template for standard solution-phase PCR with gene-specific primers, using standard molecular biology practices. The primers are listed below whereby the bracketed sequences indicate the gene-specific hybridization regions, while the remaining sequences are non-hybridizing regions which act as common universal sequences, flanking the gene inserts, to which the subsequent solid-phase bridge PCR primers are directed (the non-hybridizing regions also correspond to elements needed for later cell-free protein expression as well as epitope tag detection):

```
p53 Forward Primer:
                                          [SEQ NO. 23]
5'ggATCCTAATACgACTCACTATAgggAgAggAggTATATCAATggATT
ATAAAgACgATgATgATAAA[gAggAgCCgCAgTCAgATCCTAg
CgTC]3' p53 Reverse Primer:
                                          [SEQ NO. 24]
5'TTTTTATTACTTACCCAggCggTTCATTTCgATATCAgTgTATTTAT
TTAT[CAAggggCACAgAACgTTgTTTTCA]3'

GST A2 Forward Primer:
                                          [SEQ NO. 25]
5'ggATCCTAATACgACTCACTATAgggAgAggAggTATATCAATggATT
ATAAAgACgATgATgATAAA[gCAgAgAAgCCCAAgCTCCACTACT
CC]3'

GST A2 Reverse Primer:
                                          [SEQ NO. 26]
5'TTTTTATTACTTACCCAggCggTTCATTTCgATATCAgTgTATTTATT
TAT[CTCTTCAAACTCTACTCCAgCTgCAgCC]3'
```

Following the solution-phase PCR, the products were analyzed by standard agarose gel electrophoresis and ethidium bromide staining to ensure a single band was produced and of the correct molecular weight. Based on the primers used, gene fragments of human p53 and human GST A2, flanked by common universal sequences, are produced as the PCR product, at 221 and 212 bp respectively. The PCR products were then purified by agarose gel electrophoresis and the resultant DNA concentration was 83-84 ng/µL. From here forward, these purified PCR products are referred to as "Concentrated Stock Template DNA Solutions", and were subsequently used to make the template DNA dilutions for the solid-phase bridge PCR reactions described later in this Example.

Preparation of Agarose Beads Covalently Conjugated to PCR Primers Used for Solid-Phase Bridge PCR:

The following universal forward and reverse PCR primers, directed against the common sequences in both the human p53 and human GST A2 DNA templates (templates prepared as described earlier in this Example), were purchased from Sigma-Genosys (The Woodlands, Tex.), both with a 5' primary amine modification following a 6 carbon spacer:

```
                                          [SEQ NO. 27]
Forward: 5'[Amine]TAATACgACTCACTATAgggAgAggAgg3'

[SEQ NO. 28]
Reverse: 5'[Amine]TTACTTACCCAggCggTTCATTTC3'
```

Primary amine reactive, NHS ester activated (N-hydroxysuccinimide), 4% cross-linked agarose beads (~100 micron diameter) were purchased from Amersham Biosciences (Amersham Biosciences Corp., Piscataway, N.J.). The following procedures, unless otherwise noted, were performed in batch mode using Filtration Devices to facilitate manipulation of the beaded matrix (~100 micron beads), perform washes and otherwise exchange the buffers (Filtration Devices=Ultrafree-MC Durapore Micro-centrifuge Filtration Devices, 400 µL capacity, PVDF filtration membrane, 0.45 micron pore size; Millipore, Billerica, Mass. distributed by Sigma-Aldrich, St. Louis, Mo.). 200 µL of bead volume (400 µL of stock 50% slurry as supplied by the manufacturer) was placed in a Filtration Device, spun down briefly in a micro-centrifuge (just until reaches maximum speed of ~13,000 rpm corresponding to ~16,000×g) and the filtrate corresponding to the isopropanol storage buffer was discarded. The 200 µL of beads was then washed 4× briefly (briefly=5 sec vortex mix) with 400 µL each of ice cold 1 mM HCl prepared in MBG-Water. Unless otherwise stated, all buffers or washes in this procedure were removed from the beads (exchanged) by spinning the Filtration Devices briefly in a standard micro-centrifuge (just until reaches maximum speed of ~13,000 rpm corresponding to ~16,000×g) and discarding the filtrate. The washed bead pellet was then resuspend in 200 µL containing 125 µM of each primer (forward and reverse primers; both primers added from 1,250 µM stocks in MBG-Water) prepared in Binding Buffer (200 mM sodium bicarbonate, 2M NaCl) additionally containing 12 µM of a Biotin-Amine Linker (EZ-Link Amine-PEO3-Biotin; Pierce Biotechnology, Inc., Rockford, Ill.; added from a 40× concentrated stock in MBG-Water). As a negative control, a second set of beads received the same 200 µL of solution lacking only the forward and reverse primers. The binding reaction was allowed to proceed for 1 hour with gentle vortex mixing. The beads were then washed 1× briefly with 400 µL of Quenching Buffer (200 mM sodium bicarbonate, 200 mM glycine, 1 mM EDTA, 2M NaCl) and then 2×400 µL with Quenching Buffer for 30 min each with gentle vortex mixing. The beads were then washed 2× briefly with Binding Buffer followed by 2× for 5 min each with TE-NaCl (10 mM Tris, pH 8.0, 2M NaCl and 1 mM EDTA). Beads were lastly washed 1× briefly with SP-PCR Storage Buffer (50% glycerol, 10 mM Tris, pH 8.0, 2M NaCl, 1 mM EDTA) and then diluted to a 20% (v/v) bead suspension in SP-PCR Storage Buffer. The bead suspension was recovered from the upper chamber of the Filtration Device and stored in a 1.5 mL polypropylene micro-centrifuge tube at −20° C. From here forward, these beads are referred to as Primer-Conjugated Agarose Beads.

Qualitative Analysis of Primer Attachment:

To qualitatively verify successful primer attachment to the Primer-Conjugated Agarose Beads, an aliquot of the beads was stained with the single-stranded DNA fluorescence-based detection reagent OliGreen (Invitrogen Corporation, Carlsbad, Calif.). The manufacturer supplied reagent was diluted 1/200 in TE (10 mM Tris, pH 8.0, 1 mM EDTA) containing 0.01% (v/v) Tween-20. 5 µL of the prepared Primer-Conjugated Agarose Bead suspension (20% beads for 1 µL actual bead volume) was mixed with 100 µL of the diluted OliGreen reagent in a thin-walled 0.5 mL clear polypropylene PCR tube. As a negative control, the beads that were prepared in the same manner, except lacked any attached primer, were also tested. After approximately 1 min, the beads were spun down briefly in a micro-centrifuge (just until reaches maximum speed of ~13,000 rpm corresponding to ~16,000×g), 90 µL of the fluid supernatant was then removed and the bead pellet imaged directly in the tubes using a laser-based fluorescence scanner (FUJI FLA-2000, 473 nm solid-state laser excitation and 520 nm emissions filter) (FUJI Photo Film Co. Ltd, Japan).

First Round of Effective Single Template Molecule Solid-Phase Bridge PCR:

5 µL actual bead volume of the previously prepared Primer-Conjugated Agarose Beads was used per each sample, but first, enough beads for all 3 sample permutations were washed in bulk, with heating. To do so, 75 µL of the aforementioned 20% (v/v) Primer-Conjugated Agarose Bead suspension (15 µL actual bead volume) was placed into a 0.5 mL polypropylene thin-wall PCR tube. The beads were spun down briefly in a standard micro-centrifuge (just until reaches maximum speed of ~13,000 rpm corresponding to ~16,000× g). As much of the fluid supernatant was removed as possible by manual pipetting, with the beads nearly going to dryness. 60 µL of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 60 µL of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device. Filtration was performed and the filtrate discarded. Beads were briefly washed 1×400 µL more with TE-50 mM NaCl then 1×400 µL with MBG-Water.

To pre-hybridize the template DNA to the washed Primer-Conjugated Agarose Beads, the template DNA was first prepared by serial dilution as follows: The template DNA solutions were 1:1 mixtures of the aforementioned human p53 and human GST A2 fragments (i.e. 50% GST A2 and 50% p53). To prepare these solutions, the Concentrated Stock Template DNA Solutions for human p53 and human GST A2, prepared as described earlier in this Example, were subsequently diluted to 1 ng/µL in MBG-Water. The resultant 1 ng/µL human p53 and human GST A2 solutions were then mixed together at a 1:1 ratio. This template mixture was further diluted to 0.1 ng/µL in MBG-Water.

Next, the entire washed pellet of Primer-Conjugated Agarose Beads was then resuspended in 169.1 µL of a commercially available pre-mixed PCR reaction solution containing everything needed for PCR except template DNA and primers (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-SO$_4$ pH 8.9, 19.8 mM (NH$_4$)$_2$SO$_4$, 2.4 mM MgSO$_4$, 220 µM dNTPs and stabilizers; Invitrogen Corporation, Carlsbad, Calif.; solution used at 92% strength with remaining 8% volume being MBG-Water). 53.3 µL portions of the resultant bead suspension (containing 4.3 µL actual bead volume), which contained no soluble primers and no template DNA, was divided into separate 0.5 mL polypropylene thin-wall PCR tubes which already contained 1 µL of either 0 ng/µL (MBG-Water), 0.1 ng/mL or 1 ng/µL of the aforementioned template mixtures. This resulted in a ratio of 0, 180 and 1,800 attomoles of template per µL of actual Primer-Conjugated Agarose Bead volume. With 1 µL of Primer-Conjugated Agarose Beads determined to contain approximately 1,000 beads, 180 and 1,800 attomoles of template per µL of beads represents a ratio of approximately 100,000 and 1,000,000 template molecules added per each bead respectively (beads physically enumerated under a microscope both in diluted droplets of bead suspension and with suspensions in a hemacytometer cell counting chamber). The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing) (beads were resuspended by brief gentle vortex mixing just before and at 2.5 min of this step), ramp down to 59° C. at a rate of 0.1° C./sec then hold 1 hour at 59° C. (annealing/capture of template onto beads) (beads were resuspended by brief gentle vortex mixing at time zero of the 1 hour step and every 10 min thereafter), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 µL of ice cold MBG-Water was added to each tube and the suspensions transferred to fresh Filtration Devices. Filtration was immediately performed as described earlier in this Example and the filtrate discarded. Using the same Filtration Devices, the beads were briefly washed 2×400 µL with room temperature MBG-Water. Beads were further washed 2×400 µL for 2.5 min each with room temperature 0.1M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 50 µL of the commercial pre-mixed PCR solution (Platinum® PCR SuperMix High Fidelity; Invitrogen Corporation, Carlsbad, Calif.) which was again used at 92% strength as described earlier in this Example and contains all necessary components for PCR except template DNA and primers. However, a fluorescence BODIPY-FL-dUTP reagent was also added to a 20 µM final concentration from the manufacturer's 1 mM stock (ChromaTide® BODIPY® FL-14-dUTP; Invitrogen Corporation, Carlsbad, Calif.), in order to achieve subsequent fluorescence labeling of the PCR amplicon (PCR product). The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before and at the end of this step), and 40 cycles of 94° C. for 30 sec (denature), 59° C. for 30 sec (anneal) and 68° C. for 2 min (extend); followed by a final extension step of 68° C. for 10 min (once).

400 µL of TE-50 mM NaCl-T (10 mM Tris, pH 8.0, 1 mM EDTA, 50 mM NaCl, 0.01% v/v Tween-20) was added to each completed solid-phase bridge PCR reaction and the suspensions transferred to fresh 0.5 mL polypropylene PCR tubes. The beads were then spun down in a micro-centrifuge (just until reaches maximum speed of ~13,000 rpm corresponding to ~16,000×g) and the fluid supernatant carefully removed. The beads were washed 3×400 µL more with TE-50 mM NaCl-T; resuspending by ~5 sec vortex mixing then spinning down and discarding the fluid supernatant as above. Following the final wash, as much of the fluid supernatant as possible was removed from the bead pellet by manual pipetting, with the beads going nearly to dryness. The beads were lastly resuspended to 5% (v/v) using SP-PCR Storage Buffer (10 mM Tris, pH 8.0, 1 mM EDTA, 50 mM NaCl, all in 50% v/v glycerol). These intermediate beads could be stored at −20° C. and portions were subsequently used for a full second round of PCR thermocycling as described below.

Second Round of Solid-Phase Bridge PCR:

A portion of the above beads, following completion of the aforementioned initial full round of solid-phase bridge PCR thermocycling (i.e. all preceding steps), were subjected to a second full round of PCR thermocycling. To do so, 20 μL of the aforementioned 5% bead suspension (1 μL actual bead volume) was washed 2×400 μL with MBG-Water using a Filtration Device. Following the final filtration step on the bead samples, each washed bead pellet was resuspended in 50 μL of the commercial pre-mixed PCR solution (Platinum® PCR SuperMix High Fidelity; Invitrogen Corporation, Carlsbad, Calif.) which was again used at 92% strength as described earlier in this Example and contains all necessary components for PCR except template DNA and primers. The fluorescence BODIPY-FL-dUTP reagent was also added to a 20 μM final concentration from the manufacturer's 1 mM stock (ChromaTide® BODIPY® FL-14-dUTP; Invitrogen Corporation, Carlsbad, Calif.), in order to achieve subsequent fluorescence labeling of the PCR amplicon (PCR product). The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (beads were briefly resuspended by gentle vortex mixing just before and at the end of this step), and 40 cycles of 94° C. for 30 sec (denature), 59° C. for 30 sec (anneal) and 68° C. for 2 min (extend), followed by a final extension step of 68° C. for 10 min.

400 μL of TE-50 mM NaCl-T (10 mM Tris, pH 8.0, 1 mM EDTA, 50 mM NaCl, 0.01% v/v Tween-20) was added to each completed solid-phase bridge PCR reaction and the suspensions transferred to fresh 0.5 mL polypropylene PCR tubes. The beads were then spun down in a micro-centrifuge (just until reaches maximum speed of ~13,000 rpm corresponding to ~16,000×g) and the fluid supernatant carefully removed. The beads were washed 3×400 μL more with TE-50 mM NaCl-T; resuspending by ~5 sec vortex mixing then spinning down and discarding the fluid supernatant as above. Following the final wash, as much of the fluid supernatant as possible was removed from the bead pellet by manual pipetting, with the beads going nearly to dryness. The beads were lastly resuspended to 5% (v/v) using SP-PCR Storage Buffer (10 mM Tris, pH 8.0, 1 mM EDTA, 50 mM NaCl, all in 50% v/v glycerol). These final beads, referred to from here forward as Post-PCR Beads, could be stored at −20° C. and portions were subsequently used for fluorescence analysis as detailed below in this Example.

Embedding the Beads in a Polyacrylamide Film and Fluorescence Imaging:

Lastly, the beads were embedded in a polyacrylamide film on a microscope slide and fluorescently imaged to detect the BODIPY-FL-dUTP labeling of the PCR amplicon (PCR product). First however, beads were stained with a NeutrAvidin-Cy5 fluorescence conjugate, which binds the bead-bound biotin groups, to enable detection of all beads regardless of the presence of PCR amplicon. To do so, the NeutrAvidin-Cy5 fluorescence conjugate was prepared as described previously in Example 35. Following completion of all prior solid-phase bridge PCR reaction steps in this Example, 20 μL of the aforementioned 5% (v/v) suspension of Post-PCR Beads was taken (i.e. 1 μL Post-PCR Bead volume), combined with 100 μL of the NeutrAvidin-Cy5 conjugate (38 ng/mL in TE-50 mM NaCl-T) and mixed gently for 5 min. The beads were then spun down in a standard micro-centrifuge (just until reaches maximum speed of ~13,000 rpm corresponding to ~16,000×g) and the fluid supernatant removed. The beads were washed 3×400 μL with TE-50 mM NaCl-T; resuspending by ~5 sec vortex mixing then spinning down and discarding the fluid supernatant as above.

After removing the final wash, the beads were embedded in a polyacrylamide film on a microscope slide and fluorescently imaged. To do so, an Acrylamide Mix was prepared by combining the following reagents in order: 244 μL of TE-50 mM NaCl, 57 μL of 40% acrylamide (19:1 cross-linking) (Bio-Rad Laboratories, Hercules, Calif.), 0.5 μL TEMED (Bio-Rad Laboratories, Hercules, Calif.), and 1 μL of a 10% (w/v) ammonium persulfate stock (prepared in MBG-Water from powder obtained from Bio-Rad Laboratories, Hercules, Calif.). Each washed bead pellet was then resuspended in 50 μL of the above Acrylamide Mix and combined by brief vortex mixing. 25 μL of the bead suspension was then pipetted to a standard glass microscope slide and overlaid with a standard 18 mm square microscope cover glass (coverslip). Polymerization was allowed to occur for ~10 min protected from light. Note that the adequately slow polymerization process allows all beads to settle to the surface of the microscope slide by unit gravity. When polymerization was complete, imaging was performed using an ArrayWoRx$^e$ BioChip fluorescence microarray reader (Applied Precision, LLC, Issaquah, Wash.).

Results:

A representative field-of-view of the raw fluorescence image is shown in FIG. 33A for all 3 sample permutations, as green and red 2-color fluorescence image overlays for each. The minus template sample permutation (−Template) was prepared in the same manner as the other sample permutations except that only the template DNA was omitted from the solid-phase bridge PCR reaction. Qualitatively, it is observed that in the minus template negative control, virtually no beads have detectible amplicon as evidenced by the lack of green fluorescence signal from the BODIPY-FL-dUTP labeling, while all beads are detected by their independent red NeutrAvidin-Cy5 label. Note that a very low percentage of beads in the minus template negative control do have significant BODIPY-FL-dUTP labeling, which is believed to be non-specific amplification of non-template contaminant DNA or amplification of offset primer-dimers (so-called "false positives"). Nonetheless, at 180 and 1,800 attomoles of template per each μL of bead volume, amplicon is observed on a significantly larger percentage of the beads in comparison to the minus template negative control and at an overall greater intensity of the BODIPY-FL-dUTP (green) signal. However, significant heterogeneity in the BODIPY-FL-dUTP (green) signal strength is observed from bead-to-bead in the samples that received template. Note that all beads in all sample permutations have similar (uniform) red signal intensity to that of the minus template negative control (see below), but at higher amplicon levels, the red is masked by the green signal in the image presented. It is also important to note that the data shown in FIG. 33A is after the second round of solid-phase bridge PCR, and that no significant detectible BODIPY-FL-dUTP (green) signal was observed on the beads after the first round of solid-phase bridge PCR (see methods portion of this Example for details of the first and second rounds of solid-phase bridge PCR).

For more precise data interpretation, the non-overlaid fluorescence grayscale images were quantified by computer-assisted image analysis using the ImageQuant software package (Molecular Dynamics; Amersham Biosciences Corp., Piscataway, N.J.). Average fluorescence intensities for each bead (henceforth referred to as "bead intensity") were determined in both the green and red fluorescence channels (i.e. average fluorescence intensity over the entire area of a given individual bead). More than 350 beads were quantified for each sample permutation and the data graphed in bar chart form (each bar in the graph represents the bead intensity of a specific individual bead) (FIG. 33B). Note that the red bead intensities alone were highly consistent from bead-to-bead in all sample permutations, as expected (not shown in FIG. 33B); if the red bead intensities for all beads in the minus template negative control are averaged and normalized to 100%, the minus template negative control is 100±12% (n=353 beads), in comparison, the 180 attomoles/µL beads sample averaged 99±9% (n=517 beads) and the 1,800 attomoles/µL beads sample averaged 99±8% (n=512 beads) of the minus template negative control. Note that the fluorescence detector was not saturated in any case.

The green bead intensity, corresponding to the level of amplicon, was normalized to the red bead intensity (i.e. the green to red ratio was calculated for each bead), since the red bead intensity (biotin labeling level) is assumed to be proportional to each bead's binding capacity. The green to red ratios for all beads in the minus template negative control averaged 1±1. Based on the data patterns and background levels, the following bead scoring parameters were used: Beads were scored as "strong positive" if the green to red ratio was $\geq 10$ (red line in bar chart of FIG. 33B), thereby corresponding to a signal-to-noise ratio of $\geq 10:1$ since the green to red ratio for the minus template negative control (noise) averaged 1. Using these criteria, 4% of the beads score as "strong positive" in the 180 attomoles/µL of beads sample and 38% in the 1,800 attomoles/µL of beads sample, in strong agreement with the 10-fold difference in added template. It is critical to note that the "strong positives" in both the 180 and 1,800 attomoles template per µL of beads samples had comparable green to red ratios per each bead, averaging at 15±6 and 13±4 respectively; thus the amplicon levels in all "strong positives" of either sample were similar. Under these same criteria, the minus template negative control had 0% "strong positives".

Conversely, beads were scored as "negative" if their green to red ratio was less than or equal to the average green to red ratio for the minus template negative control plus one standard deviation of the minus template negative control (i.e. green to red ratio of $\leq 2$ is "negative"). Under these criteria, 29% of the beads score as "negative" in the 180 attomoles/µL of beads sample and 3% in the 1,800 attomoles/µL of beads sample, again in strong agreement with the 10-fold difference in added template. Under these same criteria, the minus template negative control had 96% "negatives". Together, these data suggest the amplification of only one or a few of the original template molecules per bead (e.g. 1-3 copies per bead). Note also that there are "intermediately positive" beads that fall in between the "negative" and "strong positive" cutoffs. One possible explanation is that the "negative" beads amplified zero template molecules, the "intermediately positive" beads 1 template molecule and the "strong positive" 2 template molecules. Further evidence of amplification of only one or a few of the original template molecules per bead (e.g. 1-3 copies per bead) is provided in later Examples, such as titrating the initially added template DNA below the level of 180 attomoles/µL of beads (Example 37) as well as simultaneously detecting the human p53 and human GST A2 amplicons on different beads with gene-specific oligonucleotide hybridization probes having different fluorescent labels (Examples 38 and 39).

Example 37

Effective Single Template Molecule Solid-Phase Bridge PCR and Amplicon Detection Through Fluorescence dUTP Labeling During the PCR Reaction: Lower Limits of the Added Template Amount This Example is similar to Example 36, repeating the 180 attomoles of template per µL of beads permutation and further including a permutation of 18 attomoles of template per µL of beads, to demonstrate the lower limits of template concentration in this particular model system.

Preparing the Solid-Phase Bridge PCR Template DNA:
    Performed as in Example 36.
Preparation of Agarose Beads Covalently Conjugated to PCR Primers Used for Solid-Phase Bridge PCR:
    Performed as in Example 36.
Qualitative Analysis of Primer Attachment:
    Performed as in Example 36.
First Round of Effective Single Template Molecule Solid-Phase Bridge PCR:
    Performed essentially as in Example 36, with slight modifications. The full protocol was as follows: 10 µL actual bead volume of the previously prepared Primer-Conjugated Agarose Beads was used per each sample, but first, each of the 10 µL of beads was washed separately in parallel, with heating. To do so, 50 µL each of the aforementioned 20% (v/v) Primer-Conjugated Agarose Bead suspension (10 µL actual bead volume) was placed into a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness. 40 µL each of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 40 µL each of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 1×400 µL more with TE-50 mM NaCl then 1×400 µL with MBG-Water. Each set of beads was then resuspended in 50 µL MBG-Water and transferred to a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness.

Next, to pre-hybridize the template DNA to the washed Primer-Conjugated Agarose Beads, each pellet was then resuspended in 5 µL of diluted template solution, which contained no soluble primers. The p53 and GST A2 template mixture was prepared to 1 ng/µL as described in Example 36 (except 75% GST A2 and 25% p53). This template mixture was further serially diluted to 0.05 and 0.005 ng/µL in a commercially available pre-mixed PCR reaction solution containing everything needed for PCR except template DNA and primers (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-$SO_4$ pH 8.9, 19.8 mM $(NH_4)_2SO_4$, 2.4 mM $MgSO_4$, 220 µM dNTPs and stabilizers; Invitrogen Corporation, Carlsbad, Calif.; solution used without prior dilution). This resulted in a ratio of 180 and 18 attomoles of template per µL of actual Primer-Conjugated Agarose Bead volume. With 1 µL of Primer-Conjugated Agarose Bead determined to contain approximately 1,000 beads, 180 and 18 attomoles of template per µL of beads represents a ratio of approximately 100,000 and 10,000 template molecules added per bead (beads physically enumerated under a microscope both in diluted droplets of bead suspension and with suspensions in a hemacytometer cell counting chamber). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing), ramp down to 59° C. at a rate of 0.1° C./sec then hold 1 hour at 59° C. (annealing/capture of template onto beads), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 µL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 µL with room temperature MBG-Water. Beads were further washed 2×400 µL for 2.5 min each with room temperature 0.1 M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 100 µL of the commercial pre-mixed PCR solution (Platinum® PCR SuperMix High Fidelity; Invitrogen Corporation, Carlsbad, Calif.) which was used at 92% strength (diluted with MBG-Water) and contains all necessary components for PCR except template DNA and primers. However, since it was determined in Example 36 that no detectable BODIPY-FL-dUTP fluorescence signal was observed after the first round of effective single template molecule solid-phase bridge PCR, the BODIPY-FL-dUTP reagent omitted from the PCR reaction at this stage. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before and at the end of this step), and 40 cycles of 94° C. for 30 sec (denature), 59° C. for 30 sec (anneal) and 68° C. for 2 min (extend); followed by a final extension step of 68° C. for 10 min (once).

400 µL of TE-50 mM NaCl-T (10 mM Tris, pH 8.0, 1 mM EDTA, 50 mM NaCl, 0.01% v/v Tween-20) was added to each completed solid-phase bridge PCR reaction and the suspensions transferred to fresh 0.5 mL polypropylene PCR tubes. The beads were then spun down in a micro-centrifuge (just until reaches maximum speed of ~13,000 rpm corresponding to ~16,000×g) and the fluid supernatant carefully removed. The beads were washed 3×400 µL more with TE-50 mM NaCl-T; resuspending by ~5 sec vortex mixing then spinning down and discarding the fluid supernatant as above. Following the final wash, as much of the fluid supernatant as possible was removed from the bead pellet by manual pipetting, with the beads going nearly to dryness. The beads were lastly resuspended to 5% (v/v) using SP-PCR Storage Buffer (10 mM Tris, pH 8.0, 1 mM EDTA, 50 mM NaCl, all in 50% v/v glycerol). These intermediate beads could be stored at −20° C. and portions were subsequently used for a full second round of PCR thermocycling as described below.

Second Round of Solid-Phase Bridge PCR:

Performed as described in Example 36 except that a 5 µL portion of beads (actual bead volume) was used in 100 µL of the commercially available pre-mixed PCR reaction solution (with the BODIPY-FL-dUTP labeling reagent).

Embedding the Beads in a Polyacrylamide Film and Fluorescence Imaging:

Performed as in Example 36.

Results:

A representative field-of-view of the raw fluorescence image is shown in FIG. 34A for all 3 sample permutations, as green and red 2-color fluorescence image overlays for each. The minus template sample permutation (−Template) was prepared in the same manner as the other sample permutations except that only the template DNA was omitted from the solid-phase bridge PCR reaction. Qualitatively, it is observed that in the minus template negative control, virtually no beads have detectable amplicon as evidenced by the lack of green fluorescence signal from the BODIPY-FL-dUTP labeling, while all beads are detected by their independent red NeutrAvidin-Cy5 label. Note that a very low percentage of beads in the minus template negative control do have significant BODIPY-FL-dUTP labeling, which is believed to be non-specific amplification of non-template contaminant DNA or amplification of offset primer-dimers (so-called "false positives"). At 18 attomoles of template per each µL of bead volume, the beads are indistinguishable from those of the minus template negative control. However, as in the previous Example 36, at 180 attomoles of template per each µL of bead volume, amplicon is observed on a significantly larger percentage of the beads in comparison to the minus template negative control and at an overall greater intensity of the BODIPY-FL-dUTP (green) signal. Significant heterogeneity in the BODIPY-FL-dUTP (green) signal strength is observed from bead-to-bead in this sample. Note that all beads in all sample permutations have similar (uniform) red signal intensity to that of the minus template negative control (see below), but at higher amplicon levels, the red is masked by the green signal in the image presented.

For more precise data interpretation, the non-overlaid fluorescence grayscale images were quantified by computer-assisted image analysis using the ImageQuant software package (Molecular Dynamics; Amersham Biosciences Corp., Piscataway, N.J.). Average fluorescence intensities for each bead (henceforth referred to as "bead intensity") were determined in both the green and red fluorescence channels (i.e.

average fluorescence intensity over the entire area of a given individual bead). More than 350 beads were quantified for each sample permutation and the data graphed in bar chart form (1 bar=1 bead) (FIG. 34B). As determined in Example 36, the red bead intensities alone were highly consistent from bead-to-bead in all sample permutations, as expected (not shown in FIG. 34B).

The green bead intensity, corresponding to the level of amplicon, was normalized to the red bead intensity (i.e. the green to red ratio was calculated for each bead), since the red bead intensity (biotin labeling level) is assumed to be proportional to each bead's binding capacity. The beads were scored as "strong positive" or "negative" as described previously in Example 36. Using those criteria, 5% of the beads score as "strong positive" and 55% score as "negative" in the 180 attomoles/µL of beads sample, comparable to that observed previously in Example 36. Note also that there are "intermediately positive" beads that fall in between the "negative" and "strong positive" cutoffs (see Example 36 for details). Conversely, the 18 attomoles/µL of beads sample had only 1% "strong positives" and 96% "negatives" and was indistinguishable from the minus template negative control which had 1% "strong positives" (so-called "false positives") and 95% "negatives". This indicates that 180 attomoles/mL of beads of initially added template, corresponding to roughly 100,000 template molecules initially added per bead (making no assumptions about the efficiency of template capture), is the lower limit of template concentration for this particular system.

Example 38

Effective Single Template Molecule Solid-Phase Bridge PCR: Validation of Effective Amplification of Single Template Molecules per Bead Using 2 Template Species This Example is similar to Example 37, except that the putative target template concentration of 180 attomoles of template per µL of beads is confirmed using dual fluorescence oligonucleotide hybridization probing to detect the levels of each of the 2 distinct amplicon species on each bead.
Preparing the Solid-Phase Bridge PCR Template DNA:
    Performed as in Example 36.
Preparation of Agarose Beads Covalently Conjugated to PCR Primers Used for Solid-Phase Bridge PCR
    Performed as in Example 36.
Qualitative Analysis of Primer Attachment:
    Performed as in Example 36.
First Round of Effective Single Template Molecule Solid-Phase Bridge PCR:
    Performed essentially as in Example 36, with slight modifications. The full protocol was as follows: 10 µL actual bead volume of the previously prepared Primer-Conjugated Agarose Beads was used per each sample, but first, each of the 10 µL of beads was washed separately in parallel, with heating. To do so, 50 µL each of the aforementioned 20% (v/v) Primer-Conjugated Agarose Bead suspension (10 µL actual bead volume) was placed into a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness. 40 µL each of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 40 µL each of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 1×400 µL more with TE-50 mM NaCl then 1×400 µL with MBG-Water. Each set of beads was then resuspended in 50 µL MBG-Water and transferred to a 0.5 mL polypropylene thin-wall PCR tube. The beads were spun down briefly in a standard micro-centrifuge (just until reaches maximum speed of ~13,000 rpm corresponding to ~16,000× g). As much of the fluid supernatant was removed as possible by manual pipetting, with the beads nearly going to dryness.

Next, to pre-hybridize the template DNA to the washed Primer-Conjugated Agarose Beads, each pellet was then resuspended in 5 µL of diluted template solution, which contained no soluble primers. The p53 and GST A2 template mixture was prepared to 1 ng/µL as described in Example 36 (except 75% GST A2 and 25% p53). This template mixture was further serially diluted to 0.05 ng/µL in a commercially available pre-mixed PCR reaction solution containing everything needed for PCR except template DNA and primers (Platinum® PCR SuperMix High Fidelity; contains 22 U/mL complexed recombinant Taq DNA polymerase, Pyrococcus species GB-D thermostable polymerase, Platinum® Taq Antibody, 66 mM Tris-SO$_4$ pH 8.9, 19.8 mM (NH$_4$)$_2$SO$_4$, 2.4 mM MgSO$_4$, 220 µM dNTPs and stabilizers; Invitrogen Corporation, Carlsbad, Calif.; solution used without prior dilution). This resulted in a ratio of 180 attomoles of template per µL of actual Primer-Conjugated Agarose Bead volume. With 1 µL of Primer-Conjugated Agarose Beads determined to contain approximately 1,000 beads, 180 attomoles of template per µL of beads represents a ratio of approximately 100,000 template molecules added per bead (beads physically enumerated under a microscope both in diluted droplets of bead suspension and with suspensions in a hemacytometer cell counting chamber). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing), ramp down to 59° C. at a rate of 0.1° C./sec then hold 1 hour at 59° C. (annealing/capture of template onto beads), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 µL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 µL with room temperature MBG-Water. Beads were further washed 2×400 µL for 2.5 min each with room temperature 0.1M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 100 µL of the commercial pre-mixed PCR solution (Platinum® PCR SuperMix High Fidelity; Invitrogen Corporation, Carlsbad, Calif.) which was used at 92% strength (diluted with MBG-Water) and contains all necessary components for PCR except template DNA and primers. The BODIPY-FL-dUTP labeling reagent was not used in the solid-phase bridge PCR reaction. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before and at the end of this step), and 40 cycles of 94° C. for 30 sec (denature), 59° C. for 30 sec (anneal) and 68° C. for 2 min (extend); followed by a final extension step of 68° C. for 10 min (once).

400 µL of TE-50 mM NaCl-T (10 mM Tris, pH 8.0, 1 mM EDTA, 50 mM NaCl, 0.01% v/v Tween-20) was added to each completed solid-phase bridge PCR reaction and the suspensions transferred to fresh 0.5 mL polypropylene PCR tubes. The beads were then spun down in a micro-centrifuge (just until reaches maximum speed of ~13,000 rpm corresponding to ~16,000×g) and the fluid supernatant carefully removed. The beads were washed 3×400 µL more with TE-50 mM NaCl-T; resuspending by ~5 sec vortex mixing then spinning down and discarding the fluid supernatant as above. Following the final wash, as much of the fluid supernatant as possible was removed from the bead pellet by manual pipetting, with the beads going nearly to dryness. The beads were lastly resuspended to 5% (v/v) using SP-PCR Storage Buffer (10 mM Tris, pH 8.0, 1 mM EDTA, 50 mM NaCl, all in 50% v/v glycerol). These intermediate beads could be stored at −20° C. and portions were subsequently used for a full second round of PCR thermocycling as described below.

Second Round of Solid-Phase Bridge PCR:

Performed as described in Example 36 and 37 except that a 2 µL portion of beads (actual bead volume) was used in 50 µL of the commercially available pre-mixed PCR reaction solution and without the BODIPY-FL-dUTP labeling reagent (i.e. no BODIPY-FL-dUTP labeling at any stage).

Oligonucleotide Hybridization Probing:

Fluorescently labeled oligonucleotide probes were commercially custom synthesized and HPLC purified by the manufacturer (Sigma-Genosys, The Woodlands, Tex.). The probes were reconstituted to 100 µM in MBG-Water and further desalted using MicroSpin G-25 columns according to the manufacturer's instructions (Amersham Biosciences Corp., Piscataway, N.J.), except that the columns were pre-washed 2×350 µL with MBG-Water prior to sample loading (to wash, columns were mixed briefly in the MBG-Water then spun 1 min in a standard micro-centrifuge at the proper speed). The probes were diluted to 5 µM final in TE-50 mM NaCl for hybridization experiments. Prior to use however, the 5 µM probe solution was pre-clarified by spinning 1 min at maximum speed on a micro-centrifuge (~13,000 rpm or ~16,000×g) and collecting the fluid supernatant. The supernatant was then passed though a Filtration Device (see Example 36) and the filtrate saved for use as the probing solution.

In this Example, simultaneous dual probing was performed by creating a single probing solution containing 5 µM of each probe, labeled on their 5' ends with the Cy3 or Cy5 fluorophores by the manufacturer (Sigma-Genosys, The Woodlands, Tex.). The gene-specific probes were complementary to an internal segment of the human p53 and GST A2 amplicons and had the following sequences:

[SEQ NO. 29]
Human p53: 5'[Cy5]CATTTTCAgACCTATggAAACTACTTC3'

[SEQ NO. 30]
Human GST A2: 5'[Cy3]AgAATggAgTCCATCCggTg3'

Following completion of all prior solid-phase bridge PCR reaction steps in this Example, 20 µL of the aforementioned stored 5% (v/v) stock bead suspension (i.e. 1 µL post-PCR stored beads) was taken and washed 2×400 µL with TE-50 mM NaCl using a Filtration Device (see Example 36). In the Filtration Device, each 1 µL pellet corresponding to each sample was resuspended in 25 µL of the aforementioned clarified 5 µM probe solution. The beads were resuspended by manual pipetting then transferred to 0.5 mL polypropylene thin-wall PCR tubes. Hybridization was performed as follows in a PCR machine (Mastercycler Personal; Eppendorf AG, Hamburg, Germany) (lid temperature always 105° C., no mineral oil used): 5 min 95° C. (denature) (beads resuspended by vortex mixing just before and at 2.5 min) followed by ramping down to 55° C. at a rate of 0.1° C./sec and subsequently holding 1 hour at 55° C. (anneal).

Just at the end of the above 1 hour 55° C. (anneal) step, while the tubes were still at 55° C. and still in the PCR machine, each sample was rapidly diluted with 400 µL of 55° C. TE-50 mM NaCl, the suspensions immediately transferred to a Filtration Device and filtration immediately performed. The filtrate was then discarded. The beads were washed 3×400 µL more with room temperature TE-50 mM NaCl then 1×400 µL with room temperature TE-100 mM NaCl (10 mM Tris, pH 8.0, 1 mM EDTA, 100 mM NaCl). The beads were recovered from the Filtration Devices by resuspending the pellet in 50 µL of TE-100 mM NaCl and transferring to a 0.5 mL polypropylene PCR tube. The beads were spun down in a standard micro-centrifuge (just until reaches maximum speed of 13,000 rpm corresponding to ~16,000×g) and the fluid supernatant removed.

Embedding the Beads in a Polyacrylamide Film and Fluorescence Imaging:

Lastly, the beads were embedded in a polyacrylamide film on a microscope slide and fluorescently imaged to detect the bound Cy3 and Cy5 labeled hybridization probes. To do so, an Acrylamide Mix was prepared by combining the following reagents in order: 244 µL of TE-100 mM NaCl, 57 µL of 40% acrylamide (19:1 cross-linking) (Bio-Rad Laboratories, Hercules, Calif.), 0.5 µL TEMED (Bio-Rad Laboratories, Hercules, Calif.), and 1 µL of a 10% (w/v) ammonium persulfate stock (prepared in MBG-Water from powder obtained from Bio-Rad Laboratories, Hercules, Calif.). Each aforementioned washed bead pellet was then resuspended in 50 µL of the above Acrylamide Mix and combined by brief vortex mixing. 25 µL of the bead suspension was then pipetted to a standard glass microscope slide and overlaid with a standard 18 mm square microscope cover glass (coverslip). Polymerization was allowed to occur for ~10 min protected from light. Note that the adequately slow polymerization process allows all beads to settle to the surface of the microscope slide by unit gravity. When polymerization was complete, imaging was performed using an ArrayWoRx$^e$ BioChip fluorescence microarray reader (Applied Precision, LLC, Issaquah, Wash.).

Results:

A representative field-of-view of the fluorescence image is shown in FIG. 35 for both sample permutations, as green and red 2-color fluorescence image overlays for each. The minus template sample permutation (−Template) was prepared in the same manner as the other sample permutations except that only the template DNA was omitted from the solid-phase bridge PCR reaction. In the figure, green corresponds to the GST A2 probe (Cy3) and red the p53 probe (Cy5). For the plus template sample permutation, non-overlaid green and red fluorescence images of the same selected region are also shown. Because the green and red signals arise from different binding probes (for GST A2 and p53) labeled with different fluorophores (Cy3 and Cy5), the two are not directly comparable with respect to relative quantification of the level of GST A2 and p53 amplicon on each bead. This is due to potentially different probe binding efficiencies and differences in fluorescence output and signal collection efficiencies. Therefore, for the image presented in FIG. 35, all image intensity levels of the red channel have been scaled linearly (uniformly) for normalization, such that the maximum intensity in the red channel matched the maximum intensity in the green channel. Qualitatively, it is observed that in the minus template negative control, no beads have detectible amplicon as evidenced by the lack of any significant fluorescence signal. However, the presence of beads in the minus template negative control sample can be confirmed by the extremely weak auto-fluorescence of the beads themselves, which have a uniform green:red fluorescence ratio when the image is observed at very high contrast settings (beads appearing uniformly yellow-orange in the image overlay, shown in the inset box, in the minus template negative control panel of FIG. 35). In the plus template sample, significant probing signal is observed for both GST A2 (green) and p53 (red). The data suggest amplification of only 1 or a few original template molecules per bead, otherwise, relatively uniform green:red (or visa versa) ratios would be expected from bead-to-bead. Instead, it is clear from the data that a sub-population of beads has a significantly higher green:red signal ratio (elevated GST A2 content) compared to that of the other beads. Likewise, a different sub-population of beads has a significantly higher red:green signal ratio (elevated p53 content) compared to that of the other beads. Furthermore, the proportion of these 2 sub-populations approximates that of the initially added template DNA mix (75% GST A2 and 25% p53). The subsequent Example 39 provides a more quantitative analysis of this experimental system.

Example 39

Effective Single Template Molecule Solid-Phase Bridge PCR: Validation of Effective Amplification of Single Template Molecules per Bead by Titrating Ratios of 2 Template Species This Example is similar to Example 38, except that the ratio of human GST A2 and p53 in the initially added template mix was modulated. Following dual fluorescence oligonucleotide hybridization probing to detect the level of each amplicon on each bead, the beads were quantified and enumerated.

Preparing the Solid-Phase Bridge PCR Template DNA:
Performed as in Example 36.

Preparation of Agarose Beads Covalently Conjugated to PCR Primers Used for Solid-Phase Bridge PCR:
Performed as in Example 36.

Qualitative Analysis of Primer Attachment:
Performed as in Example 36.

First Round of Effective Single Template Molecule Solid-Phase Bridge PCR:

Performed essentially as in Example 36, with slight modifications. The full protocol was as follows: 10 µL actual bead volume of the previously prepared Primer-Conjugated Agarose Beads was used per each sample, but first, each of the 10 µL of beads was washed separately in parallel, with heating. To do so, 50 µL each of the aforementioned 20% (v/v) Primer-Conjugated Agarose Bead suspension (10 µL actual bead volume) was placed into a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness. 40 µL each of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 40 µL each of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 1×400 µL more with TE-50 mM NaCl then 1×400 µL with MBG-Water. Each set of beads was then resuspended in 50 µL MBG-Water and transferred to a 0.5 mL polypropylene thin-wall PCR tube. The beads were spun down briefly in a standard micro-centrifuge (just until reaches maximum speed of 13,000 rpm corresponding to ~16,000× g). As much of the fluid supernatant was removed as possible by manual pipetting, with the beads nearly going to dryness.

Next, to pre-hybridize the template DNA to the washed Primer-Conjugated Agarose Beads, each pellet was then resuspended in 5 µL of diluted template solution, which contained no soluble primers. The p53 and GST A2 template mixture was prepared to 1 ng/µL as described in Example 36 (except at various ratios of p53 to GST A2). This template mixture was further serially diluted to 0.05 ng/µL in a commercially available pre-mixed PCR reaction solution containing everything needed for PCR except template DNA and primers (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-SO$_4$ pH 8.9, 19.8 mM (NH$_4$)$_2$SO$_4$, 2.4 mM MgSO$_4$, 220 µM dNTPs and stabilizers; Invitrogen Corporation, Carlsbad, Calif.; solution used without prior dilution). This resulted in a ratio of 180 attomoles of template per µL of actual Primer-Conjugated Agarose Bead volume. With 1 µL of Primer-Conjugated Agarose Beads determined to contain approximately 1,000 beads, 180 attomoles of template per µL of beads represents a ratio of approximately 100,000 template molecules added per bead (beads physically enumerated under a microscope both in diluted droplets of bead suspension and with suspensions in a hemacytometer cell counting chamber). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing), ramp down to 59° C. at a rate of 0.1° C./sec then hold 1 hour at 59° C. (annealing/capture of template onto beads), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 μL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 μL with room temperature MBG-Water. Beads were further washed 2×400 μL for 2.5 min each with room temperature 0.1 M NaOH, with constant vigorous vortex mixing, in order to strip off any hybridized but non-covalently bound template DNA, leaving only covalently attached unused and extended primers on the beads. The beads were then briefly washed 3×400 μL with 10×TE (100 mM Tris, pH 8.0, 10 mM EDTA), in order to neutralize the pH, followed by 3×400 μL with MBG-Water, in order to remove the components of the 10×TE which would interfere with subsequent PCR.

Following the final filtration step on the bead samples, each washed bead pellet was resuspended in 100 μL of the commercial pre-mixed PCR solution (Platinum® PCR SuperMix High Fidelity; Invitrogen Corporation, Carlsbad, Calif.) which was used at 92% strength (diluted with MBG-Water) and contains all necessary components for PCR except template DNA and primers. The PCR reaction was further supplemented with 0.15 U/μL final of additional PlatinumTaq DNA Polymerase High Fidelity added from a 5 U/μL manufacturer's stock (Invitrogen Corporation, Carlsbad, Calif.). The BODIPY-FL-dUTP labeling reagent was not used in the solid-phase bridge PCR reaction. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before and at the end of this step), and 40 cycles of 94° C. for 30 sec (denature), 59° C. for 30 sec (anneal) and 68° C. for 2 min (extend); followed by a final extension step of 68° C. for 10 min (once).

400 μL of TE-50 mM NaCl-T (10 mM Tris, pH 8.0, 1 mM EDTA, 50 mM NaCl, 0.01% v/v Tween-20) was added to each completed solid-phase bridge PCR reaction and the suspensions transferred to fresh 0.5 mL polypropylene PCR tubes. The beads were then spun down in a micro-centrifuge (just until reaches maximum speed of ~13,000 rpm corresponding to ~16,000×g) and the fluid supernatant carefully removed. The beads were washed 3×400 μL more with TE-50 mM NaCl-T; resuspending by ~5 sec vortex mixing then spinning down and discarding the fluid supernatant as above. Following the final wash, as much of the fluid supernatant as possible was removed from the bead pellet by manual pipetting, with the beads going nearly to dryness. The beads were lastly resuspended to 5% (v/v) using SP-PCR Storage Buffer (10 mM Tris, pH 8.0, 1 mM EDTA, 50 mM NaCl, all in 50% v/v glycerol). These intermediate beads could be stored at −20° C. and portions were subsequently used for a full second round of PCR thermocycling as described below.

Second Round of Solid-Phase Bridge PCR:

Performed as described in Example 36 and 37 except that a 10 μL portion of beads (actual bead volume) was used in 100 μL of the commercially available pre-mixed PCR reaction solution and without the BODIPY-FL-dUTP labeling reagent (i.e. no BODIPY-FL-dUTP labeling at any stage). Furthermore, the solid-phase bridge PCR reaction was further supplemented with 0.15 U/μL final of additional PlatinumTaq DNA Polymerase High Fidelity added from a 5 U/μL manufacturer's stock (Invitrogen Corporation, Carlsbad, Calif.).

Oligonucleotide Hybridization Probing:

Fluorescently labeled oligonucleotide probes were commercially custom synthesized and HPLC purified by the manufacturer (Sigma-Genosys, The Woodlands, Tex.). The probes were reconstituted to 100 μM in MBG-Water and further desalted using MicroSpin G-25 columns according to the manufacturer's instructions (Amersham Biosciences Corp., Piscataway, N.J.), except that the columns were pre-washed 2×350 μL with MBG-Water prior to sample loading (to wash, columns were mixed briefly in the MBG-Water then spun 1 min in a standard micro-centrifuge at the proper speed). The probes were diluted to 5 μM final in TE-50 mM NaCl for hybridization experiments. Prior to use however, the 5 μM probe solution was pre-clarified by spinning 1 min at maximum speed on a micro-centrifuge (~13,000 rpm or ~16,000×g) and collecting the fluid supernatant. The supernatant was then passed though a Filtration Device (see Example 36) and the filtrate saved for use as the probing solution.

In this Example, simultaneous dual probing was performed by creating a single probing solution containing 5 μM of each probe, labeled on their 5' ends with the Cy3 or Cy5 fluorophores by the manufacturer (Sigma-Genosys, The Woodlands, Tex.). The gene-specific probes were complementary to an internal segment of the human p53 and GST A2 amplicons and had the following sequences:

```
                                              [SEQ NO. 31]
Human p53:  5'[Cy5]CATTTTCAgACCTATggAAACTACTTC3'

[SEQ NO. 32]
Human GST A2:  5'[Cy3]AgAATggAgTCCATCCggTg3'
```

Following completion of all prior solid-phase bridge PCR reaction steps in this Example, 20 μL of the aforementioned stored 5% (v/v) stock bead suspension (i.e. 1 post-PCR stored beads) was taken and washed 2×400 μL with TE-50 mM NaCl using a Filtration Device (see Example 36). In the Filtration Device, each 1 μL pellet corresponding to each sample was resuspended in 25 μL of the aforementioned clarified 5 μM probe solution. The beads were resuspended by manual pipetting then transferred to 0.5 mL polypropylene thin-wall PCR tubes. Hybridization was performed as follows in a PCR machine (Mastercycler Personal; Eppendorf AG, Hamburg, Germany) (lid temperature always 105° C., no mineral oil used): 5 min 95° C. (denature) (beads resuspended by vortex mixing just before and at 2.5 min) followed by ramping down to 55° C. at a rate of 0.1° C./sec and subsequently holding 1 hour at 55° C. (anneal).

Just at the end of the above 1 hour 55° C. (anneal) step, while the tubes were still at 55° C. and still in the PCR machine, each sample was rapidly diluted with 400 μL of 55° C. TE-50 mM NaCl, the suspensions immediately transferred to a Filtration Device and filtration immediately performed. The filtrate was then discarded. The beads were washed 1×400 μL more with room temperature TE-50 mM NaCl. Next, to fluorescently stain all beads independently of the presence or absence of amplicon, the beads were treated 1× for 5 min with gentle mixing using 200 μL of TE-50 mM NaCl containing 0.01% (v/v) Tween-20 and 50 pg/μL of a streptavidin Alexa Fluor 488 conjugate (Invitrogen Corporation, Carlsbad, Calif.). The beads were then further washed 3×400 μL with TE-100 mM NaCl (10 mM Tris, pH 8.0, 1 mM EDTA, 100 mM NaCl). The beads were recovered from the Filtration Devices by resuspending the pellet in 50 μL of TE-100 mM NaCl and transferring to a 0.5 mL polypropylene PCR tube. The beads were spun down in a standard microcentrifuge (just until reaches maximum speed of ~13,000 rpm corresponding to ~16,000×g) and the fluid supernatant removed.

Embedding the Beads in a Polyacrylamide Film and Fluorescence Imaging:

Lastly, the beads were embedded in a polyacrylamide film on a microscope slide and fluorescently imaged to detect the bound Cy3 and Cy5 labeled oligonucleotide hybridization probes as well as the Alexa Fluor 488 labeled total bead probe (detects all beads independent of either amplicon). To do so, an Acrylamide Mix was prepared by combining the following reagents in order: 244 μL of TE-100 mM NaCl, 57 μL of 40% acrylamide (19:1 cross-linking) (Bio-Rad Laboratories, Hercules, Calif.), 0.5 μL TEMED (Bio-Rad Laboratories, Hercules, Calif.), and 1 μL of a 10% (w/v) ammonium persulfate stock (prepared in MBG-Water from powder obtained from Bio-Rad Laboratories, Hercules, Calif.). Each aforementioned washed bead pellet was then resuspended in 50 μL of the above Acrylamide Mix and combined by brief vortex mixing. 25 μL of the bead suspension was then pipetted to a standard glass microscope slide and overlaid with a standard 18 mm square microscope cover glass (coverslip). Polymerization was allowed to occur for 10 min protected from light. Note that the adequately slow polymerization process allows all beads to settle to the surface of the microscope slide by unit gravity. When polymerization was complete, imaging was performed using an ArrayWoRx$^e$ BioChip fluorescence microarray reader (Applied Precision, LLC, Issaquah, Wash.).

Results:

A representative field-of-view of the fluorescence image is shown in FIG. 36A for all sample permutations, as blue, red and green 3-color fluorescence image overlays for each. The minus template sample permutation (−Template) was prepared in the same manner as the other sample permutations except that only the template DNA was omitted from the solid-phase bridge PCR reaction. In the figure, red corresponds to the p53 probe (Cy5) and green the GST A2 probe (Cy3), while blue corresponds to the Alexa Fluor 488 labeled total bead probe (detects all beads independent of either amplicon). Because the red and green signals arise from different binding probes (for p53 and GST A2) labeled with different fluorophores (Cy5 and Cy3), the two are not directly comparable with respect to relative quantification of the level of p53 and GST A2 amplicon on each bead. This is due to potentially different probe binding efficiencies and differences in fluorescence output and signal collection efficiencies. Therefore, for the image presented in FIG. 36A, all image intensity levels of the red channel have been scaled linearly (uniformly) for normalization, such that the maximum intensity in the red channel matched the maximum intensity in the green channel.

The raw, unmodified, non-overlaid fluorescence grayscale images were quantified by computer-assisted image analysis using the ImageQuant software package (Molecular Dynamics; Amersham Biosciences Corp., Piscataway, N.J.). Average fluorescence intensities for each bead (henceforth referred to as "bead intensity") were determined in both the red and green fluorescence channels (i.e. average fluorescence intensity over the entire area of a given individual bead). More than 700 beads were quantified for each sample permutation. The beads were scored as follows: The average bead intensity for all beads in the minus template negative control (i.e. the blank), for either the red or green fluorescence channels, was taken as the "noise" level (i.e. background) for that given channel. The signal to noise ratio for all beads in the plus template sample permutations was calculated for both the red (p53) and green (GST A2) fluorescence channels. Beads were scored positive for p53 if the red signal to noise ratio was ≧10:1. Likewise, beads were scored positive for GST A2 if the green signal to noise ratio was ≧10:1. The number of p53 positive scores and GST A2 positive scores was expressed as a percent of the total positive scores. As shown graphically in FIG. 36B, when 50:50, 75:25 and 95:5 p53:GST A2 template mixtures were used, actual ratios obtained of p53 positive scores to GST A2 positive scores were 34:66, 76:24, and 97:3 respectively, in close correlation with the added template. While the 50:50 p53:GST A2 sample deviated 16 percentage points from the expected (experimental variability), the 75:25 and 95:5 p53:GST A2 samples differed by no more than 2 percentage points, for an average deviation of 6 percentage points.

These data suggest that only 1 or a few original template molecules have been amplified per bead, otherwise, relatively constant p53:GST A2 (or visa versa) signal ratios from bead-to-bead within each sample permutation would be expected. Furthermore, if amplification of significantly more than 1 or a few original template molecules per bead was occurring, decreasing GST A2 signal to noise ratios correlating with decreasing amounts of GST A2 template across the various sample permutations would be expected. Instead, the signal to noise ratios for positively scoring GST A2 beads remains relatively constant, averaging 42:1 and 56:1 for the 50:50 and 95:5 p53:GST A2 samples respectively; despite the 10-fold decrease in overall GST A2 template amount and nearly 20-fold decrease in relative GST A2 template abundance in the 95:5 p53:GST A2 sample. While the signal to noise ratios remain constant, the number of positively scoring GST A2 beads decreases in a manner consistent with the ratio of added template.

Example 40

Effective Single Template Molecule Solid-Phase Bridge PCR: Multiplexed Cell-Free Expression with In Situ Protein Capture, Contact Photo-Transfer and Antibody Detection Preparing the Solid-Phase Bridge PCR Template DNA:
Performed as in Example 36.
Preparation of Agarose Beads Covalently Conjugated to PCR Primers Used for Solid-Phase Bridge PCR:
Performed as in Example 36.
Qualitative Analysis of Primer Attachment:
Performed as in Example 36.
First Round of Effective Single Template Molecule Solid-Phase Bridge PCR:
Performed essentially as in Example 36, with slight modifications. The full protocol was as follows: 10 μL actual bead volume of the previously prepared Primer-Conjugated Agarose Beads was used per each sample, but first, each of the 10 μL of beads was washed separately in parallel, with heating. To do so, 50 μL each of the aforementioned 20% (v/v) Primer-Conjugated Agarose Bead suspension (10 μL actual bead volume) was placed into a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness. 40 µL each of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 40 µL each of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 1×400 µL more with TE-50 mM NaCl then 1×400 µL with MBG-Water. Each set of beads was then resuspended in 50 µL MBG-Water and transferred to a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness.

Next, to pre-hybridize the template DNA to the washed Primer-Conjugated Agarose Beads, each pellet was then resuspended in 5 µL of diluted template solution, which contained no soluble primers. The p53 and GST A2 template mixture was prepared to 1 ng/µL as described in Example 36 (except 75% GST A2 and 25% p53). This template mixture was further serially diluted to 0.05 ng/µL in a commercially available pre-mixed PCR reaction solution containing everything needed for PCR except template DNA and primers (Platinum® PCR SuperMix High Fidelity; contains 22 U/mL complexed recombinant Taq DNA polymerase, $Pyrococcus$ species GB-D thermostable polymerase, Platinum® Taq Antibody, 66 mM Tris-$SO_4$ pH 8.9, 19.8 mM $(NH_4)_2SO_4$, 2.4 mM $MgSO_4$, 220 µM dNTPs and stabilizers; Invitrogen Corporation, Carlsbad, Calif.; solution used without prior dilution). This resulted in a ratio of 180 attomoles of template per µL of actual Primer-Conjugated Agarose Bead volume. With 1 µL of Primer-Conjugated Agarose Beads determined to contain approximately 1,000 beads, 180 attomoles of template per µL of beads represents a ratio of approximately 100,000 template molecules added per bead (beads physically enumerated under a microscope both in diluted droplets of bead suspension and with suspensions in a hemacytometer cell counting chamber). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing), ramp down to 59° C. at a rate of 0.1° C./sec then hold 1 hour at 59° C. (annealing/capture of template onto beads), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 µL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 µL with room temperature MBG-Water. Beads were further washed 2×400 µL for 2.5 min each with room temperature 0.1M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 100 µL of the commercial pre-mixed PCR solution (Platinum® PCR SuperMix High Fidelity; Invitrogen Corporation, Carlsbad, Calif.) which was used at 92% strength (diluted with MBG-Water) and contains all necessary components for PCR except template DNA and primers. The BODIPY-FL-dUTP labeling reagent was not used during the solid-phase bridge PCR. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before and at the end of this step), and 40 cycles of 94° C. for 30 sec (denature), 59° C. for 30 sec (anneal) and 68° C. for 2 min (extend); followed by a final extension step of 68° C. for 10 min (once).

400 µL of TE-50 mM NaCl-T (10 mM Tris, pH 8.0, 1 mM EDTA, 50 mM NaCl, 0.01% v/v Tween-20) was added to each completed solid-phase bridge PCR reaction and the suspensions transferred to fresh 0.5 mL polypropylene PCR tubes. The beads were then spun down in a micro-centrifuge (just until reaches maximum speed of ~13,000 rpm corresponding to ~16,000×g) and the fluid supernatant carefully removed. The beads were washed 3×400 µL more with TE-50 mM NaCl-T; resuspending by 5 sec vortex mixing then spinning down and discarding the fluid supernatant as above. Following the final wash, as much of the fluid supernatant as possible was removed from the bead pellet by manual pipetting, with the beads going nearly to dryness. The beads were lastly resuspended to 5% (v/v) using SP-PCR Storage Buffer (10 mM Tris, pH 8.0, 1 mM EDTA, 50 mM NaCl, all in 50% v/v glycerol). These intermediate beads could be stored at −20° C. and portions were subsequently used for a full second round of PCR thermocycling as described below.

Second Round of Solid-Phase Bridge PCR:

Performed as described in Example 36 and 37 except that a 2 µL portion of beads (actual bead volume) was used in 50 µL of the commercially available pre-mixed PCR reaction solution and without the BODIPY-FL-dUTP labeling reagent (i.e. no BODIPY-FL-dUTP labeling at any stage).

Attaching the PC-Antibody to Beads Following Solid-Phase Bridge PCR:

Following the solid-phase bridge PCR reaction, 0.5 µL actual bead volume per sample was washed briefly 3×400 µL with TE-Saline (10 mM Tris-HCl, pH 8.0, 1 mM EDTA, 200 mM NaCl). Unless otherwise noted, all washes and bead manipulations were performed in batch mode using 0.45 micron pore size, PVDF membrane, micro-centrifuge Filtration Devices to facilitate manipulation of the beaded matrix (~100 micron beads) and exchange the buffers (Ultrafree-MC Durapore Micro-centrifuge Filtration Devices, 400 µL capacity; Millipore, Billerica, Mass.). NeutrAvidin (tetrameric) was then attached to the bead bound biotin-amine linker, in excess, by treatment with 200 µL of a 0.5 µg/µL solution in TE-Saline for 20 min (note: biotin-amine linker attached during previous preparation of Primer-Conjugated Agarose Beads; see Example 36). Beads were washed briefly 4×400 µL with TE-Saline.

The beads were next coated with a monoclonal mouse anti-FLAG tag capture antibody which was converted to photocleavable form by conjugation to PC-biotin. Creation of the photocleavable antibody (PC-antibody) was performed similar to as described in Example 2. To first create the PC-antibody (prepared in advance), 1 mg of antibody as supplied by the manufacturer (Mouse Anti-FLAG M2 Antibody; Sigma-Aldrich, St. Louis, Mo.) was purified on a NAP-5 desalting column according to the manufacturer's instructions (Amersham Biosciences Corp., Piscataway, N.J.) against a 200 mM sodium bicarbonate and 200 mM NaCl buffer (nuclease-free reagents). The resultant antibody was then reacted with 25 molar equivalents of AmberGen's PC-biotin-NHS labeling reagent (added from a 50 mM stock in anhydrous DMF) for 30-60 min with gentle mixing. The labeled antibody was then purified on a NAP-10 desalting column according to the manufacturer's instructions (Amersham Biosciences Corp., Piscataway, N.J.) against TE-Saline buffer. This prepared monoclonal anti-FLAG PC-biotin conjugate was then loaded onto the beads by treatment of the beads with 250 µL of 0.15 µg/µL in TE-Saline for 20 min. Beads were washed briefly 4×400 µL in TE-Saline followed by 2×400 µL in Molecular Biology Grade Water (MBG-Water).

Multiplexed Cell-Free Expression of the Beads and In Situ Protein Capture:

The 0.5 µL bead pellets were then resuspended in 25 µL of the *E. coli* based PureSystem cell-free expression mixture (mixture prepared according to the manufacturer's instructions; Post Genome Institute Co., LTD., Japan) (no soluble DNA was included in the reaction). To disperse the beads and limit diffusion during in situ capture, the expression mixture was spread over the surface of a plain glass microscope slide and overlaid with a 18×18 mm cover glass (see Examples 25 and 26 for mechanism and details of in situ capture). In situ capture was mediated by a common N-terminal FLAG epitope tag present in all expressed proteins and the anti-FLAG PC-antibody on the beads. Expression was carried out for 45 min at 42° C. in a humidified chamber without disturbance or mixing. After expression, the microscope slide (and cover glass) "sandwich" was placed in a 50 mL polypropylene centrifuge tube and sprayed at the seam with 400 µL of ice cold PBS and 10 mM EDTA (tube kept on crushed ice-water bath during this process; bead suspension collects at tube bottom). The bead suspension was recovered into the aforementioned Filtration Devices, filtration was performed and the filtrate discarded. Beads were then washed 3×400 µL briefly with PBS then 1×400 µL with PBS and 50% (v/v) glycerol. The washed bead pellets were then resuspended to 1% beads (v/v) in PBS and 50% (v/v) glycerol.

Contact Photo-Transfer from Individually Resolved Beads:

Contact photo-transfer from individually resolved beads onto epoxy activated glass microarray substrates (slides) (SuperEpoxy substrates, TeleChem International, Inc. ArrayIt™ Division, Sunnyvale, Calif.) overlaid with a cover glass was performed as described in Example 24 with the following exceptions: 40 µL of the aforementioned 1% (v/v) bead suspension was applied to the substrate and overlaid with a 18×18 mm square cover glass (coverslip). After contact photo-transfer, washing was 3×30 sec with TBS-T only (cover glass removed) and substrates were not dried. After washing, the substrates were further processed for antibody probing as described in the following paragraphs.

Antibody Probing and Detection:

Substrates were blocked for 10 min using excess 5% BSA (w/v) in TBS-T. Substrates were then probed to detect the common C-terminal VSV epitope tag present in all expressed proteins. To do so, a commercial anti-VSV antibody conjugated to the Cy3 fluorophore was used (clone P5D4; Sigma-Aldrich, St. Louis, Mo.). The antibody was diluted 1/100 from the manufacturer's stock in 5% BSA (w/v) in TBS-T. 100 µL of diluted antibody probe was added to the substrate and overlaid with a 22×60 mm microscope cover glass. Binding was performed for 30 min at 37° C. in a humidified chamber. The substrate was then washed 4× for 30 sec each with excess TBS-T followed by 4 brief washes in purified water. The substrates were dried and then probed with a commercial anti-[mouse IgG] secondary antibody conjugated to the Alexa Fluor 488 fluorophore (Invitrogen Corporation, Carlsbad, Calif.) to detect the mouse anti-FLAG antibody present on the substrate in all contact photo-transfer spots (present regardless of the presence of cell-free expressed protein). Probing was done as above except that the antibody was diluted 1/1000 and binding was overnight at +4° C. Substrates were washed and dried as above and detection of the bound antibody probes was achieved by imaging the dry microarray substrates on an ArrayWoRx$^e$ BioChip fluorescence reader (Applied Precision, LLC, Issaquah, Wash.).

Results:

Results are shown in FIG. 37 as 2-color fluorescence image overlays for each sample. Green represents signal from the anti-[mouse IgG] secondary antibody conjugated to the Alexa Fluor 488 fluorophore which detects the mouse anti-FLAG antibody present in all contact photo-transfer spots, regardless of the presence of expressed protein. The minus template (−Template) sample permutation was prepared in the same manner as the plus template (+Template) sample permutation except that only the template DNA was omitted from the solid-phase bridge PCR reaction. The red represents signal from the anti-VSV tag antibody conjugated to the Cy3 fluorophore, which detects the common C-terminal VSV epitope tag present in both expressed proteins (p53 and GST A2). A yellow-orange color indicates binding of both fluorescent antibody probes. A representative region is shown in FIG. 37, although approximately 100 spots were analyzed for each sample. Results show that if template DNA was omitted from the solid-phase bridge PCR reaction (−Template), no detectable expressed protein is observed, but regardless, all spots are detected (green) via the contact photo-transferred anti-FLAG capture antibody originally present on all beads. Expressed protein was detectible (red) only when template DNA was included in the solid-phase bridge PCR reaction (+Template). Importantly, only a fraction of the spots contain expressed protein, suggesting that 1 or a few of the original template DNA molecules were amplified per bead.

Example 41

Effective Single Template Molecule Solid-Phase Bridge PCR: Multiplexed Cell-Free Expression with In Situ Protein Capture and On-Bead Analysis by Flow Cytometry Preparing the Solid-Phase Bridge PCR Template DNA:
Performed as in Example 36.
Preparation of Agarose Beads Covalently Conjugated to PCR Primers Used for Solid-Phase Bridge PCR:
Performed as in Example 36.
Qualitative Analysis of Primer Attachment:
Performed as in Example 36.

First Round of Effective Single Template Molecule Solid-Phase Bridge PCR:

Performed essentially as in Example 36, with slight modifications. The full protocol was as follows: 10 µL actual bead volume of the previously prepared Primer-Conjugated Agarose Beads was used per each sample, but first, each of the 10 µL of beads was washed separately in parallel, with heating. To do so, 50 µL each of the aforementioned 20% (v/v) Primer-Conjugated Agarose Bead suspension (10 µL actual bead volume) was placed into a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness. 40 µL each of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 40 µL each of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 1×400 µL more with TE-50 mM NaCl then 1×400 µL with MBG-Water. Each set of beads was then resuspended in 50 µL MBG-Water and transferred to a 0.5 mL polypropylene thin-wall PCR tube. The beads were spun down briefly in a standard micro-centrifuge (just until reaches maximum speed of ~13,000 rpm corresponding to ~16,000× g). As much of the fluid supernatant was removed as possible by manual pipetting, with the beads nearly going to dryness.

Next, to pre-hybridize the template DNA to the washed Primer-Conjugated Agarose Beads, each pellet was then resuspended in 5 µL of diluted template solution, which contained no soluble primers. The p53 and GST A2 template mixture was prepared to 1 ng/µL as described in Example 36 (except 75% GST A2 and 25% p53). This template mixture was further serially diluted to 0.05 ng/µL in a commercially available pre-mixed PCR reaction solution containing everything needed for PCR except template DNA and primers (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-$SO_4$ pH 8.9, 19.8 mM $(NH_4)_2SO_4$, 2.4 mM $MgSO_4$, 220 µM dNTPs and stabilizers; Invitrogen Corporation, Carlsbad, Calif.; solution used without prior dilution). This resulted in a ratio of 180 attomoles of template per µL of actual Primer-Conjugated Agarose Bead volume. With 1 µL of Primer-Conjugated Agarose Beads determined to contain approximately 1,000 beads, 180 attomoles of template per µL of beads represents a ratio of approximately 100,000 template molecules added per bead (beads physically enumerated under a microscope both in diluted droplets of bead suspension and with suspensions in a hemacytometer cell counting chamber). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing), ramp down to 59° C. at a rate of 0.1° C./sec then hold 1 hour at 59° C. (annealing/capture of template onto beads), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 µL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 µL with room temperature MBG-Water. Beads were further washed 2×400 µL for 2.5 min each with room temperature 0.1M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 100 µL of the commercial pre-mixed PCR solution (Platinum® PCR SuperMix High Fidelity; Invitrogen Corporation, Carlsbad, Calif.) which was used at 92% strength (diluted with MBG-Water) and contains all necessary components for PCR except template DNA and primers. The BODIPY-FL-dUTP labeling reagent was not used during the solid-phase bridge PCR. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before and at the end of this step), and 40 cycles of 94° C. for 30 sec (denature), 59° C. for 30 sec (anneal) and 68° C. for 2 min (extend); followed by a final extension step of 68° C. for 10 min (once).

400 µL of TE-50 mM NaCl-T (10 mM Tris, pH 8.0, 1 mM EDTA, 50 mM NaCl, 0.01% v/v Tween-20) was added to each completed solid-phase bridge PCR reaction and the suspensions transferred to fresh 0.5 mL polypropylene PCR tubes. The beads were then spun down in a micro-centrifuge (just until reaches maximum speed of ~13,000 rpm corresponding to ~16,000×g) and the fluid supernatant carefully removed. The beads were washed 3×400 µL more with TE-50 mM NaCl-T; resuspending by ~5 sec vortex mixing then spinning down and discarding the fluid supernatant as above. Following the final wash, as much of the fluid supernatant as possible was removed from the bead pellet by manual pipetting, with the beads going nearly to dryness. The beads were lastly resuspended to 5% (v/v) using SP-PCR Storage Buffer (10 mM Tris, pH 8.0, 1 mM EDTA, 50 mM NaCl, all in 50% v/v glycerol). These intermediate beads could be stored at −20° C. and portions were subsequently used for a full second round of PCR thermocycling as described below.

Second Round of Solid-Phase Bridge PCR:

Performed as described in Example 36 and 37 except that a 2 µL portion of beads (actual bead volume) was used in 50 µL of the commercially available pre-mixed PCR reaction solution and without the BODIPY-FL-dUTP labeling reagent (i.e. no BODIPY-FL-dUTP labeling at any stage).

Attaching the PC-Antibody to Beads Following Solid-Phase Bridge PCR:

Beads following the solid-phase bridge PCR reaction were used as the test samples (−Template and +Template permutations) and, in addition, primer coated beads that were not subjected to the solid-phase bridge PCR reaction were used to generate the positive control. In all cases, 1 µL actual bead volume per sample was washed briefly 3×400 µL with TE-T [10 mM Tris-HCl, pH 8.0, 1 mM EDTA, 50 mM NaCl and 0.01% Tween-20 (v/v)]. Unless otherwise noted, all washes and bead manipulations were performed in batch mode using 0.45 micron pore size, PVDF membrane, micro-centrifuge Filtration Devices to facilitate manipulation of the beaded matrix (~100 micron beads) and exchange the buffers (Ultrafree-MC Durapore Micro-centrifuge Filtration Devices, 400 µL capacity; Millipore, Billerica, Mass.). NeutrAvidin (tetrameric) was then attached to the bead bound biotin-amine linker, in excess, by treatment with 200 µL of a 0.5 µg/µL solution in TE-T for 20 min (note: biotin-amine linker attached during previous preparation of Primer-Conjugated Agarose Beads; see Example 36). Beads were washed briefly 4×400 µL with TE-Saline (10 mM Tris-HCl, pH 8.0, 1 mM EDTA and 200 mM NaCl.

The beads were next coated with a monoclonal mouse anti-FLAG tag capture antibody which was converted to photocleavable form by conjugation to PC-biotin. The antibody was additionally labeled with fluorescence to allow tracking of all beads, independent of the presence of expressed protein (see later in this Example). To first create the fluorescently labeled PC-antibody (prepared in advance), 1 mg of antibody as supplied by the manufacturer (Mouse Anti-FLAG M2 Antibody; Sigma-Aldrich, St. Louis, Mo.) was purified on a NAP-10 desalting column according to the manufacturer's instructions (Amersham Biosciences Corp., Piscataway, N.J.) against a 200 mM sodium bicarbonate and 200 mM NaCl buffer (nuclease-free reagents). 1 mL of the antibody elutate at 0.6 µg/µL was labeled by adding 2 molar equivalents of a commercial Alexa Fluor 488 TFP labeling reagent (Invitrogen Corporation, Carlsbad, Calif.) added from a 12.5 mM stock in dimethylformamide (DMF). The reaction was carried out for 30 min with gentle mixing. The antibody was then reacted with 20 molar equivalents of AmberGen's PC-biotin-NHS labeling reagent (added from a 50 mM stock in anhydrous DMF) for 30 min with gentle mixing. The labeled antibody was then purified on a NAP-10 desalting column according to the manufacturer's instructions (Amersham Biosciences Corp., Piscataway, N.J.) against TBS. This prepared monoclonal anti-FLAG PC-biotin fluorescent conjugate was then loaded onto the beads by treatment of the beads with 250 µL of 0.04 µg/µL in TE-Saline for 20 min. Beads were washed briefly 4×400 µL in TE-Saline followed by 2×400 µL in Molecular Biology Grade Water (MBG-Water).

Multiplexed Cell-Free Expression of the Beads and In Situ Protein Capture:

For the test samples (−Template and +Template solid-phase bridge PCR permutations), the 1 µL bead pellets were then resuspended in 25 µL of the *E. coli* based PureSystem cell-free expression mixture (mixture prepared according to the manufacturer's instructions; Post Genome Institute Co., LTD., Japan) (no soluble DNA was included in the reaction except for the positive control sample; see below). To disperse the beads and limit diffusion during in situ capture, the expression mixture was spread over the surface of a plain glass microscope slide and overlaid with a 18×18 mm cover glass (see Examples 25 and 26 for mechanism and details of in situ capture). In situ capture was mediated by a common N-terminal FLAG epitope tag present in all expressed proteins and the fluorescent anti-FLAG PC-antibody on the beads. Expression was carried out for 1 hr at 42° C. in a humidified chamber without disturbance or mixing. After expression, the microscope slide (and cover glass) "sandwich" was placed in a 50 mL polypropylene centrifuge tube and sprayed at the seam with 400 µL of ice cold 5% BSA (w/v) in TBS-T (tube kept on crushed ice-water bath during this process; bead suspension collects at tube bottom). The bead suspension was recovered into the aforementioned Filtration Devices, filtration was performed and the filtrate discarded. Beads were then further washed 2×400 µL briefly and 1×400 µL for 10 min in 5% BSA (w/v) in TBS-T.

The positive control beads, which were not previously subjected to solid-phase bridge PCR, but were coated with PC-antibody as detailed earlier in this Example, were expressed similarly as above except: Expression was not performed on a glass microscope slide but in a tube (with mixing) by adding approximately 200 ng of the GST A2 soluble template DNA (see Example 36 for soluble GST A2 template DNA). Positive control beads were then simply washed 1×400 µL with the ice cold 5% BSA (w/v) in TBS-T using the Filtration Devices then further washed 2×400 µL briefly and 1×400 µL for 10 min in 5% BSA (w/v) in TBS-T.

Antibody Probing and Detection:

The beads were then probed to detect the common C-terminal VSV epitope tag present in all expressed proteins. To do so, a commercial anti-VSV antibody conjugated to the Cy3 fluorophore was used (clone P5D4; Sigma-Aldrich, St. Louis, Mo.). The antibody was diluted ½₅₀ from the manufacturer's stock in 5% BSA (w/v) in TBS-T. 250 µL of diluted antibody probe was used to resuspend the washed bead pellets and binding was performed for 1 hr at 37° C. with mixing. Beads were washed briefly 3×400 µL in TBS-T the 2×400 µL in PBS. Beads were then recovered from the Filtration Devices in 25 µL of PBS and analyzed in a BD FACSArray (BD Biosciences, San Jose, Calif.) flow cytometer.

Results:

Results are shown graphically in FIG. 38, whereby the X-axis is the intensity of the Cy3 labeled anti-VSV tag detection antibody and the Y-axis the side-scatter (detection of all beads based on light scattering). Based on the side-scatter, beads are identified in the lower left and lower right quadrants of each plot in FIG. 38, regardless of fluorescence intensity. The minus template (−Template) sample permutation was prepared in the same manner as the plus template (+Template) sample permutation except that only the template DNA was omitted from the solid-phase bridge PCR reaction. The positive control sample did not utilize solid-phase bridge PCR to generate the expressible DNA, but instead used soluble PCR product for cell-free expression (did use capture on antibody coated beads) (for details see "Attaching the PC-Antibody to Beads Following Solid-Phase Bridge PCR" and "Multiplexed Cell-Free Expression of the Beads and In Situ Protein Capture" sub-sections earlier in this Example). Beads were scored positive for detection with the Cy3 labeled anti-VSV tag antibody if the fluorescence intensity was sufficient such that they fell within the lower right quadrant of the plots in FIG. 38. The fluorescence intensity threshold was set based on the positive control, such that the percent of positive beads in that sample was 20-fold greater than the percent of positive beads in the minus template negative control sample (−Template). In other words, the threshold was set to yield a 20:1 signal to noise ratio for the positive control sample. Based on these criteria, 4% of the beads scored as positive in the plus template test sample (+Template) while 2% scored positive in the minus template negative control sample (−Template) for a 2:1 signal to noise ratio. Importantly, only a fraction of the beads contain expressed protein, suggesting that 1 or a few of the original template DNA molecules were amplified per bead. This Example is similar to the previous Example 40 except that here, final analysis directly on the beads via flow cytometry is demonstrated.

Example 42

Contact Photo-Transfer for Molecular Diagnostic Assays: Cell-Free Expression of the APC Gene Associated with Colorectal Cancer Followed by a Microarray Protein Truncation Test Based on Fluorescence Antibody Detection Preparation of a Photocleavable Antibody Affinity Matrix:

A polyclonal rabbit anti-HSV epitope tag capture antibody (Bethyl Laboratories, Montgomery, Tex.) was converted to photocleavable form by conjugation to photocleavable biotin (PC-biotin) as described in Example 31. The resultant photocleavable antibody (PC-antibody) was then loaded onto a beaded affinity matrix. The following procedures, unless otherwise noted, were performed in batch mode using Filtration Devices to facilitate manipulation of the beaded matrix (~100 micron beads), perform washes and otherwise exchange the buffers (Filtration Devices=Ultrafree-MC Durapore Microcentrifuge Filtration Devices, 400 µL capacity, PVDF filtration membrane, 0.45 micron pore size; Millipore, Billerica, Mass. distributed by Sigma-Aldrich, St. Louis, Mo.). Unless otherwise stated, all washes of the affinity matrix were by brief (~5 sec) vortex mixing in the Filtration Device, spinning down briefly in a micro-centrifuge (just until reaches maximum speed of ~13,000 rpm corresponding to ~16,000×g) and discarding the filtrate. 4 µL packed volume of NeutrAvidin biotin binding agarose beads (Pierce Biotechnology, Inc., Rockford, Ill.) was washed 3×400 µL with TE-Saline (10 mM Tris-HCl, pH 8.0, 1 mM EDTA, 200 mM NaCl). Beads were then resuspended in 100 µL of 0.2 µg/µL PC-antibody in TE-Saline. Binding was allowed to occur for 20 min with gentle mixing. Beads were then washed 3×400 µL with TE-Saline and 1×400 µL with TE-Saline-T [10 mM Tris-HCl, pH 8.0, 1 mM EDTA, 200 mM NaCl, 0.1% (v/v) Tween-20]. Beads were then recovered from the Filtration Devices in 40 µL total by re-suspension in TE-Saline-T. The resultant 10% (v/v) PC-antibody beads were used immediately for capture of cell-free expressed proteins (see later in this Example).

PCR Amplification of an APC Segment from Genomic DNA:

So-called segment 3 of either the wild-type or mutant APC gene was amplified by PCR on genomic DNA from cell-lines as described in Example 28 and reported by AmberGen in the scientific literature [Gite et al. (2003) Nat Biotechnol 21, 194-197]. The mutant APC gene contains a truncation mutation (nonsense mutation), in segment 3, that results in a truncated protein product upon translation.

Cell-Free Expression:

The PCR amplified APC segment 3 was expressed in a cell-free translation reaction as described by AmberGen in the scientific literature [Gite et al. (2003) *Nat Biotechnol* 21, 194-197].

Capture of the Cell-Free Expressed APC Segment on the Photocleavable Antibody Affinity Matrix:

Following cell-free protein expression, 25 µL of the reaction mixture was mixed with equal volume of Translation Dilution Buffer (TDB) [2×PBS pH 7.5, 0.4% (v/v) of a mammalian protease inhibitor cocktail (cocktail in DMSO, Sigma-Aldrich Corp., St. Louis, Mo.) and 20 mM EDTA added from a 500 mM pH 8.0 stock]. The samples were gently mixed for 10 min, supplemented with a final 0.1% (v/v) Tween-20 from a 10% (v/v) stock and mixed for an additional 5 min. The samples were clarified by spinning on a microcentrifuge for 1 min (~13,000 rpm corresponding to ~16,000×g) and subsequently collecting the supernatant. 10 µL of the aforementioned prepared 10% (v/v) PC-antibody beads was then added to each sample (1 µL packed bead volume) and mixed for 30 min gently. Beads were then washed 3×400 µL with PBS and 1×400 µL with 50% glycerol (v/v) in PBS using the aforementioned Filtration Devices. Beads were resuspended to 1% (v/v) with 50% glycerol (v/v) in PBS. Beads could be stored for at least 2 days at −20° C. in this buffer.

Contact Photo-Transfer from Individually Resolved Beads:

Contact photo-transfer from individually resolved beads onto epoxy activated glass microarray substrates (slides) (SuperEpoxy substrates, TeleChem International, Inc. ArrayIt™ Division, Sunnyvale, Calif.) overlaid with a cover glass was performed as described in Example 24 with the following exceptions: 50 µL of the aforementioned 1% (v/v) bead suspension was applied to the substrate and overlaid with a 18×18 mm square cover glass (coverslip). After contact photo-transfer, TBS-T washes were 2×2 min (cover glass removed). After washing and drying, the substrates were further processed for antibody probing as described in the following paragraphs.

Antibody Probing and Detection:

Substrates were blocked for 10 min using excess 5% BSA (w/v) in TBS-T. Substrates were then probed to detect the N-terminal VSV epitope tag (YTDIEMNRLGK [SEQ NO. 33]), present in all APC segment 3 protein products, as well as a C-terminal p53-derived epitope tag (TFSDLHKLL [SEQ NO. 34]), present only in non-truncated (full-length) APC segment 3 protein products. To do so, a commercial anti-VSV antibody conjugated to the Cy3 fluorophore (clone P5D4; Sigma-Aldrich, St. Louis, Mo.) and an in-house prepared anti-p53 antibody conjugated to the Cy5 fluorophore (Example 26) were used. Both antibodies were added to the same solution for dual simultaneous probing. The anti-VSV-Cy3 antibody was diluted 1/500 and the anti-p53-Cy5 antibody 1/50 with 5% BSA (w/v) in TBS-T. 100 µL of the antibody probing solution was added to the substrate and overlaid with a 22×60 mm microscope cover glass. Binding was performed for 30 min at 37° C. in a humidified chamber. The substrate was then washed 3× for 2 min each with excess TBS-T followed by 4 brief washes in purified water. The substrates were dried and detection of the bound antibody probes was achieved by imaging the dry microarray substrates on an ArrayWoRx$^e$ BioChip fluorescence reader (Applied Precision, LLC, Issaquah, Wash.).

Results:

Results are shown in FIG. 39A as 2-color fluorescence image overlays for each sample permutation. Green corresponds to signal from the anti-VSV-Cy3 N-terminal epitope tag antibody and red the anti-p53-Cy5 C-terminal epitope tag antibody. The yellow-orange color indicates the presence of both the green and red signals in the 2-color fluorescence image overlay. The minus DNA (−DNA) sample permutation is identical to the other sample permutations except that expressible APC DNA was omitted from the cell-free translation reaction. Qualitatively, as expected, the APC wild-type (APC WT) shows signals for both the N- and C-terminal epitope tags (green and red), while the APC mutant (i.e. truncated) shows only the N-terminal signal (green only).

For more precise data interpretation, the non-overlaid raw fluorescence grayscale images were quantified by computer-assisted image analysis using the ImageQuant software package (Molecular Dynamics; Amersham Biosciences Corp., Piscataway, N.J.). Average fluorescence intensities for each spot (henceforth referred to as "spot intensity") were determined in both the green and red fluorescence channels (i.e. average fluorescence intensity over the entire area of a given individual spot). More than 300 spots were quantified for each sample permutation (except the –DNA negative control where no discrete spots were discernable). Using these data, without background subtraction, the C-terminal to N-terminal ratios (so-called C:N ratio) for each spot were calculated (i.e. ratio of red to green spot intensities) and averaged. The data were uniformly normalized to such that the C:N ratio of the APC wild-type (APC WT) was set to 100%. As shown graphically in FIG. 39B, the average C:N ratio of the APC WT was 100±12% and the APC mutant 5±1%, a 20-fold difference. N-terminal signal to noise ratios were an average 186:1 and 246:1 for the APC WT and APC mutant respectively. C-terminal signal to noise ratios were an average 21:1 and 1:1 for the APC WT and APC mutant respectively.

Example 43

Solid-Phase Bridge PCR on the APC Gene Associated with Colorectal Cancer: Cell-free Expression and Contact Photo-Transfer Followed by a Microarray Protein Truncation Test Based on Fluorescence Antibody Detection This Example is similar to the previous Example 42, except that solid-phase bridge PCR was used to generate the expressible APC DNA. The beads carrying the APC solid-phase bridge PCR product (amplicon) were coated with a photocleavable antibody (PC-antibody) for downstream protein capture, the beads then used directly in a cell-free expression reaction and translated APC proteins were captured onto the same beads via the PC-antibody. Contact photo-transfer was then performed to fabricate random microarrays and the resultant spots were then probed with fluorescent antibodies against N- and C-terminal epitope tags, which can allow detection of truncated APC protein products as shown previously in Example 42.

The integration of solid-phase bridge PCR into this process affords several advantages, including but not limited to: a) The ability to multiplex, in a single solid-phase bridge PCR reaction, the amplification of various APC segments (e.g. different exons or fragments there of) or b) the ability to perform amplification of 1 or a few APC template molecules per each bead, in order to facilitate for example, high sensitivity detection of a few mutant APC template molecules in the presence of an excess of wild-type APC template molecules, based on a single solid-phase bridge PCR reaction. These processes are not intended to be limited to the APC gene, but are applicable to other nucleic acid sequences.

Preparing the Solid-Phase Bridge PCR Template DNA:

Note: All buffers and reagents used throughout this entire Example, unless otherwise noted, were minimally DNAse, RNAse and protease free, referred to as Molecular Biology Grade (MBG), including the water, referred to as MBG-Water.

Soluble wild-type (WT) and mutant (nonsense, i.e. truncation) versions of APC segment 3, of approximately 1.7 kb in size, were produced from cell-line genomic DNA as described in Example 28 and as described by AmberGen in the scientific literature [Gite et al. (2003) *Nat Biotechnol* 21, 194-197]. This DNA product was further amplified using standard solution-phase PCR practices using the following APC-specific primer set (APC-specific hybridizing sequences are bracketed and the remaining sequences are a portion of those necessary for efficient cell-free expression and incorporation of epitope tags. The remaining sequences needed for efficient cell-free expression and incorporation of epitope tags are introduced via the solid-phase bridge PCR primers used later):

Forward Primer:
[SEQ NO. 35]
5'ATgAACCgCCTgggCAAgggAggAggAggACAgCCTgAACTCgCTC
CAgAggATCCggAAgAT[CAggAAgCAgATTCTgCTAAT]3'

Reverse Primer:
[SEQ NO. 36]
5'TTACAgCAgCTTgTgCAggTCgCTgAAggT[gggTgTCTgAgCACC
ACTTTT]3'

This resulted in a 321 bp APC product, from within the so-called APC mutation cluster region (MCR), that was used (without purification) as the template for solid-phase bridge PCR. The 321 bp product covers APC codons 1,294-1,369 with the truncation mutation located at site 1,338 (CAg→TAg).

Preparation of Agarose Beads Covalently Conjugated to PCR Primers Used for Solid-Phase Bridge PCR:

Performed as in Example 36 except that 25 µM final concentration of each primer was used and 90 µL of the primer solution (containing 25 µM each primer) was added to 50 µL packed bead volume for attachment (12 µM final of the Biotin-Amine Linker was used as in Example 36). Sequences of the 5' primary amine modified (6 carbon spacer) primers used for attachment to the beads were as follows:

Forward Primer:
[SEQ NO. 37]
5'[Amine]TAATACgACTCACTATAgggAgAggAggTATATCAATg
TACACCgACATCgAgATgAACCgCCTgggCAAgggAggAggAggA3'

Reverse Primer:
[SEQ NO. 38]
5'[Amine]TTACAgCAgCTTgTgCAggTCgCTgAAggTgggTgTCTgA
gCACCACTTTT3'

Based on the primers used, the final APC solid-phase bridge PCR product (on the beads) would contain additional untranslated sequences for efficient cell-free expression as well as sequences for epitope tags. Specifically, an N-terminal VSV epitope tag (YTDIEMNRLGK [SEQ NO. 39]) for detection, followed by a 4 glycine spacer, an N-terminal HSV epitope tag (QPELAPEDPED [SEQ NO. 40]) for protein capture and a C-terminal p53-derived epitope tag (TFSDLH-KLL [SEQ NO. 41]) for detection. The N- and C-terminal epitope tags flank the APC gene fragment insert.

Qualitative Analysis of Primer Attachment:
Performed as in Example 36.

First Round of Solid-Phase Bridge PCR:
Performed essentially as in Example 36, with slight modifications. The full protocol was as follows: 5 µL actual bead volume of the previously prepared Primer-Conjugated Agarose Beads was used per each sample, but first, each of the 5 µL of beads was washed separately in parallel, with heating. To do so, 25 µL each of the aforementioned 20% (v/v) Primer-Conjugated Agarose Bead suspension (5 µL actual bead volume) was placed into a 0.5 mL polypropylene thin-wall PCR tube. The beads were spun down briefly in a standard microcentrifuge (just until reaches maximum speed of ~13,000 rpm corresponding to ~16,000×g). As much of the fluid supernatant was removed as possible by manual pipetting, with the beads nearly going to dryness. 20 µL, each of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 20 µL each of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 1×400 µL more with TE-50 mM NaCl then 1×400 µL with MBG-Water. Each set of beads was then resuspended in 50 µL MBG-Water and transferred to a 0.5 mL polypropylene thin-wall PCR tube. The beads were spun down briefly in a standard micro-centrifuge (just until reaches maximum speed of ~13,000 rpm corresponding to ~16,000× g). As much of the fluid supernatant was removed as possible by manual pipetting, with the beads nearly going to dryness.

Next, to pre-hybridize the template DNA to the washed Primer-Conjugated Agarose Beads, each pellet was then resuspended in 2.5 µL of diluted template solution, which contained no soluble primers. The APC template was prepared to 0.16 ng/µL at a 75% wild-type and 25% mutant mixture. The template was prepared in a commercially available pre-mixed PCR reaction solution containing everything needed for PCR except template DNA and primers (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-$SO_4$ pH 8.9, 19.8 mM $(NH_4)_2SO_4$, 2.4 mM $MgSO_4$, 220 µM dNTPs and stabilizers; Invitrogen Corporation, Carlsbad, Calif.; solution used without prior dilution). This resulted in a ratio of 400 attomoles of template per µL of actual Primer-Conjugated Agarose Bead volume. With 1 µL of Primer-Conjugated Agarose Beads determined to contain approximately 1,000 beads, 400 attomoles of template per µL of beads represents a ratio of roughly 200,000 template molecules added per bead (beads physically enumerated under a microscope both in diluted droplets of bead suspension and with suspensions in a hemacytometer cell counting chamber). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing), ramp down to 55° C. at a rate of 0.1° C./sec then hold 1 hour at 55° C. (annealing/capture of template onto beads), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 µL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 µL with room temperature MBG-Water. Beads were further washed 2×400 µL for 2.5 min each with room temperature 0.1M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 100 µL of the commercial pre-mixed PCR solution (Platinum® PCR SuperMix High Fidelity; Invitrogen Corporation, Carlsbad, Calif.) which was used at 92% strength (diluted with MBG-Water) and contains all necessary components for PCR except template DNA and primers. The BODIPY-FL-dUTP labeling reagent was not used in the solid-phase bridge PCR reaction. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before and at the end of this step), and 40 cycles of 94° C. for 30 sec (denature), 59° C. for 30 sec (anneal) and 68° C. for 2 min (extend); followed by a final extension step of 68° C. for 10 min (once).

400 µL of TE-50 mM NaCl-T (10 nM Tris, pH 8.0, 1 mM EDTA, 50 mM NaCl, 0.01% v/v Tween-20) was added to each completed solid-phase bridge PCR reaction and the suspensions transferred to the aforementioned Filtration Devices for washing. The beads were washed 3×400 µL with the TE-50 mM NaCl-T then 3×400 µL with MBG-Water; resuspending by ~5 sec vortex mixing then performing filtration and discarding the filtrate. The washed beads were immediately used for a full second round of PCR thermocycling as described below.

Second Round of Solid-Phase Bridge PCR:

Performed as described in Example 37 except that the washed bead pellets from above, still in their Filtration Devices, were directly resuspended in the solid-phase bridge PCR reaction mixture and transferred to 0.5 mL thin-walled polypropylene PCR tubes for thermocycling.

Attaching the PC-Antibody to Beads Following Solid-Phase Bridge PCR:

Following completion of the solid-phase bridge PCR, NeutrAvidin and then a photocleavable antibody (PC-antibody) were loaded onto the beads. This was performed as described in Example 40 with the following exceptions. 2 µL packed bead volume per sample was used and was pre-washed only 2×400 µL with TE-Saline (10 mM Tris-HCl, pH 8.0, 1 mM EDTA, 200 mM NaCl) instead of 3×. NeutrAvidin was used at 0.2 µg/µL instead of 0.5 µg/µL. Instead of coating with an anti-FLAG capture antibody, the beads were coated with a polyclonal rabbit anti-HSV tag capture antibody (Bethyl Laboratories, Montgomery, Tex.) which was converted to photocleavable form by conjugation to PC-biotin. Creation of the photocleavable antibody (PC-antibody) was performed as described in Example 31. The PC-antibody as added at 0.1 µg/µL (100 µL/sample) and binding was allowed to occur for 30 min. In addition to the washes described in Example 40, the beads were finally washed additionally 1×400 µL with 50% glycerol in TE (10 mM Tris-HCl, pH 8.0, 1 mM EDTA) and resuspended to 4% (v/v) beads in the same buffer. Beads were stored overnight at −20° C. prior to continuation of the procedure as described below.

Multiplexed Cell-Free Expression of the Beads and In Situ Protein Capture:

Performed as in Example 40 with the following exceptions: The stored beads from above (1 μL packed volume) were first pre-washed, prior to expression, 2×400 μL in MBG-Water using the Filtration Devices (see Example 40 for washing with Filtration Devices). The expression reaction was carried out for 60 min at 37° C. After expression, the beads were initially recovered in 400 μL of ice cold PBS and 10 mM EDTA as in Example 40 except the buffer was additionally supplemented with 0.05% (v/v) Tween-20. The washed bead pellets were ultimately resuspended to 1.25% beads (v/v) in PBS and 50% (v/v) glycerol prior to performing contact photo-transfer, instead of 1% (v/v) beads.

Contact Photo-Transfer from Individually Resolved Beads:

Performed as in Example 40 except that the 1.25% (v/v) beads suspension was used for contact photo-transfer.

Antibody Probing and Detection:

Performed as in Example 42 except: The anti-VSV-Cy3 antibody was diluted 1/100 and the anti-p53-Cy5 antibody 1/100, instead of 1/500 and 1/50 respectively. After antibody probing, the TBS-T washes were for 30 sec each instead of 2 min each.

Results:

Results are shown in FIG. 40 as non-overlaid fluorescence grayscale images of the same microarray region for each sample permutation. Qualitatively, it is observed that both the C-terminal p53-derived and the N-terminal VSV epitope tags are detectible in each contact photo-transferred spot, only in the sample permutation where template DNA was included in the solid-phase bridge PCR reaction (+Template). If only the template DNA was omitted at the level of the solid-phase bridge PCR reaction, neither epitope tag is detected at the protein level on the contact photo-transfer microarray (-Template). The wild-type (WT) and mutant (truncated) APC protein products were not measurably segregated on different beads (spots), hence the detection of both epitope tags in each spot. This data therefore suggests significantly more than 1 or few original template DNA molecules were amplified per bead during solid-phase bridge PCR, with this particular experimental setup. This APC experimental system is comprised of a different template species and a different primer pair compared to the p53-GST A2 solid-phase bridge PCR system used in Examples 36-41, and additionally used altered solid-phase bridge PCR conditions relative to the p53-GST A2 system (e.g. longer primers with different $T_m$ values and lower temperature during initial template capture step). Therefore, the added template:bead ratio needed to achieve amplification of 1 or few original template DNA molecules per bead is significantly different, as evidenced in the subsequent Example 44.

The images were quantified by computer-assisted image analysis using the ImageQuant software package (Molecular Dynamics; Amersham Biosciences Corp., Piscataway, N.J.). Average fluorescence intensities for each spot (henceforth referred to as "spot intensity") were determined in both fluorescence channels (i.e. average fluorescence intensity over the entire area of a given individual spot). More than 300 spots were quantified in the plus template (+Template) sample permutation. Average signal to noise ratios were 3±1:1 and 179±29:1 for the C-terminal p53-derived and the N-terminal VSV epitope tags respectively.

Example 44

Effective Single Template Molecule Solid-Phase Bridge PCR on the APC Gene Associated with Colorectal Cancer: Validation of Effective Amplification of Single Template Molecules per Bead Using 2 Template Species and a Single-Base Extension Reaction as the Ultimate Assay Preparing the Solid-Phase Bridge PCR Template DNA:

Note: All buffers and reagents used throughout this entire Example, unless otherwise noted, were minimally DNAse, RNAse and protease free, referred to as Molecular Biology Grade (MBG), including the water, referred to as MBG-Water.

Templates used for solid-phase bridge PCR were generated via initial standard solution-phase PCR. A segment of Exon 15 of the human APC gene (codons 1,294-1,369) (see GeneBank M74088 for full APC open reading frame) was amplified using solution-phase PCR with gene-specific primers, essentially via standard PCR and molecular biology practices. For the solution-phase PCR, genomic DNA from the HeLa cell line was used as the wild-type template and genomic DNA from the SW480 colorectal cancer cell line as mutant template. The SW480 cell line possesses a nonsense mutation (CAg→TAg) in the APC gene at codon 1,338 resulting in a truncated gene product (protein) upon expression. Isolation of genomic DNA from cultured cells and solution-phase PCR amplification of the human APC gene was essentially performed as reported by AmberGen in the scientific literature [Gite et al. (2003) *Nat Biotechnol* 21, 194-197] with the following exceptions: PCR primers used in this Example are listed below this paragraph. In the primers below, the bracketed sequences indicate the gene-specific hybridization regions, while the remaining sequences are non-hybridizing regions which act as common universal sequences, flanking the gene fragment, to which the subsequent solid-phase bridge PCR primers are directed (the non-hybridizing regions also correspond to partial elements needed for later cell-free protein expression as well as epitope tag detection; the remaining portion of these elements are introduced via the solid-phase bridge PCR primers detailed later in this Example). 0.1 μM of each primer was used and the PCR system was a commercially available pre-mixed PCR reaction solution containing everything needed for PCR except template DNA and primers (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-SO$_4$ pH 8.9, 19.8 mM (NH$_4$)$_2$SO$_4$, 2.4 mM MgSO$_4$, 220 μM dNTPs and stabilizers; Invitrogen Corporation, Carlsbad, Calif.; solution used at 90% strength). The following thermocycling steps were used: Initially 94° C. 2 min (once) and then 35 cycles of 94° C. 30 s, 60° C. 30 s and 68° C. 30 s, followed by a final 68° C. 5 min (once).

```
Solution-Phase PCR APC Forward Primer:
                                          [SEQ NO. 42]
5'ATgAACCgCCTgggCAAgggAggAggAggACAgCCTgAACTCgCTCCA
gAggATCCggAAgAT[CAggAAgCAgATTCTgCTAAT]3'

Solution-Phase PCR APC Reverse Primer:
                                          [SEQ NO. 43]
5'TTACAgCAgCTTgTgCAggTCgCTgAAggT[gggTgTCTgAgCACCAC
TTTT]3'
```

Following the solution-phase PCR, the products were analyzed by standard agarose gel electrophoresis and ethidium bromide staining to ensure a single band was produced and of the correct molecular weight. Based on the primers used, the PCR products are 321 bp. The PCR products were then purified by agarose gel electrophoresis. These purified PCR products subsequently served as template DNA for the solid-phase bridge PCR reactions described later in this Example.

Preparation of Agarose Beads Covalently Conjugated to PCR Primers Used for Solid-Phase Bridge PCR:

Performed as in Example 36 with the following exceptions: PCR primers used in this Example are listed below this paragraph. In the primers below, the bracketed sequences indicate the template-specific hybridization regions, while the remaining sequences are non-hybridizing regions which correspond to the remaining portions of the elements needed for later cell-free protein expression as well as epitope tag detection (the initial portion of these elements was introduced during the template preparation earlier in this Example). During conjugation to the beads, concentration of each primer was 29 µM instead of 125 µM.

```
Solid-Phase Bridge PCR APC Forward Primer:
                                        [SEQ NO. 44]
5'[Amine]TAATACgACTCACTATAgggAgAggAggTATATCAATgTAC
ACCgACATCgAg[ATgAACCgCCTgggCAAgggAggAggAggA]3'

Solid-Phase Bridge PCR APC Reverse Primer:
                                        [SEQ NO. 45]
5'[Amine]TTTTTTTTTTTTTTTTTTATTATCCTCCTCCTgCgTAgT
CTggTACgTCgTATgggTA[CAgCAgCTTgTgCAggTCgCTgAAggTgg]
3'
```

Qualitative Analysis of Primer Attachment:

Performed as in Example 36.

First Round of Effective Single Template Molecule Solid-Phase Bridge PCR:

Performed essentially as in Example 36, with slight modifications. The full protocol was as follows: 10 µL actual bead volume of the previously prepared Primer-Conjugated Agarose Beads was used per each sample, but first, each of the 10 µL of beads was washed separately in parallel, with heating. To do so, 50 µL each of the aforementioned 20% (v/v) Primer-Conjugated Agarose Bead suspension (10 µL actual bead volume) was placed into a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness. 40 µL each of TE-50 mM NaCl (10 mM Tris, pH 8.0, 1 mM EDTA, 50 mM NaCl) was added to the pellet, to bring the volume back to the original 20% beads (v/v). The beads were briefly vortex mixed then spun down and all fluid removed as described before. 40 µL each of TE-50 mM NaCl was again added to the pellet as above and the tube placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 1×400 µL more with TE-50 mM NaCl then 1×400 µL with MBG-Water. Each set of beads was then resuspended in 50 µL MBG-Water and transferred to a 0.5 mL polypropylene thin-wall PCR tube. The beads were spun down briefly in a standard micro-centrifuge (just until reaches maximum speed of ~13,000 rpm corresponding to ~16,000× g). As much of the fluid supernatant was removed as possible by manual pipetting, with the beads nearly going to dryness.

Next, to pre-hybridize the template DNA to the washed Primer-Conjugated Agarose Beads, each pellet was then resuspended in 5 µL of diluted template solution, which contained no soluble primers. The aforementioned APC template, prepared as described in this Example, was diluted to $8 \times 10^{-7}$ ng/µL, mixed at a ratio of 50% wild-type (WT) and 50% mutant APC. The template was prepared in a commercially available pre-mixed PCR reaction solution containing everything needed for PCR except template DNA and primers (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-$SO_4$ pH 8.9, 19.8 mM $(NH_4)_2SO_4$, 2.4 mM $MgSO_4$, 220 µM dNTPs and stabilizers; Invitrogen Corporation, Carlsbad, Calif.; solution used without prior dilution). This resulted in a ratio of 0.002 attomoles of template per µL of actual Primer-Conjugated Agarose Bead volume. With 1 µL of Primer-Conjugated Agarose Beads determined to contain approximately 1,000 beads, 0.002 attomoles of template per µL of beads represents a ratio of approximately 1 template molecule added per bead (beads physically enumerated under a microscope both in diluted droplets of bead suspension and with suspensions in a hemacytometer cell counting chamber). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C. and no mineral oil used): 5 min 95° C. (denaturing), ramp down to 55° C. at a rate of 0.1° C./sec then hold 1 hour at 55° C. (annealing/capture of template onto beads), 10 min 68° C. (fully extend any hybridized template-primer complexes once; no mixing). Immediately upon completion of the previous steps above, while the tubes were still at 68° C., the tubes were immediately transferred from the PCR machine to a crushed ice water bath. 400 µL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 µL with room temperature MBG-Water. Beads were further washed 2×400 µL for 2.5 min each with room temperature 0.1M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 100 µL of the commercial pre-mixed PCR solution (Platinum® PCR SuperMix High Fidelity; Invitrogen Corporation, Carlsbad, Calif.) which was used at 92% strength (diluted with MBG-Water) and contains all necessary components for PCR except template DNA and primers. The solid-phase bridge PCR reaction was further supplemented with 0.15 U/µL final of additional PlatinumTaq DNA Polymerase High Fidelity added from a 5 U/µL manufacturer's stock (Invitrogen Corporation, Carlsbad, Calif.). The BODIPY-FL-dUTP labeling reagent was not used in the solid-phase bridge PCR reaction. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 94° C. for 2 min (once) (beads were briefly resuspended by gentle vortex mixing just before this step), and 35 cycles of 94° C. for 1 min (denature), 68° C. for 2 min (anneal and extend); followed by a final extension step of 68° C. for 10 min (once).

400 μL of TE-50 mM NaCl (10 mM Tris, pH 8.0, 1 mM EDTA, 50 mM NaCl) was added to each completed solid-phase bridge PCR reaction and the suspensions transferred to Filtration Devices (Ultrafree-MC Durapore Micro-centrifuge Filtration Devices, 400 μL capacity; Millipore, Billerica, Mass.). Filtration was performed in a micro-centrifuge (just until reaches maximum speed of ~13,000 rpm corresponding to ~16,000×g) and the filtrate discarded. The beads were washed 3×400 μL more with TE-50 mM NaCl; resuspending by ~5 sec vortex mixing then performing filtration and discarding the filtrate as above. Beads were used immediately for a full second round of PCR thermocycling as described below.

Second Round of Solid-Phase Bridge PCR:

Performed as described in Example 36 and 37 except that a 10 μL portion of beads (actual bead volume) was used in 100 μL of the commercially available pre-mixed PCR reaction solution and without the BODIPY-FL-dUTP labeling reagent (i.e. no BODIPY-FL-dUTP labeling at any stage). Furthermore, the solid-phase bridge PCR reaction was further supplemented with 0.15 U/μL final of additional PlatinumTaq DNA Polymerase High Fidelity added from a 5 U/μL manufacturer's stock (Invitrogen Corporation, Carlsbad, Calif.). Thermocycling was performed as above in this Example.

400 μL of TE-50 mM NaCl (10 mM Tris, pH 8.0, 1 mM EDTA, 50 mM NaCl) was added to each completed solid-phase bridge PCR reaction and the suspensions transferred to fresh Filtration Devices (Ultrafree-MC Durapore Micro-centrifuge Filtration Devices, 400 μL capacity; Millipore, Billerica, Mass.). Filtration was performed and the filtrate discarded. The beads were washed briefly 3×400 μL more with TE-50 mM NaCl. Beads were additionally washed 2×400 μL briefly with MBG-Water before processing further as described below in this Example.

Single-Base Extension Reaction to Detect Mutant and Wild-Type APC:

A single-base extension (SBE) reaction was performed with fluorescent dideoxynucleotide triphosphates (ddNTPs) in order to distinguish the mutant (TAg at codon 1,338) from the wild-type (CAg at codon 1,338) APC amplicon on the solid-phase bridge PCR beads. Hence, a hybridization oligonucleotide probe was used in the SBE reaction which hybridizes up to (just before), but not overlapping with, the mutation site on the solid-phase bridge PCR amplicon (product). Cy5 labeled ddUTP and Cy3 labeled ddCTP were used in the extension reaction to detect the mutant and wild-type APC respectively.

First however, several prior measures were taken to eliminate background in the SBE reaction. The beads were first treated with Exonuclease I (New England Biolabs, Inc., Ipswich, Mass.) to remove any unused primers. To do so, following the final washes as detailed above, beads were resuspended in 30 μL of 1× reaction buffer (67 mM Glycine-KOH, 6.7 mM MgCl2, 10 mM 2-Mercaptoethanol, pH 9.5@25° C.) containing 0.7 U/μL final concentration of Exonuclease I. The reaction was incubated for 1 hr at 37° C. and the enzyme then heat inactivated for 10 min at 90° C. Using the aforementioned Filtration Devices, the beads were then washed 2×400 μL in 0.1 N NaOH for 3 mM each with gentle mixing. Beads were then washed briefly 3×400 μL in 10×TE (100 mM Tris, pH 8.0, 10 mM EDTA) then 3×400 μL, in TE-50 mM NaCl.

Next, the solid-phase bridge PCR amplicon on the beads was pre-capped using unlabeled ddNTP terminators. To do so, the beads were placed in 80 μL of 1× ThermoSequenase Reaction Buffer (150 mM Tris-HCl, pH 9.5, 67 mM MgCl$_2$) with 25 μM of each of the 4 ddNTPs, and 0.5 U/μL of the ThermoSequenase DNA Polymerase (Amersham Biosciences Corp., Piscataway, N.J.). Thermocycling was as follows: An initial denaturing step of 94° C. for 2 min (once), and 20 cycles of 94° C. for 30 sec (denature), 58° C. for 30 sec (anneal/extend); followed by a final extension step of 58° C. for 10 min (once). Again using the aforementioned Filtration Devices, the beads were washed briefly 3×400 μL with TE-50 mM NaCl then 3×400 μL MBG-Water. At this stage, beads could be stored by washing 1×400 μL in 1×TE buffer containing 50% glycerol and 50 mM NaCl, then resuspending to 5% beads (v/v) in the same buffer for storage at −20° C.

Next, the solid-phase bridge PCR product on the beads was hybridized with a fluorescently labeled complementary oligonucleotide corresponding to the SBE probe (i.e. primer). The SBE probe was commercially custom synthesized with a 5' fluorescein label and PAGE purified by the manufacturer (Sigma-Genosys, The Woodlands, Tex.). The SBE probe was diluted to 5 μM final in TE-50 mM NaCl for hybridization experiments. Prior to use however, the 5 μM SBE probe solution was pre-clarified by spinning 1 min at maximum speed on a micro-centrifuge (~13,000 rpm or ~16,000×g) and collecting the fluid supernatant. The supernatant was then passed though a Filtration Device (see earlier in this Example for Filtration Devices) and the filtrate saved for use as the SBE probe solution. The sequence of the SBE probe was as follows:

```
SBE Probe:
                                          [SEQ NO. 46]
5'[Fluorescein]gCACCCTAgAACCAAATCCAgCAgACTg3'
```

1 μL bead volume per sample was washed 2×400 μL with TE-50 mM NaCl using the aforementioned Filtration Devices. In the Filtration Device, each 1 μL pellet corresponding to each sample was resuspended in 25 μL of the aforementioned clarified 5 μM SBE probe solution. The beads were resuspended by manual pipetting then transferred to 0.5 mL polypropylene thin-wall PCR tubes. Hybridization was performed as follows in a PCR machine: 2 min 94° C. (denature) (beads resuspended by vortex mixing just before and at 2.5 min) followed by ramping down to 68° C. at a rate of 0.1° C./sec and subsequently holding 1 hour at 68° C. (anneal).

Just at the end of the above 1 hour 68° C. (anneal) step, while the tubes were still at 68° C. and still in the PCR machine, each sample was rapidly diluted with 400 μL of 68° C. TE-50 mM NaCl, the suspensions immediately transferred to a Filtration Device and filtration immediately performed. The filtrate was then discarded. The beads were washed 2×400 μL more with 68° C. TE-50 mM NaCl then 2×400 μL with room temperature TE-50 mM NaCl. Beads were lastly washed 2×400 μL with 50 mM NaCl. The beads were recovered from the Filtration Devices by resuspending the pellet in 50 μL of 50 mM NaCl and transferring to a 0.5 mL polypropylene PCR tube. The beads were spun down in a standard micro-centrifuge (just until reaches maximum speed of ~13,000 rpm corresponding to ~16,000×g) and the fluid supernatant removed.

The 1 μL washed bead pellet was resuspended in 20 μL of 1× ThermoSequenase Reaction Buffer (150 mM Tris-HCl, pH 9.5, 67 mM $MgCl_2$) with 2.5 μM each of Cy3 labeled ddCTP and Cy5 labeled ddUTP, 25 μM each of unlabeled ddATP and ddGTP, and 0.5 U/μL of the ThermoSequenase DNA Polymerase (Amersham Biosciences Corp., Piscataway, N.J.). The single base extension reaction was incubated for 20 min at 68° C. Again using the aforementioned Filtration Devices, the beads were washed briefly 3×400 μL with 68° C. TE-50 mM NaCl then 1×400 μL with room temperature TE-100 mM NaCl (10 mM Tris, pH 8.0, 1 mM EDTA, 100 mM NaCl).

Embedding the Beads in a Polyacrylamide Film and Fluorescence Imaging:

Lastly, the beads were embedded in a polyacrylamide film on a microscope slide and fluorescently imaged to detect the bound Fluorescein labeled SBE probe as well as the Cy3 and Cy5 extension products corresponding to the wild-type and mutant respectively. To do so, an Acrylamide Mix was prepared by combining the following reagents in order: 244 μL of TE-100 mM NaCl, 57 μL of 40% acrylamide (19:1 crosslinking) (Bio-Rad Laboratories, Hercules, Calif.), 0.5 μL TEMED (Bio-Rad Laboratories, Hercules, Calif.), and 1 μL of a 10% (w/v) ammonium persulfate stock (prepared in MBG-Water from powder obtained from Bio-Rad Laboratories, Hercules, Calif.). Each aforementioned washed bead pellet was then resuspended in 50 μL of the above Acrylamide Mix and combined by brief vortex mixing. 25 μL of the bead suspension was then pipetted to a standard glass microscope slide and overlaid with a standard 18 mm square microscope cover glass (coverslip). Polymerization was allowed to occur for ~10 min protected from light. Note that the adequately slow polymerization process allows all beads to settle to the surface of the microscope slide by unit gravity. When polymerization was complete, imaging was performed using an ArrayWoRx$^e$ BioChip fluorescence microarray reader (Applied Precision, LLC, Issaquah, Wash.).

Results:

The fluorescence images are shown in FIG. 41 whereby the top pair of image panels correspond the minus template (blank) sample permutation and the bottom pair of image panels the plus template sample (50:50 wild-type:mutant template mix initially added to beads at ratio of ~1 original template molecule initially added per each bead).

The top images in each panel pair ("SBE Probe Binding") are a single fluorescence channel corresponding to detection of binding of the fluorescein labeled SBE probe. Results show essentially no significant SBE probe binding in the case of the minus template blank. The presence of beads in this sample however is confirmed by extremely weak auto-fluorescence (visible only at extremely high image intensity settings; see inset box). Conversely, in the plus template sample, significant SBE probe binding is observed with an average signal-to-noise ratio of 33:1 (n>27 beads randomly sampled).

The bottom images of each panel pair ("SBE Probe Extension") are 2-color fluorescence image overlays corresponding to the wild-type (Cy3 fluorescence channel; green) and mutant (Cy5 fluorescence channel; red) extension products. Compared to the minus template blank, the plus template beads have an average signal-to-noise ratio of 14:1 and 11:1 for the Cy3 and Cy5 fluorescence channels respectively (n>50 beads sampled).

As a measure of relative mutant and wild-type APC content on each bead, the fluorescence images were quantified and the green:red fluorescence ratios calculated. Beads with a higher green:red ratio have a higher relative wild-type content compared to beads with a lower green:red ratio, and visa versa. Green:red ratios of a sampling of beads are shown in FIG. 41, indicated by arrows. Beads classified as wild-type had a 3-4 fold higher green:red ratio than beads classified as mutant APC. The number of beads classified as wild-type and mutant in the image shown approximates the 50:50 ratio of wild-type and mutant template initially added to the solid-phase bridge PCR reaction. Taken together, these data suggest effective solid-phase bridge PCR amplification of one or a few original template molecules per bead.

Example 45

Solid-Phase Bridge PCR for Multiplexed Detection of Methylated DNA

DNA methylation, which silences genes via repression of transcription and also maintains genomic stability, occurs primarily on CpG dinucleotides at the C5 position of cytosine and plays a critical role in both normal function of mammalian organisms as well as in disease (Reviewed in [Robertson. (2005) *Nat Rev Genet.* 6, 597-610]). In particular, aberrant DNA methylation has been associated with human cancers. Such methylation patterns aid in understanding the mechanisms of disease and act as specific biomarkers for molecularly based diagnostic or prognostic assays.

This Example pertains to the detection (analysis) of the methylation status of one or many regions of DNA, as biomarkers for colorectal cancer diagnostic or prognostic assays. The overall approach however, is not intended to be limited to any one specific disease or specific biomarker.

A multitude of analytical methods have been developed to detect DNA methylation patterns in biological samples (e.g. reviewed in [Fraga & Esteller. (2002) *Biotechniques* 33, 632, 634, 636-649]). Despite this variety, virtually all methods are based on a few common principals:

First, current methods extract information on DNA methylation status by exploiting either methylation-sensitive/resistant/dependent restriction enzymes (or nucleases) (e.g. [Singer-Sam et al. (1990) *Nucleic Acids Res* 18, 687]) or sodium bisulfite conversion of DNA (e.g. [Frommer et al. (1992) *Proc Natl Acad Sci USA* 89, 1827-1831]). The DNA cutting activity of methylation-sensitive restriction enzymes (or nucleases) is blocked by methylation, whereas methylation-resistant enzymes cut regardless of methylation state and methylation-dependent enzymes cut only if the recognition site(s) is methylated. On the other hand, sodium bisulfite treatment converts unmethylated cytosines to uracils, whereas methylated cytosines are protected from this chemical reaction, hence remaining as cytosines; thus creating methylation-dependent sequence differences.

Second, virtually all such methods subsequently utilize PCR either as the detection step itself, or as a pre-amplification step prior to detection. Hence, these approaches are amenable to adaptation to solid-phase bridge PCR based assays. The use of solid-phase bridge PCR affords several advantages, including but not limited to: a) The ability to multiplex, in a single solid-phase bridge PCR reaction, the amplification of various distinct biomarkers or b) the ability to perform amplification of 1 or a few template DNA molecules per each bead, in order to facilitate for example, high sensitivity detection of a few aberrantly methylated DNA molecules in the presence of an excess of normal.

In this Example, DNA from biological samples (e.g. stool, blood, plasma, serum, tissue or urine) of colorectal cancer patients (or normal patients as controls) will be subjected to methylation-sensitive/resistant/dependent restriction enzyme (or nuclease) digestion [e.g. using methylation-sensitive Hpa II, MspA1 I or Hha I; or methylation-resistant Msp I; or methylation-dependent Dpn I or McrBC enzymes from New England Biolabs, Inc., Ipswich, Mass.; or methylation-dependent Gla I, Bls I, Bis I or Glu I enzymes from SibEnzyme Ltd., Academtown, Russia]. Alternatively, sodium bisulfite conversion of the sample DNA will be employed alone or will be used in conjunction with methylation-sensitive/resistant/dependent enzyme digestion.

In colorectal cancer, aberrant methylation patterns in the CDKN2A, MLH1, HTLF, SLC5A8, RASSF2A and vimentin genes, among others, have been identified and have diagnostic potential [Kane et al. (1997) Cancer Res 57, 808-811; Ahuja et al. (1997) Cancer Res 57, 3370-3374; Moinova et al. (2002) Proc Natl Acad Sci USA 99, 4562-4567; Li et al. (2003) Proc Natl Acad Sci USA 100, 8412-8417; Chen et al. (2005) J Natl Cancer Inst 97, 1124-1132; Hesson et al. (2005) Oncogene 24, 3987-3994]. Such genes, and their relevant regions of aberrant methylation will be targeted in this Example, based on the literature reports. In some cases, multiple genes (biomarkers) or segments thereof, will be targeted in a single solid-phase bridge PCR reaction, to facilitate multiplexing hence increasing specificity and sensitivity of the colorectal cancer diagnostic or prognostic assays.

In one scenario, a methylation-sensitive enzyme will be selected that does not digest the targeted template DNA region if methylated, allowing subsequent amplification of the targeted methylated region by solid-phase bridge PCR. Separately, a methylation-resistant or methylation-dependent enzyme will also be selected that cuts within the template DNA region targeted by the solid-phase bridge PCR primers, either regardless of methylation status or only if methylation is present, thereby preventing amplification of the targeted methylated region by solid-phase bridge PCR. Positive formation of solid-phase bridge PCR product in the former case, coupled with lack of (or reduced) formation of solid-phase bridge PCR product in the latter case indicates the targeted region is methylated. Sample DNA not treated with any restriction enzymes (or nucleases), as well as fully methylated or unmethylated DNA treated with restriction enzymes (or nucleases) will be used as additional controls. Alternatively, following digestion with any such enzymes, the cut ends of the DNA (one or both ends) will be selectively attached to oligonucleotide adaptors to facilitate downstream amplification of the targeted region by directing at least one of the solid-phase bridge PCR primers against at least one adaptor (other primer will be biomarker region specific). Again, depending on the enzymes selected, formation or lack of (or reduced) formation of solid-phase bridge PCR product will indicate the methylation status. Enzyme treatments will be performed similar to as described in the scientific literature (e.g. [Singer-Sam et al. (1990) Nucleic Acids Res 18, 687; Liu et al. (2002) Otolaryngol Head Neck Surg 126, 548-553; Badal et al. (2003) J Virol 77, 6227-6234]). Solid-phase bridge PCR will be performed (individually or multiplexed for various biomarkers in one reaction) either as in Example 31 (where initial soluble template DNA is present throughout the entire solid-phase bridge PCR amplification) or Examples 36-41 (where after initial capture of the soluble template DNA onto the primer-coated beads and extension of the primers once, the initial template DNA is washed away prior to subsequent solid-phase bridge PCR amplification). Detection of the solid-phase bridge PCR product (amplicon) will be directly on the beads at the DNA level, via labeling with fluorescence deoxynucleotides during the solid-phase bridge PCR reaction (e.g. as in Example 36) or probing with fluorescently labeled complementary oligonucleotides (e.g. as in Example 38). Alternatively, detection will be indirect, by cell-free expression of the solid-phase bridge PCR product into protein, capture of the protein onto the same beads, in some cases contact-photo transfer of the proteins onto a second surface and detection of the protein, either on or off the original beads. Detection in this case will be via antibody (e.g. readout by microarray reader as in Example 40 or by flow cytometry as in Example 41) or mass spectrometry (e.g. Example 34).

In a second scenario, enzyme digestion will not be performed, instead, the sample DNA will be subjected to sodium bisulfite conversion to create methylation-dependent sequence differences. Sodium bisulfite treatment will be performed according to the scientific literature (e.g. [Frommer et al. (1992) Proc Natl Acad Sci USA 89, 1827-1831]). Fully unmethylated or fully methylated DNA, as well as DNA not treated with sodium bisulfite will be used as additional controls. Solid-phase bridge PCR will then be performed on all samples (individually or multiplexed for various biomarkers in one reaction) using primers that specifically target the methylation-dependent sequence differences (i.e. after bisulfite treatment, primers target unconverted and therefore methylated sequences) (called Methylation-Specific PCR or MSP). In this case, positive formation of solid-phase bridge PCR product indicates the targeted region(s) is methylated. Detection of the solid-phase bridge PCR product will be directly at the DNA level or following expression of the DNA into protein, as detailed above for the methylation-sensitive/resistant/dependent enzyme digestion approach. Alternatively, the bisulfate treated DNA will be amplified via solid-phase bridge PCR using primers which do not target any potentially methylated regions, and detection of the methylation-dependent sequence differences will be achieved by various methods including restriction enzyme digestion (COBRA), single nucleotide primer extension (Ms-SNuPE) or DNA sequencing according to the scientific literature [Frommer et al. (1992) Proc Natl Acad Sci USA 89, 1827-1831; Gonzalgo & Jones. (1997) Nucleic Acids Res 25, 2529-2531; Xiong & Laird. (1997) Nucleic Acids Res 25, 2532-2534].

Example 46

Solid-Phase Bridge PCR for Multiplexed Detection of Methylated DNA in Vimentin and RASSF2A Markers for Colorectal Cancer Diagnosis Methylation of the vimentin and RASSF2A markers and the detection of colorectal cancer, using methylation-specific PCR (MSP), is reported in the scientific literature [Chen et al. (2005) J Natl Cancer Inst 97, 1124-1132; Hesson et al. (2005) Oncogene 24, 3987-3994; Park et al. (2007) Int J Cancer 120, 7-12]. This Example will demonstrate the ability to use solid-phase bridge PCR to multiplex MSP assays for multiple diagnostic markers, such as the vimentin and RASSF2A markers shown here.

Preparation of Agarose Beads Covalently Conjugated to PCR Primers Used for Solid-Phase Bridge PCR:

Production of Primer-Conjugated Agarose Beads will be performed as in Example 36 except beads with the following primer pairs will be prepared (each primer pair bead set prepared separately).

```
Vimentin Unmethylated Primer Pair:
                                            [SEQ NO. 47]
Forward: 5'[Amine]TTgAggTTTTTgTgTTAgAgATgTAgTTgT3'
                                            [SEQ NO. 48]
Reverse:  5'[Amine]ACTCCAACTAAAACTCAACCAACTCACA3'
```

```
-continued
Vimentin Methylated Primer Pair:
                                               [SEQ NO. 48]
Forward: 5'[Amine]TCgTTTCgAggTTTTCgCgTTAgAgAC3'
                                               [SEQ NO. 50]
Reverse: 5'[Amine]CgACTAAAACTCgACCgACTCgCgA3'

RASSF2A Unmethylated Primer Pair:
                                               [SEQ NO. 51]
Forward: 5'[Amine]AgTTTgTTgTTgTTTTTTAggTgg3'
                                               [SEQ NO. 52]
Reverse: 5'[Amine]AAAAAACCAACAACCCCCACA3'

RASSF2A Methylated Primer Pair:
                                               [SEQ NO. 53]
Forward: 5'[Amine]AgTTCgTCgTCgTTTTTTAggC3'
                                               [SEQ NO. 54]
Reverse: 5'[Amine]AAAAACCAACgACCCCCgCg3'
```

Qualitative Analysis of Primer Attachment:

Performed as in Example 36

Template for Solid-Phase Bridge PCR and Bisulfite Conversion.

Fully methylated genomic DNA (CpGenome™ Universal Methylated DNA; Chemicon-Millipore, Billerica, Mass.), i.e. "mutant" DNA, and normal human blood genomic DNA (wild-type DNA; i.e. unmethylated at vimentin and RASSF2A marker regions) (Clontech, Mountain View, Calif.) will be purchased commercially to be used as the template solid-phase bridge PCR.

Prior to bisulfite conversion, genomic DNA will be mechanically fragmented into an average size of roughly 500 bp via direct probe sonication. Fragmentation will be verified by standard agarose gel electrophoresis. The fragmented genomic DNA will then be mixed in the following ratios of wild-type (unmethylated) to "mutant" (methylated): 0:100, 50:50, 95:5, 99:1, 99.9:0.1, 99.99:0.01 and 100:0.

For bisulfite conversion, the aforementioned fragmented DNA mixtures will first be denatured by preparing the following reaction: 12.5 ng/µL single-stranded carrier DNA (lambda DNA, *E. coli* genomic DNA or salmon sperm DNA), 0.3N NaOH, and 1-50 ng of the aforementioned fragmented genomic DNA mixtures. The denaturation reaction will then be incubated for 10 min at 37° C. Next, 30 µL of 10 mM hydroquinone will be added (10 mM hydroquinone prepared fresh from 25× stock which is stored at −20° C.) followed by 500 µL of a 3M sodium bisulfite stock (stock adjusted to pH 5.0 with NaOH). Lastly, 200 µL of mineral oil will be added and the reaction will be incubated at 50° C. for 16 hrs.

The resultant bisulfite converted DNA will be purified using the commercially available Wizard® DNA Clean-Up System (Promega, Madison, Wis.) according to the manufacturer's instructions. After elution from the Wizard® DNA Clean-Up System mini-columns in 90 µL 0.1×TE (1 mM Tris-HCl, pH 8.0, 0.1 mM EDTA), the DNA will be ethanol precipitated. Ethanol precipitation will be carried out as follows: 45 µL of 1 N NaOH will be added to each sample and briefly vortex mixed. After 5 min, 15 µL of 3M sodium acetate, pH 5.2, will be added to each tube. Next, 1 µL of 20 mg/mL glycogen will be added followed by 300 µL of ethanol. The mixture will then be incubated at −80° C. for 20 min and spun in a micro-centrifuge for 10 min (maximum speed of ~13,000 rpm corresponding to ~16,000×g). The ethanol will be removed and the DNA pellet air dried at room temperature for 15 min. The DNA will then be re-dissolved in 0.1×TE for immediate use or storage at −20° C.

Solid-Phase Bridge PCR:

2.5 µL actual total bead volume of the previously prepared Primer-Conjugated Agarose Beads will be used per each sample. The 2.5 µL beads for each sample will be comprised of equal quantities of each of the 4 aforementioned Primer-Conjugated Agarose Bead species (0.625 µL each of vimentin and RASSF2A primer pair beads, methylated and unmethylated directed versions) to allow multiplexed solid-phase bridge PCR of the 2 markers. First, enough beads for all sample permutations will be pre-washed in bulk. Beads will be washed using 0.45 micron pore size, PVDF membrane, micro-centrifuge Filtration Devices (Ultrafree-MC Durapore Micro-centrifuge Filtration Devices, 400 µL capacity; Millipore, Billerica, Mass.). Unless otherwise noted, all washes involving the Filtration Devices will be by brief vortex mixing (~5 sec), spinning down briefly in a micro-centrifuge (just until reaches maximum speed of ~13,000 rpm corresponding to ~16,000×g) and discarding of the filtrate. Beads will first be washed 2×400 µL with TE-50 mM NaCl (10 mM Tris, pH 8.0, 1 mM EDTA, 50 mM NaCl). Beads will then be resuspended in TE-50 mM NaCl to 20% (v/v) and the suspension recovered into a 0.5 mL thin-walled polypropylene PCR tube. The tube will be placed in a PCR machine at 95° C. for 10 min to allow heat-mediated washing (lid temperature 105° C. and no mineral oil used) (beads were resuspended by brief gentle vortex mixing just before this step). After heating, the tube will immediately be removed from the PCR machine, the beads will be diluted to 400 µL with TE-50 mM NaCl and the bead suspension will then be transferred to a Filtration Device. Filtration will be performed and the filtrate will be discarded. Beads will be briefly washed 1×400 µL more with TE-50 mM NaCl then 1×400 µL with MBG-Water.

Following the final filtration step on the bead samples, the bulk washed bead pellet will be resuspended in a commercially available PCR reaction mixture (HotStarTaq DNA Polymerase; Qiagen, Valencia, Calif.) which will prepared according to the manufacturer's instructions except with a 0.2 U/µL final DNA polymerase concentration and no soluble primers (and no template added yet). Additionally, a fluorescence BODIPY-FL-dUTP reagent will also be added to a 20 µM final concentration from the manufacturer's 1 mM stock (ChromaTide® BODIPY® FL-14-dUTP; Invitrogen Corporation, Carlsbad, Calif.), in order to achieve subsequent fluorescence labeling of the PCR amplicon (PCR product). The beads will be resuspended with 10 µL of PCR reaction mixture per each 1 µL actual bead volume. The suspension will then be recovered from the Filtration Device into fresh 0.5 mL polypropylene thin-wall PCR tubes, divided up at 25 µL total suspension volume per tube (i.e. per sample). At this point, 1-2 µL of the various fragmented genomic DNA template mixtures will be added to the appropriate tubes (a minus template negative control will also be performed). The samples will be subjected to the following thermocycling in a PCR machine (lid temperature 105° C. and no mineral oil used): An initial denaturing step (once) of 95° C. for 15 min (beads will briefly be resuspended by gentle vortex mixing just before this step), and 40 cycles of 94° C. for 30 sec (denature), 58° C. for 30 sec (anneal) and 72° C. for 30 sec (extend); followed by a final extension step of 72° C. for 5 min.

400 µL of TE-50 mM NaCl-T (10 mM Tris, pH 8.0, 1 mM EDTA, 50 mM NaCl, 0.01% v/v Tween-20) will be added to each completed solid-phase bridge PCR reaction and the suspensions transferred to fresh 0.5 mL polypropylene PCR tubes. The beads will then be spun down in a micro-centrifuge (just until reaches maximum speed of ~13,000 rpm corresponding to ~16,000×g) and the fluid supernatant carefully removed. The beads will be washed 3×400 µL more with TE-50 mM NaCl-T; resuspending by ~5 sec vortex mixing then spinning down and discarding the fluid supernatant as above. Following the final wash, as much of the fluid supernatant as possible will be removed from the bead pellet by manual pipetting. The beads will be lastly resuspended to 5% (v/v) using SP-PCR Storage Buffer (10 mM Tris, pH 8.0, 1 mM EDTA, 50 mM NaCl, all in 50% v/v glycerol).

If necessary, a second full round of solid-phase bridge PCR will be performed to increase product formation to detectible levels. To do so, the bead samples will be washed 2×400 µL with MBG-Water using a Filtration Device as described earlier in this Example. Following the final filtration step on the bead samples, each washed bead pellet will be resuspended in 25 µL of a fresh batch of PCR reaction mixture as detailed above in this Example (again containing the BODIPY-FL-dUTP reagent). The suspensions will then be recovered from their Filtration Devices into fresh 0.5 mL polypropylene thin-wall PCR tubes and again subjected to thermocycling as detailed above in this Example (40 cycles). After the second round of solid-phase bridge PCR thermocycling is complete, the beads will again be washed. To do so, 400 µL of TE-50 mM NaCl-T (10 mM Tris, pH 8.0, 1 mM EDTA, 50 mM NaCl, 0.01% v/v Tween-20) will be added to each completed solid-phase bridge PCR reaction and the suspensions transferred to fresh 0.5 mL polypropylene PCR tubes. The beads will then be spun down in a micro-centrifuge (just until reaches maximum speed of ~13,000 rpm corresponding to ~16,000×g) and the fluid supernatant carefully removed. The beads will be washed 3×400 µL more with TE-50 mM NaCl-T; resuspending by ~5 sec vortex mixing then spinning down and discarding the fluid supernatant as above. Following the final wash, as much of the fluid supernatant as possible will be removed from the bead pellet by manual pipetting. Beads are then resuspended to 5% (v/v) in SP-PCR Storage Buffer (10 mM Tris, pH 8.0, 1 mM EDTA, 50 mM NaCl, all in 50% v/v glycerol) for storage at −20° C.

Oligonucleotide Hybridization Probing:

Fluorescently labeled oligonucleotide probes will be commercially custom synthesized and HPLC purified by the manufacturer (Sigma-Genosys, The Woodlands, Tex.). The probes will be reconstituted to 100 µM in MBG-Water and further desalted using MicroSpin G-25 columns according to the manufacturer's instructions (Amersham Biosciences Corp., Piscataway, N.J.), except that the columns will be pre-washed 2×350 µL with MBG-Water prior to sample loading (to wash, columns will be mixed briefly in the MBG-Water then spun 1 min in a standard micro-centrifuge at the proper speed). The probes will be diluted to 5 µM final in TE-50 mM NaCl for hybridization experiments. Prior to use however, the 5 µM probe solution will be pre-clarified by spinning 1 min at maximum speed on a micro-centrifuge (~13,000 rpm or ~16,000×g) and collecting the fluid supernatant. The supernatant will then be passed though a Filtration Device (see earlier in this Example for Filtration Devices) and the filtrate will be saved for use as the probe solution.

In this Example, simultaneous dual probing will be performed by creating a single probing solution containing 5 µM of each probe, labeled on their 5' ends with the Cy3 or Cy5 fluorophores by the manufacturer (Sigma-Genosys, The Woodlands, Tex.). The gene-specific probes will complementary to an internal segment of the vimentin and RASSF2A solid-phase bridge PCR amplicons, corresponding to the "mutant" (i.e. methylated) bisulfite converted forms:

Human Vimentin Methylated & Bisulfite Converted:
[SEQ NO. 55]
5'[Cy3]gTAggATgTTCggCggTTCg3'

Human RASSF2A Methylated & Bisulfite Converted:
[SEQ NO. 56]
5'[Cy5]gTTTTAgTTTTCggCgCggg3'

Following completion of all prior solid-phase bridge PCR reaction steps in this Example, 20 µL of the aforementioned stored 5% (v/v) stock bead suspension (i.e. 1 post-PCR stored beads) will be taken and washed 2×400 µL with TE-50 mM NaCl using the aforementioned Filtration Devices. In the Filtration Device, each 1 µL pellet corresponding to each sample will be resuspended in 25 µL of the aforementioned clarified 5 µM probe solution. The beads will be resuspended by manual pipetting then transferred to 0.5 mL polypropylene thin-wall PCR tubes. Hybridization will be performed as follows in a PCR machine (lid temperature always 105° C., no mineral oil used): 5 min 95° C. (denature) (beads will be resuspended by vortex mixing just before this step) followed by ramping down to 60° C. at a rate of 0.1° C./sec and subsequently holding 1 hour at 60° C. (anneal).

Just at the end of the above 1 hour 60° C. (anneal) step, while the tubes are still at 60° C. and still in the PCR machine, each sample will be rapidly diluted with 400 µL of 60° C. TE-50 mM NaCl, the suspensions immediately transferred to a Filtration Device and filtration immediately performed. The filtrate will then be discarded. The beads will be washed 3×400 µL more with room temperature TE-50 mM NaCl then 1×400 µL with room temperature TE-100 mM NaCl (10 mM Tris, pH 8.0, 1 mM EDTA, 100 mM NaCl). The beads will be recovered from the Filtration Devices by resuspending the pellets in 50 µL of TE-100 mM NaCl and transferring to a 0.5 mL polypropylene PCR tube. The beads will be spun down in a standard micro-centrifuge (just until reaches maximum speed of ~13,000 rpm corresponding to ~16,000×g) and the fluid supernatant will be removed.

Embedding the Beads in a Polyacrylamide Film and Fluorescence Imaging:

Lastly, the beads will be embedded in a polyacrylamide film on a microscope slide and fluorescently imaged to detect the bound Cy3 and Cy5 labeled hybridization probes. To do so, an Acrylamide Mix will be prepared by combining the following reagents in order: 244 µL of TE-100 mM NaCl, 57 µL of 40% acrylamide (19:1 cross-linking) (Bio-Rad Laboratories, Hercules, Calif.), 0.5 µL TEMED (Bio-Rad Laboratories, Hercules, Calif.), and 1 µL of a 10% (w/v) ammonium persulfate stock (prepared in MBG-Water from powder obtained from Bio-Rad Laboratories, Hercules, Calif.). Each aforementioned washed bead pellet will then be resuspended in 50 µL of the above Acrylamide Mix and combined by brief vortex mixing. 25 µL of the bead suspension will then be pipetted to a standard glass microscope slide and overlaid with a standard 18 mm square microscope cover glass (coverslip). Polymerization will be allowed to occur for ~10 min protected from light. Note that the adequately slow polymerization process will allow all beads to settle to the surface of the microscope slide by unit gravity. When polymerization is complete, imaging will be performed using an ArrayWoRx$^e$ BioChip fluorescence microarray reader (Applied Precision, LLC, Issaquah, Wash.). The beads will be imaged in 3 different fluorescence channels to detect the BODIPY-FL dUTP labels as well as the Cy3 and Cy5 hybridization probes.

Results:

Results are anticipated to show proof-of-principal for multiplexing MSP of several disease biomarkers, in this case for colorectal cancer, by using a single solid-phase bridge PCR reaction. Multiplexing is achieved by using a mixture of PCR primer coated beads in the single solid-phase bridge PCR reaction, with each bead species targeting the various biomarkers, methylated or unmethylated versions (following bisulfite conversion) (i.e. 4 bead species in this case, with a multitude replicates of each bead species). In this Example, "mutant" (methylated; bisulfite converted) vimentin and RASSF2A amplicons are detected on their corresponding beads using selective complementary hybridization probes, each labeled with a different fluorophore (Cy3 and Cy5). These amplicons will also carry the BODIPY-FL dUTP fluorescence label. Selective formation of PCR product on these beads indicates the aberrant methylated state of at least a fraction of the biomarker present in the sample and hence the presence of disease (in the case where actual patient samples are assayed). Wild-type (unmethylated; bisulfite converted) vimentin and RASSF2A amplicons are detected on their corresponding beads by the presence of the BODIPY-FL dUTP fluorescence label, but absence of any hybridization probe signal. Detection of the wild-type amplicons serves only as a positive control and could be detected more specifically using additional hybridization probes bearing different fluorophores (in which case BODIPY-FL dUTP fluorescence labeling could be omitted). Because the methylation directed primer beads will selectively amplify any methylated biomarker present in the sample, detection of very low percentages of the methylated ("mutant") biomarker is expected among a large background of wild-type (unmethylated). In this Example, detection is expected at ratios at least as low as 1 "mutant" (methylated) DNA biomarker molecule out of every 10,000 DNA biomarker molecules (9,999 wild-type DNA biomarker molecules).

Note that the method in this Example could be modified to provide for effective solid-phase bridge PCR amplification of single DNA molecules per bead, in which case the initially added soluble template DNA is washed out following a single primer extension step on the solid-phase bridge PCR beads (e.g. as done in Examples 36-39 for instance). This would be expected to reduce background from unintended amplification of wild-type DNA on "mutant" (methylated) directed primer beads (via non-specific hybridization).

Ultimately, in the case where a multitude of biomarkers are to be multiplexed (e.g. more than 2), the beads themselves could carry a unique readable intrinsic code which identifies the specific primer pair on each bead. Different hybridization probes, specifically directed against the different biomarker amplicons, could be used to simultaneously probe the bead population. In this case, the different hybridization probes could all carry the same fluorophore (or other reporter), while determination of which biomarkers were positively amplified could be made by reading the code of the specific primer coated bead species. Coded bead platforms manufactured by Luminex Corporation (Austin, Tex.) and Illumina Incorporated (San Diego, Calif.), for example, would be suitable for this purpose.

Example 47

Solid-Phase Bridge PCR for Multiplexed Detection of Bisulfite Converted Wild-Type Vimentin and RASSF2A DNA Markers: Applications in Colorectal Cancer Diagnosis Methylation of the vimentin and RASSF2A markers and the detection of colorectal cancer, using methylation-specific PCR (MSP), is reported in the scientific literature [Chen et al. (2005) *J Natl Cancer Inst* 97, 1124-1132; Hesson et al. (2005) *Oncogene* 24, 3987-3994; Park et al. (2007) *Int J Cancer* 120, 7-12]. This Example demonstrates the ability to use solid-phase bridge PCR to multiplex MSP assays for multiple diagnostic markers. In this Example, multiplexed detection of the wild-type vimentin and RASSF2A markers is demonstrated. However, the technique is equally applicable to the detection of the "mutant", i.e. methylated markers, simply by changing the primer sequences.

Preparation of Agarose Beads Covalently Conjugated to PCR Primers Used for Solid-Phase Bridge PCR:

Production of Primer-Conjugated Agarose Beads was performed as in Example 36 except beads with the following primer pairs were prepared (each primer pair bead set prepared separately).

Vimentin Unmethylated Primer Pair:
[SEQ NO. 57]
Forward: 5'[Amine]TTgAggTTTTTgTgTTAgAgATgTAgTTgT3'
[SEQ NO. 58]
Reverse: 5'[Amine]ACTCCAACTAAAACTCAACCAACTCACA3'

RASSF2A Unmethylated Primer Pair:
[SEQ NO. 59]
Forward: 5'[Amine]AgTTTgTTgTTgTTTTTTAggTgg3'
[SEQ NO. 60]
Reverse: 5'[Amine]AAAAAACCAACAACCCCCACA3'

Qualitative Analysis of Primer Attachment:
Performed as in Example 36

Template for Solid-Phase Bridge PCR and Bisulfate Conversion:

Normal human blood genomic DNA (wild-type DNA; i.e. unmethylated at vimentin and RASSF2A marker regions) (Clontech, Mountain View, Calif.) was purchased commercially. For bisulfite conversion, the normal human blood genomic DNA was first denatured by preparing the following reaction: 12.5 ng/µL single-stranded carrier DNA (lambda DNA, *E. coli* genomic DNA or salmon sperm DNA), 0.3N NaOH, and 1-50 ng of the aforementioned normal human blood genomic DNA. The denaturation reaction was then incubated for 10 min at 37° C. Next, 30 µL of 10 mM hydroquinone was added (10 mM hydroquinone prepared fresh from 25× stock which is stored at −20° C.) followed by 500 µL of a 3M sodium bisulfite stock (stock adjusted to pH 5.0 with NaOH). Lastly, 200 µL of mineral oil was added and the reaction incubated at 50° C. for 16 hrs.

The resultant bisulfite converted DNA was purified using the commercially available Wizard® DNA Clean-Up System (Promega, Madison, Wis.) according to the manufacturer's instructions. After elution from the Wizard® DNA Clean-Up System mini-columns in 90 µL 0.1×TE (1 mM Tris-HCl, pH 8.0, 0.1 mM EDTA), the DNA was ethanol precipitated. Ethanol precipitation was carried out as follows: 45 µL of 1 N NaOH was added to each sample and briefly vortex mixed. After 5 min, 15 µL of 3M sodium acetate, pH 5.2, was added to each tube. Next, 1 µL of 20 mg/mL glycogen was added followed by 300 µL of ethanol. The mixture was then incubated at −80° C. for 20 min and spun in a micro-centrifuge for 10 min (maximum speed of ~13,000 rpm corresponding to ~16,000×g). The ethanol was removed and the DNA pellet air dried at room temperature for 15 min. The DNA was then re-dissolved in 0.1×TE for immediate use or storage at −20° C.

Following bisulfite conversion of the normal human blood genomic DNA as described above in this Example, standard solution-phase PCR was performed with the following MSP primers directed against the bisulfite converted wild-type DNA markers:

```
Vimentin Unmethylated Primer Pair:
                                       [SEQ NO. 61]
Forward: 5'TTgAggTTTTTgTgTTAgAgATgTAgTTgT3'
                                       [SEQ NO. 62]
Reverse: 5'ACTCCAACTAAAACTCAACCAACTCACA3'

RASSF2A Unmethylated Primer Pair:
                                       [SEQ NO. 63]
Forward: 5'AgTTTgTTgTTgTTTTTTAggTgg3'
                                       [SEQ NO. 64]
Reverse: 5'AAAAAACCAACAACCCCCACA3'
```

The standard solution-phase PCR was carried out in a commercially available PCR reaction mixture (HotStarTaq DNA Polymerase; Qiagen, Valencia, Calif.) which was prepared according to the manufacturer's instructions. The reactions were subjected to the following thermocycling in a PCR machine: An initial denaturing step (once) of 95° C. for 15 min, and 40 cycles of 94° C. for 30 sec (denature), 58° C. for 30 sec (anneal) and 72° C. for 30 sec (extend); followed by a final extension step of 72° C. for 5 min. The PCR products from the MSP reaction were purified by agarose gel electrophoresis using standard practices and these purified products were used as template for solid-phase bridge PCR as described below.

Solid-Phase Bridge PCR:

2.5 µL actual total bead volume of the previously prepared Primer-Conjugated Agarose Beads was used per each sample. The 2.5 µL beads for each sample was comprised of equal quantities of each of the 2 aforementioned Primer-Conjugated Agarose Bead species (1.25 µL each of vimentin and RASSF2A primer pair beads, unmethylated directed versions) to allow multiplexed solid-phase bridge PCR of the 2 markers. Additional non-multiplexed sample permutations were prepared which comprised 2.5 µL bead volume of either the vimentin or the RASSF2A primer pair beads only. Beads were pre-washed to remove any non-covalently attached primers. Beads were initially washed using 0.45 micron pore size, PVDF membrane, micro-centrifuge Filtration Devices (Ultrafree-MC Durapore Micro-centrifuge Filtration Devices, 400 µL capacity; Millipore, Billerica, Mass.). Unless otherwise noted, all washes involving the Filtration Devices were by brief vortex mixing (~5 sec), spinning down briefly in a micro-centrifuge (just until reaches maximum speed of ~13,000 rpm corresponding to ~16,000×g) and discarding the filtrate. Initial washes were 2×400 µL with TE-50 mM NaCl (10 mM Tris, pH 8.0, 1 mM EDTA, 50 mM NaCl). Beads were then resuspended in TE-50 mM NaCl to 20% (v/v) and the suspensions recovered into 0.5 mL thin-walled polypropylene PCR tubes. The tubes were placed in a PCR machine at 95° C. for 10 min to allow heat-mediated washing (lid temperature 105° C. and no mineral oil used) (beads were resuspended by brief gentle vortex mixing just before this step). After heating, the tubes were immediately removed from the PCR machine, the beads were diluted to 400 µL with TE-50 mM NaCl and the bead suspensions were then transferred to Filtration Devices. Filtration was performed and the filtrate discarded. Beads were briefly washed 1×400 µL more with TE-50 mM NaCl then 1×400 µL with MBG-Water.

Following the final filtration step (wash) on the bead samples, the washed bead pellets were resuspended in a commercially available PCR reaction mixture (HotStarTaq DNA Polymerase; Qiagen, Valencia, Calif.) which was prepared according to the manufacturer's instructions except with a 3 mM total magnesium concentration and no soluble primers (and no template added yet). The beads were resuspended with 10 µL of PCR reaction mixture per each 1 µL actual bead volume. The suspensions (~25 µL) were placed into 0.5 mL polypropylene thin-wall PCR tubes. At this point, 1 µL of the aforementioned template DNA was added (a minus template negative control was also performed). The resultant template concentration was 0.4 ng/µL and was a 50:50 mix of the vimentin and RASSF2A templates for the multiplexed sample (0.2 ng/µL final of each template for 0.4 ng/µL total template). 0.4 ng/µL of the corresponding single template species was used for the non-multiplexed samples. For the multiplexed sample, this resulted in a ratio of 28,000 and 54,000 attomoles of template per µL of actual Primer-Conjugated Agarose Bead volume for vimentin and RASSF2A respectively. With 1 µL of Primer-Conjugated Agarose Beads determined to contain approximately 1,000 beads, 28,000 and 54,000 attomoles of template per µL of beads represents a ratio of approximately $2 \times 10^7$ and $3 \times 10^7$ template molecules added per bead for vimentin and RASSF2A respectively, in the multiplexed sample (beads physically enumerated under a microscope both in diluted droplets of bead suspension and with suspensions in a hemacytometer cell counting chamber). The samples were subjected to the following thermocycling in a PCR machine (lid temperature 105° C. and no mineral oil used): An initial denaturing step (once) of 95° C. for 15 min (beads were briefly resuspended by gentle vortex mixing just before this step), and 40 cycles of 94° C. for 30 sec (denature), 58° C. for 2 min (anneal) and 72° C. for 1 min (extend); followed by a final extension step of 72° C. for 5 min.

400 µL of TE-50 mM NaCl (10 mM Tris, pH 8.0, 1 mM EDTA, 50 mM NaCl) was added to each completed solid-phase bridge PCR reaction and the suspensions transferred to Filtration Devices (Ultrafree-MC Durapore Micro-centrifuge Filtration Devices, 400 µL capacity; Millipore, Billerica, Mass.). Filtration was performed in a micro-centrifuge (just until reaches maximum speed of ~13,000 rpm corresponding to ~16,000×g) and the filtrate discarded. The beads were washed 3×400 µL more with TE-50 mM NaCl; resuspending by ~5 sec vortex mixing then performing filtration and discarding the filtrate as described earlier in this Example.

Oligonucleotide Hybridization Probing:

Fluorescently labeled oligonucleotide probes were commercially custom synthesized and HPLC purified by the manufacturer (Sigma-Genosys, The Woodlands, Tex.). The probes were reconstituted to 100 µM in MBG-Water and further desalted using MicroSpin G-25 columns according to the manufacturer's instructions (Amersham Biosciences Corp., Piscataway, N.J.), except that the columns were pre-washed 2×350 µL with MBG-Water prior to sample loading (to wash, columns were mixed briefly in the MBG-Water then spun 1 min in a standard micro-centrifuge at the proper speed). The probes were diluted in TE-50 mM NaCl for hybridization experiments. Prior to use however, the diluted probe solution was pre-clarified by spinning 1 min at maximum speed on a micro-centrifuge (~13,000 rpm or ~16,000×g) and collecting the fluid supernatant. The supernatant was then passed though a Filtration Device (see earlier in this Example for Filtration Devices) and the filtrate was saved for use as the clarified probe solution.

In this Example, simultaneous dual hybridization probing was performed by creating a single probing solution containing 1 µM of each probe, labeled on their 5' ends with the Cy3 or Cy5 fluorophores by the manufacturer (Sigma-Genosys, The Woodlands, Tex.). The gene-specific probes were complementary to an internal segment of the vimentin and RASSF2A solid-phase bridge PCR amplicons:

Human Vimentin Unmethylated & Bisulfite Converted:
[SEQ NO. 65]
5'[Cy3]TgTAggATgTTTggTggTTTggg3'

Human RASSF2A Unmethylated & Bisulfite Converted:
[SEQ NO. 66]
5'[Cy5]TTTTggTgTggggAggTggT3'

After solid-phase bridge PCR and washing of the beads as described earlier in this Example, the bead pellets corresponding to each sample were resuspended in 25 µL of the aforementioned clarified probe solution (containing both probes, for vimentin and RASSF2A). The beads were resuspended by manual pipetting then transferred to 0.5 mL polypropylene thin-wall PCR tubes. Hybridization was performed as follows in a PCR machine (lid temperature always 105° C., no mineral oil used): 5 min 95° C. (denature) (beads were be resuspended by vortex mixing just before this step) followed by ramping down to 60° C. at a rate of 0.1° C./sec and subsequently holding 1 hour at 60° C. (anneal).

Just at the end of the above 1 hour 60° C. (anneal) step, while the tubes were still at 60° C. and still in the PCR machine, each sample was rapidly diluted with 400 µL of 60° C. TE-50 mM NaCl, the suspensions immediately transferred to a Filtration Device and filtration immediately performed. The filtrate was then discarded. The beads were washed 2×400 µL more with 60° C. TE-50 mM NaCl then 1×400 µL with room temperature TE-50 mM NaCl. Beads were lastly washed 1×400 µL with TE-100 mM NaCl (10 mM Tris, pH 8.0, 1 mM EDTA, 100 mM NaCl). The beads were recovered from the Filtration Devices by resuspending the pellets in 50 µL of TE-100 mM NaCl and transferring to a 0.5 mL polypropylene PCR tube. The beads were spun down in a standard micro-centrifuge (just until reaches maximum speed of ~13, 000 rpm corresponding to ~16,000×g) and the fluid supernatant was removed.

Embedding the Beads in a Polyacrylamide Film and Fluorescence Imaging:

Lastly, the beads were embedded in a polyacrylamide film on a microscope slide and fluorescently imaged to detect the bound Cy3 and Cy5 labeled hybridization probes. To do so, an Acrylamide Mix was prepared by combining the following reagents in order: 244 µL of TE-100 mM NaCl, 57 µL of 40% acrylamide (19:1 cross-linking) (Bio-Rad Laboratories, Hercules, Calif.), 0.5 µL TEMED (Bio-Rad Laboratories, Hercules, Calif.), and 1 µL of a 10% (w/v) ammonium persulfate stock (prepared in MBG-Water from powder obtained from Bio-Rad Laboratories, Hercules, Calif.). Each aforementioned washed bead pellet was then resuspended to 2% (v/v) beads in the above Acrylamide Mix and combined by brief vortex mixing. 25 µL of the bead suspension was then pipetted to a standard glass microscope slide and overlaid with a standard 18 mm square microscope cover glass (coverslip). Polymerization was allowed to occur for ~10 min protected from light. Note that the adequately slow polymerization process allows all beads to settle to the surface of the microscope slide by unit gravity. When polymerization was complete, imaging was performed using an ArrayWoRx$^e$ BioChip fluorescence microarray reader (Applied Precision, LLC, Issaquah, Wash.). The beads were imaged in 2 different fluorescence channels to detect the Cy3 and Cy5 hybridization probes.

Results:

Results show proof-of-principal for multiplexing MSP of multiple disease biomarkers, in this case for colorectal cancer, by using a single solid-phase bridge PCR reaction. FIG. 42 is a 2-color fluorescence image overlay of the solid-phase bridge PCR beads following dual hybridization probing for both vimentin (Cy3; green in FIG. 42) and RASSF2A (Cy5; red in FIG. 42) amplicons. In FIG. 42, panels marked as "Multiplex" pertain to where both vimentin and RASSF2A primer coated beads were included in the solid-phase bridge PCR reaction at a 50:50 ratio. If only the template DNA was omitted ["–Template (Multiplex)"], no significant signal was observed. If both templates were included in the reaction ["+Vimentin & +RASSF2A (Multiplex)"], both amplicons were observed and were segregated on their respective beads, with the two bead populations in an approximate 50:50 ratio as expected. Controls where only one primer coated bead species and the corresponding template were used in the solid-phase bridge PCR reaction show that only the respective amplicon was produced and detected (two right most panels in FIG. 42).

Example 48

Solid-Phase Bridge PCR on the APC Gene Associated with Colorectal Cancer: Direct Use of Genomic DNA Templates in the Solid-Phase Bridge PCR Reaction This Example illustrates 3 important aspects of the presented solid-phase bridge PCR methodology compared to previous Examples: i) All, rather than partial untranslated regions and epitope tag sequences of the solid-phase bridge PCR amplicon are introduced by the solid-phase bridge PCR primers which allows ii) the direct use of native (i.e. no exogenous sequence modifications) genomic DNA templates, such as those obtained from patients, in the solid-phase bridge PCR reaction, and iii) the benefit of magnesium supplementation to improve the efficiency of the solid-phase bridge PCR reaction is demonstrated.

Preparing the Solid-Phase Bridge PCR Template DNA:

Note: All buffers and reagents used throughout this entire Example, unless otherwise noted, were minimally DNAse, RNAse and protease free, referred to as Molecular Biology Grade (MBG), including the water, referred to as MBG-Water.

Normal human blood genomic DNA (Clontech, Mountain View, Calif.) was purchased commercially to be used as the template for solid-phase bridge PCR. The genomic DNA was first mechanically fragmented into an average size of roughly 500 bp via direct probe sonication. Fragmentation was verified by standard agarose gel electrophoresis.

Preparation of Agarose Beads Covalently Conjugated to PCR Primers Used for Solid-Phase Bridge PCR:

Performed as in Example 36 with the following exceptions: PCR primers used in this Example are listed below this paragraph. In the primers below, the bracketed sequences indicate the gene-specific APC directed hybridization regions, while the remaining sequences are non-hybridizing regions which correspond to all of the elements needed for later cell-free protein expression as well as epitope tag detection. During conjugation to the beads, concentration of each primer was 29 µM instead of 125 µM.

```
Solid-Phase Bridge PCR APC Forward Primer:
                                         [SEQ NO. 67]
5'TAATACgACTCACTATAgggAgAggAggTATATCAATgTACACCgACA
TCgAgATgAACCgCCTgggCAgggAggACAgCCTgAACTCgCTCCAgAg
gATCCggAAgAT[CAggAAgCAgATTCTgCTAAT]3'

Solid-Phase Bridge PCR APC Reverse Primer:
                                         [SEQ NO. 68]
5'TTTTTTTTTTTTTTTTTTTATTATCCTCCTCCTTTATCATCATCgTC
TTTATAATCCAgCAgCTTgTgCAggTCgCTgAAggT[TggACTTTTgggT
gTCTgAgCACCACTTTT]3'
```

Qualitative Analysis of Primer Attachment.
Performed as in Example 36.
First Round of Effective Single Template Molecule Solid-Phase Bridge PCR:

Performed essentially as in Example 36, with slight modifications. The full protocol was as follows: 4 µL actual bead volume of the previously prepared Primer-Conjugated Agarose Beads was used per each sample, but first, the beads were washed in bulk, with heating. To do so, 65 µL (in duplicate) of the aforementioned 20% (v/v) Primer-Conjugated Agarose Bead suspension (~13 µL actual bead volume) was placed into a 0.5 mL polypropylene thin-wall PCR tube. The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness. 50 µL of TE-50 mM NaCl (10 mM Tris, pH 8.0, 1 mM EDTA, 50 mM NaCl) was added to the pellets, to bring the volume approximately back to the original 20% beads (v/v). The beads were briefly vortex mixed then spun down and all fluid removed as described before. 50 µL of TE-50 mM NaCl was again added to the pellets as above and the tubes placed in a PCR machine (Mastercycler Personal; Eppendorf AG, Hamburg, Germany) at 95° C. for 10 min (lid temperature 105° C. and no mineral oil used) (beads were resuspended by brief gentle vortex mixing just before and at 5 min of this step). After heating, the tube was immediately removed from the PCR machine, the beads diluted in 400 µL of TE-50 mM NaCl and the bead suspension then transferred to a Filtration Device (see Example 36). Filtration was performed and the filtrate discarded. Beads were briefly washed 2×400 µL more with TE-50 mM NaCl then 2×400 µL with MBG-Water. Each set of beads was then resuspended in 50 µL MBG-Water and then pooled. The pooled bead suspension was divided up into 0.5 mL polypropylene thin-wall PCR tubes such that 4 µL actual bead volume was added per tube (i.e. per sample). The beads were spun down briefly in a standard micro-centrifuge (just until reaches maximum speed of ~13,000 rpm corresponding to ~16,000×g). As much of the fluid supernatant was removed as possible by manual pipetting, with the beads nearly going to dryness.

Next, to pre-hybridize the template DNA to the washed Primer-Conjugated Agarose Beads, each 4 µL bead pellet was then resuspended in 2.5 µL of diluted fragmented genomic DNA template solution, which contained no soluble primers. The aforementioned fragmented genomic DNA template, prepared as described in this Example, was diluted to 33.2 ng/µL directly in a commercially available pre-mixed PCR reaction solution containing everything needed for PCR except template DNA and primers (Phusion™ High Fidelity PCR Master Mix; 1× contains 0.02 U/µL Phusion DNA Polymerase, 200 µM dNTPs, 1.5 mM MgCl$_2$ and other optimized buffer constituents; New England Biolabs, Ipswich, Mass.; solution provided as 2× concentrate and used at 1×). This resulted in a ratio of ~3,000 genome equivalents per µL of actual Primer-Conjugated Agarose Bead volume. With 1 µL of Primer-Conjugated Agarose Beads determined to contain approximately 1,000 beads, ~3,000 genome equivalents per µL of beads represents a ratio of approximately 6 actual APC template molecules (gene copies) added per bead (beads physically enumerated under a microscope both in diluted droplets of bead suspension and with suspensions in a hemacytometer cell counting chamber). It should be noted that although a ratio of 6 APC gene copies per bead was used, the fragmentation of the genomic DNA will statistically reduce the number of amplifiable APC templates per bead (average genomic DNA template fragment ~500 bp; targeted APC region for amplification 237 bp). A minus template negative control was also prepared. The bead suspensions were only mixed manually by gentle stirring with a pipette tip.

The resultant bead suspensions, now containing added template but no soluble (free) primers (only bead-bound primers), were then treated as follows in a PCR machine (Mastercycler Personal; Eppendorf AG, Hamburg, Germany) (lid temperature 105° C., and no mineral oil used): 5 min 95° C. (denaturing), ramp down to 55° C. at a rate of 0.1° C./sec and then hold 1 hour at 55° C. (annealing/capture of template onto beads). Next, 30 µL of fresh 1× Phusion™ High Fidelity PCR Master Mix was added to each sample (without removal of previous solution and without letting samples cool). At this stage, some samples also received magnesium supplementation beyond what was provided in the aforementioned 1× Phusion™ High Fidelity PCR Master Mix. The 3 sample permutations at this stage were as follows: 1) Minus template; no supplementation 2) plus template; no supplementation 3) plus template; magnesium supplementation to 3 mM total (duplicate sample). Before adding the 30 µL solutions to each sample, the solutions were pre-treated on a PCR machine at 98° C. for 3.7 min followed by 65° C. for 40 seconds; and the solutions then added while at 65° C. After addition of the solutions to the samples, the samples were treated at 72° C. for 10 min on the PCR machine to fully extend any primers which were hybridized to a template molecule. Immediately upon completion of the previous steps above, while the tubes were still at 72° C., the tubes were immediately transferred from the PCR machine to a crushed ice water bath. 400 µL of ice cold MBG-Water was added to each tube, the suspensions transferred to fresh Filtration Devices, filtration was immediately performed and the filtrate discarded (see Example 36). Using the same Filtration Devices, the beads were briefly washed 2×400 µL with room temperature MBG-Water. Beads were further washed 2×400 µL for 3 min each with room temperature 0.1M NaOH, with constant vigorous vortex mixing, in order to strip off any hybridized but non-covalently bound template DNA, leaving only covalently attached unused and extended primers on the beads. The beads were then briefly washed 3×400 µL with 10×TE (100 mM Tris, pH 8.0, 10 mM EDTA), in order to neutralize the pH, followed by 3×400 µL with MBG-Water, in order to remove the components of the 10×TE which would interfere with subsequent PCR.

Following the final filtration step on the bead samples, each washed bead pellet was resuspended in 50 µL of the aforementioned commercial Phusion™ High Fidelity PCR Master Mix pre-mixed PCR solution. The magnesium supplementation detailed earlier was also maintained at this stage for the corresponding samples. Also at this stage, some samples additionally received Phusion DNA polymerase supplementation beyond what was provided in the aforementioned 1×

Phusion™ High Fidelity PCR Master Mix. The 4 sample permutations at this stage were as follows: 1) Minus template; no supplementation 2) plus template; no supplementation 3) plus template; magnesium supplementation to 3 mM total and 4) plus template; magnesium supplementation to 3 mM total with Phusion DNA polymerase supplementation to 0.1 U/µL total. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 98° C. for 2 min (once) (beads were briefly resuspended by gentle vortex mixing just before this step), and 40 cycles of 98° C. for 40 sec (denature), 65° C. for 40 sec (anneal), and 72° C. for 1 min (extend); followed by a final extension step of 72° C. for 5 min (once).

400 µL of TE-50 mM NaCl (10 mM Tris, pH 8.0, 1 mM EDTA, 50 mM NaCl) was added to each completed solid-phase bridge PCR reactions and the suspensions transferred to Filtration Devices (Ultrafree-MC Durapore Micro-centrifuge Filtration Devices, 400 µL capacity; Millipore, Billerica, Mass.). Filtration was performed in a micro-centrifuge (just until reaches maximum speed of ~13,000 rpm corresponding to ~16,000×g) and the filtrate discarded. The beads were washed 2×400 µL more with TE-50 mM NaCl; resuspending by ~5 sec vortex mixing then performing filtration and discarding the filtrate as above. Beads were used immediately for a full second round of PCR thermocycling as described below.

Second Round of Solid-Phase Bridge PCR:

A portion of the above beads, following completion of the aforementioned initial full round of solid-phase bridge PCR thermocycling (i.e. all preceding steps), were subjected to a second full round of PCR thermocycling. To do so, 2.5 µL actual bead volume was washed 3×400 µL with MBG-Water using a Filtration Device. Following the final filtration step on the bead samples, each washed bead pellet was resuspended in 50 µL of the aforementioned commercial Phusion™ High Fidelity PCR Master Mix pre-mixed PCR solution. The magnesium and Phusion DNA polymerase supplementation detailed earlier was also maintained at this stage for the corresponding samples. Therefore, the 4 sample permutations at this stage remained as follows: 1) Minus template; no supplementation 2) plus template; no supplementation 3) plus template; magnesium supplementation to 3 mM total and 4) plus template; magnesium supplementation to 3 mM total with Phusion DNA polymerase supplementation to 0.1 U/µL total. The suspensions were then recovered from their Filtration Devices into fresh 0.5 mL polypropylene thin-wall PCR tubes and subjected to the following thermocycling in a PCR machine (Mastercycler Personal; Eppendorf AG, Hamburg, Germany) (lid temperature 105° C. and no mineral oil used): An initial denaturing step of 98° C. for 2 min (once) (beads were briefly resuspended by gentle vortex mixing just before this step), and 40 cycles of 98° C. for 40 sec (denature), 65° C. for 40 sec (anneal), and 72° C. for 1 min (extend); followed by a final extension step of 72° C. for 5 min (once).

Next, the solid-phase bridge PCR product on the beads was hybridized with a fluorescently labeled complementary oligonucleotide directed against internal APC sequences. The oligonucleotide probe was commercially custom synthesized with a 5' Cy5 label and PAGE purified by the manufacturer (Sigma-Genosys, The Woodlands, Tex.). The probe was diluted to 5 µM final in TE-50 mM NaCl for hybridization experiments. Prior to use however, the 5 µM probe solution was pre-clarified by spinning 1 min at maximum speed on a micro-centrifuge (~13,000 rpm or ~16,000×g) and collecting the fluid supernatant. The supernatant was then passed though a Filtration Device (see earlier in this Example for Filtration Devices) and the filtrate saved for use as the probe solution. The sequence of the probe was as follows:

```
Internal APC Probe:
                                         [SEQ NO. 69]
5'[Cy5]gCACCCTAgAACCAAATCCAgCAgACTg3'
```

To perform the hybridization probing, following completion of the solid-phase bridge PCR reaction, 400 µL of TE-50 mM NaCl (10 mM Tris, pH 8.0, 1 mM EDTA, 50 mM NaCl) was added to each completed solid-phase bridge PCR reaction and the suspensions transferred to fresh Filtration Devices (Ultrafree-MC Durapore Micro-centrifuge Filtration Devices, 400 µL capacity; Millipore, Billerica, Mass.). Filtration was performed and the filtrate discarded. The beads were washed briefly 2×400 µL more with TE-50 mM NaCl. Prior to performing filtration on the final wash, enough of the suspension was removed from the Filtration Device (for storage) thereby leaving 1 µL actual bead volume per sample. Following filtration, each 1 µL pellet corresponding to each sample was resuspended in 25 µL of the aforementioned clarified 5 µM probe solution. The beads were resuspended by manual pipetting then transferred to 0.5 mL polypropylene thin-wall PCR tubes. Hybridization was performed as follows in a PCR machine: 2 min 94° C. (denature) (beads resuspended by vortex mixing just before this step) followed by ramping down to 68° C. at a rate of 0.1° C./sec and subsequently holding 1 hour at 68° C. (anneal).

Just at the end of the above 1 hour 68° C. (anneal) step, while the tubes were still at 68° C. and still in the PCR machine, each sample was rapidly diluted with 400 µL of 68° C. TE-50 mM NaCl, the suspensions immediately transferred to a Filtration Device and filtration immediately performed. The filtrate was then discarded. The beads were washed 2×400 µL more with 68° C. TE-50 mM NaCl then 2×400 µL with room temperature TE-50 mM NaCl. Next, to fluorescently stain all beads independently of the presence or absence of amplicon, the beads were treated 1× for 5 min with gentle mixing using 200 µL of TE-50 mM NaCl containing 50 pg/µL of a streptavidin Alexa Fluor 488 conjugate (Invitrogen Corporation, Carlsbad, Calif.). The beads were then further washed 2×400 µL with TE-50 mM NaCl and then 1× 400 µL with TE-100 mM NaCl (10 mM Tris, pH 8.0, 1 mM EDTA, 100 mM NaCl). The beads were recovered from the Filtration Devices by resuspending the pellet in 50 µL of TE-100 mM NaCl and transferring to a 0.5 mL polypropylene PCR tube. The beads were spun down in a standard micro-centrifuge (just until reaches maximum speed of ~13,000 rpm corresponding to ~16,000×g) and the fluid supernatant removed.

Embedding the Beads in a Polyacrylamide Film and Fluorescence Imaging:

Lastly, the beads were embedded in a polyacrylamide film on a microscope slide and fluorescently imaged to detect the bound Cy5 labeled hybridization probe as well as the Alexa Fluor 488 total bead staining. To do so, an Acrylamide Mix was prepared by combining the following reagents in order: 244 µL of TE-100 mM NaCl, 57 µL of 40% acrylamide (19:1 cross-linking) (Bio-Rad Laboratories, Hercules, Calif.), 0.5 µL TEMED (Bio-Rad Laboratories, Hercules, Calif.), and 1 µL of a 10% (w/v) ammonium persulfate stock (prepared in MBG-Water from powder obtained from Bio-Rad Laboratories, Hercules, Calif.). Each aforementioned washed bead pellet was then resuspended in 50 µL of the above Acrylamide Mix and combined by brief vortex mixing. 25 µL of the bead suspension was then pipetted to a standard glass microscope slide and overlaid with a standard 18 mm square microscope cover glass (coverslip). Polymerization was allowed to occur for ~10 min protected from light. Note that the adequately slow polymerization process allows all beads to settle to the surface of the microscope slide by unit gravity. When polymerization was complete, imaging was performed using an ArrayWoRx$^e$ BioChip fluorescence microarray reader (Applied Precision, LLC, Issaquah, Wash.).

Results:

The fluorescence images are shown in FIG. 43 as 2-color overlays. The green signal in FIG. 43 is the total bead stain, independent of the presence or absence of amplicon, while the red signal is the APC-specific hybridization probing of the solid-phase bridge PCR amplicon on the beads. Without magnesium supplementation in the solid-phase bridge PCR reaction, essentially no amplicon is detectible on the beads above the minus template background control sample. With magnesium supplementation to 3 mM total, solid-phase bridge PCR amplicon (APC) is detected in the plus template sample permutation, with a signal-to-noise ratio of approximately 5:1 when quantified. 3 mM total magnesium plus DNA polymerase supplementation to 0.1 U/µL further improves solid-phase bridge PCR efficiency approximately 2-3 fold above the 3 mM magnesium alone. These results confirm the compatibility of the presented solid-phase bridge PCR method with amplification of fragmented genomic DNA templates, and also demonstrates the benefits of magnesium supplementation in the solid-phase bridge PCR reaction. Magnesium supplementation is beneficial likely due to the high concentration of primers on the beads, which chelate the magnesium thereby reducing the free magnesium concentration in the reaction. Sufficient free magnesium however, is needed as a co-factor for the DNA polymerase activity.

Example 49

Solid-Phase Bridge PCR on 6 Micron Diameter, Non-Porous, Fluorescently Bar-Coded Plastic Beads from Luminex Corporation: Detection of the Solid-Phase Bridge PCR Amplicon on the Beads by Biotin-dUTP Labeling This Example demonstrates the compatibility of solid-phase bridge PCR with multiplexed assay platforms, more specifically, the Luminex xMAP® platform (Luminex Corporation; Austin, Tex.) which currently can use approximately 100 different fluorescently bar-coded bead species for multiplexed assays based on a flow cytometric readout.

Primer Conjugation to Luminex Beads

Note: All buffers and reagents used throughout this entire Example, unless otherwise noted, were minimally DNAse, RNAse and protease free, referred to as Molecular Biology Grade (MBG), including the water, referred to as MBG-Water.

xMAP Multi-Analyte Carboxylated Microspheres® and SeroMAP Carboxylated Microspheres® were purchased commercially from Luminex Corporation (Austin, Tex.). The beads are non-porous, polystyrene based, contain carboxyl functional moieties and have a diameter of approximately 6 microns.

These carboxylated beads were covalently conjugated to the 5' amine modified solid-phase bridge PCR primers. The forward and reverse solid-phase bridge PCR primers, directed against a prepared template corresponding to a segment of the human APC gene Mutation Cluster Region (MCR), were purchased from Sigma-Genosys (The Woodlands, Tex.), both with a 5' primary amine modification following a 6 carbon spacer. The primer sequences are listed below. In the primers below, the bracketed sequences indicate the template-specific hybridization regions, while the remaining sequences are non-hybridizing regions which correspond to the remaining portions of the elements needed for later cell-free protein expression as well as epitope tag detection (the initial portion of these elements was introduced during the template preparation; template prepared as in Example 44).

```
Solid-Phase Bridge PCR APC Forward Primer:
                                        [SEQ NO. 70]
5'[Amine]TAATACgACTCACTATAgggAgAggAggTATATCAATgTAC
ACCgACATCgAg[ATgAACCgCCTgggCAAgggAggAggAggA]3'

Solid-Phase Bridge PCR APC Reverse Primer:
                                        [SEQ NO. 71]
5'[Amine]TTTTTTTTTTTTTTTTTTTATTATCCTCCTCCTgCgTAgT
CTggTACgTCgTATgggTA[CAgCAgCTTgTgCAggTCgCTgAAggTgg]
3'
```

To wash and manipulate the beads or exchange the buffers, 0.45 micron pore size, PVDF membrane, micro-centrifuge Filtration Devices were used unless otherwise noted (Ultrafree-MC Durapore Micro-centrifuge Filtration Devices, 400 µL capacity; Millipore, Billerica, Mass.). Using the aforementioned Filtration Devices, 5 µL of actual bead volume was washed 5×400 µL with MES Buffer (0.1 M MES, pH 4.7, 0.9% NaCl; Pierce Biotechnology, Inc., Rockford, Ill.). Unless otherwise noted, all washes are brief, 1-3 sec, by vortex mixing followed by spinning the Filtration Devices briefly in a standard micro-centrifuge (just until reaches maximum speed of ~13,000 rpm corresponding to ~16,000× g) and discarding the filtrate. The washed bead pellets were then recovered into 0.5 mL polypropylene PCR tubes by resuspending in 120 µL of MES Buffer. Each suspension was then split into 20 µL and 100 µL portions for the minus primer and plus primer permutations respectively (roughly 1 µL and 4 µL actual bead volumes respectively). To the 100 µL bead suspensions, 5.1 µL of a solution of 625 µM each primer (forward and reverse; prepared in MBG-Water) was added, resulting in a final concentration of 30 µM each primer (forward and reverse) (plus primer permutation). Nothing was added to the 20 µL bead suspensions (minus primer permutation).

EDC (1-Ethyl-3-[3-dimethylaminopropyl]carbodiimide hydrochloride powder; Pierce Biotechnology, Inc., Rockford, Ill.) was dissolved to 100 mg/mL in ice-cold MBG-Water then 5 µL and 25 µL immediately added to the above minus primer and plus primer bead suspensions respectively. The reaction was carried out for 1 hour at room temperature with gentle mixing.

In Filtration Devices, the beads were then washed 3×400 µL with TE-Saline-Glycine Buffer (10 mM Tris-HCl, pH 8.0, 1 mM EDTA, 200 mM NaCl, 0.1M glycine) and quenched by treatment for 30 min with mixing in a fresh 400 µL of the same buffer. Beads were then washed 4×400 µL with TE-50 mM NaCl-T Buffer (10 mM Tris-HCl, pH 8.0, 1 mM EDTA, 50 mM NaCl, 0.01% Tween-20) and lastly resuspended to 5% beads (v/v) in the same buffer for storage at +4° C. protected from light.

Qualitative Analysis of Primer Attachment:

To qualitatively verify successful primer attachment to the beads, an aliquot of the beads was stained with the single-stranded DNA fluorescence-based detection reagent Oli-Green (Invitrogen Corporation, Carlsbad, Calif.). The manufacturer supplied reagent was diluted 1/200 in TE (10 mM Tris, pH 8.0, 1 mM EDTA) containing 0.01% (v/v) Tween-20. 2.5

µL of the prepared primer-conjugated bead suspension (5% beads for 0.125 µL actual bead volume) was mixed with 100 µL of the diluted OliGreen reagent in a thin-walled 0.5 mL clear polypropylene PCR tube. As a negative control, the beads that were prepared in the same manner, except lacked any attached primer, were also tested. After approximately 1 min, the beads were spun down briefly in a micro-centrifuge (just until reaches maximum speed of ~13,000 rpm corresponding to ~16,000×g) and the bead pellet imaged directly in the tubes using a laser-based fluorescence scanner (FUJI FLA-2000, 473 nm solid-state laser excitation and 520 nm emissions filter) (FUJI Photo Film Co. Ltd, Japan).

Template Preparation and Solid-Phase Bridge PCR

Template was prepared and purified as described in Example 44.

0.25 µL of actual bead volume of each of the 2 primer bead types (xMAP and SeroMAP) was washed in bulk in the aforementioned Filtration Devices 1×400 µL with MBG-Water. Only beads containing primer were used in the solid-phase bridge PCR reactions. Each bead type was then resuspended in 400 µL of 0.1% (w/v) nuclease-free BSA (Invitrogen Corporation, Carlsbad, Calif.), in the top chamber of the Filtration Device, and allowed to stand for 15 min. Filtration was then performed and each bead pellet resuspended in 55 µL of PCR Master Mix (SuperTaq™ DNA Polymerase Kit; Ambion, Austin, Tex.; prepared according to the manufacturer's instructions except with 0.25 U/µL final SuperTaq™ DNA polymerase and 5% v/v PCR grade DMSO). Biotin-16-dUTP (Roche Applied Science, Indianapolis, Ind.) was also included in the PCR Master Mix at a final concentration of 20 µM, in order to label the solid-phase bridge PCR amplicon. Each bead suspension was then split into two 25 µL portions into 0.5 mL thin-wall polypropylene PCR tubes for the minus template and plus template sample permutations (approximately 0.125 µL/tube actual bead volume for approximately 300,000 beads/tube). For the plus template sample permutations, 4 ng in 1 µL of the aforementioned template was added to the appropriate bead suspensions. Minus template sample permutations received nothing further. The bead suspensions were subjected to thermocycling as follows: Initially 94° C. 2 min (once); then 35 cycles of 94° C. 30 s, 65° C. 30 s and 72° C. 2 min; followed by a final 72° C. 10 min (once). Beads were resuspended by vortex mixing just before thermocycling and then periodically every 5 cycles during the 72° C. 2 min extension step. After thermocycling, beads were washed directly in their tubes 5×400 µL with TE-50 mM NaCl-T Buffer. Beads were ultimately resuspended in approximately 25 µL of TE-50 mM NaCl-T Buffer for storage at +4° C.

Chemiluminescence Based Detection of Biotin dUTP Labeled Amplicon on Beads

The above beads were blocked 30 min with gentle mixing by adding 400 µL of Blocking Buffer [1% (w/v) nuclease-free BSA in 10 mM Tris-HCl, pH 8.0, 1 mM EDTA, 200 mM NaCl, 0.05% (v/v) Tween-20]. Beads were spun down briefly in a standard micro-centrifuge (just until reaches maximum speed of ~13,000 rpm corresponding to ~16,000×g) and the supernatant discarded. Beads were then treated with 200 µL of 50 ng/mL of a NeutrAvidin-HRP conjugate (Pierce Biotechnology, Inc., Rockford, Ill.) diluted in Blocking Buffer. Treatment was for 30 min with gentle mixing. Beads were then spun down briefly in a standard micro-centrifuge (just until reaches maximum speed of ~13,000 rpm corresponding to ~16,000×g) and the supernatant discarded. Beads were washed 4×400 µL in TE-Saline-Tween (10 mM Tris-HCl, pH 8.0, 1 mM EDTA, 200 mM NaCl, 0.05% (v/v) Tween-20). All washes were by brief (1-3 sec) vortex mixing followed by spinning the beads down briefly in a standard micro-centrifuge (just until reaches maximum speed of ~13,000 rpm corresponding to ~16,000×g) and discarding the supernatant. Beads were then resuspended in 400 µL of Tris-Saline (10 mM Tris-HCl, pH 8.0, 200 mM NaCl) and transferred to the aforementioned Filtration Devices (fresh devices). Filtration was performed as before and the filtrate discarded. Beads were then recovered from the Filtration Devices in 50 µL of Tris-Saline and placed into the wells of a 96-well opaque white microtiter plate. Next, 200 µL/well was added of freshly prepared SuperSignal Femto chemiluminescent HRP substrate (Pierce Biotechnology, Inc., Rockford, Ill.), the plates shaken for 10 s and immediately read on a LumiCount luminescence plate reader (Packard/PerkinElmer Life and Analytical Sciences, Inc., Boston, Mass.).

Results:

Primer attachment to the beads was first verified by staining the beads with OliGreen, which fluorescently detects single-stranded DNA. The stained bead pellets were imaged directly in 0.5 mL thin-wall polypropylene PCR tubes and the image shown in FIG. 44A. The results clearly show that attached primer is only detected when the primers were included in the chemical conjugation reaction ("+Primer"), but not when the primers were omitted from the reaction ("−Primer").

Following verification or primer attachment, the beads (not stained with OliGreen) were used in solid-phase bridge PCR reactions (only beads containing primer used in solid-phase bridge PCR). The resultant amplicon on the beads, which was labeled using biotin dUTP during the solid-phase bridge PCR, was detected via a chemiluminescent assay. The data was plotted and is shown graphically in FIG. 44B. Results show that solid-phase bridge PCR amplicon is clearly detected on both the xMAP and SeroMAP beads only when the template DNA is added to the solid-phase bridge PCR reaction, with signal-to-noise ratios of 133:1 and 250:1 respectively.

Example 50

Solid-Phase Bridge PCR for Detection of the Bisulfite Converted Wild-Type Vimentin DNA Marker Directly from Genomic DNA: Applications in Colorectal Cancer Diagnosis Methylation of the vimentin and RASSF2A markers and the detection of colorectal cancer, using methylation-specific PCR (MSP), is reported in the scientific literature [Chen et al. (2005) *J Natl Cancer Inst* 97, 1124-1132; Hesson et al. (2005) *Oncogene* 24, 3987-3994; Park et al. (2007) *Int J Cancer* 120, 7-12]. This Example demonstrates the ability to use solid-phase bridge PCR for MSP assays on diagnostic markers. In this Example, detection of the wild-type vimentin marker is demonstrated. However, the technique is equally applicable to the detection of the "mutant", i.e. methylated marker(s), simply by changing the primer sequences.

Importantly, this example differs from Example 47 in that fragmented and bisulfite converted genomic DNA was used directly as the solid-phase bridge PCR (MSP) template, instead of a purified PCR product as done previously.

Preparation of Agarose Beads Covalently Conjugated to PCR Primers Used for Solid-Phase Bridge PCR:

Production of Primer-Conjugated Agarose Beads was performed as in Example 36 except beads with the following primer pair were prepared.

```
Vimentin Unmethylated Primer Pair:
                                            [SEQ NO. 72]
Forward: 5'[Amine]TTgAggTTTTTgTgTTAgAgATgTAgTTgT3'
                                            [SEQ NO. 73]
Reverse: 5'[Amine]ACTCCAACTAAAACTCAACCAACTCACA3'
```

Qualitative Analysis of Primer Attachment:

Performed as in Example 36

Template for Solid-Phase Bridge PCR and Bisulfate Conversion:

Normal human blood genomic DNA (wild-type DNA; i.e. unmethylated at vimentin marker region) (Clontech, Mountain View, Calif.) was purchased commercially to be used as the template for solid-phase bridge PCR. The genomic DNA was first mechanically fragmented into an average size of roughly 500 bp via direct probe sonication. Fragmentation was verified by standard agarose gel electrophoresis.

For bisulfite conversion, the fragmented normal human blood genomic DNA was first denatured by preparing the following reaction: 12.5 ng/µL single-stranded carrier DNA (lambda DNA, E. coli genomic DNA or salmon sperm DNA), 0.3N NaOH, and 1-50 ng of the aforementioned normal human blood genomic DNA. The denaturation reaction was then incubated for 10 min at 37° C. Next, 30 µL of 10 mM hydroquinone was added (10 mM hydroquinone prepared fresh from 25× stock which is stored at −20° C.) followed by 500 µL of a 3M sodium bisulfite stock (stock adjusted to pH 5.0 with NaOH). Lastly, 200 µL of mineral oil was added and the reaction incubated at 50° C. for 16 hrs.

The resultant bisulfite converted DNA was purified using the commercially available Wizard® DNA Clean-Up System (Promega, Madison, Wis.) according to the manufacturer's instructions. After elution from the Wizard® DNA Clean-Up System mini-columns in 90 µL 0.1×TE (1 mM Tris-HCl, pH 8.0, 0.1 mM EDTA), the DNA was ethanol precipitated. Ethanol precipitation was carried out as follows: 45 µL of 1 N NaOH was added to each sample and briefly vortex mixed. After 5 min, 15 µL of 3M sodium acetate, pH 5.2, was added to each tube. Next, 1 µL of 20 mg/mL glycogen was added followed by 300 µL of ethanol. The mixture was then incubated at −80° C. for 20 min and spun in a micro-centrifuge for 10 min (maximum speed of ~13,000 rpm corresponding to ~16,000×g). The ethanol was removed and the DNA pellet air dried at room temperature for 15 min. The DNA was then re-dissolved in 0.1×TE for immediate use or storage at −20° C. This fragmented and bisulfite converted genomic DNA directly served as template for the solid-phase bridge PCR reactions described below.

Solid-Phase Bridge PCR:

10 µL actual total bead volume of the previously prepared Primer-Conjugated Agarose Beads was pre-washed in bulk. Beads were pre-washed to remove any non-covalently attached primers. Beads were initially washed using 0.45 micron pore size, PVDF membrane, micro-centrifuge Filtration Devices (Ultrafree-MC Durapore Micro-centrifuge Filtration Devices, 400 µL capacity; Millipore, Billerica, Mass.). Unless otherwise noted, all washes involving the Filtration Devices were by brief vortex mixing (~5 sec), spinning down briefly in a micro-centrifuge (just until reaches maximum speed of ~13,000 rpm corresponding to ~16,000×g) and discarding the filtrate. Initial washes were 2×400 µL with TE-50 mM NaCl (10 mM Tris, pH 8.0, 1 mM EDTA, 50 mM NaCl). Beads were then resuspended in TE-50 mM NaCl to 20% (v/v) and the suspensions recovered into 0.5 mL thin-walled polypropylene PCR tubes. The tubes were placed in a PCR machine at 95° C. for 10 min to allow heat-mediated washing (lid temperature 105° C. and no mineral oil used) (beads were resuspended by brief gentle vortex mixing just before this step). After heating, the tubes were immediately removed from the PCR machine, the beads were diluted to 400 µL with TE-50 mM NaCl and the bead suspensions were then transferred to Filtration Devices. Filtration was performed and the filtrate discarded. Beads were briefly washed 1×400 µL more with TE-50 mM NaCl then 1×400 µL with MBG-Water.

Prior to the final filtration step (wash), bead suspensions were split into 2.5 µL and 7.5 µL portions (actual bead volume) in separate Filtration Devices. Following the final filtration step (wash) on the bead samples, the washed bead pellets were resuspended in a commercially available PCR reaction buffer (HotStarTaq DNA Polymerase kit; Qiagen, Valencia, Calif.). To do so, first, the 2.5 and 7.5 µL bead pellets were resuspended in 100 µL each of the 1× HotStarTaq reaction buffer (i.e. just the provided buffer; no dNTPs or DNA polymerase yet) containing either no template or roughly 150 ng of the aforementioned fragmented and bisulfite converted genomic DNA template, respectively. This resulted in a ratio of ~3,000 genome equivalents per µL of actual Primer-Conjugated Agarose Bead volume. With 1 µL of Primer-Conjugated Agarose Beads determined to contain approximately 1,000 beads, ~3,000 genome equivalents per µL of beads represents a ratio of approximately 6 actual vimentin template molecules (gene copies) added per bead (beads physically enumerated under a microscope both in diluted droplets of bead suspension and with suspensions in a hemacytometer cell counting chamber). It should be noted that although a ratio of 6 vimentin gene copies per bead was used, the fragmentation of the genomic DNA will statistically reduce the number of amplifiable vimentin templates per bead (average genomic DNA template fragment ~500 bp; targeted vimentin region for amplification 217 bp). The suspensions were placed into 0.5 mL polypropylene thin-wall PCR tubes and mixed at 57° C. for 18 hrs to selectively capture the targeted vimentin template by hybridization to the bead-bound primers. Using the aforementioned Filtration Devices, the beads were then washed 2×400 µL with TE-50 mM NaCl then 1×400 µL with the 1× HotStarTaq reaction buffer (i.e. just the provided buffer; no dNTPs or DNA polymerase yet) to remove any unbound DNA. Then, 2.5 µL actual bead volume, from each sample, was each resuspended in 25 µL of HotStarTaq DNA Polymerase PCR reaction mix which was prepared according to the manufacturer's instructions (with dNTPs and DNA polymerase at this stage) and pre-activated (95° C. for 15 min then cool to room temperature) prior to addition to the beads. The samples were then subjected to the following thermocycling in a PCR machine (lid temperature 105° C. and no mineral oil used): An initial extension step (once) of 72° C. for 10 min followed by an initial denaturing step (once) of 95° C. for 5 min, and 70 cycles of 94° C. for 30 sec (denature), 58° C. for 2 min (anneal) and 72° C. for 1 min (extend) whereby a fresh aliquot of HotStarTaq DNA polymerase was added to 0.05 U/µL final concentration after 40 cycles; followed by a final extension step of 72° C. for 5 min after all 70 cycles.

400 µL of TE-50 mM NaCl (10 mM Tris, pH 8.0, 1 mM EDTA, 50 mM NaCl) was added to each completed solid-phase bridge PCR reaction and the suspensions transferred to Filtration Devices (Ultrafree-MC Durapore Micro-centrifuge Filtration Devices, 400 µL capacity; Millipore, Billerica, Mass.). Filtration was performed in a micro-centrifuge (just until reaches maximum speed of ~13,000 rpm corresponding to ~16,000×g) and the filtrate discarded. The beads were washed 3×400 μL more with TE-50 mM NaCl; resuspending by ~5 sec vortex mixing then performing filtration and discarding the filtrate as described earlier in this Example.
Oligonucleotide Hybridization Probing:

Fluorescently labeled oligonucleotide probes were commercially custom synthesized and HPLC purified by the manufacturer (Sigma-Genosys, The Woodlands, Tex.). The probes were reconstituted to 100 μM in MBG-Water and further desalted using MicroSpin G-25 columns according to the manufacturer's instructions (Amersham Biosciences Corp., Piscataway, N.J.), except that the columns were prewashed 2×350 μL with MBG-Water prior to sample loading (to wash, columns were mixed briefly in the MBG-Water then spun 1 min in a standard micro-centrifuge at the proper speed). The probes were diluted in TE-50 mM NaCl for hybridization experiments. Prior to use however, the diluted probe solution was pre-clarified by spinning 1 min at maximum speed on a micro-centrifuge (~13,000 rpm or ~16,000× g) and collecting the fluid supernatant. The supernatant was then passed though a Filtration Device (see earlier in this Example for Filtration Devices) and the filtrate was saved for use as the clarified probe solution.

In this Example, hybridization probing was performed by creating a probing solution containing 1 μM of the vimentin probe, labeled on its 5' end with the Cy3 fluorophore by the manufacturer (Sigma-Genosys, The Woodlands, Tex.). The gene-specific probe was complementary to an internal segment of the vimentin solid-phase bridge PCR amplicon:

Human Vimentin Unmethylated & Bisulfite Converted:
[SEQ NO. 74]
5'[Cy3]TgTAggATgTTTggTggTTTggg3'

After solid-phase bridge PCR and washing of the beads as described earlier in this Example, the bead pellets corresponding to each sample were resuspended in 25 μL of the aforementioned clarified probe solution. The beads were resuspended by manual pipetting then transferred to 0.5 mL polypropylene thin-wall PCR tubes. Hybridization was performed as follows in a PCR machine (lid temperature always 105° C., no mineral oil used): 5 min 95° C. (denature) (beads were be resuspended by vortex mixing just before this step) followed by ramping down to 60° C. at a rate of 0.1° C./sec and subsequently holding 1 hour at 60° C. (anneal).

Just at the end of the above 1 hour 60° C. (anneal) step, while the tubes were still at 60° C. and still in the PCR machine, each sample was rapidly diluted with 400 μL of 60° C. TE-50 mM NaCl, the suspensions immediately transferred to a Filtration Device and filtration immediately performed. The filtrate was then discarded. The beads were washed 2×400 μL more with 60° C. TE-50 mM NaCl then 1×400 μL with room temperature TE-50 mM NaCl. Beads were lastly washed 1×400 μL with TE-100 mM NaCl (10 mM Tris, pH 8.0, 1 mM EDTA, 100 mM NaCl). The beads were recovered from the Filtration Devices by resuspending the pellets in 50 μL of TE-100 mM NaCl and transferring to a 0.5 mL polypropylene PCR tube. The beads were spun down in a standard micro-centrifuge (just until reaches maximum speed of ~43, 000 rpm corresponding to ~16,000×g) and the fluid supernatant was removed.
Embedding the Beads in a Polyacrylamide Film and Fluorescence Imaging:

Lastly, the beads were embedded in a polyacrylamide film on a microscope slide and fluorescently imaged to detect the bound Cy3 labeled hybridization probe. To do so, an Acrylamide Mix was prepared by combining the following reagents in order: 244 μL of TE-100 mM NaCl, 57 μL of 40% acrylamide (19:1 cross-linking) (Bio-Rad Laboratories, Hercules, Calif.), 0.5 μL TEMED (Bio-Rad Laboratories, Hercules, Calif.), and 1 μL of a 10% (w/v) ammonium persulfate stock (prepared in MBG-Water from powder obtained from Bio-Rad Laboratories, Hercules, Calif.). Each aforementioned washed bead pellet was then resuspended to 2% (v/v) beads in the above Acrylamide Mix and combined by brief vortex mixing. 25 μL of the bead suspension was then pipetted to a standard glass microscope slide and overlaid with a standard 18 mm square microscope cover glass (coverslip). Polymerization was allowed to occur for ~10 min protected from light. Note that the adequately slow polymerization process allows all beads to settle to the surface of the microscope slide by unit gravity. When polymerization was complete, imaging was performed using an ArrayWoRx$^e$ BioChip fluorescence microarray reader (Applied Precision, LLC, Issaquah, Wash.).
Results:

Results show proof-of-principal for performing methylation-specific PCR (MSP) on disease biomarkers (in this case for colorectal cancer), using solid-phase bridge PCR, by directly using fragmented and bisulfite converted genomic DNA as the template. FIG. 45 shows the solid-phase bridge PCR beads following fluorescence hybridization probing for the vimentin amplicon. Amplicon is detected on the beads when the fragmented and bisulfite converted genomic DNA template is added to the solid-phase bridge PCR reaction ("+gDNA Template"), with a signal-to-noise ratio of approximately 10:1 (following quantification) versus the negative control sample where only the template DNA was omitted ("−Template").

Example 51

Effective Single Template Molecule Solid-Phase Bridge PCR on the APC Gene Associated with Colorectal Cancer: Multiplexing of Various APC Gene Segments Using Patient DNA as Template and Followed by a Downstream Bead-Based High-Sensitivity Protein Truncation Test The overall goal of this Example is molecular diagnostics of colorectal cancer based on detection of truncating mutations in the APC gene from various types of patient samples (e.g. stool, urine or blood samples). These patient samples are the source of template DNA molecules used in the solid-phase bridge PCR and cell-free protein expression based diagnostic test. This Example will combine the effective amplification of single template DNA molecules per bead in solid-phase bridge PCR, e.g. similar to as in Example 44, with the inherent multiplexing capabilities of solid-phase bridge PCR (e.g. Example 47), that is, to use different primer bead species in a single reaction to target (amplify) single molecules from different segments of the APC gene associated with colorectal cancer. Following solid-phase bridge PCR, multiplexed cell-free expression, with in situ capture, e.g. as in Example 31, will be performed on the bead population to convert the DNA beads to beads carrying the cognate protein. Lastly, the beads, or bead-derived contact photo-transfer spots, will be probed with fluorescently labeled antibodies to N-terminal and C-terminal detection epitopes to measure the presence of beads (or bead-derived spots) carrying truncated proteins, e.g. as in Example 42, indicating the presence of a truncation mutation in APC in at least a fraction of the template DNA molecules from the patient sample.

Solid-Phase Bridge PCR Template DNA:

DNA will be isolated from various biological fluids and biological samples from both normal human subjects as well as those known to have colorectal cancer at various stages (e.g. as identified by colonoscopy). Fluids and samples will include, but are not limited to tissue, stool, blood, serum, plasma or urine.

Preparation of Agarose Beads Covalently Conjugated to PCR Primers Used for Solid-Phase Bridge PCR:

Several different Primer-Conjugated Agarose Bead sets will be prepared separately, each set targeting different regions of Exon 15 of the APC gene, with all sets combined covering the entire Mutation Cluster Region (MCR). Primer-Conjugated Agarose Bead preparation will be performed as in Example 48, except using the PCR primer pairs listed below this paragraph. In the primers below, the bracketed sequences indicate the gene-specific APC directed hybridization regions, while the remaining sequences are non-hybridizing regions which correspond to all of the elements needed for later cell-free protein expression as well as epitope tag binding and detection. Epitope tags include an N-terminal VSV-G detection tag, an N-terminal HSV capture/binding tag and a C-terminal p53-tag for detection. For the reference APC template sequence (mRNA), see for example GeneBank Accession NM_000038.

```
APC Segment 1 (Forward and Reverse):
                                                         [SEQ NO. 75]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[ggACAAAgCAgT
AAAACCgAA]3'

[SEQ NO. 76]
5'TTATTACAgCAgCTTgTgCAggTCgCTgAAggT[AgCCTTTTgAggCTgACCACT]3'

APC Segment 2 (Forward and Reverse):
                                                         [SEQ NO. 77]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[CCAAgTTCTgCA
CAgAgTAgA]3'

[SEQ NO. 78]
5'TTATTACAgCAgCTTgTgCAggTCgCTgAAggT[TgAACTACATCTTgAAAAACA]3'

APC Segment 3 (Forward and Reverse):
                                                         [SEQ NO. 79]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[TgTgTAgAAgATA
CTCCAATA]3'

[SEQ NO. 80]
5'TTATTACAgCAgCTTgTgCAggTCgCTgAAggT[TATTTCTgCTATTTgCAgggT]3'

APC Segment 4 (Forward and Reverse):
                                                         [SEQ NO. 81]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[CAggAAgCAgATT
CTgCTAAT]3'

[SEQ NO. 82]
5'TTATTACAgCAgCTTgTgCAggTCgCTgAAggT[CTgCAgTCTgCTggATTTggT]3'

APC Segment 5 (Forward and Reverse):
                                                         [SEQ NO. 83]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[gCAgTgTCACAgC
ACCCTAgA]3'

[SEQ NO. 84]
5'TTATTACAgCAgCTTgTgCAggTCgCTgAAggT[gggTgTCTgAgCACCACTTTT]3'

APC Segment 6 (Forward and Reverse):
                                                         [SEQ NO. 85]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[TCAggAgCgAAAT
CTCCCTCC]3'

[SEQ NO. 86]
5'TTATTACAgCAgCTTgTgCAggTCgCTgAAggT[CgAACgACTCTCAAAACTATC]3'

APC Segment 7 (Forward and Reverse):
                                                         [SEQ NO. 87]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[TgTACTTCTgTCA
gTTCACTT]3'
```

-continued
```
                                                         [SEQ NO. 88]
5'TTATTACAgCAgCTTgTgCAggTCgCTgAAggT[CATggTTTgTCCAgggCTATC]3'

APC Segment 8 (Forward and Reverse):
                                                         [SEQ NO. 89]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[ATAAgCCCCAgT
gATCTTCCA]3'

[SEQ NO. 90]
5'TTATTACAgCAgCTTgTgCAggTCgCTgAAggT[CTTTTCAgCAgTAggTgCTTT]3'

APC Segment 9 (Forward and Reverse):
                                                         [SEQ NO. 91]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[AAgCgAgAAgTA
CCTAAAAAT]3'

[SEQ NO. 92]
5'TTATTACAgCAgCTTgTgCAggTCgCTgAAggT[CgTggCAAAATgTAATAAAgT]3'

APC Segment 10 (Forward and Reverse):
                                                         [SEQ NO. 93]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[CAggTTCTTCCAg
ATgCTgAT]3'

[SEQ NO. 94]
5'TTATTACAgCAgCTTgTgCAggTCgCTgAAggT[TATTCTTAATTCCACATCTTT]3'

APC Segment 11 (Forward and Reverse):
                                                         [SEQ NO. 95]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[CTCgATgAgCCAT
TTATACag]3'

[SEQ NO. 96]
5'TTATTACAgCAgCTTgTgCAggTCgCTgAAggT[TTTTTCTgCCTCTTTCTCTTg]3'

APC Segment 12 (Forward and Reverse):
                                                         [SEQ NO. 97]
5'TAATACgACTCACTATAgggAgAggAggTATATCAATgTACACCgACATCgAgATgAACC
gCCTgggCAAgggAggACAgCCTgAACTCgCTCCAgAggATCCggAAgAT[CCTAAAgAATCA
AATgAAAAC]3'

[SEQ NO. 98]
5'TTATTACAgCAgCTTgTgCAggTCgCTgAAggT[TgACTTTgTTggCATggCAgA]3'
```

Qualitative Analysis of Primer Attachment:

Will be performed as in Example 36.

First Round of Effective Single Template Molecule Solid-Phase Bridge PCR:

Will be performed as in Example 48, using the conditions corresponding to the optimal permutation from that Example, that is, 3 mM total magnesium and 0.1 U/μL final DNA polymerase at the various steps as detailed in Example 48. In this Example however, the template DNA sources will be the various patient samples as described earlier in this Example. In some cases, the isolated patient DNA will be naturally fragmented, in which case it will not be further fragmented if of the proper size (e.g. approximate average 100 to 500 bp) (e.g. freely circulating DNA in blood or urine, not arising from blood cells or bladder cells respectively, but from arising non-local sources). In other cases, isolated patient DNA will not be naturally fragmented (e.g. from properly preserved tissue samples), in which case the DNA will be fragmented by direct probe sonication as in Example 48 (e.g. to approximate average 100 to 500 bp), or via mechanical shearing, enzymatic digestion or nebulization for example, prior to use in solid-phase bridge PCR.

Critically, using the criteria developed in previous Examples, the template DNA will be added to the beads in specific amounts so as to achieve effective amplification of one or a few initially added template molecules per bead.

Another important difference from Example 48 is that all of the different Primer-Conjugated Agarose beads sets described earlier in this Example will be combined into one solid-phase bridge PCR reaction, so as to allow multiplexed amplification of the different primer-targeted segments of the APC gene, using the same template mixture.

The template amount, reaction volume and numbers of beads will be scaled accordingly from that used in Example 48, so as to allow detection down to at least 1 mutant APC molecule out of 1,000 total (i.e. 999 wild-type molecules) for each bead set (each gene segment), with a 5-fold bead redundancy for each bead set. For example, this would entail 5,000 beads of each bead set and 60,000 beads total per reaction for all 12 APC segments, corresponding to approximately 60 μL of actual bead volume (see Example 48 for number of beads per μL).

Second Round of Solid-Phase Bridge PCR:

Will be performed as in Example 48, except that following solid-phase bridge PCR, the beads will not be hybridized with an oligonucleotide probe, but will instead be subjected to antibody coating and multiplexed cell-free protein expression, using in situ capture, as described see below.

Attaching the PC-Antibody to Beads Following Solid-Phase Bridge PCR:

The photocleavable binding/capture anti-HSV antibody (the PC-antibody) will be attached to the post solid-phase bridge PCR beads as performed in Example 31.

Multiplexed Cell-Free Protein Expression with In Situ Capture:

Will be performed as in Example 31 using the rabbit reticulocyte cell-free expression system (TNT® T7 Quick for PCR DNA; Promega, Madison, Wis.) or as in Example 40, using the PureSystem cell-free expression mixture (mixture prepared according to the manufacturer's instructions; Post Genome Institute Co., LTD., Japan).

Contact Photo-Transfer and Antibody Probing:

Following protein synthesis with in situ capture, the entire bead population will be photo-printed onto a microarray substrate (contact photo-transfer) and the printed substrate simultaneously probed with an anti-VSV Cy3 labeled N-terminal detection antibody and an anti-p53 Cy5 labeled C-terminal detection antibody as done in Example 42. The probing is performed to detect mutant truncated proteins missing the N-terminal as described in Example 42. Fluorescence imaging is performed as in Example 42. Note that contact photo-transfer can be omitted and the antibody probing performed directly on the beads (e.g. similar to Example 41).

Results:

Beads which originally amplify single APC template molecules corresponding to a particular APC segment having a truncating mutation, are expected to ultimately carry the truncated protein product following multiplexed cell-free protein expression with in situ capture. Hence, following antibody probing for the N-terminal and C-terminal epitope tags, these beads (or bead-derived microarray spots) will be detected as lacking a C-terminus on the expressed protein, as determined by the presence of the N-terminal antibody probe signal but absence of the C-terminal antibody probe signal. Conversely, beads or bead-derived microarray spots with wild-type APC proteins will have both N-terminal and C-terminal antibody probe signals. The ratio of mutant to wild-type beads or bead-derived microarray spots is expected to mirror the ratio of mutant and wild-type APC molecules present in the patient sample.

Instead of antibody probing of the protein containing beads or bead-derived spots, other protein-based analyses are possible, such as mass spectrometric analysis, which would detect missense mutations in addition to truncation (nonsense) mutations, based on a precise mass shift of the protein/peptide.

Lastly, protein expression of the beads can be omitted, in favor of DNA level assays on the post solid-phase bridge PCR beads. For example, single-base extension or massively parallel DNA sequencing could be employed for mutation detection on the beads.

Overall, the methodology is expected to allow non-invasive early diagnosis of colorectal cancer at the molecular level, with high sensitivity and high throughput screening abilities. The effective single-molecule amplification per bead will facilitate detection of low abundance mutant DNA molecules (relative to wild-type) in various types of patient samples. The full multiplexing of the solid-phase bridge PCR and cell-free protein expression (with in situ capture) will allow simultaneous analysis of different segments of a gene or template as well as different genes or markers for example.

Example 52

Solid-Phase Bridge PCR Followed by Cell-Free Expression with In Situ Protein Capture on PC-Antibodies: Background Reduction in Mass Spectrometry Analysis by Subsequent Photo-Release Preparing the Solid-Phase Bridge PCR Template DNA:

K562 cell-line total RNA was purchased from the ATCC (Manassas, Va.) and subjected to RT-PCR using the Advantage RT-PCR Kit (Clontech, Mountain View, Calif.) according to the manufacturer's instructions. The second step reaction of the RT-PCR was directed against the BCR-ABL transcript expressed in K562 cells with the following primers, which result in an approximate 1.8 kb product:

```
BCR-ABL RT-PCR Forward:
                                        [SEQ NO. 99]
5'gCgAACAAgggCAgCAAggCTACg3'

BCR-ABL RT-PCR Reverse:
                                        [SEQ NO. 100]
5'ACTggATTCCTggAACATTgTTTCAAAggCTTg3'
```

The resultant ~1.8 kb product was used directly as template in the solid-phase bridge PCR reaction without purification.

Preparation of Agarose Beads Covalently Conjugated to PCR Primers Used for Solid-Phase Bridge PCR:

Primer-Conjugated Agarose Beads prepared as in Example 36, except that the concentration of each primer during conjugation to the beads was 62.5 µM in 100 mM sodium bicarbonate, 1M NaCl as the Binding Buffer. The following primer pair was used for conjugation to the beads:

```
Forward:
                                        [SEQ NO. 101]
5'[Amine]TAATACgACTCACTATAgggAgAggAggTATATCAATgg
ATTATAAAgACgATgATgATAAAAACTACgACAAgTgggAgATg3'

Reverse:
                                        [SEQ NO. 102]
5'[Amine]TTATTTATTTATCACCgTCAggCTgTATTTCTT3'
```

The above primers amplify a region of the BCR-ABL tyrosine kinase domain designated in this Example as Segment 1. The primers also incorporate an N-terminal FLAG epitope tag for purification of the expressed peptide.

Qualitative Analysis of Primer Attachment:

Performed as in Example 36.

Solid-Phase Bridge PCR:

5 µL actual total bead volume of the previously prepared Primer-Conjugated Agarose Beads was used per each sample. Beads were initially washed using 0.45 micron pore size, PVDF membrane, micro-centrifuge Filtration Devices (Ultrafree-MC Durapore Micro-centrifuge Filtration Devices, 400 µL capacity; Millipore, Billerica, Mass.). Unless otherwise noted, all washes involving the Filtration Devices were by brief vortex mixing (~5 sec), spinning down briefly in a micro-centrifuge (just until reaches maximum speed of ~13,000 rpm corresponding to ~16,000×g) and discarding the filtrate. Initial washes were 2×400 µL with TE-50 mM NaCl (10 mM Tris, pH 8.0, 1 mM EDTA, 50 mM NaCl). Beads were then resuspended in TE-50 mM NaCl to 20% (v/v) and the suspensions recovered into 0.5 mL thin-walled polypropylene PCR tubes. The tubes were placed in a PCR machine at 95° C. for 10 min to allow heat-mediated washing (lid temperature 105° C. and no mineral oil used) (beads were resuspended by brief gentle vortex mixing just before this step). After heating, the tubes were immediately removed from the PCR machine, the beads were diluted to 400 µL with TE-50 mM NaCl and the bead suspensions were then transferred to Filtration Devices. Filtration was performed and the filtrate discarded. Beads were briefly washed 1×400 µL more with TE-50 mM NaCl then 1×400 µL with MBG-Water.

Following the final filtration step (wash) on the bead samples, the washed bead pellets were resuspended in a commercially available pre-mixed PCR reaction solution (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-$SO_4$ pH 8.9, 19.8 mM $(NH_4)_2SO_4$, 2.4 mM $MgSO_4$, 220 μM dNTPs and stabilizers; Invitrogen Corporation, Carlsbad, Calif.; solution used without prior dilution), which was supplemented with 0.2 U/μL additional DNA polymerase (same polymerase as in aforementioned PCR mix) and ~10 ng of the aforementioned RT-PCR product as template. 10 μL of this mixture was used per each 1 μL actual bead volume. No soluble primers were used. The suspensions (~50 μL) were placed into 0.5 mL polypropylene thin-wall PCR tubes. The samples were subjected to the following thermocycling in a PCR machine (lid temperature 105° C. and no mineral oil used): An initial denaturing step (once) of 94° C. for 2 min (beads were briefly resuspended by gentle vortex mixing just before this step), and 40 cycles of 94° C. for 30 sec (denature), 65° C. for 30 sec (anneal) and 68° C. for 30 sec (extend); followed by a final extension step of 68° C. for 10 mM.

400 μL of TE-50 mM NaCl (10 mM Tris, pH 8.0, 1 mM EDTA, 50 mM NaCl) was added to each completed solid-phase bridge PCR reaction and the suspensions transferred to Filtration Devices (Ultrafree-MC Durapore Micro-centrifuge Filtration Devices, 400 μL capacity; Millipore, Billerica, Mass.). Filtration was performed in a micro-centrifuge (just until reaches maximum speed of ~13,000 rpm corresponding to ~16,000×g) and the filtrate discarded. The beads were washed 3×400 μL more with TE-50 mM NaCl; resuspending by ~5 sec vortex mixing then performing filtration and discarding the filtrate as described earlier in this Example. At this point beads could either be placed in SP-PCR Storage Buffer (50% glycerol, TE-50 mM NaCl) and stored at −20° C. (5% beads v/v) or processed immediately as detailed below in this Example.

Attaching the PC-Antibody to Beads Following Solid-Phase Bridge PCR:

Following the solid-phase bridge PCR reaction, the 5 μL actual bead volume per sample was washed briefly 3×400 μL with TE-Saline (10 mM Tris-HCl, pH 8.0, 1 mM EDTA, 200 mM NaCl). Unless otherwise noted, all washes and bead manipulations were performed in batch mode using 0.45 micron pore size, PVDF membrane, micro-centrifuge Filtration Devices to facilitate manipulation of the beaded matrix (~100 micron beads) and exchange the buffers (Ultrafree-MC Durapore Micro-centrifuge Filtration Devices, 400 μL capacity; Millipore, Billerica, Mass.). NeutrAvidin (tetrameric) was then attached to the bead bound biotin-amine linker, in excess, by treatment with 400 μL of a 0.2 μg/μL solution in TE-Saline for 20 min (note: biotin-amine linker attached during previous preparation of Primer-Conjugated Agarose Beads; see Example 36). Beads were washed briefly 4×400 μL with TE-Saline.

The beads were next coated with a monoclonal mouse anti-FLAG tag capture antibody which was converted to photocleavable form by conjugation to PC-biotin. Creation of the photocleavable antibody (PC-antibody) was performed similar to as described in Example 2. To first create the PC-antibody (prepared in advance), 1 mg of antibody as supplied by the manufacturer (Mouse Anti-FLAG M2 Antibody; Sigma-Aldrich, St. Louis, Mo.) was purified on a NAP-5 desalting column according to the manufacturer's instructions (Amersham Biosciences Corp., Piscataway, N.J.) against a 200 mM sodium bicarbonate and 200 mM NaCl buffer (nuclease-free reagents). The resultant antibody was then reacted with 25 molar equivalents of AmberGen's PC-biotin-NHS labeling reagent (added from a 50 mM stock in anhydrous DMF) for 30-60 min with gentle mixing. The labeled antibody was then purified on a NAP-10 desalting column according to the manufacturer's instructions (Amersham Biosciences Corp., Piscataway, N.J.) against TE-Saline buffer. This prepared monoclonal anti-FLAG PC-biotin conjugate was then loaded onto the beads by treatment of the beads (still in Filtration Devices) with 200 μL of 0.15 μg/μL in TE-Saline for 20 mM. Beads were washed briefly 4×400 μL in TE-Saline followed by 2×400 μL in Molecular Biology Grade Water (MBG-Water).

Cell-Free Protein Expression of the Beads and In Situ Protein Capture:

Still in the Filtration Devices, the 5 μL bead pellets were then resuspended in 50 μL of the *E. coli* based PureSystem cell-free protein expression mixture (mixture prepared according to the manufacturer's instructions; Post Genome Institute Co., LTD., Japan) (no soluble DNA was included in the reaction). The expression mixture was additionally supplemented with 250 mM final Betaine concentration from a 5M stock (Sigma-Aldrich, St. Louis, Mo.) to minimize mRNA secondary structure. Protein expression was carried out for 1-2 hr at 42° C. in with gentle mixing (in the upper chamber of the Filtration Devices). After expression, filtration was performed and the filtrate discarded. Still in the Filtration Devices, the beads were washed 1×400 μL with PBS-T [standard PBS with 0.2% Triton X-100 (v/v)]. Beads were then washed 2×400 μL with mass spectrometry grade water (MSG-Water). Beads were re-suspended 50 μL of MSG-Water and recovered from the Filtration Devices.

Elution of Bead Bound Peptides and Mass Spectrometry Analysis:

The aforementioned 50 μL bead suspension was split into equal portions of 25 μL with each portion going into separate micro-columns. Micro-columns consist of 10 μL volume polypropylene pipette tips crimped at the end in order to trap the beads (i.e. prevent beads from flowing out of column). Essentially all of the MSG-Water was drained from the column by gravity (although agarose beads remain partially hydrated). One micro-column was eluted by denaturation of the capture antibody while the other was photo-eluted (photo-release of the photocleavable capture antibody). For denaturing elution, 5 μL of MALDI-TOF mass spectrometry matrix solution (20 mg/mL sinapinic acid matrix in 50% acetonitrile and 0.1% trifluoroacetic acid) was applied to the micro-column and the first ~14 eluted droplet collected directly onto a stainless steel MALDI-TOF plate. The droplet was then allowed to dry/crystallize under ambient conditions. For photo-elution, the beads, still in the micro-column, were exposed to near-UV light (365 nm peak UV lamp, Blak-Ray Lamp, Model XX-15, UVP, Upland, Calif.) at a 5 cm distance for 10 minutes. Importantly, the polypropylene micro-columns transmit the necessary light. The power output under these conditions was 2.6 mW/$cm^2$ at 360 nm, 1.0 mW/$cm^2$ at 310 nm and 0.16 mW/$cm^2$ at 250 nm. Following photo-elution, approximately 5 μL of MSG-Water was applied to the micro-column and the first ~1 μL eluted droplet collected directly onto a stainless steel MALDI-TOF plate. The droplet was mixed with equal volume of the aforementioned MALDI-TOF mass spectrometry matrix solution and the droplet was then allowed to dry/crystallize under ambient conditions. Once dried, the spots were analyzed using a Voyager-DE MALDI-TOF mass spectrometer (Applied Biosystems; Foster City, Calif.).

Results:

Results are shown in FIG. 46. With both the denaturing elution and photo-elution methods, the correct peptide peak corresponding to the so-called Segment 1 of the BCR-ABL tyrosine kinase domain was identified with a mass accuracy of ±1 Dalton (0.02% mass error). However, in the denaturing elution method, several contaminating background peaks are observed which are not present in the photo-eluted sample. Background is believed to be caused by 2 mechanisms: First, the highly charged DNA and (strept)avidin on the bead surface, as well as the agarose bead surface itself, can mediate non-specific binding of components in the highly concentrated cell-free protein expression system. These components can remain bound to the beads even after extensive washing, but are striped from the beads by the denaturing elution, contaminating target peptide and creating background in the mass spectrometry analysis. Second, the DNA and (strept) avidin, present at high concentrations on the beads, can themselves leach from beads hence directly causing background (especially minor degradation products falling in the mass range of interest). The gentle and highly selective photo-elution avoids these problems, leaving such contaminants behind on the beads. Lastly, likely because of the contaminating materials in the denaturing elution method, the magnitude of the target peak (Segment 1) is 4-fold less than that of the photo-eluted peptide.

Example 53

Solid-Phase Bridge PCR Followed by Cell-Free Expression and Mass Spectrometry Analysis Multiplex Cell-Free Expression Preparing the Solid-Phase Bridge PCR Template DNA:

K562 cell-line total RNA was purchased from the ATCC (Manassas, Va.) and subjected to RT-PCR using the Advantage RT-PCR Kit (Clontech, Mountain View, Calif.) according to the manufacturer's instructions. The second step reaction of the RT-PCR was directed against the BCR-ABL transcript expressed in K562 cells with the following primers, which result in an approximate 1.8 kb product:

```
BCR-ABL RT-PCR Forward:
                                           [SEQ NO. 99]
5'gCgAACAAgggCAgCAAggCTACg3'

BCR-ABL RT-PCR Reverse:
                                           [SEQ NO. 100]
5'ACTggATTCCTggAACATTgTTTCAAAggCTTg3'
```

The resultant ~1.8 kb product was used directly as template in the solid-phase bridge PCR reaction without purification. Preparation of Agarose Beads Covalently Conjugated to PCR Primers Used for Solid-Phase Bridge PCR:

Primer-Conjugated Agarose Beads prepared as in Example 36, except that the concentration of each primer during conjugation to the beads was 62.5 µM in 100 mM sodium bicarbonate, 1M NaCl as the Binding Buffer. The following primer pairs were used for conjugation to the beads (one primer pair per batch of beads):

```
Forward Segment 1:
                                           [SEQ NO. 105]
5'[Amine]TAATACgACTCACTATAgggAgAggAggTATATCAATggAT
TATAAAgACgATgATgATAAAAACTACgACAAgTgggAgATg3'
Reverse Segment 1:
                                           [SEQ NO. 106]
5'[Amine]TTATTTATTTATCACCgTCAggCTgTATTTCTT3'

Forward Segment 2:
                                           [SEQ NO. 107]
5'[Amine]TAATACgACTCACTATAgggAgAggAggTATATCAATggAT
TATAAAgACgATgATgATAAAgTgTACgAgggCgTgTgg3'
Reverse Segment 2:
                                           [SEQ NO. 108]
5'[Amine]TTATTTATTTATTTCTTTCAAgAACTCTTCCACCTC3'

Forward Segment 3:
                                           [SEQ NO. 109]
5'[Amine]TAATACgACTCACTATAgggAgAggAggTATATCAATggAT
TATAAAgACgATgATgATAAAgCCgTgAAgACCTTgAAggAg3'
Reverse Segment 3:
                                           [SEQ NO. 110]
5'[Amine]TTATTTATTTATAAggAgCTgCACCAggTTAgg3'

Forward Segment 4:
                                           [SEQ NO. 111]
5'[Amine]TAATACgACTCACTATAgggAgAggAggTATATCAATggAT
TATAAAgACgATgATgATAAAgTCTgCACCCgggAgCC3'
Reverse Segment 4:
                                           [SEQ NO. 112]
5'[Amine]TTATTTATTTATCACCACggCgTTCACCT3'

Forward Segment 7:
                                           [SEQ NO. 113]
5'[Amine]TAATACgACTCACTATAgggAgAggAggTATATCAATggAT
TATAAAgACgATgATgATAAAAACTgCCTggTAggggAgAAC3'
Reverse Segment 7:
                                           [SEQ NO. 114]
5'[Amine]TTATTTATTTATAgTCCATTTgATggggAACTTg3'

Forward Segment 10:
                                           [SEQ NO. 115]
5'[Amine]TAATACgACTCACTATAgggAgAggAggTATATCAATggAT
TATAAAgACgATgATgATAAACAgTggAATCCCTCTgACC3'
Reverse Segment 10:
                                           [SEQ NO. 116]
5'[Amine]TTATTTATTTATgCCTTgTTTCCCCAgCTCCTTTTC3'
```

The above primers amplify regions of the BCR-ABL tyrosine kinase domain designated in this Example as Segments 1, 2, 3, 4, 7, 10. The primers also incorporate a common N-terminal FLAG epitope tag for purification of all expressed peptides.

Qualitative Analysis of Primer Attachment:

Performed as in Example 36.

Multiplexed Solid-Phase Bridge PCR:

5 µL actual total bead volume of the previously prepared Primer-Conjugated Agarose Beads was used per each sample. The 5 µL total bead volume was a mixture of equal amounts of the different bead species, prepared as described earlier in this Example, each bead species carrying different primer pairs for the different BCR-ABL segments. Therefore, the subsequently described procedure corresponds to a single multiplexed solid-phase bridge PCR reaction. Beads were initially washed using 0.45 micron pore size, PVDF membrane, micro-centrifuge Filtration Devices (Ultrafree-MC Durapore Micro-centrifuge Filtration Devices, 400 µL capacity; Millipore, Billerica, Mass.). Unless otherwise noted, all washes involving the Filtration Devices were by brief vortex mixing (~5 sec), spinning down briefly in a micro-centrifuge (just until reaches maximum speed of ~43,000 rpm corresponding to ~16,000×g) and discarding the filtrate. Initial washes were 2×400 µL with TE-50 mM NaCl (10 mM Tris, pH 8.0, 1 mM EDTA, 50 mM NaCl). Beads were then resuspended in TE-50 mM NaCl to 20% (v/v) and the suspensions recovered into 0.5 mL thin-walled polypropylene PCR tubes. The tubes were placed in a PCR machine at 95° C. for 10 min to allow heat-mediated washing (lid temperature 105° C. and no mineral oil used) (beads were resuspended by brief gentle vortex mixing just before this step). After heating, the tubes were immediately removed from the PCR machine, the beads were diluted to 400 µL with TE-50 mM NaCl and the bead suspensions were then transferred to Filtration Devices. Filtration was performed and the filtrate discarded. Beads were briefly washed 1×400 µL more with TE-50 mM NaCl then 1×400 µL with MBG-Water.

Following the final filtration step (wash) on the bead samples, the washed bead pellets were resuspended in a commercially available pre-mixed PCR reaction solution (Platinum® PCR SuperMix High Fidelity; contains 22 U/mL complexed recombinant Taq DNA polymerase, *Pyrococcus* species GB-D thermostable polymerase, Platinum® Taq Antibody, 66 mM Tris-$SO_4$ pH 8.9, 19.8 mM $(NH_4)_2SO_4$, 2.4 mM $MgSO_4$, 220 µM dNTPs and stabilizers; Invitrogen Corporation, Carlsbad, Calif.; solution used without prior dilution), which was supplemented with 0.2 U/µL additional DNA polymerase (same polymerase as in aforementioned PCR mix) and ~10 ng of the aforementioned RT-PCR product as template. 10 µL of this mixture was used per each 1 µL actual bead volume. No soluble primers were used. The suspensions (~50 µL) were placed into 0.5 mL polypropylene thin-wall PCR tubes. The samples were subjected to the following thermocycling in a PCR machine (lid temperature 105° C. and no mineral oil used): An initial denaturing step (once) of 94° C. for 2 min (beads were briefly resuspended by gentle vortex mixing just before this step), and 40 cycles of 94° C. for 30 sec (denature), 65° C. for 30 sec (anneal) and 68° C. for 30 sec (extend); followed by a final extension step of 68° C. for 10 min.

400 µL of TE-50 mM NaCl (10 mM Tris, pH 8.0, 1 mM EDTA, 50 mM NaCl) was added to each completed solid-phase bridge PCR reaction and the suspensions transferred to Filtration Devices (Ultrafree-MC Durapore Micro-centrifuge Filtration Devices, 400 µL capacity; Millipore, Billerica, Mass.). Filtration was performed in a micro-centrifuge (just until reaches maximum speed of ~13,000 rpm corresponding to ~16,000×g) and the filtrate discarded. The beads were washed 3×400 µL more with TE-50 mM NaCl; resuspending by ~5 sec vortex mixing then performing filtration and discarding the filtrate as described earlier in this Example. At this point beads could either be placed in SP-PCR Storage Buffer (50% glycerol, TE-50 mM NaCl) and stored at −20° C. (5% beads v/v) or processed immediately as detailed below in this Example.

Multiplexed Cell-Free Protein Expression of the Beads:

Using the aforementioned Filtration Devices, 1 µL total of the post solid-phase bridge PCR beads was washed 3×400 µL more with MBG-Water and then resuspended in 15 µL of the *E. coli* based PureSystem cell-free protein expression mixture (mixture prepared according to the manufacturer's instructions; Post Genome Institute Co., LTD., Japan) (no soluble DNA was included in the reaction). The expression mixture was additionally supplemented with 250 mM final Betaine concentration from a 5M stock (Sigma-Aldrich, St. Louis, Mo.) to minimize mRNA secondary structure. The bead suspensions were then recovered from their Filtration Devices and transferred to 0.5 mL polypropylene PCR tubes. Protein expression was carried out for 1-2 hr at 42° C. in with gentle mixing. Because the post solid-phase bridge PCR beads were a mixture of beads corresponding to 6 different BCR-ABL segments, a single multiplexed cell-free protein expression reaction was used. After expression, beads were spun down in a micro-centrifuge (just until reaches maximum speed of ~13,000 rpm corresponding to ~16,000×g) and the fluid supernatant containing the cell-free expressed peptide mixture was collected and combined with 40 µL of PBS-T [standard PBS with 0.2% Triton X-100 (v/v)].

Purification and Elution of Bead Bound Peptides and Mass Spectrometry Analysis:

Micro-columns were used to affinity purify the cell-free expressed peptides via their common N-terminal FLAG epitope tag. Micro-columns consisted of 10 µL volume polypropylene pipette tips crimped at the end in order to trap the affinity beads (i.e. prevent beads from flowing out of column). Micro-columns were pre-loaded with ~2 µL mouse anti-FLAG antibody coated agarose affinity beads (EZ-view™ Red Anti-FLAG® M2 Affinity Gel, Sigma-Aldrich, St. Louis, Mo.) and pre-washed in excess PBS-T, allowing the liquid to flow by unit gravity. Next, the crude cell-free expressed peptide mixtures were injected into micro-columns and allowed to flow through by unit gravity. Micro-columns were then washed 2×100 µL in PBS-T followed by 2×100 µL mass spectrometry grade water (MSG-Water). Essentially all of the MSG-Water was drained from the column by unit gravity (although agarose beads remain partially hydrated). To elute the peptides from the affinity beads, 5 µL of MALDI-TOF mass spectrometry matrix solution (20 mg/mL sinapinic acid matrix in 50% acetonitrile and 0.1% trifluoroacetic acid) was applied to the micro-column and the first ~1 µL eluted droplet collected directly onto a stainless steel MALDI-TOF plate. The droplet was then allowed to dry/crystallize under ambient conditions without disturbance. Once completely dried, the spots were analyzed using a Voyager-DE MALDI-TOF mass spectrometer (Applied Biosystems; Foster City, Calif.).

Results:

Results are shown in FIG. 47. The correct peptide peaks corresponding to all 6 segments (Segments 1, 2, 3, 4, 7, and 10) of the BCR-ABL tyrosine kinase domain were identified with a mass accuracy of 1±1 Dalton (0.01% mass error; average error over all 6 peptides). These data demonstrate proof-of-principal that a single multiplexed solid-phase bridge PCR reaction can then be used to mediate a single multiplexed cell-free protein expression reaction, which was then followed peptide purification and mass spectrometry analysis. Note that the additional +75 Da peak, relative to the peak of Segment 7 (determined by non-multiplex samples), is putatively identified as a SNP, resulting in a G to E amino acid substitution (+72 Da), which was also identified in preliminary DNA sequencing experiments.

Example 54

Affinity Purification of Cell-Free Expressed Peptides onto an Agarose Bead Affinity Resin Followed by Mass Spectrometry Detection from Single Beads PCR to Create Template DNA for Cell-Free Protein Expression:

Conventional solution-phase PCR was performed on cell-line genomic DNA using standard molecular biology practices. The PCR product was confirmed by conventional agarose gel electrophoresis and used for template in the cell-free protein expression reactions without purification. The following primer pairs were used to amplify so-called Segment 7 of the APC mutation cluster region (MCR) of Exon 15:

```
Forward APC Segment 7:
                                              [SEQ NO. 117]
5'TAATACgACTCACTATAgggAgAggAggTATATCAATgAAAgATTATA
AAgACgATgATgATAAATgTACTTCTgTCAgTTCACTT3'

Reverse APC Segment 7:
                                              [SEQ NO. 118]
5'TTATTTATTTATCATggTTTgTCCAgggCTATC3'
```

Cell-Free Protein Expression:

Cell-free protein expression was carried out using 1 µL of the aforementioned soluble PCR product in 10 µL of the *E. coli* based PureSystem cell-free protein expression mixture (mixture prepared according to the manufacturer's instructions; Post Genome Institute Co., LTD., Japan). The expression mixtures were additionally supplemented with 250 mM final Betaine concentration from a 5M stock (Sigma-Aldrich, St. Louis, Mo.) to minimize mRNA secondary structure. Protein expression was carried out for 1-2 hr at 42° C. in with gentle mixing.

Purification and Elution of Bead Bound Peptides and Mass Spectrometry Analysis:

The crude cell-free expression mixtures were then diluted with 50 µL of AB-T [100 mM ammonium bicarbonate with 0.1% Triton X-100 (v/v)]. Mouse anti-FLAG antibody coated agarose affinity beads were used in batch mode to purify the cell-free expressed peptides (EZview™ Red Anti-FLAG® M2 Affinity Gel, Sigma-Aldrich, St. Louis; binding capacity for FLAG-tagged proteins is >100 ng per 1 µL of packed gel). The diluted crude cell-free expression mixtures were combined directly with ~1 µL beads in 0.5 mL polypropylene PCR tubes. The mixtures were then incubated for 20 minutes at room temperature with gentle mixing to keep the beads suspended. The beads were then spun down in a micro-centrifuge (just until reaches maximum speed of ~13,000 rpm corresponding to ~16,000×g) and the fluid supernatant removed and discarded. The beads were then washed 2×10 minutes each in mass spectrometry grade water (MSG-Water), removing the fluid supernatant as before. After removing the final wash, beads were resuspended in 50 mL MSG-Water and individual beads were selected from suspension by careful pipetting and deposited onto a stainless steel MALDI-TOF plate. A small volume (0.2-0.5 µL) of MALDI-TOF matrix solution (20 mg/mL sinapinic acid matrix in 50% acetonitrile and 0.1% trifluoroacetic acid) was immediately applied directly on top of the beads. The droplet was then allowed to dry/crystallize under ambient conditions without disturbance. The size of the final spot was approximately 2 mm in diameter with the beads near the center of spot. Once completely dried, the spots were analyzed using a Voyager-DE MALDI-TOF mass spectrometer (Applied Biosystems; Foster City, Calif.). The MALDI-TOF spectra were acquired on the outer edge of the spot, inside the spot in the immediate vicinity of the beads and also directly from the beads. The signal intensity was typically higher near the beads, although the matrix solution can elute peptides from the beads resulting in peptide spreading prior to drying of the matrix solution spot.

Results:

FIG. 48 shows that the expected peptide, corresponding to so-called Segment 7 of the APC gene, was observed at the correct mass (expected peptide mass 6,203 Da including N-terminal formylation produced in the cell-free expression system). These data confirm that the amount of peptide that can be bound to single agarose beads of roughly 100 microns in diameter, is sufficient to be detected by MALDI-TOF mass spectrometry. This is consistent with the reported capacity of the agarose beads, which at >100 ng/µL beads and approximately 1,000 individual beads per 1 µL bead volume, would amount to approximately 20 femtomoles of a 6,000 Da peptide. This falls within range of the sensitivity of MALDI-TOF mass spectrometry.

Template Sequences for Experimental
Template: Example 25 p53 in pETBlue-2 Plasmid; p53 portion is GeneBank NM_000546

[SEQ NO. 119]

```
5'gCCggCACCTgTCCTACgAgTTgCATgATAAAgAAgACAgTCATAAgTgCggCgACgACCggTgAATTgTgAgCgCTCACAATTC

TCgTgACATCATAACgTCCCgCgAAATTAATACgACTCACTATAggggAATTgTgAgCggATAACAATTCCCCTCTAgACTTAC AATTTCCATTCgCCATTCAggCTgCgCAACTgTTgggAAgggCgATCggTACgggCCTCTTCgCTATTACgCCAgCTTgCgAACggT gggTgCgCTgCAAggCgATTAAgTTgggTAACgCCAggATTCTCCCAgTCACgACgTTgTAAAACgACggCCAgCgAgAgATCTTgA TTggCTAgCAgAATAATTTTgTTTAACTTTAAgAAggAgATATACCATggCgATAgAggAgCCgCAgTCAgATCCTAgCgTCgAgC CCCCTCTgAgTCAggAAACATTTTCAgACCTATggAAACTACTTCCTgAAAACAACgTTCTgTCCCCCTTgCCgTCCCAAgCA ATggATgATTTgATgCTgTCCCCggACgATATTgAACAATggTTCACTgAAgACCCAggTCCAgATgAAgCTCCCAgAATgCCAgA ggCTgCTCCCCgCgTggCCCCTgCACCAgCAgCTCCTACACCggCggCCCCTgCACCAgCCCCCTCCTggCCCCTgTCATCTTCTg TCCCTTCCCAgAAAACCTACCAgggCAgCTACggTTTCCgTCTgggCTTCTTgCATTCTgggACAgCCAAgTCTgTgACTTgCACg TACTCCCCTgCCCTCAACAAgATgTTTTgCCAACTggCCAAgACCTgCCCTgTgCAgCTgTgggTTgATTCCACACCCCCgCCCgg CACCCgCgTCCgCgCCATggCCATCTACAAgCAgTCACAgCACATgACggAggTTgTgAggCgCTgCCCCCACCATgAgCgCTgCT CAgATACgATggTCTggCCCCTCCTCAgCATCTTATCCgAgTggAAggAAATTTgCgTgTggAgTATTTggATgACAgAAACACTT TTCgACATAgTgTggTggTgCCCTATgAgCCgCCTgAggTTggCTCTgACTgTACCACCATCCACTACAACTACATgTgTAACAgT TCCTgCATgggCggCATgAACCggAggCCCATCCTCACCATCATCACACTggAAgACTCCAgTggTAATCTACTgggACggAACAg CTTTgAggTgCgTgTTTgTgCCTgTCCTgggAgAgACCggCACAgAggAAgAgAATCTCCgCAAgAAAggggAgCCTCACCACgAg CTgCCCCCAgggAgCACTAAgCgAgCACTgCCCAACAACACCAgCTCCTCTCCCCAgCCAAAgAAgAAACCACTggATggAgA ATATTTCACCCTTCAgATCCgTgggCgTgAgCgCTTCgAgATgTTCCgAgAgCTgAATgAggCCTTggAACTCAAggATgCCCAggC TgggAAggAgCCAgggggggAgCAgggCTCACTCCAgCCACCTgAAgTCCAAAAAgggTCAgTCTACCTCCCgCCATAAAAAACTC ATgTTCAAgACAgAAgggCCTgACTCAgACTCCCgggAgCTCgTggATCCgAATTCTgTACAggCgCgCCTgCAggACgTCgACggT
```

-continued

ACCATCgATACgCgTTCgAAgCTTgCggCCgCACAgCTgTATACACgTgCAAgCCAgCCAgAACTCgCTCCTgAAgACCCAgAgg
ATCTCgAgCACCACCACCACCACCACTAATgTTAATTAAgTTgggCgTTgTAATCATAgTCATAATCAATACTCCTgACTgCgT
TAgCAATTTAACTgTgATAAACTACCgCATTAAAgCTATTCgATgATAAgCTgTCAAACATgATAATTCTTgAAgACgAAAggg
CCTAggCTgATAAAACAgAATTTgCCTggCggCAgTAgCgCggTggTCCCACCTgACCCCATgCCgAACTCAgAAgTgAAACgCCg
TAgCgCCgATggTAgTgTggggTCTCCCCATgCgAgAgTAgggAACTgCCAggCATCAAATAAAACgAAAggCTCAgTCgAAAgAC
TgggCCTTTCgTTTTATCTgTTgTTTgTCggTgAACgCTCTCCTgAgTAggACAAATCCgCCgggAgCggATTTgAACgTTgCgAAgC
AACggCCCggAgggTggCgggCAggACgCCCACCATAAACTgCCAggCATCAAATTAAgCAgAAggCCATCCTgACggATTggCCTTT
TTgCgTTTCTACAAACTCTTTTgTTTATTTTTCTAAATACATTCAAATATgTATCCgCTgAgCAATAACTAgCATAACCCCTTg
gggCCTCTAAACgggTCTTgAggggTTTTTTgCTgAAAggAggAACTATATCCggATTggCgAATgggACgCgCCCTgTAgCggCgCAT
TAAgCgCggCgggTgTggTggTTACgCgCAgCgTgACCgCTACACTTgCCAgCgCCCTAgCgCCCgCTCCTTTCgCTTTCTTCCCTTC
CTTTCTCgCCACgTTCgCCggCTTTCCCCgTCAAgCTCTAAATCgggggCTCCCTTTAgggTTCCgATTTAgTgCTTTACggCACCT
CgACCCCAAAAAACTTgATTAgggTgATggTTCACgTAgTgggCCATCgCCCTgATAgACggTTTTTCgCCCTTTgACgTTggAgTC
CACgTTCTTTAATAgTggACTCTTgTTCCAAACTggAACAACACTCAACCCTATCTCggTCTATTCTTTTgATTTATAAgggATT
TTgCCgATTTCggCCTATTggTTAAAAAATgAgCTgATTTAACAAAAATTTAACgCgAATTTTAACAAAATATTAACgTTTAC
AATTTCTggCggCACgATggCATgAgATTATCAAAAAggATCTTCACCTAgATCCTTTTAAATTAAAAATgAAgTTTTAAATCA
ATCTAAAgTATATATgAgTAAACTTggTCTgACAgTTACCAATgCTTAATCAgTgAggCACCTATCTCAgCgATCTgTCTATTTC
gTTCATCCATAgTTgCCTgACTCCCCgTCgTgTAgATAACTACgATACgggAgggCTTACCATCTggCCCCAgTgCTgCAATgATA
CCgCAgACCCACgCTCACCggCTCCAgATTTATCAgCAATAAACCAgCCAgCCggAAgggCCgAgCgCAgAAgTggTCCTgCAA
CTTTATCCgCCTCCATCCAgTCTATTAATTgTTgCCgggAAgCTAgAgTAAgTAgTTCgCCAgTTAATAgTTTgCgCAACgTTgTT
gCCATTgCTACAggCATCgTggTgTCACgCTCgTCgTTTggTATggCTTCATTCAgCTCCggTTCCCAACgATCAAggCgAgTTACA
TgATCCCCCATgTTgTgCAAAAAAgCggTTAgCTCCTTCggTCCTCCgATCgTTgTCAgAAgTAAgTTggCCgCAgTgTTATCACT
CATggTTATggCAgCACTgCATAATTCTCTTACTgTCATgCCATCCgTAAgATgCTTTTCTgTgACTggTgAgTACTCAACCAAgT
CATTCTgAgAATAgTgTATgCggCgACCgAgTTgCTCTTgCCCggCgTCAATACgggATAATACCgCgCCACATAgCAgAACTTTA
AAAgTgCTCATCATTggAAAACgTTCTTCggggCgAAAACTCTCAAggATCTTACCgCTgTTgAgATCCAgTTCgATgTAACCCA
CTCgTgCACCCAACTgATCTTCAgCATCTTTTACTTTCACCAgCgTTTCTgggTgAgCAAAAACAggAAggCAAAATgCCgCAA
AAAAgggAATAAgggCgACACggAAATgTTgAATACTCATACTCTTCCTTTTTCAATCATgACCAAAATCCCTTAACgTgAgTT
TTCgTTCCACTgAgCgTCAgACCCCgTAgAAAAgATCAAAggATCTTCTTgAgATCCTTTTTTTCTgCgCgTAATCTgCTgCTTgC
AAACAAAAAAACCACCgCTACCAgCggTggTTTgTTTgCCggATCAAgAgCTACCAACTCTTTTTCCgAAggTAACTggCTTCAg
CAgAgCgCAgATACCAAATACTgTCCTTCTAgTgTAgCCgTAgTTAggCCACCACTTCAAgAACTCTgTAgCACCgCCTACATA
CCTCgCTCTgCTAATCCTgTTACCAgTggCTgCTgCCAgTggCgATAAgTCgTgTCTTACCgggTTggACTCAAgACgATAgTTACC
ggATAAggCgCAgCggTCgggCTgAACggggggTTCgTgCACACAgCCCAgCTTggAgCgAACgACCTACACCgAACTgAgATACCT
ACAgCgTgAgCTATgAgAAAgCgCCACgCTTCCCgAAgggAgAAAggCggACAggTATCCggTAAgCggCAgggTCggAACAggAgAg
CgCACgAgggAgCTTCCAggggAAACgCCTggTATCTTTATAgTCCTgTCgggTTTCgCCACCTCTgACTTgAgCgTCgATTTTTgT
gATgCTCgTCAgggggCggAgCCTATggAAAAACgCCAgCAACgCggCCTTTTTACggTTCCTggCCTTTTgCTggCCTTTTgCTCA
CATgTTCTTTCCTgCgTTATCCCCTgATTCTgTggATAACCgTATTACCgCCTTTgAgTgAgCTgATACCgCTCgCCgCAgCCgAA
CgACCgAgCgCAgCgAgTCAgTgAgCgAggAAgCggCgATAATggCCTgCTTCTCgCCgAAACgTTTggTggCgggACCAgTgACgA
AggCTTgAgCgAgggCgTgCAAgATTCCgAATACCgCAAgCgACAggCCgATCATCgTCgCgCTCCAgCgAAAgCggTCCTCgCCgA
AAATgACCCAgAgCgCT3'

Template; Example 25 and 30 (Solution PCR Template) GST A2 in pETBlue-2 Plasmid; GST A2 portion is GeneBank NM_000846

[SEQ NO. 120]

5'gCCggCACCTgTCCTACgAgTTgCATgATAAAgAAgACAgTCATAAgTgCggCgACgACCggTgAATTgTgAgCgCTCACAATTC

TCgTgACATCATAACgTCCCgCgAAATTAATACgACTCACTATAggggAATTgTgAgCggATAACAATTCCCCTCTAgACTTAC AATTTCCATTCgCCATTCAggCTgCgCAACTgTTgggAAgggCgATCggTACgggCCTCTTCgCTATTACgCCAgCTTgCgAACggT gggTgCgCTgCAAggCgATTAAgTTgggTAACgCCAggATTCTCCCAgTCACgACgTTgTAAAACgACggCCAgCgAgAgATCTTgA TTggCTAgCAgAATAATTTTgTTTAACTTTAAgAAggAgATATACCATggCgATAgCAgAgAAgCCCAAgCTCCACTACTCCAA TATACggggCAgAATggAgTCCATCCggTggCTCCTggCTgCAgCTggAgTAgAgTTTgAAgAgAAATTTATAAAATCTgCAgAAgA TTTggACAAgTTAAgAAATgATggATATTTgATgTTCCAgCAAgTgCCAATggTTgAgATTgATgggATgAAgCTggTgCAgACCAg AgCCATTCTCAACTACATTgCCAgCAAATACAACCTCTATgggAAAgACATAAAggAgAAAgCCCTgATTgATATgTATATAg AAggTATAgCAgATTTgggTgAAATgATCCTTCTTCTgCCCTTTACTCAACCTgAggAACAAgATgCCAAgCTTgCCTTgATCCA AgAgAAAACAAAAAATCgCTACTTCCCTgCCTTTgAAAAAgTCTTAAAgAgCCACggACAAgACTACCTTgTTggCAACAAgC TgAgCCgggCTgACATTCACCTggTggAACTTCTCTACTACgTggAAgAgCTTgACTCTAgCCTTATTTCCAgCTTCCCTCTgCTg AAggCCCTgAAAACCAgAATCAgTAACCTgCCCACAgTgAAgAAgTTTCTACAgCCTggCAgCCCAAggAAgCCTCCCATggAT gAgAAATCTTTAgAAgAATCAAggAAgATTTTCAggTTTTCCCgggAgCTCgTggATCCgAATTCTgTACAggCgCgCCTgCAggAC gTCgACggTACCATCgATACgCgTTCgAAgCTTgCggCCgCACAgCTgTATACACgTgCAAgCCAgCCAgAACTCgCTCCTgAAgA CCCAgAggATCTCgAgCACCACCACCACCACCACTAATgTTAATTAAgTTgggCgTTgTAATCATAgTCATAATCAATACTCC TgACTgCgTTAgCAATTTAACTgTgATAAACTACCgCATTAAAgCTATTCgATgATAAgCTgTCAAACATgATAATTCTTgAAg ACgAAAgggCCTAggCTgATAAAACAgAATTTgCCTggCggCAgTAgCgCggTggTCCCACCTgACCCCATgCCgAACTCAgAAgT gAAACgCCgTAgCgCCgTggTAgTgTggggTCTCCCCATgCgAgAgTAgggAACTgCCAggCATCAAATAAAACgAAAggCTCAgT CgAAAgACTgggCCTTTCgTTTTATCTgTTgTTTgTCggTgAACgCTCTCCTgAgTAggACAAATCCgCCgggAgCggATTTgAACgT TgCgAAgCAACggCCCggAgggTggCgggCAggACgCCCgCCATAAACTgCCAggCATCAAATTAAgCAgAAggCCATCCTgACgg ATggCCTTTTTgCgTTTCTACAAACTCTTTTgTTTATTTTTCTAAATACATTCAAATATgTATCCgCTgAgCAATAACTAgCAT AACCCCTTggggCCTCTAAACgggTCTTgAggggTTTTTTgCTgAAAggAggAACTATATCCggATTggCgAATgggACgCgCCCTgT AgCggCgCATTAAgCgCggCgggTgTggTggTTACgCgCAgCgTgACCgCTACACTTgCCAgCgCCCTAgCgCCCgCTCCTTTCgCTT TCTTCCCTTCCTTTCTCgCCACgTTCgCCggCTTTCCCCgTCAAgCTCTAAATCggggggCTCCCTTTAgggTTCCgATTTAgTgCTT TACgCACCTCgACCCCAAAAAACTTgATTAgggTgATgGTTCACgTAgTgggCCATCgCCCTgATAgACggTTTTTCgCCCTTTg ACgTTggAgTCCACgTTCTTTAATAgTggACTCTTgTTCCAAACTggAACAACACTCAACCCTATCTCggTCTATTCTTTTgATT TATAAgggATTTTgCCgATTTCggCCTATTggTTAAAAAATgAgCTgATTTAACAAAAATTTAACgCgAATTTTAACAAAATAT TAACgTTTACAATTTCTggCggCACgATggCATgAgATTATCAAAAAggATCTTCACCTAgATCCTTTTAAATTAAAAATgAAg TTTTAAATCAATCTAAAgTATATATgAgTAAACTTggTCTgACAgTTACCAATgCTTAATCAgTgAggCACCTATCTCAgCgAT CTgTCTATTCgTTCATCCATAgTTgCCTgACTCCCCgTCgTgTAgATAACTACgATACgggAgggCTTACCATCTggCCCCAgTg CTgCAATgATACCgCgAgACCCACgCTCACCggCTCCAgATTTATCAgCAATAAACCAgCCAgCggAAgggCCgAgCgCAgAAg TggTCCTgCAACTTTATCCgCCTCCATCCAgTCTATTAATTgTTgCCgggAAgCTAgAgTAAgTAgTTCgCCAgTTAATAgTTTgC gCAACgTTgTTgCCATTgCTACAggCATCgTggTgTCACgCTCgTCgTTTggTATggCTTCATTCAgCTCCggTTCCCAACgATCAA ggCgAgTTACATgATCCCCCATgTTgTgCAAAAAgCggTTAgCTCCTTCggTCCTCCgATCgTTgTCAgAAgTAAgTTggCCgCAg TgTTATCACTCATggTTATggCAgCACTgCATAATTCTCTTACTgTCATgCCATCCgTAAgATgCTTTTCTgTgACTggTgAgTAC TCAACCAAgTCATTCTgAgAATAgTgTATgCggCgACCgAgTTgCTCTTgCCCggCgTCAATACgggATAATACCgCgCCACATAg CAgAACTTTAAAAgTgCTCATCATTggAAAACgTTCTTCggggCgAAAACTCTCAAggATCTTACCgCTgTTgAgATCCAgTTCg ATgTAACCCACTCgTgCACCCAACTgATCTTCAgCATCTTTTACTTTCACCAgCgTTTCTgggTgAgCAAAAACAggAAggCAA -continued

```
AATgCCgCAAAAAAgggAATAAgggCgACACggAAATgTTgAATACTCATACTCTTCCTTTTTCAATCATgACCAAAATCCCT
TAACgTgAgTTTTCgTTCCACTgAgCgTCAgACCCCgTAgAAAAgATCAAAggATCTTCTTgAgATCCTTTTTTTCTgCgCgTAAT
CTgCTgCTTgCAAACAAAAAAACCACCgCTACCAgCggTggTTTgTTTgCCggATCAAgAgCTACCAACTCTTTTTCCgAAggTA
ACTggCTTCAgCAgAgCgCAgATACCAAATACTgTCCTTCTAgTgTAgCCgTAgTTAggCCACCACTTCAAgAACTCTgTAgCAC
CgCCTACATACCTCgCTCTgCTAATCCTgTTACCAgTggCTgCTgCCAgTggCgATAAgTCgTgTCTTACCgggTTggACTCAAgAC
gATAgTTACCggATAAggCgCAgCggTCgggCTgAACggggggTTCgTgCACACAgCCCAgCTTggAgCgAACgACCTACACCgAAC
TgAgATACCTACAgCgTgAgCTATgAgAAAgCgCCACgCTTCCCgAAgggAgAAAggCggACAggTATCCggTAAgCggCAgggTCg
gAACAggAgAgCgCACgAgggAgCTTCCAggggAAACgCCTggTATCTTTATAgTCCTgTCgggTTTCgCCACCTCTgACTTgAgCg
TCgATTTTTgTgATgCTCgTCAgggggCggAgCCTATggAAAAACgCCAgCAACgCggCCTTTTTACggTTCCTggCCTTTTgCTgg
CCTTTTgCTCACATgTTCTTTCCTgCgTTATCCCCTgATTCTgTggATAACCgTATTACCgCCTTTgAgTgAgCTgATACCgCTCg
CCgCAgCCgAACgACCgAgCgCAgCgAgTCAgTgAgCgAggAAgCCggCgATAATggCCTgCTTCTCgCCgAAACgTTTggTggCggg
ACCAgTgACgAAggCTTgAgCgAgggCgTgCAAgATTCCgAATACCgCAAgCgACAggCCgATCATCgTCgCgCTCCAgCgAAAgC
ggTCCTCgCCgAAAATgACCCAgAgCgCT3'
```

Template: Example 30 GST A2 Solid-Phase Bridge PCR Template; Template is linear construct derived from GST A2 in pETBlue-2 plasmid; GST A2 portion is GeneBank NM_000846

[SEQ NO. 121]
```
5'TgAgCgCTCACAATTCTCgTgCATCATAACgTCCCgCgAAATTAATACgACTCACTATAggggAATTgTgAgCggATAACAA
TTCCCCTCTAgACTTACAATTTCCATTCgCCATTCAggCTgCgCAACTgTTgggAAgggCgATCggTACgggCCTCTTCgCTATTA
CgCCAgCTTgCgAACggTgggTgCgCTgCAAggCgATTAAgTTgggTAACgCCAggATTCTCCCAgTCACgACgTTgTAAAACgACg
gCCAgCgAgAgATCTTgATTggCTAgCAgAATAATTTTgTTTAACTTTAAgAAggAgATATACCATggCgATAgCAgAgAAgCCC
AAgCTCCACTACTCCAATATACggggCAgAATggAgTCCATCCggTggCTCCTggCTgCAgCTggAgTAgAgTTTgAAgAgAAATTT
ATAAAATCTgCAgAAgATTTggACAAgTTAAgAAATgATggATATTTgATgTTCCAgCAAgTgCCAATggTTgAgATTgATgggAT
gAAgCTggTgCAgACCAgAgCCATTCTCAACTACATTgCCAgCAAATACAACCTCTATgggAAAgACATAAAggAgAAAgCCCT
gATTgATATgTATATAgAAggTATAgCAgATTTgggTgAAATgATCCTTCTTCTgCCCTTTACTCAACCTgAggAACAAgATgCC
AAgCTTgCCTTgATCCAAgAgAAAACAAAAAATCgCTACTTCCCTgCCTTTgAAAAAgTCTTAAAgAgCCACggACAAgACTA
CCTTgTTggCAACAAgCTgAgCCgggCTgACATTCACCTggTggAACTTCTCTACTACgTggAAgAgCTTgACTCTAgCCTTATTT
CCAgCTTCCCTCTgCTgAAggCCCTgAAAACCAgAATCAgTAACCTgCCCACAgTgAAgAAgTTTCTACAgCCTggCAgCCCAA
ggAAgCCTCCCATggATgAgAAATCTTTAgAAgAATCAAggAAgATTTTCAggTTTTCCCgggAgCTCgTggATCCgAATTCTgTA
CAggCgCgCCTgCAggACgTCgACggTACCATCgATACgCgTTCgAAgCTTCggCCgCACAgCTgTATACACgTgCAAgCCAgCC
AgAACTCgCTCCTgAAgACCCAgAggATCTCgAgCACCACCACCACCACCACTAATgTTAATTAAgTTgggCgTTgTAATCATA
gTCATAATCAATACTCCTgACTgCgTTAgCAATTTAACTgTgATAAACTACCgCATTAAgCTATTCg3'
```

Template: Example 28 & 44 APC Segment 3 of Exon 15; GeneBank of full APC coding sequence is M74088; Example 54 APC Segment 7 also within below sequence [bracketed region]

[SEQ NO. 122]
```
5'gTTTCTCCATACAggTCACggggAgCCAATggTTCAgAAACAAATCgAgTgggTTCTAATCATggAATTAATCAAAATgTAAgC
CAgTCTTTgTgTCAAgAAgATgACTATgAAgATgATAAgCCTACCAATTATAgTgAACgTTACTCTgAAgAAgAACAgCATgAA
gAAgAAgAgAgACCAACAAATTATAgCATAAAATATAATgAAgAgAAACgTCATgTggATCAgCCTATTgATTATAgTTTAAA
```

-continued

ATATgCCACAgATATTCCTTCATCACAgAAACAgTCATTTTCATTCTCAAAgAgTTCATCTggACAAAgCAgTAAAACCgAA

CATATgTCTTCAAgCAgTgAgAATACgTCCACACCTTCATCTAATgCCAAgAggCAgAATCAgCTCCATCCAAgTTCTgCACAg

AgTAgAAgTggTCAgCCTCAAAAggCTgCCACTTgCAAAgTTTCTTCTATTAACCAAgAAACAATACAgACTTATTgTgTAgAA gATACTCCAATATgTTTTTCAAgATgTAgTTCATTATCATCTTTgTCATCAgCTgAAgATgAAATAggATgTAATCAgACgACA

CAggAAgCAgATTCTgCTAATACCCTgCAAATAgCAgAAATAAAAgAAAAgATTggAACTAggTCAgCTgAAgATCCTgTgAgC gAAgTTCCAgCAgTgTCACAgCACCCTAgAACCAAATCCAgCAgACTgCAgggTTCTAgTTTATCTTCAgAATCAgCCAggCAC AAAgCTgTTgAATTTTCTTCAggAgCgAAATCTCCCTCCAAAgTggTgCTCAgACACCCAAAgTCCACCTgAACACTATgTT CAggAgACCCCACTCATgTTTAgCAgA[TgTACTTCTgTCAgTTCACTTgATAgTTTTgAgAgTCgTTCgATTgCCAgCTCCgTTCA gAgTgAACCATgCAgTggAATggTAAgTggCATTATAAgCCCCAgTgATCTTCCAgATAgCCCTggACAAACCATg]CCACCAAg CAgAAgTAAAACACCTCCACCACCTCCTCAAACAgCTCAAACCAAgCgAgAAgTACCTAAAAATAAAgCACCTACTgCTgA AAAgAgAgAgTggACCTAAgCAAgCTgCAgTAAATgCTgCAgTTCAgAgggTCCAggTTCTTCCAgATgCTgATACTTTATTAC ATTTTgCCACggAAAgTACTCCAgATggATTTTCTTgTTCATCCAgCCTgAgTgCTCTgAgCCTCgATgAgCCATTTATACAgAA AgATgTggAATTAAgAATAATgCCTCCAgTTCAggAAAATgACAATgggAATgAAACAgAATCAgAgCAgCCTAAAgAATCAA ATgAAAACCAAgAgAAAgAggCAgAAAAAACTATTgATTCTgAAAAggACCTATTAgATgATTCAgATgATgATgATATTgAA ATACTAgAAgAATgTATTATTTCTgCCATgCCAACAAgTCATCACgTAAAgCAAAAAgCCAgCCCAgACTgCTTCAAAAT TACCTCCACCTgTggCAAggAAACCAAgTCAgCTgCCTgTgTACAAACTTCTACCATCACAAAACAggTTgCAACCCCAAAg CATgTTAgTTTTACACCggggATgATATgCCACgggTgTATTgTgTTgAAgggACACCTATAAACTTTTCCACAgCTACATCTCT AAgTgATCTAACAATCgAATCCCTCCAAATgAgTTAgCTgCTggAgAAggAgTTAgAggAggAgCACAgTCAggTgAATTTgAAA AACgAgATACCATTCCTACAgAAggCAgAAgT3'

Template: Example 31 Gamma-Actin GeneBank NM_001614; Full coding sequence

[SEQ NO. 123]

5'ATggAAgAAgAgATCgCCgCgCTggTCATTgACAATggCTCCggCATgTgCAAAgCTggTTTTgCTggggACgACgCTCCCCgAgC CgTgTTTCCTTCCATCgTCgggCgCCCCAgACACCAgggCgTCATggTgggCATgggCCAgAAggACTCCTACgTgggCgACgAggCC CAgAgCAAgCgTggCATCCTgACCCTgAAgTACCCCATTgAgCATggCATCgTCACCAACTgggACgACATggAgAAgATCTggCA CCACACCTTCTACAACgAgCTgCgCgTggCCCCggAggAgCACCCAgTgCTgCTgACCgAggCCCCCCTgAACCCCAAggCCAAC AgAgAgAAgATgACTCAgATTATgTTTgAgACCTTCAACACCCCggCCATgTACgTggCCATCCAggCCgTgCTgTCCCTCTACgC CTCTgggCgCACCACTggCATTgTCATggACTCTggAgACggggTCACCCACACggTgCCCATCTACgAgggCTACgCCCTCCCCC ACgCCATCCTgCgTCTggACCTggCTggCCgggACCTgACCgACTACCTCATgAAgATCCTCACTgAgCgAggCTACAgCTTCACC ACCACggCCgAgCgggAAATCgTgCgCgACATCAAggAgAAgCTgTgCTACgTCgCCCTggACTTCgAgCAggAgATggCCACCgCC gCATCCTCCTCTTCTCTggAgAAgAgCTACgAgCTgCCCgATggCCAggTCATCACCATTggCAATgAgCggTTCCggTgTCCggAg gCgCTgTTCCAgCCTTCCTTCCTgggTATggAATCTTgCggCATCCACgAgACCACCTTCAACTCCATCATgAAgTgTgACgTggA CATCCgCAAAgACCTgTACgCCAACACggTgCTgTCgggCggCACCACCATgTACCCgggCATTgCCgACAggATgCAgAAggAgA TCACCgCCCTggCgCCCAgCACCATgAAgATCAAgATCATCgCACCCCCAgAgCgCAAgTACTCggTgTggATCggTggCTCCATC CTggCCTCACTgTCCACCTTCCAgCAgATgTggATTAgCAAgCAggAgTACgACgAgTCgggCCCCTCCATCgTCCACCgCAAATg

CTTCTAA3'

Template: Example 31 p53 GeneBank NM_000546; Full coding sequence

[SEQ NO. 124]

5'ATggAggAgCCgCAgTCAgATCCTAgCgTCgAgCCCCCTCTgAgTCAggAAACATTTTCAgACCTATggAAACTACTTCCTgAA

AACAACgTTCTgTCCCCCTTgCCgTCCCAAgCAATggATgATTTgATgCTgTCCCCggACgATATTgAACAATggTTCACTgAAg

ACCCAggTCCAgATgAAgCTCCCAgAATgCCAgAggCTgCTCCCCgCgTggCCCCTgCACCAgCAgCTCCTACACCggCggCCCCT gCACCAgCCCCCTCCTggCCCCTgTCATCTTCTgTCCCTTCCCAgAAAACCTACCAgggCAgCTACggTTTCCgTCTgggCTTCTT gCATTCTgggACAgCCAAgTCTgTgACTTgCACgTACTCCCCTgCCCTCAACAAgATgTTTTgCCAACTggCCAAgACCTgCCCT gTgCAgCTgTgggTTgATTCCACACCCCCgCCCggCACCCgCgTCCgCgCCATggCCATCTACAAgCAgTCACAgCACATgACggA ggTTgTgAggCgCTgCCCCCACCATgAgCgCTgCTCAgATAgCgATggTCTggCCCCTCCTCAgCATCTTATCCgAgTggAAggAAA TTTgCgTgTggAgTATTTggATgACAgAAACACTTTTCgACATAgTgTggTggTgCCCTATgAgCCgCCTgAggTTggCTCTgACTgT ACCACCATCCACTACAACTACATgTgTAACAgTTCCTgCATgggCggCATgAACCggAggCCCATCCTCACCATCATCACACTg gAAgACTCCAgTggTAATCTACTgggACggAACAgCTTTgAggTgCgTgTTTgTgCCTgTCCTgggAgAgACCggCgCACAgAggAAg AgAATCTCCgCAAgAAAggggAgCCTCACCACgAgCTgCCCCCAgggAgCACTAAgCgCACTgCCCAACAACACCAgCTCCT CTCCCCAgCCAAAgAAgAAACCACTggATggAgAATATTTCACCCTTCAgATCCgTgggCgTgAgCgCTTCgAgATgTTCCgAgAg CTgAATgAggCCTTggAACTCAAggATgCCCAggCTgggAAggAgCCAggggggAgCAgggCTCACTCCAgCCACCTgAAgTCCAAA AAgggTCAgTCTACCTCCCgCCATAAAAAACTCATgTTCAAgACAgAAgggCCTgACTCAgACTgA3'

Template: Example 34 BRCA2 GeneBank NM_000059, exon 11; Full coding sequence

[SEQ NO. 125]

ATgCCTATTggATCCAAAgAgAggCCAACATTTTTTgAAATTTTTAAgACACgCTgCAACAAAgCAgATTTAggACCAATAAgT

CTTAATTggTTTgAAgAACTTTCTTCAgAAgCTCCACCCTATAATTCTgAACCTgCAgAAgAATCTgAACATAAAAACAACA

ATTACgAACCAAACCTATTTAAAACTCCACAAAggAAACCATCTTATAATCAgCTggCTTCAACTCCAATAATATTCAAAg

AgCAAgggCTgACTCTgCCgCTgTACCAATCTCCTgTAAAAgAATTAgATAAATTCAAATTAgACTTAggAAggAATgTTCCCA ATAgTAgACATAAAAgTCTTCgCACAgTgAAAACTAAAATggATCAAgCAgATgATgTTTCCTgTCCACTTCTAAATTCTTgTC TTAgTgAAAgTCCTgTTgTTCTACAAATgTACACATgTAACACCACAAAgAgATAAgTCAgTggTATgTgggAgTTTgTTTCATAC ACCAAAgTTTgTgAAgggTCgTCAgACACCAAAACATATTTCTgAAAgTCTAggAgCTgAggTggATCCTgATATgTCTTggTCAA gTTCTTTAgCTACACCACCCACCCTTAgTTCTACTgTgCTCATAgTCAgAAATgAAgAAgCATCTgAAACTgTATTTCCTCATg ATACTACTgCTAATgTgAAAAgCTATTTTTCCAATCATgATgAAAgTCTgAAgAAAATgATAgATTTATCgCTTCgTgACAg ACAgTgAAAACACAAATCAAAgAgAAgCTgCAAgTCATggATTTggAAAAACATCAgggAATTCATTTAAAgTAAATAgCTgC AAAgACCACATTggAAAgTCAATgCCAAATgTCCTAgAAgATgAAgTATATgAAACAgTTgTAgATACCTCTgAAgAAgATAgT TTTTCATTATgTTTTTCTAAATgTAgAACAAAAAATCTACAAAAAgTAAgAACTAgCAAgACTAggAAAAAATTTTCCATg AAgCAAACgCTgATgAATgTgAAAAATCTAAAAACCAAgTgAAAgAAAAATACTCATTTgTATCTgAAgTggAACCAAATgAT ACTgATCCATTAgATTCAAATgTAgCACATCAgAAgCCCTTTgAgAgTggAAgTgACAAAATCTCCAAggAAgTTgTACCgTCTT TggCCTgTgAATggTCTCAACTAACCCTTTCAggTCTAAATggCCCAgATggAgAAAATACCCCTATTgCATATTTCTTCATg TgACCAAAATATTTCAgAAAAAgACCTATTAgACACAgAACAAAAgAAAgATTTTCTTACTTCAgAgAATTCTTTg CCACgTATTTCTAgCCTACCAAAATCAgAgAAgCCATTAAATgAgggAAACAgTggTAAATAAgAgAgATgAAgAgCAgCATCTT gAATCTCATACAgACTgCATTCTTgCAgTAAAgCAggCAATATCTggAACTTCTCCAgTggCTTCTTCATTTCAgggTATCAAAA AgTCTATATTCAgAATAAgAgAATCACCTAAgAgACTTTCAATgCAAgTTTTTCAggTCATATgACTgATCCAAACTTTAAA AAAgAAACTgAAgCCTCTgAAAgTggACTggAAATACATACTgTTTgCTCACAgAAggAggACTCCTTATgTCCAAATTTAATT gATAATggAAgCTggCCAgCCACCACCACAgAATTCTgTAgCTTTgAAgAATgCAggTTTAATATCCACTTTgAAAAAgAAA -continued ACAAATAAgTTTATTTATgCTATACATgATgAAACATTTTATAAAggAAAAAAAATACCgAAAgACCAAAAATCAgAACTA ATTAACTgTTCAgCCCAgTTTgAAgCAAATgCTTTTgAAgCACCACTTACATTTgCAAATgCTgATTCAggTTTATTgCATTCTT CTgTgAAAAgAAgCTgTTCACAgAATgATTCTgAAgAACCAACTTTgTCCTTAACTAgCTCTTTTgggACAATTCTgAggAAATg TTCTAgAAATgAAACATgTTCTAATAATACAgTAATCTCTCAggATCTTgATTATAAAgAAgCAAAATgTAATAAggAAAAA CTACAgTTATTTATTACCCCAgAAgCTgATTCTCTgTCATgCCTgCAggAAggACAgTgTgAAAATgATCCAAAAAgCAAAAAA gTTTCAgATATAAAAgAAgAggTCTTggCTgCAgCATgTCACCCAgTACAACATTCAAAAgTggAATACAgTgATACTgACTTT CAATCCCAgAAAAgTCTTTTATATgATCATgAAAATgCCAgCACTCTTATTTTAACTCCTACTTCCAAggATgTTCTgTCAAA CCTAgTCATgATTTCTAgAggCAAAgAATCATACAAAATgTCAgACAAgCTCAAAggTAACAATTATgAATCTgATgTTgAAT TAACCAAAAATATTCCCATggAAAAgAATCAAgATgTATgTgCTTTAAATgAAAATTATAAAAACgTTgAgCTgTTgCCACCT gAAAATACATgAgAgTAgCATCACCTTCAAgAAAggTACAATTCAACCAAAACACAAATCTAAgAgTAATCCAAAAAAAT CAAgAAgAAACTACTTCAATTTCAAAAATAACTgTCAATCCAgACTCTgAAgAACTTTTCTCAgACAATgAgAATAATTTTg TCTTCCAAgTAgCTAATgAAAggAATAATCTTgCTTTAggAAATACTAAggAACTTCATgAAACAgACTTgACTTgTgTAAACg AACCCATTTTCAAgAACTCTACCATggTTTTATATggAgACACAggTgAAACAAgCAACCCAAgTgTCAATTAAAAAgAT TTggTTTATgTTCTTgCAgAggAgAACAAAAATAgTgTAAAgCAgCATATAAAAATgACTCTAggTCAAgATTTAAAATCggAC ATCTCCTTgAATATAgATAAAATACCAgAAAAAAATAATgATTACATgAACAAATgggCAggACTCTTAggTCCAATTTCAA ATCACAgTTTTggAggTAgCTTCAgAACAgCTTCAAATAAggAAATCAAgCTCTCTgAACATAACATTAAgAAgAgCAAAATg TTCTTCAAAgATATTgAAgAACAATATCCTACTAgTTTAgCTTgTgTTgAAATTgTAAATACCTTggCATTAgATAATCAAAAg AAACTgAgCAAgCCTCAgTCAATTAATACTgTATCTgCACATTTACAgAgTAgTgTAgTTgTTTCTgATTgTAAAAATAgTCAT ATAACCCCTCAgATgTTATTTTCCAAgCAggATTTTAATTCAAACCATAATTTAACACCTAgCCAAAAggCAgAAATTACAg AACTTTCTACTATATTAgAAgAATCAggAAgTCAgTTTgAATTTACTCAgTTTAgAAAACCAAgCTACATATTgCAgAAgAgT ACATTTgAAgTgCCTgAAAACCAgATgACTATCTTAAAgACCCACTTCTgAggAATgCAgAgATgCTgATCTTCATgTCATAATg AATgCCCCATCgATTggTCAggTAgACAgCAgCAAgCAATTTgAAggTACAgTTgAAATTAAACggAAgTTTgCTggCCTgTTgAA AAATgACTgTAACAAAAgTgCTTCTggTTATTTAACAgATgAAAATgAAgTggggTTTAggggCTTTTATTCTgCTCATggCACAA AACTgAATgTTTCTACTgAAgCTCTgCAAAAAgCTgTgAAACgTTTAgTgATATTgAgAATATTAgTgAggAAACTTCTgCAgA ggTACATCCAATAAgTTTATCTTCAAgTAAATgTCATgATTCTgTTgTTTCAATgTTTAAgATAgAAAATCATAATgATAAAA CTgTAAgTgAAAAAAATAATAAATgCCAACTgATATTACAAAATAATATTgAAATgACTACTggCACTTTTgTTgAAgAAATT ACTgAAAATTACAAgAgAAATACTgAAAATgAAgATAACAAATATACTgCTgCCAgTAgAAATTCTCATAACTTAgAATTTg ATggCAgTgATTCAAgTAAAAATgATACTgTTTgTATTCATAAAgATgAAACggACTTgCTATTTACTgATCAgCACAACATAT gTCTTAAATTATCTggCCAgTTTATgAAggAgggAAACACTCAgATTAAAgAAgATTTgTCAgATTTAACTTTTTTggAAgTTgCg AAAgCTCAAgAAgCATgTCATggTAATACTTCAAATAAAgAACAgTTAACTgCTACTAAAACggAgCAAAATATAAAAgATT TTgAgACTTCTgATACATTTTTTCAgACTgCAAgTgggAAAAATATTAgTgTCgCCAAAgAgTCATTTAATAAAATTgTAAATT TCTTTgATCAgAAACCAgAAgAATTgCATAACTTTTCCTTAAATTCTgAATTACATTCTgACATAAgAAAgAACAAAATggA CATTCTAAgTTATgTgAggAAACAgACATAgTTAAACACAAAATACTgAAAgAAAgTgTCCCAgTTggTACTggAAATCAACTAg TgACCTTCCAgggACAACCCgAACgTgATgAAAAgATCAAAgAACCTACTCTgTTgggTTTTCATACAgCTAgCgggAAAAAgT TAAAATTgCAAAggAATCTTTggACAAAgTgAAAAACCTTTTTgATgAAAAAgAgCAAggTACTAgTgAAATCACCAgTTTTAg CCATCAATgggCAAAgACCCTAAAgTACAgAgAggCCTgTAAAgACCTTgAATTAgCATgTgAgACCATTgAgATCACAgCTgC CCCAAAgTgTAAAgAAATgCAgAATTCTCTCAATAATgTATAAAAACCTTgTTTCTATTgAgACTgTggTgCCACCTAAgCTCTT AAgTgATAATTTATgTAgACAAACTgAAAATCTCAAAACATCAAAAAgTATCTTTTTgAAAgTTAAAgTACATgAAAATgTA gAAAAAgAAACAgCAAAAAgTCCTgCAACTTgTTACACAAATCAgTCCCCTTATTCAgTCATTgAAAATTCAgCCTTAgCTTT TTACACAAgTTgTAgTAgAAAAACTTCTgTgAgTCAgACTTCATTACTTgAAgCAAAAAAATggCTTAgAgAAggAATATTTgA TggTCAACCAgAAAgAATAAATACTgCAgATTATgTAggAAATTATTTgTATgAAAATAATTCAAACAgTACTATAgCTgAAA -continued

```
ATgACAAAAATCATCTCTCCgAAAAACAAgATACTTATTTAAgTAACAgTAgCATgTCTAACAgCTATTCCTACCATTCTgA
TgAggTATATAATgATTCAggATATCTCTCAAAAAATAAACTTgATTCTggTATTgAgCCAgTATTgAAgAATgTTgAAgATCA
AAAAAACACTAgTTTTTCCAAAgTAATATCCAATgTAAAAgATgCAAATgCATACCCACAAACTgTAAATgAAgATATTTgC
gTTgAggAACTTgTgACTAgCTCTTCACCCTgCAAAAATAAAAATgCAgCCATTAAATTgTCCATATCTAATAgTAATAATTT
TgAggTAgggCCACCTgCATTTAggATAgCCAgTggTAAAATCgTTTgTgTTTCACATgAAACAATTAAAAAAgTgAAAgACATA
TTTACAgACAgTTTCAgTAAAgTAATTAAggAAAACAACgAgAATAAATCAAAAATTTgCCAAACgAAAATTATggCAggTTg
TTACgAggCATTggATgATTCAgAggATATTCTTCATAACTCTCTAgATAATgATgAATgTAgCACgCATTCACATAAggTTTTT
gCTgACATTCAgAgTgAAgAAATTTTACAACATAACCAAAATATgTCTggATTggAgAAAgTTTCTAAAATATCACCTTgTgAT
gTTAgTTTggAAACTTCAgATATATgTAAATgTAgTATAgggAAgCTTCATAAgTCAgTCTCATCTgCAAATACTTgTgggATTTT
TAgCACAgCAAgTggAAAATCTgTCCAggTATCAgATgCTTCATTACAAAACgCAAgACAAgTgTTTTCTgAAATAgAAgATAg
TACCAAgCAAgTCTTTTCCAAAgTATTgTTTAAAAgTAACgAACATTCAgACCAgCTCACAAgAgAAgAAAATACTgCTATA
CgTACTCCAgAACATTTAATATCCCAAAAAggCTTTTCATATAATgTggTAAATTCATCTgCTTTCTCTggATTTAgTACAgCA
AgTggAAAgCAAgTTTCCATTTTAgAAAgTTCCTTACACAAAgTTAAgggAgTgTTAgAggAATTTgATTTAATCAgAACTgAgC
ATAgTCTTCACTATTCACCTACgTCTAgACAAAATgTATCAAAAATACTTCCTCgTgTTgATAAgAgAAACCCAgAgCACTgT
gTAAACTCAgAAATggAAAAAACCTgCAgTAAAgAATTTAAATTATCAAATAACTTAAATgTTgAAggTggTTCTTCAgAAAA
TAATCACTCTATTAAAgTTTCTCCATATCTCTCTCAATTTCAACAAgACAAACAACAgTTggTATTAggAACCAAAgTCTCA
CTTgTTgAgAACATTCATgTTTTgggAAAAgAACAggCTTCACCTAAAAACgTAAAAATggAAATTggTAAAACTgAAACTTTT
TCTgATgTTCCTgTgAAAACAAATATAgAAgTTTgTTCTACTTACTCCAAAgATTCAgAAAACTACTTTgAAACAgAAgCAgT
AgAAATTgCTAAAgCTTTTATggAAgATgATgAACTgACAgATTCTAAACTgCCAAgTCATgCCACACATTCTCTTTTTACATg
TCCCgAAAATgAggAAATggTTTTgTCAAATTCAAgAATTggAAAAAgAAgAgggAgAgCCCCTTATCTTAgTgggAgAACCCTCA
ATCAAAAgAAACTTATTAAATgAATTTgACAggATAATAgAAAATCAAgAAAAATCCTTAAAggCTTCAAAAAgCACTCCA
gATggCACAATAAAAgATCgAAgATTgTTTATgCATCATgTTTCTTTAgAgCCgATTACCTgTgTACCCTTTCgCACAACTAAgg
AACgTCAAgAgATACAgAATCCAAATTTTACCgCACCTggTCAAgAATTTCTgTCTAAATCTCATTTgTATgAACATCTgACT
TTggAAAAATCTTCAAgCAATTTAgCAgTTTCAggACATCCATTTTATCAAgTTTCTgCTACAAgAAATgAAAAAATgAgACA
CTTgATTACTACAggCAgACCAACCAAAgTCTTTgTTCCACCTTTTAAAACTAAATCACATTTTCACAgAgTTgAACAgTgTg
TTAggAATATTAACTTggAggAAAACAgACAAAAgCAAAACATTgATggACATggCTCTgATgATAgTAAAAATAAgATTAATg
ACAATgAgATTCATCAgTTTAACAAAAACAACTCCAATCAAgCAgCAgCTgTAACTTTCACAAAgTgTgAAgAAgAACCTTT
AgATTTAATTACAAgTCTTCAgAATgCCAgAgATATACAggATATgCgAATTAAgAAgAAACAAAggCAACgCgTCTTTCCAC
AgCCAggCAgTCTgTATCTTgCAAAAACATCCACTCTgCCTCgAATCTCTCTgAAAgCAgCAgTAggAggCCAAgTTCCCTCTgC
gTgTTCTCATAAACAgCTgTATACgTATggCgTTTCTAAACATTgCATAAAAATTAACAgCAAAAATgCAgAgTCTTTTCAgTT
TCACACTgAAgATTATTTTggTAAggAAAgTTTATggACTggAAAAggAATACAgTTggCTgATggTggATggCTCATACCCTCCA
ATgATggAAAggCTggAAAAgAAgAATTTTATAgggCTCTgTgTgACACTCCAggTgTggATCCAAAgCTTATTTCTAgAATTTggg
TTTATAATCACTATAgATggTCATATggAAACTggCAgCTATgAATgTgCCTTTCCTAAggAATTTgCTAATAgATgCCTAAg
CCCAgAAAgggTgCTTCTTCAACTAAAATACAgATATgATACggAAATTgATAgAAgCAgAAgATCggCTATAAAAAAgATAA
TggAAAgggATgACACAgCTgCAAAAACACTTgTTCTCTgTgTTTCTgACATAATTTCATTgAgCgCAAATATATCTgAAACTT
CTAgCAATAAAACTAgTAgTgCAgATACCCAAAAAgTggCCATTATTgAACTTACAgATgggTggTATgCTgTTAAggCCCAgTT
AgATCCTCCCCTCTTAgCTgTCTTAAAgAATggCAgACTgACAgTTggTCAgAAgATTATTCTTCATggAgCAgAACTggTgggCT
CTCCTgATgCCTgTACACCTCTTgAAgCCCCAgAATCTCTTATgTTAAAgATTTCTgCTAACAgTACTCggCCTgCTCgCTggTA
TACCAAACTTggATTCTTTCCTgACCCTAgACCTTTTCCTCTgCCCTTATCATCgCTTTTCAgTgATggAggAAATgTTggTTgTg
TTgATgTAATTATTCAAAgAgCATACCCTATACAgTggATggAgAAgACATCATCTggATTATACATATTTCgCAATgAAAgAg
```

-continued

AggAAgAAAAggAAgCAgCAAAATATgTggAggCCCAACAAAAgAgACTAgAAgCCTTATTCACTAAAATTCAggAggAATTTg

AAgAACATgAAgAAAACACAACAAAACCATATTTACCATCACgTgCACTAACAAgACAgCAAgTTCgTgCTTTgCAAgATgg

TgCAgAgCTTTATgAAgCAgTgAAgAATgCAgCAgACCCAgCTTACCTTgAgggTTATTTCAgTgAAgAgCAgTTAAgAgCCTTgA ATAATCACAggCAAATgTTgAATgATAAgAAACAAgCTCAgATCCAgTTggAAATTAggAAggCCATggAATCTgCTgAACAAA AggAACAAggTTTATCAAgggATgTCACAACCgTgTggAAgTTgCgTATTgTAAgCTATTCAAAAAAAgAAAAAgATTCAgTTAT ACTgAgTATTTggCgTCCATCATCAgATTTATATTCTCTgTTAACAgAAggAAAgAgATACAgAATTTATCATCTTgCAACTTC AAAATCTAAAAgTAAATCTgAAAgAgCTAACATACAgTTAgCAgCgACAAAAAAAACTCAgTATCAACAACTACCggTTTC AgATgAAATTTTATTTCAgATTTACCAgCCAcggAgCCCCTTCACTTCAgCAAATTTTTAgATCCAgACTTTCAgCCATCTTg TTCTgAggTggACCTAATAggATTTgTCgTTTCTgTTgTgAAAAAACAggACTTgCCCCTTTCgTCTATTTgTCAgACgAATgTT ACAATTTACTggCAATAAAgTTTTggATAgACCTTAATgAggACATTATTAAgCCTCATATgTTAATTgCTgCAAgCAACCTCC AgTggCgACCAgAATCCAAATCAggCCTTCTTACTTTATTTgCTggAgATTTTTCTgTgTTTTCTgCTAgTCCAAAAgAgggCCAC TTTCAAgAgACATTCAACAAAATgAAAAATACTgTTgAgAATATTgACATACTTTgCAATgAAgCAgAAAACAAgCTTATgC ATATACTgCATgCAAATgATCCCAAgTggTCCACCCCAACTAAAgACTgTACTTCAgggCCgTACACTgCTCAAATCATTCCTg gTACAggAAACAAgCTTCTgATgTCTTCTCCTAATTgTgAgATATATTATCAAAgTCCTTTATCACTTTgTATgggCCAAAAggA AgTCTgTTTCCACACCTgTCTCAgCCCAgATgACTTCAAAgTCTTgTAAAggggAgAAAgAgATTgATgACCAAAAgAACTgCA AAAAgAgAAgAgCCTTggATTTCTTgAgTAgACTgCCTTTACCTCCACCTgTTAgTCCCATTTgTACATTTgTTTCTCCggCTgCA CAgAAggCATTTCAgCCACCAAggAgTTgTggCACCAAATACgAAACACCCATAAAgAAAAAAgAACTgAATTCTCCTCAgAT gACTCCATTTAAAAAATTCAATgAAATTTCTCTTTTggAAAgTAATTCAATAgCTgACgAAgAACTTgCATTgATAAATACCC AAgCTCTTTTgTCTggTTCAACAggAgAAAAACAATTTATATCTgTCAgTgAATCCATCTAggACTgCTCCCACCAgTTCAgAAg ATTATCTCAgACTgAAACgACgTTgTACTACATCTCTgATCAAAgAACAggAgTTCCCAggCCAgTACggAAgAATgTgAgAA AAATAAgCAggACACAATTACAACTAAAAAATATATCTAAgCATTTgCAAAggCgACAATAAATTATTgACgCTTAACCTTT CCAgTTTATAAgACTggAATATAATTTCAAACCACACATTAgTACTTATgTTgCACAATgAgAAAAgAAATTAgTTTCAAATT TACCTCAgCgTTTgTgTATCgggCAAAAATCgTTTTgCCCgATTCCgTATTggTATACTTTTgCTTCAgTTgCATACTTAAAACT AAATgTAATTTATTAACTAATCAAgAAAAACATCTTTggCTgAgCTCggTggCTCATgCCTgTAATCCCAACACTTTgAgAAgC TgAggTgggAggAgTgCTTgAggCCAggAgTTCAAgACCAgCCTgggCAACATAgggAgACCCCCATCTTTACgAAgAAAAAAAAA AAggggAAAAgAAAATCTTTTAAATCTTggATTTgATCACTACAAgTATTATTTTACAATCAACAAAATggTCATCCAAACT CAAACTTgAgAAAATATCTTgCTTTCAAATTgACACTA 45
Template: Example 52 and 53 BCR-ABL b3a2 transcript:
Full coding sequence

[SEQ NO. 126]
ATggTggACCCggTgggCTTCgCggAggCgTggAAggCgCAgTTCCCggACTCAgAgCCCCCgCgCATggAgCTgCgCTCAgTgggCgAC ATCgAgCAggAgCTggAgCgCTgCAAggCCTCCATTCggCgCCTggAgCAggAggTgAACCAggAgCgCTTCCgCATgATCTACCTgC AgACgTTgCTggCCAAggAAAAgAAgAgCTATgACCggCAgCgATggggCTTCCggCgCgCggCgCAggCCCCCgACggCgCCTCCgA gCCCCgAgCgTCCgCgTCgCgCCCgCAgCCAgCgCCCgCCgACgAgCCgACCCgCCgCCCgCCgAggAgCCgAggCCCggCCCgAC ggCgAgggTTCTCCgggTAAggCCAggCCCgggACCgCCCgCAggCCCggggCAgCCgCgTCggggAACgggACgACCggggACCCCCC gCCAgCgTggCggCgCTCAggTCCAACTTCgAgCggATCCgCAAgggCCATggCCAgCCCgggCggACgCCgAgAAgCCCTTCTACg TgAACgTCgAgTTTCACCACgAgCgCggCCTggTgAAggTCAACgACAAAgAggTgTCgACCgCATCAgCTCCCTgggCAgCCAgg CCATgCAgATggAgCgCAAAAAgTCCCAgCACggCgCgggCTCgAgCgTggggATgCATCCAggCCCCCTTACCggggACgCTCCT CggAgAgCAgCTgCggCgTCgACgCgACTACgAggACgCCgAgTTgAACCCCCgCTTCCTgAAggACAACCTgATCgACgCCAATg gCggTAgCAggCCCCCTTggCCgCCCCTggAgTACCAgCCCTACCAgAgCATCTACgTCggggCATgATggAAggggAgggCAAggg -continued CCCgCTCCTgCgCAgCCAgAgCACCTCTgAgCAggAgAAgCgCCTTACCTggCCCCgCAggTCCTACTCCCCCggAgTTTTgAgg
ATTgCggAggCggCTATACCCCggACTgCAgCTCCAATgAgAACCTCACCTCCAgCgAggAggACTTCTCCTCTggCCAgTCCAgC
CgCgTgTCCCCAAgCCCCACCACCTACCgCATgTTCCgggACAAAAgCCgCTCTCCCTCgCAgAACTCgCAACAgTCCTTCgAC
AgCAgCAgTCCCCCACgCCgCAgTgCCATAAgCggCACCggCACTgCCCggTTgTCgTgTCCgAggCCACCATCgTgggCgTCCgC
AAgACCgggCAgATCTggCCCAACgATggCgAgggCgCCTTCCATggAgACgCAgATggCTCgTTCggAACACCACCTggATACggC
TgCgCTgCAgACCgggCAgAggAgCAgCgCCggCACCAAgATgggCTgCCCTACATTgATgACTCgCCCTCCTCATCgCCCCACCT
CAgCAgCAAgggCAggggCAgCCgggATgCgCTggTCTCgggAgCCCTggAgTCCACTAAAgCgAgTgAgCTggACTTggAAAAgggCT
TggAgATgAgAAAATgggTCCTgTCgggAATCCTggCTAgCAggAgACTTACCTgAgCCACCTggAggCACTgCTgCTgCCCATgA
AgCCTTTgAAAgCCgCTgCCACCACCTCTCAgCCggTgCTgACgAgTCAgCAgATCgAgACCATCTTCTTCAAAgTgCCTgAgCT
CTACgAgATCCACAAggAgTTCTATgATgggCTCTTCCCCCgCgTgCAgCAgTggAgCCACCAgCAgCgggTgggCgACCTCTTCCA
gAAgCTggCCAgCCAgCTgggTgTgTACCgggCCTTCgTggACAACTACggAgTTgCCATggAAATggCTgAgAAgTgCTgTCAggCC
AATgCTCAgTTTgCAgAAATCTCCgAgAACCTgAgAgCCAgAAgCAACAAAgATgCCAAggATCCAACgACCAAgAACTCTCT
ggAAACTCTgCTCTACAAgCCTgTggACCgTgTgACgAggAgCACgCTggTCCTCCATgACTTgCTgAAgCACACTCCTgCCAgCC
ACCCTgACCACCCCTTgCTgCAggACgCCCTCCgCATCTCACAgAACTTCCTgTCCAgCATCAATgAggAgATCACACCCCgAC
ggCAgTCCATgACggTgAAgAAgggAgAgCACCggCAgCTgCTgAAggACAgCTTCATgTggAgCTggTggAgggggCCCgCAAgCTg
CgCCACgTCTTCCTgTTCACCgACCTgCTTCTCTgCACCAAgCTCAAgAAgCAgAgCggAggCAAAACgCAgCAgTATgACTgCA
AATggTACATTCCgCTCACggATCTCAgCTTCCAgATggTggATgAACTggAggCAgTgCCCAACATCCCCCTggTgCCCgATgAgg
AgCTggACgCTTTgAAgATCAAgATCTCCCAgATCAAgAATgACATCCAgAgAgAgAAgAgggCgAACAAgggCAgCAAggCTAC
ggAgAggCTgAAgAAgAAgCTgTCggAgCAggAgTCACTgCTgCTgCTTATgTCTCCCAgCATggCCTTCAgggTgCACAgCCgCAA
CggCAAgAgTTACACgTTCCTgATCTCCTCTgACTATgAgCgTgCAgAgTggAgggAgAACATCCgggAgCAgCAgAAgAAgTgTTT
CAgAAgCTTCTCCCTgACATCCgTggAgCTgCAgATgCTgACCAACTCgTgTgTgAAACTCCAgACTgTCCACAgCATTCCgCTg
ACCATCAATAAggAAgATgATgAgTCTCCggggCTCTATgggTTTCTgAATgTCATCgTCCACTCAgCCACTggATTTAAgCAgAg
TTCAAAAgCCCTTCAgCggCCAgTAgCATCTgACTTTgAgCCTCAgggTCTgAgTgAAgCCgCTCgTTggAACTCCAAggAAAACC
TTCTCgCTggACCCAgTgAAAATgACCCCAACCTTTTCgTTgCACTgTATgATTTTgTggCCAgTggAgATAACACTCTAAgCAT
AACTAAggTgAAAAgCTCCgggTCTTAggCTATAATCACAATggggAATggTgTgAAgCCCAAACCAAAAATggCCAAggCTggg
TCCCAAgCAACTACATCACgCCAgTCAACAgTCTggAgAAACACTCCTggTACCATgggCCTgTgTCCCgCAATgCCgCTgAgTA
TCTgCTgAgCAgCgggATCAATggCAgCTTCTTggTgCgTgAgAgTgAgAgCAgTCCTggCCAgAggTCCATCTCgCTgAgATACgAA
gggAgggTgTACCATTACAggATCAACACTgCTTCTgATggCAAgCTCTACgTCTCCTCCgAgAgCCgCTTCAACACCCTggCCgA
gTTggTTCATCATCATTCAACggTggCCgACgggCTCATCACCACgCTCCATTATCCAgCCCCAAAgCgCAACAAgCCCACTgT
CTATggTgTgTCCCCCAACTACgACAAgTgggAgATggAACgCACggACATCACCATgAAgCACAAgCTgggCggggCCAgTACgg
ggAggTgTACgAgggCgTgTggAAgAAATACAgCCTgACggTggCCgTgAAgACCTTgAAggAggACACCATggAggTggAAgAgTTCT
TgAAAgAAgCTgCAgTCATgAAgAgATCAAACACCCTAACCTggTgCAgCTCCTTggggTCTgCACCCgggAgCCCCCgTTCTAT
ATCATCACTgAgTTCATgACCTACgggAACCTCCTggACTACCTggggAgTgCAACCggCAggAggTgAACgCCgTggTgCTgCTg
TACATggCCACTCAgATCTCgTCAgCCATggAgTACCTggAgAAgAAAAACTTCATCCACAgAgATCTTgCTgCCCgAAACTgC
CTggTAggggAgAACCACTTggTgAAggTAgCTgATTTTggCCTgAgCAggTTgATgACAggggACACCTACACAgCCCATgCTggAg
CCAAgTTCCCCATCAAATggACTgCACCCgAgAgCCTggCCTACAACAAgTTCTCCATCAAgTCCgACgTCTgggCATTTggAgT
ATTgCTTTgggAAATTgCTACCTATggCATgTCCCCTTACCCgggAATTgACCTgTCCCAggTgTATgAgCTgCTAgAgAAggACTA
CCgCATggAgCgCCCAgAAggCTgCCCAgAgAAggTCTATgAACTCATgCgAgCATgTTggCAgTggAATCCCTCTgACCggCCCTC
CTTTgCTgAAATCCACCAAgCCTTTgAAACAATgTTCCAggAATCCAgTATCTCAgACgAAgTggAAAAggAgCTggggAAACA
AggCgTCCgTggggCTgTgAgTACCTTgCTgCAggCCCCAgCTgCCCACCAAgACggAggACCTCCAggAgAgCTgCAgAgCACAg
AgACACCACTgACgTgCCTgAgATgCCTCACTCCAAgggCCAgggAgAgAgCgATCCTCTggACCATgAgCCTgCCgTgTCTCCAT

```
TgCTCCCTCgAAAAgAgCgAggTCCCCCggAgggCggCCTgAATgAAgATgAgCgCCTTCTCCCCAAAgACAAAAgACCAACTT gTTCAgCgCCTTgATCAAgAAgAAgAAgAAgACAgCCCCAACCCCTCCCAAACgCAgCAgCTCCTTCCgggAgATggACggCCAg CCggAgCgCAgAggggCCggCgAggAAgAgggCCgAgACATCAgCAACggggCACTggCTTTCACCCCCTTggACACAgCTgACCCA gCCAAgTCCCCAAAgCCCAgCAATggggCTggggTCCCCAATggAgCCCTCCgggAgTCCggggCTCAggCTTCCggTCTCCCCAC CTgTggAAgAAgTCCAgCACgCTgACCAgCAgCCgCCTAgCCACCggCgAggAggAgggCggTggCAgCTCCAgCAAgCgCTTCCTgC gCTCTTgCTCCgCCTCCTgCgTTCCCCATggggCCAAggACACggAgTggAggTCAgTCACgCTgCCTCgggACTTgCAgTCCACggg AAgACAgTTTgACTCgTCCACATTTggAgggCACAAAAgTgAgAAgCCggCTCTgCCTCggAAgAgggCAggggAgAACAggTCTgA CCAggTgACCCgAggCACAgTAACgCCTCCCCCCAggCTggTgAAAAAgAATgAggAAgCTgCTgATgAggTCTTCAAAgACATC ATggAgTCCAgCCCgggCTCCAgCCCgCCCAACCTgACTCCAAAACCCCTCCggCggCAggTCACCgTggCCCCTgCCTgggCCT CCCCCACAAggAAgAAgCTggAAAgggCAgTgCCTTAgggACCCCTgCTgCAgCTgAgCCAgTgACCCCCACCAgCAAAgCAggCT CAggTgCACCAggggCACCAgCAAgggCCCCgCCgAggAgTCCAgAgTgAggAggCACAAgCACTCCTCTgAgTCgCCAgggAgggA CAAggggAAATTgTCCAggCTCAAACCTgCCCCgCCgCCCCCACCAgCAgCCTCTgCAgggAAggCTggAggAAAgCCCTCgCAgA gCCCgAgCCAggAggCggCCggggAggCAgTCCTgggCgCAAAgACAAAAgCCACgAgTCTggTTgATgCTgTgAACAgTgACgCTgC CAAgCCCAgCCAgCCgggAgAgggCCTCAAAAAgCCCgTgCTCCCggCCACTCCAAAgCCACAgTCCgCCAAgCCgTCggggACC CCCATCAgCCCAgCCCCCgTTCCCTCCACgTTgCCATCAgCATCCTCggCCCTggCAggggACCAgCCgTCTTCCACCgCCTTCA TCCCTCTCATATCAACCCgAgTgTCTCTTCggAAAACCCgCCAgCCTCCAgAgCggATCgCCAgCggCgCCATCACCAAgggCgT ggTCCTggACAgCACCgAggCgCTgTgCCTCgCCATCTCTAggAACTCCgAgCAgATggCCAgCCACAgCgCAgTgCTggAggCCggC AAAAACCTCTACACgTTCTgCgTgAgCTATgTggATTCCATCCAgCAAATgAggAACAAgTTTgCCTTCCgAgAggCCATCAAC AAACTggAgAATAATCTCCgggAgCTTCAgATCTgCCCggCgACAgCAggCAgTggTCCggCggCCACTCAggACTTCAgCAAgCT CCTCAgTTCggTgAAggAAATCAgTgACATAgTgCAgAggTAg
```

REFERENCES

1. Ramachandran, N., Hainsworth, E., Bhullar, B., Eisenstein, S., Rosen, B., Lau, A. Y., Walter, J. C., and LaBaer, J. (2004) Self-Assembling Protein Microarrays. Science 305, 86-90
2. Zhu, H., Bilgin, M., Bangham, R., Hall, D., Casamayor, A., Bertone, P., Lan, N., Jansen, R., Bidlingmaier, S., Houfek, T., Mitchell, T., Miller, P., Dean, R. A., Gerstein, M., and Snyder, M. (2001) Global analysis of protein activities using proteome chips. Science 293, 2101-2105
3. MacBeath, G., and Schreiber, S. L. (2000) Printing proteins as microarrays for high-throughput function determination. Science 289, 1760-1763
4. Zhu, H., Klemic, J. F., Chang, S., Bertone, P., Casamayor, A., Klemic, K. G., Smith, D., Gerstein, M., Reed, M. A., and Snyder, M. (2000) Analysis of yeast protein kinases using protein chips. Nat Genet. 26, 283-289
5. Michaud, G. A., Salcius, M., Zhou, F., Bangham, R., Bonin, J., Guo, H., Snyder, M., Predki, P. F., and Schweitzer, B. I. (2003) Analyzing antibody specificity with whole proteome microarrays. Nat Biotechnol 21, 1509-1512
6. Sheridan, C. (2005) Protein chip companies turn to biomarkers. Nat Biotechnol 23, 3-4
7. Robinson, W. H., Fontoura, P., Lee, B. J., de Vegvar, H. E., Tom, J., Pedotti, R., DiGennaro, C. D., Mitchell, D. J., Fong, D., Ho, P. P., Ruiz, P. J., Maverakis, E., Stevens, D. B., Bernard, C. C., Martin, R., Kuchroo, V. K., van Noort, J. M., Genain, C. P., Amor, S., Olsson, T., Utz, P. J., Garren, H., and Steinman, L. (2003) Protein microarrays guide tolerizing DNA vaccine treatment of autoimmune encephalomyelitis. Nat Biotechnol 21, 1033-1039
8. Robinson, W. H., DiGennaro, C., Hueber, W., Haab, B. B., Kamachi, M., Dean, E. J., Fournel, S., Fong, D., Genovese, M. C., de Vegvar, H. E., Skriner, K., Hirschberg, D. L., Morris, R. I., Muller, S., Pruijn, G. J., van Venrooij, W. J., Smolen, J. S., Brown, P. O., Steinman, L., and Utz, P. J. (2002) Autoantigen microarrays for multiplex characterization of autoantibody responses. Nat Med 8, 295-301
9. Xiao, Y., Segal, M. R., Yang, Y. H., and Yeh, R. F. (2007) A multi-array multi-SNP genotyping algorithm for Affymetrix SNP microarrays. Bioinformatics 23, 1459-1467
10. Hughes, L., O'Brien, S. L., Gallagher, W. M., and McDonnell, S. (2007) DNA microarray-based transcriptomic profiling of an isogenic cell culture model of breast tumour cell invasion. Anticancer Res 27, 1353-1359
11. Barone, A. D., Beecher, J. E., Bury, P. A., Chen, C., Doede, T., Fidanza, J. A., and McGall, G. H. (2001) Photolithographic synthesis of high-density oligonucleotide probe arrays. Nucleosides Nucleotides Nucleic Acids 20, 525-531
12. Michael, K. L., Taylor, L. C., Schultz, S. L., and Walt, D. R. (1998) Randomly ordered addressable high-density optical sensor arrays. Anal Chem 70, 1242-1248
13. Han, M., Gao, X., Su, J. Z., and Nie, S. (2001) Quantum-dot-tagged microbeads for multiplexed optical coding of biomolecules. Nat Biotechnol 19, 631-635
14. Olejnik, J., Sonar, S., Krzymanska-Olejnik, E., and Rothschild, K. J. (1995) Photocleavable Biotin derivatives: A Versatile Approach for the Isolation of Biomolecules. Proceedings of the National Academy of Science (USA) 92, 7590-7594

15. Pandori, M. W., Hobson, D. A., Olejnik, J., Krzymanska-Olejnik, E., Rothschild, K. J., Palmer, A. A., Phillips, T. J., and Sano, T. (2002) Photochemical control of the infectivity of adenoviral vectors using a novel photocleavable biotinylation reagent. *Chem Biol* 9, 567-573

16. Gunderson, K. L., Kruglyak, S., Graige, M. S., Garcia, F., Kermani, B. G., Zhao, C., Che, D., Dickinson, T., Wickham, E., Bierle, J., Doucet, D., Milewski, M., Yang, R., Siegmund, C., Haas, J., Zhou, L., Oliphant, A., Fan, J. B., Barnard, S., and Chee, M. S. (2004) Decoding randomly ordered DNA arrays. *Genome Res* 14, 870-877

17. Olejnik, J., Ludemann, H. C., Krzymanska-Olejnik, E., Berkenkamp, S., Hillenkamp, F., and Rothschild, K. J. (1999) Photocleavable peptide-DNA conjugates: synthesis and applications to DNA analysis using MALDI-MS. *Nucleic Acids Res* 27, 4626-4631

18. Hahner, S., Olejnik, J., Ludemann, H. C., Krzymanska-Olejnik, E., Hillenkamp, F., and Rothschild, K. J. (1999) Matrix-assisted laser desorption/ionization mass spectrometry of DNA using photocleavable biotin. *Biomol Eng* 16, 127-133

19. Nord, O., Uhlen, M., and Nygren, P. A. (2003) Microbead display of proteins by cell-free expression of anchored DNA. *J Biotechnol* 106, 1-13

20. Gite, S., Lim, M., Carlson, R., Olejnik, J., Zehnbauer, B., and Rothschild, K. (2003) A high-throughput nonisotopic protein truncation test. *Nat Biotechnol* 21, 194-197

21. Dressman, D., Yan, H., Traverso, G., Kinzler, K. W., and Vogelstein, B. (2003) Transforming single DNA molecules into fluorescent magnetic particles for detection and enumeration of genetic variations. *Proc Natl Acad Sci USA* 100, 8817-8822

22. Diehl, F., Li, M., Dressman, D., He, Y., Shen, D., Szabo, S., Diaz, L. A., Jr., Goodman, S, N., David, K. A., Juhl, H., Kinzler, K. W., and Vogelstein, B. (2005) Detection and quantification of mutations in the plasma of patients with colorectal tumors. *Proc Natl Acad Sci USA* 102, 16368-16373

23. Den Dunnen, J. T., and Van Ommen, G. J. (1999) The protein truncation test: A review. *Hum Mutat* 14, 95-102

24. Powell, S. M., Petersen, G. M., Krush, A. J., Booker, S., Jen, J., Giardiello, F. M., Hamilton, S. R., Vogelstein, B., and Kinzler, K. W. (1993) Molecular diagnosis of familial adenomatous polyposis. *N Engl J Med* 329, 1982-1987.

25. van der Luijt, R., Khan, P. M., Vasen, H., van Leeuwen, C., Tops, C., Roest, P., den Dunnen, J., and Fodde, R. (1994) Rapid detection of translation-terminating mutations at the adenomatous polyposis coli (APC) gene by direct protein truncation test. *Genomics* 20, 1-4.

26. Traverso, G., Shuber, A., Levin, B., Johnson, C., Olsson, L., Schoetz, D. J., Jr., Hamilton, S. R., Boynton, K., Kinzler, K. W., and Vogelstein, B. (2002) Detection of APC mutations in fecal DNA from patients with colorectal tumors. *N Engl J Med* 346, 311-320.

27. Kinzler, K. W., Nilbert, M. C., Vogelstein, B., Bryan, T. M., Levy, D. B., Smith, K. J., Preisinger, A. C., Hamilton, S. R., Hedge, P., Markham, A., and et al. (1991) Identification of a gene located at chromosome 5q21 that is mutated in colorectal cancers. *Science* 251, 1366-1370.

28. Groden, J., Thliveris, A., Samowitz, W., Carlson, M., Gelbert, L., Albertsen, H., Joslyn, G., Stevens, J., Spirio, L., Robertson, M., and et al. (1991) Identification and characterization of the familial adenomatous polyposis coli gene. *Cell* 66, 589-600.

29. Hogervorst, F. B., Cornelis, R. S., Bout, M., van Vliet, M., Oosterwijk, J. C., Olmer, R., Bakker, B., Klijn, J. G., Vasen, H. F., Meijers-Heijboer, H., and et al. (1995) Rapid detection of BRCA1 mutations by the protein truncation test. *Nat Genet.* 10, 208-212.

30. Garvin, A. M. (1998) A complete protein truncation test for BRCA1 and BRCA2. *Eur J Hum Genet.* 6, 226-234.

31. Futreal, P. A., Liu, Q., Shattuck-Eidens, D., Cochran, C., Harshman, K., Tavtigian, S., Bennett, L. M., Haugen-Strano, A., Swensen, J., Miki, Y., and et al. (1994) BRCA1 mutations in primary breast and ovarian carcinomas. *Science* 266, 120-122.

32. Peral, B., Gamble, V., Strong, C., Ong, A. C., Sloane-Stanley, J., Zerres, K., Winearls, C. G., and Harris, P. C. (1997) Identification of mutations in the duplicated region of the polycystic kidney disease 1 gene (PKD1) by a novel approach. *Am J Hum Genet.* 60, 1399-1410.

33. Heim, R. A., Kam-Morgan, L. N., Binnie, C. G., Corns, D. D., Cayouette, M. C., Farber, R. A., Aylsworth, A. S., Silverman, L. M., and Luce, M. C. (1995) Distribution of 13 truncating mutations in the neurofibromatosis 1 gene. *Hum Mol Genet.* 4, 975-981.

34. Parry, D. M., MacCollin, M. M., Kaiser-Kupfer, M. I., Pulaski, K., Nicholson, H. S., Bolesta, M., Eldridge, R., and Gusella, J. F. (1996) Germ-line mutations in the neurofibromatosis 2 gene: correlations with disease severity and retinal abnormalities. *Am J Hum Genet.* 59, 529-539.

35. Roest, P. A., Roberts, R. G., van der Tuijn, A. C., Heikoop, J. C., van Ommen, G. J., and den Dunnen, J. T. (1993) Protein truncation test (PTT) to rapidly screen the DMD gene for translation terminating mutations. *Neuromuscul Disord* 3, 391-394.

36. Rothschild, K. J., and Gite, S. (1999) tRNA-mediated protein engineering. *Curr Opin Biotechnol* 10, 64-70.

37. Gite, S., Marnaev, S., Olejnik, J., and Rothschild, K. (2000) Ultrasensitive fluorescence-based detection of nascent proteins in gels. *Anal Biochem* 279, 218-225.

38. Johansson, M. K., Cook, R. M., Xu, J., and Raymond, K. N. (2004) Time gating improves sensitivity in energy transfer assays with terbium chelate/dark quencher oligonucleotide probes. *J Am Chem Soc* 126, 16451-16455

39. Kojima, T., Takei, Y., Ohtsuka, M., Kawarasaki, Y., Yamane, T, and Nakano, H. (2005) PCR amplification from single DNA molecules on magnetic beads in emulsion: application for high-throughput screening of transcription factor targets. *Nucleic Acids Res* 33, e150

40. Nakano, M., Komatsu, J., Matsuura, S., Takashima, K., Katsura, S., and Mizuno, A. (2003) Single-molecule PCR using water-in-oil emulsion. *J Biotechnol* 102, 117-124

41. Nakano, M., Nakai, N., Kurita, H., Komatsu, J., Takashima, K., Katsura, S., and Mizuno, A. (2005) Single-molecule reverse transcription polymerase chain reaction using water-in-oil emulsion. *J Biosci Bioeng* 99, 293-295

42. Shendure, J., Porreca, G. J., Reppas, N. B., Lin, X., McCutcheon, J. P., Rosenbaum, A. M., Wang, M. D., Zhang, K., Mitra, R. D., and Church, G. M. (2005) Accurate multiplex polony sequencing of an evolved bacterial genome. *Science* 309, 1728-1732

43. Thomas, R. K., Nickerson, E., Simons, J. F., Janne, P. A., Tengs, T., Yuza, Y., Garraway, L. A., Laframboise, T., Lee, J. C., Shah, K., O'Neill, K., Sasaki, H., Lindeman, N., Wong, K. K., Borras, A. M., Gutmann, E. J., Dragnev, K. H., Debiasi, R., Chen, T. H., Glatt, K. A., Greulich, H., Desany, B., Lubeski, C. K., Brockman, W., Alvarez, P., Hutchison, S. K., Leamon, J. H., Ronan, M. T., Turenchalk, G. S., Egholm, M., Sellers, W. R., Rothberg, J. M., and Meyerson, M. (2006) Sensitive mutation detection in heterogeneous cancer specimens by massively parallel picoliter reactor sequencing. *Nat Med* 12, 852-855

The invention claimed is:

1. A method of amplifying nucleic acid on a solid support, comprising:
   a) providing a population of a known number of beads, each bead comprising forward and reverse amplification primers, wherein said forward primer comprises a portion encoding an N-terminal epitope tag and said reverse primer comprises a portion encoding a C-terminal epitope tag, a population of a known number of nucleic acid template molecules, wherein said nucleic acid template molecules have been treated with bisulfite; and
   b) contacting said population of beads with said population of nucleic acid template molecules under conditions such that at least a portion of said nucleic acid is amplified to create loaded beads comprising immobilized amplified nucleic acid.

2. The method of claim 1, further comprising: c) treating said immobilized amplified nucleic acid so as to release at least a portion from said loaded beads so as to create free amplified nucleic acid.

3. The method of claim 1, further comprising: c) transferring at least a portion of said immobilized amplified nucleic acid to a non-bead solid support.

4. The method of claim 1, further comprising: c) detecting at least a portion of said immobilized amplified nucleic acid.

5. The method of claim 1, further comprising: c) determining at least a portion of the sequence of the immobilized amplified nucleic acid on one or more beads.

6. The method of claim 5, wherein determining at least a portion of the sequence comprises use of nucleic acid hybridization probes, single base extension, DNA sequencing and mass spectrometry.

7. The method of claim 1, further comprising: c) transcribing and translating the immobilized amplified nucleic acid.

8. The method of claim 1, wherein prior to step a) said forward and reverse PCR primers comprise 5' amine modifications and are attached to agarose beads comprising a plurality of primary amine reactive functional groups.

9. The method of claim 1, wherein said forward and reverse PCR primers have a region that is completely complementary to a portion of the vimentin gene.

10. The method of claim 1, wherein said forward and reverse PCR primers have a region that is completely complementary to a portion of the RASF2A gene.

11. The method of claim 1, wherein the known number of beads and the known number of nucleic acid template molecules is such that less than five template molecules contact any one bead.

12. The method of claim 1, wherein the known number of beads and the known number of nucleic acid template molecules is such that less than two template molecules contact any one bead.

13. The method of claim 1, wherein the known number of beads and the known number of nucleic acid template molecules is such that less than one template molecule contacts any one bead.

14. The method of claim 1, wherein the bisulfite is an aqueous solution of a bisulfite salt.

15. The method of claim 14, wherein the bisulfite salt comprises sodium bisulfite.

16. The method of claim 14, wherein the bisulfite salt comprises magnesium bisulfite.

17. A method of amplifying nucleic acid on a solid support, comprising:
   a) providing a population of a known number of beads, each bead comprising forward and reverse amplification primers, wherein said forward primer comprises a portion encoding an N-terminal epitope tag and said reverse primer comprises a portion encoding a C-terminal epitope tag, and a population of a known number of nucleic acid template molecules treated with bisulfite, wherein said known number of nucleic acid template molecules is less than the known number of beads;
   b) contacting said population of beads with said population of nucleic acid template molecules under conditions such that at least a portion of said nucleic acid is non-covalently attached so as to create loaded beads comprising immobilized template; and
   c) amplifying at least a portion of said immobilized template so as to create immobilized amplified nucleic acid.

18. The method of claim 17, further comprising: d) treating said immobilized amplified nucleic acid so as to release at least a portion from said loaded beads so as to create free amplified nucleic acid.

19. The method of claim 17, further comprising: d) transferring at least a portion of said immobilized amplified nucleic acid to a non-bead solid support.

20. The method of claim 17, further comprising: d) detecting at least a portion of said immobilized amplified nucleic acid.

21. The method of claim 17, further comprising: d) determining at least a portion of the sequence of the immobilized amplified nucleic acid on one or more beads.

22. The method of claim 21, wherein determining a least a portion of the sequence comprises use of nucleic acid hybridization probes, single base extension, DNA sequencing and mass spectrometry.

23. The method of claim 17, further comprising: c) transcribing and translating the immobilized amplified nucleic acid.

24. The method of claim 17, wherein prior to step a) said forward and reverse PCR primers comprise 5' amine modifications and are attached to agarose beads comprising a plurality of primary amine reactive functional groups.

25. The method of 17, wherein said forward and reverse PCR primers have a region that is completely complementary to a portion of the vimentin gene.

26. The method of 17, wherein said forward and reverse PCR primers have a region that is completely complementary to a portion of the RASF2A gene.

27. The method of claim 17, wherein the bisulfite is an aqueous solution of a bisulfite salt.

28. The method of claim 27, wherein the bisulfite salt comprises sodium bisulfite.

29. The method of claim 27, wherein the bisulfite salt comprises magnesium bisulfite.

30. A method of amplifying nucleic acid on a solid support, comprising:
   a) providing a population of a known number of beads, each bead comprising forward and reverse PCR primers linked to the bead through a photocleavable linker, wherein said forward primer comprises a portion encoding an N-terminal epitope tag and said reverse primer comprises a portion encoding a C-terminal epitope tag, a population of a known number of nucleic acid template molecules treated with bisulfite, wherein said known number of nucleic acid template molecules is less than the known number of beads; and
   b) contacting said population of beads with said population of nucleic acid template molecules under conditions such that at least a portion of said nucleic acid is amplified to create loaded beads comprising immobilized amplified nucleic acid linked to the beads through a photocleavable linker.

31. The method of claim 30 further comprising: c) exposing at least a portion of said immobilized amplified nucleic acid to light so as to create free amplified nucleic acid.

32. The method of claim 30, further comprising: c) detecting at least a portion of said immobilized amplified nucleic acid.

33. The method of claim 30, further comprising: c) determining at least a portion of the sequence of the immobilized amplified nucleic acid on one or more beads.

34. The method of claim 33, wherein determining a least a portion of the sequence comprises use of nucleic acid hybridization probes, single base extension, DNA sequencing and mass spectrometry.

35. The method of claim 30, further comprising: c) transcribing and translating the immobilized amplified nucleic acid.

36. The method of claim 30, further comprising: c) exposing at least a portion of said immobilized amplified nucleic acid to light so as to transfer at least a portion of said immobilized amplified nucleic acid to a non-bead solid support.

37. The method of claim 30, wherein prior to step a) said forward and reverse PCR primers comprise 5' amine modifications and are attached to agarose beads comprising a plurality of primary amine reactive functional groups.

38. The method of claim 30, wherein said forward and reverse PCR primers have a region that is completely complementary to a portion of the vimentin gene.

39. The method of claim 30, wherein said forward and reverse PCR primers have a region that is completely complementary to a portion of the RASF2A gene.

* * * * *

SEQUENCE LISTING

<160> NUMBER OF SEQ ID NOS: 126

<210> SEQ ID NO 1
<211> LENGTH: 26
<212> TYPE: DNA
<213> ORGANISM: Homo sapiens

<400> SEQUENCE: 1
cgtcccgcga aattaatacg actcac                                          26

<210> SEQ ID NO 2
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Biotin conjugated nucleotide

<400> SEQUENCE: 2
gttaaattgc taacgcagtc aggag                                           25

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Gln Pro Glu Leu Ala Pro Glu Asp Pro Glu Asp
1               5                   10

<210> SEQ ID NO 4
<211> LENGTH: 133
<212> TYPE: DNA
<213> ORGANISM: Artificial Sequence
<220> FEATURE:
<223> OTHER INFORMATION: Synthetic

<400> SEQUENCE: 4
ggatcctaat acgactcact atagggagac caccatgtac accgacatcg agatgaaccg     60
cctgggcaag ggaggacagc ctgaactcgc tccagaggat ccggaagatg tttctccata   120
caggtcacgg gga                                                       133

<210> SEQ ID NO 5
<211> LENGTH: 60
<212> TYPE: DNA
<213> ORGANISM: Homo sapiens

<400> SEQUENCE: 5
ttattacagc agcttgtgca ggtcgctgaa ggtacttctg ccttctgtag gaatggtatc     60

<210> SEQ ID NO 6
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide

<400> SEQUENCE: 6
cgtcccgcga aattaatacg actcac    26

<210> SEQ ID NO 7
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide

<400> SEQUENCE: 7
gttaaattgc taacgcagtc aggag    25

<210> SEQ ID NO 8
<211> LENGTH: 26
<212> TYPE: DNA
<213> ORGANISM: Homo sapiens

<400> SEQUENCE: 8
cgtcccgcga aattaatacg actcac    26

<210> SEQ ID NO 9
<211> LENGTH: 25
<212> TYPE: DNA
<213> ORGANISM: Homo sapiens

<400> SEQUENCE: 9
gttaaattgc taacgcagtc aggag    25

<210> SEQ ID NO 10
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine Conjugated Nucleotide

<400> SEQUENCE: 10
ggatcctaat acgactcact atagggagcc accatggaag aagagatcgc cgcgctggtc    60
attgac    66

<210> SEQ ID NO 11
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine Conjugated Nucleotide

<400> SEQUENCE: 11
ttaatcctct gggtcttcag gagcgagttc tggctggctg aagcatttgc ggtggacgat    60
ggaggggcc    69

<210> SEQ ID NO 12
<211> LENGTH: 58

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine Conjugated Nucleotide

<400> SEQUENCE: 12
ggatcctaat acgactcact atagggagac caccatggag gagccgcagt cagatcct      58

<210> SEQ ID NO 13
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine Conjugated Nucleotide

<400> SEQUENCE: 13
ttttaatcct ctgggtcttc aggagcgagt tctggctggc tgtctgagtc aggcccttct      60
gtc                                                                  63

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Asp Tyr Lys Asp Asp Asp Asp Lys
1               5

<210> SEQ ID NO 15
<211> LENGTH: 83
<212> TYPE: DNA
<213> ORGANISM: Artificial Sequence
<220> FEATURE:
<223> OTHER INFORMATION: Synthetic

<400> SEQUENCE: 15
taatacgact cactataggg agaggaggta tatcaatgga ttataaagac gatgatgata      60
aaagtacagc aagtggaaag caa                                            83

<210> SEQ ID NO 16
<211> LENGTH: 33
<212> TYPE: DNA
<213> ORGANISM: Homo sapiens

<400> SEQUENCE: 16
ttatttattt attttttgata cattttgtct aga                                33

<210> SEQ ID NO 17
<211> LENGTH: 83
<212> TYPE: DNA
<213> ORGANISM: Artificial Sequence
<220> FEATURE:
<223> OTHER INFORMATION: Synthetic

<400> SEQUENCE: 17
taatacgact cactataggg agaggaggta tatcaatgga ttataaagac gatgatgata      60
```

-continued aacttcataa gtcagtctca tct    83

<210> SEQ ID NO 18
<211> LENGTH: 33
<212> TYPE: DNA
<213> ORGANISM: Homo sapiens

<400> SEQUENCE: 18
ttatttattt atttctattt cagaaaacac ttg    33

<210> SEQ ID NO 19
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine Conjugated Nucleotide

<400> SEQUENCE: 19
gttaaattgc taacgcagtc aggag    25

<210> SEQ ID NO 20
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy5 Conjugated Nucleotide

<400> SEQUENCE: 20
ctcctgactg cgttagcaat ttaac    25

<210> SEQ ID NO 21
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Biotin Conjugated Nucleotide

<400> SEQUENCE: 21
ctcctgactg cgttagcaat ttaac    25

<210> SEQ ID NO 22
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy5 Conjugated Nucleotide

<400> SEQUENCE: 22
ctcctgactg cgttagcaat ttaac    25

<210> SEQ ID NO 23
<211> LENGTH: 95
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<222> LOCATION: (69)..(95)
<223> OTHER INFORMATION: The nucleotides in these positions indicate the
      gene-specific hybridization regions.

<400> SEQUENCE: 23
ggatcctaat acgactcact atagggagag gaggtatatc aatggattat aaagacgatg    60
atgataaaga ggagccgcag tcagatccta gcgtc                              95

<210> SEQ ID NO 24
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(76)

<400> SEQUENCE: 24
tttttattac ttacccaggc ggttcatttc gatatcagtg tatttattta tcaaggggga    60
cagaacgttg ttttca                                                   76

<210> SEQ ID NO 25
<211> LENGTH: 95
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (69)..(95)
<223> OTHER INFORMATION: The nucleotides at these positions indicate the
      gene-specific hybridization regions.

<400> SEQUENCE: 25
ggatcctaat acgactcact atagggagag gaggtatatc aatggattat aaagacgatg    60
atgataaagc agagaagccc aagctccact actcc                              95

<210> SEQ ID NO 26
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(79)
<223> OTHER INFORMATION: The nucleotides at these positions indicate the
      gene-specific hybridization regions.

<400> SEQUENCE: 26
tttttattac ttacccaggc ggttcatttc gatatcagtg tatttattta tctcttcaaa    60
ctctactcca gctgcagcc                                                79

<210> SEQ ID NO 27
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

```
<223> OTHER INFORMATION: Amine
<220> FEATURE:
<221> NAME/KEY: misc_feature
<222> LOCATION: (1)..(1)
<223> OTHER INFORMATION: Amine conjugated nucleotide

<400> SEQUENCE: 27
taatacgact cactataggg agaggagg                                      28

<210> SEQ ID NO 28
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide

<400> SEQUENCE: 28
ttacttaccc aggcggttca tttc                                          24

<210> SEQ ID NO 29
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy5 conjugated nucleotide

<400> SEQUENCE: 29
cattttcaga cctatggaaa ctacttc                                       27

<210> SEQ ID NO 30
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy3 conjugated nucleotide

<400> SEQUENCE: 30
agaatggagt ccatccggtg                                               20

<210> SEQ ID NO 31
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy5 conjugated nucleotide

<400> SEQUENCE: 31
cattttcaga cctatggaaa ctacttc                                       27

<210> SEQ ID NO 32
<211> LENGTH: 20
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(1)
<223> OTHER INFORMATION: Cy3 conjugated nucleotide

<400> SEQUENCE: 32
agaatggagt ccatccggtg                                                  20

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Tyr Thr Asp Ile Glu Met Asn Arg Leu Gly Lys
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Thr Phe Ser Asp Leu His Lys Leu Leu
1               5

<210> SEQ ID NO 35
<211> LENGTH: 84
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (64)..(84)
<223> OTHER INFORMATION: APC-specific hybridizing sequences.

<400> SEQUENCE: 35
atgaaccgcc tgggcaaggg aggaggagga cagcctgaac tcgctccaga ggatccggaa      60
gatcaggaag cagattctgc taat                                             84

<210> SEQ ID NO 36
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(51)
<223> OTHER INFORMATION: APC-specific hybridizing sequences.

<400> SEQUENCE: 36
ttacagcagc ttgtgcaggt cgctgaaggt gggtgtctga gcaccacttt t               51

<210> SEQ ID NO 37
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

<223> OTHER INFORMATION: Amine conjugated nucleotide.

<400> SEQUENCE: 37
taatacgact cactataggg agaggaggta tatcaatgta caccgacatc gagatgaacc    60
gcctgggcaa gggaggagga gga    83

<210> SEQ ID NO 38
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 38
ttacagcagc ttgtgcaggt cgctgaaggt gggtgtctga gcaccacttt t    51

<210> SEQ ID NO 39
<211> LENGTH: 11
<212> TYPE: PRT
<213> ORGANISM: Homo sapiens

<400> SEQUENCE: 39

Tyr Thr Asp Ile Glu Met Asn Arg Leu Gly Lys
1               5                   10

<210> SEQ ID NO 40
<211> LENGTH: 11
<212> TYPE: PRT
<213> ORGANISM: Homo sapiens

<400> SEQUENCE: 40

Gln Pro Glu Leu Ala Pro Glu Asp Pro Glu Asp
1               5                   10

<210> SEQ ID NO 41
<211> LENGTH: 9
<212> TYPE: PRT
<213> ORGANISM: Homo sapiens

<400> SEQUENCE: 41

Thr Phe Ser Asp Leu His Lys Leu Leu
1               5

<210> SEQ ID NO 42
<211> LENGTH: 84
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (64)..(84)
<223> OTHER INFORMATION: The nucleotides at these positions indicate the
      gene-specific hybridization regions.

<400> SEQUENCE: 42
atgaaccgcc tgggcaaggg aggaggagga cagcctgaac tcgctccaga ggatccggaa    60
gatcaggaag cagattctgc taat    84

<210> SEQ ID NO 43
<211> LENGTH: 51
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(51)
<223> OTHER INFORMATION: The nucleotides at these positions indicate the
      gene-specific hybridization regions.

<400> SEQUENCE: 43
ttacagcagc ttgtgcaggt cgctgaaggt gggtgtctga gcaccacttt t            51

<210> SEQ ID NO 44
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.
<220> FEATURE:
<221> NAME/KEY: misc_feature
<222> LOCATION: (54)..(83)
<223> OTHER INFORMATION: The nucleotides in these positions indicate the
      template-specific hybridization regions.

<400> SEQUENCE: 44
taatacgact cactataggg agaggaggta tatcaatgta caccgacatc gagatgaacc   60
gcctgggcaa gggaggagga gga                                          83

<210> SEQ ID NO 45
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.
<220> FEATURE:
<221> NAME/KEY: misc_feature
<222> LOCATION: (61)..(89)
<223> OTHER INFORMATION: The nucleotides in these positions indicate the
      template-specific hybridization regions.

<400> SEQUENCE: 45 ttttttttt tttttttttt attatcctcc tcctgcgtag tctggtacgt cgtatgggta    60
cagcagcttg tgcaggtcgc tgaaggtgg                                     89

<210> SEQ ID NO 46
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fluorescein conjugated nucleotide.

<400> SEQUENCE: 46
gcaccctaga accaaatcca gcagactg                                      28

<210> SEQ ID NO 47
<211> LENGTH: 30
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 47
ttgaggtttt tgtgttagag atgtagttgt                                          30

<210> SEQ ID NO 48
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 48
actccaacta aaactcaacc aactcaca                                            28

<210> SEQ ID NO 49
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 49
tcgtttcgag gttttcgcgt tagagac                                             27

<210> SEQ ID NO 50
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 50
cgactaaaac tcgaccgact cgcga                                               25

<210> SEQ ID NO 51
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 51
agtttgttgt tgtttttag gtgg                                                 24

<210> SEQ ID NO 52
<211> LENGTH: 21
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 52
aaaaaaccaa caaccccac a                                              21

<210> SEQ ID NO 53
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 53
agttcgtcgt cgttttttag gc                                            22

<210> SEQ ID NO 54
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 54
aaaaaccaac gaccccgcg                                                20

<210> SEQ ID NO 55
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy3 conjugated nucleotide.

<400> SEQUENCE: 55
gtaggatgtt cggcggttcg                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy5 conjugated nucleotide.

<400> SEQUENCE: 56
gttttagttt tcggcgcggg                                               20

<210> SEQ ID NO 57
<211> LENGTH: 30
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 57
ttgaggtttt tgtgttagag atgtagttgt                                          30

<210> SEQ ID NO 58
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 58
actccaacta aaactcaacc aactcaca                                            28

<210> SEQ ID NO 59
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 59
agtttgttgt tgtttttag gtgg                                                 24

<210> SEQ ID NO 60
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 60
aaaaaaccaa caaccccac a                                                    21

<210> SEQ ID NO 61
<211> LENGTH: 30
<212> TYPE: DNA
<213> ORGANISM: Homo sapiens

<400> SEQUENCE: 61
ttgaggtttt tgtgttagag atgtagttgt                                          30

<210> SEQ ID NO 62
<211> LENGTH: 28
<212> TYPE: DNA
<213> ORGANISM: Homo sapiens

<400> SEQUENCE: 62
actccaacta aaactcaacc aactcaca                                            28
```

<210> SEQ ID NO 63
<211> LENGTH: 24
<212> TYPE: DNA
<213> ORGANISM: Homo sapiens

<400> SEQUENCE: 63
agtttgttgt tgttttttag gtgg                                              24

<210> SEQ ID NO 64
<211> LENGTH: 21
<212> TYPE: DNA
<213> ORGANISM: Homo sapiens

<400> SEQUENCE: 64
aaaaaaccaa caacccccac a                                                 21

<210> SEQ ID NO 65
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy3 conjugated nucleotide.

<400> SEQUENCE: 65
tgtaggatgt ttggtggttt ggg                                               23

<210> SEQ ID NO 66
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy5 conjugated nucleotide.

<400> SEQUENCE: 66
ttttggtgtg gggaggtggt                                                   20

<210> SEQ ID NO 67
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 67
taatacgact cactataggg agaggaggta tatcaatgta caccgacatc gagatgaacc        60
gcctgggcaa gggaggacag cctgaactcg ctccagagga tccggaagat caggaagcag      120
attctgctaa t                                                           131

<210> SEQ ID NO 68
<211> LENGTH: 114
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (85)..(114)
<223> OTHER INFORMATION: The nucleotides at these positions indicate the
      gene-specific APC directed hybridization regions.

<400> SEQUENCE: 68
tttttttttt tttttttttt attatcctcc tcctttatca tcatcgtctt tataatccag      60
cagcttgtgc aggtcgctga aggttggact tttgggtgtc tgagcaccac tttt           114

<210> SEQ ID NO 69
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy5 conjugated nucleotide.

<400> SEQUENCE: 69
gcaccctaga accaaatcca gcagactg                                         28

<210> SEQ ID NO 70
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.
<220> FEATURE:
<221> NAME/KEY: misc_feature
<222> LOCATION: (54)..(83)
<223> OTHER INFORMATION: The nucleotides at these positions indicate the
      template-specific hybridization regions.

<400> SEQUENCE: 70
taatacgact cactataggg agaggaggta tatcaatgta caccgacatc gagatgaacc      60
gcctgggcaa gggaggagga gga                                              83

<210> SEQ ID NO 71
<211> LENGTH: 89
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.
<220> FEATURE:
<221> NAME/KEY: misc_feature
<222> LOCATION: (61)..(89)
<223> OTHER INFORMATION: The nucleotides at these positions indicate the
      template-specific hybridization regions.

<400> SEQUENCE: 71
tttttttttt tttttttttt attatcctcc tcctgcgtag tctggtacgt cgtatgggta      60
cagcagcttg tgcaggtcgc tgaaggtgg                                        89

<210> SEQ ID NO 72
<211> LENGTH: 30
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: Amine conjugated nucleotide.

<400> SEQUENCE: 72
ttgaggtttt tgtgttagag atgtagttgt                                          30

<210> SEQ ID NO 73
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 73
actccaacta aaactcaacc aactcaca                                            28

<210> SEQ ID NO 74
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Cy3 conjugated nucleotide.

<400> SEQUENCE: 74
tgtaggatgt ttggtggttt ggg                                                 23

<210> SEQ ID NO 75
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 75
taatacgact cactataggg agaggaggta tatcaatgta caccgacatc gagatgaacc         60
gcctgggcaa gggaggacag cctgaactcg ctccagagga tccggaagat ggacaaagca        120
gtaaaaccga a                                                            131

<210> SEQ ID NO 76
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 76
ttattacagc agcttgtgca ggtcgctgaa ggtagccttt tgaggctgac cact               54
```

```
<210> SEQ ID NO 77
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 77
taatacgact cactataggg agaggaggta tatcaatgta caccgacatc gagatgaacc    60
gcctgggcaa gggaggacag cctgaactcg ctccagagga tccggaagat ccaagttctg   120
cacagagtag a                                                        131

<210> SEQ ID NO 78
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 78
ttattacagc agcttgtgca ggtcgctgaa ggttgaacta catcttgaaa aaca           54

<210> SEQ ID NO 79
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 79
taatacgact cactataggg agaggaggta tatcaatgta caccgacatc gagatgaacc    60
gcctgggcaa gggaggacag cctgaactcg ctccagagga tccggaagat tgtgtagaag   120
atactccaat a                                                        131

<210> SEQ ID NO 80
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 80
ttattacagc agcttgtgca ggtcgctgaa ggttatttct gctatttgca gggt           54

<210> SEQ ID NO 81
<211> LENGTH: 131
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 81
taatacgact cactataggg agaggaggta tatcaatgta caccgacatc gagatgaacc      60
gcctgggcaa gggaggacag cctgaactcg ctccagagga tccggaagat caggaagcag    120
attctgctaa t                                                         131

<210> SEQ ID NO 82
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 82
ttattacagc agcttgtgca ggtcgctgaa ggtctgcagt ctgctggatt tggt           54

<210> SEQ ID NO 83
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 83
taatacgact cactataggg agaggaggta tatcaatgta caccgacatc gagatgaacc      60
gcctgggcaa gggaggacag cctgaactcg ctccagagga tccggaagat gcagtgtcac    120
agcaccctag a                                                         131

<210> SEQ ID NO 84
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 84
ttattacagc agcttgtgca ggtcgctgaa ggtgggtgtc tgagcaccac tttt           54

<210> SEQ ID NO 85
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<222> LOCATION: (111)..(131)
<223> OTHER INFORMATION: The nucleotides at these positions indicate the
      gene-specific APC directed hybridization regions.

<400> SEQUENCE: 85
taatacgact cactataggg agaggaggta tatcaatgta caccgacatc gagatgaacc    60
gcctgggcaa gggaggacag cctgaactcg ctccagagga tccggaagat tcaggagcga   120
aatctccctc c                                                       131

<210> SEQ ID NO 86
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 86
ttattacagc agcttgtgca ggtcgctgaa ggtcgaacga ctctcaaaac tatc          54

<210> SEQ ID NO 87
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 87
taatacgact cactataggg agaggaggta tatcaatgta caccgacatc gagatgaacc    60
gcctgggcaa gggaggacag cctgaactcg ctccagagga tccggaagat tgtacttctg   120
tcagttcact t                                                       131

<210> SEQ ID NO 88
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 88
ttattacagc agcttgtgca ggtcgctgaa ggtcatggtt tgtccagggc tatc          54

<210> SEQ ID NO 89
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 89
taatacgact cactataggg agaggaggta tatcaatgta caccgacatc gagatgaacc    60
gcctgggcaa gggaggacag cctgaactcg ctccagagga tccggaagat ataagcccca   120
gtgatcttcc a                                                       131

<210> SEQ ID NO 90
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 90
ttattacagc agcttgtgca ggtcgctgaa ggtcttttca gcagtaggtg cttt          54

<210> SEQ ID NO 91
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 91
taatacgact cactataggg agaggaggta tatcaatgta caccgacatc gagatgaacc    60
gcctgggcaa gggaggacag cctgaactcg ctccagagga tccggaagat aagcgagaag   120
tacctaaaaa t                                                       131

<210> SEQ ID NO 92
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 92
ttattacagc agcttgtgca ggtcgctgaa ggtcgtggca aaatgtaata aagt          54

<210> SEQ ID NO 93
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 93
taatacgact cactataggg agaggaggta tatcaatgta caccgacatc gagatgaacc    60

```
gcctgggcaa gggaggacag cctgaactcg ctccagagga tccggaagat caggttcttc    120
cagatgctga t                                                         131

<210> SEQ ID NO 94
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 94
ttattacagc agcttgtgca ggtcgctgaa ggttattctt aattccacat cttt           54

<210> SEQ ID NO 95
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 95
taatacgact cactataggg agaggaggta tatcaatgta caccgacatc gagatgaacc     60
gcctgggcaa gggaggacag cctgaactcg ctccagagga tccggaagat ctcgatgagc    120
catttataca g                                                         131

<210> SEQ ID NO 96
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 96
ttattacagc agcttgtgca ggtcgctgaa ggttttttct gcctctttct cttg           54

<210> SEQ ID NO 97
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(131)
<223> OTHER INFORMATION: The nucleotides at these positions indicate the
      gene-specific APC directed hybridization regions.

<400> SEQUENCE: 97
taatacgact cactataggg agaggaggta tatcaatgta caccgacatc gagatgaacc     60
gcctgggcaa gggaggacag cctgaactcg ctccagagga tccggaagat cctaaagaat    120
caaatgaaaa c                                                         131
```

```
<210> SEQ ID NO 98
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(54)
<223> OTHER INFORMATION: The nucleotides at these positions indicate the
      gene-specific APC directed hybridization regions.

<400> SEQUENCE: 98
ttattacagc agcttgtgca ggtcgctgaa ggttgacttt gttggcatgg caga          54

<210> SEQ ID NO 99
<211> LENGTH: 24
<212> TYPE: DNA
<213> ORGANISM: Homo sapiens

<400> SEQUENCE: 99
gcgaacaagg gcagcaaggc tacg                                           24

<210> SEQ ID NO 100
<211> LENGTH: 33
<212> TYPE: DNA
<213> ORGANISM: Homo sapiens

<400> SEQUENCE: 100
actggattcc tggaacattg tttcaaaggc ttg                                 33

<210> SEQ ID NO 101
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 101
taatacgact cactataggg agaggaggta tatcaatgga ttataaagac gatgatgata    60
aaaactacga caagtgggag atg                                            83

<210> SEQ ID NO 102
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 102
ttatttattt atcaccgtca ggctgtattt ctt                                 33

<210> SEQ ID NO 103
<211> LENGTH: 24
<212> TYPE: DNA
<213> ORGANISM: Homo sapiens

<400> SEQUENCE: 103
gcgaacaagg gcagcaaggc tacg                                           24
```

<210> SEQ ID NO 104
<211> LENGTH: 33
<212> TYPE: DNA
<213> ORGANISM: Homo sapiens

<400> SEQUENCE: 104
actggattcc tggaacattg tttcaaaggc ttg                                  33

<210> SEQ ID NO 105
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 105
taatacgact cactataggg agaggaggta tatcaatgga ttataaagac gatgatgata     60
aaaactacga caagtgggag atg                                            83

<210> SEQ ID NO 106
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 106
ttatttattt atcaccgtca ggctgtattt ctt                                 33

<210> SEQ ID NO 107
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 107
taatacgact cactataggg agaggaggta tatcaatgga ttataaagac gatgatgata     60
aagtgtacga gggcgtgtgg                                                80

<210> SEQ ID NO 108
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 108
ttatttattt atttctttca agaactcttc cacctc                              36

```
<210> SEQ ID NO 109
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 109
taatacgact cactataggg agaggaggta tatcaatgga ttataaagac gatgatgata      60
aagccgtgaa gaccttgaag gag                                             83

<210> SEQ ID NO 110
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 110
ttatttattt ataaggagct gcaccaggtt agg                                  33

<210> SEQ ID NO 111
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 111
taatacgact cactataggg agaggaggta tatcaatgga ttataaagac gatgatgata      60
aagtctgcac ccgggagcc                                                  79

<210> SEQ ID NO 112
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 112
ttatttattt atcaccacgg cgttcacct                                       29

<210> SEQ ID NO 113
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 113
```

-continued

```
taatacgact cactataggg agaggaggta tcaatggga ttataaagac gatgatgata    60
aaaactgcct ggtaggggag aac                                          83
```

<210> SEQ ID NO 114
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 114

```
ttatttattt atagtccatt tgatggggaa cttg                              34
```

<210> SEQ ID NO 115
<211> LENGTH: 81
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 115

```
taatacgact cactataggg agaggaggta tcaatggga ttataaagac gatgatgata    60
aacagtggaa tccctctgac c                                            81
```

<210> SEQ ID NO 116
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Amine conjugated nucleotide.

<400> SEQUENCE: 116

```
ttatttattt atgccttgtt tccccagctc cttttc                            36
```

<210> SEQ ID NO 117
<211> LENGTH: 86
<212> TYPE: DNA
<213> ORGANISM: Homo sapiens

<400> SEQUENCE: 117

```
taatacgact cactataggg agaggaggta tcaatgaa agattataaa gacgatgatg    60
ataaatgtac ttctgtcagt tcactt                                       86
```

<210> SEQ ID NO 118
<211> LENGTH: 33
<212> TYPE: DNA
<213> ORGANISM: Homo sapiens

<400> SEQUENCE: 118

```
ttatttattt atcatggttt gtccagggct atc                               33
```

<210> SEQ ID NO 119
<211> LENGTH: 4829

```
<212> TYPE: DNA
<213> ORGANISM: Homo sapiens

<400> SEQUENCE: 119
gccggcacct gtcctacgag ttgcatgata agaagacag tcataagtgc ggcgacgacc      60
ggtgaattgt gagcgctcac aattctcgtg acatcataac gtcccgcgaa attaatacga     120
ctcactatag ggaattgtg agcggataac aattcccctc tagacttaca atttccattc      180
gccattcagg ctgcgcaact gttgggaagg gcgatcggta cgggcctctt cgctattacg     240
ccagcttgcg aacggtgggt gcgctgcaag gcgattaagt tgggtaacgc caggattctc     300
ccagtcacga cgttgtaaaa cgacggccag cgagagatct tgattggcta gcagaataat     360
tttgtttaac tttaagaagg agatatacca tggcgataga ggagccgcag tcagatccta     420
gcgtcgagcc ccctctgagt caggaaacat tttcagacct atggaaacta cttcctgaaa     480
acaacgttct gtccccttg ccgtcccaag caatggatga tttgatgctg tcccggacg      540
atattgaaca atggttcact gaagaccag gtccagatga agctcccaga atgccagagg      600
ctgctcccg cgtggcccct gcaccagcag ctcctacacc ggcggcccct gcaccagccc      660
cctcctggcc cctgtcatct tctgtccctt cccagaaaac ctaccagggc agctacggtt     720
tccgtctggg cttcttgcat tctgggacag ccaagtctgt gacttgcacg tactccctg      780
ccctcaacaa gatgttttgc caactggcca agacctgccc tgtgcagctg tgggttgatt     840
ccacaccccc gcccggcacc cgcgtccgcg ccatggccat ctacaagcag tcacagcaca     900
tgacggaggt tgtgaggcgc tgccccccac catgagcgctg ctcagatagc gatggtctgg     960
ccctcctca gcatcttatc cgagtggaag gaaatttgcg tgtggagtat ttggatgaca    1020
gaaacacttt tcgacatagt gtggtggtgc cctatgagcc gcctgaggtt ggctctgact    1080
gtaccaccat ccactacaac tacatgtgta acagttcctg catgggcggc atgaaccgga    1140
ggcccatcct caccatcatc acactggaag actccagtgg taatctactg ggacggaaca    1200
gctttgaggt gcgtgtttgt gcctgtcctg ggagagaccg gcgcacagag aagagaatc     1260
tccgcaagaa aggggagcct caccacgagc tgcccccagg gagcactaag cgagcactgc    1320
ccaacaacac cagctcctct ccccagccaa agaagaaacc actggatgga gaatatttca    1380
cccttcagat ccgtgggcgt gagcgcttcg agatgttccg agagctgaat gaggccttgg    1440
aactcaagga tgcccaggct gggaaggagc caggggggag cagggctcac tccagccacc    1500
tgaagtccaa aaagggtcag tctacctccc gccataaaaa actcatgttc aagacagaag    1560
ggcctgactc agactcccgg gagctcgtgg atccgaattc tgtacaggcg cgcctgcagg    1620
acgtcgacgg taccatcgat acgcgttcga agcttgcggc cgcacagctg tatacacgtg    1680
caagccagcc agaactcgct cctgaagacc cagaggatct cgagcaccac caccaccacc    1740
actaatgtta attaagttgg gcgttgtaat catagtcata atcaatactc ctgactgcgt    1800
tagcaattta actgtgataa actaccgcat taaagctatt cgatgataag ctgtcaaaca    1860
tgataattct tgaagacgaa agggcctagg ctgataaaac agaatttgcc tggcggcagt    1920
agcgcggtgg tcccacctga ccccatgccg aactcagaag tgaaacgccg tagcgccgat    1980
ggtagtgtgg ggtctcccca tgcgagagta gggaactgcc aggcatcaaa taaaacgaaa    2040
ggctcagtcg aaagactggg cctttcgttt tatctgttgt ttgtcggtga acgctctcct    2100
gagtaggaca atccgccgg gagcggattt gaacgttgcg aagcaacggc ccggagggtg    2160
gcgggcagga cgcccgccat aaactgccag gcatcaaatt aagcagaagg ccatcctgac    2220
ggatggcctt tttgcgtttc tacaaactct tttgtttatt tttctaaata cattcaaata    2280
```

```
tgtatccgct gagcaataac tagcataacc ccttggggcc tctaaacggg tcttgagggg   2340
ttttttgctg aaaggaggaa ctatatccgg attggcgaat gggacgcgcc ctgtagcggc   2400
gcattaagcg cggcggtgt ggtggttacg cgcagcgtga ccgctacact tgccagcgcc    2460
ctagcgcccg ctcctttcgc tttcttccct tcctttctcg ccacgttcgc cggctttccc   2520
cgtcaagctc taaatcgggg ctcccttta gggttccgat ttagtgcttt acggcacctc    2580
gaccccaaaa aacttgatta gggtgatggt tcacgtagtg ggccatcgcc ctgatagacg   2640 gttttcgcc ctttgacgtt ggagtccacg ttctttaata gtggactctt gttccaaact    2700
ggaacaacac tcaaccctat ctcggtctat tcttttgatt tataagggat tttgccgatt   2760
tcggcctatt ggttaaaaaa tgagctgatt taacaaaaat ttaacgcgaa ttttaacaaa   2820
atattaacgt ttacaatttc tggcggcacg atggcatgag attatcaaaa aggatcttca   2880
cctagatcct ttaaattaa aaatgaagtt ttaaatcaat ctaaagtata tatgagtaaa    2940
cttggtctga cagttaccaa tgcttaatca gtgaggcacc tatctcagcg atctgtctat   3000
ttcgttcatc catagttgcc tgactccccg tcgtgtagat aactacgata cgggagggct   3060
taccatctgg ccccagtgct gcaatgatac cgcgagaccc acgctcaccg gctccagatt   3120
tatcagcaat aaaccagcca gccggaaggg ccgagcgcag aagtggtcct gcaactttat   3180
ccgcctccat ccagtctatt aattgttgcc gggaagctag agtaagtagt tcgccagtta   3240
atagtttgcg caacgttgtt gccattgcta caggcatcgt ggtgtcacgc tcgtcgtttg   3300
gtatggcttc attcagctcc ggttcccaac gatcaaggcg agttacatga tcccccatgt   3360
tgtgcaaaaa agcggttagc tccttcggtc ctccgatcgt tgtcagaagt aagttggccg   3420
cagtgttatc actcatggtt atggcagcac tgcataattc tcttactgtc atgccatccg   3480
taagatgctt ttctgtgact ggtgagtact caaccaagtc attctgagaa tagtgtatgc   3540
ggcgaccgag ttgctcttgc ccggcgtcaa tacgggataa taccgcgcca tagcagaa    3600 ctttaaaagt gctcatcatt ggaaaacgtt cttcggggcg aaaactctca aggatcttac   3660
cgctgttgag atccagttcg atgtaaccca ctcgtgcacc caactgatct tcagcatctt   3720
ttactttcac cagcgtttct gggtgagcaa aaacaggaag gcaaaatgcc gcaaaaaagg   3780
gaataagggc gacacggaaa tgttgaatac tcatactctt cctttttcaa tcatgaccaa   3840
aatcccttaa cgtgagtttt cgttccactg agcgtcagac cccgtagaaa agatcaaagg   3900
atcttcttga tcctttttt tctgcgcgt aatctgctgc ttgcaaacaa aaaaaccacc    3960
gctaccagcg gtggtttgtt tgccggatca agagctacca actctttttc cgaaggtaac   4020
tggcttcagc agagcgcaga taccaaatac tgtccttcta gtgtagccgt agttaggcca   4080
ccacttcaag aactctgtag caccgcctac atacctcgct ctgctaatcc tgttaccagt   4140
ggctgctgcc agtggcgata agtcgtgtct taccggggttg gactcaagac gatagttacc   4200
ggataaggcg cagcggtcgg gctgaacggg gggttcgtgc acacagccca gcttggagcg   4260
aacgacctac accgaactga gatacctaca gcgtgagcta tgagaaagcg ccacgcttcc   4320
cgaagggaga aaggcggaca ggtatccggt aagcggcagg gtcggaacag gagagcgcac   4380
gagggagctt ccagggggaa acgcctggta tctttatagt cctgtcgggt ttcgccacct   4440
ctgacttgag cgtcgatttt tgtgatgctc gtcagggggg cggagcctat ggaaaaacgc   4500
cagcaacgcg gccttttac ggttcctggc cttttgctgg cctttgctc acatgttctt    4560 tcctgcgtta tccctgatt ctgtggataa ccgtattacc gcctttgagt gagctgatac    4620
cgctcgccgc agccgaacga ccgagcgcag cgagtcagtg agcgaggaag ccggcgataa   4680
```

```
tggcctgctt ctcgccgaaa cgtttggtgg cgggaccagt gacgaaggct tgagcgaggg      4740
cgtgcaagat tccgaatacc gcaagcgaca ggccgatcat cgtcgcgctc cagcgaaagc      4800
ggtcctcgcc gaaaatgacc cagagcgct                                        4829

<210> SEQ ID NO 120
<211> LENGTH: 4316
<212> TYPE: DNA
<213> ORGANISM: Homo sapiens

<400> SEQUENCE: 120
gccggcacct gtcctacgag ttgcatgata aagaagacag tcataagtgc ggcgacgacc        60
ggtgaattgt gagcgctcac aattctcgtg acatcataac gtcccgcgaa attaatacga       120
ctcactatag gggaattgtg agcggataac aattcccctc tagacttaca atttccattc       180
gccattcagg ctgcgcaact gttgggaagg gcgatcggta cgggcctctt cgctattacg       240
ccagcttgcg aacggtgggt gcgctgcaag gcgattaagt tgggtaacgc caggattctc       300
ccagtcacga cgttgtaaaa cgacggccag cgagagatct tgattggcta gcagaataat       360
tttgtttaac tttaagaagg agatatacca tggcgatagc agagaagccc aagctccact       420
actccaatat acggggcaga atggagtcca tccggtggct cctggctgca gctggagtag       480
agtttgaaga gaaatttata aaatctgcag aagatttgga caagttaaga aatgatggat       540
atttgatgtt ccagcaagtg ccaatggttg agattgatgg gatgaagctg gtgcagacca       600
gagccattct caactacatt gccagcaaat acaacctcta tggaaaagac ataaaggaga       660
aagccctgat tgatatgtat atagaaggta tagcagattt gggtgaaatg atccttcttc       720
tgccctttac tcaacctgag gaacaagatg ccaagcttgc cttgatccaa gagaaaacaa       780
aaaatcgcta cttccctgcc tttgaaaaag tcttaaagag ccacggacaa gactaccttg       840
ttggcaacaa gctgagccgg gctgacattc acctggtgga acttctctac tacgtggaag       900
agcttgactc tagccttatt ccagcttccc ctctgctgaa ggccctgaaa accagaatca       960
gtaacctgcc cacagtgaag aagtttctac agcctggcag cccaaggaag cctcccatgg      1020
atgagaaatc tttagaagaa tcaaggaaga ttttcaggtt ttcccgggag ctcgtggatc      1080
cgaattctgt acaggcgcgc ctgcaggacg tcgacggtac catcgatacg cgttcgaagc      1140
ttgcggccgc acagctgtat acacgtgcaa gccagccaga actcgctcct gaagacccag      1200
aggatctcga gcaccaccac caccaccact aatgttaatt aagttgggcg ttgtaatcat      1260
agtcataatc aatactcctg actgcgttag caatttaact gtgataaact accgcattaa      1320
agctattcga tgataagctg tcaaacatga taattcttga agacgaaagg gcctaggctg      1380
ataaaacaga atttgcctgg cggcagtagc gcggtggtcc cacctgaccc catgccgaac      1440
tcagaagtga aacgccgtag cgccgatggt agtgtggggt ctccccatgc gagagtaggg      1500
aactgccagg catcaaataa aacgaaaggc tcagtcgaaa gactgggcct ttcgttttat      1560
ctgttgtttg tcggtgaacg ctctcctgag taggacaaat ccgccgggag cggatttgaa      1620
cgttgcgaag caacggcccg gagggtggcg gcaggacgc ccgccataaa ctgccaggca      1680
tcaaattaag cagaaggcca tcctgacgga tggcctttt gcgtttctac aaactctttt      1740
gtttattttt ctaaatacat tcaaatatgt atccgctgag caataactag cataacccct      1800
tggggcctct aaacgggtct tgaggggttt tttgctgaaa ggaggaacta tatccggatt      1860
ggcgaatggg acgcgccctg tagcggcgca ttaagcgcgg cgggtgtggt ggttacgcgc      1920
agcgtgaccg ctacacttgc cagcgcccta gcgcccgctc ctttcgcttt cttcccttcc      1980
```

```
tttctcgcca cgttcgccgg cttttcccgt caagctctaa atcggggggct ccctttaggg   2040 ttccgattta gtgctttacg gcacctcgac cccaaaaaac ttgattaggg tgatggttca   2100
cgtagtgggc catcgccctg atagacggtt tttcgcccct tgacgttgga gtccacgttc   2160
tttaatagtg gactcttgtt ccaaactgga acaacactca accctatctc ggtctattct   2220
tttgatttat aagggatttt gccgatttcg gcctattggt taaaaaatga gctgatttaa   2280
caaaaattta acgcgaattt taacaaaata ttaacgttta caatttctgg cggcacgatg   2340
gcatgagatt atcaaaaagg atcttcacct agatcctttt aaattaaaaa tgaagtttta   2400
aatcaatcta agtatatat gagtaaactt ggtctgacag ttaccaatgc ttaatcagtg   2460
aggcacctat ctcagcgatc tgtctatttc gttcatccat agttgcctga ctccccgtcg   2520
tgtagataac tacgatacgg gagggcttac catctggccc cagtgctgca atgataccgc   2580
gagacccacg ctcaccggct ccagatttat cagcaataaa ccagccagcc ggaagggccg   2640
agcgcagaag tggtcctgca actttatccg cctccatcca gtctattaat tgttgccggg   2700
aagctagagt aagtagttcg ccagttaata gtttgcgcaa cgttgttgcc attgctacag   2760
gcatcgtggt gtcacgctcg tcgtttggta tggcttcatt cagctccggt tcccaacgat   2820
caaggcgagt tacatgatcc cccatgttgt gcaaaaaagc ggttagctcc ttcggtcctc   2880
cgatcgttgt cagaagtaag ttggccgcag tgttatcact catggttatg gcagcactgc   2940
ataattctct tactgtcatg ccatccgtaa gatgcttttc tgtgactggt gagtactcaa   3000
ccaagtcatt ctgagaatag tgtatgcggc gaccgagttg ctcttgcccg gcgtcaatac   3060
gggataatac cgcgccacat agcagaactt taaaagtgct catcattgga aaacgttctt   3120
cggggcgaaa actctcaagg atcttaccgc tgttgagatc cagttcgatg taacccactc   3180
gtgcacccaa ctgatcttca gcatctttta ctttcaccag cgtttctggg tgagcaaaaa   3240
caggaaggca aaatgccgca aaaaagggaa taagggcgac acggaaatgt tgaatactca   3300
tactcttcct ttttcaatca tgaccaaaat cccttaacgt gagttttcgt tccactgagc   3360
gtcagacccc gtagaaaaga tcaaggatc ttcttgagat ccttttttc tgcgcgtaat   3420 ctgctgcttg caaacaaaaa aaccaccgct accagcggtg gtttgtttgc cggatcaaga   3480
gctaccaact cttttccga aggtaactgg cttcagcaga gcgcagatac caaatactgt   3540
ccttctagtg tagccgtagt taggccacca cttcaagaac tctgtagcac cgcctacata   3600
cctcgctctg ctaatcctgt taccagtggc tgctgccagt ggcgataagt cgtgtcttac   3660
cgggttggac tcaagacgat agttaccgga taaggcgcag cggtcgggct gaacgggggg   3720
ttcgtgcaca cagcccagct tggagcgaac gacctacacc gaactgagat acctacagcg   3780
tgagctatga gaaagcgcca cgcttcccga agggagaaag gcggacaggt atccggtaag   3840
cggcagggtc ggaacaggag agcgcacgag ggagcttcca gggggaaacg cctggtatct   3900
ttatagtcct gtcgggtttc gccacctctg acttgagcgt cgatttttgt gatgctcgtc   3960 agggggggcgg agcctatgga aaaacgccag caacgcggcc ttttacggt tcctggcctt   4020 ttgctggcct tttgctcaca tgttctttcc tgcgttatcc cctgattctg tggataaccg   4080
tattaccgcc tttgagtgag ctgataccgc tcgccgcagc cgaacgaccg agcgcagcga   4140
gtcagtgagc gaggaagcgg cgataatgg cctgcttctc gccgaaacgt ttggtggcgg   4200
gaccagtgac gaaggcttga gcgagggcgt gcaagattcc gaataccgca agcgacaggc   4260
cgatcatcgt cgcgctccag cgaaagcggg cctcgccgaa aatgacccag agcgct   4316
```

```
<210> SEQ ID NO 121
<211> LENGTH: 1260
<212> TYPE: DNA
<213> ORGANISM: Homo sapiens

<400> SEQUENCE: 121
tgagcgctca caattctcgt gacatcataa cgtcccgcga aattaatacg actcactata      60
ggggaattgt gagcggataa caattcccct ctagacttac aatttccatt cgccattcag     120
gctgcgcaac tgttgggaag ggcgatcggt acgggcctct tcgctattac gccagcttgc     180
gaacggtggg tgcgctgcaa ggcgattaag ttgggtaacg ccaggattct cccagtcacg     240
acgttgtaaa acgacggcca gcgagagatc ttgattggct agcagaataa ttttgtttaa     300
ctttaagaag gagatatacc atggcgatag cagagaagcc caagctccac tactccaata     360
tacggggcag aatggagtcc atccggtggc tcctggctgc agctggagta gagttttgaag   420 agaaatttat aaaatctgca gaagatttgg acaagttaag aaatgatgga tatttgatgt     480
tccagcaagt gccaatggtt gagattgatg ggatgaagct ggtgcagacc agagccattc     540
tcaactacat tgccagcaaa tacaacctct atgggaaaga cataaggag aaagccctga       600 ttgatatgta tatagaaggt atagcagatt tgggtgaaat gatccttctt ctgccctta      660 ctcaacctga ggaacaagat gccaagcttg ccttgatcca agagaaaaca aaaaatcgct     720
acttccctgc ctttgaaaaa gtcttaaaga gccacggaca agactacctt gttggcaaca     780
agctgagccg ggctgacatt cacctggtgg aacttctcta ctacgtggaa gagcttgact     840
ctagccttat ttccagcttc cctctgctga aggccctgaa accagaatc agtaacctgc       900 ccacagtgaa gaagtttcta cagcctggca gcccaaggaa gcctcccatg gatgagaaat     960
ctttagaaga atcaaggaag attttcaggt tttcccggga gctcgtggat ccgaattctg    1020
tacaggcgcg cctgcaggac gtcgacggta ccatcgatac gcgttcgaag cttgcggccg    1080
cacagctgta tacacgtgca agccagccag aactcgctcc tgaagaccca gaggatctcg    1140
agcaccacca ccaccaccac taatgttaat taagttgggc gttgtaatca tagtcataat    1200
caatactcct gactgcgtta gcaatttaac tgtgataaac taccgcatta aagctattcg    1260

<210> SEQ ID NO 122
<211> LENGTH: 1794
<212> TYPE: DNA
<213> ORGANISM: Homo sapiens

<400> SEQUENCE: 122
gtttctccat acaggtcacg gggagccaat ggttcagaaa caaatcgagt gggttctaat      60
catggaatta atcaaaatgt aagccagtct ttgtgtcaag aagatgacta tgaagatgat     120
aagcctacca attatagtga acgttactct gaagaagaac agcatgaaga agaagagaga     180
ccaacaaatt atagcataaa atataatgaa gagaaacgtc atgtggatca gcctattgat     240
tatagtttaa aatatgccac agatattcct tcatcacaga aacagtcatt ttcattctca     300
aagagttcat ctggacaaag cagtaaaacc gaacatatgt cttcaagcag tgagaatacg     360
tccacacctt catctaatgc caagaggcag aatcagctcc atccaagttc tgcacagagt     420
agaagtggtc agcctcaaaa ggctgccact tgcaaagttt cttctattaa ccaagaaaca     480
atacagactt attgtgtaga agatactcca atatgttttt caagatgtag ttcattatca     540
tctttgtcat cagctgaaga tgaaatagga tgtaatcaga cgacacagga agcagattct     600
gctaataccc tgcaaatagc agaaataaaa gaaaagattg gaactaggtc agctgaagat     660
cctgtgagcg aagttccagc agtgtcacag cacccctagaa ccaaatccag cagactgcag    720
```

```
ggttctagtt tatcttcaga atcagccagg cacaaagctg ttgaattttc ttcaggagcg    780
aaatctccct ccaaaagtgg tgctcagaca cccaaaagtc cacctgaaca ctatgttcag    840
gagaccccac tcatgtttag cagatgtact tctgtcagtt cacttgatag ttttgagagt    900
cgttcgattg ccagctccgt tcagagtgaa ccatgcagtg aatggtaagt ggcattata     960
agccccagtg atcttccaga tagccctgga caaaccatgc caccaagcag aagtaaaaca   1020
cctccaccac ctcctcaaac agctcaaacc aagcgagaag tacctaaaaa taaagcacct   1080
actgctgaaa agagagagag tggacctaag caagctgcag taaatgctgc agttcagagg   1140
gtccaggttc ttccagatgc tgatacttta ttacattttg ccacggaaag tactccagat   1200
ggattttctt gttcatccag cctgagtgct ctgagcctcg atgagccatt tatacagaaa   1260
gatgtggaat taagaataat gcctccagtt caggaaaatg acaatgggaa tgaaacagaa   1320
tcagagcagc ctaaagaatc aaatgaaaac caagagaaag aggcagaaaa aactattgat   1380
tctgaaaagg acctattaga tgattcagat gatgatgata ttgaaatact agaagaatgt   1440
attatttctg ccatgccaac aaagtcatca cgtaaagcaa aaaagccagc ccagactgct   1500
tcaaaattac ctccacctgt ggcaaggaaa ccaagtcagc tgcctgtgta caaacttcta   1560
ccatcacaaa acaggttgca accccaaaag catgttagtt ttacaccggg ggatgatatg   1620
ccacgggtgt attgtgttga agggacacct ataaactttt ccacagctac atctctaagt   1680
gatctaacaa tcgaatcccc tccaaatgag ttagctgctg agaaggagt tagaggagga   1740
gcacagtcag gtgaatttga aaaacgagat accattccta cagaaggcag aagt         1794

<210> SEQ ID NO 123
<211> LENGTH: 1128
<212> TYPE: DNA
<213> ORGANISM: Homo sapiens

<400> SEQUENCE: 123
atggaagaag agatcgccgc gctggtcatt gacaatggct ccggcatgtg caaagctggt    60
tttgctgggg acgacgctcc ccgagccgtg tttccttcca tcgtcgggcg ccccagacac   120
cagggcgtca tggtgggcat gggccagaag gactcctacg tgggcgacga ggcccagagc   180
aagcgtggca tcctgacccc tgaagtaccc cattgagcatg gcatcgtcac caactgggac   240
gacatggaga gatctggca ccacaccttc tacaacgagc tgcgcgtggc cccggaggag   300
cacccagtgc tgctgaccga ggccccctg aaccccaagg ccaacagaga gaagatgact   360
cagattatgt ttgagacctt caacacccg gccatgtacg tggccatcca ggccgtgctg   420
tccctctacg cctctgggcg caccactggc attgtcatgg actctggaga cggggtcacc   480
cacacggtgc ccatctacga gggctacgcc ctcccccacg ccatcctgcg tctggacctg   540
gctggccggg acctgaccga ctacctcatg aagatcctca ctgagcgagg ctacagcttc   600
accaccacgg ccgagcggga aatcgtgcgc gacatcaagg agaagctgtg ctacgtcgcc   660
ctggacttcg agcaggagat ggccaccgcc gcatcctcct cttctctgga aagagctac   720
gagctgcccg atgccaggt catcaccatt ggcaatgagc ggttccggtg tccggaggcg   780
ctgttccagc cttccttcct gggtatggaa tcttgcggca tccacgagac caccttcaac   840
tccatcatga agtgtgacgt ggacatccgc aaagacctgt acgccaacac ggtgctgtcg   900
ggcggcacca ccatgtaccc gggcattgcc gacaggatgc agaaggagat caccgccctg   960
gcgcccagca ccatgaagat caagatcatc gcaccccag agcgcaagta ctcggtgtgg  1020
atcggtggct ccatcctggc ctcactgtcc accttccagc agatgtggat tagcaagcag  1080
```

```
gagtacgacg agtcgggccc ctccatcgtc caccgcaaat gcttctaa         1128
```

<210> SEQ ID NO 124
<211> LENGTH: 1182
<212> TYPE: DNA
<213> ORGANISM: Homo sapiens

<400> SEQUENCE: 124

```
atggaggagc cgcagtcaga tcctagcgtc gagccccctc tgagtcagga aacatttcca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccgcgtgg ccctgcacc agcagctcct     240
acaccggcgg ccctgcacc agcccctcc tggcccctgt catcttctgt cccttcccag     300
aaaacctacc agggcagcta cggtttccgt ctgggcttct gcattctggg acagccaag    360
tctgtgactt gcacgtactc ccctgccctc aacaagatgt tttgccaact ggccaagacc     420
tgccctgtgc agctgtgggt tgattccaca ccccgcccg caccgcgt ccgcgccatg       480
gccatctaca gcagtcaca gcacatgacg gaggttgtga ggcgctgccc ccaccatgag      540
cgctgctcag atagcgatgg tctggcccct cctcagcatc ttatccgagt ggaaggaaat     600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg aacagctttt gaggtgcgtg tttgtgcctg tcctgggaga    840
gaccggcgca cagaggaaga gaatctccgc aagaagggg agcctcacca cgagctgccc     900
ccagggagca ctaagcgagc actgcccaac aacaccagct cctctcccca gccaagaag     960
aaaccactgg atggagaata tttcacccctt cagatccgtg ggcgtgagcg cttcgagatg    1020
ttccgagagc tgaatgaggc cttggaactc aaggatgccc aggctgggaa ggagccaggg    1080
gggagcaggg ctcactccag ccacctgaag tccaaaaagg gtcagtctac ctcccgccat    1140
aaaaaactca tgttcaagac agaagggcct gactcagact ga                       1182
```

<210> SEQ ID NO 125
<211> LENGTH: 10759
<212> TYPE: DNA
<213> ORGANISM: Homo sapiens

<400> SEQUENCE: 125

```
atgcctattg gatccaaaga gaggccaaca tttttgaaa tttttaagac acgctgcaac      60
aaagcagatt taggaccaat aagtcttaat tggtttgaag aactttcttc agaagctcca     120
ccctataatt ctgaacctgc agaagaatct gaacataaaa acaacaatta cgaaccaaac     180
ctatttaaaa ctccacaaag gaaaccatct tataatcagc tggcttcaac tccaataata     240
ttcaaagagc aagggctgac tctgccgctg taccaatctc ctgtaaaaga attagataaa     300
ttcaaattag acttaggaag gaatgttccc aatagtagac ataaaagtct tcgcacagtg    360
aaaactaaaa tggatcaagc agatgatgtt tcctgtccac ttctaaattc ttgtcttagt    420
gaaagtcctg ttgttctaca atgtacacat gtaacaccac aaagagataa gtcagtggta    480
tgtgggagtt tgtttcatac accaaagttt gtgaagggtc gtcagacacc aaaacatatt    540
tctgaaagtc taggagctga ggtggatcct gatatgtctt ggtcaagttc tttagctaca    600
ccacccaccc ttagttctac tgtgctcata gtcagaaatg aagaagcatc tgaaactgta    660
```

```
tttcctcatg atactactgc taatgtgaaa agctattttt ccaatcatga tgaaagtctg    720
aagaaaaatg atagatttat cgcttctgtg acagacagtg aaaacacaaa tcaaagagaa    780
gctgcaagtc atggatttgg aaaaacatca gggaattcat ttaaagtaaa tagctgcaaa    840
gaccacattg gaaagtcaat gccaaatgtc ctagaagatg aagtatatga aacagttgta    900
gatacctctg aagaagatag ttttcatta tgttttcta aatgtagaac aaaaaatcta    960 caaaagtaa gaactagcaa gactaggaaa aaaattttcc atgaagcaaa cgctgatgaa   1020
tgtgaaaaat ctaaaaacca agtgaaagaa aaatactcat ttgtatctga agtggaacca   1080
aatgatactg atccattaga ttcaaatgta gcacatcaga agcccctttga gagtggaagt   1140 gacaaaatct ccaaggaagt tgtaccgtct ttggcctgtg aatggtctca actaacccctt   1200 tcaggtctaa atggagccca gatggagaaa ataccctat tgcatatttc ttcatgtgac   1260
caaaatattt cagaaaaga cctattagac acagagaaca aaagaaagaa agattttctt   1320
acttcagaga attctttgcc acgtatttct agcctaccaa aatcagagaa gccattaaat   1380
gaggaaacag tggtaaataa gagagatgaa gagcagcatc ttgaatctca tacagactgc   1440
attcttgcag taaagcaggc aatatctgga acttctccag tggcttcttc atttcagggt   1500
atcaaaaagt ctatattcag aataagagaa tcacctaaag agactttcaa tgcaagtttt   1560
tcaggtcata tgactgatcc aaactttaaa aagaaactg aagcctctga agtggactg   1620 gaaatacata ctgtttgctc acagaaggag gactccttat gtccaaattt aattgataat   1680
ggaagctggc cagccaccac cacacagaat tctgtagctt tgaagaatgc aggtttaata   1740 tccacttga aaagaaaac aaataagttt atttatgcta tacatgatga aacattttat   1800
aaaggaaaaa aaataccgaa agaccaaaaa tcagaactaa ttaactgttc agcccagttt   1860
gaagcaaatg cttttgaagc accacttaca tttgcaaatg ctgattcagg tttattgcat   1920
tcttctgtga aaagaagctg ttcacagaat gattctgaag aaccaactt gtccttaact   1980 agctcttttg ggacaattct gaggaaatgt tctagaaatg aaacatgttc taataataca   2040
gtaatctctc aggatcttga ttataaagaa gcaaatgta ataaggaaaaa actacagtta   2100 tttattaccc cagaagctga ttctctgtca tgcctgcagg aaggacagtg tgaaaatgat   2160
ccaaaaagca aaaagttttc agatataaaa gaagaggtct tggctgcagc atgtcaccca   2220
gtacaacatt caaaagtgga atacagtgat actgactttc aatcccagaa aagtcttta   2280 tatgatcatg aaaatgccag cactcttatt ttaactccta cttccaagga tgttctgtca   2340
aacctagtca tgatttctag aggcaaagaa tcatacaaaa tgtcagacaa gctcaaaggt   2400
aacaattatg aatctgatgt tgaattaacc aaaaatattc ccatggaaaa gaatcaagat   2460
gtatgtgctt taaatgaaaa ttataaaaac gttgagctgt tgccacctga aaaatacatg   2520
agagtagcat caccttcaag aaaggtacaa ttcaaccaaa acacaaatct aagagtaatc   2580 caaaaaatc aagaagaaac tacttcaatt tcaaaaataa ctgtcaatcc agactctgaa   2640 gaactttct cagacaatga gaataatttt gtcttccaag tagctaatga aaggaataat   2700
cttgctttag gaaatactaa ggaacttcat gaaacagact tgacttgtgt aaacgaaccc   2760
attttcaaga actctaccat ggttttatat ggagacacag gtgataaaca agcaacccaa   2820
gtgtcaatta aaaaagattt ggtttatgtt cttcagaggg agaacaaaaa tagtgtaaag   2880
cagcatataa aaatgactct aggtcaagat ttaaaatcgg acatctcctt gaatatagat   2940
aaaataccag aaaaaaataa tgattacatg aacaaatggg caggactctt aggtccaatt   3000
tcaaatcaca gttttggagg tagcttcaga acagcttcaa ataaggaaat caagctctct   3060
```

```
gaacataaca ttaagaagag caaaatgttc ttcaaagata ttgaagaaca atatcctact   3120
agtttagctt gtgttgaaat tgtaaatacc ttggcattag ataatcaaaa gaaactgagc   3180
aagcctcagt caattaatac tgtatctgca catttacaga gtagtgtagt tgtttctgat   3240
tgtaaaaata gtcatataac ccctcagatg ttattttcca agcaggattt taattcaaac   3300
cataatttaa cacctagcca aaaggcagaa attacagaac tttctactat attagaagaa   3360
tcaggaagtc agtttgaatt tactcagttt agaaaaccaa gctacatatt gcagaagagt   3420
acatttgaag tgcctgaaaa ccagatgact atcttaaaga ccacttctga ggaatgcaga   3480
gatgctgatc ttcatgtcat aatgaatgcc ccatcgattg gtcaggtaga cagcagcaag   3540
caatttgaag gtacagttga aattaaacgg aagtttgctg gcctgttgaa aaatgactgt   3600
aacaaaagtg cttctggtta tttaacagat gaaaatgaag tggggtttag gggcttttat   3660
tctgctcatg gcacaaaact gaatgtttct actgaagctc tgcaaaaagc tgtgaaactg   3720
tttagtgata ttgagaatat tagtgaggaa acttctgcag aggtacatcc aataagttta   3780
tcttcaagta aatgtcatga ttctgttgtt tcaatgttta agatagaaaa tcataatgat   3840
aaaactgtaa gtgaaaaaaa taataaatgc caactgatat tacaaaataa tattgaaatg   3900
actactggca cttttgttga agaaattact gaaaattaca agagaaatac tgaaaatgaa   3960
gataacaaat atactgctgc cagtagaaat tctcataact tagaatttga tggcagtgat   4020
tcaagtaaaa atgatactgt ttgtattcat aaagatgaaa cggacttgct atttactgat   4080
cagcacaaca tatgtcttaa attatctggc cagtttatga aggagggaaa cactcagatt   4140
aaagaagatt tgtcagattt aacttttttg gaagttgcga agctcaagag agcatgtcat   4200
ggtaatactt caaataaaga acagttaact gctactaaaa cggagcaaaa tataaaagat   4260
tttgagactt ctgatacatt ttttcagact gcaagtggga aaaatattag tgtcgccaaa   4320
gagtcattta taaaaattgt aaatttcttt gatcagaaac cagaagaatt gcataacttt   4380
tccttaaatt ctgaattaca ttctgacata agaaagaaca aaatggacat tctaagttat   4440
gaggaaacag acatagttaa acacaaaata ctgaaagaaa gtgtcccagt tggtactgga   4500
aatcaactag tgaccttcca gggacaaccc gaacgtgatg aaaagatcaa agaacctact   4560
ctgttgggtt ttcatacagc tagcgggaaa aagttaaaa ttgcaaagga atctttggac   4620
aaagtgaaaa acctttttga tgaaaagag caaggtacta gtgaaatcac cagttttagc   4680
catcaatggg caaagaccct aaagtacaga gaggcctgta aagaccttga attagcatgt   4740
gagaccattg agatcacagc tgccccaaag tgtaaagaaa tgcagaattc tctcaataat   4800
gataaaaacc ttgttctat tgagactgtg gtgccaccta agctcttaag tgataattta   4860
tgtagacaaa ctgaaaatct caaaacatca aaaagtatct ttttgaaagt taaagtacat   4920
gaaaatgtag aaaagaaac agcaaaaagt cctgcaactt gttacacaaa tcagtcccct   4980
tattcagtca ttgaaaattc agccttagct ttttacacaa gttgtagtag aaaaacttct   5040
gtgagtcaga cttcattact tgaagcaaaa aaatggctta gagaaggaat atttgatggt   5100
caaccagaaa gaataaatac tgcagattat gtaggaaatt atttgtatga aataattca   5160 aacagtacta tagctgaaaa tgacaaaaat catctctccg aaaaacaaga tacttattta   5220
agtaacagta gcatgtctaa cagctattcc taccattctg atgaggtata taatgattca   5280
ggatatctct caaaaaataa acttgattct ggtattgagc cagtattgaa gaatgttgaa   5340
gatcaaaaaa acactagttt ttccaaagta atatccaatg taaagatgc aaatgcatac   5400 ccacaaactg taaatgaaga tatttgcgtt gaggaacttg tgactagctc ttcaccctgc   5460
```

-continued

```
aaaaataaaa atgcagccat taaattgtcc atatctaata gtaataattt tgaggtaggg    5520
ccacctgcat ttaggatagc cagtggtaaa atcgtttgtg tttcacatga aacaattaaa    5580
aaagtgaaag acatatttac agacagtttc agtaaagtaa ttaaggaaaa caacgagaat    5640
aaatcaaaaa tttgccaaac gaaaattatg gcaggttgtt acgaggcatt ggatgattca    5700
gaggatattc ttcataactc tctagataat gatgaatgta gcacgcattc acataaggtt    5760
tttgctgaca ttcagagtga agaaatttta caacataacc aaaatatgtc tggattggag    5820
aaagtttcta aaatatcacc ttgtgatgtt agtttggaaa cttcagatat atgtaaatgt    5880
agtataggga agcttcataa gtcagtctca tctgcaaata cttgtgggat ttttagcaca    5940
gcaagtggaa atctgtcca ggtatcagat gcttcattac aaaacgcaag acaagtgttt    6000
tctgaaatag aagatagtac caagcaagtc ttttccaaag tattgtttaa aagtaacgaa    6060
cattcagacc agctcacaag agaagaaaat actgctatac gtactccaga acatttaata    6120
tcccaaaaag gcttttcata taatgtggta aattcatctg ctttctctgg atttagtaca    6180
gcaagtggaa agcaagtttc cattttagaa agttccttac acaaagttaa gggagtgtta    6240
gaggaatttg atttaatcag aactgagcat agtcttcact attcacctac gtctagacaa    6300
aatgtatcaa aaatacttcc tcgtgttgat aagagaaacc cagagcactg tgtaaactca    6360
gaaatggaaa aaacctgcag taagaatttt aaattatcaa ataacttaaa tgttgaaggt    6420
ggttcttcag aaaataatca ctctattaaa gtttctccat atctctctca atttcaacaa    6480
gacaaacaac agttggtatt aggaaccaaa gtctcacttg ttgagaacat tcatgttttg    6540
ggaaaagaac aggcttcacc taaaaacgta aaaatggaaa ttggtaaaac tgaaactttt    6600
tctgatgttc ctgtgaaaac aaatatagaa gtttgttcta cttactccaa agattcagaa    6660
aactactttg aaacagaagc agtagaaatt gctaaagctt ttatggaaga tgatgaactg    6720
acagattcta aactgccaag tcatgccaca cattctcttt ttacatgtcc cgaaaatgag    6780
gaaatggttt tgtcaaattc aagaattgga aaaagaagag gagagcccct tatcttagtg    6840
ggagaaccct caatcaaaag aaacttatta atgaatttg acaggataat agaaaatcaa    6900
gaaaaatcct taaggcttc aaaaagcact ccagatggca aataaaaga tcgaagattg    6960 tttatgcatc atgtttcttt agagccgatt acctgtgtac cctttcgcac aactaaggaa    7020
cgtcaagaga tacagaatcc aaatttacc gcacctggtc aagaatttct gtctaaatct    7080
catttgtatg aacatctgac tttgaaaaa tcttcaagca atttagcagt ttcaggacat    7140 ccatttatc aagtttctgc tacaagaaat gaaaaaatga gacacttgat tactacaggc    7200
agaccaacca aagtctttgt tccaccttt aaaactaaat cacattttca cagagttgaa    7260
cagtgtgtta ggaatattaa cttggaggaa acagacaaa agcaaaacat tgatggacat    7320
ggctctgatg atagtaaaaa taagattaat gacaatgaga ttcatcagtt taacaaaaac    7380
aactccaatc aagcagcagc tgtaactttc acaaagtgtg aagaagaacc tttagattta    7440
attacaagtc ttcagaatgc cagagatata caggatgtgc gaattaagaa gaaacaaagg    7500
caacgcgtct ttccacagcc aggcagtctg tatcttgcaa aaacatccac tctgcctcga    7560
atctctctga aagcagcagt aggaggccaa gttccctctg cgtgttctca taacagctg    7620 tatacgtatg gcgtttctaa acattgcata aaaattaaca gcaaaatgc agagtctttt    7680 cagtttcaca ctgaagatta ttttggtaag aaagttttat ggactggaaa aggaatacag    7740
ttggctgatg gtggatggct catacccctcc aatgatggaa aggctggaaa agaagaattt    7800
tatagggctc tgtgtgacac tccaggtgtg gatccaaagc ttatttctag aatttgggtt    7860
```

```
tataatcact atagatggat catatggaaa ctggcagcta tggaatgtgc ctttcctaag    7920
gaatttgcta atagatgcct aagcccagaa agggtgcttc ttcaactaaa atacagatat    7980
gatacggaaa ttgatagaag cagaagatcg gctataaaaa agataatgga aagggatgac    8040
acagctgcaa aaacacttgt tctctgtgtt tctgacataa tttcattgag cgcaaatata    8100
tctgaaactt ctagcaataa aactagtagt gcagataccc aaaaagtggc cattattgaa    8160
cttacagatg ggtggtatgc tgttaaggcc cagttagatc ctcccctctt agctgtctta    8220
aagaatggca gactgacagt tggtcagaag attattcttc atggagcaga actggtgggc    8280
tctcctgatg cctgtacacc tcttgaagcc ccagaatctc ttatgttaaa gatttctgct    8340
aacagtactc ggcctgctcg ctggtatacc aaacttggat tctttcctga ccctagacct    8400
tttcctctgc ccttatcatc gcttttcagt gatggaggaa atgttggttg tgttgatgta    8460
attattcaaa gagcataccc tatacagtgg atggagaaga catcatctgg attatacata    8520
tttcgcaatg aaagagagga agaaaaggaa gcagcaaaat atgtggaggc ccaacaaaag    8580
agactagaag ccttattcac taaaattcag gaggaatttg aagaacatga agaaaacaca    8640
acaaaaccat atttaccatc acgtgcacta acaagacagc aagttcgtgc tttgcaagat    8700
ggtgcagagc tttatgaagc agtgaagaat gcagcagacc cagcttacct tgagggttat    8760
ttcagtgaag agcagttaag agccttgaat aatcacaggc aaatgttgaa tgataagaaa    8820
caagctcaga tccagttgga aattaggaag gccatggaat ctgctgaaca aaaggaacaa    8880
ggtttatcaa gggatgtcac aaccgtgtgg aagttgcgta ttgtaagcta ttcaaaaaaa    8940
gaaaaagatt cagttatact gagtatttgg cgtccatcat cagatttata ttctctgtta    9000
acagaaggaa agagatacag aatttatcat cttgcaactt caaaatctaa aagtaaatct    9060
gaaagagcta acatacagtt agcagcgaca aaaaaaactc agtatcaaca actaccggtt    9120
tcagatgaaa ttttatttca gatttaccag ccacgggagc cccttcactt cagcaaatttt    9180
ttagatccag actttcagcc atcttgttct gaggtggacc taataggatt tgtcgtttct    9240
gttgtgaaaa aaacaggact tgcccctttc gtctatttgt cagacgaatg ttacaattta    9300
ctggcaataa agttttggat agaccttaat gaggacatta ttaagcctca tatgttaatt    9360
gctgcaagca acctccagtg gcgaccagaa tccaaatcag gccttcttac tttatttgct    9420
ggagattttt ctgtgttttc tgctagtcca aaagagggcc actttcaaga gacattcaac    9480
aaaatgaaaa atactgttga gaatattgac atactttgca atgaagcaga aaacaagctt    9540
atgcatatac tgcatgcaaa tgatcccaag tggtccaccc caactaaaga ctgtacttca    9600
gggccgtaca ctgctcaaat cattcctggt acaggaaaca agcttctgat gtcttctcct    9660
aattgtgaga tatattatca aagtccttta tcactttgta tggccaaaag gaagtctgtt    9720
tccacacctg tctcagccca gatgacttca aagtcttgta aggggagaa agagattgat    9780
gaccaaaaga actgcaaaaa gagaagagcc ttggatttct tgagtagact gccttaccct    9840
ccacctgtta gtcccatttg tacatttgtt tctccggctg cacagaaggc atttcagcca    9900
ccaaggagtt gtggcaccaa atacgaaaca cccataaaga aaaagaact gaattctcct    9960
cagatgactc catttaaaaa attcaatgaa atttctcttt tggaaagtaa ttcaatagct   10020
gacgaagaac ttgcattgat aaatacccaa gctcttttgt ctggttcaac aggagaaaaa   10080
caatttatat ctgtcagtga atccactagg actgctccca ccagttcaga agattatctc   10140
agactgaaac gacgttgtac tacatctctg atcaaagaac aggagagttc ccaggccagt   10200
acggaagaat gtgagaaaaa taagcaggac acaattacaa ctaaaaaata tatctaagca   10260
```

| | |
|---|---|
| tttgcaaagg cgacaataaa ttattgacgc ttaacctttc cagtttataa gactggaata | 10320 |
| taatttcaaa ccacacatta gtacttatgt tgcacaatga gaaagaaat tagtttcaaa | 10380 |
| tttacctcag cgtttgtgta tcgggcaaaa atcgttttgc ccgattccgt attggtatac | 10440 |
| ttttgcttca gttgcatatc ttaaaactaa atgtaattta ttaactaatc aagaaaaaca | 10500 |
| tctttggctg agctcggtgg ctcatgcctg taatcccaac actttgagaa gctgaggtgg | 10560 |
| gaggagtgct tgaggccagg agttcaagac cagcctgggc aacatagga gaccccatc | 10620 |
| tttacgaaga aaaaaaaaa ggggaaaaga aatcttttta aatctttgga tttgatcact | 10680 |
| acaagtatta ttttacaatc aacaaaatgg tcatccaaac tcaaacttga gaaaatatct | 10740 |
| tgctttcaaa ttgacacta | 10759 |

<210> SEQ ID NO 126
<211> LENGTH: 6096
<212> TYPE: DNA
<213> ORGANISM: Homo sapiens

<400> SEQUENCE: 126

| | |
|---|---|
| atggtggacc cggtgggctt cgcggaggcg tggaaggcgc agttcccgga ctcagagccc | 60 |
| ccgcgcatgg agctgcgctc agtgggcgac atcgagcagg agctggagcg ctgcaaggcc | 120 |
| tccattcggc gcctggagca ggaggtgaac caggagcgct tccgcatgat ctacctgcag | 180 |
| acgttgctgg ccaaggaaaa gaagagctat gaccggcagc gatgggcctt ccggcgcgcg | 240 |
| gcgcaggccc ccgacggcgc ctccgagccc cgagcgtccg cgtcgcgccc gcagccagcg | 300 |
| cccgccgacg gagccgaccc gccgcccgcc gaggagcccg aggcccggcc cgacggcgag | 360 |
| ggttctccgg gtaaggccag gcccgggacc gcccgcaggc ccggggcagc cgcgtcgggg | 420 |
| gaacgggacg accggggacc ccccgccagc gtggcggcgc tcaggtccaa cttcgagcgg | 480 |
| atccgcaagg ccatggcca gcccggggcg gacgccgaga agcccttcta cgtgaacgtc | 540 |
| gagtttcacc acgagcgcgg cctggtgaag gtcaacgaca aagaggtgtc ggaccgcatc | 600 |
| agctccctgg gcagccaggc catgcagatg gagcgcaaaa agtcccagca cggcgcgggc | 660 |
| tcgagcgtgg gggatgcatc caggcccct taccggggac gctcctcgga gagcagctgc | 720 |
| ggcgtcgacg gcgactacga ggacgccgag ttgaaccccc gcttcctgaa ggacaacctg | 780 |
| atcgacgcca atggcggtag caggcccccct tggccgcccc tggagtacca gccctaccag | 840 |
| agcatctacg tcgggggcat gatggaaggg gagggcaagg gccgctcct gcgcagccag | 900 |
| agcacctctg agcaggagaa gcgccttacc tggccccgca ggtcctactc cccccggagt | 960 |
| tttgaggatt gcggaggcgg ctatacccg gactgcagct ccaatgagaa cctcacctcc | 1020 |
| agcgaggagg acttctcctc tggccagtcc agccgcgtgt ccccaagccc caccacctac | 1080 |
| cgcatgttcc gggacaaaag ccgctctccc tcgcagaact cgcaacagtc cttcgacagc | 1140 |
| agcagtcccc ccacgccgca gtgccataag cggcaccggc actgcccggt tgtcgtgtcc | 1200 |
| gaggccacca tcgtgggcgt ccgcaagacc gggcagatct ggcccaacga tggcgagggc | 1260 |
| gccttccatg gagacgcaga tggctcgttc ggaacaccac tggatacgg ctgcgctgca | 1320 |
| gaccgggcag aggagcagcg ccggcaccaa gatgggctgc cctacattga tgactcgccc | 1380 |
| tcctcatcgc cccacctcag cagcaagggc aggggcagcc gggatgcgct ggtctcggga | 1440 |
| gccctggagt ccactaaagc gagtgagctg gacttggaaa agggcttgga gatgagaaaa | 1500 |
| tgggtcctgt cgggaatcct ggctagcgag gagacttacc tgagccacct ggaggcactg | 1560 |
| ctgctgccca tgaagccttt gaaagccgct gccaccacct ctcagccggt gctgacgagt | 1620 |

```
cagcagatcg agaccatctt cttcaaagtg cctgagctct acgagatcca caaggagttc    1680
tatgatgggc tcttcccccg cgtgcagcag tggagccacc agcagcgggt gggcgacctc    1740
ttccagaagc tggccagcca gctgggtgtg taccgggcct tcgtggacaa ctacggagtt    1800
gccatggaaa tggctgagaa gtgctgtcag gccaatgctc agtttgcaga aatctccgag    1860
aacctgagag ccagaagcaa caaagatgcc aaggatccaa cgaccaagaa ctctctggaa    1920
actctgctct acaagcctgt ggaccgtgtg acgaggagca cgctggtcct ccatgacttg    1980
ctgaagcaca ctcctgccag ccaccctgac cacccccttgc tgcaggacgc cctccgcatc    2040
tcacagaact tcctgtccag catcaatgag gagatcacac cccgacggca gtccatgacg    2100
gtgaagaagg gagagcaccg gcagctgctg aaggacagct tcatggtgga gctggtggag    2160
ggggcccgca agctgcgcca cgtcttcctg ttcaccgacc tgcttctctg caccaagctc    2220
aagaagcaga gcggaggcaa aacgcagcag tatgactgca aatggtacat tccgctcacg    2280
gatctcagct tccagatggt ggatgaactg gaggcagtgc ccaacatccc cctggtgccc    2340
gatgaggagc tggacgcttt gaagatcaag atctcccaga tcaagaatga catccagaga    2400
gagaagaggg cgaacaaggg cagcaaggct acggagaggc tgaagaagaa gctgtcggag    2460
caggagtcac tgctgctgct tatgtctccc agcatggcct tcaggtgcac agccgcaac     2520
ggcaagagtt acacgttcct gatctcctct gactatgagc gtgcagagtg gagggagaac    2580
atccgggagc agcagaagaa gtgtttcaga agcttctccc tgacatccgt ggagctgcag    2640
atgctgacca ctcgtgtgt gaaactccag actgtccaca gcattccgct gaccatcaat    2700
aaggaagatg atgagtctcc ggggctctat gggtttctga atgtcatcgt ccactcagcc    2760
actggattta agcagagttc aaaagccctt cagcggccag tagcatctga ctttgagcct    2820
cagggtctga gtgaagccgc tcgttggaac tccaaggaaa accttctcgc tggacccagt    2880
gaaaatgacc ccaaccttttt cgttgcactg tatgattttg tggccagtgg agataacact    2940
ctaagcataa ctaaaggtga aaagctccgg gtcttaggct ataatcacaa tggggaatgg    3000
tgtgaagccc aaaccaaaaa tggccaaggc tgggtcccaa gcaactacat cacgccagtc    3060
aacagtctgg agaaacactc ctggtaccat gggcctgtgt cccgcaatgc cgctgagtat    3120
ctgctgagca gcgggatcaa tggcagcttc ttggtgcgtg agagtgagag cagtcctggc    3180
cagaggtcca tctcgctgag atacgaaggg agggtgtacc attacaggat caacactgct    3240
tctgatggca agtctacgt ctcctccgag agccgcttca cacccctggc cgagttggtt    3300
catcatcatt caacggtggc cgacgggctc atcaccacgc tccattatcc agccccaaag    3360
cgcaacaagc ccactgtcta tggtgtgtcc cccaactacg acaagtggga gatgaacgc    3420
acggacatca ccatgaagca caagctgggc ggggccagt acggggaggt gtacgagggc    3480
gtgtggaaga aatacagcct gacggtggcc gtgaagacct tgaaggagga caccatggag    3540
gtggaagagt tcttgaaaga agctgcagtc atgaaagaga tcaaacaccc taacctggtg    3600
cagctccttg ggtctgcac ccgggagccc ccgttctata tcatcactga gttcatgacc    3660
tacgggaacc tcctggacta cctgaggag tgcaaccggc aggaggtgaa cgccgtggtg    3720
ctgctgtaca tggccactca gatctcgtca gccatggagt acctggagaa gaaaaacttc    3780
atccacagag atcttgctgc ccgaaactgc ctggtagggg agaaccactt ggtgaaggta    3840
gctgattttg gcctgagcag gttgatgaca ggggacacct acacagccca tgctggagcc    3900
aagttcccca tcaaatggac tgcacccgag agcctggcct acaacaagtt ctccatcaag    3960
tccgacgtct gggcatttgg agtattgctt tgggaaattg ctacctatgg catgtcccct    4020
```

```
tacccgggaa ttgacctgtc ccaggtgtat gagctgctag agaaggacta ccgcatggag    4080
cgcccagaag gctgcccaga gaaggtctat gaactcatgc gagcatgttg gcagtggaat    4140
ccctctgacc ggccctcctt tgctgaaatc caccaagcct ttgaaacaat gttccaggaa    4200
tccagtatct cagacgaagt ggaaaaggag ctggggaaac aaggcgtccg tggggctgtg    4260
agtaccttgc tgcaggcccc agagctgccc accaagacga ggacctccag gagagctgca    4320
gagcacagag acaccactga cgtgcctgag atgcctcact ccaagggcca gggagagagc    4380
gatcctctgg accatgagcc tgccgtgtct ccattgctcc ctcgaaaaga gcgaggtccc    4440
ccggagggcg gcctgaatga agatgagcgc cttctcccca agacaaaaa gaccaacttg    4500 ttcagcgcct tgatcaagaa gaagaagaag acagccccaa cccctcccaa acgcagcagc    4560
tccttccggg agatggacgg ccagccggag cgcagagggg ccggcgagga gagggccga    4620 gacatcagca acgggcact ggctttcacc cccttggaca cagctgaccc agccaagtcc    4680
ccaaagccca gcaatggggc tggggtcccc aatggagccc tccgggagtc cggggggctca    4740 ggcttccggt ctccccacct gtggaagaag tccagcacgc tgaccagcag ccgcctagcc    4800
accggcgagg aggagggcgg tggcagctcc agcaagcgct tcctgcgctc ttgctccgcc    4860
tcctgcgttc cccatggggc caaggacacg gagtggaggt cagtcacgct gcctcgggac    4920
ttgcagtcca cggaagaca gtttgactcg tccacatttg gagggcacaa aagtgagaag    4980
ccggctctgc ctcggaagag ggcaggggag aacaggtctg accaggtgac ccgaggcaca    5040
gtaacgcctc cccccaggct ggtgaaaaag aatgaggaag ctgctgatga ggtcttcaaa    5100
gacatcatgg agtccagccc gggctccagc ccgcccaacc tgactccaaa acccctccgg    5160
cggcaggtca ccgtggcccc tgcctcgggc ctcccccaca aggaagaagc tggaaagggc    5220
agtgccttag ggaccctgc tgcagctgag ccagtgaccc ccaccagcaa agcaggctca    5280
ggtgcaccag ggggcaccag caagggcccc gccgaggagt ccagagtgag gaggcacaag    5340
cactcctctg agtcgccagg gagggacaag gggaaattgt ccaggctcaa acctgccccg    5400
ccgcccccac cagcagcctc tgcagggaag gctggaggaa agccctcgca gagcccgagc    5460
caggaggcgg ccggggaggc agtcctgggc gcaaagacaa aagccacgag tctggttgat    5520
gctgtgaaca gtgacgctgc caagcccagc cagccgggag agggcctcaa aaagcccgtg    5580
ctcccggcca ctccaaagcc acagtccgcc aagccgtcgg ggacccccat cagcccagcc    5640
cccgttccct ccacgttgcc atcagcatcc tcggccctgg caggggacca gccgtcttcc    5700
accgccttca tccctctcat atcaacccga gtgtctcttc ggaaaacccg ccagcctcca    5760
gagcggatcg ccagcggcgc catcaccaag gcgtggtcc tggacagcac cgaggcgctg    5820
tgcctcgcca tctctaggaa ctccgagcag atggccagcc acagcgcagt gctggaggcc    5880
ggcaaaaacc tctacacgtt ctgcgtgagc tatgtggatt ccatccagca aatgaggaac    5940
aagtttgcct tccgagaggc catcaacaaa ctggagaata atctccggga gcttcagatc    6000
tgcccggcga cagcaggcag tggtccggcg gccactcagg acttcagcaa gctcctcagt    6060
tcggtgaagg aaatcagtga catagtgcag aggtag                             6096
```